US009828379B2

(12) United States Patent
Jones et al.

(10) Patent No.: US 9,828,379 B2
(45) Date of Patent: Nov. 28, 2017

(54) PYRROLO-PYRROLE CARBAMATE AND RELATED ORGANIC COMPOUNDS, PHARMACEUTICAL COMPOSITIONS, AND MEDICAL USES THEREOF

(71) Applicant: Abide Therapeutics, Inc., San Diego, CA (US)

(72) Inventors: Todd K. Jones, Solana Beach, CA (US); Justin S. Cisar, San Diego, CA (US); Cheryl A. Grice, Encinitas, CA (US); Dong-Hui Wang, San Diego, CA (US); Olivia D. Weber, San Diego, CA (US)

(73) Assignee: ABIDE THERAPEUTICS, INC., San Diego, CA (US)

( * ) Notice: Subject to any disclaimer, the term of this patent is extended or adjusted under 35 U.S.C. 154(b) by 0 days.

(21) Appl. No.: 14/902,324

(22) PCT Filed: Jul. 1, 2014

(86) PCT No.: PCT/US2014/045145
§ 371 (c)(1),
(2) Date: Dec. 30, 2015

(87) PCT Pub. No.: WO2015/003002
PCT Pub. Date: Jan. 8, 2015

(65) Prior Publication Data
US 2016/0137649 A1 May 19, 2016

Related U.S. Application Data

(60) Provisional application No. 61/842,543, filed on Jul. 3, 2013.

(51) Int. Cl.
*C07D 487/04* (2006.01)
*C07D 519/00* (2006.01)
*A61K 31/407* (2006.01)

(52) U.S. Cl.
CPC ......... *C07D 487/04* (2013.01); *C07D 519/00* (2013.01)

(58) Field of Classification Search
CPC ... C07D 487/04; C07D 519/00; A61K 31/407
USPC .................... 548/453, 454; 514/412, 414
See application file for complete search history.

(56) References Cited

U.S. PATENT DOCUMENTS

2005/0234090 A1  10/2005  Colon-Cruz et al.
2011/0071180 A1   3/2011  Akireddy et al.
2012/0208812 A1   8/2012  Chai et al.

FOREIGN PATENT DOCUMENTS

ES   WO 2012052730 A1 *  4/2012  ............ A61K 31/35
WO   WO 2011109277 A1 *  9/2011  ........... C07D 285/14
WO   WO-2014048865 A1    4/2014
WO   WO-2015003002 A1    1/2015

OTHER PUBLICATIONS

Berge et al. Pharmaceutical Salts. Journal of Pharmaceutical Sciences 66(1):1-19 (Jan. 1977).
Brun et al. Drug sensitivity of Chinese Trypanosoma evansi and Trypanosoma equiperdum isolates. Vet. Parasitol. 52:37-46 (1994).
Changsen et al. Improved green fluorescent protein reporter gene-based microplate screening for antituberculosis compounds by utilizing an acctamidasc promoter. Antimicrobial Agents and Chemotherapy 47:3682-3687 (2003).
Chen et al. SAP102 mediates synaptic clearance of NMDA receptors. Cell Rep. 2(5):1120-1128 (2012).
Cho et al. Low-oxygen-recovery assay for high-throughput screening of compounds against nonreplicating *Mycobacterium tuberculosis*. Antimicrobial Agents and Chemotherapy 51:1380-1385 (2007).
Collins et al. Microplate alamar blue assay versus BACTEC 460 system for high-throughput screening of compounds against *Mycobacterium tuberculosis* and *Mycobacterium avium*. Antimicrobial Agents and Chemotherapy 41:1004-1009 (1997).
Long et al. Selective blockade of 2-arachidonoylglycerol hydrolysis produces cannabinoid behavioral effects. Nat Chem Biol. 5(1):37-44 (2009).
Niphakis et al. O-Hydroxyacetamide Carbamates as a Highly Potent and Selective Class of Endocannabinoid Hydrolase Inhibitors ACS Chem. Neurosci. 3(5):418-426 (2012/Web2011).
Nomura et al. Activation of the endocannabinoid system by organophosphorus nerve agents. Nat Chem Biol. 4(6):373-378 (2008).
Nomura et al. Endocannabinoid hydrolysis generates brain prostaglandins that promote neuroinflammation. Science. 334(6057):809-813 (2011).
Nomura et al. Monoacylglycerol lipase regulates 2-arachidonoylglycerol action and arachidonic acid levels. Bioorg Med Chem Lett. 18(22):5875-5878 (2008).
PCT/US2014045145 International Preliminary Report on Patentability dated Jan. 14, 2016.
PCT/US2014045145 International Search Report and Written Opinion dated Dec. 10, 2014.
Piro et al. A dysregulated endocannabinoid-eicosanoid network supports pathogenesis in a mouse model of Alzheimer's disease. Cell Rep. 1(6):617-623 (2012).
Raz et al. The Alamar Blue® assay to determine drug sensitivity of African trypanosomes (T.b. rhodesiense and T.b. gambiense) in vitro. Acta Tropica 68:139-147 (1997).

(Continued)

*Primary Examiner* — Matthew Coughlin
*Assistant Examiner* — Sagar Patel
(74) *Attorney, Agent, or Firm* — Wilson Sonsini Goodrich & Rosati

(57) ABSTRACT

The invention provides pyrrolo-pyrrole carbamate and related organic compounds, compositions containing such compounds, medical kits, and methods for using such compounds and compositions to treat medical disorders, e.g., solid tumor cancer, obesity, Down's syndrome, Alzheimer's disease, or pain, in a patient. The octahydropyrrolo pyrrole carbamates could be derived from hexafluoroisopropanol, N,N-disuccinimide and such. The activity of carbamates in MAGL, FAAH, and ABHD6 assays are also described.

18 Claims, No Drawings

(56) References Cited

OTHER PUBLICATIONS

Snewin et al. Assessment of immunity to mycobacterial infection with luciferase reporter constructs. Infection and Immunity 67:4586-4593 (1999).
Chang et al. Highly Selective Inhibitors of Monoacylglycerol Lipase Bearing a Reactive Group that is Bioisosteric with Endocannabinoid Substrates. ChemBiol 19(5):579-588 (2012).
Niphakis et al. Evaluation of NHS carbamates as a potent and selective class of endocannabinoid hydrolase inhibitors. ACS Chem Neurosci 4(9):1322-1332 (2013).

* cited by examiner

PYRROLO-PYRROLE CARBAMATE AND RELATED ORGANIC COMPOUNDS, PHARMACEUTICAL COMPOSITIONS, AND MEDICAL USES THEREOF

CROSS-REFERENCE

This application is a U.S. National Stage Entry of PCT/US2014/045145, filed Jul. 1, 2014; which claims the benefit of priority from U.S. Provisional Patent Application No. 61/842,543, filed Jul. 3, 2013, all of which are hereby incorporated by reference in their entirety.

FIELD OF THE INVENTION

The invention provides pyrrolo-pyrrole carbamate and related organic compounds, compositions containing such compounds, medical kits, and methods for using such compounds and compositions to treat medical disorders in a patient.

BACKGROUND

Monoacylglycerol lipase (MAGL) is an enzyme responsible for hydrolyzing endocannabinoids such as 2-AG (2-arachidonoylglycerol), an arachidonate based lipid, in the nervous system. The endocannabinoid system regulates a range of physiological processes, including for example, appetite, pain sensation, inflammation, and memory. Further, disorders such as obesity, chronic pain, anxiety and depression have been linked to regulation of endocannabinoid system signaling activities. It has also recently been discovered that MAGL and its free fatty acid products are upregulated in aggressive cancer cells and in primary tumors, where it regulates a fatty acid network that promotes cancer cell migration and tumor growth.

Accordingly, MAGL modulating compounds may be useful in modulating 2-AG mediated signaling activities, and disorders associated with such signaling activities, including pain, inflammation, metabolic disorders, cancer, and the like. However, MAGL modulating compounds to date have typically lacked the selectivity required for general use as in vivo pharmaceutically acceptable agents, particularly, agents that are selective over fatty acid amide hydrolase (FAAH), a primary N-arachidonoyl ethanolamide (AEA) hydrolyzing enzyme. Genetic or pharmacological disruption of FAAH may result in one or more cannabinoid dependent behavioral effects, for example, inflammation, anxiety, depression, or reduction in pain sensation.

MAGL also serves as a source of arachidonic acid in the nervous system (Nomura, Nat. Chem. Bio. 2008; Nomura, Bioorg. Med. Chem. Lett. 2008; Long, Nat. Chem. Bio. 2009) and controls brain levels of pro-inflammatory arachidonic acid derivatives such as prostaglandins (Nomura Science 2011). Blockade of MAGL reduces molecular and cellular signs of neuroinflammation and is protective in models of neurodegeneration (Nomura, Science 2011; Chen, Cell Rep. 2012; Piro Cell Rep. 2012).

The serine hydrolase α-β-hydrolase domain 6 (ABHD6) is another lipid mediator and also may control accumulation and efficacy of 2-AG at cannabinoid receptors. ABHD6 may be a rate-limiting step of 2-AG signaling and thus is a member of the endocannabinoid signaling system. Therefore, ABHD6 may also be a useful target for cannabinoid dependent disorders, alone or in conjunction with MAGL and/or another serine hydrolase.

SUMMARY

The invention provides, for example, pyrrolo-pyrrole carbamate and related organic compounds, compositions containing such compounds, medical kits, processes to prepare such compounds, methods for using such compounds and compositions to treat medical disorders, e.g., pain, in a patient. Various aspects and embodiments of the invention are described in further detail below.

One aspect of the invention provides a family of pyrrolo-pyrrole carbamate and related organic compounds embraced by Formula (I) that may be used in the methods, compositions and kits described herein, wherein Formula (I) is represented by:

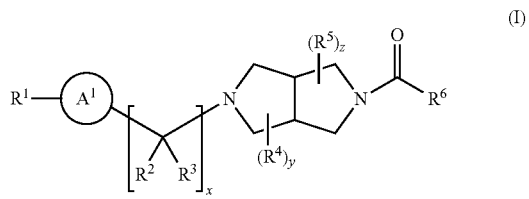

wherein, $A^1$ is arylene or heteroarylene, each of which is optionally substituted with 1 or 2 substituents independently selected from the group consisting of halogen, alkyl, haloalkyl, cycloalkyl, hydroxyl, alkoxy, haloalkoxy, and -alkylene-cycloalkyl;

$R^1$ is one of the following:
(a) heterocycloalkyl optionally substituted with 1, 2, or 3 substituents independently selected from the group consisting of alkyl, cycloalkyl, —N($R^7$)C(O)$R^8$, —N($R^7$)SO$_2$$R^8$, —C(O)$R^8$, —C(O)N($R^9$)($R^{10}$), —SO$_2$$R^8$, oxo, heteroaryl, halogen, haloalkyl, hydroxyl, alkoxyl, and -alkylene-cycloalkyl;
(b) aryl, heteroaryl, a fused heterocyclyl-heteroaryl, or cycloalkyl, each of which is optionally substituted with 1, 2, or 3 substituents independently selected from the group consisting of halogen, —N($R^7$)C(O)$R^8$, —N($R^7$)SO$_2$$R^8$, —C(O)$R^8$, —C(O)N($R^9$)($R^{10}$), —SO$_2$$R^8$, heterocycloalkyl, alkyl, haloalkyl, cycloalkyl, hydroxyl, and alkoxy; or
(c) alkyl, alkoxy, halogen, —C(O)N($R^9$)($R^{10}$), or -alkylene-heterocycloalkyl optionally substituted with 1 or more substituents independently selected from the group consisting of alkyl, cycloalkyl, —N($R^7$)C(O)$R^8$, —N($R^7$)SO$_2$$R^8$, —C(O)$R^8$, —C(O)N($R^9$)($R^{10}$), —SO$_2$$R^8$, oxo, heteroaryl, halogen, haloalkyl, hydroxyl, alkoxyl, and -alkylene-cycloalkyl;

$R^2$ is independently for each occurrence hydrogen or an alkyl optionally substituted with 1, 2, or 3 substituents independently selected from the group consisting of halogen, alkyl, haloalkyl, and cycloalkyl;

$R^3$ is independently for each occurrence hydrogen, or $R^3$ is independently for each occurrence alkyl or aryl, each of which is optionally substituted with 1, 2, or 3 substituents independently selected from the group consisting of halogen, alkyl, haloalkyl, and cycloalkyl;

$R^4$ and $R^5$ each represent independently for each occurrence alkyl, haloalkyl, or oxo; $R^6$ is one of the following:
(a) —O-haloalkyl or —O—C($R^{11}$)(haloalkyl)C(O)N($R^{12}$)($R^{13}$);

(b)

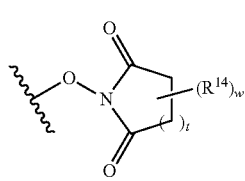

(c)

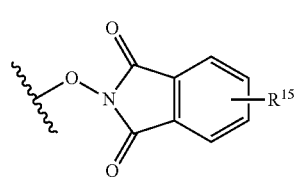

wherein t is 1 or 2; w is 0, 1, 2, 3, or 4; and $R^{14}$ represents independently for each occurrence one of the following:
(i) alkyl optionally substituted by 1, 2, or 3 substituents independently selected from the group consisting of halogen, cyano, phenyl, and hydroxyl;
(ii) alkoxy optionally substituted by 1, 2, or 3 substituents independently selected from the group consisting of halogen, cyano, and hydroxyl;
(iii) cycloalkyl optionally substituted by 1, 2, or 3 substituents independently selected from the group consisting of alkyl, halogen, cyano, phenyl, and hydroxyl; or
(iv) phenyl optionally substituted by 1, 2, or 3 substituents independently selected from the group consisting of halogen, cyano, hydroxyl, nitro, $C_{1-6}$alkyl (optionally substituted by one, two, or three halogens, cyano, or hydroxyl), $C_{2-6}$alkenyl (optionally substituted by one, two, or three halogens), $C_{3-6}$cycloalkyl, $C_{1-6}$alkoxy (optionally substituted by one, two, or three halogens), $(R^a)(R^b)N—$, $(R^a)(R^b)N—SO_2—$, $(R^a)(R^b)N—C(O)—$, $C_{1-6}$alkyl-C(O)—, $C_{1-6}$alkyl-O—C(O)—, $R^a—S(O)_2—N(R^b)—$, $R^a—S(O)—$, and $R^a—S(O)_2—$; wherein $R^a$ and $R^b$ each represent independently for each occurrence hydrogen, $C_{1-3}$alkyl, or phenyl; wherein $C_{1-3}$alkyl is optionally substituted by one or more substituents independently selected from the group consisting of halogen, cyano, oxo, phenyl, heterocyclyl and hydroxyl, and wherein phenyl or heterocyclyl is optionally substituted by one, two or three substituents each independently selected from the group consisting of halogen, cyano, hydroxyl, nitro, $C_{1-6}$alkyl (optionally substituted by one, two, or three halogens, cyano, or hydroxyl), $C_{2-6}$alkenyl (optionally substituted by one, two, or three halogens), $C_{3-6}$cycloalkyl, $C_{1-6}$alkoxy (optionally substituted by one, two, or three halogens), oxo, amino, sulfonamide, amide, $C_{1-6}$alkyl-C(O)—, and $C_{1-6}$alkyl-O—C(O)—; or $R^a$ and $R^b$ are taken together with the nitrogen atom to which they are attached to form a 4-6 membered heterocyclic ring, a 9-10 membered bicyclic heterocycle or spirocyclic ring, or a 7-9 membered bridged ring, which in addition to the first heteroatom may have a second heteroatom selected from O, S, or N; wherein the 4-6 membered heterocyclic ring, 9-10 membered bicyclic heterocycle or spirocycle, or the 7-9 membered bridged ring is optionally substituted by one or more substituents independently selected from the group consisting of halogen, cyano, oxo, $C_{1-6}$alkyl, $—S(O)_2—C_{1-6}$alkyl, hydroxyl, $—C(O)—C_{1-6}$alkyl, $—NH_2$, $—N(H)—C_{1-6}$alkyl, $—N(H)—C(O)—C_{1-6}$alkyl, $—N(H)—S(O)_2—C_{1-6}$alkyl, and $—C(O)$-heterocycle; or where $R^{15}$ is hydrogen, alkyl, or halogen;
$R^7$ is hydrogen or alkyl;
$R^8$ is alkyl, cycloalkyl, or -alkylene-cycloalkyl;
$R^9$ is hydrogen or alkyl;
$R^{10}$ is hydrogen, alkyl, cycloalkyl, heterocycloalkyl, aryl, aralkyl, -alkylene-heterocycloalkyl, or -alkylene-cycloalkyl, wherein alkyl, cycloalkyl, heterocycloalkyl, aryl, aralkyl, -alkylene-heterocycloalkyl, and -alkylene-cycloalkyl are optionally substituted with 1 or more substituents selected from the group consisting of alkyl, alkenyl, alkynyl, alkoxyl, hydroxyl, halogen, and haloalkyl; or $R^9$ and $R^{10}$ are taken together with the nitrogen atom to which they are attached to form a 4-7 membered heterocyclic ring optionally substituted with 1 or more substituents selected from the group consisting of alkyl, alkoxyl, hydroxyl, haloalkyl, halogen, $—N(R^7)C(O)R^8$, $—N(R^7)SO_2R^8$, $—C(O)R^8$, $—C(O)N(R^9)(R^{10})$, $—SO_2R^8$, and oxo;
$R^{11}$ is hydrogen or alkyl;
$R^{12}$ is hydrogen, alkyl, cycloalkyl, -alkylene-cycloalkyl, or aralkyl;
$R^{13}$ is alkyl, cycloalkyl, -alkylene-cycloalkyl, or aralkyl; or $R^{12}$ and $R^{13}$ are taken together with the nitrogen atom to which they are attached to form a 4-7 membered heterocyclic ring;
x is 1, 2, or 3; and
y and z are independently 0, 1, 2, 3, or 4;
wherein the stereochemical configuration at any stereocenter in a compound of Formula I is R, S, or a mixture thereof; or a pharmaceutically acceptable salt, solvate, hydrate, tautomer, or N-oxide thereof.

Another aspect of the invention provides a pharmaceutical composition, comprising a pharmaceutically acceptable carrier and a pyrrolo-pyrrole carbamate or related organic compound described herein, such as a compound of Formula (I).

Another aspect of the invention provides a method of treating a medical disorder, e.g., a solid tumor cancer, obesity, Downs syndrome, Alzheimer's disease, or an infection, in a patient. The method comprises administering to a patient in need thereof a therapeutically effective amount of a pyrrolo-pyrrole carbamate or related organic compound described herein, such as a compound of Formula (I), to treat the medical disorder. In some embodiments, the disorder is a solid tumor cancer. In some embodiments, the disorder is obesity. In some embodiments, the disorder is Down's syndrome or Alzheimer's disease. In some embodiments, the disorder is an infection by a bacterium, fungus, parasite, or virus.

Another aspect of the invention provides a method of treating pain in a patient. The method comprises administering to a patient in need thereof a therapeutically effective amount of a pyrrolo-pyrrole carbamate or related organic compound described herein, such as a compound of Formula (I), to treat the pain.

Yet another aspect of the invention provides a method of reducing the amount of adipose tissue in a patient. The method comprises administering to a patient in need thereof an effective amount of a pyrrolo-pyrrole carbamate or related organic compound described herein, such as a compound of Formula (I), to reduce the amount of adipose tissue in the patient.

DETAILED DESCRIPTION

The invention provides, for example, pyrrolo-pyrrole carbamate and related organic compounds, compositions containing such compounds, medical kits, and methods for using such compounds and compositions to treat medical disorders in a patient. Various aspects of the invention are set forth below in sections; however, aspects of the invention described in one particular section are not to be limited to any particular section.

I. Definitions

To facilitate an understanding of the present invention, a number of terms and phrases are defined below.

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

"Cyano" refers to the —CN radical.

"Nitro" refers to the —NO$_2$ radical.

"Oxa" refers to the —O— radical.

The term "alkyl" as used herein refers to a saturated straight or branched hydrocarbon. Exemplary alkyl groups include, but are not limited to, straight or branched hydrocarbons of 1-15, 1-12, 1-10, 1-8, 1-6, 1-5, 1-4, or 1-3 carbon atoms, referred to herein as $C_{1-15}$alkyl, $C_{1-12}$alkyl, $C_{1-10}$alkyl, $C_{1-8}$alkyl, $C_{1-6}$alkyl, $C_{1-5}$alkyl, $C_{1-4}$alkyl, and $C_{1-3}$alkyl, respectively. In certain embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). Exemplary alkyl groups include, but are not limited to, methyl, ethyl, propyl (n-propyl), isopropyl, 2-methyl-1-butyl, 3-methyl-2-butyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, etc. The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^f$, —OC(O)— NR$^a$R$^f$, —N(R$^a$)C(O)R$^f$, —N(R$^a$)S(O)$_t$R$^f$ (where t is 1 or 2), —S(O)$_t$OR$^a$ (where t is 1 or 2), —S(O)$_t$R$^f$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl, and each R$^f$ is independently alkyl, fluoroalkyl, carbocyclyl, carbocyclylalkyl, aryl, aralkyl, heterocyclyl, heterocyclylalkyl, heteroaryl or heteroarylalkyl.

The terms "alkylene" or "alkylene chain" refer to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^f$, —OC(O)— NR$^a$R$^f$, —N(R$^a$)C(O)R$^f$, —N(R$^a$)S(O)$_t$R$^f$ (where t is 1 or 2), —S(O)$_t$OR$^a$ (where t is 1 or 2), —S(O)$_t$R$^f$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl, and each R$^f$ is independently alkyl, fluoroalkyl, carbocyclyl, carbocyclylalkyl, aryl, aralkyl, heterocyclyl, heterocyclylalkyl, heteroaryl or heteroarylalkyl.

The term "haloalkyl" refers to an alkyl group that is substituted with at least one halogen. For example, —CH$_2$F, —CHF$_2$, —CF$_3$, —CH$_2$CF$_3$, —CF$_2$CF$_3$, CH(CF$_3$)$_2$ and the like.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. The alkyl part of the fluoroalkyl radical may be optionally substituted as defined above for an alkyl group.

The term "cycloalkyl" refers to a monovalent saturated cyclic, bicyclic, or multicyclic (e.g., a bridged cyclic, such as, adamantyl) hydrocarbon group of 3-12, 3-8, 4-8, or 4-6 carbons, referred to herein, e.g., as "$C_{4-8}$cycloalkyl," derived from a cycloalkane. Unless specified otherwise, cycloalkyl groups are optionally substituted at one or more ring positions by alkyl. Exemplary cycloalkyl groups include cyclohexyl, cyclopentyl, cyclobutyl, and cyclopropyl.

The term "cycloalkylene" refers to a diradical of an cycloalkyl group. An exemplary cycloalkylene group is

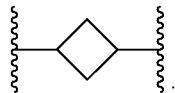

The term "alkenyl" as used herein refers to an unsaturated straight or branched hydrocarbon having at least one carbon-carbon double bond, and having from two to twelve carbon atoms. In certain embodiments, an alkenyl comprises two to eight carbon atoms. In other embodiments, an alkenyl comprises two to four carbon atoms. Exemplary alkenyl groups include, but are not limited to, a straight or branched group of 2-6 or 3-4 carbon atoms, referred to herein as $C_{2-6}$alkenyl, and $C_{3-4}$alkenyl, respectively. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —$OR^a$, —$SR^a$, —$OC(O)$—$R^a$, —$N(R^a)_2$, —$C(O)R^a$, —$C(O)OR^a$, —$C(O)N(R^a)_2$, —$N(R^a)C(O)OR^f$, —$OC(O)$—$NR^aR^f$, —$N(R^a)C(O)R^f$, —$N(R^a)S(O)_tR^f$ (where t is 1 or 2), —$S(O)_tOR^a$ (where t is 1 or 2), —$S(O)_tR^f$ (where t is 1 or 2) and —$S(O)_tN(R^a)_2$ (where t is 1 or 2) where each $R^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl, and each $R^f$ is independently alkyl, fluoroalkyl, carbocyclyl, carbocyclylalkyl, aryl, aralkyl, heterocyclyl, heterocyclylalkyl, heteroaryl or heteroarylalkyl.

The term "alkynyl" as used herein refers to an unsaturated straight or branched hydrocarbon having at least one carbon-carbon triple bond, having from two to twelve carbon atoms. In certain embodiments, an alkynyl comprises two to eight carbon atoms. In other embodiments, an alkynyl has two to four carbon atoms. Exemplary alkynyl groups include, but are not limited to, straight or branched groups of 2-6, or 3-6 carbon atoms, referred to herein as $C_{2-6}$alkynyl, and $C_{3-6}$alkynyl, respectively. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —$OR^a$, —$SR^a$, —$OC(O)$—$R^a$, —$N(R^a)_2$, —$C(O)R^a$, —$C(O)OR^a$, —$C(O)N(R^a)_2$, —$N(R^a)C(O)OR^f$, —$OC(O)$—$NR^aR^f$, —$N(R^a)C(O)R^f$, —$N(R^a)S(O)_tR^f$ (where t is 1 or 2), —$S(O)_tOR^a$ (where t is 1 or 2), —$S(O)_tR^f$ (where t is 1 or 2) and —$S(O)_tN(R^a)_2$ (where t is 1 or 2) where each $R^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl, and each $R^f$ is independently alkyl, fluoroalkyl, carbocyclyl, carbocyclylalkyl, aryl, aralkyl, heterocyclyl, heterocyclylalkyl, heteroaryl or heteroarylalkyl.

The term "aryl" is art-recognized and refers to a carbocyclic aromatic monocyclic or multicyclic ring system containing five to eighteen carbon atoms, where at least one of the rings in the ring system is fully unsaturated, i.e., it contains a cyclic, delocalized (4n+2) π-electron system in accordance with the Hückel theory. Representative aryl groups include phenyl, naphthyl, anthracenyl, and the like. The carbocyclic aromatic group may be a six-membered monocyclic ring, or the carbocyclic aromatic group may be a ten-membered bicyclic ring. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, haloalkyl (e.g., fluoroalkyl), cyano, azide, nitro, alkylthio, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$OC(O)$—$R^a$, —$R^b$—$OC(O)$—$OR^a$, —$R^b$—$OC(O)$—$N(R^a)_2$, —$R^b$—$N(R^a)_2$, —$R^b$—$C(O)R^a$, —$R^b$—$C(O)OR^a$, —$R^b$—$C(O)N(R^a)_2$, —$R^b$—$O$—$R^c$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tOR^a$ (where t is 1 or 2), —$R^b$—$S(O)_tR^a$ (where t is 1 or 2) and —$R^b$—$S(O)_tN(R^a)_2$ (where t is 1 or 2), where each $R^a$ is independently hydrogen, alkyl, fluoroalkyl, cycloalkyl, cycloalkylalkyl, aryl (optionally substituted with one or more halo groups), aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated. The term "aryl" also includes polycyclic ring systems having two or more carbocyclic rings in which two or more carbons are common to two adjoining rings (the rings are "fused rings") wherein all rings of the polycyclic ring system are aromatic. In certain embodiments, the aromatic group is not substituted, i.e., it is unsubstituted.

The term "aryloxy" refers to a radical bonded through an oxygen atom of the formula O-aryl, where aryl is as defined above.

The term "arylene" refers to a diradical of an aryl group. An exemplary arylene group is phenylene, which is represented by

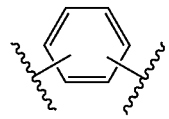

The term "aralkyl" refers to a radical of the formula —$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

The term "aralkenyl" refers to a radical of the formula $R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

The term "aralkynyl" refers to a radical of the formula —$R^e$-aryl, where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

The term "carbocyclyl" refers to a stable non-aromatic monocyclic or polycyclic hydrocarbon radical consisting solely of carbon and hydrogen atoms, which may include fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl may be saturated, (i.e., containing single C—C bonds only) or unsaturated (i.e., containing one or more double bonds or triple bonds.) A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. In certain embodiments, a cycloalkyl comprises three to eight carbon atoms (e.g., $C_3$-$C_8$ cycloalkyl). In other embodiments, a cycloalkyl comprises three to seven carbon atoms (e.g., $C_3$-$C_7$ cycloalkyl). In other embodiments, a cycloalkyl comprises three to six carbon atoms (e.g., $C_3$-$C_6$ cycloalkyl). In other embodiments, a cycloalkyl comprises three to five carbon atoms (e.g., $C_3$-$C_5$ cycloalkyl). In other embodiments, a cycloalkyl comprises three to four carbon atoms (e.g., $C_3$-$C_4$ cycloalkyl). An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$OC(O)$—$R^a$, —$R^b$—$OC(O)$—$OR^a$, —$R^b$—$OC(O)$—$N(R^a)_2$, —$R^b$—$N(R^a)_2$, —$R^b$—$C(O)R^a$, —$R^b$—$C(O)OR^a$, —$R^b$—$C(O)N(R^a)_2$, —$R^b$—$O$—$R^c$—$C(O)N(R^a)_2$, —$R^b$—$N(R^a)C(O)OR^a$, —$R^b$—$N(R^a)$ $C(O)R^a$, —$R^b$—$N(R^a)S(O)_tR^a$ (where t is 1 or 2), —$R^b$—$S(O)_tOR^a$ (where t is 1 or 2), —$R^b$—$S(O)_tR^a$ (where t is 1 or 2) and —$R^b$—$S(O)_tN(R^a)_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

The term "carbocyclylalkyl" refers to a radical of the formula —$R^c$-carbocyclyl where $R^c$ is an alkylene chain as defined above. The alkylene chain and the carbocyclyl radical is optionally substituted as defined above.

The terms "heteroaryl" or "heteroaromatic group" as used herein refers to a radical derived from a 5- to 18-membered aromatic ring radical that comprises two to seventeen carbon atoms and from one to six heteroatoms selected from nitrogen, oxygen and sulfur. As used herein, the heteroaryl radical may be a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused ring systems. The heteroatom(s) in the heteroaryl radical is optionally oxidized. One or more nitrogen atoms, if present, are optionally quaternized. The heteroaryl is attached to the rest of the molecule through any atom of the ring(s). In some embodiments, "heteroaryl" or "heteroaromatic group" as used herein refers to a monocyclic aromatic 5-6 membered or bicyclic 9-10 membered ring system containing one or more heteroatoms, for example one to three heteroatoms, such as nitrogen, oxygen, and sulfur. Where possible, said heteroaryl ring may be linked to the adjacent radical though a carbon or nitrogen atom. Examples of heteroaryls include, but are not limited to, azepinyl, acridinyl, benzimidazolyl, benzindolyl, 1,3-benzodioxolyl, benzofuranyl, benzoxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetra-hydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, azido, alkylthio, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$OC(O)$—$R^a$, —$R^b$—$OC(O)$—$OR^a$, —$R^b$—$OC(O)$—$N(R^a)_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$OR$^a$ (where t is 1 or 2), —R$^b$—S(O)$_t$R$^a$ (where t is 1 or 2) and —R$^b$—S(O)$_t$N(R$^a$)$_2$ (where t is 1 or 2), where each R$^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each R$^b$ is independently a direct bond or a straight or branched alkylene or alkenylene chain, and R$^c$ is a straight or branched alkylene or alkenylene chain, and where each of the above substituents is unsubstituted unless otherwise indicated. In certain embodiments, the heteroaryl group is not substituted, i.e., it is unsubstituted.

The term "heteroarylene" refers to a diradical of an heteroaryl group. Exemplary heteroarylene groups are (i) pyrazolylene, which is represented by

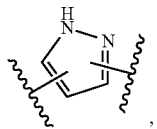

and (ii) pyridinylene, which is represented by

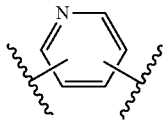

The term "heteroaryloxy" refers to radical bonded through an oxygen atom of the formula —O-heteroaryl, where heteroaryl is as defined above.

The term "heteroarylalkyl" refers to a radical of the formula —R$^c$-heteroaryl, where R$^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

The term "heteroarylalkoxy" refers to a radical bonded through an oxygen atom of the formula —O—R$^c$-heteroaryl, where R$^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

The terms "heterocycle", "heterocyclyl", or "heterocyclic group" are art-recognized and refer to saturated or partially unsaturated 3-12 membered ring structures, whose ring structures include one to four heteroatoms, such as nitrogen, oxygen, and sulfur. The ring structure may be monocyclic ring, bicyclic ring, spirocyclic ring, or other multi-cyclic ring systems, which may include fused or bridged ring systems. Where possible, heterocyclyl rings may be linked to the adjacent radical through a carbon or nitrogen atom. Examples of heterocyclyl groups include, but are not limited to, pyrrolidine, piperidine, morpholine, thiomorpholine, piperazine, oxetane, azetidine, tetrahydrofuran, dihydrofuran, tetrahydropyan, indoline, benzodioxole, dihydrobenzofuran, pyrazolidinyl, tetrahydroquinolyl, thiazolidinyl, etc. Exemplary heterocyclyl groups that are bicyclic include, but are not limited to, octahydropyrrolo[1,2-a]pyrazinyl, 8-oxa-3-azabicyclo[3.2.1]octanyl, 3-oxa-8-azabicyclo[3.2.1]octanyl, and octahydrocyclopenta[b][1,4]oxazinyl. Graphical illustrations of exemplary heterocyclyl groups that are bicyclic are provided below:

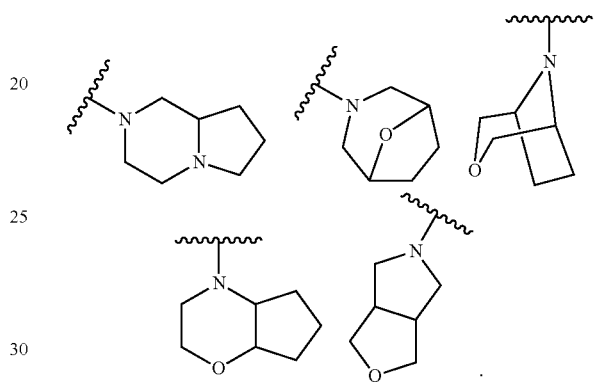

Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substitutedheteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$OR$^a$ (where t is 1 or 2), —R$^b$—S(O)$_t$R$^a$ (where t is 1 or 2) and —R$^b$—S(O)$_t$N(R$^a$)$_2$ (where t is 1 or 2), where each R$^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each R$^b$ is independently a direct bond or a straight or branched alkylene or alkenylene chain, and R$^c$ is a straight or branched alkylene or alkenylene chain, and where each of the above substituents is unsubstituted unless otherwise indicated.

Exemplary heterocyclyl groups that are spirocyclic include, but are not limited to, 2,8-diazaspiro[4.5]decanyl; 2-oxa-8-azaspiro[4.5]decanyl; 2-oxa-7-azaspiro[4.4]nonanyl; 8-oxa-2-azaspiro[4.5]decanyl; and 2,7-diazaspiro[4.4]nonanyl. Graphical illustrations of exemplary heterocyclyl groups that are spirocyclic are provided below:

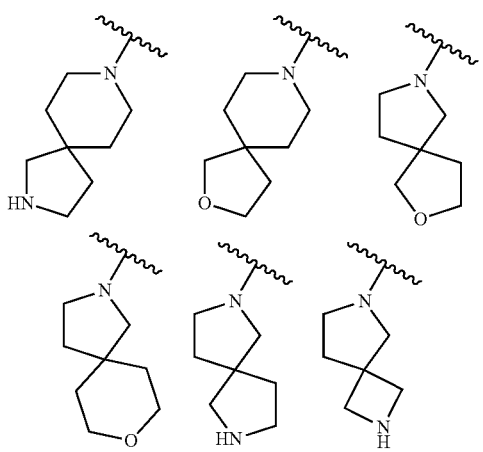

Unless specified otherwise, the heterocyclyl may be substituted at one or more ring positions with, for example, halogen, azide, alkyl, haloalkyl, aralkyl, alkenyl, alkynyl, cycloalkyl, hydroxyl, alkoxyl, amino, nitro, sulfhydryl, imino, amido, cyano, —CO$_2$H, —C(O)alkyl, —CO$_2$alkyl, alkylthio, sulfonyl, sulfonamido, sulfonamide, formyl, oxo, ester, aryl, heteroaryl, or the like.

The term "heterocycloalkyl" refers to a radical of the formula —R$^c$-heterocyclyl where R$^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

The term "heterocyclylalkoxy" refers to a radical bonded through an oxygen atom of the formula —O—R$^c$-heterocyclyl where R$^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkoxy radical is optionally substituted as defined above for an alkylene chain. The heterocyclyl part of the heterocyclylalkoxy radical is optionally substituted as defined above for a heterocyclyl group.

The term "fused heterocyclyl-heteroaryl" refers to a bicyclic ring consisting of a monocyclic heterocyclyl group fused to a monocyclic heteroaryl group. Exemplary fused heterocyclyl-heteroaryl include, but are not limited to, 6,7-dihydro-5H-pyrrolo[3,4-b]pyridinyl; 5,6,7,8-tetrahydro-[1,2,4]triazolo[1,5-c]pyrazinyl; and 5,6,7,8-tetrahydroimidazo[1,2-a]pyrazine. Graphical illustrations of exemplary fused heterocyclyl-heteroaryl groups are provided below:

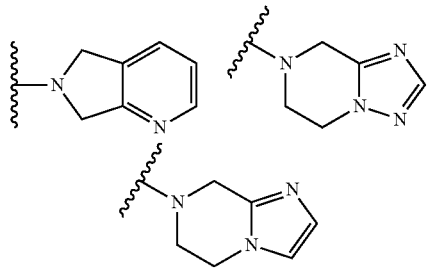

The terms "alkoxy" and "alkoxyl" are used interchangeably and refer to a straight or branched alkyl group attached to oxygen (alkyl-O—), wherein alkyl is as defined above. Exemplary alkoxy groups include, but are not limited to, alkoxy groups of 1-6 or 2-6 carbon atoms, referred to herein as C$_{1-6}$alkoxy, and C$_{2-6}$alkoxy, respectively. Exemplary alkoxy groups include, but are not limited to methoxy, ethoxy, isopropoxy, etc.

The term "haloalkoxy" refers to an alkoxy group that is substituted with at least one halogen. For example, —O—CH$_2$F, —O—CHF$_2$, —O—CF$_3$, —O—CH$_2$CF$_3$, —O—CF$_2$CF$_3$, and the like.

The terms "halo" or "halogen" as used herein refer to F, Cl, Br, or I.

The term "oxo" as used herein refers to the radical =O.

The terms "amine" and "amino" are art-recognized and refer to both unsubstituted and substituted amines, e.g., a moiety that may be represented by the general formula:

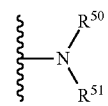

wherein R$^{50}$ and R$^{51}$ each independently represent hydrogen, alkyl, alkenyl, or —(CH$_2$)$_m$—R$^{61}$; or R$^{50}$ and R$^{51}$, taken together with the N atom to which they are attached complete a heterocycle having from 4 to 8 atoms in the ring structure; wherein R$^{61}$ is aryl, cycloalkyl, cycloalkenyl, a heterocycle or a polycycle; and m is zero or an integer in the range of 1 to 8. In certain embodiments, R$^{50}$ and R$^{51}$ each independently represent hydrogen or alkyl. In certain embodiments, R$^{50}$ and R$^{51}$ are both hydrogen.

The term "amide" or "amido" as used herein refers to a radical of the form —R$_a$C(O)N(R$_b$)—, —R$_a$C(O)N(R$_b$)R$_c$—, —C(O)NR$_b$R$_c$, or —C(O)NH$_2$, wherein R$_a$, R$_b$ and R$_c$ are each independently selected from alkoxy, alkyl, alkenyl, alkynyl, amide, amino, aryl, arylalkyl, carbamate, cycloalkyl, ester, formyl, halogen, haloalkyl, heteroaryl, heterocyclyl, and hydrogen. The amide can be attached to another group through the carbon, the nitrogen, R$_b$, R$_c$, or R$_a$. The amide also may be cyclic, for example R$_b$ and R$_c$, R$_a$ and R$_b$, or R$_a$ and R$_c$ may be joined to form a 3- to 12-membered ring, such as a 3- to 10-membered ring or a 5- to 6-membered ring.

The symbol " ∼∼∼ " indicates a point of attachment.

The compounds of the disclosure may contain one or more chiral centers and, therefore, exist as stereoisomers. The term "stereoisomers" when used herein consist of all enantiomers or diastereomers. These compounds may be designated by the symbols "(+)," "(−)," "R" or "S," depending on the configuration of substituents around the stereogenic carbon atom, but the skilled artisan will recognize that a structure may denote a chiral center implicitly. The present invention encompasses various stereoisomers of these compounds and mixtures thereof. Mixtures of enantiomers or diastereomers may be designated "(±)" in nomenclature, but the skilled artisan will recognize that a structure may denote a chiral center implicitly. It is understood that graphical depictions of chemical structures, e.g., generic chemical structures, encompass all stereoisomeric forms of the specified compounds, unless indicated otherwise.

Individual enantiomers and diastereomers of contemplated compounds can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns or (4) kinetic resolution using stereoselective chemical or enzymatic reagents. Racemic mixtures can also be resolved into their component enantiomers by well-known methods, such as chiral-phase liquid chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations, and may involve the use of chiral auxiliaries. For examples, see Carreira and Kvaerno, *Classics in Stereoselective Synthesis*, Wiley-VCH: Weinheim, 2009.

Geometric isomers can also exist in the compounds of the present invention. The symbol ═══ denotes a bond that may be a single, double or triple bond as described herein. The present invention encompasses the various geometric isomers and mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers.

Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring are designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. The compounds presented herein may, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

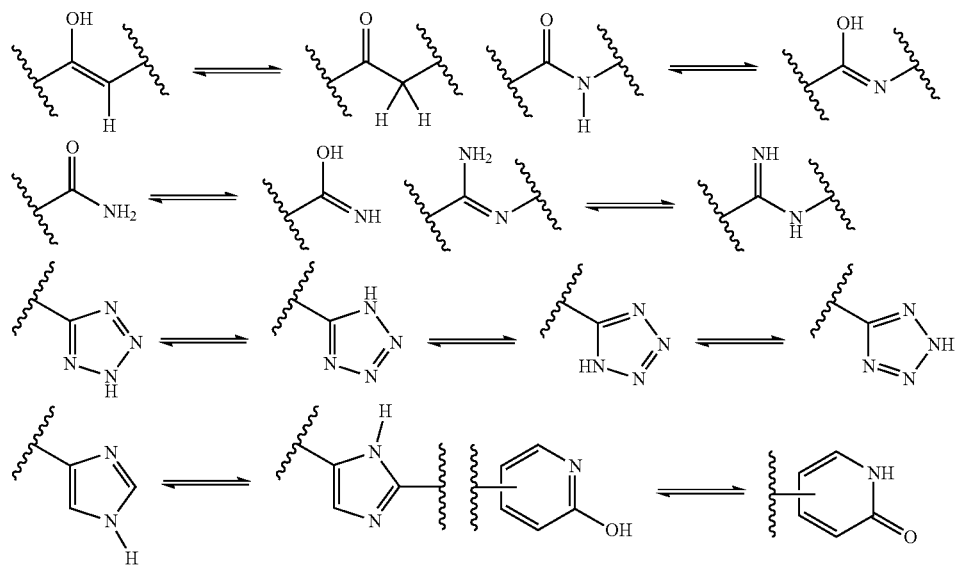

"Optional" or "optionally" means that a subsequently described event or circumstance may or may not occur and that the description includes instances when the event or circumstance occurs and instances in which it does not. For example, "optionally substituted aryl" means that the aryl radical may or may not be substituted and that the description includes both substituted aryl radicals and aryl radicals having no substitution.

The compounds disclosed herein can exist in solvated as well as unsolvated forms with pharmaceutically acceptable solvents such as water, ethanol, and the like, and it is intended that the invention embrace both solvated and unsolvated forms. In one embodiment, the compound is amorphous. In one embodiment, the compound is a single polymorph. In another embodiment, the compound is a mixture of polymorphs. In another embodiment, the compound is in a crystalline form.

Generic chemical formulae presented herein define collections of compounds based on the definitions of various substituents. Combinations of substituents envisioned are those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

As used herein, the terms "subject" and "patient" refer to organisms to be treated by the methods of the present invention. Such organisms are preferably mammals (e.g., murines, simians, equines, bovines, porcines, canines, felines, and the like), and more preferably humans.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. [1975]).

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts. Also contemplated are salts of amino acids, such as arginates, gluconates, and galacturonates (see, for example, Berge S. M. et al., "Pharmaceutical Salts," *Journal of Pharmaceutical Science*, 66:1-19 (1997), which is hereby incorporated by reference in its entirety). Acid addition salts of basic compounds may be prepared by contacting the free base forms with a sufficient amount of the desired acid to produce the salt according to methods and techniques with which a skilled artisan is familiar.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

Throughout the description, where compositions and kits are described as having, including, or comprising specific components, or where processes and methods are described as having, including, or comprising specific steps, it is contemplated that, additionally, there are compositions and kits of the present invention that consist essentially of, or consist of, the recited components, and that there are processes and methods according to the present invention that consist essentially of, or consist of, the recited processing steps.

As a general matter, compositions specifying a percentage are by weight unless otherwise specified. Further, if a variable is not accompanied by a definition, then the previous definition of the variable controls.

As used herein, "treatment" or "treating" or "palliating" or "ameliorating" are used interchangeably herein. These terms refers to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

II. Pyrrolo-Pyrrole Carbamate And Related Organic Compounds

One aspect of the invention provides pyrrolo-pyrrole carbamate and related organic compounds. The pyrrolo-pyrrole carbamate and related organic compounds are contemplated to be useful in the methods, compositions, and kits described herein.

In certain embodiments, the pyrrolo-pyrrole carbamate or related organic compound is a compound embraced by Formula (I):

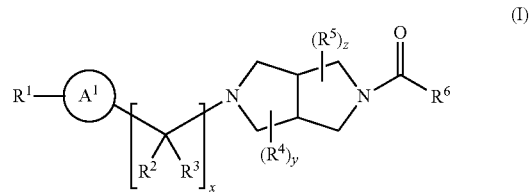

wherein,
$A^1$ is arylene or heteroarylene, each of which is optionally substituted with 1 or 2 substituents independently selected from the group consisting of halogen, alkyl, haloalkyl, cycloalkyl, hydroxyl, alkoxy, haloalkoxy, and -alkylene-cycloalkyl;
$R^1$ is one of the following:
  (a) heterocycloalkyl optionally substituted with 1, 2, or 3 substituents independently selected from the group consisting of alkyl, cycloalkyl, —N(R⁷)C(O)R⁸, —N(R⁷)SO₂R⁸, —C(O)R⁸, —C(O)N(R⁹)(R¹⁰) SO₂R⁸, oxo, heteroaryl, halogen, haloalkyl, hydroxyl, alkoxyl, and -alkylene-cycloalkyl;
(b) aryl, heteroaryl, a fused heterocyclyl-heteroaryl, or cycloalkyl, each of which is optionally substituted with 1, 2, or 3 substituents independently selected from the group consisting of halogen, —N(R⁷)C(O)R⁸, —N(R⁷)SO₂R⁸, —C(O)R⁸, —C(O)N(R⁹)(R¹⁰), —SO₂R⁸, heterocycloalkyl, alkyl, haloalkyl, cycloalkyl, hydroxyl, and alkoxy; or
(c) alkyl, alkoxy, halogen, —C(O)N(R⁹)(R¹⁰) or -alkylene-heterocycloalkyl optionally substituted with 1 or more substituents independently selected from the group consisting of alkyl, cycloalkyl, —N(R⁷)C(O)R⁸, —N(R⁷)SO₂R⁸, —C(O)R⁸, —C(O)N(R⁹)(R¹⁰), —SO₂R⁸, oxo, heteroaryl, halogen, haloalkyl, hydroxyl, alkoxyl, and -alkylene-cycloalkyl;

R² is independently for each occurrence hydrogen or an alkyl optionally substituted with 1, 2, or 3 substituents independently selected from the group consisting of halogen, alkyl, haloalkyl, and cycloalkyl;

R³ is independently for each occurrence hydrogen, or R³ is independently for each occurrence alkyl or aryl, each of which is optionally substituted with 1, 2, or 3 substituents independently selected from the group consisting of halogen, alkyl, haloalkyl, and cycloalkyl;

R⁴ and R⁵ each represent independently for each occurrence alkyl, haloalkyl, or oxo;

R⁶ is one of the following:
(a) —O-haloalkyl or —O—C(R¹¹)(haloalkyl)C(O)N(R¹²)(R¹³);

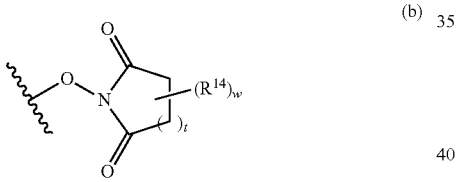

(b)

wherein t is 1 or 2; w is 0, 1, 2, 3, or 4; and R¹⁴ represents independently for each occurrence one of the following:
(i) alkyl optionally substituted by 1, 2, or 3 substituents independently selected from the group consisting of halogen, cyano, phenyl, and hydroxyl;
(ii) alkoxy optionally substituted by 1, 2, or 3 substituents independently selected from the group consisting of halogen, cyano, and hydroxyl;
(iii) cycloalkyl optionally substituted by 1, 2, or 3 substituents independently selected from the group consisting of alkyl, halogen, cyano, phenyl, and hydroxyl; or
(iv) phenyl optionally substituted by 1, 2, or 3 substituents independently selected from the group consisting of halogen, cyano, hydroxyl, nitro, C₁₋₆alkyl (optionally substituted by one, two, or three halogens, cyano, or hydroxyl), C₂₋₆alkenyl (optionally substituted by one, two, or three halogens), C₃₋₆cycloalkyl, C₁₋₆alkoxy (optionally substituted by one, two, or three halogens), (Rᵃ)(Rᵇ)N—, (Rᵃ)(Rᵇ)N—SO₂—, (Rᵃ)(Rᵇ)N—C(O)—, C₁₋₆alkyl-C(O)—, C₁₋₆alkyl-O—C(O)—, Rᵃ—S(O)₂—N(Rᵇ)—, Rᵃ—S(O)—, and Rᵃ—S(O)₂—; wherein Rᵃ and Rᵇ each represent independently for each occurrence hydrogen, C₁₋₃alkyl, or phenyl; wherein C₁₋₃alkyl is optionally substituted by one or more substituents independently selected from the group consisting of halogen, cyano, oxo, phenyl, heterocyclyl and hydroxyl, and wherein phenyl or heterocyclyl is optionally substituted by one, two or three substituents each independently selected from the group consisting of halogen, cyano, hydroxyl, nitro, C₁₋₆alkyl (optionally substituted by one, two, or three halogens, cyano, or hydroxyl), C₂₋₆alkenyl (optionally substituted by one, two, or three halogens), C₃₋₆cycloalkyl, C₁₋₆alkoxy (optionally substituted by one, two, or three halogens), oxo, amino, sulfonamide, amide, C₁₋₆alkyl-C(O)—, and C₁₋₆alkyl-O—C(O)—; or Rᵃ and Rᵇ are taken together with the nitrogen atom to which they are attached to form a 4-6 membered heterocyclic ring, a 9-10 membered bicyclic heterocycle or spirocyclic ring, or a 7-9 membered bridged ring, which in addition to the first heteroatom may have a second heteroatom selected from O, S, or N; wherein the 4-6 membered heterocyclic ring, 9-10 membered bicyclic heterocycle or spirocycle, or the 7-9 membered bridged ring is optionally substituted by one or more substituents independently selected from the group consisting of halogen, cyano, oxo, C₁₋₆alkyl, —S(O)₂—C₁₋₆alkyl, hydroxyl, —C(O)—C₁₋₆alkyl, —NH₂, —N(H)—C₁₋₆alkyl, —N(H)—C(O)—C₁₋₆alkyl, —N(H)—S(O)₂—C₁₋₆alkyl, and —C(O)-heterocycle; or

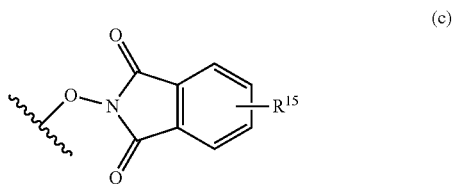

(c)

where R¹⁵ is hydrogen, alkyl, or halogen;
R⁷ is hydrogen or alkyl;
R⁸ is alkyl, cycloalkyl, or -alkylene-cycloalkyl;
R⁹ is hydrogen or alkyl;
R¹⁰ is hydrogen, alkyl, cycloalkyl, heterocycloalkyl, aryl, aralkyl, -alkylene-heterocycloalkyl, or -alkylene-cycloalkyl, wherein alkyl, cycloalkyl, heterocycloalkyl, aryl, aralkyl, -alkylene-heterocycloalkyl, and -alkylene-cycloalkyl are optionally substituted with 1 or more substituents selected from the group consisting of alkyl, alkenyl, alkynyl, alkoxyl, hydroxyl, halogen, and haloalkyl; or R⁹ and R¹⁰ are taken together with the nitrogen atom to which they are attached to form a 4-7 membered heterocyclic ring optionally substituted with 1 or more substituents selected from the group consisting of alkyl, alkoxyl, hydroxyl, haloalkyl, halogen, —N(R⁷)C(O)R⁸, —N(R⁷)SO₂R⁸, —C(O)R⁸, —C(O)N(R⁹)(R¹⁰), —SO₂R⁸, and oxo;
R¹¹ is hydrogen or alkyl;
R¹² is hydrogen, alkyl, cycloalkyl, -alkylene-cycloalkyl, or aralkyl;
R¹³ is alkyl, cycloalkyl, -alkylene-cycloalkyl, or aralkyl; or R¹² and R¹³ are taken together with the nitrogen atom to which they are attached to form a 4-7 membered heterocyclic ring;

x is 1, 2, or 3; and y and z are independently 0, 1, 2, 3, or 4;

wherein the stereochemical configuration at any stereocenter in a compound of Formula (I) is R, S, or a mixture thereof; or a pharmaceutically acceptable salt, solvate, hydrate, tautomer, or N-oxide thereof.

In certain embodiments, the pyrrolo-pyrrole carbamate or related organic compound is a compound embraced by Formula (Ia):

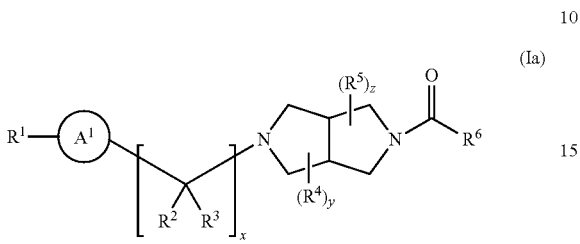

(Ia)

wherein, $A^1$ is arylene or heteroarylene, each of which is optionally substituted with 1 or 2 substituents independently selected from the group consisting of halogen, alkyl, haloalkyl, cycloalkyl, hydroxyl, alkoxy, haloalkoxy, and -alkylene-cycloalkyl;

$R^1$ is one of the following:
 (a) heterocycloalkyl optionally substituted with 1, 2, or 3 substituents independently selected from the group consisting of alkyl, cycloalkyl, —N($R^7$)C(O)$R^8$, —N($R^7$)SO$_2$$R^8$, —C(O)$R^8$, —C(O)N($R^9$)($R^{10}$), —SO$_2$$R^8$, oxo, heteroaryl, halogen, haloalkyl, hydroxyl, alkoxyl, and -alkylene-cycloalkyl;
 (b) aryl, heteroaryl, a fused heterocyclyl-heteroaryl, or cycloalkyl, each of which is optionally substituted with 1, 2, or 3 substituents independently selected from the group consisting of halogen, heterocycloalkyl, alkyl, haloalkyl, cycloalkyl, hydroxyl, and alkoxy; or
 (c) alkyl, alkoxy, halogen, or —C(O)N($R^9$)($R^{10}$);

$R^2$ is independently for each occurrence hydrogen or an alkyl optionally substituted with 1, 2, or 3 substituents independently selected from the group consisting of halogen, alkyl, haloalkyl, and cycloalkyl;

$R^3$ is independently for each occurrence hydrogen, or $R^3$ is independently for each occurrence alkyl or aryl, each of which is optionally substituted with 1, 2, or 3 substituents independently selected from the group consisting of halogen, alkyl, haloalkyl, and cycloalkyl;

$R^4$ and $R^5$ each represent independently for each occurrence alkyl, haloalkyl, or oxo;

$R^6$ is one of the following:
 (a) —O-haloalkyl or —O—C($R^{11}$)(haloalkyl)C(O)N ($R^{12}$)($R^{13}$);

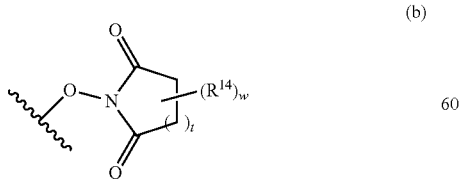

(b)

wherein t is 1 or 2; w is 0, 1, 2, 3, or 4; and $R^{14}$ represents independently for each occurrence one of the following:

(i) alkyl optionally substituted by 1, 2, or 3 substituents independently selected from the group consisting of halogen, cyano, phenyl, and hydroxyl;

(ii) alkoxy optionally substituted by 1, 2, or 3 substituents independently selected from the group consisting of halogen, cyano, and hydroxyl;

(iii) cycloalkyl optionally substituted by 1, 2, or 3 substituents independently selected from the group consisting of alkyl, halogen, cyano, phenyl, and hydroxyl; or (iv) phenyl optionally substituted by 1, 2, or 3 substituents independently selected from the group consisting of halogen, cyano, hydroxyl, nitro, $C_{1-6}$alkyl (optionally substituted by one, two, or three halogens, cyano, or hydroxyl), $C_{2-6}$alkenyl (optionally substituted by one, two, or three halogens), $C_{3-6}$cycloalkyl, $C_{1-6}$alkoxy (optionally substituted by one, two, or three halogens), ($R^a$)($R^b$)N—, ($R^a$)($R^b$)N—SO$_2$—, ($R^a$)($R^b$)N—C(O)—, $C_{1-6}$alkyl-C(O)—, $C_{1-6}$alkyl-O—C(O)—, $R^a$—S(O)$_2$—N($R^b$)—, $R^a$—S(O)—, and $R^a$—S(O)$_2$—; wherein $R^a$ and $R^b$ each represent independently for each occurrence hydrogen, $C_{1-3}$alkyl, or phenyl; wherein $C_{1-3}$alkyl is optionally substituted by one or more substituents independently selected from the group consisting of halogen, cyano, oxo, phenyl, heterocyclyl and hydroxyl, and wherein phenyl or heterocyclyl is optionally substituted by one, two or three substituents each independently selected from the group consisting of halogen, cyano, hydroxyl, nitro, $C_{1-6}$alkyl (optionally substituted by one, two, or three halogens, cyano, or hydroxyl), $C_{2-6}$alkenyl (optionally substituted by one, two, or three halogens), $C_{3-6}$cycloalkyl, $C_{1-6}$alkoxy (optionally substituted by one, two, or three halogens), oxo, amino, sulfonamide, amide, $C_{1-6}$alkyl-C(O)—, and $C_{1-6}$alkyl-O—C(O)—; or $R^a$ and $R^b$ are taken together with the nitrogen atom to which they are attached to form a 4-6 membered heterocyclic ring, a 9-10 membered bicyclic heterocycle or spirocyclic ring, or a 7-9 membered bridged ring, which in addition to the first heteroatom may have a second heteroatom selected from O, S, or N; wherein the 4-6 membered heterocyclic ring, 9-10 membered bicyclic heterocycle or spirocycle, or the 7-9 membered bridged ring is optionally substituted by one or more substituents independently selected from the group consisting of halogen, cyano, oxo, $C_{1-6}$alkyl, —S(O)$_2$—$C_{1-6}$alkyl, hydroxyl, —C(O)—$C_{1-6}$alkyl, —NH$_2$, —N(H)—$C_{1-6}$alkyl, —N(H)—C(O)—$C_{1-6}$alkyl, —N(H)—S(O)$_2$—$C_{1-6}$alkyl, and —C(O)-heterocycle; or (c)

where $R^{15}$ is hydrogen, alkyl, or halogen;

$R^7$ is hydrogen or alkyl;

$R^8$ is alkyl, cycloalkyl, or -alkylene-cycloalkyl;

R⁹ is hydrogen or alkyl;

R¹⁰ is hydrogen, alkyl, cycloalkyl, aryl, aralkyl, or -alkylene-cycloalkyl; or R⁹ and R¹⁰ are taken together with the nitrogen atom to which they are attached to form a 4-7 membered heterocyclic ring;

R¹¹ is hydrogen or alkyl;

R¹² is hydrogen, alkyl, cycloalkyl, -alkylene-cycloalkyl, or aralkyl;

R¹³ is alkyl, cycloalkyl, -alkylene-cycloalkyl, or aralkyl; or R¹² and R¹³ are taken together with the nitrogen atom to which they are attached to form a 4-7 membered heterocyclic ring;

x is 1, 2, or 3; and y and z are independently 0, 1, 2, 3, or 4;

wherein the stereochemical configuration at any stereocenter in a compound of Formula (Ia) is R, S, or a mixture thereof; or a pharmaceutically acceptable salt, solvate, hydrate, tautomer, or N-oxide thereof.

In certain embodiments of a compound of Formula (I) or Formula (Ia), A¹ is phenylene optionally substituted with 1 or 2 substituents independently selected from the group consisting of halogen, alkyl, haloalkyl, cycloalkyl, hydroxyl, alkoxy, and haloalkoxy. In certain other embodiments of a compound of Formula (I) or Formula (Ia), A¹ is phenylene optionally substituted with 1 or 2 substituents independently selected from the group consisting of halogen, methyl, —CF₃, and —O—CF₃. In certain other embodiments of a compound of Formula (I) or Formula (Ia), A¹ is a 5-membered or 6-membered heteroarylene optionally substituted with 1 or 2 substituents independently selected from the group consisting of halogen, alkyl, haloalkyl, cycloalkyl, hydroxyl, alkoxy, and haloalkoxy. In certain embodiments of a compound of Formula (I) or Formula (Ia), A¹ is a 5-membered heteroarylene optionally substituted with 1 or 2 substituents independently selected from the group consisting of halogen, alkyl, haloalkyl, cycloalkyl, hydroxyl, alkoxy, and haloalkoxy. In certain embodiments of a compound of Formula (I) or Formula (Ia), A¹ is a 6-membered heteroarylene optionally substituted with 1 or 2 substituents independently selected from the group consisting of halogen, alkyl, haloalkyl, cycloalkyl, hydroxyl, alkoxy, and haloalkoxy. In certain other embodiments of a compound of Formula (I) or Formula (Ia), A¹ is pyridinylene or pyrazolylene, each of which is optionally substituted with 1 or 2 substituents independently selected from the group consisting of halogen, alkyl, haloalkyl, cycloalkyl, hydroxyl, alkoxy, and haloalkoxy. In certain other embodiments of a compound of Formula (I) or Formula (Ia), A¹ is pyrazolylene optionally substituted with 1 or 2 substituents independently selected from the group consisting of halogen, methyl, ethyl, n-propyl, isopropyl, butyl, —CF₃, and —O—CF₃.

In certain embodiments of a compound of Formula (I) or Formula (Ia), R¹ is heterocycloalkyl optionally substituted with 1, 2, or 3 substituents independently selected from the group consisting of alkyl, cycloalkyl, —N(R⁷)C(O)R⁸, —N(R⁷)SO₂R⁸, —C(O)R⁸, —C(O)N(R⁹)(R¹⁰), —SO₂R⁸, oxo, heteroaryl, halogen, haloalkyl, hydroxyl, alkoxyl, and -alkylene-cycloalkyl. In certain other embodiments of a compound of Formula (I) or Formula (Ia), R¹ is tetrahydropyranyl, morpholinyl, piperidinyl, pyrrolidinyl, piperizindyl, or azetidinyl, each of which is optionally substituted with 1, 2, or 3 substituents independently selected from the group consisting of alkyl, cycloalkyl, —N(R⁷)C(O)R⁸, —N(R⁷)SO₂R⁸, —C(O)R⁸, —C(O)N(R⁹)(R¹⁰), —SO₂R⁸, oxo, and heteroaryl. In certain embodiments of a compound of Formula (I) or Formula (Ia), any substituent attached to the heterocycloalkyl (e.g., the tetrahydropyranyl, morpholinyl, piperidinyl, pyrrolidinyl, piperizindyl, or azetidinyl) is attached via C—C bond or a C—N bond. In certain embodiments of a compound of Formula (I) or Formula (Ia), R¹ is a heterocycloalkyl selected from:

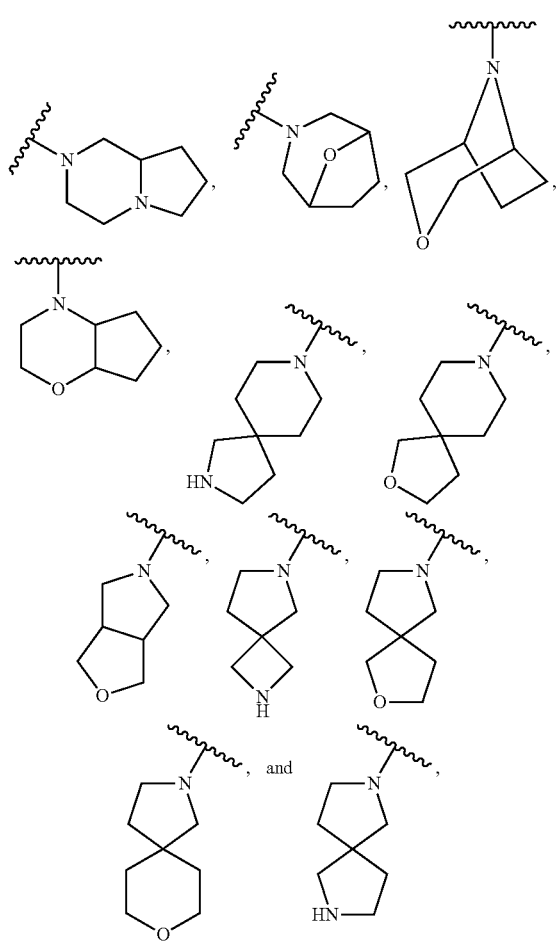

each of which is optionally substituted with 1 or 2 substituents independently selected from the group consisting of alkyl, —N(R⁷)C(O)R⁸, —N(R⁷)SO₂R⁸, —C(O)R⁸, —C(O)N(R⁹)(R¹⁰), —SO₂R⁸, and oxo. In certain other embodiments of a compound of Formula (I) or Formula (Ia), R¹ is aryl, heteroaryl, or a fused heterocyclyl-heteroaryl, each of which is optionally substituted with 1, 2, or 3 substituents independently selected from the group consisting of halogen, heterocycloalkyl, alkyl, and haloalkyl. In certain other embodiments of a compound of Formula (I) or Formula (Ia), R¹ is phenyl, pyridinyl, pyrazolyl, or a fused heterocyclyl-heteroaryl, each of which is optionally substituted with 1, 2, or 3 substituents independently selected from the group consisting of halogen, heterocycloalkyl, alkyl, and haloalkyl, wherein the fused heterocyclyl-heteroaryl is one of the following:

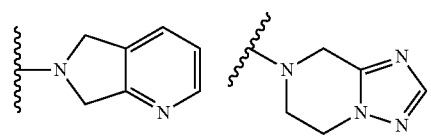

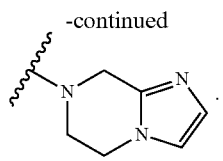

In certain other embodiments of a compound of Formula (I) or Formula (Ia), $R^1$ is alkyl. In certain other embodiments of a compound of Formula (I) or Formula (Ia), $R^1$ is alkoxy. In certain other embodiments of a compound of Formula (I) or Formula (Ia), $R^1$ is halogen. In certain other embodiments of a compound of Formula (I) or Formula (Ia), $R^1$ is —C(O)N($R^9$)($R^{10}$). In certain other embodiments of a compound of Formula (I), $R^1$ is -alkylene-heterocycloalkyl optionally substituted with 1 or more substituents independently selected from the group consisting of alkyl, cycloalkyl, —N($R^7$)C(O)$R^8$, —N($R^7$)SO$_2$$R^8$, —C(O)$R^8$, —C(O)N($R^9$)($R^{10}$), —SO$_2$$R^8$, oxo, heteroaryl, halogen, haloalkyl, hydroxyl, alkoxyl, and -alkylene-cycloalkyl. In certain other embodiments of a compound of Formula (I), $R^1$ is -alkylene-heterocycloalkyl.

In certain embodiments of a compound of Formula (I) or Formula (Ia), $R^2$ is hydrogen. In certain embodiments of a compound of Formula (I) or Formula (Ia), $R^2$ is alkyl.

In certain embodiments of a compound of Formula (I) or Formula (Ia), $R^3$ is hydrogen. In other certain embodiments of a compound of Formula (I) or Formula (Ia), $R^3$ is aryl optionally substituted by 1 or 2 halogens.

In certain embodiments of a compound of Formula (I) or Formula (Ia), $R^4$ and $R^5$ are alkyl.

In certain embodiments of a compound of Formula (I) or Formula (Ia), $R^6$ is —O— haloalkyl. In certain other embodiments of a compound of Formula (I) or Formula (Ia), $R^6$ is —O—C(H)(CF$_3$)$_2$. In certain other embodiments of a compound of Formula (I) or Formula (Ia), $R^6$ is —O—C($R^{11}$)(haloalkyl)C(O)N($R^{12}$)($R^{13}$). In certain other embodiments of a compound of Formula (I) or Formula (Ia), $R^6$ is —O—C(H)(CF$_3$)C(O)N(H)(CH$_3$). In certain other embodiments of a compound of Formula (I) or Formula (Ia), $R^6$ is

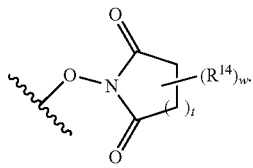

In certain embodiments of a compound of Formula (I) or Formula (Ia), $R^{14}$ alkyl. In certain other embodiments of a compound of Formula (I) or Formula (Ia), $R^6$ is

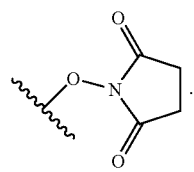

In certain embodiments of a compound of Formula (I) or Formula (Ia), $R^7$ is hydrogen. In certain embodiments of a compound of Formula (I) or Formula (Ia), $R^7$ is alkyl.

In certain embodiments of a compound of Formula (I) or Formula (Ia), $R^8$ is alkyl. In certain embodiments of a compound of Formula (I) or Formula (Ia), $R^8$ is cycloalkyl. In certain embodiments of a compound of Formula (I) or Formula (Ia), $R^8$ is -alkylene-cycloalkyl.

In certain embodiments of a compound of Formula (I) or Formula (Ia), $R^9$ is hydrogen. In certain embodiments of a compound of Formula (I) or Formula (Ia), $R^9$ is alkyl.

In certain embodiments of a compound of Formula (I), $R^{10}$ is hydrogen, alkyl, cycloalkyl, heterocycloalkyl, aralkyl, -alkylene-heterocycloalkyl, or -alkylene-cycloalkyl. In certain embodiments of a compound of Formula (I), $R^{10}$ is alkyl, cycloalkyl, heterocycloalkyl, aralkyl, -alkylene-heterocycloalkyl, or -alkylene-cycloalkyl. In certain embodiments of a compound of Formula (I), $R^{10}$ is alkyl, aralkyl, -alkylene-heterocycloalkyl, or -alkylene-cycloalkyl. In certain embodiments of a compound of Formula (I) or Formula (Ia), $R^{10}$ is alkyl. In certain embodiments of a compound of Formula (I) or Formula (Ia), $R^{10}$ is cycloalkyl. In certain embodiments of a compound of Formula (I), $R^{10}$ is heterocycloalkyl. In certain embodiments of a compound of Formula (I) or Formula (Ia), $R^{10}$ is aryl. In certain embodiments of a compound of Formula (I) or Formula (Ia), $R^{10}$ is aralkyl. In certain embodiments of a compound of Formula (I), $R^{10}$ is -alkylene-heterocycloalkyl. In certain embodiments of a compound of Formula (I) or Formula (Ia), $R^{10}$ is -alkylene-cycloalkyl.

In certain other embodiments of a compound of Formula (I) or Formula (Ia), $R^7$ is hydrogen, $R^8$ is alkyl, $R^9$ is hydrogen, and $R^{10}$ is alkyl.

In certain other embodiments of a compound of Formula (I), $R^9$ and $R^{10}$ are taken together with the nitrogen atom to which they are attached to form a 4-7 membered heterocyclic ring optionally substituted with 1 or more substituents selected from the group consisting of alkyl, alkoxyl, hydroxyl, haloalkyl, halogen, —N($R^7$)C(O)$R^8$, —N($R^7$)SO$_2$$R^8$, —C(O)$R^8$, —C(O)N($R^9$)($R^{10}$), —SO$_2$$R^8$, and oxo. In certain other embodiments of a compound of Formula (I) or Formula (Ia), $R^9$ and $R^{10}$ are taken together with the nitrogen atom to which they are attached to form a 4-7 membered heterocyclic ring.

In certain embodiments of a compound of Formula (I) or Formula (Ia), $R^{11}$ is hydrogen. In certain embodiments of a compound of Formula (I) or Formula (Ia), $R^{11}$ is alkyl.

In certain embodiments of a compound of Formula (I) or Formula (Ia), $R^{12}$ is hydrogen. In certain embodiments of a compound of Formula (I) or Formula (Ia), $R^{12}$ is alkyl. In certain embodiments of a compound of Formula (I) or Formula (Ia), $R^{12}$ is cycloalkyl. In certain embodiments of a compound of Formula (I) or Formula (Ia), $R^{12}$ is -alkylene-cycloalkyl. In certain embodiments of a compound of Formula (I) or Formula (Ia), $R^{12}$ is aralkyl.

In certain embodiments of a compound of Formula (I) or Formula (Ia), $R^{13}$ is alkyl. In certain other embodiments of a compound of Formula (I) or Formula (Ia), $R^{12}$ is hydrogen and $R^{13}$ is alkyl.

In certain embodiments of a compound of Formula (I) or Formula (Ia), x is 1. In certain embodiments of a compound of Formula (I) or Formula (Ia), x is 2. In certain embodiments of a compound of Formula (I) or Formula (Ia), x is 3.

In certain embodiments of a compound of Formula (I) or Formula (Ia), y and z are 0. In certain embodiments of a compound of Formula (I) or Formula (Ia), y is 1 and z is 0. In certain embodiments of a compound of Formula (I) or Formula (Ia), y is 0 and z is 1.

In certain embodiments of a compound of Formula (I) or Formula (Ia), the compound is in the form or a pharmaceutically acceptable salt. In certain embodiments of a compound of Formula (I) or Formula (Ia), the compound is in the form of a free base.

The description above describes multiple embodiments relating to compounds of Formula (I) and Formula (Ia). The patent application specifically contemplates all combinations of the embodiments. For example, the invention contemplates a compound of Formula (Ia) wherein $A^1$ is phenylene optionally substituted with 1 or 2 substituents independently selected from the group consisting of halogen, methyl, —$CF_3$, and —O—$CF_3$; $R^2$ is hydrogen; $R^3$ is hydrogen; and $R^6$ is —O-haloalkyl.

Another aspect of the invention provides a compound represented by Formula (Ib):

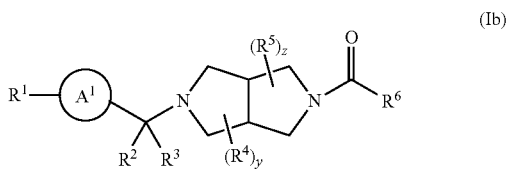

(Ib)

wherein,
  $A^1$ is phenylene or pyrazolylene, each of which is optionally substituted with 1 or 2 substituents independently selected from the group consisting of halogen, alkyl, haloalkyl, cycloalkyl, hydroxyl, alkoxy, and haloalkoxy;
  $R^1$ is one of the following:
    (a) a heterocycloalkyl selected from the group consisting of morpholinyl, piperidinyl, pyrrolidinyl, piperizindyl, and azetidinyl; each of which is optionally substituted with 1, 2, or 3 substituents independently selected from the group consisting of alkyl, cycloalkyl, —$N(R^7)C(O)R^8$, —$N(R^7)SO_2R^8$, —$C(O)R^8$, —$C(O)N(R^9)(R^{10})$, —$SO_2R^8$, and heteroaryl;
    (b) phenyl, pyridinyl, pyrazolyl, a fused heterocyclyl-heteroaryl, or cyclohexyl, each of which is optionally substituted with 1, 2, or 3 substituents independently selected from the group consisting of halogen and heterocycloalkyl; or
    (c) alkyl, alkoxy, halogen, —$C(O)N(R^9)(R^{10})$, or -alkylene-heterocycloalkyl;
  $R^2$ is hydrogen;
  $R^3$ is hydrogen or a phenyl substituted with 1 or 2 halogens;
  $R^4$ and $R^5$ each represent independently for each occurrence alkyl or haloalkyl;

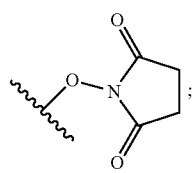 [SMILES: *ON1C(=O)CCC1=O]

$R^6$ is —O-haloalkyl, —O—$C(R^{11})$(haloalkyl)$C(O)N(R^{12})(R^{13})$, or
  $R^7$ is hydrogen or alkyl;
  $R^8$ is alkyl or cycloalkyl;
  $R^9$ is hydrogen;

$R^{10}$ is alkyl, cycloalkyl, heterocycloalkyl, -alkylene-heterocycloalkyl, aryl, or aralkyl, each of which is optionally substituted with 1 or more substituents selected from the group consisting of alkyl, alkenyl, alkynyl, alkoxyl, hydroxyl, halogen, and haloalkyl; or $R^9$ and $R^{10}$ are taken together with the nitrogen atom to which they are attached to form a 4-7 membered heterocyclic ring optionally substituted with 1 or more substituents selected from the group consisting of alkyl, alkoxyl, hydroxyl, haloalkyl, halogen, —$N(R^7)C(O)R^8$, —$N(R^7)SO_2R^8$, —$C(O)R^8$, —$C(O)N(R^9)(R^{10})$, —$SO_2R^8$, and oxo;
  $R^{11}$ is hydrogen or alkyl;
  $R^{12}$ is hydrogen, alkyl, cycloalkyl, -alkylene-cycloalkyl, or aralkyl;
  $R^{13}$ is alkyl, cycloalkyl, -alkylene-cycloalkyl, or aralkyl; or $R^{12}$ and $R^{13}$ are taken together with the nitrogen atom to which they are attached to form a 4-7 membered heterocyclic ring; and y and z are independently 0 or 1;
wherein the stereochemical configuration at any stereocenter in a compound of Formula (Ib) is R, S, or a mixture thereof; or a pharmaceutically acceptable salt, solvate, hydrate, tautomer, or N-oxide thereof.

Another aspect of the invention provides a compound represented by Formula (Ic):

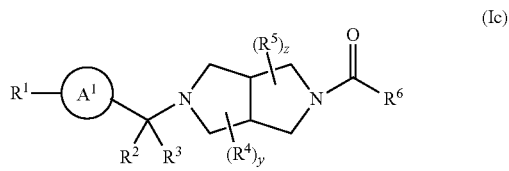

(Ic)

wherein,
  $A^1$ is phenylene or pyrazolylene, each of which is optionally substituted with 1 or 2 substituents independently selected from the group consisting of halogen, alkyl, haloalkyl, cycloalkyl, hydroxyl, alkoxy, and haloalkoxy;
  $R^1$ is one of the following:
    (a) a heterocycloalkyl selected from the group consisting of morpholinyl, piperidinyl, pyrrolidinyl, piperizindyl, and azetidinyl; each of which is optionally substituted with 1, 2, or 3 substituents independently selected from the group consisting of alkyl, cycloalkyl, —$N(R^7)C(O)R^8$, —$N(R^7)SO_2R^8$, —$C(O)R^8$, —$C(O)N(R^9)(R^{10})$, —$SO_2R^8$, and heteroaryl;
    (b) phenyl, pyridinyl, pyrazolyl, a fused heterocyclyl-heteroaryl, or cyclohexyl, each of which is optionally substituted with 1, 2, or 3 substituents independently selected from the group consisting of halogen and heterocycloalkyl; or
    (c) alkyl, alkoxy, halogen, or —$C(O)N(R^9)(R^{10})$;
  $R^2$ is hydrogen;
  $R^3$ is hydrogen or a phenyl substituted with 1 or 2 halogens;
  $R^4$ and $R^5$ each represent independently for each occurrence alkyl or haloalkyl;
  $R^6$ is —O-haloalkyl, —O—$C(R^{11})$(haloalkyl)$C(O)N(R^{12})(R^{13})$, or

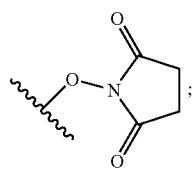 [SMILES: *ON1C(=O)CCC1=O]

R[7] is hydrogen or alkyl;
R[8] is alkyl or cycloalkyl;
R[9] is hydrogen;
R[10] is alkyl, cycloalkyl, aryl, or aralkyl; or R[9] and R[10] are taken together with the nitrogen atom to which they are attached to form a 4-7 membered heterocyclic ring;
R[11] is hydrogen or alkyl;
R[12] is hydrogen, alkyl, cycloalkyl, -alkylene-cycloalkyl, or aralkyl;
R[13] is alkyl, cycloalkyl, -alkylene-cycloalkyl, or aralkyl; or R[12] and R[13] are taken together with the nitrogen atom to which they are attached to form a 4-7 membered heterocyclic ring; and
y and z are independently 0 or 1;
wherein the stereochemical configuration at any stereocenter in a compound of Formula (Ic) is R, S, or a mixture thereof; or a pharmaceutically acceptable salt, solvate, hydrate, tautomer, or N-oxide thereof.

In certain embodiments of a compound of Formula (Ib) or Formula (Ic), $A^1$ is pyrazolylene optionally substituted with 1 or 2 substituents independently selected from the group consisting of halogen, alkyl, haloalkyl, cycloalkyl, hydroxyl, alkoxy, and haloalkoxy. In certain other embodiments of a compound of Formula (Ib) or Formula (Ic), $A^1$ is phenylene optionally substituted with 1 or 2 substituents independently selected from the group consisting of halogen, alkyl, haloalkyl, cycloalkyl, hydroxyl, alkoxy, and haloalkoxy.

In certain embodiments of a compound of Formula (Ib) or Formula (Ic), $R^1$ is a heterocycloalkyl selected from the group consisting of morpholinyl, piperidinyl, pyrrolidinyl, piperizindyl, and azetidinyl; each of which is optionally substituted with 1, 2, or 3 substituents independently selected from the group consisting of alkyl, cycloalkyl, —N(R[7])C(O)R[8], —N(R[7])SO$_2$R[8], —C(O)R[8], —C(O)N(R[9])(R[10]), and —SO$_2$R[8]. In certain other embodiments of a compound of Formula (Ib) or Formula (Ic), $R^1$ is phenyl, pyridinyl, pyrazolyl, a fused heterocyclyl-heteroaryl, or cyclohexyl, each of which is optionally substituted with 1, 2, or 3 substituents independently selected from the group consisting of halogen and heterocycloalkyl. In certain other embodiments of a compound of Formula (Ib) or Formula (Ic), $R^1$ is alkyl, alkoxy, halogen, or —C(O)N(R[9])(R[10]). In certain other embodiments of a compound of Formula (Ib) or Formula (Ic), $R^1$ is alkyl. In certain other embodiments of a compound of Formula (Ib) or Formula (Ic), $R^1$ is alkoxy. In certain other embodiments of a compound of Formula (Ib) or Formula (Ic), $R^1$ is halogen. In certain other embodiments of a compound of Formula (Ib) or Formula (Ic), $R^1$ is —C(O)N(R[9])(R[10]). In certain other embodiments of a compound of Formula (Ib), $R^1$ is -alkylene-heterocycloalkyl.

In certain embodiments of a compound of Formula (Ib) or Formula (Ic), $R^3$ is hydrogen. In certain embodiments of a compound of Formula (Ib) or Formula (Ic), $R^3$ is phenyl substituted with 1 or 2 halogens.

In certain embodiments of a compound of Formula (Ib) or Formula (Ic), $R^6$ is —O-haloalkyl. In certain embodiments of a compound of Formula (Ib) or Formula (Ic), $R^6$ is —O—C(R[11])(haloalkyl)C(O)N(R[12])(R[13]). In certain embodiments of a compound of Formula (Ib) or Formula (Ic), $R^6$ is —O-haloalkyl or —O—C(R[11])(haloalkyl)C(O)N(R[12])(R[13]). In certain embodiments of a compound of Formula (Ib) or Formula (Ic), $R^6$ is

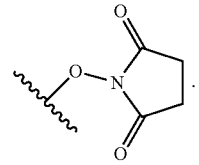

In certain embodiments of a compound of Formula (Ib) or Formula (Ic), $R^7$ is hydrogen. In certain embodiments of a compound of Formula (Ib) or Formula (Ic), $R^7$ is alkyl.

In certain embodiments of a compound of Formula (Ib) or Formula (Ic), $R^8$ is alkyl. In certain embodiments of a compound of Formula (Ib) or Formula (Ic), $R^8$ is cycloalkyl.

In certain embodiments of a compound of Formula (Ib), $R^{10}$ is hydrogen, alkyl, cycloalkyl, heterocycloalkyl, aralkyl, -alkylene-heterocycloalkyl, or -alkylene-cycloalkyl. In certain embodiments of a compound of Formula (Ib), $R^{10}$ is alkyl, cycloalkyl, heterocycloalkyl, aralkyl, -alkylene-heterocycloalkyl, or -alkylene-cycloalkyl. In certain embodiments of a compound of Formula (Ib), $R^{10}$ is alkyl, aralkyl, -alkylene-heterocycloalkyl, or -alkylene-cycloalkyl. In certain embodiments of a compound of Formula (Ib) or Formula (Ic), $R^{10}$ is alkyl. In certain embodiments of a compound of Formula (Ib) or Formula (Ic), $R^{10}$ is cycloalkyl. In certain embodiments of a compound of Formula (Ib), $R^{10}$ is heterocycloalkyl. In certain embodiments of a compound of Formula (Ib) or Formula (Ic), $R^{10}$ is aryl. In certain embodiments of a compound of Formula (Ib) or Formula (Ic), $R^{10}$ is aralkyl. In certain embodiments of a compound of Formula (Ib), $R^{10}$ is -alkylene-heterocycloalkyl. In certain embodiments of a compound of Formula (Ib), $R^{10}$ is -alkylene-cycloalkyl.

In certain embodiments of a compound of Formula (Ib), $R^9$ and $R^{10}$ are taken together with the nitrogen atom to which they are attached to form a 4-7 membered heterocyclic ring optionally substituted with 1 or more substituents selected from the group consisting of alkyl, alkoxyl, hydroxyl, haloalkyl, halogen, —N(R[7])C(O)R[8], —N(R[7])SO$_2$R[8], —C(O)R[8], —C(O)N(R[9])(R[10]), —SO$_2$R[8], and oxo. In certain embodiments of a compound of Formula (Ib) or Formula (Ic), $R^9$ and $R^{10}$ are taken together with the nitrogen atom to which they are attached to form a 4-7 membered heterocyclic ring.

In certain other embodiments of a compound of Formula (Ib) or Formula (Ic), $R^7$ is hydrogen, $R^8$ is alkyl, and $R^{10}$ is alkyl.

In certain embodiments of a compound of Formula (Ib) or Formula (Ic), $R^{11}$ is hydrogen. In certain embodiments of a compound of Formula (Ib) or Formula (Ic), $R^{11}$ is alkyl.

In certain embodiments of a compound of Formula (Ib) or Formula (Ic), $R^{12}$ is hydrogen. In certain embodiments of a compound of Formula (Ib) or Formula (Ic), $R^{12}$ is alkyl. In certain embodiments of a compound of Formula (Ib) or Formula (Ic), $R^{12}$ is cycloalkyl. In certain embodiments of a compound of Formula (Ib) or Formula (Ic), $R^{12}$ is -alkylene-cycloalkyl. In certain embodiments of a compound of Formula (Ib) or Formula (Ic), $R^{12}$ is aralkyl.

In certain embodiments of a compound of Formula (Ib) or Formula (Ic), $R^{13}$ is alkyl. In certain other embodiments of a compound of Formula (Ib) or Formula (Ic), $R^{12}$ is hydrogen and $R^{13}$ is alkyl. In certain other embodiments of a compound of Formula (Ib) or Formula (Ic), $R^{12}$ and $R^{13}$ are taken together with the nitrogen atom to which they are attached to form a 4-7 membered heterocyclic ring.

In certain embodiments of a compound of Formula (Ib) or Formula (Ic), y and z are 0.

In certain embodiments of a compound of Formula (Ib), $A^1$ is phenylene optionally substituted with 1 or 2 substituents independently selected from the group consisting of halogen, alkyl, haloalkyl, cycloalkyl, hydroxyl, alkoxy, and haloalkoxy; and $R^1$ is alkyl, alkoxy, halogen, —C(O)N($R^9$)($R^{10}$), or -alkylene-heterocycloalkyl. In certain embodiments of a compound of Formula (Ib), $A^1$ is phenylene optionally substituted with 1 or 2 substituents independently selected from the group consisting of halogen, alkyl, haloalkyl, cycloalkyl, hydroxyl, alkoxy, and haloalkoxy; and $R^1$ is alkyl. In certain embodiments of a compound of Formula (Ib), $A^1$ is phenylene optionally substituted with 1 or 2 substituents independently selected from the group consisting of halogen, alkyl, haloalkyl, cycloalkyl, hydroxyl, alkoxy, and haloalkoxy; and $R^1$ is halogen. In certain embodiments of a compound of Formula (Ib), $A^1$ is phenylene optionally substituted with 1 or 2 substituents independently selected from the group consisting of halogen, alkyl, haloalkyl, cycloalkyl, hydroxyl, alkoxy, and haloalkoxy; and $R^1$ is —C(O)N($R^9$)($R^{10}$). In certain embodiments of a compound of Formula (Ib), $A^1$ is phenylene optionally substituted with 1 or 2 substituents independently selected from the group consisting of halogen, alkyl, haloalkyl, cycloalkyl, hydroxyl, alkoxy, and haloalkoxy; and $R^1$ is -alkylene-heterocycloalkyl.

In certain embodiments of a compound of Formula (Ib), $A^1$ is pyrazolylene optionally substituted with 1 or 2 substituents independently selected from the group consisting of halogen, alkyl, haloalkyl, cycloalkyl, hydroxyl, alkoxy, and haloalkoxy; and $R^1$ is alkyl, alkoxy, halogen, —C(O)N($R^9$)($R^{10}$) or -alkylene-heterocycloalkyl. In certain embodiments of a compound of Formula (Ib), $A^1$ is pyrazolylene optionally substituted with 1 or 2 substituents independently selected from the group consisting of halogen, alkyl, haloalkyl, cycloalkyl, hydroxyl, alkoxy, and haloalkoxy; and $R^1$ is alkyl. In certain embodiments of a compound of Formula (Ib), $A^1$ is pyrazolylene optionally substituted with 1 or 2 substituents independently selected from the group consisting of halogen, alkyl, haloalkyl, cycloalkyl, hydroxyl, alkoxy, and haloalkoxy; and $R^1$ is halogen. In certain embodiments of a compound of Formula (Ib), $A^1$ is pyrazolylene optionally substituted with 1 or 2 substituents independently selected from the group consisting of halogen, alkyl, haloalkyl, cycloalkyl, hydroxyl, alkoxy, and haloalkoxy; and $R^1$ is —C(O)N($R^9$)($R^{10}$). In certain embodiments of a compound of Formula (Ib), $A^1$ is pyrazolylene optionally substituted with 1 or 2 substituents independently selected from the group consisting of halogen, alkyl, haloalkyl, cycloalkyl, hydroxyl, alkoxy, and haloalkoxy; and $R^1$ is -alkylene-heterocycloalkyl.

In certain embodiments of a compound of Formula (Ib) or Formula (Ic), the compound is in the form or a pharmaceutically acceptable salt. In certain embodiments of a compound of Formula (Ib) or Formula (Ic), the compound is in the form of a free base.

The description above describes multiple embodiments relating to compounds of Formula (Ib) or Formula (Ic). The patent application specifically contemplates all combinations of the embodiments. For example, the invention contemplates a compound of Formula (Ic) wherein $A^1$ is pyrazolylene optionally substituted with 1 or 2 substituents independently selected from the group consisting of halogen, alkyl, haloalkyl, cycloalkyl, hydroxyl, alkoxy, and haloalkoxy; $R^3$ is hydrogen; and $R^6$ is —O-haloalkyl.

Another aspect of the invention provides a compound represented by Formula (Id):

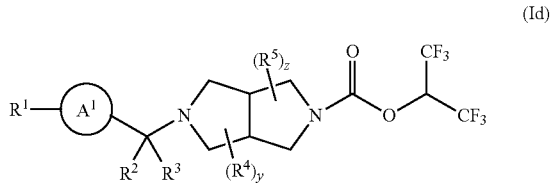

wherein,
$A^1$ is phenylene or pyrazolylene, each of which is optionally substituted with 1 or 2 substituents independently selected from the group consisting of halogen, alkyl, haloalkyl, cycloalkyl, hydroxyl, alkoxy, and haloalkoxy;

$R^1$ is one of the following:
(a) a heterocycloalkyl selected from the group consisting of morpholinyl, piperidinyl, pyrrolidinyl, piperizindyl, and azetidinyl; each of which is optionally substituted with 1, 2, or 3 substituents independently selected from the group consisting of alkyl, cycloalkyl, —N($R^7$)C(O)$R^8$, —N($R^7$)SO$_2$$R^8$, —C(O)$R^8$, —C(O)N($R^9$)($R^{10}$), —SO$_2$$R^8$, and heteroaryl;
(b) phenyl, pyridinyl, pyrazolyl, a fused heterocyclyl-heteroaryl, or cyclohexyl, each of which is optionally substituted with 1, 2, or 3 substituents independently selected from the group consisting of halogen and heterocycloalkyl; or
(c) alkyl, alkoxy, halogen, —C(O)N($R^9$)($R^{10}$), or alkylene-heterocycloalkyl;

$R^2$ is hydrogen;
$R^3$ is hydrogen or a phenyl substituted with 1 or 2 halogens;
$R^4$ and $R^5$ each represent independently for each occurrence alkyl or haloalkyl;
$R^7$ is hydrogen or alkyl;
$R^8$ is alkyl or cycloalkyl;
$R^9$ is hydrogen;
$R^{10}$ is alkyl, cycloalkyl, heterocycloalkyl, -alkylene-heterocycloalkyl, -alkylene-cycloalkyl, aryl, or aralkyl, each of which is optionally substituted with 1 or more substituents selected from the group consisting of alkyl, alkenyl, alkynyl, alkoxyl, hydroxyl, halogen, and haloalkyl; or $R^9$ and $R^{10}$ are taken together with the nitrogen atom to which they are attached to form a 4-7 membered heterocyclic ring optionally substituted with 1 or more substituents selected from the group consisting of alkyl, alkoxyl, hydroxyl, haloalkyl, halogen, —N($R^7$)C(O)$R^8$, —N($R^7$)SO$_2$$R^8$, —C(O)$R^8$, —C(O)N($R^9$)($R^{10}$), —SO$_2$$R^8$, and oxo; and
y and z are independently 0 or 1;
wherein the stereochemical configuration at any stereocenter in a compound of Formula (Id) is R, S, or a mixture thereof; or a pharmaceutically acceptable salt, solvate, hydrate, tautomer, or N-oxide thereof.

Another aspect of the invention provides a compound represented by Formula (Ie):

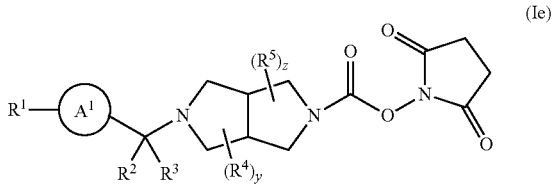

wherein,
- $A^1$ is phenylene or pyrazolylene, each of which is optionally substituted with 1 or 2 substituents independently selected from the group consisting of halogen, alkyl, haloalkyl, cycloalkyl, hydroxyl, alkoxy, and haloalkoxy;
- $R^1$ is one of the following:
  - (a) a heterocycloalkyl selected from the group consisting of morpholinyl, piperidinyl, pyrrolidinyl, piperizindyl, and azetidinyl; each of which is optionally substituted with 1, 2, or 3 substituents independently selected from the group consisting of alkyl, cycloalkyl, —N($R^7$)C(O)$R^8$, —N($R^7$)SO$_2$$R^8$, —C(O)$R^8$, —C(O)N($R^9$)($R^{10}$), —SO$_2$$R^8$, and heteroaryl;
  - (b) phenyl, pyridinyl, pyrazolyl, a fused heterocyclyl-heteroaryl, or cyclohexyl, each of which is optionally substituted with 1, 2, or 3 substituents independently selected from the group consisting of halogen and heterocycloalkyl; or
  - (c) alkyl, alkoxy, halogen, —C(O)N($R^9$)($R^{10}$), or alkylene-heterocycloalkyl;
- $R^2$ is hydrogen;
- $R^3$ is hydrogen or a phenyl substituted with 1 or 2 halogens;
- $R^4$ and $R^5$ each represent independently for each occurrence alkyl or haloalkyl;
- $R^7$ is hydrogen or alkyl;
- $R^8$ is alkyl or cycloalkyl;
- $R^9$ is hydrogen;
- $R^{10}$ is alkyl, cycloalkyl, heterocycloalkyl, -alkylene-heterocycloalkyl, -alkylene-cycloalkyl, aryl, or aralkyl, each of which is optionally substituted with 1 or more substituents selected from the group consisting of alkyl, alkenyl, alkynyl, alkoxyl, hydroxyl, halogen, and haloalkyl; or $R^9$ and $R^{10}$ are taken together with the nitrogen atom to which they are attached to form a 4-7 membered heterocyclic ring optionally substituted with 1 or more substituents selected from the group consisting of alkyl, alkoxyl, hydroxyl, haloalkyl, halogen, —N($R^7$)C(O)$R^8$, —N($R^7$)SO$_2$$R^8$, —C(O)$R^8$, —C(O)N($R^9$)($R^{10}$), —SO$_2$$R^8$, and oxo; and
- y and z are independently 0 or 1;

wherein the stereochemical configuration at any stereocenter in a compound of Formula (Ie) is R, S, or a mixture thereof; or a pharmaceutically acceptable salt, solvate, hydrate, tautomer, or N-oxide thereof.

In certain embodiments of a compound of Formula (Id) or Formula (Ie), $A^1$ is pyrazolylene optionally substituted with 1 or 2 substituents independently selected from the group consisting of halogen, alkyl, haloalkyl, cycloalkyl, hydroxyl, alkoxy, and haloalkoxy. In certain other embodiments of a compound of Formula (Id) or Formula (Ie), $A^1$ is phenylene optionally substituted with 1 or 2 substituents independently selected from the group consisting of halogen, alkyl, haloalkyl, cycloalkyl, hydroxyl, alkoxy, and haloalkoxy.

In certain embodiments of a compound of Formula (Id) or Formula (Ie), $R^1$ is a heterocycloalkyl selected from the group consisting of morpholinyl, piperidinyl, pyrrolidinyl, piperizindyl, and azetidinyl; each of which is optionally substituted with 1, 2, or 3 substituents independently selected from the group consisting of alkyl, cycloalkyl, —N($R^7$)C(O)$R^8$, —N($R^7$)SO$_2$$R^8$, —C(O)$R^8$, —C(O)N($R^9$)($R^{10}$), —SO$_2$$R^8$, and heteroaryl. In certain embodiments of a compound of Formula (Id) or Formula (Ie), $R^1$ is phenyl, pyridinyl, pyrazolyl, a fused heterocyclyl-heteroaryl, or cyclohexyl, each of which is optionally substituted with 1, 2, or 3 substituents independently selected from the group consisting of halogen and heterocycloalkyl. In certain embodiments of a compound of Formula (Id) or Formula (Ie), $R^1$ is alkyl, alkoxy, halogen, —C(O)N($R^9$)($R^{10}$), or -alkylene-heterocycloalkyl. In certain embodiments of a compound of Formula (Id) or Formula (Ie), $R^1$ is alkyl. In certain embodiments of a compound of Formula (Id) or Formula (Ie), $R^1$ is alkoxy. In certain embodiments of a compound of Formula (Id) or Formula (Ie), $R^1$ is halogen. In certain embodiments of a compound of Formula (Id) or Formula (Ie), $R^1$ is —C(O)N($R^9$)($R^{10}$). In certain embodiments of a compound of Formula (Id) or Formula (Ie), $R^1$ is -alkylene-heterocycloalkyl.

Another aspect of the invention provides a compound represented by Formula (If):

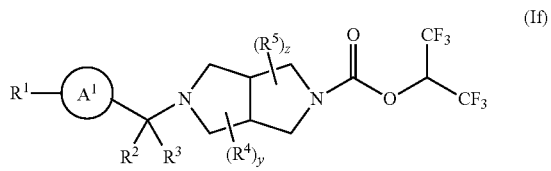

wherein,
- $A^1$ is phenylene optionally substituted with 1 or 2 substituents independently selected from the group consisting of halogen, alkyl, haloalkyl, cycloalkyl, hydroxyl, alkoxy, and haloalkoxy;
- $R^1$ is a heterocycloalkyl selected from the group consisting of morpholinyl, piperidinyl, pyrrolidinyl, piperizindyl, and azetidinyl; each of which is optionally substituted with 1, 2, or 3 substituents independently selected from the group consisting of alkyl, cycloalkyl, —N($R^7$)C(O)$R^8$, —N($R^7$)SO$_2$$R^8$, —C(O)$R^8$, —C(O)N($R^9$)($R^{10}$), —SO$_2$$R^8$, and heteroaryl;
- $R^2$ is hydrogen;
- $R^3$ is hydrogen or a phenyl substituted with 1 or 2 halogens;
- $R^4$ and $R^5$ each represent independently for each occurrence alkyl or haloalkyl;
- $R^7$ is hydrogen or alkyl;
- $R^8$ is alkyl or cycloalkyl;
- $R^9$ is hydrogen;
- $R^{10}$ is alkyl, cycloalkyl, heterocycloalkyl, -alkylene-heterocycloalkyl, -alkylene-cycloalkyl, aryl, or aralkyl, each of which is optionally substituted with 1 or more substituents selected from the group consisting of alkyl, alkenyl, alkynyl, alkoxyl, hydroxyl, halogen, and haloalkyl; or $R^9$ and $R^{10}$ are taken together with the nitrogen atom to which they are attached to form a 4-7 membered heterocyclic ring optionally substituted with 1 or more substituents selected from the group consisting of alkyl, alkoxyl, hydroxyl, haloalkyl, halogen, —N(R⁷)C(O)R⁸, —N(R⁷)SO₂R⁸, —C(O)R⁸, —C(O)N(R⁹)(R¹⁰), —SO₂R⁸, and oxo; and y and z are independently 0 or 1;

wherein the stereochemical configuration at any stereocenter in a compound of Formula (If) is R, S, or a mixture thereof; or a pharmaceutically acceptable salt, solvate, hydrate, tautomer, or N-oxide thereof.

Another aspect of the invention provides a compound represented by Formula (Ig):

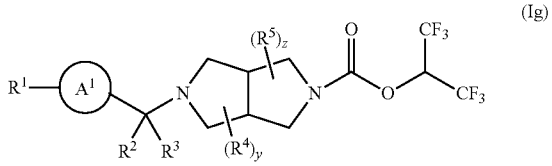

wherein,
- A¹ is phenylene optionally substituted with 1 or 2 substituents independently selected from the group consisting of halogen, alkyl, haloalkyl, cycloalkyl, hydroxyl, alkoxy, and haloalkoxy;
- R¹ is phenyl, pyridinyl, pyrazolyl, a fused heterocyclyl-heteroaryl, or cyclohexyl, each of which is optionally substituted with 1, 2, or 3 substituents independently selected from the group consisting of halogen and heterocycloalkyl;
- R² is hydrogen;
- R³ is hydrogen or a phenyl substituted with 1 or 2 halogens;
- R⁴ and R⁵ each represent independently for each occurrence alkyl or haloalkyl;
- R⁷ is hydrogen or alkyl;
- R⁸ is alkyl or cycloalkyl;
- R⁹ is hydrogen;
- R¹⁰ is alkyl, cycloalkyl, heterocycloalkyl, -alkylene-heterocycloalkyl, -alkylene-cycloalkyl, aryl, or aralkyl, each of which is optionally substituted with 1 or more substituents selected from the group consisting of alkyl, alkenyl, alkynyl, alkoxyl, hydroxyl, halogen, and haloalkyl; or R⁹ and R¹⁰ are taken together with the nitrogen atom to which they are attached to form a 4-7 membered heterocyclic ring optionally substituted with 1 or more substituents selected from the group consisting of alkyl, alkoxyl, hydroxyl, haloalkyl, halogen, —N(R⁷)C(O)R⁸, —N(R⁷)SO₂R⁸, —C(O)R⁸, —C(O)N(R⁹)(R¹⁰), —SO₂R⁸, and oxo; and y and z are independently 0 or 1;

wherein the stereochemical configuration at any stereocenter in a compound of Formula (Ig) is R, S, or a mixture thereof; or a pharmaceutically acceptable salt, solvate, hydrate, tautomer, or N-oxide thereof.

Another aspect of the invention provides a compound represented by Formula (Ih):

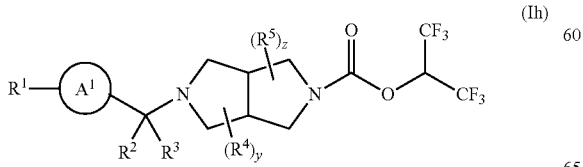

wherein,
- A¹ is pyrazolylene optionally substituted with 1 or 2 substituents independently selected from the group consisting of halogen, alkyl, haloalkyl, cycloalkyl, hydroxyl, alkoxy, and haloalkoxy;
- R¹ is a heterocycloalkyl selected from the group consisting of morpholinyl, piperidinyl, pyrrolidinyl, piperizindyl, and azetidinyl; each of which is optionally substituted with 1, 2, or 3 substituents independently selected from the group consisting of alkyl, cycloalkyl, —N(R⁷)C(O)R⁸, —N(R⁷)SO₂R⁸, —C(O)R⁸, —C(O)N(R⁹)(R¹⁰), —SO₂R⁸, and heteroaryl;
- R² is hydrogen;
- R³ is hydrogen or a phenyl substituted with 1 or 2 halogens;
- R⁴ and R⁵ each represent independently for each occurrence alkyl or haloalkyl;
- R⁷ is hydrogen or alkyl;
- R⁸ is alkyl or cycloalkyl;
- R⁹ is hydrogen;
- R¹⁰ is alkyl, cycloalkyl, heterocycloalkyl, -alkylene-heterocycloalkyl, -alkylene-cycloalkyl, aryl, or aralkyl, each of which is optionally substituted with 1 or more substituents selected from the group consisting of alkyl, alkenyl, alkynyl, alkoxyl, hydroxyl, halogen, and haloalkyl; or R⁹ and R¹⁰ are taken together with the nitrogen atom to which they are attached to form a 4-7 membered heterocyclic ring optionally substituted with 1 or more substituents selected from the group consisting of alkyl, alkoxyl, hydroxyl, haloalkyl, halogen, —N(R⁷)C(O)R⁸, —N(R⁷)SO₂R⁸, —C(O)R⁸, —C(O)N(R⁹)(R¹⁰), —SO₂R⁸, and oxo; and y and z are independently 0 or 1;

wherein the stereochemical configuration at any stereocenter in a compound of Formula (Ih) is R, S, or a mixture thereof; or a pharmaceutically acceptable salt, solvate, hydrate, tautomer, or N-oxide thereof.

Another aspect of the invention provides a compound represented by Formula (Ii):

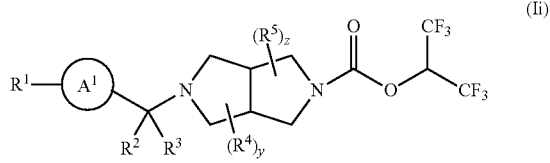

wherein,
- A¹ is pyrazolylene optionally substituted with 1 or 2 substituents independently selected from the group consisting of halogen, alkyl, haloalkyl, cycloalkyl, hydroxyl, alkoxy, and haloalkoxy;
- R¹ is phenyl, pyridinyl, pyrazolyl, a fused heterocyclyl-heteroaryl, or cyclohexyl, each of which is optionally substituted with 1, 2, or 3 substituents independently selected from the group consisting of halogen and heterocycloalkyl;
- R² is hydrogen;
- R³ is hydrogen or a phenyl substituted with 1 or 2 halogens;
- R⁴ and R⁵ each represent independently for each occurrence alkyl or haloalkyl;
- R⁷ is hydrogen or alkyl;
- R⁸ is alkyl or cycloalkyl;
- R⁹ is hydrogen;

R¹⁰ is alkyl, cycloalkyl, heterocycloalkyl, -alkylene-heterocycloalkyl, -alkylene-cycloalkyl, aryl, or aralkyl, each of which is optionally substituted with 1 or more substituents selected from the group consisting of alkyl, alkenyl, alkynyl, alkoxyl, hydroxyl, halogen, and haloalkyl; or R⁹ and R¹⁰ are taken together with the nitrogen atom to which they are attached to form a 4-7 membered heterocyclic ring optionally substituted with 1 or more substituents selected from the group consisting of alkyl, alkoxyl, hydroxyl, haloalkyl, halogen, —N(R⁷)C(O)R⁸, —N(R⁷)SO₂R⁸, —C(O)R⁸, —C(O)N(R⁹)(R¹⁰), —SO₂R⁸, and oxo; and
y and z are independently 0 or 1;
wherein the stereochemical configuration at any stereocenter in a compound of Formula (Ii) is R, S, or a mixture thereof; or a pharmaceutically acceptable salt, solvate, hydrate, tautomer, or N-oxide thereof.

Another aspect of the invention provides a compound represented by Formula (Ij):

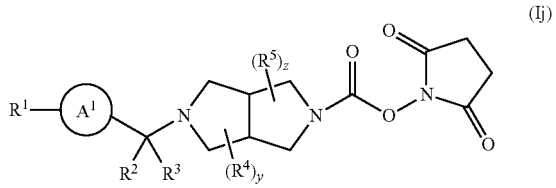

wherein,
A¹ is phenylene optionally substituted with 1 or 2 substituents independently selected from the group consisting of halogen, alkyl, haloalkyl, cycloalkyl, hydroxyl, alkoxy, and haloalkoxy;
R¹ is a heterocycloalkyl selected from the group consisting of morpholinyl, piperidinyl, pyrrolidinyl, piperizindyl, and azetidinyl; each of which is optionally substituted with 1, 2, or 3 substituents independently selected from the group consisting of alkyl, cycloalkyl, —N(R⁷)C(O)R⁸, —N(R⁷)SO₂R⁸, —C(O)R⁸, —C(O)N(R⁹)(R¹⁰), —SO₂R⁸, and heteroaryl;
R² is hydrogen;
R³ is hydrogen or a phenyl substituted with 1 or 2 halogens;
R⁴ and R⁵ each represent independently for each occurrence alkyl or haloalkyl;
R⁷ is hydrogen or alkyl;
R⁸ is alkyl or cycloalkyl;
R⁹ is hydrogen;
R¹⁰ is alkyl, cycloalkyl, heterocycloalkyl, -alkylene-heterocycloalkyl, -alkylene-cycloalkyl, aryl, or aralkyl, each of which is optionally substituted with 1 or more substituents selected from the group consisting of alkyl, alkenyl, alkynyl, alkoxyl, hydroxyl, halogen, and haloalkyl; or R⁹ and R¹⁰ are taken together with the nitrogen atom to which they are attached to form a 4-7 membered heterocyclic ring optionally substituted with 1 or more substituents selected from the group consisting of alkyl, alkoxyl, hydroxyl, haloalkyl, halogen, —N(R⁷)C(O)R⁸, —N(R⁷)SO₂R⁸, —C(O)R⁸, —C(O)N(R⁹)(R¹⁰), —SO₂R⁸, and oxo; and
y and z are independently 0 or 1;
wherein the stereochemical configuration at any stereocenter in a compound of Formula (Ij) is R, S, or a mixture thereof; or a pharmaceutically acceptable salt, solvate, hydrate, tautomer, or N-oxide thereof.

Another aspect of the invention provides a compound represented by Formula (Ik):

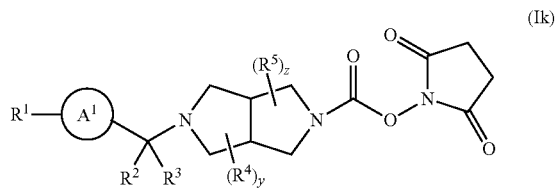

wherein,
A¹ is phenylene optionally substituted with 1 or 2 substituents independently selected from the group consisting of halogen, alkyl, haloalkyl, cycloalkyl, hydroxyl, alkoxy, and haloalkoxy;
R¹ is phenyl, pyridinyl, pyrazolyl, a fused heterocyclylheteroaryl, or cyclohexyl, each of which is optionally substituted with 1, 2, or 3 substituents independently selected from the group consisting of halogen and heterocycloalkyl;
R² is hydrogen;
R³ is hydrogen or a phenyl substituted with 1 or 2 halogens;
R⁴ and R⁵ each represent independently for each occurrence alkyl or haloalkyl;
R⁷ is hydrogen or alkyl;
R⁸ is alkyl or cycloalkyl;
R⁹ is hydrogen;
R¹⁰ is alkyl, cycloalkyl, heterocycloalkyl, -alkylene-heterocycloalkyl, -alkylene-cycloalkyl, aryl, or aralkyl, each of which is optionally substituted with 1 or more substituents selected from the group consisting of alkyl, alkenyl, alkynyl, alkoxyl, hydroxyl, halogen, and haloalkyl; or R⁹ and R¹⁰ are taken together with the nitrogen atom to which they are attached to form a 4-7 membered heterocyclic ring optionally substituted with 1 or more substituents selected from the group consisting of alkyl, alkoxyl, hydroxyl, haloalkyl, halogen, —N(R⁷)C(O)R⁸, —N(R⁷)SO₂R⁸, —C(O)R⁸, —C(O)N(R⁹)(R¹⁰), —SO₂R⁸, and oxo; and
y and z are independently 0 or 1;
wherein the stereochemical configuration at any stereocenter in a compound of Formula (Ik) is R, S, or a mixture thereof; or a pharmaceutically acceptable salt, solvate, hydrate, tautomer, or N-oxide thereof.

Another aspect of the invention provides a compound represented by Formula (Im):

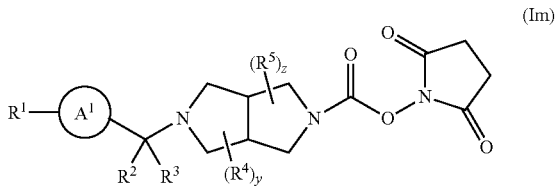

wherein,
A¹ is pyrazolylene optionally substituted with 1 or 2 substituents independently selected from the group consisting of halogen, alkyl, haloalkyl, cycloalkyl, hydroxyl, alkoxy, and haloalkoxy;

R¹ is a heterocycloalkyl selected from the group consisting of morpholinyl, piperidinyl, pyrrolidinyl, piperizindyl, and azetidinyl; each of which is optionally substituted with 1, 2, or 3 substituents independently selected from the group consisting of alkyl, cycloalkyl, —N(R⁷)C(O)R⁸, —N(R⁷)SO₂R⁸, —C(O)R⁸, —C(O)N(R⁹)(R¹⁰), —SO₂R⁸, and heteroaryl;

R² is hydrogen;

R³ is hydrogen or a phenyl substituted with 1 or 2 halogens;

R⁴ and R⁵ each represent independently for each occurrence alkyl or haloalkyl;

R⁷ is hydrogen or alkyl;

R⁸ is alkyl or cycloalkyl;

R⁹ is hydrogen;

R¹⁰ is alkyl, cycloalkyl, heterocycloalkyl, -alkylene-heterocycloalkyl, -alkylene-cycloalkyl, aryl, or aralkyl, each of which is optionally substituted with 1 or more substituents selected from the group consisting of alkyl, alkenyl, alkynyl, alkoxyl, hydroxyl, halogen, and haloalkyl; or R⁹ and R¹⁰ are taken together with the nitrogen atom to which they are attached to form a 4-7 membered heterocyclic ring optionally substituted with 1 or more substituents selected from the group consisting of alkyl, alkoxyl, hydroxyl, haloalkyl, halogen, —N(R⁷)C(O)R⁸, —N(R⁷)SO₂R⁸, —C(O)R⁸, —C(O)N(R⁹)(R¹⁰), —SO₂R⁸, and oxo; and y and z are independently 0 or 1;

wherein the stereochemical configuration at any stereocenter in a compound of Formula (Im) is R,
S, or a mixture thereof;
or a pharmaceutically acceptable salt, solvate, hydrate, tautomer, or N-oxide thereof.

Another aspect of the invention provides a compound represented by Formula (Io):

$$R^1-A^1-\underset{R^2\ R^3\ (R^4)_y}{C}-N \overset{(R^5)_z}{\underset{}{\bigcirc\hspace{-2pt}\bigcirc}} N-C(O)-O-N(succinimide)$$ (Io)

wherein,

A¹ is pyrazolylene optionally substituted with 1 or 2 substituents independently selected from the group consisting of halogen, alkyl, haloalkyl, cycloalkyl, hydroxyl, alkoxy, and haloalkoxy;

R¹ is phenyl, pyridinyl, pyrazolyl, a fused heterocyclyl-heteroaryl, or cyclohexyl, each of which is optionally substituted with 1, 2, or 3 substituents independently selected from the group consisting of halogen and heterocycloalkyl;

R² is hydrogen;

R³ is hydrogen or a phenyl substituted with 1 or 2 halogens;

R⁴ and R⁵ each represent independently for each occurrence alkyl or haloalkyl;

R⁷ is hydrogen or alkyl;

R⁸ is alkyl or cycloalkyl;

R⁹ is hydrogen;

R¹⁰ is alkyl, cycloalkyl, heterocycloalkyl, -alkylene-heterocycloalkyl, -alkylene-cycloalkyl, aryl, or aralkyl, each of which is optionally substituted with 1 or more substituents selected from the group consisting of alkyl, alkenyl, alkynyl, alkoxyl, hydroxyl, halogen, and haloalkyl; or R⁹ and R¹⁰ are taken together with the nitrogen atom to which they are attached to form a 4-7 membered heterocyclic ring optionally substituted with 1 or more substituents selected from the group consisting of alkyl, alkoxyl, hydroxyl, haloalkyl, halogen, —N(R⁷)C(O)R⁸, —N(R⁷)SO₂R⁸, —C(O)R⁸, —C(O)N(R⁹)(R¹⁰), —SO₂R⁸, and oxo; and y and z are independently 0 or 1;

wherein the stereochemical configuration at any stereocenter in a compound of Formula (Io) is R, S, or a mixture thereof;
or a pharmaceutically acceptable salt, solvate, hydrate, tautomer, or N-oxide thereof.

In certain embodiments of a compound of Formulas (Ig), (Ii), (Ik), or (Io), R¹ is phenyl, pyridinyl, pyrazolyl, or a fused heterocyclyl-heteroaryl, each of which is optionally substituted with 1, 2, or 3 substituents independently selected from the group consisting of halogen and heterocycloalkyl. In certain embodiments of a compound of Formulas (Ig), (Ii), (Ik), or (Io), R¹ is phenyl optionally substituted with 1, 2, or 3 substituents independently selected from the group consisting of halogen and heterocycloalkyl. In certain embodiments of a compound of Formulas (Ig), (Ii), (Ik), or (Io), R¹ is pyridinyl optionally substituted with 1, 2, or 3 substituents independently selected from the group consisting of halogen and heterocycloalkyl. In certain embodiments of a compound of Formulas (Ig), (Ii), (Ik), or (Io), R¹ is pyrazolyl or a fused heterocyclyl-heteroaryl. In certain embodiments of a compound of Formulas (Ig), (Ii), (Ik), or (Io), R¹ is cyclohexyl.

In certain embodiments of a compound of Formulas (If), (Ig), (Ih), (Ii), (IJ), (Ik), (Im), or (Io), R³ is hydrogen. In certain embodiments of a compound of Formulas (If), (Ig), (Ih), (Ii), (IJ), (Ik), (Im), or (Io), R³ is a phenyl substituted with 1 or 2 halogens.

In certain embodiments of a compound of Formulas (If), (Ig), (Ih), (Ii), (IJ), (Ik), (Im), or (Io), R⁷ is hydrogen. In certain embodiments of a compound of Formulas (If), (Ig), (Ih), (Ii), (Im), (Ik), (Im), or (Io), R⁷ is alkyl.

In certain embodiments of a compound of Formulas (If), (Ig), (Ih), (Ii), (IJ), (Ik), (Im), or (Io), R⁸ is alkyl. In certain embodiments of a compound of Formulas (If), (Ig), (Ih), (Ii), (IJ), (Ik), (Im), or (Io), R⁸ is cycloalkyl.

In certain embodiments of a compound of Formulas (If), (Ig), (Ih), (Ii), (IJ), (Ik), (Im), or (Io), R¹⁰ is alkyl, cycloalkyl, heterocycloalkyl, -alkylene-heterocycloalkyl, aryl, or aralkyl, each of which is optionally substituted with 1 or more substituents selected from the group consisting of alkyl, alkenyl, alkynyl, alkoxyl, hydroxyl, halogen, and haloalkyl. In certain embodiments of a compound of Formulas (If), (Ig), (Ih), (Ii), (IJ), (Ik), (Im), or (Io), R¹⁰ is alkyl. In certain embodiments of a compound of Formulas (If), (Ig), (Ih), (Ii), (IJ), (Ik), (Im), or (Io), R¹⁰ is cycloalkyl. In certain embodiments of a compound of Formulas (If), (Ig), (Ih), (Ii), (IJ), (Ik), (Im), or (Io), R¹⁰ is heterocycloalkyl optionally substituted with 1 or more substituents selected from the group consisting of alkyl, alkenyl, alkynyl, alkoxyl, hydroxyl, halogen, and haloalkyl. In certain embodiments of a compound of Formulas (If), (Ig), (Ih), (Ii), (IJ), (Ik), (Im), or (Io), R¹⁰ is -alkylene-cycloalkyl. In certain embodiments of a compound of Formulas (If), (Ig), (Ih), (Ii), (IJ), (Ik), (Im), or (Io), R¹⁰ is -alkylene-heterocycloalkyl optionally substituted with 1 or more substituents selected from the group consisting of alkyl, alkenyl, alkynyl, alkoxyl, hydroxyl, halogen, and haloalkyl. In certain embodiments of a compound of Formulas (If), (Ig), (Ih), (Ii), (IJ), (Ik), (Im), or (Io), R¹⁰ is aryl optionally substituted with 1 or more substituents selected from the group consisting of alkyl, alkenyl, alkynyl, alkoxyl, hydroxyl, halogen, and haloalkyl. In certain embodiments of a compound of Formulas (If), (Ig), (Ih), (Ii), (ID, (Ik), (Im), or (Io), R¹⁰ is aralkyl optionally substituted with 1 or more substituents selected from the group consisting of alkyl, alkenyl, alkynyl, alkoxyl, hydroxyl, halogen, and haloalkyl.

In certain embodiments of a compound of Formulas (If), (Ig), (Ih), (Ii), (Ij), (Ik), (Im), or (Io), R⁹ and R¹⁰ are taken together with the nitrogen atom to which they are attached to form a 4-7 membered heterocyclic ring optionally substituted with 1 or more substituents selected from the group consisting of alkyl, alkoxyl, hydroxyl, haloalkyl, halogen, —N(R⁷)C(O)R⁸, —N(R⁷)SO₂R⁸, —C(O)R⁸, —C(O)N(R⁹)(R¹⁰), —SO₂R⁸, and oxo.

In certain embodiments of a compound of Formulas (If), (Ig), (Ih), (Ii), (Ij), (Ik), (Im), or (Io), y and z are both 0. In certain embodiments of a compound of Formulas (If), (Ig), (Ih), (Ii), (Ij), (Ik), (Im), or (Io), y is 0 and z is 1. In certain embodiments of a compound of Formulas (If), (Ig), (Ih), (Ii), (Ij), (Ik), (Im), or (Io), y is 1 and z is 0. In certain embodiments of a compound of Formulas (If), (Ig), (Ih), (Ii), (Ij), (Ik), (Im), or (Io), y and z are both 1.

In yet other embodiments, the compound is one of the following: 1,1,1,3,3,3-hexafluoropropan-2-yl 5-({1-ethyl-3-[3-(morpholin-4-yl)phenyl]-1H-pyrazol-4-yl}methyl)-octahydropyrrolo[3,4-c]pyrrole-2-carboxylate; 1,1,1,3,3,3-hexafluoropropan-2-yl 5-((1-methyl-3-phenyl-1H-pyrazol-4-yl)methyl)hexahydropyrrolo[3,4-c]pyrrole-2(1H)-carboxylate; 1,1,1,3,3,3-hexafluoropropan-2-yl 5-{[3-phenyl-1-(propan-2-yl)-1H-pyrazol-4-yl]methyl}-octahydropyrrolo[3,4-c]pyrrole-2-carboxylate; 1,1,1,3,3,3-hexafluoropropan-2-yl 5-{[3-(2-chlorophenyl)-1-(propan-2-yl)-1H-pyrazol-4-yl]methyl}-octahydropyrrolo[3,4-c]pyrrole-2-carboxylate; 1,1,1,3,3,3-hexafluoropropan-2-yl 5-[(3-chloro-2-{2-oxa-7-azaspiro[4.4]nonan-7-yl}phenyl)methyl]-octahydropyrrolo[3,4-c]pyrrole-2-carboxylate; 1,1,1,3,3,3-hexafluoropropan-2-yl 5-[(3-phenylphenyl)methyl]-octahydropyrrolo[3,4-c]pyrrole-2-carboxylate; 1,1,1,3,3,3-hexafluoropropan-2-yl 5-[(3-methyl-2-{2-oxa-7-azaspiro[4.4]nonan-7-yl}phenyl)methyl]-octahydropyrrolo[3,4-c]pyrrole-2-carboxylate; 1,1,1,3,3,3-hexafluoropropan-2-yl 5-{[3-(2-chlorophenyl)-1-methyl-1H-pyrazol-4-yl]methyl}-octahydropyrrolo[3,4-c]pyrrole-2-carboxylate; 1,1,1,3,3,3-hexafluoropropan-2-yl 5-(2-(8-oxa-3-azabicyclo[3.2.1]octan-3-yl)-4-chlorobenzyl)hexahydropyrrolo[3,4-c]pyrrole-2(1H)-carboxylate; 1,1,1,3,3,3-hexafluoropropan-2-yl 5-{[1-cyclohexyl-3-(propan-2-yl)-1H-pyrazol-5-yl]methyl}-octahydropyrrolo[3,4-c]pyrrole-2-carboxylate; 1,1,1,3,3,3-hexafluoropropan-2-yl 5-(2-chloro-4-morpholinobenzyl)hexahydro-pyrrolo[3,4-c]pyrrole-2(1H)-carboxylate; 1,1,1,3,3,3-hexafluoropropan-2-yl 5-{[2-(morpholin-4-yl)-3-(trifluoromethyl)phenyl]methyl}-octahydropyrrolo[3,4-c]pyrrole-2-carboxylate; 1,1,1,3,3,3-hexafluoropropan-2-yl 5-{[2-methyl-3-(morpholin-4-yl)phenyl]methyl}-octahydropyrrolo[3,4-c]pyrrole-2-carboxylate; 1,1,1,3,3,3-hexafluoropropan-2-yl 5-(2-(3-acetamidoazetidin-1-yl)-5-chlorobenzyl)hexahydropyrrolo[3,4-c]pyrrole-2(1H)-carboxylate; 1,1,1,3,3,3-hexafluoropropan-2-yl 5-{[1-(oxan-4-yl)-3-(propan-2-yl)-1H-pyrazol-5-yl]methyl}-octahydropyrrolo[3,4-c]pyrrole-2-carboxylate; 1,1,1,3,3,3-hexafluoropropan-2-yl 5-{[2-methyl-3-(piperidin-1-yl)phenyl]methyl}-octahydropyrrolo[3,4-c]pyrrole-2-carboxylate; 1,1,1,3,3,3-hexafluoropropan-2-yl 5-(4-chloro-2-(5,6-dihydro-[1,2,4]triazolo[1,5-a]pyrazin-7(8H)-yl)benzyl)-hexahydropyrrolo[3,4-c]pyrrole-2(1H)-carboxylate; 1,1,1,3,3,3-hexafluoropropan-2-yl 5-{[2-(azetidin-1-yl)-4-chlorophenyl]methyl}-octahydropyrrolo[3,4-c]pyrrole-2-carboxylate; 1,1,1,3,3,3-hexafluoropropan-2-yl 5-{[2-(4-acetylpiperazin-1-yl)-4-chlorophenyl]methyl}-octahydropyrrolo[3,4-c]pyrrole-2-carboxylate; 1,1,1,3,3,3-hexafluoropropan-2-yl 5-[(1-cyclohexyl-3-methyl-1H-pyrazol-5-yl)methyl]-octahydropyrrolo[3,4-c]pyrrole-2-carboxylate; 1,1,1,3,3,3-hexafluoropropan-2-yl 5-[(2-phenylphenyl)methyl]-octahydropyrrolo[3,4-c]pyrrole-2-carboxylate; 1,1,1,3,3,3-hexafluoropropan-2-yl 5-{[2-chloro-4-(3-methylmorpholin-4-yl)phenyl]methyl}-octahydropyrrolo[3,4-c]pyrrole-2-carboxylate; 1,1,1,3,3,3-hexafluoropropan-2-yl 5-[(3-chloro-2-{3-oxa-8-azabicyclo[3.2.1]octan-8-yl}phenyl)methyl]-octahydropyrrolo[3,4-c]pyrrole-2-carboxylate; 1,1,1,3,3,3-hexafluoropropan-2-yl 5-{[4-(morpholin-4-yl)-2-(trifluoromethoxy)phenyl]methyl}-octahydropyrrolo[3,4-c]pyrrole-2-carboxylate; 1,1,1,3,3,3-hexafluoropropan-2-yl 5-{[4-(4-acetylpiperazin-1-yl)-2-chlorophenyl]methyl}-octahydropyrrolo[3,4-c]pyrrole-2-carboxylate; 1,1,1,3,3,3-hexafluoropropan-2-yl 5-{[1-ethyl-3-(pyridin-3-yl)-1H-pyrazol-4-yl]methyl}-octahydropyrrolo[3,4-c]pyrrole-2-carboxylate; 1,1,1,3,3,3-hexafluoropropan-2-yl 5-[(2-methyl-3-{2-oxa-7-azaspiro[4.4]nonan-7-yl}phenyl)methyl]-octahydropyrrolo[3,4-c]pyrrole-2-carboxylate; 1,1,1,3,3,3-hexafluoropropan-2-yl 5-(4-chloro-2-(hexahydrocyclopenta[b][1,4]oxazin-4(4aH)-yl)benzyl)hexahydropyrrolo[3,4-c]pyrrole-2(1H)-carboxylate; 1,1,1,3,3,3-hexafluoropropan-2-yl 5-{[4-(morpholin-4-yl)-2-(trifluoromethyl)phenyl]methyl}-octahydropyrrolo[3,4-c]pyrrole-2-carboxylate; 1,1,1,3,3,3-hexafluoropropan-2-yl 5-{[4-fluoro-2-(3-methylmorpholin-4-yl)phenyl]methyl}-octahydropyrrolo[3,4-c]pyrrole-2-carboxylate; 1,1,1,3,3,3-Hexafluoropropan-2-yl 5-[(4-chloro-2-[4-[(pyrrolidin-1-yl)carbonyl]piperidin-1-yl]phenyl)methyl]-octahydropyrrolo[3,4-c]pyrrole-2-carboxylate; 1,1,1,3,3,3-hexafluoropropan-2-yl 5-({1-ethyl-3-[4-(morpholin-4-yl)phenyl]-1H-pyrazol-4-yl}methyl)-octahydropyrrolo[3,4-c]pyrrole-2-carboxylate; 1,1,1,3,3,3-hexafluoropropan-2-yl 5-{[2-(4-acetylpiperazin-1-yl)-4-(propan-2-yl)phenyl]methyl}-octahydropyrrolo[3,4-c]pyrrole-2-carboxylate; 1,1,1,3,3,3-hexafluoropropan-2-yl 5-{[2-chloro-3-(morpholin-4-yl)phenyl]methyl}-octahydropyrrolo[3,4-c]pyrrole-2-carboxylate; 1,1,1,3,3,3-hexafluoropropan-2-yl 5-(2-fluoro-4-morpholinobenzyl)hexahydropyrrolo[3,4-c]pyrrole-2(1H)-carboxylate; 1,1,1,3,3,3-hexafluoropropan-2-yl 5-[(4-chloro-2-{5H,6H,7H,8H-imidazo[1,2-a]pyrazin-7-yl}phenyl)methyl]-octahydropyrrolo[3,4-c]pyrrole-2-carboxylate; 1,1,1,3,3,3-hexafluoropropan-2-yl 5-[(4-chloro-2-{5H,6H,7H-pyrrolo[3,4-b]pyridin-6-yl}phenyl)methyl]-octahydropyrrolo[3,4-c]pyrrole-2-carboxylate; 1,1,1,3,3,3-hexafluoropropan-2-yl 5-{[3-chloro-2-(morpholin-4-yl)phenyl]methyl}-octahydropyrrolo[3,4-c]pyrrole-2-carboxylate; 1,1,1,3,3,3-hexafluoropropan-2-yl 5-{[1-ethyl-3-(pyridin-4-yl)-1H-pyrazol-4-yl]methyl}-octahydropyrrolo[3,4-c]pyrrole-2-carboxylate; 1,1,1,3,3,3-hexafluoropropan-2-yl 5-({1-ethyl-3-[4-(pyrrolidin-1-yl)phenyl]-1H-pyrazol-4-yl}methyl)-octahydropyrrolo[3,4-c]pyrrole-2-carboxylate; 1,1,1,3,3,3-hexafluoro-propan-2-yl 5-{[3-(1-methanesulfonylpiperidin-4-yl)-1-(propan-2-yl)-1H-pyrazol-4-yl]methyl}-octahydropyrrolo[3,4-c]pyrrole-2-carboxylate; 1,1,1,3,3,3-hexafluoropropan-2-yl 5-{[4-chloro-2-(3-methylmorpholin-4-yl)phenyl]methyl}-octahydropyrrolo[3,4-c]pyrrole-2-carboxylate; 1,1,1,3,3,3-hexafluoropropan-2-yl 5-[(4-chloro-2-{1-oxo-2,8-diazaspiro[4.5]decan-8-yl}phenyl)methyl]-octahydropyrrolo[3,4-c]pyrrole-2-carboxylate; 1,1,1,3,3,3-hexafluoropropan-2-yl 5-{[2-fluoro-4-(3-methylmorpholin- 4-yl)phenyl]methyl}-octahydropyrrolo[3,4-c]pyrrole-2-carboxylate; 1,1,1,3,3,3-hexafluoropropan-2-yl 5-[(4-chloro-2-{8-oxa-2-azaspiro[4.5]decan-2-yl}phenyl)methyl]-octahydropyrrolo[3,4-c]pyrrole-2-carboxylate; 1,1,1,3,3,3-hexafluoropropan-2-yl 5-{[4-chloro-2-(pyrrolidin-1-yl)phenyl]methyl}-octahydropyrrolo[3,4-c]pyrrole-2-carboxylate; 1,1,1,3,3,3-hexafluoropropan-2-yl 5-{[4-chloro-2-(4-methanesulfonylpiperazin-1-yl)phenyl]methyl}-octahydropyrrolo[3,4-c]pyrrole-2-carboxylate; 1,1,1,3,3,3-hexafluoropropan-2-yl 5-[(2-chloro-3-{2-oxa-7-azaspiro[4.4]nonan-7-yl}phenyl)methyl]-octahydropyrrolo[3,4-c]pyrrole-2-carboxylate; 1,1,1,3,3,3-hexafluoropropan-2-yl 5-(5-chloro-2-(4-(methyl-sulfonamido)piperidin-1-yl)benzyl)hexahydropyrrolo[3,4-c]pyrrole-2(1H)-carboxylate; 1,1,1,3,3,3-hexafluoropropan-2-yl 5-{[2-(4-acetylpiperazin-1-yl)-4-fluorophenyl]methyl}-octahydropyrrolo[3,4-c]pyrrole-2-carboxylate; 1,1,1,3,3,3-hexafluoropropan-2-yl 5-{[4-fluoro-2-(pyrrolidin-1-yl)phenyl]methyl}-octahydropyrrolo[3,4-c]pyrrole-2-carboxylate; 1,1,1,3,3,3-Hexafluoropropan-2-yl 5-(4-chloro-2-((R)-hexahydropyrrolo[1,2-a]pyrazin-2(1H)-yl)benzyl)-hexahydropyrrolo[3,4-c]pyrrole-2(1H)-carboxylate; 1,1,1,3,3,3-hexafluoropropan-2-yl 5-{[3-methyl-2-(morpholin-4-yl)phenyl]methyl}-octahydropyrrolo[3,4-c]pyrrole-2-carboxylate; 1,1,1,3,3,3-hexafluoropropan-2-yl 5-{[3-(1-acetylpiperidin-4-yl)-1-(propan-2-yl)-1H-pyrazol-4-yl]methyl}-octahydropyrrolo[3,4-c]pyrrole-2-carboxylate; 1,1,1,3,3,3-hexafluoropropan-2-yl 5-{[2-(morpholin-4-yl)-4-(propan-2-yl)phenyl]methyl}-octahydropyrrolo[3,4-c]pyrrole-2-carboxylate; 1,1,1,3,3,3-hexafluoropropan-2-yl 5-{[4-(4-acetylpiperazin-1-yl)-2-fluoro-phenyl]methyl}-octahydropyrrolo[3,4-c]pyrrole-2-carboxylate; 1,1,1,3,3,3-hexafluoropropan-2-yl 5-{[1-(1-acetylpiperidin-4-yl)-3-methyl-1H-pyrazol-5-yl]methyl}-octahydropyrrolo[3,4-c]pyrrole-2-carboxylate; 1,1,1,3,3,3-hexafluoropropan-2-yl 5-(2-(4-acetamidopiperidin-1-yl)-5-chlorobenzyl)hexahydropyrrolo[3,4-c]pyrrole-2(1H)-carboxylate; 1,1,1,3,3,3-hexafluoropropan-2-yl 5-{[3-methyl-1-(propan-2-yl)-1H-pyrazol-5-yl]methyl}-octahydropyrrolo[3,4-c]pyrrole-2-carboxylate; 1,1,1,3,3,3-hexafluoropropan-2-yl 5-{[4-(propan-2-yl)-2-(pyrrolidin-1-yl)phenyl]methyl}-octahydropyrrolo[3,4-c]pyrrole-2-carboxylate; 1,1,1,3,3,3-hexafluoropropan-2-yl 5-{[3-methyl-2-(piperidin-1-yl)phenyl]methyl}-octahydropyrrolo[3,4-c]pyrrole-2-carboxylate; 1,1,1,3,3,3-hexafluoropropan-2-yl 5-((1-ethyl-5-(morpholine-4-carbonyl)-1H-pyrazol-4-yl)methyl)hexahydropyrrolo[3,4-c]pyrrole-2(1H)-carboxylate; 1,1,1,3,3,3-hexafluoropropan-2-yl 5-[bis(4-chlorophenyl)methyl]octahydropyrrolo[3,4-c]pyrrole-2-carboxylate; 1,1,1,3,3,3-hexafluoropropan-2-yl 5-[(4-phenylphenyl)methyl]-octahydropyrrolo[3,4-c]pyrrole-2-carboxylate; 1,1,1,3,3,3-hexafluoropropan-2-yl 5-{[4-fluoro-2-(morpholin-4-yl)phenyl]methyl}-octahydropyrrolo[3,4-c]pyrrole-2-carboxylate; 1,1,1,3,3,3-hexafluoropropan-2-yl 5-{[4-chloro-2-(morpholin-4-yl)phenyl]methyl}-octahydropyrrolo[3,4-c]pyrrole-2-carboxylate; 1,1,1,3,3,3-hexafluoropropan-2-yl 5-{[3-(1-acetylpiperidin-4-yl)-1-methyl-1H-pyrazol-4-yl]methyl}-octahydropyrrolo[3,4-c]pyrrole-2-carboxylate; 1,1,1,3,3,3-hexafluoropropan-2-yl 5-{[3-(1-methanesulfonylpiperidin-4-yl)-1-methyl-1H-pyrazol-4-yl]methyl}-octahydropyrrolo[3,4-c]pyrrole-2-carboxylate; 1,1,1,3,3,3-hexafluoropropan-2-yl 5-({3-[2-(azetidin-1-yl)phenyl]-1-ethyl-1H-pyrazol-4-yl}methyl)-octahydropyrrolo[3,4-c]pyrrole-2-carboxylate; 1,1,1,3,3,3-hexafluoropropan-2-yl 5-({1-ethyl-3-[3-(pyrrolidin-1-yl)phenyl]-1H-pyrazol-4-yl}methyl)-octahydropyrrolo[3,4-c]pyrrole-2-carboxylate; 1,1,1,3,3,3-hexafluoropropan-2-yl 5-({3-[3-(azetidin-1-yl)phenyl]-1-ethyl-1H-pyrazol-4-yl}methyl)-octahydropyrrolo[3,4-c]pyrrole-2-carboxylate; 1,1,1,3,3,3-hexafluoropropan-2-yl 5-({3-[4-(azetidin-1-yl)phenyl]-1-ethyl-1H-pyrazol-4-yl}methyl)-octahydropyrrolo[3,4-c]pyrrole-2-carboxylate; 1,1,1,3,3,3-hexafluoropropan-2-yl 5-{[1-ethyl-3-(pyridin-2-yl)-1H-pyrazol-4-yl]methyl}-octahydropyrrolo[3,4-c]pyrrole-2-carboxylate; 1,1,1,3,3,3-hexafluoropropan-2-yl 5-((5-(cyclopropylcarbamoyl)-1-ethyl-1H-pyrazol-4-yl)methyl)hexahydropyrrolo[3,4-c]pyrrole-2(1H)-carboxylate; 1,1,1,3,3,3-hexafluoropropan-2-yl 5-((5-(benzylcarbamoyl)-1-ethyl-1H-pyrazol-4-yl)methyl)hexahydro-pyrrolo[3,4-c]pyrrole-2(1H)-carboxylate; 1,1,1,3,3,3-Hexafluoropropan-2-yl 5-((1-ethyl-3-(morpholine-4-carbonyl)-1H-pyrazol-4-yl)methyl)hexahydropyrrolo[3,4-c]pyrrole-2(1H)-carboxylate; 1,1,1,3,3,3-Hexafluoropropan-2-yl 5-((3-(cyclopropylcarbamoyl)-1-ethyl-1H-pyrazol-4-yl)methyl)hexahydropyrrolo[3,4-c]pyrrole-2(1H)-carboxylate; 1,1,1,3,3,3-Hexafluoropropan-2-yl 5-((3-(benzylcarbamoyl)-1-ethyl-1H-pyrazol-4-yl)methyl)hexa-hydropyrrolo[3,4-c]pyrrole-2(1H)-carboxylate; 2,5-dioxopyrrolidin-1-yl 5-{[2-methyl-3-(piperidin-1-yl)phenyl]methyl}-octahydropyrrolo[3,4-c]pyrrole-2-carboxylate; 2,5-dioxopyrrolidin-1-yl 5-[(3-phenylphenyl)methyl]-octahydropyrrolo[3,4-c]pyrrole-2-carboxylate; 2,5-dioxopyrrolidin-1-yl 5-{[4-(morpholin-4-yl)-2-(trifluoromethoxy)phenyl]methyl}-octahydropyrrolo[3,4-c]pyrrole-2-carboxylate; 2,5-dioxopyrrolidin-1-yl 5-[(2-phenylphenyl)methyl]-octahydropyrrolo[3,4-c]pyrrole-2-carboxylate; 2,5-dioxopyrrolidin-1-yl 5-{[4-(morpholin-4-yl)-2-(trifluoromethyl)phenyl]methyl}-octahydropyrrolo[3,4-c]pyrrole-2-carboxylate; 2,5-dioxopyrrolidin-1-yl 5-(2-(8-oxa-3-azabicyclo[3.2.1]octan-3-yl)-4-chlorobenzyl)hexahydropyrrolo[3,4-c]pyrrole-2(1H)-carboxylate; 2,5-dioxopyrrolidin-1-yl 5-(2-chloro-4-morpholinobenzyl)hexahydropyrrolo[3,4-c]pyrrole-2(1H)-carboxylate; 2,5-dioxopyrrolidin-1-yl 5-(4-chloro-2-(hexahydrocyclopenta[b][1,4]oxazin-4(4aH)-yl)benzyl)hexahydropyrrolo[3,4-c]pyrrole-2(1H)-carboxylate; 2,5-dioxopyrrolidin-1-yl 5-{[2-chloro-4-(3-methylmorpholin-4-yl)phenyl]methyl}-octahydropyrrolo[3,4-c]pyrrole-2-carboxylate; 2,5-dioxopyrrolidin-1-yl 5-((1-methyl-3-phenyl-1H-pyrazol-4-yl)methyl)hexahydropyrrolo[3,4-c]pyrrole-2(1H)-carboxylate; 2,5-dioxopyrrolidin-1-yl 5-(2-fluoro-4-morpholinobenzyl)hexa-hydropyrrolo[3,4-c]pyrrole-2(1H)-carboxylate; 2,5-dioxopyrrolidin-1-yl 5-[bis(4-chlorophenyl)methyl]octahydropyrrolo[3,4-c]pyrrole-2-carboxylate; 2,5-dioxopyrrolidin-1-yl 5-[(4-phenylphenyl)methyl]-octahydropyrrolo[3,4-c]pyrrole-2-carboxylate; 2,5-dioxopyrrolidin-1-yl 5-{[4-fluoro-2-(morpholin-4-yl)phenyl]methyl}-octahydropyrrolo[3,4-c]pyrrole-2-carboxylate; 2,5-dioxopyrrolidin-1-yl 5-{[4-fluoro-2-(pyrrolidin-1-yl)phenyl]methyl}-octahydropyrrolo[3,4-c]pyrrole-2-carboxylate; 2,5-dioxopyrrolidin-1-yl 5-{[4-fluoro-2-(3-methylmorpholin-4-yl)phenyl]methyl}-octahydropyrrolo[3,4-c]pyrrole-2-carboxylate; 2,5-dioxopyrrolidin-1-yl 5-{[2-(4-acetylpiperazin-1-yl)-4-fluorophenyl]methyl}-octahydropyrrolo[3,4-c]pyrrole-2-carboxylate; 2,5-dioxopyrrolidin-1-yl 5-{[4-chloro-2-(morpholin-4-yl)phenyl]methyl}-octahydropyrrolo[3,4-c]pyrrole-2-carboxylate; 2,5-dioxopyrrolidin-1-yl 5-{[4-chloro-2-(pyrrolidin-1-yl)phenyl]methyl}-octahydropyrrolo[3,4-c]pyrrole-2-carboxylate; 2,5-dioxopyrrolidin-1-yl 5-{[4-chloro-2-(3-methylmorpholin-4-yl)phenyl]methyl}-octahydro-pyrrolo[3,4-c]pyrrole-2-carboxylate; 2,5-dioxopyrrolidin-1-yl 5-{[2-(4-acetyl-piperazin-1-yl)-4-chlorophenyl]methyl}-octahydropyrrolo[3,4-c]pyrrole-2-carboxylate; 2,5-dioxopyrrolidin-1-yl 5-{[2-(morpholin-4-yl)-4-(propan-2- yl)phenyl]methyl}-octahydropyrrolo[3,4-c]pyrrole-2-carboxylate; 2,5-dioxopyrrolidin-1-yl 5-{[4-(propan-2-yl)-2-(pyrrolidin-1-yl)phenyl]methyl}-octahydropyrrolo[3,4-c]pyrrole-2-carboxylate; 2,5-dioxopyrrolidin-1-yl 5-{[2-(4-acetyl-piperazin-1-yl)-4-(propan-2-yl)phenyl]methyl}-octahydropyrrolo[3,4-c]pyrrole-2-carboxylate; 2,5-dioxopyrrolidin-1-yl 5-{[2-fluoro-4-(3-methylmorpholin-4-yl)phenyl]methyl}-octahydro-pyrrolo[3,4-c]pyrrole-2-carboxylate; 2,5-dioxopyrrolidin-1-yl 5-{[4-(4-acetylpiperazin-1-yl)-2-fluorophenyl]methyl}-octahydropyrrolo[3,4-c]pyrrole-2-carboxylate; 2,5-dioxopyrrolidin-1-yl 5-{[4-(4-acetylpiperazin-1-yl)-2-chlorophenyl]methyl}-octahydropyrrolo[3,4-c]pyrrole-2-carboxylate; 2,5-dioxopyrrolidin-1-yl 5-{[3-methyl-2-(piperidin-1-yl)phenyl]methyl}-octahydro-pyrrolo[3,4-c]pyrrole-2-carboxylate; 2,5-dioxopyrrolidin-1-yl 5-[(4-chloro-2-{8-oxa-2-azaspiro[4.5]decan-2-yl}phenyl)methyl]-octahydropyrrolo[3,4-c]pyrrole-2-carboxylate; 2,5-dioxopyrrolidin-1-yl 5-[(4-chloro-2-{5H,6H,7H-pyrrolo[3,4-b]pyridin-6-yl}phenyl)methyl]-octahydropyrrolo[3,4-c]pyrrole-2-carboxylate; 2,5-Dioxopyrrolidin-1-yl 5-(4-chloro-2-(5,6-dihydro-[1,2,4]triazolo[1,5-a]pyrazin-7(8H)-yl)benzyl)-hexahydropyrrolo[3,4-c]pyrrole-2(1H)-carboxylate; 2,5-Dioxopyrrolidin-1-yl 5-(4-chloro-2-((R)-hexahydropyrrolo[1,2-a]pyrazin-2(1H)-yl)benzyl)-hexahydropyrrolo[3,4-c]pyrrole-2(1H)-carboxylate; 2,5-dioxopyrrolidin-1-yl 5-{[4-chloro-2-(4-methanesulfonylpiperazin-1-yl)phenyl]methyl}-octahydropyrrolo[3,4-c]pyrrole-2-carboxylate; 2,5-Dioxopyrrolidin-1-yl 5-[(4-chloro-2-[4-[(pyrrolidin-1-yl)carbonyl]piperidin-1-yl]phenyl)methyl]-octahydropyrrolo[3,4-c]pyrrole-2-carboxylate; 2,5-dioxopyrrolidin-1-yl 5-[(4-chloro-2-{1-oxo-2,8-diazaspiro[4.5]decan-8-yl}phenyl)methyl]-octahydropyrrolo[3,4-c]pyrrole-2-carboxylate; 2,5-dioxopyrrolidin-1-yl 5-{[2-(azetidin-1-yl)-4-chlorophenyl]methyl}-octahydropyrrolo[3,4-c]pyrrole-2-carboxylate; 2,5-dioxopyrrolidin-1-yl 5-{[3-(2-chlorophenyl)-1-methyl-1H-pyrazol-4-yl]methyl}-octahydropyrrolo[3,4-c]pyrrole-2-carboxylate; 2,5-dioxopyrrolidin-1-yl 5-{[3-(1-acetylpiperidin-4-yl)-1-methyl-1H-pyrazol-4-yl]methyl}-octahydropyrrolo[3,4-c]pyrrole-2-carboxylate; 2,5-dioxopyrrolidin-1-yl 5-{[3-phenyl-1-(propan-2-yl)-1H-pyrazol-4-yl]methyl}-octahydropyrrolo[3,4-c]pyrrole-2-carboxylate; 2,5-dioxopyrrolidin-1-yl 5-{[3-(2-chlorophenyl)-1-(propan-2-yl)-1H-pyrazol-4-yl]methyl}-octahydropyrrolo[3,4-c]pyrrole-2-carboxylate; 2,5-dioxopyrrolidin-1-yl 5-{[3-(1-acetylpiperidin-4-yl)-1-(propan-2-yl)-1H-pyrazol-4-yl]methyl}-octahydropyrrolo[3,4-c]pyrrole-2-carboxylate; 2,5-dioxopyrrolidin-1-yl 5-{[3-(1-methanesulfonylpiperidin-4-yl)-1-(propan-2-yl)-1H-pyrazol-4-yl]methyl}-octahydropyrrolo[3,4-c]pyrrole-2-carboxylate; 2,5-dioxopyrrolidin-1-yl 5-{[3-methyl-1-(propan-2-yl)-1H-pyrazol-5-yl]methyl}-octahydropyrrolo[3,4-c]pyrrole-2-carboxylate; 2,5-dioxopyrrolidin-1-yl 5-{[1-(1-acetylpiperidin-4-yl)-3-methyl-1H-pyrazol-5-yl]methyl}-octahydropyrrolo[3,4-c]pyrrole-2-carboxylate; 2,5-dioxopyrrolidin-1-yl 5-{[1-cyclohexyl-3-(propan-2-yl)-1H-pyrazol-5-yl]methyl}-octahydropyrrolo[3,4-c]pyrrole-2-carboxylate; 2,5-dioxopyrrolidin-1-yl 5-{[1-(oxan-4-yl)-3-(propan-2-yl)-1H-pyrazol-5-yl]methyl}-octahydro-pyrrolo[3,4-c]pyrrole-2-carboxylate; 2,2,2-trifluoro-1-(methylcarbamoyl)ethyl 5-[bis(4-chlorophenyl)methyl]-octahydropyrrolo[3,4-c]pyrrole-2-carboxylate; 2,2,2-trifluoro-1-(methylcarbamoyl)ethyl 5-[(4-phenylphenyl)methyl]-octahydropyrrolo[3,4-c]pyrrole-2-carboxylate; 1,1,1,3,3,3-hexafluoropropan-2-yl 5-[(2-methyl-3-[3-oxa-8-azabicyclo[3.2.1]octan-8-yl]phenyl)methyl]-octahydropyrrolo[3,4-c]pyrrole-2-carboxylate; 1,1,1,3,3,3-hexafluoro-propan-2-yl 5-[(3-[2-oxa-7-azaspiro[4.4]nonan-7-yl]-2-(trifluoromethyl)phenyl)methyl]-octahydropyrrolo[3,4-c]pyrrole-2-carboxylate; 1,1,1,3,3,3-hexafluoropropan-2-yl 5-[[3-(morpholin-4-yl)-2-(trifluoromethyl)phenyl]methyl]-octahydropyrrolo[3,4-c]pyrrole-2-carboxylate; 1,1,1,3,3,3-hexafluoropropan-2-yl 5-([1-ethyl-3-[2-(piperidin-1-yl)phenyl]-1H-pyrazol-4-yl]methyl)-octahydropyrrolo[3,4-c]pyrrole-2-carboxylate; 1,1,1,3,3,3-hexafluoropropan-2-yl 5-([1-ethyl-3-[2-(morpholin-4-yl)phenyl]-1H-pyrazol-4-yl]methyl)-octahydropyrrolo[3,4-c]pyrrole-2-carboxylate; 1,1,1,3,3,3-hexafluoropropan-2-yl 5-([1-ethyl-3-[3-(piperidin-1-yl)phenyl]-1H-pyrazol-4-yl]methyl)-octahydropyrrolo[3,4-c]pyrrole-2-carboxylate; 1,1,1,3,3,3-hexafluoropropan-2-yl 5-([1-ethyl-3-[4-(piperidin-1-yl)phenyl]-1H-pyrazol-4-yl]methyl)-octahydropyrrolo[3,4-c]pyrrole-2-carboxylate; 1,1,1,3,3,3-hexafluoro-propan-2-yl 5-[(2-[7-methanesulfonyl-2,7-diazaspiro[4.4]nonan-2-yl]phenyl)methyl]-octahydropyrrolo[3,4-c]pyrrole-2-carboxylate; 1,1,1,3,3,3-hexafluoropropan-2-yl 5-[(2-[7-acetyl-2,7-diazaspiro[4.4]nonan-2-yl]phenyl)methyl]-octahydropyrrolo[3,4-c]pyrrole-2-carboxylate; 1,1,1,3,3,3-hexafluoropropan-2-yl 5-[(2-[2-methanesulfonyl-2,6-diazaspiro[3.4]octan-6-yl]phenyl)methyl]-octahydropyrrolo[3,4-c]pyrrole-2-carboxylate; 1,1,1,3,3,3-hexafluoropropan-2-yl 5-[(2-[2-acetyl-2,6-diazaspiro[3.4]octan-6-yl]phenyl)methyl]-octahydropyrrolo[3,4-c]pyrrole-2-carboxylate; 2,5-dioxopyrrolidin-1-yl 5-[[3-methyl-2-(4-methylpiperazin-1-yl)phenyl]methyl]-octahydropyrrolo[3,4-c]pyrrole-2-carboxylate; 2,5-dioxopyrrolidin-1-yl 5-[[2-(4-ethylpiperazin-1-yl)-3-methylphenyl]methyl]-octahydropyrrolo[3,4-c]pyrrole-2-carboxylate; 2,5-dioxopyrrolidin-1-yl 5-[[3-(4-methanesulfonamidopiperidin-1-yl)-2-methylphenyl]methyl]-octahydropyrrolo[3,4-c]pyrrole-2-carboxylate; 2,5-dioxopyrrolidin-1-yl 5-[[3-(4-methane-sulfonylpiperazin-1-yl)-2-methylphenyl]methyl]-octahydropyrrolo[3,4-c]pyrrole-2-carboxylate; 2,5-dioxopyrrolidin-1-yl 5-[[3-(4-acetamidopiperidin-1-yl)-2-methylphenyl]methyl]-octahydropyrrolo[3,4-c]pyrrole-2-carboxylate; 2,5-dioxopyrrolidin-1-yl 5-[[3-(4-acetylpiperazin-1-yl)-2-methylphenyl]methyl]-octahydropyrrolo[3,4-c]pyrrole-2-carboxylate; 2,5-dioxo-pyrrolidin-1-yl 5-[[3-(4,4-difluoropiperidin-1-yl)-2-methylphenyl]methyl]-octahydropyrrolo[3,4-c]pyrrole-2-carboxylate; 2,5-dioxocyclopentyl 5-[[2-methyl-3-(4-methylpiperazin-1-yl)phenyl]methyl]-octahydropyrrolo[3,4-c]pyrrole-2-carboxylate; 2,5-dioxocyclopentyl 5-[[3-(4-ethylpiperazin-1-yl)-2-methylphenyl]methyl]-octahydropyrrolo[3,4-c]pyrrole-2-carboxylate; 1,1,1,3,3,3-hexafluoropropan-2-yl 5-[[3-methyl-2-(4-methylpiperazin-1-yl)phenyl]methyl]-octahydropyrrolo[3,4-c]pyrrole-2-carboxylate; 1,1,1,3,3,3-hexafluoropropan-2-yl 5-[[2-(4-ethylpiperazin-1-yl)-3-methylphenyl]methyl]-octahydropyrrolo[3,4-c]pyrrole-2-carboxylate; 1,1,1,3,3,3-hexafluoropropan-2-yl 5-[[3-(4-methanesulfonamidopiperidin-1-yl)-2-methylphenyl]methyl]-octahydropyrrolo[3,4-c]pyrrole-2-carboxylate; 1,1,1,3,3,3-hexafluoro-propan-2-yl 5-[3-(4-methanesulfonylpiperazin-1-yl)-2-methylphenyl]methyl]-octahydropyrrolo[3,4-c]pyrrole-2-carboxylate; 1,1,1,3,3,3-hexafluoropropan-2-yl 5-[[3-(4-acetamidopiperidin-1-yl)-2-methylphenyl]methyl]-octahydropyrrolo[3,4-c]pyrrole-2-carboxylate; 1,1,1,3,3,3-hexafluoropropan-2-yl 5-[[3-(4-acetylpiperazin-1-yl)-2-methylphenyl]]-octahydropyrrolo[3,4-c]pyrrole-2-carboxylate; 1,1,1,3,3,3-hexafluoropropan-2-yl 5-[[3-(4,4-difluoropiperidin-1-yl)-2-methylphenyl]

methyl]-octahydropyrrolo[3,4-c]pyrrole-2-carboxylate; 1,1, 1,3,3,3-hexafluoropropan-2-yl 5-[[2-methyl-3-(4-methyl-piperazin-1-yl)phenyl]methyl]-octahydropyrrolo[3,4-c]pyrrole-2-carboxylate; 1,1,1,3,3,3-hexafluoropropan-2-yl 5-[[3-(4-ethylpiperazin-1-yl)-2-methylphenyl]methyl]-octahydropyrrolo[3,4-c]pyrrole-2-carboxylate; 1,1,1,3,3,3-hexafluoropropan-2-yl 5-[[3-ethyl-1-(oxan-4-yl)-1H-pyrazol-5-yl]methyl]-octahydropyrrolo[3,4-c]pyrrole-2-carboxylate; 1,1,1,3,3,3-hexafluoropropan-2-yl 5-[[3-tert-butyl-1-(oxan-4-yl)-1H-pyrazol-5-yl]methyl]-octahydropyrrolo[3,4-c]pyrrole-2-carboxylate; 1,1,1,3,3,3-hexafluoropropan-2-yl 5-[[3-chloro-2-(4,4-difluoropiperidin-1-yl)phenyl]methyl]-octahydropyrrolo[3,4-c]pyrrole-2-carboxylate; 1,1,1,3,3,3-hexafluoropropan-2-yl 5-[[3-chloro-2-(4-fluoropiperidin-1-yl)phenyl]methyl]-octahydropyrrolo[3,4-c]pyrrole-2-carboxylate; 2,5-dioxopyrrolidin-1-yl 5-[[3-chloro-2-(4-fluoropiperidin-1-yl)phenyl]methyl]-octahydropyrrolo[3,4-c]pyrrole-2-carboxylate; 2,5-dioxopyrrolidin-1-yl 5-([2-chloro-4-[(piperidin-1-yl)carbonyl]phenyl]methyl)-octahydropyrrolo[3,4-c]pyrrole-2-carboxylate; 2,5-dioxopyrrolidin-1-yl 5-(2-chloro-4-(4-methylpiperazine-1-carbonyl)benzyl)-hexahydropyrrolo[3,4-c]pyrrole-2(1H)-carboxylate; 2,5-dioxopyrrolidin-1-yl 5-(2-chloro-4-(morpholine-4-carbonyl)benzyl)-hexahydro-pyrrolo[3,4-c]pyrrole-2(1H)-carboxylate; 2,5-dioxopyrrolidin-1-yl5-(2-chloro-4-(pyrrolidine-1-carbonyl)benzyl)-hexahydropyrrolo[3,4-c]pyrrole-2(1H)-carboxylate; 2,5-dioxopyrrolidin-1-yl-5-(4-(azetidine-1-carbonyl)-2-chlorobenzyl)-hexahydropyrrolo[3,4-c]pyrrole-2(1H)-carboxylate; 2,5-dioxopyrrolidin-1-yl 5-(2-fluoro-4-(piperidine-1-carbonyl)benzyl)-hexahydropyrrolo[3,4-c]pyrrole-2(1H)-carboxylate; 2,5-dioxopyrrolidin-1-yl5-(2-fluoro-4-(pyrrolidine-1-carbonyl)benzyl)-hexahydropyrrolo[3,4-c]pyrrole-2(1H)-carboxylate; 2,5-dioxopyrrolidin-1-yl 5-(4-(azetidine-1-carbonyl)-2-fluorobenzyl)-hexahydropyrrolo[3,4-c]pyrrole-2(1H)-carboxylate; 1,1,1,3,3,3-hexafluoropropan-2-yl 5-[[1-(2-chlorophenyl)-3-ethyl-1H-pyrazol-5-yl]methyl]-octahydropyrrolo[3,4-c]pyrrole-2-carboxylate; 1,1,1,3,3,3-hexafluoropropan-2-yl 5-[[3-tert-butyl-1-(2-chlorophenyl)-1H-pyrazol-5-yl]methyl]-octahydropyrrolo[3,4-c]pyrrole-2-carboxylate; 1,1,1,3,3,3-hexafluoropropan-2-yl 5-[[3-chloro-2-(4-methylpiperazin-1-yl)phenyl]methyl]-octahydropyrrolo[3,4-c]pyrrole-2-carboxylate; 1,1,1,3,3,3-hexafluoropropan-2-yl 5-[(3-chloro-2-[8-oxa-2-azaspiro[4.5]decan-2-yl]phenyl)methyl]-octahydropyrrolo[3,4-c]pyrrole-2-carboxylate; 1,1,1,3,3,3-hexafluoropropan-2-yl 5-([3-chloro-2-[(3S)-3-(fluoromethyl)pyrrolidin-1-yl]phenyl]methyl)-octahydropyrrolo[3,4-c]pyrrole-2-carboxylate; 1,1,1,3,3,3-hexafluoropropan-2-yl 5-[[3-(3-chlorophenyl)-1-(propan-2-yl)-1H-pyrazol-4-yl]methyl]-octahydropyrrolo[3,4-c]pyrrole-2-carboxylate; 1,1,1,3,3,3-hexafluoropropan-2-yl 5-[(2-chlorophenyl)methyl]-octahydropyrrolo[3,4-c]pyrrole-2-carboxylate; 1,1,1,3,3,3-hexafluoropropan-2-yl 5-[(3-chlorophenyl)methyl]-octahydropyrrolo[3,4-c]pyrrole-2-carboxylate; 1,1,1,3,3,3-hexafluoropropan-2-yl 5-[(4-chlorophenyl)methyl]-octahydropyrrolo[3,4-c]pyrrole-2-carboxylate; 1,1,1,3,3,3-hexafluoropropan-2-yl 5-((1-ethyl-3-(prop-2-yn-1-ylcarbamoyl)-1H-pyrazol-4-yl)methyl)hexahydropyrrolo[3,4-c]pyrrole-2(1H)-carboxylate; 1,1,1,3,3,3-hexafluoropropan-2-yl 5-((5-((cyclopropylmethyl)carbamoyl)-1-ethyl-1H-pyrazol-4-yl)methyl)hexahydropyrrolo[3,4-c]pyrrole-2(1H)-carboxylate; 1,1,1,3,3,3-hexafluoropropan-2-yl 5-((5-((3-chlorophenethyl)carbamoyl)-1-ethyl-1H-pyrazol-4-yl)methyl)hexahydropyrrolo[3,4-c]pyrrole-2(1H)-carboxylate; 1,1,1,3,3,3-hexafluoropropan-2-yl 5-((1-ethyl-5-(((tetrahydro-2H-pyran-4-yl)methyl)carbamoyl)-1H-pyrazol-4-yl)methyl)hexahydropyrrolo[3,4-c]pyrrole-2(1H)-carboxylate; 1,1,1,3,3,3-hexafluoropropan-2-yl 5-((1-ethyl-5-((tetrahydro-2H-pyran-4-yl)carbamoyl)-1H-pyrazol-4-yl)methyl)hexahydropyrrolo[3,4-c]pyrrole-2(1H)-carboxylate; 1,1,1,3,3,3-hexafluoropropan-2-yl 5-(3-(morpholinomethyl)-5-(trifluoromethoxy)benzyl)hexa-hydropyrrolo[3,4-c]pyrrole-2(1H)-carboxylate; 1,1,1,3,3,3-hexafluoropropan-2-yl 5-(3-(piperidin-1-ylmethyl)-5-(trifluoromethoxy)benzyl)hexahydropyrrolo[3,4-c]pyrrole-2(1H)-carboxylate; 1,1,1,3,3,3-hexafluoropropan-2-yl 5-(3-(pyrrolidin-1-ylmethyl)-5-(trifluoromethoxy)benzyl)hexahydropyrrolo[3,4-c]pyrrole-2(1H)-carboxylate; 1,1,1,3,3,3-hexafluoropropan-2-yl 5-(3-(pyrrolidin-1-ylmethyl)-5-(trifluoromethoxy)benzyl)hexahydropyrrolo[3,4-c]pyrrole-2(1H)-carboxylate; 1,1,1,3,3,3-hexafluoropropan-2-yl 5-(2-methyl-3-(piperidine-1-carbonyl)benzyl)hexahydropyrrolo[3,4-c]pyrrole-2(1H)-carboxylate; 1,1,1,3,3,3-hexafluoropropan-2-yl 5-(5-(morpholinomethyl)-2-(trifluoromethoxy)benzyl)hexahydropyrrolo[3,4-c]pyrrole-2(1H)-carboxylate; 1,1,1,3,3,3-hexafluoropropan-2-yl 5-(5-(piperidin-1-ylmethyl)-2-(trifluoromethoxy)benzyl)hexahydro-pyrrolo[3,4-c]pyrrole-2(1H)-carboxylate; 1,1,1,3,3,3-hexafluoropropan-2-yl 5-(5-(pyrrolidin-1-ylmethyl)-2-(trifluoromethoxy)benzyl)hexahydropyrrolo[3,4-c]pyrrole-2(1H)-carboxylate; 1,1,1,3,3,3-hexafluoropropan-2-yl 5-(4-(morpholine-4-carbonyl)-3-(trifluoromethoxy)benzyl)hexahydropyrrolo[3,4-c]pyrrole-2(1H)-carboxylate; 1,1,1,3,3,3-hexafluoropropan-2-yl 5-(4-(piperidine-1-carbonyl)-3-(trifluoromethoxy)benzyl)hexahydropyrrolo[3,4-c]pyrrole-2(1H)-carboxylate; 1,1,1,3,3,3-hexafluoropropan-2-yl 5-(4-(pyrrolidine-1-carbonyl)-3-(trifluoromethoxy)benzyl)hexa-hydropyrrolo[3,4-c]pyrrole-2(1H)-carboxylate; 1,1,1,3,3,3-hexafluoropropan-2-yl 5-((1-methyl-3-phenyl-1H-pyrazol-5-yl)methyl)hexahydropyrrolo[3,4-c]pyrrole-2(1H)-carboxylate; 1,1,1,3,3,3-hexafluoropropan-2-yl 5-((3-(3-fluorophenyl)-1-methyl-1H-pyrazol-5-yl)methyl)hexa-hydropyrrolo[3,4-c]pyrrole-2(1H)-carboxylate; 1,1,1,3,3,3-hexafluoropropan-2-yl 5-((1-methyl-3-(m-tolyl)-1H-pyrazol-5-yl)methyl)hexahydropyrrolo[3,4-c]pyrrole-2(1H)-carboxylate; 2,5-dioxopyrrolidin-1-yl 5-((1-methyl-3-phenyl-1H-pyrazol-5-yl)methyl)hexahydropyrrolo[3,4-c]pyrrole-2(1H)-carboxylate; 2,5-dioxopyrrolidin-1-yl 5-((3-(3-fluorophenyl)-1-methyl-1H-pyrazol-5-yl)methyl) hexahydropyrrolo[3,4-c]pyrrole-2(1H)-carboxylate; 2,5-dioxopyrrolidin-1-yl 5-((1-methyl-3-(m-tolyl)-1H-pyrazol-5-yl)methyl)hexa-hydropyrrolo[3,4-c]pyrrole-2 (1H)-carboxylate; 1,1,1,3,3,3-hexafluoropropan-2-yl 5-(2-(difluoromethyl)-4-morpholinobenzyl)hexahydropyrrolo[3,4-c]pyrrole-2(1H)-carboxylate; 1,1,1,3,3,3-hexafluoropropan-2-yl 5-(2-(difluoromethyl)-4-(piperidin-1-yl)benzyl)hexa-hydropyrrolo[3,4-c]pyrrole-2(1H)-carboxylate; 1,1,1,3,3,3-hexafluoropropan-2-yl 5-(2-(difluoromethyl)-4-(pyrrolidin-1-yl)benzyl)hexahydropyrrolo[3,4-c]pyrrole-2 (1H)-carboxylate; 1,1,1,3,3,3-hexafluoropropan-2-yl 5-(4-(difluoromethyl)-2-morpholinobenzyl)hexa-hydropyrrolo[3,4-c]pyrrole-2(1H)-carboxylate; 1,1,1,3,3,3-hexafluoropropan-2-yl 5-(4-(difluoromethyl)-2-(piperidin-1-yl)benzyl)hexahydropyrrolo[3,4-c]pyrrole-2(1H)-carboxylate; 1,1,1,3,3,3-hexafluoropropan-2-yl 5-(4-(difluoromethyl)-2-(pyrrolidin-1-yl)benzyl)hexahydro-pyrrolo[3,4-c]pyrrole-2 (1H)-carboxylate; 1,1,1,3,3,3-hexafluoropropan-2-yl 5-((6-methyl-[1,1'-biphenyl]-3-yl)methyl)hexa-hydropyrrolo[3,4-c]pyrrole-2(1H)-carboxylate; 1,1,1,3,3,3-hexafluoropropan-2-yl 5-((1-methyl-3-phenyl-1H-pyrazol-5-yl)methyl)hexahydropyrrolo[3,4-c]pyrrole-2(1H)-carboxylate; 1,1,1,3, 3,3-hexafluoropropan-2-yl 5-(4-chloro-2-(tetrahydro-1H-furo[3,4-c]pyrrol-5(3H)-yl)benzyl)hexa-hydropyrrolo[3,4-c]pyrrole-2(1H)-carboxylate; 1,1,1,3,3,3-hexafluoropropan-2-yl 5-(2-(tetrahydro-1H-furo[3,4-c]pyrrol-5(3H)-yl)-6-(trifluoromethyl)benzyl)hexahydropyrrolo[3,4-c]pyrrole-2 (1H)-carboxylate; or 1,1,1,3,3,3-hexafluoropropan-2-yl 5-(2-(tetrahydro-1H-furo[3,4-c]pyrrol-5(3H)-yl)-4-(trifluoromethyl)benzyl)hexahydropyrrolo[3,4-c]pyrrole-2(1H)-carboxylate; or a pharmaceutically acceptable salt thereof.

Preparation of the Compounds

The compounds used in the reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, Pa.), Aldrich Chemical (Milwaukee, Wis., including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, Pa.), Crescent Chemical Co. (Hauppauge, N.Y.), Eastman Organic Chemicals, Eastman Kodak Company (Rochester, N.Y.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Spectrum Quality Product, Inc. (New Brunswick, N.J.), TCI America (Portland, Oreg.), Trans World Chemicals, Inc. (Rockville, Md.), and Wako Chemicals USA, Inc. (Richmond, Va.).

Methods known to one of ordinary skill in the art are identified through various reference books and databases. Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants may also be identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs may be prepared by custom chemical synthesis houses, where many of the standard chemical supply houses (e.g., those listed above) provide custom synthesis services. A reference for the preparation and selection of pharmaceutical salts of the pyrazole compounds described herein is P. H. Stahl & C. G. Wermuth "Handbook of Pharmaceutical Salts", Verlag Helvetica Chimica Acta, Zurich, 2002.

Methods for preparing carbamate compounds encompassed by Formula I and the other Formulas disclosed herein are provided in the examples. Further synthetic methods for preparing various compounds described herein are provided by the following SCHEMES. The SCHEMES are given for the purpose of illustrating the invention, but not for limiting the scope or spirit of the invention. Starting materials shown in the SCHEMES can be obtained from commercial sources or can be prepared based on procedures described in the literature. SCHEME 1, SCHEME 2 and SCHEME 3 provide general methods for preparing the carbamate compounds of Formula I and/or the other Formulas disclosed herein. The activated hexafluoroisopropyl chloroformate, C, can be prepared by reacting hexafluoroisopropanol (HFIP), B, with triphosgene, A, in the presence of a base such as diisopropylethyl amine (Hunig's base, DIEA, DIPEA, $^i$Pr$_2$NEt) or 2,6-lutidine with catalytic 4-(NN-dimethylamino)pyridine (DMAP) in a solvent such as methylene chloride (CH$_2$Cl$_2$, DCM) or acetonitrile (CH$_3$CN) as shown in SCHEME 1. The desired carbamate, E, can be formed by reacting the activated chloroformate with the appropriate amine D.

SCHEME 1

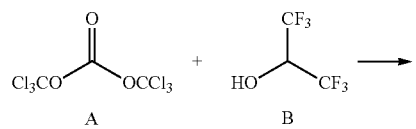

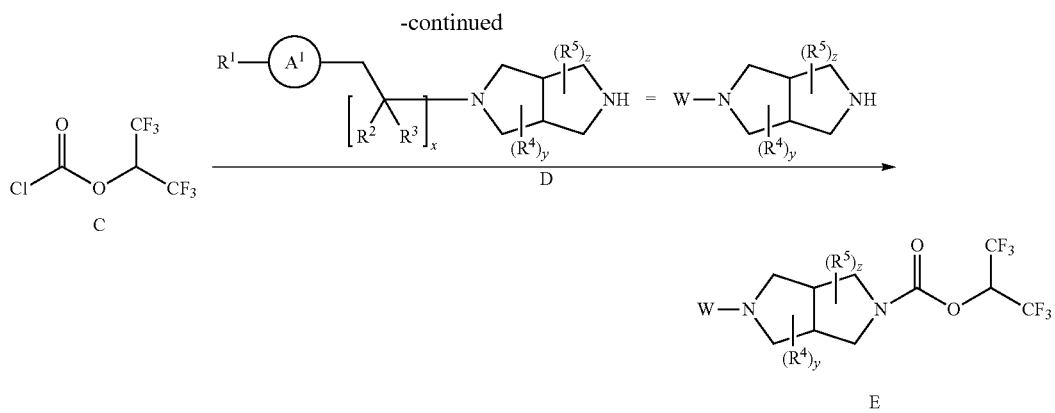

As shown in SCHEME 2, a desired carbamate, G, can be prepared using an amine D and bis(2,5-dioxopyrrolidin-1-yl)carbonate (N,N'-disuccinimidyl carbonate, DSC) in the presence of a base such as N-methylmorpoholine (NMM), DIEA or triethylamine (TEA, $Et_3N$) in a solvent such as acetonitrile or dichloromethane. Compounds of the general structure G can also be prepared by treating F (including those with substitution with $R^{14}$), with an in-situ prepared carbamoyl chloride. The carbamoyl chloride can be prepared by reaction of triphosgene, A, and amine D in the presence of pyridine. Compounds G can further be prepared by treating the N-hydroxysuccinimide intermediates, F, including N-hydroxyphthalimide, with triphosgene, A, in the presence of DIEA. Compounds G can then be prepared by subsequent addition of the desired amine D to the above in-situ prepared acyl chloride.

Compounds of the general formula L can be prepared according to SCHEME 3. The activated methyl 2-((chlorocarbonyl)oxy)-3,3,3-trifluoropropanoate I can be prepared by allowing methyl 3,3,3-trifluoro-2-hydroxypropanoate, H, to react with triphosgene A in the presence of a base such as DIEA, 2,6-lutidine or $Et_3N$ optionally with catalytic DMAP in a solvent such as methylene chloride or acetonitrile. The carbamate, J can be prepared by reacting I with the appropriate amine D. Further modification of J under conditions of hydrolysis using NaOH or similar base in a solvent such as dioxane mixed with water provides K. Conversion to amide L can be achieved under standard amide coupling conditions using an appropriately substituted amine and 1-ethyl-3-(3-dimethylaminopropyl)carbodiimide or similar reagent and hydroxybenzotriazole in a solvent such as

SCHEME 2

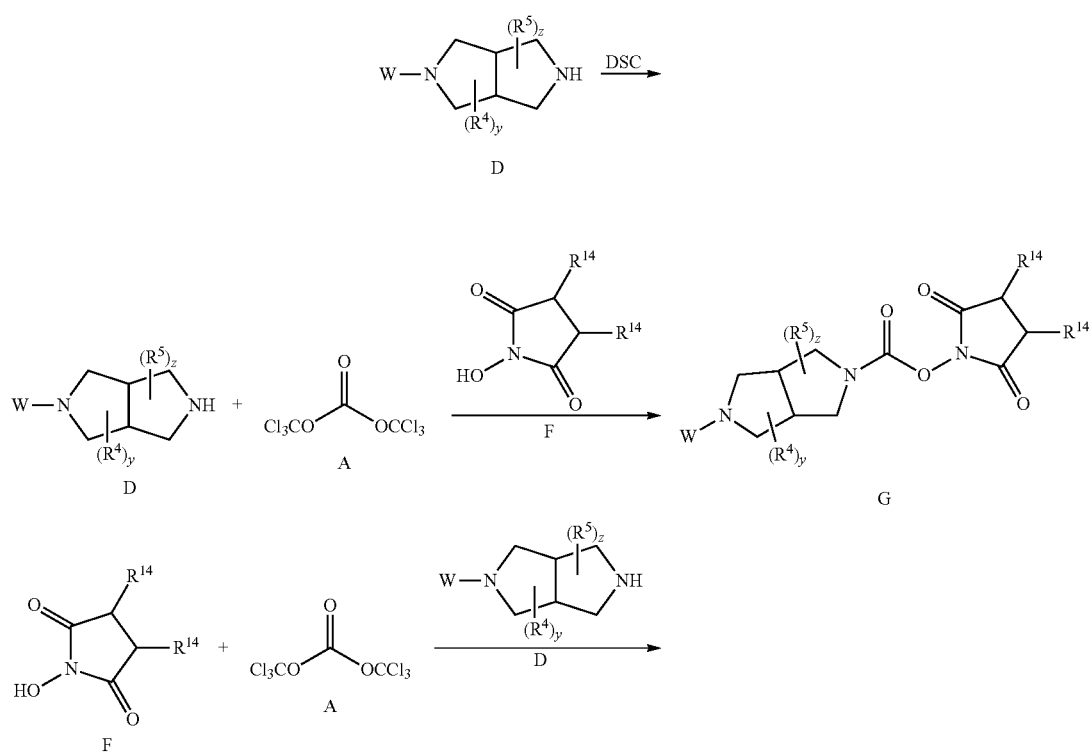

CH$_2$Cl$_2$ or by treatment with methylamine in THF wherein R$^{12}$ is equal to hydrogen and R$^{13}$ is equal to Me.

SCHEME 3

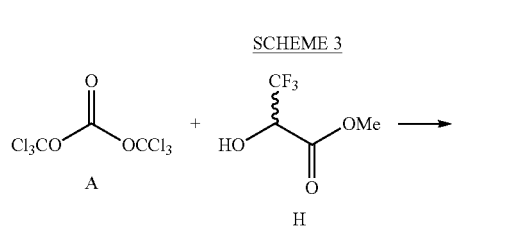

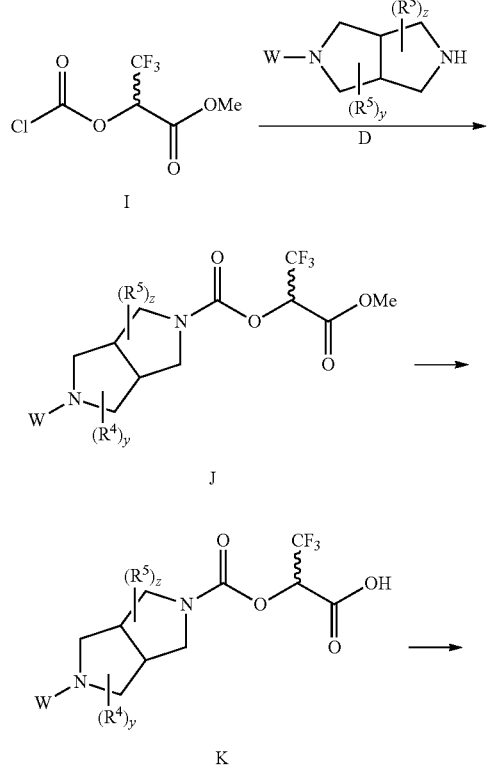

SCHEME 4

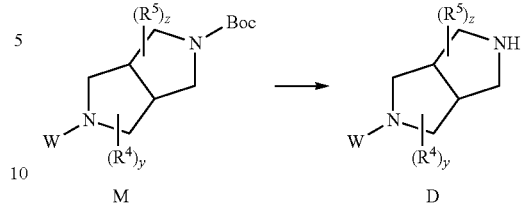

SCHEME 5 provides a detailed exemplary synthetic procedure for making protected amine derivatives of the general structure R. Arylbromide N, optionally substituted, can be converted to an aryllithium using either tert-butyllithium or n-butyllithium at reduced temperatures or the Grignard reagent using standard conditions familiar to those skilled in the art. Allowing the aryllithium or the Grignard reagent to react with ethyl formate or an appropriate aldehyde O provides alcohol P, which can be symmetrical (utilizing ethyl formate, wherein optional substitutions are equivalent) or unsymmetrical (wherein optional substitutions of aldehyde O and aryl bromide N are not equivalent). Alcohol P can be converted to the chloro variant Q using thionyl chloride, in a solvent such as CH$_2$Cl$_2$ optionally in the presence of DMF, followed by treatment with tert-butyl hexahydropyrrolo[3,4-c]pyrrole-2(1H)-carboxylate, or a substituted variant, in a solvent, such as acetonitrile, with or without an added base, such as potassium carbonate, to give R. Alternatively, alcohol P can be obtained from a ketone after reduction with NaBH$_4$ or similar reagent in solvents such as MeOH or CH$_2$Cl$_2$. The protected amine R can be converted to compounds of Formula I and/or the other Formulas disclosed herein according to the representative protocols described above for SCHEME 1, SCHEME 2, SCHEME 3 and SCHEME 4.

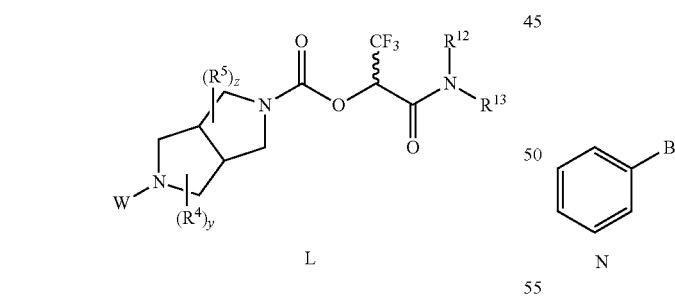

SCHEME 5

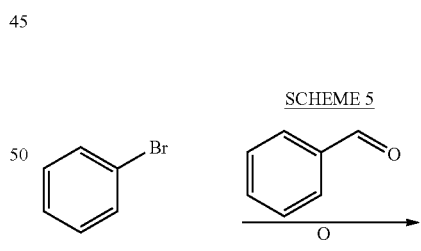

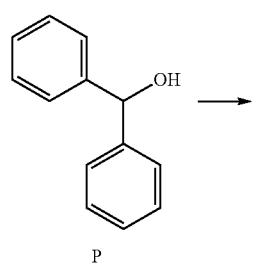

SCHEME 4 provides an exemplary synthetic procedure for making the amine starting material utilized in SCHEME 1, SCHEME 2 and SCHEME 3. The desired amine, D, can be derived from the Boc-protected variant M. Removal of the Boc-group can be achieved by reaction of the Boc-protected amine with NMM and iodotrimethylsilane or alternatively, by treatment with a 4N solution of HCl in dioxane in a solvent such as CH$_2$Cl$_2$ at temperatures ranging from 0 to 25° C. or by treatment with trifluoroacetic acid (TFA) in a solvent such as CH$_2$Cl$_2$.

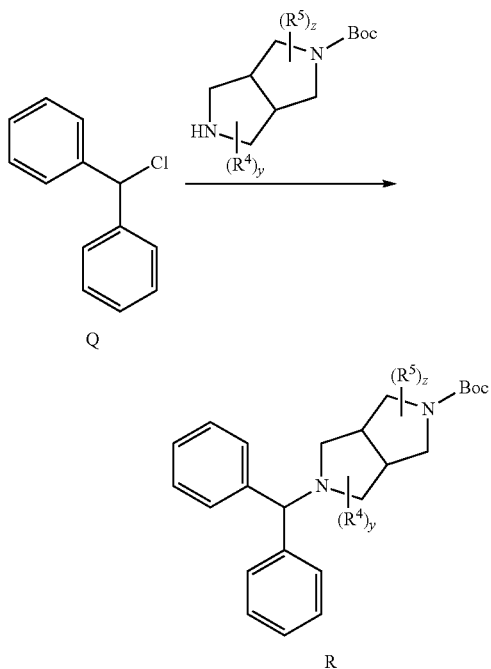

Fluorobenzaldehydes, optionally substituted, S, may be subjected to nucleophilic aromatic substitution conditions according to the exemplary synthetic procedure described in SCHEME 6 in the presence of a base such as potassium carbonate in DMSO or dimethylacetamide at elevated temperature to provide aldehydes T, wherein $R^1$ is a heterocycloalkyl, optionally substituted as defined above. These aldehydes can be used as variants of aldehydes O in SCHEME 8, below.

SCHEME 6

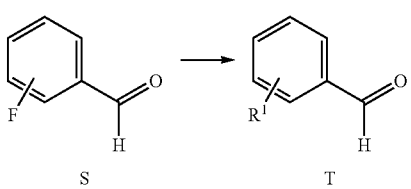

Substituted aldehydes V, wherein $R^1$ is a heterocycloalkyl, optionally substituted as defined above, may be prepared under palladium cross coupling conditions according to the exemplary synthetic procedure described in SCHEME 7 using the appropriately substituted bromobenzaldehyde, U, and the desired amine in the presence of a Pd catalyst such as $Pd_2(dba)_3$, a ligand such as BINAP or Davephos, and a base such as sodium tert-butoxide, and in a solvent such as toluene at elevated temperature. These aldehydes can be used as variants of aldehydes O in SCHEME 8 below. Similar chemistry can be executed using heteroaryl aldehydes.

SCHEME 7

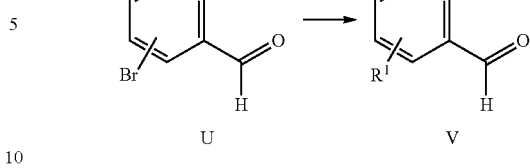

SCHEME 8 provides a detailed exemplary synthetic procedure for making amine intermediates X. Aldehyde O, optionally substituted as described above can be allowed to react with amines using a reducing agent such as NaBH(OAc)$_3$, in dichloromethane, dichloroethane (DCE), N,N-dimethylformamide (DMF) or the like in the presence or absence of molecular sieves to yield intermediates X. The protected amine X can be converted to compounds of Formula I and/or the other Formulas disclosed herein according to the representative protocols described above for SCHEME 1, SCHEME 2, SCHEME 3 and SCHEME 4.

SCHEME 8

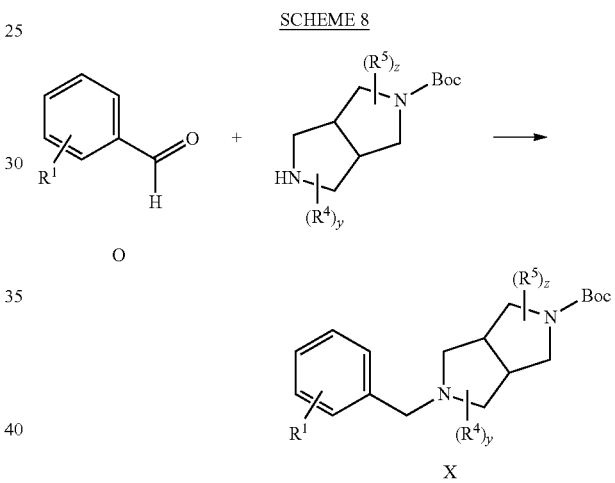

Alternatively, a palladium catalyzed cross coupling can be performed on a substituted aryl bromide after reductive amination with tert-butyl hexahydropyrrolo[3,4-c]pyrrole-2(1H)-carboxylate, or suitably substituted variant as described in SCHEME 8. An appropriately substituted arylhalide or aryltriflate carboxaldehyde, for example aryl bromide U, can be allowed to react with tert-butyl hexahydropyrrolo[3,4-c]pyrrole-2(1H)-carboxylate as described in SCHEME 8 to provide Y. Arylbromide Y can be treated with a desired amine in the presence of a Pd catalyst such as $Pd_2(dba)_3$ or $Pd(OAc)_2$, a ligand such as BINAP or Davephos, and a base such as sodium tert-butoxide or $Cs_2CO_3$, and in a solvent such as toluene at elevated temperature to provide intermediate Z. Intermediate Y can also be treated with an appropriately substituted arylboronic acid optionally substituted under palladium cross coupling conditions in the presence of a Pd catalyst such as $Pd(PPh_3)_4$ or $PdCl_2(dppf)$ $CH_2Cl_2$ in the presence of a base such as potassium carbonate and a solvent such as dioxane or THF/water mixtures at elevated temperatures to generate AA. Intermediates Z and AA can be converted to compounds of Formula I and/or the other Formulas disclosed herein according to the representative protocols described above for SCHEME 1, SCHEME 2, SCHEME 3 and SCHEME 4.

SCHEME 9

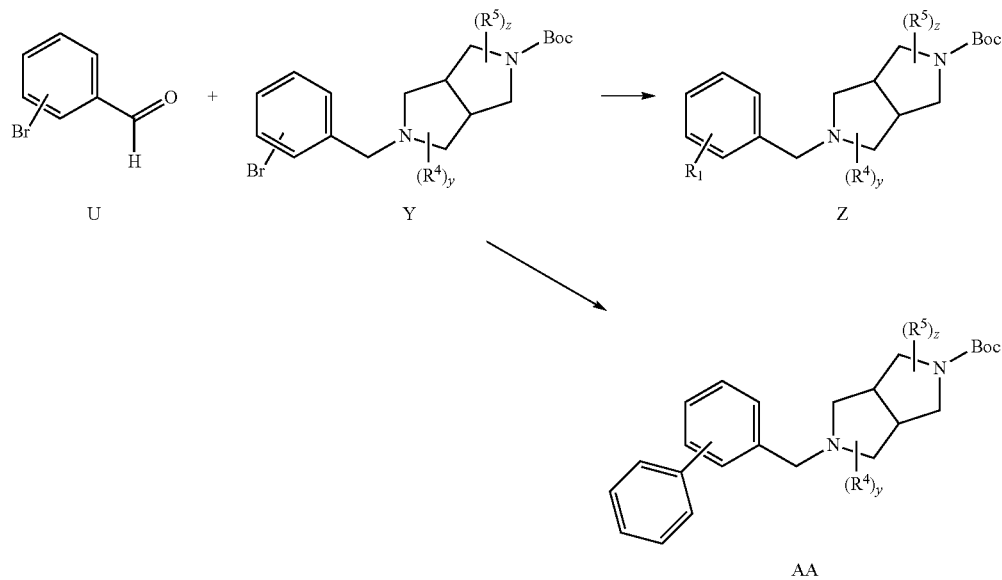

Substituted heteroaryl aldehydes of the general formula AE can be prepared as shown in SCHEME 10 as heteroaryl analogues of U. $R^i$ and $R^j$ may be independently selected, and are intended to be consistent with $R^1$ and allowed substitutions on $A^1$ as defined above. Commercially available methyl ketones AB can be condensed with hydrazines or hydrazine salts AC in an alcoholic solvent at room temperature to reflux for hours to overnight to provide hydrazines AD. The hydrazines can then be treated with N-(chloromethylene)-N-methyl-methanaminium chloride (also known as (chloromethylidene)dimethylazanium chloride) or phosphoryl chloride ($POCl_3$) and DMF in a solvent such as DMF and stirred at room temperature to 100° C. overnight. After an aqueous workup, aldehydes AE are generated which can be used as shown in SCHEME 9 to prepare compounds of Formula I and/or the other Formulas disclosed herein.

Substituted heteroaryl aldehydes of the general formula AI can also be prepared as shown in SCHEME 11 as heteroaryl analogues of U. $R^i$ and $R^j$ may be independently selected, and are intended to be consistent with $R^1$ and allowed substitutions on $A^1$ as defined above. Commercially available 2,4-dioxo-pentanoic acid esters AF can be condensed with commercially available O-methylhydroxylamine or its salts in an alcoholic solvent at room temperature to reflux for hours to overnight in the presence of molecular sieves to provide oximes AG. The oximes can then be treated with hydrazines or hydrazine salts in an alcoholic solvent such as ethanol and stirred at room temperature to reflux overnight to provide esters AH. The esters can be converted to aldehydes AI through various routes known to those skilled in the art, including direct reduction with diisobutylaluminum hydride in a solvent such as toluene or dichloromethane at −78° C. to 0° C. followed by aqueous workup, or by reducing to the alcohol with a reducing agent such as lithium borohydride or lithium aluminum hydride in a solvent such as tetrahydrofuran or diethyl ether at −78° C. to room temperature followed by an aqueous workup and oxidizing to the aldehyde with a reagent such as pyridinium chlorochromate or pyridinium dichromate in a solvent such as dichloromethane at 0° C. to reflux. Other appropriate oxidants include dimethylsulfoxide with an appropriate activating agent, such as oxalyl chloride at −78° C. to 0° C. in a solvent such as dichloromethane or Dess-Martin periodinane in a solvent such as dichloromethane at room temperature. The aldehydes AI can be used as shown in SCHEME 9 to prepare compounds of Formula I and/or the other Formulas disclosed herein.

SCHEME 10

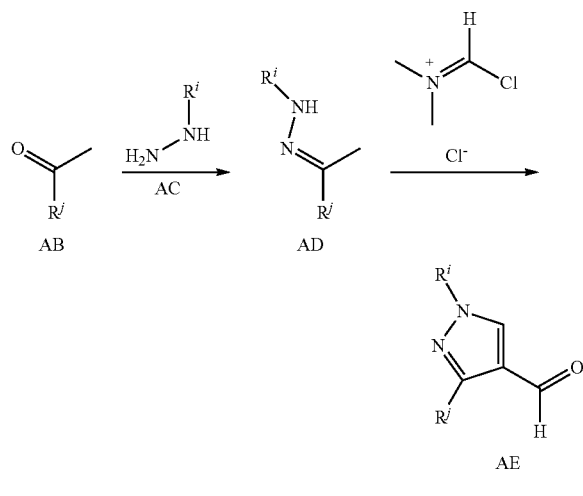

SCHEME 11

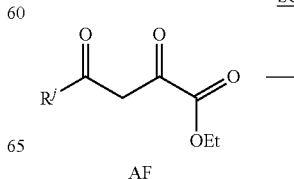

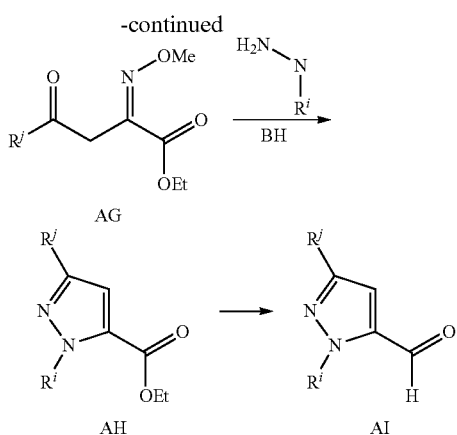

Additionally, substituted heteroaryl aldehydes of the general formula AN can be prepared as shown in SCHEME 12 as heteroaryl analogues of U. $R^i$ and $R^j$ may be independently selected, and are intended to be consistent with $R^1$ and allowed substitutions on $A^1$ as defined above. Hydrazine or hydrazine salts, AC can be condensed with appropriately substituted aldehydes, AJ in an alcoholic solvent at room temperature to reflux for hours to overnight in the presence or absence of molecular sieves to provide hydrazines AK. The hydrazine, AK can be allowed to react with a (E)-N-methoxy-N-methyl-3-nitroacrylamide, for example AL, in an alcoholic solvent at room temperature to reflux for hours to overnight to yield the appropriately substituted pyrazole amide AM. Reduction of the amide moiety to the desired pyrazole aldehyde, AN, can be accomplished through various routes known to those skilled in the art, including direct reduction with diisobutylaluminum hydride in a solvent such as THF at −78° C. followed by aqueous workup. Aldehydes AN can be used as shown in SCHEME 9 to prepare compounds of Formula I and/or the other Formulas disclosed herein.

Heterocyclic variants of X, such as AO, can be further modified according to SCHEME 13. $R^i$ may be independently selected, and is intended to be consistent with $R^1$ and allowed substitutions on $A^1$ as defined above. AO may be allowed to react with benzyl bromide (BnBr) in a solvent such as acetone at elevated temperature for hours to overnight to obtain the pyridinium bromide AP. Reduction of the phenyl ring and subsequent removal of the benzyl group can be achieved via a two-step reduction/hydrogenation process first using sodium borohydride ($NaBH_4$) in a solvent such as ethanol at 0° C. to obtain intermediate AQ followed by hydrogenation using hydrogen gas in the presence of Pd/C in a solvent such as ethyl acetate to obtain AR. Subsequent acylation of the 2° nitrogen can be accomplished through various routes known to those skilled in the art. For example, AR can be allowed to react with acetic anhydride ($Ac_2O$) in the presence of a base such as $Et_3N$ in a solvent such as $CH_2Cl_2$ as room temperature to prepare AS. Alternatively, the use of methanesulfonyl chloride under similar conditions would result in the corresponding sulfonamide.

SCHEME 12

SCHEME 13

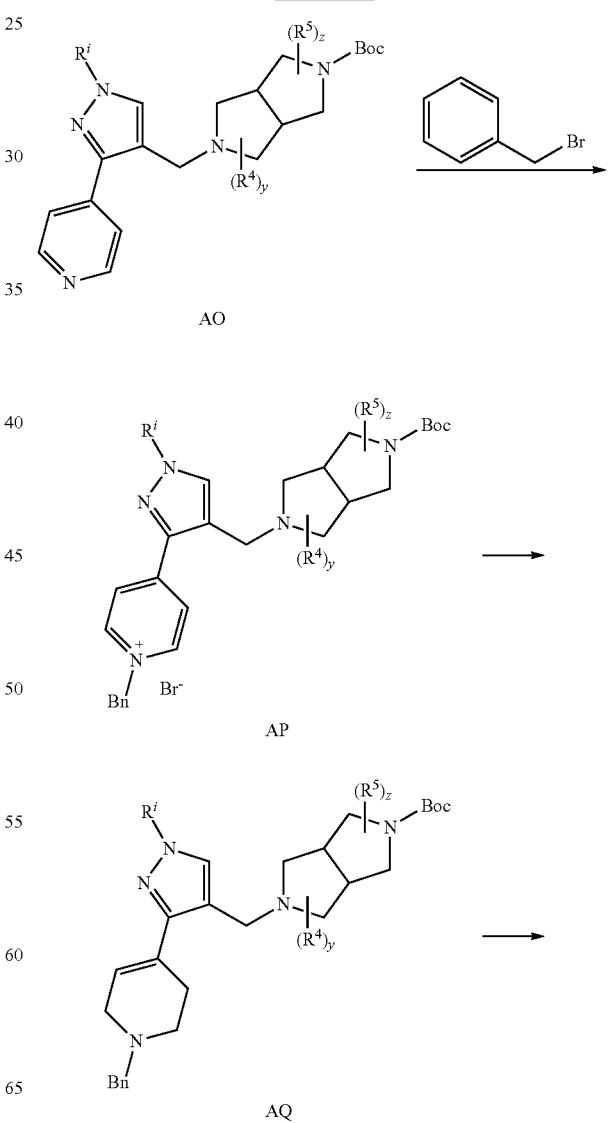

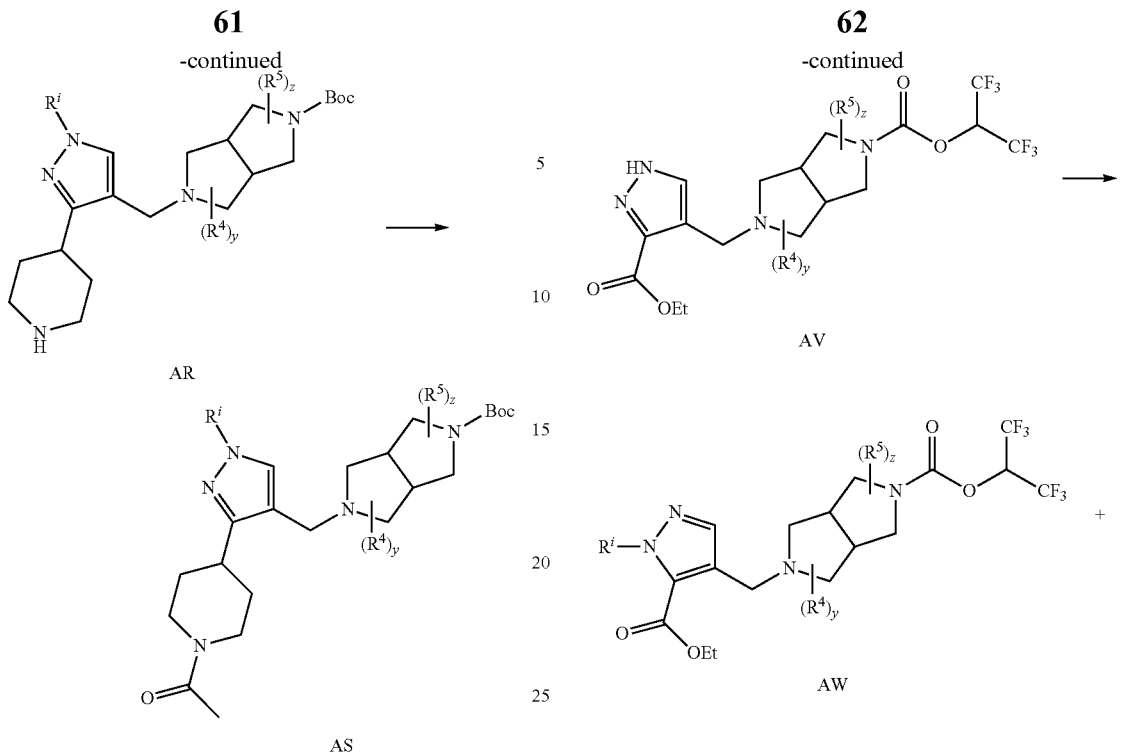

Substituted heteroaryl esters AW and AX can be prepared as shown in SCHEME 14. AT can be prepared from tert-butyl hexahydropyrrolo[3,4-c]pyrrole-2(1H)-carboxylate according to the methods outlined in SCHEME 1 and SCHEME 4. AV can be prepared according to the methods outlined in SCHEME 8 using commercially available pyrazole AU. An appropriate electrophile such as an alkyl methanesulfonate, alkyl bromide, or alkyl iodide, $R^iI$ for example, in the presence of base such as cesium carbonate in a solvent such as acetonitrile can be allowed to react with pyrazole AV to yield a mixture of isomers, AW and AX which can be isolated using standard methods of purification known to those skilled in the art. $R^i$ may be independently selected, and is intended to be consistent with allowed substitutions on $A^1$ as defined above.

Further modification of AW under conditions of hydrolysis using NaOH or similar base in a solvent such as dioxane mixed with water provides AY as shown in SCHEME 15. Conversion to amide BA can be achieved under standard amide coupling conditions using 1-ethyl-3-(3-dimethylaminopropyl)carbodiimide or (dimethylamino)-N,N-dimethyl(3H-[1,2,3]triazolo[4,5-b]pyridin-3-yloxy)methaniminium hexafluorophosphate (HATU) or similar reagent in a solvent such as DMF or $CH_2Cl_2$, optionally in the presence of a base such as DIEA. Isomer AX can, similarly, be converted to isomers of BA.

SCHEME 14

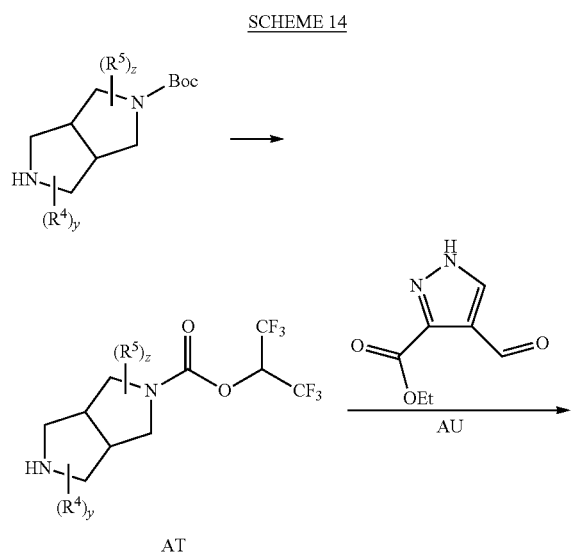

SCHEME 15

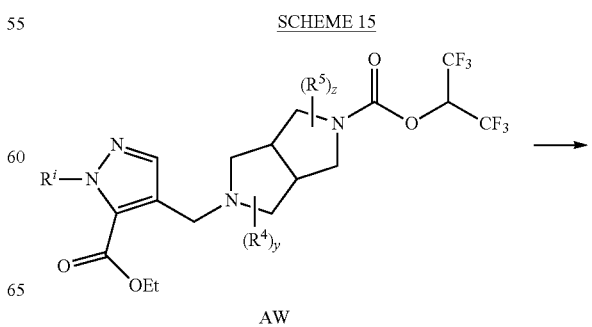

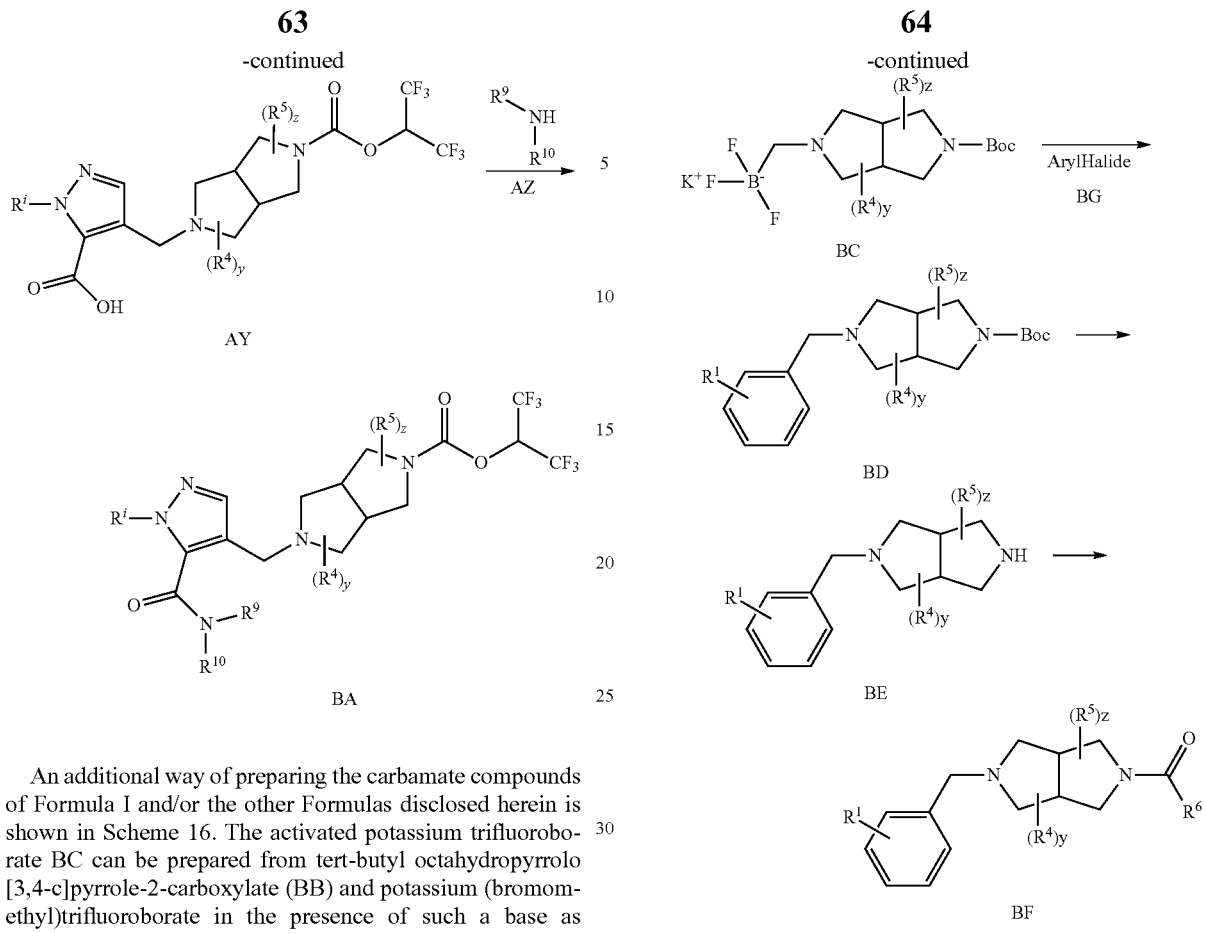

An additional way of preparing the carbamate compounds of Formula I and/or the other Formulas disclosed herein is shown in Scheme 16. The activated potassium trifluoroborate BC can be prepared from tert-butyl octahydropyrrolo[3,4-c]pyrrole-2-carboxylate (BB) and potassium (bromomethyl)trifluoroborate in the presence of such a base as potassium carbonate in a solvent such as THF. Compound of general formula BD can be prepared by reacting BC with an appropriate aryl halide (BG) in the presence of a palladium catalyst such as Pd(OAc)$_2$, a ligand such as XPhos (2-dicyclohexylphosphino-2',4',6'-triisopropylbiphenyl), a base such as cesium or potassium carbonate in a solvent such as THF/water. Carbamates of general formula BF can be obtained after deprotection of the Boc protecting group and reaction with hexafluoropropan-2-ol and triphosgene in the presence of a base such as DIEA in a solvent such as DCM. Alternatively the carbamates of general formula BF can be obtained after deprotection of the Boc protecting group and reaction with bis(2,5-dioxopyrrolidin-1-yl)carbonate is the presence of a base such as Et$_3$N in a solvent such as ACN. The order of these reactions can be reversed. BB can be first reacted with hexafluoropropan-2-ol or bis(2,5-dioxopyrrolidin-1-yl)carbonate followed by deprotection of the Boc protecting group. Subsequent reaction of the free amine with potassium (bromomethyl)trifluoroborate followed by palladium coupling with an aryl halide BG to afford the desired carbamate BF.

The appropriate aryl halides (BG) of scheme 16 can be either commercially available or synthesized as shown in Scheme 17. Compound BH can either be reacted with an amine (HNR$^9$R$^{10}$) in the presence of a palladium catalyst, a ligand and a base suitable for a Buchwald type reaction to form BG-1 or it can be reacted with a boronic acid in the presence of a palladium catalyst and a base suitable for a Suzuki type reaction to form BG-2. Alternatively aldehyde BI can be reacted with an amine (HNR$^9$R$^{10}$) in the presence of a reducing agent such as NaBH(OAc)$_3$, in DCM, DCE, DMF or the like in the presence or absence of molecular sieves to yield intermediate BG-3.

SCHEME 17

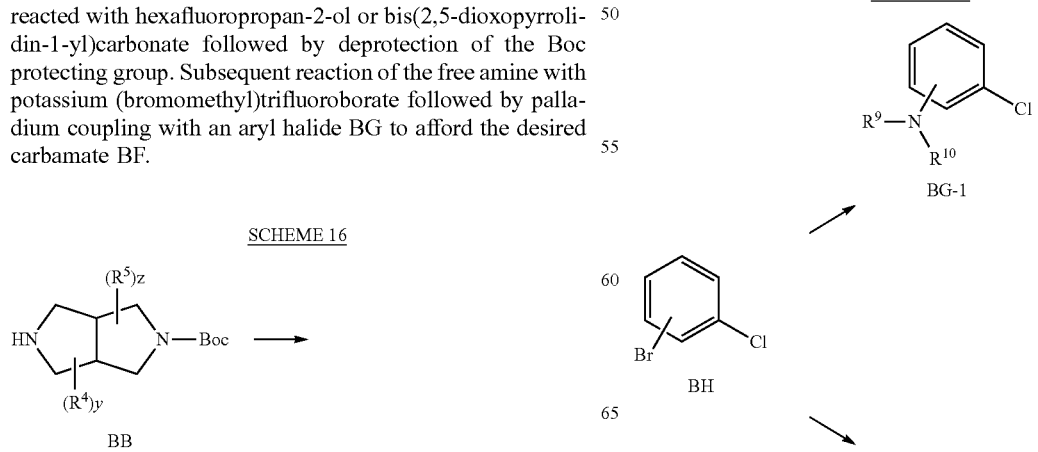

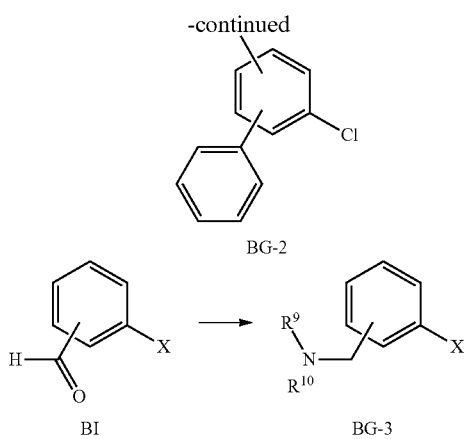

Further Forms of Pyrazole Compounds Disclosed Herein

Isomers

Furthermore, in some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, compounds exist as tautomers. The compounds described herein include all possible tautomers within the formulas described herein. In some situations, the compounds described herein possess one or more chiral centers and each center exists in the R configuration, or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that would not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, sulfur, fluorine and chloride, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds described herein, and the metabolites, pharmaceutically acceptable salts, esters, prodrugs, solvate, hydrates or derivatives thereof which contain the aforementioned isotopes and/or other isotopes of other atoms are within the scope of this invention. Certain isotopically-labeled compounds, for example those into which radioactive isotopes such as $^{3}H$ and $^{14}C$ are incorporated, are useful in drug and/or substrate tissue distribution assays. Tritiated, i.e., $^{3}H$ and carbon-14, i.e., $^{14}C$, isotopes are particularly preferred for their ease of preparation and detectability. Further, substitution with heavy isotopes such as deuterium, i.e., $^{2}H$, produces certain therapeutic advantages resulting from greater metabolic stability, for example increased in vivo half-life or reduced dosage requirements. In some embodiments, the isotopically labeled compounds, pharmaceutically acceptable salt, ester, prodrug, solvate, hydrate or derivative thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds of the invention, or by separately reacting a purified compound in its free form with a suitable acid or base, and isolating the salt thus formed.

Solvates

In some embodiments, the compounds described herein exist as solvates. The invention provides for methods of treating diseases by administering such solvates. The invention further provides for methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein can be conveniently prepared or formed during the processes described herein. By way of example only, hydrates of the compounds described herein can be conveniently prepared by recrystallization from an aqueous/organic solvent mixture, using organic solvents including, but not limited to, dioxane, tetrahydrofuran or methanol. In addition, the compounds provided herein can exist in unsolvated as well as solvated forms. In general, the solvated forms are considered equivalent to the unsolvated forms for the purposes of the compounds and methods provided herein.

Metabolites

In some embodiments, pyrazole compounds described herein are susceptible to various metabolic reactions. Therefore, in some embodiments, incorporation of appropriate substituents into the structure will reduce, minimize, or eliminate a metabolic pathway. In specific embodiments, the appropriate substituent to decrease or eliminate the susceptibility of an aromatic ring to metabolic reactions is, by way of example only, a halogen, or an alkyl group.

In additional or further embodiments, pyrazole compounds described herein are metabolized upon administration to an organism in need to produce a metabolite that is then used to produce a desired effect, including a desired therapeutic effect III. Therapeutic Applications The invention provides methods of modulating the activity of MAGL and/or ABHD6. Contemplated methods, for example, comprise exposing said enzyme to a compound described herein. In some embodiments, the compound utilized by one or more of the foregoing methods is one of the generic, subgeneric, or specific compounds described herein, such as a compound of Formulas (I), (Ia), (Ib), (Ic), (Id), (Ie), (If), (Ig), (Ih), (Ii), (Ij), (Ik), (Im), or (Io). The ability of compounds described herein to modulate or inhibit MAGL and/or ABHD6 can be evaluated by procedures known in the art and/or described herein. In some embodiments, the exposing of the enzyme is in vivo. In other embodiments, the exposing of the enzyme is in vitro.

Another aspect of this disclosure provides methods of treating a disease associated with expression or activity of MAGL and/or ABHD6 in a patient. For example, provided herein are compounds that may be selective in inhibiting MAGL or ABHD6, or both, as compared to inhibition of other serine hydrolases e.g., FAAH, e.g., 10, 100, 1000 or more fold inhibition of MAGL over FAAH. In other embodiments, disclosed compounds may be more selective in inhibition of MAGL as compared to ABHD6.

The invention also provides methods of treating medical disorders, such as pain, a solid tumor cancer, obesity, Downs syndrome, Alzheimer's disease, and an infection, using a pyrrolo-pyrrole carbamate, related compound, or pharmaceutical composition described herein. Treatment methods include the use of the pyrrolo-pyrrole carbamate or related organic compound described herein as stand-alone therapy and/or as part of a combination therapy with another therapeutic agent.

Methods of Treating Medical Disorders

Accordingly, one aspect of the invention provides a method of treating a disorder selected from the group consisting of a solid tumor cancer, obesity, Downs syndrome, Alzheimer's disease, and an infection. The method comprises administering to a patient in need thereof a therapeutically effective amount of a pyrrolo-pyrrole carbamate or related organic compound described herein, such as a compound of Formulas (I), (Ia), (Ib), (Ic), (Id), (Ie), (If), (Ig), (Ih), (Ii), (Ij), (Ik), (Im), or (Io). In certain embodiments, the method consists essentially of administering to a patient in need thereof a therapeutically effective amount of a pyrrolo-pyrrole carbamate or related organic compound described herein, such as a compound of Formulas (I), (Ia), (Ib), (Ic), (Id), (Ie), (If), (Ig), (Ih), (Ii), (Ij), (Ik), (Im), or (Io).

In certain embodiments, the disorder is a solid tumor cancer. In certain embodiments, the solid tumor cancer may be, for example, brain cancer, bladder cancer, breast cancer, cervical cancer, colon cancer, colorectal cancer, endometrial cancer, esophageal cancer, lung cancer, liver cancer, melanoma, ovarian cancer, pancreatic cancer, prostate cancer, rectal cancer, renal cancer, stomach cancer, testicular cancer, or uterine cancer.

In certain embodiments, the disorder is obesity.

In certain embodiments, the disorder is Downs syndrome or Alzheimer's disease.

In certain embodiments, the disorder is an infection by a bacterium, fungus, parasite, or virus.

Another aspect of the invention provides a method of treating pain in a patient. The method comprises administering a pyrrolo-pyrrole carbamate or related organic compound described herein, such as a compound of Formulas (I), (Ia), (Ib), (Ic), (Id), (Ie), (If), (Ig), (Ih), (Ii), (Ij), (Ik), (Im), or (Io), to a patient in need thereof to treat said pain. In certain embodiments, the method consists essentially of administering to a patient in need thereof a therapeutically effective amount of a pyrrolo-pyrrole carbamate or related organic compound described herein, such as a compound of Formulas (I), (Ia), (Ib), (Ic), (Id), (Ie), (If), (Ig), (Ih), (Ii), (Ij), (Ik), (Im), or (Io). In certain embodiments, the pain is acute pain. In certain other embodiments, the pain is chronic pain. In certain other embodiments, the pain is a chronic pain such as inflammatory pain, visceral pain, post operative pain, back pain, lower back pain, joint pain, abdominal pain, chest pain, or menstrual pain. In certain other embodiments, the pain is pain due to labor, a musculoskeletal disease, a skin disease, toothache, pyresis, burn, sunburn, snake bite, venomous snake bite, spider bite, insect sting, neurogenic bladder, interstitial cystitis, urinary tract infection, rhinitis, contact dermatitis/hypersensitivity, itch, eczema, pharyngitis, mucositis, enteritis, irritable bowel syndrome, cholecystitis, pancreatitis, postmastectomy pain syndrome, endometriosis, physical trauma, headache, sinus headache, tension headache, arachnoiditis, migraine, osteoarthritis, or rheumatoid arthritis, In certain other embodiments, the pain is a neuropathic pain (e.g., neuropathic low back pain, complex regional pain syndrome, post trigeminal neuralgia, causalgia, toxic neuropathy, reflex sympathetic dystrophy, diabetic neuropathy, or chronic neuropathy caused by a chemotherapeutic agent).

Another aspect of the invention provides a method of reducing the amount of adipose tissue in a patient, comprising administering an effective amount of a pyrrolo-pyrrole carbamate or related organic compound described herein, such as a compound of Formulas (I), (Ia), (Ib), (Ic), (Id), (Ie), (If), (Ig), (Ih), (Ii), (Ij), (Ik), (Im), or (Io), to a patient in need thereof to reduce the amount of adipose tissue in the patient. In certain embodiments, the method of reducing the amount of adipose tissue in a patient, consists essentially of administering an effective amount of a pyrrolo-pyrrole carbamate or related organic compound described herein, such as a compound of Formulas (I), (Ia), (Ib), (Ic), (Id), (Ie), (If), (Ig), (Ih), (Ii), (Ij), (Ik), (Im), or (Io), to a patient in need thereof to reduce the amount of adipose tissue in the patient.

Another aspect of the invention provides a method of treating a disorder selected from the group consisting of a metabolic disorder (such as syndrome X), vomiting, nausea, eating disorders such as anorexia and/or bulimia; dislipidaemia, neuropathy such as diabetic neuropathy, pellagric neuropathy, alcoholic neuropathy, Beriberi neuropathy, burning feet syndrome, neurodegenerative disorders such as multiple sclerosis, Parkinson's disease, Huntington's chorea, Alzheimer's disease, amyotrophic lateral sclerosis, epilepsy, sleep disorders, cardiovascular diseases, hypertension, dyslipidemia, atherosclerosis, osteoporosis, osteoarthritis, emesis, epilepsy, mental disorders such as schizophrenia and depression, glaucoma, cachexia, insomnia, traumatic brain injury, spinal cord injury, seizures, excitotoxin exposure, ischemia, AIDS wasting syndrome, renal ischaemia, cancers (e.g., solid tumor cancers such as breast, lung, head and neck, ovarian, sarcoma, melanoma, and/or prostate cancer); cancers such as melanoma, metastatic tumors, kidney or bladder cancers, brain, gastrointestinal cancers (e.g., colon cancer), leukemia or blood cancers (e.g. myeloid, lymphoid or monocytic cancers), inflammatory disorders (e.g. bladder inflammation), including inflammatory pain, and/or psychological disorders including anxiety disorders (e.g., panic disorder, acute stress disorder, post-traumatic stress disorder, substance-induced anxiety disorders, obsessive-compulsive disorder, agoraphobia, specific phobia, or social phobia. The method comprises administering to a patient in need thereof a therapeutically effective amount of a pyrrolo-pyrrole carbamate or related organic compound described herein, such as a compound of Formulas (I), (Ia), (Ib), (Ic), (Id), (Ie), (If), (Ig), (Ih), (Ii), (Ij), (Ik), (Im), or (Io), to treat the disorder. In certain embodiments, the method consists essentially of administering to a patient in need thereof a therapeutically effective amount of a pyrrolo-pyrrole carbamate or related organic compound described herein, such as a compound of Formulas (I), (Ia), (Ib), (Ic), (Id), (Ie), (If), (Ig), (Ih), (Ii), (Ij), (Ik), (Im), or (Io), to treat the disorder.

Also contemplated herein are methods for ameliorating cognitive function in a patient suffering from Down's syndrome or Alzheimer's disease, comprising administering an effective amount of a disclosed compound. Exemplary patients suffering from Down's syndrome may be a pediatric patient (e.g., a patient of age 0-11 years, 0-18 years, 0-6 years, or e.g., 12 to 18 years), an adult patient (e.g., 18 years or older), or e.g., an older patient e.g., 18-40 years, 20-50 years). Such patients may also suffer from further cognitive impairment and/or dementia, and/or seizures which may or may not be due to production of prostaglandins and/or amyloid beta. For example, such patients may also be suffering from, or may have one or more of the following symptoms associated with early, mid, or late-stage cognitive impairment: loss of language, impairment of social skills, progressive loss of activities of daily living, and may include psychotic behavior. Provided herein, for example, is a method for treating a patient having Down's syndrome or Alzheimer's disease with cognitive impairment, comprising administering an effective amount of a disclosed compound. Such disclosed methods may result in cognitive improvement, for example, measured by IQ or the Arizona Cognitive Test Battery (e.g., measured with a cognitive test battery designed for use in individuals with Down's syndrome). For example, a treated patient using a disclosed method may have at least one of: increased memory, improved memory or improved speech. In some embodiments, such disclosed methods may result in a patient having an increased quality of life as measured by an adaptive behavior scale after said administration.

In other embodiments, a method for at least partially providing a Down's syndrome patient a neuroprotective (such as a disclosed compound), that may result in delayed onset of neurodegeneration or may substantially prevent neurodegeneration, is provided. Administration to a patient may be initiated before onset of neurodegeneration and/or onset of neurodegeneration symptoms. Contemplated herein are methods for treating and/or ameliorating cognitive decline, improving sleep duration and/or quality, and/or treating PANDAS (pediatric autoimmune neuropsychiatric disorders associated with streptococcal infections) in a patient in need thereof, comprising administering a disclosed compound.

Another aspect of the invention provides methods of treating an infectious disease comprising administering to a patient in need thereof an effective amount of a disclosed compound herein. An infectious disease is understood to be an illness in a patient resulting from the infection, presence, and/or growth of a pathogenic biological agent. A pathogenic biological agent may be, for example, a bacterium, a fungus, or a parasite. An illness may be symptomatic or asymptomatic. In some embodiments, a disclosed compound may be administered to a patient in need thereof to treat a local infection and/or a systemic infection. The ability of compounds described herein to treat an infectious disease can be evaluated by procedures known in the art and/or described herein. In certain embodiments, the method consists essentially of administering to a patient in need thereof an effective amount of a compound disclosed herein.

In certain embodiments, a disclosed compound may be administered to a patient in need thereof to treat an infectious disease caused by a bacterium (e.g., a bacterial infection). In some cases, the bacterial infection may be caused by a Gram negative bacterium. In other cases, the bacterial infection may be caused by a Gram positive bacterium. In yet other embodiments, the bacterial infection may not Gram stain (e.g., the bacteria may be a *Mycobacterium* or *Mycoplasma*). In some embodiments, the bacterial infection may be caused by at least one bacterial strain, e.g., one, two, or more bacterial strains. In another embodiment, contemplated compounds may be used to treat complications of a bacterial infection including, but not limited to, sepsis, sepsis syndrome, septic shock, endotoxaemia, systemic inflammatory response syndrome (SIRS), multi-organ dysfunction syndrome, toxic shock syndrome, acute lung injury, ARDS (adult respiratory distress syndrome), acute renal failure, post-surgical infections, and meningitis. In certain embodiments, a contemplated compound may be bacteriostatic. In other embodiments, a contemplated compound may be bactericidal.

In another embodiment, the compounds contemplated herein may be used in a method of inhibiting bacterial growth on a surface. In yet another embodiment, the compounds contemplated herein may be used in a method of inhibiting bacterial growth in a medium, e.g., as a biocide, anti-fouling agent, etc.

Non-limiting examples of bacterial genera that may cause an infectious disease include: *Acinetobacter, Bacillus, Bacteroides, Bordetella, Borrelia, Brucella, Campylobacter, Chlamydia, Chlamydophila, Clostridium, Corynebacterium, Enterobacter, Enterococcus, Escherichia, Francisella, Gardnerella, Haemophilus, Helicobacter, Klebsiella, Legionella, Leptospira, Listeria, Mycobacterium, Mycoplasma, Neisseria, Proteus, Providencia, Pseudomonas, Rickettsia, Salmonella, Seratia, Shigella, Staphylococcus, Streptococcus, Treponema, Ureaplasma, Vibrio*, and *Yersinia*.

Non-limiting examples of bacterial species that may cause an infectious disease include strains of: *Acinetobacter baumannii, Bacillus anthracis, Bacteroides fragilis, Bordetella pertussis, Borrelia burgdorferi, Brucella abortus, Brucella canis, Brucella melitensis, Brucella suis, Campylobacter jejuni, Chlamydia pneumonia, Chlamydia trachomatis, Chlamydophila psittaci, Clostridium botulinum, Clostridium difficile, Clostridium perfringens, Clostridium tetani, Corynebacterium diphtheria, Enterobacter aerogenes, Enterobacter cloacae, Enterococcus faecalis, Enterococcus faecium, Escherichia coli, Francisella tularensis,*

*Gardnerella vaginalis, Haemophilus influenza, Helicobacter pylori, Klebsiella pneumonia, Legionella pneumophila, Leptospira interrogans, Listeria monocytogenes,* MRSA, MRSE, *Mycobacterium leprae, Mycobacterium tuberculosis, Mycobacterium ulcerans, Mycoplasma hominis, Mycoplasma pneumonia, Neisseria gonorrhoeae, Neisseria meningitides, Proteus mirabilis, Proteus vulgaris, Providencia rettgeri, Providencia stuartii, Pseudomonas aeruginosa, Rickettsia rickettsia, Salmonella typhi, Salmonella typhimurium, Seratia marcescens, Shigella sonnei, Staphylococcus aureus, Staphylococcus epidermidis, Staphylococcus hemolyticus, Staphylococcus saprophyticus, Streptococcus agalactiae, Streptococcus pneumonia, Streptococcus pyogenes, Streptococcus viridans, Treponema pallidum, Ureaplasma urealyticum, Vibrio cholerae, Vibrio vulnificus,* and *Yersinia pestis.*

In some embodiments, a disclosed compound may be administered to a patient in need thereof to treat an infectious disease caused by a fungus. Non-limiting examples of fungi that may cause an infectious disease include: *Candida* (e.g., *Candida albicans*), *Aspergillus* (e.g., *Aspergillus fumigatus, Aspergillus flavus,* and *Aspergillus clavatus*), *Cryptococcus* (e.g., *Cryptococcus neoformans, Cryptococcus laurentii, Cryptococcus albidus,* and *Cryptococcus gattii*), *Histoplasma* (e.g., *Histoplasma capsulatum*), *Pneumocystis* (e.g., *Pneumocystis jirovecii* and *Pneumocystis carinii*), and *Stachybotrys* (e.g., *Stachybotrys chartarum*).

In certain embodiments, a disclosed compound may be administered to a patient in need thereof to treat an infectious disease caused by a parasite (e.g., a parasitic infection). For example, a disclosed compound may be used to treat an infection caused by, but not limited to, protozoa, helminths, and ectoparasites.

Non-limiting examples of protozoa that may cause an infectious disease include those classified as amoebozoa and excavata. For instance, non-limiting examples of amoebozoa that may be sensitive (e.g., susceptible) to the contemplated compounds include *Entamoeba histolytica, Acanthamoeba,* and *Balamuthia mandrillaris.* Non-limiting examples of excavata that may cause an infectious disease include *Giardia* (e.g., *Giardia lamblia*), *Carpediemonas,* and *Trichomonas* (e.g., *Trichomonas vaginalis*). Other examples of protozoa that may cause an infectious disease include, but are not limited to, *Babesia* (e.g., *Babesia divergens, Babesia bigemina, Babesia equi, Babesia microfti,* and *Babesia duncani*), *Balantidium coli, Blastocystis, Cryptosporidium, Dientamoeba fragilis, Entamoeba histolytica, Isospora belli, Leishmania* (e.g., *Leishmania donovani*), *Naegleria fowleri, Plasmodium* (e.g., *Plasmodium falciparum, Plasmodium vivax, Plasmodium ovale, Plasmodium malariae,* and *Plasmodium knowlesi*), *Rhinosporidium seeberi, Sarcocystis* (e.g., *Sarcocystis bovihominis* and *Sarcocystis suihominis*), *Toxoplasma gondii,* and *Trypanosoma* (e.g., *Trypanosoma cruzi, Trypanosoma brucei,* and *Trypanosoma brucei brucei*).

Non-limiting examples of helminthes that may cause an infectious disease include those classified as tapeworms, flukes, and roundworms. For instance, non-limiting examples of tapeworms that may cause an infectious disease include *Cestoda, Taenia multiceps, Diphyllobothrium latum, Echinococcus* (e.g., *Echinococcus granulosus, Echinococcus multilocularis, Echinococcus vogeli, Echinococcus oligarthrus*), *Hymenolepis* (e.g., *Hymenolepis nana* and *Hymenolepis diminuta*), *Taenia* (e.g., *Taenia saginata* and *Taenia solium*), *Bertiella* (e.g., *Bertiella mucronata* and *Bertiella studeri*), and *Spirometra erinaceieuropaei.*

Non-limiting examples of flukes that may cause an infectious disease include *Clonorchis* (e.g., *Clonorchis sinensis* and *Clonorchis viverrini*), *Dicrocoelium dendriticum, Fasciola* (e.g., *Fasciola hepatica* and *Fasciola gigantica*), *Fasciolopsis buski, Gnathostoma* (e.g., *Gnathostoma spinigerum* and *Gnathostoma hispidum*), *Metagonimus yokogawai, Opisthorchis* (e.g., *Opisthorchis viverrini* and *Opisthorchis felineus*), *Clonorchis sinensis, Paragonimus* (e.g., *Paragonimus westermani, Paragonimus africanus, Paragonimus caliensis, Paragonimus kellicotti, Paragonimus skrjabini,* and *Paragonimus uterobilateralis*), *Schistosoma* (e.g., *Schistosoma mansoni, Schistosoma haematobium, Schistosoma japonicum,* and *Schistosoma mekongi*), *Echinostoma echinatum, Trichobilharzia regenti,* and *Schistosomatidae.*

Non-limiting examples of roundworms that may cause an infectious disease include *Ancylostoma duodenale, Necator americanus, Angiostrongylus costaricensis, Anisakis, Ascaris* (e.g., *Ascaris lumbricoides*), *Baylisascaris procyonis, Brugia* (e.g., *Brugia malayi* and *Brugia timori*), *Dioctophyme renale, Dirofilaria immitis, Dracunculus medinensis, Enterobius* (e.g., *Enterobius vermicularis* and *Enterobius gregorii*), *Haemonchus contortus, Halicephalobus gingivalis, Loa boa filaria, Mansonella streptocerca, Onchocerca volvulus, Strongyloides stercoralis, Thelazia* (e.g., *Thelazia californiensis* and *Thelazia callipaeda*), *Toxocara* (e.g., *Toxocara canis* and *Toxocara cati*), *Trichinella* (e.g., *Trichinella spiralis, Trichinella britovi, Trichinella nelsoni, Trichinella nativa*), *Trichuris* (e.g., *Trichuris trichiura* and *Trichuris vulpis*), and *Wuchereria bancrofti.*

Still other examples of pathogens that may cause an infectious disease include *Archiacanthocephala, Moniliformis moniliformis, Linguatula serrate, Oestroidea, Calliphoridae, Sarcophagidae, Tunga penetrans,* and *Dermatobia hominis.*

Also contemplated are methods of treating a viral infection comprising administering a disclosed compound herein to a patient in need thereof. In certain embodiments, the method consists essentially of administering a compound disclosed herein to a patient in need thereof. Non-limiting examples of viruses that may cause an infectious disease include Adeno-associated virus, Aichi virus, Australian bat lyssavirus, BK polyomavirus, Banna virus, Barmah forest virus, Bunyamwera virus, Bunyavirus La Crosse, Bunyavirus snowshoe hare, Cercopithecine herpesvirus, Chandipura virus, Chikungunya virus, Cowpox virus, Coxsackievirus, Crimean-Congo hemorrhagic fever virus, Dengue virus, Dhori virus, Dugbe virus, Duvenhage virus, Ebolavirus, Echovirus, Encephalomyocarditis virus, Epstein-Barr virus, European bat lyssavirus, GB virus C, Hantaan virus, Hendra virus, Hepatitis A virus, Hepatitis B virus, Hepatitis C virus, Hepatitis E virus, Hepatitis delta virus, Horsepox virus, Human adenovirus, Human astrovirus, Human coronavirus, Human cytomegalovirus, Human enterovirus 68, 70, Human herpesvirus 1, Human herpesvirus 2, Human herpesvirus 6, Human herpesvirus 7, Human herpesvirus 8, Human immunodeficiency virus, Human papillomavirus 1, Human papillomavirus 2, Human papillomavirus 16, 18, Human parainfluenza, Human parvovirus B 19, Human respiratory syncytial virus, Human rhinovirus, Human SARS coronavirus, Human spumaretrovirus, Human T-lymphotropic virus, Human torovirus, Influenza A virus, Influenza B virus, Influenza C virus, Isfahan virus, JC polyomavirus, Japanese encephalitis virus, Junin arenavirus, KI Polyomavirus, Kunjin virus, Lagos bat virus, Lake Victoria marburgvirus, Langat virus, Lassa virus, Lordsdale virus, Louping ill virus, Lymphocytic choriomeningitis virus, Machupo virus, Mayaro virus, Measles virus, Mengo encephalomyocarditis virus, Merkel cell polyomavirus, Mokola virus, Molluscum contagiosum virus, Monkeypox virus, Mumps virus, Murray valley encephalitis virus, New York virus, Nipah virus, Norwalk virus, O'nyong-nyong virus, Orf virus, Oropouche virus, Pichinde virus, Poliovirus, Punta toro phlebovirus, Puumala virus, Rabies virus, Rift valley fever virus, Ross river virus, Rotavirus A, Rotavirus B, Rotavirus C, Rubella virus, Sagiyama virus, Sandfly fever sicilian virus, Sapporo virus, Semliki forest virus, Seoul virus, Simian foamy virus, Simian virus 5, Sindbis virus, Southampton virus, St. louis encephalitis virus, Tick-borne powassan virus, Torque teno virus, Toscana virus, Uukuniemi virus, Vaccinia virus, Varicella-zoster virus, Variola virus, Venezuelan equine encephalitis virus, Vesicular stomatitis virus, Western equine encephalitis virus, WU polyomavirus, West Nile virus, Yaba monkey tumor virus, Yaba-like disease virus, and Yellow fever virus.

Also contemplated herein are combination therapies, for example, co-administering a disclosed compound and an additional active agent, as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually weeks, months or years depending upon the combination selected). Combination therapy is intended to embrace administration of multiple therapeutic agents in a sequential manner, that is, wherein each therapeutic agent is administered at a different time, as well as administration of these therapeutic agents, or at least two of the therapeutic agents, in a substantially simultaneous manner.

Substantially simultaneous administration can be accomplished, for example, by administering to the subject a single formulation or composition, (e.g., a tablet or capsule having a fixed ratio of each therapeutic agent or in multiple, single formulations (e.g., capsules) for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection.

Combination therapy also can embrace the administration of the therapeutic agents as described above in further combination with other biologically active ingredients and non-drug therapies. Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The components of the combination may be administered to a patient simultaneously or sequentially. It will be appreciated that the components may be present in the same pharmaceutically acceptable carrier and, therefore, are administered simultaneously. Alternatively, the active ingredients may be present in separate pharmaceutical carriers, such as, conventional oral dosage forms, that can be administered either simultaneously or sequentially.

For example, e.g., for contemplated treatment of pain or other contemplated indications (e.g., Alzheimer' or Down's syndrome), a disclosed compound can be co-administered with another therapeutic for pain such as an opioid, a cannabinoid receptor (CB-1 or CB-2) modulator, a COX-2 inhibitor, acetaminophen, and/or a non-steroidal anti-inflammatory agent. Additional therapeutics e.g., for the treatment of pain that may be co-administered include morphine, codeine, hydromorphone, hydrocodone, oxymorphone, fentanyl, tramadol, and levorphanol.

Other contemplated therapeutics for co-administration include aspirin, naproxen, ibuprofen, salsalate, diflunisal, dexibuprofen, fenoprofen, ketoprofen, oxaprozin, loxoprofen, indomethacin, tolmetin, sulindac, etodolac, ketorolac, piroxicam, meloxicam, tenoxicam, droxicam, lornoxicam, celecoxib, parecoxib, rimonabant, and/or etoricoxic.

In certain embodiments, the patient is a mammal. In certain embodiments, the patient is a human.

In certain embodiments, the compound is one of the generic or specific compounds described in Section II, such as a compound of Formulas (I), (Ia), (Ib), (Ic), (Id), (Ie), (If), (Ig), (Ih), (Ii), (Ij), (Ik), (Im), or (Io), or a compound embraced by one of the further embodiments describing definitions for certain variables of Formulas (I), (Ia), (Ib), (Ic), (Id), (Ie), (If), (Ig), (Ih), (Ii), (Ij), (Ik), (Im), or (Io).

The description above describes multiple embodiments relating to methods of treating various disorders using certain pyrrolo-pyrrole carbamate or related organic compounds. The patent application specifically contemplates all combinations of the embodiments. For example, the invention contemplates treating for treating a solid tumor cancer by administering a therapeutically effective amount of a compound of Formula (Ic).

IV. Pharmaceutical Compositions

The invention provides pharmaceutical compositions comprising a pyrrolo-pyrrole carbamate or related organic compound described herein, such as a compound of Formulas (I), (Ia), (Ib), (Ic), (Id), (Ie), (If), (Ig), (Ih), (Ii), (Ij), (Ik), (Im), or (Io).

One embodiment provides a pharmaceutical composition comprising a pharmaceutically acceptable carrier and a compound of Formula (I), or a pharmaceutically acceptable salt or solvate thereof. One embodiment provides a pharmaceutical composition comprising a pharmaceutically acceptable carrier and a compound of Formula (Ia), or a pharmaceutically acceptable salt or solvate thereof. One embodiment provides a pharmaceutical composition comprising a pharmaceutically acceptable carrier and a compound of Formula (Ib), or a pharmaceutically acceptable salt or solvate thereof. One embodiment provides a pharmaceutical composition comprising a pharmaceutically acceptable carrier and a compound of Formula (Ic), or a pharmaceutically acceptable salt or solvate thereof. One embodiment provides a pharmaceutical composition comprising a pharmaceutically acceptable carrier and a compound of Formula (Id), or a pharmaceutically acceptable salt or solvate thereof. One embodiment provides a pharmaceutical composition comprising a pharmaceutically acceptable carrier and a compound of Formula (Ie), or a pharmaceutically acceptable salt or solvate thereof. One embodiment provides a pharmaceutical composition comprising a pharmaceutically acceptable carrier and a compound of Formula (If), or a pharmaceutically acceptable salt or solvate thereof. One embodiment provides a pharmaceutical composition comprising a pharmaceutically acceptable carrier and a compound of Formula (Ig), or a pharmaceutically acceptable salt or solvate thereof. One embodiment provides a pharmaceutical composition comprising a pharmaceutically acceptable carrier and a compound of Formula (Ih), or a pharmaceutically acceptable salt or solvate thereof. One embodiment provides a pharmaceutical composition comprising a pharmaceutically acceptable carrier and a compound of Formula (Ii), or a pharmaceutically acceptable salt or solvate thereof. One embodiment provides a pharmaceutical composition comprising a pharmaceutically acceptable carrier and a compound of Formula (Ij), or a pharmaceutically acceptable salt or solvate thereof. One embodiment provides a pharmaceutical composition comprising a pharmaceutically acceptable carrier and a compound of Formula (Ik), or a pharmaceutically acceptable salt or solvate thereof. One embodiment provides a pharmaceutical composition comprising a pharmaceutically acceptable carrier and a compound of Formula (Im), or a pharmaceutically acceptable salt or solvate thereof. One embodiment provides a pharmaceutical composition comprising a pharmaceutically acceptable carrier and a compound of Formula (Io), or a pharmaceutically acceptable salt or solvate thereof.

Another embodiment provides a pharmaceutical composition consisting essentially of a pharmaceutically acceptable carrier and a compound of Formula (I), or a pharmaceutically acceptable salt or solvate thereof. Another embodiment provides a pharmaceutical composition consisting essentially of a pharmaceutically acceptable carrier and a compound of Formula (Ia), or a pharmaceutically acceptable salt or solvate thereof. Another embodiment provides a pharmaceutical composition consisting essentially of a pharmaceutically acceptable carrier and a compound of Formula (Ib), or a pharmaceutically acceptable salt or solvate thereof. Another embodiment provides a pharmaceutical composition consisting essentially of a pharmaceutically acceptable carrier and a compound of Formula (Ic), or a pharmaceutically acceptable salt or solvate thereof. Another embodiment provides a pharmaceutical composition consisting essentially of a pharmaceutically acceptable carrier and a compound of Formula (Id), or a pharmaceutically acceptable salt or solvate thereof. Another embodiment provides a pharmaceutical composition consisting essentially of a pharmaceutically acceptable carrier and a compound of Formula (Ie), or a pharmaceutically acceptable salt or solvate thereof. Another embodiment provides a pharmaceutical composition consisting essentially of a pharmaceutically acceptable carrier and a compound of Formula (If), or a pharmaceutically acceptable salt or solvate thereof. Another embodiment provides a pharmaceutical composition consisting essentially of a pharmaceutically acceptable carrier and a compound of Formula (Ig), or a pharmaceutically acceptable salt or solvate thereof. Another embodiment provides a pharmaceutical composition consisting essentially of a pharmaceutically acceptable carrier and a compound of Formula (Ih), or a pharmaceutically acceptable salt or solvate thereof. Another embodiment provides a pharmaceutical composition consisting essentially of a pharmaceutically acceptable carrier and a compound of Formula (Ii), or a pharmaceutically acceptable salt or solvate thereof. Another embodiment provides a pharmaceutical composition consisting essentially of a pharmaceutically acceptable carrier and a compound of Formula (Ij), or a pharmaceutically acceptable salt or solvate thereof. Another embodiment provides a pharmaceutical composition consisting essentially of a pharmaceutical acceptable carrier and a compound of Formula (Ik), or a pharmaceutically acceptable salt or solvate thereof. Another embodiment provides a pharmaceutical composition consisting essentially of a pharmaceutically acceptable carrier and a compound of Formula (Im), or a pharmaceutically acceptable salt or solvate thereof. Another embodiment provides a pharmaceutical composition consisting essentially of a pharmaceutically acceptable carrier and a compound of Formula (Io), or a pharmaceutically acceptable salt or solvate thereof.

In certain embodiments, the compound as described herein is substantially pure, in that it contains less than about 5%, or less than about 1%, or less than about 0.1%, of other organic small molecules, such as contaminating intermediates or by-products that are created, for example, in one or more of the steps of a synthesis method.

In certain embodiments, the pharmaceutical compositions preferably comprise one or more of the pyrrolo-pyrrole carbamate or related organic compounds described above, formulated together with one or more pharmaceutically acceptable carriers. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets (e.g., those targeted for buccal, sublingual, and/or systemic absorption), boluses, powders, granules, pastes for application to the tongue; (2) parenteral administration by, for example, subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment. A therapeutically effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

In particular, the present disclosure provides pharmaceutical compositions comprising compounds as disclosed herein formulated together with one or more pharmaceutically acceptable carriers. These formulations include those suitable for oral, rectal, topical, buccal, parenteral (e.g., subcutaneous, intramuscular, intradermal, or intravenous) rectal, vaginal, or aerosol administration, although the most suitable form of administration in any given case will depend on the degree and severity of the condition being treated and on the nature of the particular compound being used. For example, disclosed compositions may be formulated as a unit dose, and/or may be formulated for oral or subcutaneous administration.

Exemplary pharmaceutical compositions may be used in the form of a pharmaceutical preparation, for example, in solid, semisolid or liquid form, which includes one or more of a disclosed compound, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

For preparing solid compositions such as tablets, the principal active ingredient may be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a disclosed compound or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Compositions for inhalation or insufflation include solutions and suspensions in pharmaceutically acceptable, aqueous or organic solvents, or mixtures thereof, and powders. Liquid dosage forms for oral administration include pharmaceutically acceptable emulsions, microemulsions, solutions, suspensions, syrups and elixirs. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

Suspensions, in addition to the subject composition, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent.

Dosage forms for transdermal administration of a subject composition include powders, sprays, ointments, pastes, creams, lotions, gels, solutions, patches and inhalants. The active component may be mixed under sterile conditions with a pharmaceutically acceptable carrier, and with any preservatives, buffers, or propellants which may be required.

The ointments, pastes, creams and gels may contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a subject composition, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Compositions and compounds disclosed herein may alternatively be administered by aerosol. This is accomplished by preparing an aqueous aerosol, liposomal preparation or solid particles containing the compound. A non-aqueous (e.g., fluorocarbon propellant) suspension could be used. Sonic nebulizers may be used because they minimize exposing the agent to shear, which may result in degradation of the compounds contained in the subject compositions. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity may be maintained, for example, by the use of coating materials, such as lecithin, by the maintenance of the required particle size in the case of dispersions, and by the use of surfactants Also contemplated are enteral pharmaceutical formulations including a disclosed compound and an enteric material; and a pharmaceutically acceptable carrier or excipient thereof. Enteric materials refer to polymers that are substantially insoluble in the acidic environment of the stomach, and that are predominantly soluble in intestinal fluids at specific pHs. The small intestine is the part of the gastrointestinal tract (gut) between the stomach and the large intestine, and includes the duodenum, jejunum, and ileum. The pH of the duodenum is about 5.5, the pH of the jejunum is about 6.5 and the pH of the distal ileum is about 7.5. Accordingly, enteric materials are not soluble, for example, until a pH of about 5.0, of about 5.2, of about 5.4, of about 5.6, of about 5.8, of about 6.0, of about 6.2, of about 6.4, of about 6.6, of about 6.8, of about 7.0, of about 7.2, of about 7.4, of about 7.6, of about 7.8, of about 8.0, of about 8.2, of about 8.4, of about 8.6, of about 8.8, of about 9.0, of about 9.2, of about 9.4, of about 9.6, of about 9.8, or of about 10.0. Exemplary enteric materials include cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, cellulose acetate maleate, cellulose acetate butyrate, cellulose acetate propionate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylate-chlorotrimethylammonium ethyl acrylate copolymer, natural resins such as zein, shellac and copal collophorium, and several commercially available enteric dispersion systems (e. g., Eudragit L30D55, Eudragit FS30D, Eudragit L100, Eudragit S100, Kollicoat EMM30D, Estacryl 30D, Coateric, and Aquateric). The solubility of each of the above materials is either known or is readily determinable in vitro. The foregoing is a list of possible materials, but one of skill in the art with the benefit of the disclosure would recognize that it is not comprehensive and that there are other enteric materials that would meet the objectives of the present disclosure The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Preferably, the compounds are administered at about 0.01 mg/kg to about 200 mg/kg, more preferably at about 0.1 mg/kg to about 100 mg/kg, even more preferably at about 0.5 mg/kg to about 50 mg/kg. When the compounds described herein are co-administered with another agent, the effective amount may be less than when the agent is used alone.

If desired, the effective daily dose of the active compound may be administered as two, three, four, five, six or more sub-doses administered separately at appropriate intervals throughout the day, optionally, in unit dosage forms. Preferred dosing is one administration per day.

V. Kits for Use in Medical Applications

Another aspect of the invention provides a kit for treating a disorder. The kit comprises: i) instructions for treating a medical disorder, such as a solid tumor cancer, obesity, Downs syndrome, Alzheimer's disease, or an infection; and ii) a pyrrolo-pyrrole carbamate or related organic compound described herein, such as a compound of Formulas (I), (Ia), (Ib), (Ic), (Id), (Ie), (If), (Ig), (Ih), (Ii), (Ij), (Ik), (Im), or (Io). The kit may comprise one or more unit dosage forms containing an amount of a pyrrolo-pyrrole carbamate or related organic compound described herein, such as a compound of Formulas (I), (Ia), (Ib), (Ic), (Id), (Ie), (If), (Ig), (Ih), (Ii), (Ij), (Ik), (Im), or (Io), that is effective for treating said medical disorder, e.g., a solid tumor cancer, obesity, Downs syndrome, Alzheimer's disease, or an infection.

The description above describes multiple aspects and embodiments of the invention, including pyrrolo-pyrrole carbamate and related organic compounds, compositions comprising pyrrolo-pyrrole carbamate or related organic compounds, methods of using the pyrrolo-pyrrole carbamate or related organic compounds, and kits. The patent application specifically contemplates all combinations and permutations of the aspects and embodiments. For example, the invention contemplates treating a solid tumor cancer, obesity, Downs syndrome, Alzheimer's disease, or an infection in a human patient by administering a therapeutically effective amount of a compound of Formula (Ic).

EXAMPLES

List of Abbreviations

As used above, and throughout the description of the invention, the following abbreviations, unless otherwise indicated, shall be understood to have the following meanings:

ACN or MeCN acetonitrile
Ac acetyl
Ac$_2$O acetic anhydride
BINAP 2,2'-bis(diphenylphosphino)-1,1'-binaphthyl
Bn benzyl
BOC or Boc tert-butyl carbamate
t-Bu tert-butyl
Dba dibenzylideneacetone
DCE dichloroethane (ClCH$_2$CH$_2$Cl)
DCM dichloromethane (CH$_2$Cl$_2$)
DIPEA or DIEA diisopropylethylamine
DMAP 4-(N,N-dimethylamino)pyridine
DMF dimethylformamide
DMSO dimethylsulfoxide
Dppf or dppf 1,1'-bis(diphenylphosphino)ferrocene
EDCI 1-ethyl-3-(3-dimethylaminopropyl)carbodiimide
equiv equivalent(s)
Et ethyl
Et$_2$O diethyl ether
Et$_3$N triethylamine
EtOH ethanol
EtOAc ethyl acetate
ESI electrospray ionization HATU 1-[bis(dimethylamino)methylene]-1H-1,2,3-triazolo[4,5-b]pyridinium 3-oxid hexafluorophosphate
HFIP hexafluoroisopropanol
HOBt hydroxybenzotriazole
HPLC high performance liquid chromatography
LCMS liquid chromatography/mass spectrometry
Me methyl
MeOH methanol
MS mass spectroscopy
MsCl methanesulfonyl chloride (mesyl chloride)
NMR nuclear magnetic resonance
NMM N-methyl-morpholine
NMP N-methyl-pyrrolidin-2-one
Ph phenyl
RP-HPLC reverse phase-high pressure liquid chromatography
rt room temperature
TBAF tetra-N-butylammonium fluoride
TFA trifluoroacetic acid
THF tetrahydrofuran
TLC thin layer chromatography
TsCl p-toluenesulfonyl chloride (tosyl chloride)

The invention now being generally described, will be more readily understood by reference to the following examples, which are included merely for purposes of illustration of certain aspects and embodiments of the present invention, and are not intended to limit the invention.

Example 1

1,1,1,3,3,3-Hexafluoropropan-2-yl 5-(2-fluoro-4-morpholinobenzyl)hexahydropyrrolo[3,4-c]pyrrole-2(1H)-carboxylate

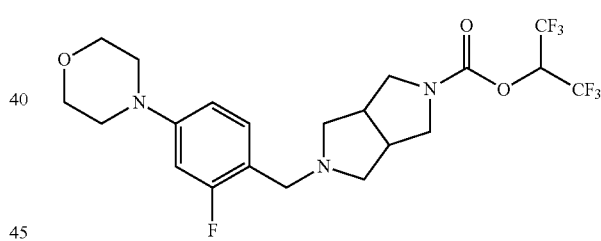

Step 1: Preparation of tert-butyl 5-(2-fluoro-4-morpholinobenzyl)hexahydropyrrolo[3,4-c]pyrrole-2(1H)-carboxylate

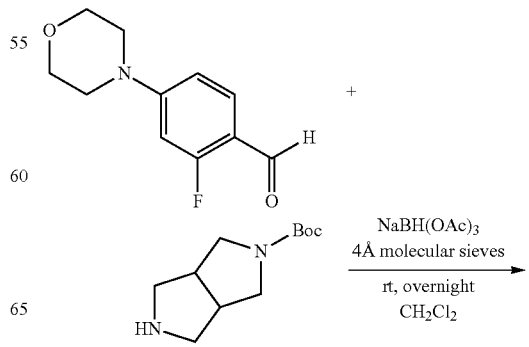

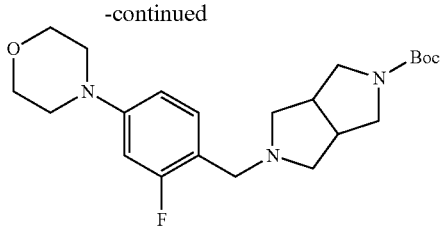

A 50-mL round-bottom flask, equipped with a magnetic stir bar, was charged with tert-butyl hexahydropyrrolo[3,4-c]pyrrole-2(1H)-carboxylate (500 mg, 2.36 mmol) under nitrogen. The solid was dissolved in 10 mL dichloromethane (anhydrous) and stirred at room temperature. 2-Fluoro-4-morpholinobenzaldehyde (493 mg, 2.36 mmol) was added followed by molecular sieves (490 mg, 8-12 mesh beads). The reaction mixture was allowed to continue to stir at room temperature for 1 h. At that point, sodium triacetoxyborohydride (549 mg, 2.59 mmol, 1.10 equiv) was added. The reaction was monitored for disappearance of aldehyde by thin layer chromatography. After 15 h, the reaction was quenched with saturated sodium bicarbonate (15 mL). After the addition of dichloromethane (15 mL), the mixture was partitioned into two phases. The aqueous phase was extracted twice with dichloromethane (15 mL). The combined organic layers were dried over anhydrous sodium sulfate, filtered, and concentrated. The crude mixture was applied to a chromatography column containing 24 g silica and dichloromethane. A gradient solvent was used from 100% dichloromethane to 10% methanol in dichloromethane to provide 915 mg (96%) of tert-butyl 5-(2-fluoro-4-morpholinobenzyl)hexahydropyrrolo[3,4-c]pyrrole-2(1H)-carboxylate as a pale yellow oil. $^1$H NMR (400 MHz, Chloroform-d) δ 7.23 (t, J=8.6 Hz, 1H), 6.66 (dd, J=8.5, 2.2 Hz, 1H), 6.57 (dd, J=13.0, 2.1 Hz, 1H), 3.96-3.81 (m, 4H), 3.56 (d, J=31.6 Hz, 4H), 3.38-3.04 (m, 6H), 2.86-2.64 (m, 4H), 2.38 (s, 2H), 1.78 (s, 1H), 1.47 (d, J=1.6 Hz, 9H).

Step 2: Preparation of 4-(3-fluoro-4-((hexahydropyrrolo[3,4-c]pyrrol-2(1H)-yl)methyl)phenyl)morpholine

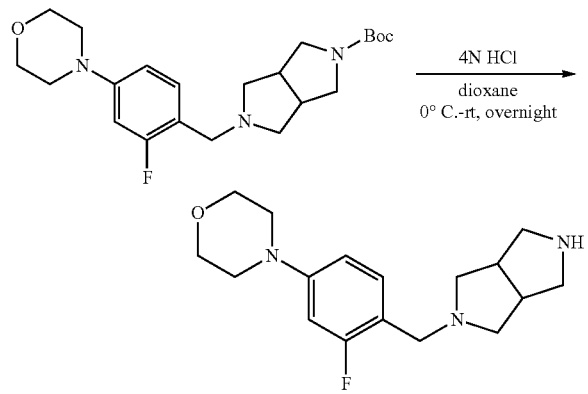

A 100-mL round-bottom flask, equipped with a magnetic stir bar, was charged with tert-butyl 4-(2-fluoro-4-morpholinobenzyl)piperazine-1-carboxylate (819 mg, 2.16 mmol) and dichloromethane (14 mL). The resulting solution was cooled to 0° C. Hydrochloric acid (3.2 mL, 4 N in dioxane) was added via syringe. The ice bath was removed and the resulting cloudy suspension was allowed to stir at room temperature overnight. After 20 h, the white suspension was transferred to a 250-mL Erlenmeyer flask and stirred with saturated aqueous sodium carbonate (30 mL), water (20 mL) and dichloromethane (30 mL) for 30 min. The layers were separated and the aqueous layer was extracted twice with dichloromethane (30 mL). The organic layers were washed with saturated aqueous sodium bicarbonate (30 mL), combined, dried over sodium sulfate, and concentrated. The resulting yellow oil was chromatographed on a 24-g silica column with a gradient (100% dichloromethane to 90% dichloromethane/10% methanol containing 2 M ammonia) to provide 4-(3-fluoro-4-((hexahydropyrrolo[3,4-c]pyrrol-2(1H)-yl)methyl)phenyl)morpholine as a yellow oil (620 mg, 91%). $^1$H NMR (400 MHz, Chloroform-d) δ 7.21 (t, J=8.6 Hz, 1H), 6.65 (dd, J=8.5, 2.4 Hz, 1H), 6.56 (dd, J=13.0, 2.4 Hz, 1H), 3.86 (t, J=4.8 Hz, 4H), 3.52 (s, 2H), 3.15 (t, J=4.8 Hz, 4H), 2.85 (dd, J=11.5, 5.5 Hz, 2H), 2.75 (d, J=10.7 Hz, 2H), 2.72-2.62 (m, 4H), 2.29 (d, J=5.7 Hz, 2H), 1.97 (br s, 1H).

Step 3: Preparation of 1,1,1,3,3,3-hexafluoropropan-2-yl 5-(2-fluoro-4-morpholinobenzyl)hexahydropyrrolo[3,4-c]pyrrole-2(1H)-carboxylate

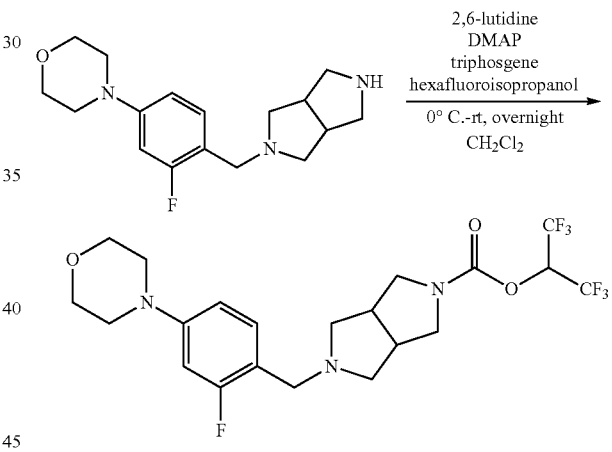

A 10-mL screw cap vial equipped with a magnetic stir bar was charged with triphosgene (16 mg, 0.055 mmol, 0.35 equiv) and dichloromethane (1 mL) under nitrogen and cooled to 0° C. 1,1,1,3,3,3-Hexafluoroisopropanol (21 µL, 0.17 mmol) was added via syringe over 1 min followed by addition of 2,6-lutidine, (38 µL, 2.1 equiv) over 1 min. The latter addition is exothermic, and the internal temperature was maintained below 5° C. during the addition. N,N-dimethylaminopyridine (2 mg, 0.1 equiv) was then added to the reaction mixture. The solution remained colorless and the ice bath was removed. The resulting clear solution was allowed to stir at room temperature for 1 h. A separate 10-mL vial, equipped with a magnetic stir bar, was charged with 4-(3-fluoro-4-((hexahydropyrrolo[3,4-c]pyrrol-2(1H)-yl)methyl)phenyl)morpholine (47.7 mg, 0.156 mmol) and dichloromethane (1 mL). The chloroformate solution was re-cooled to 0° C., and the amine solution was added to the chloroformate solution over 1 min via syringe. The amine-containing flask was rinsed with dichloromethane (0.25 mL), and the rinsing solution was added to the reaction flask. The ice bath was removed, and the clear, colorless reaction mixture was stirred at room temperature overnight. Saturated aqueous sodium bicarbonate (1 mL) was added, and the layers were separated. The aqueous layer was washed with dichloromethane (1 mL). The organic layers were combined, concentrated, and applied to a 12-g silica gel column to afford 1,1,1,3,3,3-hexafluoropropan-2-yl 5-(2-fluoro-4-morpholinobenzyl)hexahydropyrrolo[3,4-c]pyrrole-2(1H)-carboxylate, 37 mg (47%), as the second peak to elute. The first peak to elute was 2,6-lutidine. $^1$H NMR (400 MHz, Chloroform-d) δ 7.12 (t, J=8.5 Hz, 1H), 6.57 (dd, J=8.5, 2.4 Hz, 1H), 6.48 (dd, J=13.0, 2.4 Hz, 1H), 5.66 (hep, J=6.3 Hz, 1H), 3.80-3.77 (m, 4H), 3.62 (dd, J=11.4, 8.3 Hz, 2H), 3.51 (s, 2H), 3.30 (ddd, J=11.6, 7.8, 4.2 Hz, 2H), 3.10-3.05 (m, 4H), 2.85-2.75 (m, 2H), 2.59-2.52 (m, 2H), 2.40 (td, J=10.2, 3.2 Hz, 2H). LCMS (ESI, m/z): 194.1 (4-morpholino-2-fluorobenzyl cation).

Example 2

1,1,1,3,3,3-Hexafluoropropan-2-yl 5-(2-chloro-4-morpholinobenzyl)hexahydropyrrolo[3,4-c]pyrrole-2(1H)-carboxylate

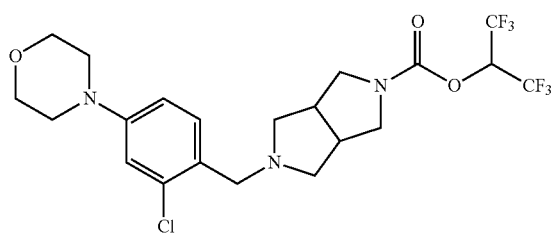 [SMILES: O=C(OC(C(F)(F)F)C(F)(F)F)N1CC2CN(Cc3ccc(N4CCOCC4)cc3Cl)CC2C1]

The title compound was synthesized directly from commercially available 2-chloro-4-morpholinobenzaldehyde and tert-butyl hexahydropyrrolo[3,4-c]pyrrole-2(1H)-carboxylate according to the representative procedures of Example 1 Steps (1-3) to provide 1,1,1,3,3,3-hexafluoropropan-2-yl 5-(2-chloro-4-morpholinobenzyl)hexahydropyrrolo[3,4-c]pyrrole-2(1H)-carboxylate as a white solid: $^1$H NMR (400 MHz, Chloroform-d) δ 7.28 (d, J=8.4 Hz, 2H), 6.87 (d, J=2.5 Hz, 1H), 6.78 (dd, J=8.5, 2.5 Hz, 1H), 5.74 (hept, J=6.3 Hz, 1H), 3.92-3.80 (m, 4H), 3.72 (dd, J=11.3, 8.3 Hz, 2H), 3.65 (s, 2H), 3.38 (m, 2H), 3.23-3.08 (m, 4H), 2.94-2.81 (m 2H), 2.67-2.48 (m, 4H). LCMS (ESI, m/z): 210.0 $[C_{11}H_{13}ClNO]^+$ (4-morpholino-2-chlorobenzyl cation).

Example 3

1,1,1,3,3,3-Hexafluoropropan-2-yl 5-(2-(8-oxa-3-azabicyclo[3.2.1]octan-3-yl)-4-chlorobenzyl)hexahydropyrrolo[3,4-c]pyrrole-2(1H)-carboxylate

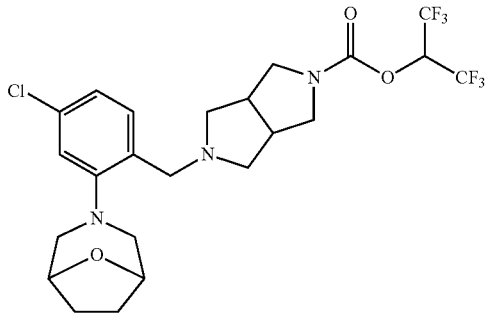 [SMILES: O=C(OC(C(F)(F)F)C(F)(F)F)N1CC2CN(Cc3ccc(Cl)cc3N3CC4CCC(C3)O4)CC2C1]

Step 1: Preparation of 2-(8-oxa-3-azabicyclo[3.2.1]octan-3-yl)-4-chlorobenzaldehyde

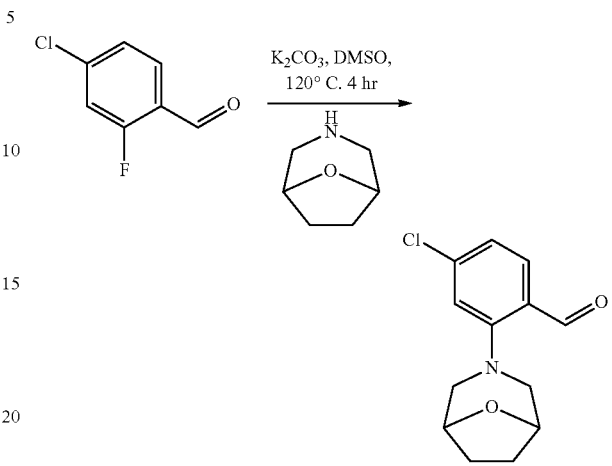

A round bottom flask was charged with 8-oxa-3-azabicyclo[3.2.1]octane (495 mg, 3.32 mmol), $K_2CO_3$ (436 mg, 3.16 mmol) and 4-chloro-2-fluorobenzaldehyde (500 mg, 3.15 mmol), and the contents were dissolved in DMSO (10 mL) and heated to 120° C. After 4 h, the reaction mixture was diluted in DCM (200 mL) and washed 3× with brine. The organics were dried over anhydrous $Na_2SO_4$ and concentrated. The resulting orange oil was chromatographed on a silica column with a gradient (100% hexanes to 80% Hexanes/20% EtOAc) to provide 2-(8-oxa-3-azabicyclo[3.2.1]octan-3-yl)-4-chlorobenzaldehyde as a yellow solid (336 mg, 43%). $^1$H NMR (400 MHz, Chloroform-d) δ 10.32 (s, 1H), 7.72 (s, 1H), 7.46 (ddd, J=8.7, 3.3, 1.7 Hz, 1H), 7.08 (dd, J=8.7, 1.3 Hz, 1H), 4.47-4.41 (m, 2H), 3.21 (d, J=11.5 Hz, 2H), 2.91 (d, J=11.7 Hz, 2H), 2.19-2.06 (m, 2H), 2.06-1.96 (m, 2H). LCMS (ESI, m/z): 252.1 [M+H]$^+$.

Steps 2-4: Preparation of 1,1,1,3,3,3-hexafluoropropan-2-yl 5-(2-(8-oxa-3-azabicyclo[3.2.1]octan-3-yl)-4-chlorobenzyl)hexahydropyrrolo[3,4-c]pyrrole-2(1H)-carboxylate

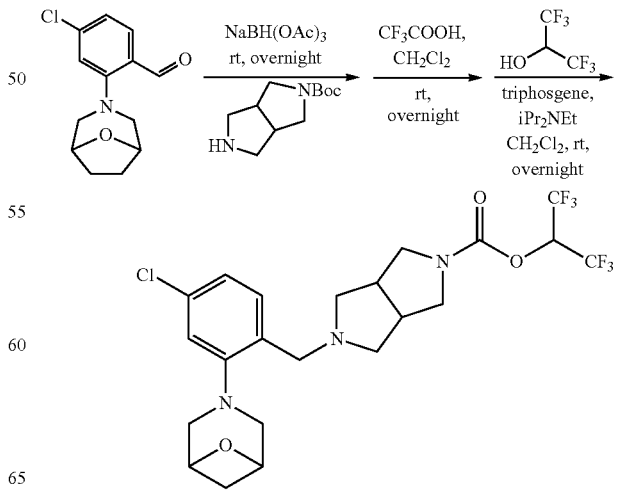

The title compound was synthesized from 2-(8-oxa-3-azabicyclo[3.2.1]octan-3-yl)-4-chlorobenzaldehyde according to the representative procedures of Example 1, Steps 1-3 to provide 1,1,1,3,3,3-hexafluoropropan-2-yl 5-(2-(8-oxa-3-azabicyclo[3.2.1]octan-3-yl)-4-chlorobenzyl)hexahydropyrrolo[3,4-c]pyrrole-2(1H)-carboxylate as an oil: $^1$H NMR (400 MHz, Chloroform-d) δ 7.32 (d, J=8.0 Hz, 1H), 7.10-7.02 (m, 2H), 5.81-5.69 (m, 1H), 4.42-4.37 (m, 2H), 3.78-3.57 (m, 4H), 3.42-3.30 (m, 2H), 3.08-2.98 (m, 2H), 2.93-2.83 (m, 4H), 2.64-2.54 (m, 4H), 2.15-2.03 (m, 2H), 2.03-1.96 (m, 2H). LCMS (ESI, m/z): 542.2 [M+H]$^+$.

Example 4

1,1,1,3,3,3-Hexafluoropropan-2-yl 5-(4-chloro-2-(hexahydrocyclopenta[b][1,4]oxazin-4(4aH)-yl)benzyl)hexahydropyrrolo[3,4-c]pyrrole-2(1H)-carboxylate

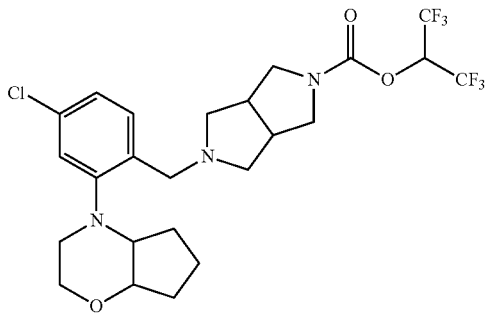 [SMILES: O=C(OC(C(F)(F)F)C(F)(F)F)N1CC2CN(Cc3ccc(Cl)cc3N3CCOC4CCCC43)CC2C1]

The title compound was synthesized directly from commercially available octahydro cyclopenta[b][1,4]oxazine and tert-butyl hexahydropyrrolo[3,4-c]pyrrole-2(1H)-carboxylate according to the representative procedures of Example 3 (Step 1) and Example 1 Steps (1-3) to provide 1,1,1,3,3,3-hexafluoropropan-2-yl 5-(4-chloro-2-(hexahydrocyclopenta[b][1,4]oxazin-4(4aH)-yl)benzyl)hexahydropyrrolo[3,4-c]pyrrole-2(1H)-carboxylate as an oil. $^1$H NMR (400 MHz, Chloroform-d) δ 7.25 (d, J=8.2 Hz, 1H), 7.03-6.97 (m, 2H), 5.66 (ddt, J=10.1, 6.2, 3.8 Hz, 1H), 3.97-3.72 (m, 3H), 3.73-3.56 (m, 2H), 3.47-3.15 (m, 4H), 3.00 (s, 1H), 2.88-2.66 (m, 3H), 2.64-2.32 (m, 5H), 2.01-1.83 (m, 1H), 1.78-1.46 (m, 5H). LCMS (ESI, m/z): 556.2 [M+H]$^+$.

Example 5

1,1,1,3,3,3-Hexafluoropropan-2-yl 5-(2-(4-acetamidopiperidin-1-yl)-5-chlorobenzyl)hexahydropyrrolo[3,4-c]pyrrole-2(1H)-carboxylate

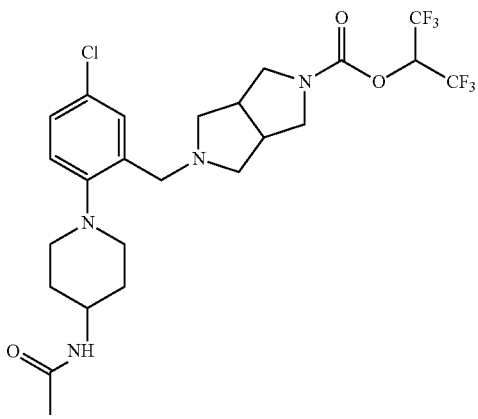 [SMILES: CC(=O)NC1CCN(c2ccc(Cl)cc2CN2CC3CN(C(=O)OC(C(F)(F)F)C(F)(F)F)CC3C2)CC1]

Step 1: Preparation of tert-butyl(1-(4-chloro-2-formylphenyl)piperidin-4-yl)carbamate

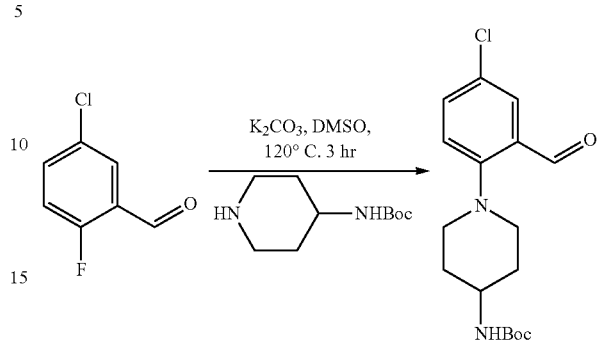

The title compound was synthesized from 5-chloro-2-fluorobenzaldehyde in a similar manner as described in Example 3 (Step 1) to provide tert-butyl(1-(4-chloro-2-formylphenyl)piperidin-4-yl)carbamate as a yellow solid (2.14 g, 70%). $^1$H NMR (400 MHz, Chloroform-d) δ 10.17 (s, 1H), 7.68 (d, J=2.6 Hz, 1H), 7.40 (dd, J=8.7, 2.7 Hz, 1H), 7.02 (d, J=8.7 Hz, 1H), 4.72 (d, J=7.8 Hz, 1H), 3.59 (br s, 1H), 3.23-3.14 (m, 2H), 2.97-2.86 (m, 2H), 2.11-1.98 (m, 2H), 1.70-1.55 (m, 2H), 1.42 (s, 9H). LCMS (ESI, m/z): 339.1 [M+H]$^+$.

Step 2: Preparation of 2-tert-butyl 5-(1,1,1,3,3,3-hexafluoropropan-2-yl)tetrahydropyrrolo[3,4-c]pyrrole-2,5(1H,3H)-dicarboxylate

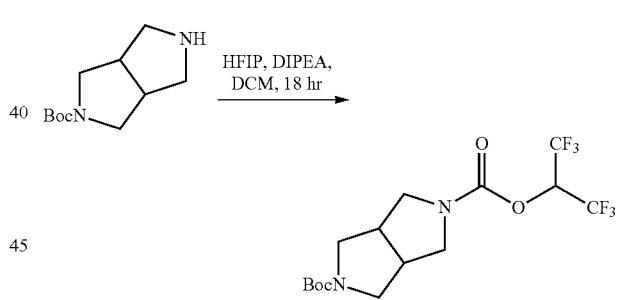

A round-bottom flask was charged with triphosgene (1.68 g, 5.66 mmol) and DCM (200 mL). Hexafluoroisopropanol (1.93 mL, 18.4 mmol) was added dropwise over 1 min DIPEA (4.9 mL, 28.0 mmol) was added dropwise over 3 min. The flask contents were stirred at rt for 2 h. tert-Butyl hexahydropyrrolo[3,4-c]pyrrole-2(1H)-carboxylate (3.00 g, 14.2 mmol) was added in one portion, and the reaction mixture was allowed to stir for 18 h at rt. The reaction mixture was then washed with 1 N HCl and brine. The organics were dried over anhydrous Na$_2$SO$_4$ and concentrated. The resulting oil was chromatographed on a silica column with a gradient (100% hexanes to 80% hexanes/20% acetone) to provide 2-tert-butyl 5-(1,1,1,3,3,3-hexafluoropropan-2-yl)tetrahydropyrrolo[3,4-c]pyrrole-2,5(1H,3H)-dicarboxylate (5.74 g, 82%). $^1$H NMR (400 MHz, Chloroform-d) δ 5.87-5.66 (m, 1H), 3.85-3.70 (m, 2H), 3.70-3.55 (m, 2H), 3.46-3.37 (m, 2H), 3.37-3.17 (m, 2H), 2.96 (br s, 2H), 1.52 (s, 9H).). LCMS (ESI, m/z): 429.0 [M+H]$^+$.

Step 3: Preparation of 1,1,1,3,3,3-hexafluoropropan-2-yl hexahydropyrrolo[3,4-c]pyrrole-2(1H)-carboxylate

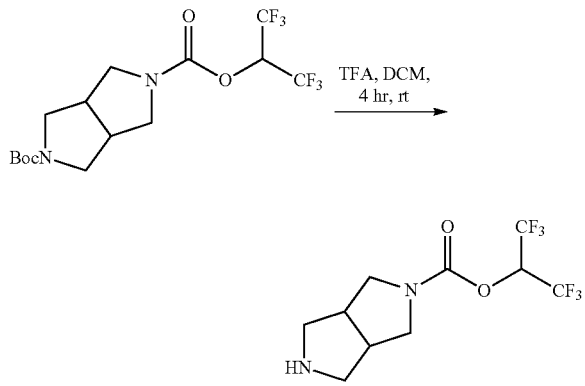

A round-bottom flask was charged with 2-tert-butyl 5-(1,1,1,3,3,3-hexafluoropropan-2-yl)tetrahydropyrrolo[3,4-c]pyrrole-2,5(1H,3H)-dicarboxylate (4.7 g, 11.6 mmol) and DCM (30 mL). TFA (15 mL) was then added, and the reaction mixture was stirred at rt for 4 h. The reaction mixture was concentrated, diluted in DCM (200 mL), and washed with 1 N NaOH (3×). The organics were dried over anhydrous $Na_2SO_4$ and concentrated, yielding crude 1,1,1,3,3,3-hexafluoropropan-2-yl hexahydropyrrolo[3,4-c]pyrrole-2(1H)-carboxylate, which was used without further purification. LCMS (ESI, m/z): 307.0 $[M+H]^+$.

Step 4: Preparation of 1,1,1,3,3,3-hexafluoropropan-2-yl 5-(2-(4-((tert-butoxy carbonyl)amino)piperidin-1-yl)-5-chlorobenzyl)hexahydropyrrolo[3,4-c]pyrrole-2(1H)-carboxylate

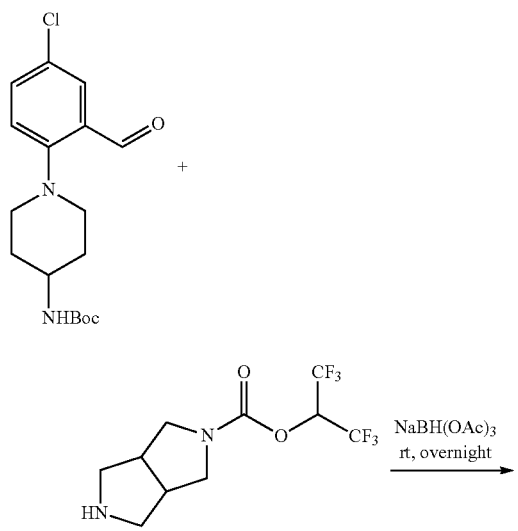

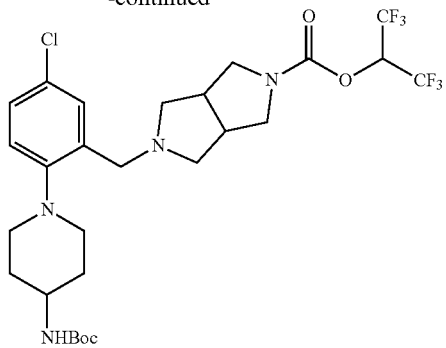

The title compound was synthesized from tert-butyl(1-(4-chloro-2-formylphenyl)piperidin-4-yl)carbamate as described for Example 1 (Step 1) to provide 1,1,1,3,3,3-hexafluoropropan-2-yl 5-(2-(4-((tert-butoxycarbonyl)amino)piperidin-1-yl)-5-chlorobenzyl)hexahydropyrrolo[3,4-c]pyrrole-2(1H)-carboxylate (1.00 g, 71%).

Step 5: Preparation of 1,1,1,3,3,3-hexafluoropropan-2-yl 5-(2-(4-acetamidopiperidin-1-yl)-5-chlorobenzyl)hexahydropyrrolo[3,4-c]pyrrole-2(1H)-carboxylate

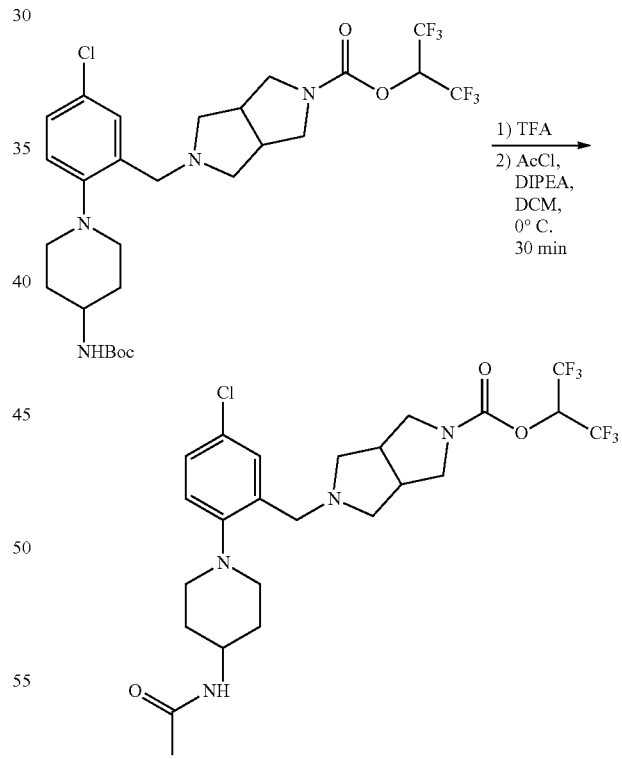

A round-bottom flask was charged with 1,1,1,3,3,3-hexafluoropropan-2-yl 5-(2-(4-((tert-butoxycarbonyl)amino)piperidin-1-yl)-5-chlorobenzyl)hexahydropyrrolo[3,4-c]pyrrole-2(1H)-carboxylate (230 mg, 0.311 mmol) and DCM (10 mL). TFA (5 mL) was added, and the reaction was stirred at rt for 2 h. The reaction mixture was concentrated; toluene was added and the solution was concentrated again, yielding crude amine. To the crude product, DCM (2 mL)

and DIPEA (213 µL) were added, and the reaction mixture was cooled to 0° C. Acetyl chloride (36 µL, 0.342 mmol) was added dropwise, and the reaction mixture was stirred at 0° C. for 30 min. The reaction was quenched by the addition of 100 µL of MeOH, and the solution was subsequently concentrated. The resulting oil was chromatographed on a silica column with a gradient (100% DCM to 95% DCM/5% MeOH) to provide 1,1,1,3,3,3-hexafluoropropan-2-yl 5-(2-(4-acetamidopiperidin-1-yl)-5-chlorobenzyl)hexahydropyrrolo[3,4-c]pyrrole-2(1H)-carboxylate as an orange solid (73 mg, 41%). $^1$H NMR (400 MHz, Chloroform-d) δ 7.35 (d, J=2.5 Hz, 1H), 7.18 (dd, J=8.5, 2.6 Hz, 1H), 6.98 (d, J=8.6 Hz, 1H), 5.74 (hept, J=6.3 Hz, 1H), 5.61 (d, J=7.9 Hz, 1H), 3.99-3.84 (m, 1H), 3.71 (dd, J=11.6, 8.1 Hz, 2H), 3.66-3.55 (m, 2H), 3.36 (td, J=11.5, 4.0 Hz, 2H), 3.09 (t, J=10.9 Hz, 2H), 2.97-2.81 (m, 2H), 2.81-2.71 (m, 3H), 2.71-2.61 (m, 3H), 2.59-2.46 (m, 2H), 2.07-1.98 (m, 5H). LCMS (ESI, m/z): 571.2 [M+H]$^+$.

Example 6

1,1,1,3,3,3-Hexafluoropropan-2-yl 5-(5-chloro-2-(4-(methylsulfonamido)piperidin-1-yl)benzyl)hexahydropyrrolo[3,4-c]pyrrole-2(1H)-carboxylate

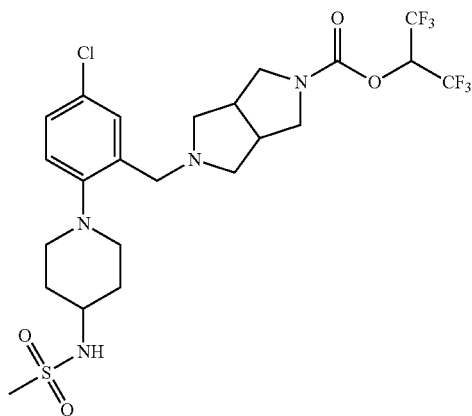 [SMILES: CS(=O)(=O)NC1CCN(c2ccc(Cl)cc2CN2CC3CN(C(=O)OC(C(F)(F)F)C(F)(F)F)CC3C2)CC1]

The title compound was prepared from 1,1,1,3,3,3-hexafluoropropan-2-yl 5-(2-(4-((tert-butoxycarbonyl)amino)piperidin-1-yl)-5-chlorobenzyl)hexahydropyrrolo[3,4-c]pyrrole-2(1H)-carboxylate and mesyl chloride according to the representative procedure of Example 5 (Step 5) to provide 1,1,1,3,3,3-hexafluoropropan-2-yl 5-(5-chloro-2-(4-(methylsulfonamido)piperidin-1-yl)benzyl)hexahydropyrrolo[3,4-c]pyrrole-2(1H)-carboxylate as a white solid. $^1$H NMR (400 MHz, Chloroform-d) δ 7.32 (d, J=2.5 Hz, 1H), 7.16 (dd, J=8.5, 2.6 Hz, 1H), 6.97 (d, J=8.6 Hz, 1H), 5.73 (hept, J=6.2 Hz, 1H), 5.19 (d, J=7.5 Hz, 1H), 3.70 (dd, J=11.0, 8.2 Hz, 2H), 3.58 (q, J=13.0 Hz, 2H), 3.47-3.28 (m, 3H), 3.14 (t, J=11.0 Hz, 2H), 2.99 (s, 3H), 2.86 (d, J=13.9 Hz, 2H), 2.71 (q, J=11.4, 10.9 Hz, 2H), 2.64-2.49 (m, 4H), 2.05 (d, J=12.4 Hz, 2H), 1.76-1.63 (m, 2H). LCMS (ESI, m/z): 607.1 [M+H]$^+$.

Example 7

1,1,1,3,3,3-Hexafluoropropan-2-yl 5-(2-(3-acetamidoazetidin-1-yl)-5-chlorobenzyl)hexahydropyrrolo[3,4-c]pyrrole-2(1H)-carboxylate

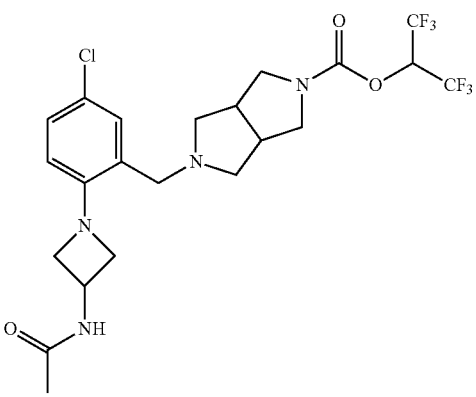 [SMILES: CC(=O)NC1CN(c2ccc(Cl)cc2CN2CC3CN(C(=O)OC(C(F)(F)F)C(F)(F)F)CC3C2)C1]

The title compound was prepared from N-(azetidin-3-yl)acetamide and 1,1,1,3,3,3-hexafluoropropan-2-yl hexahydropyrrolo[3,4-c]pyrrole-2(1H)-carboxylate according to the representative procedures of Example 5 (Steps 1-5) to provide 1,1,1,3,3,3-hexafluoropropan-2-yl 5-(2-(3-acetamidoazetidin-1-yl)-5-chlorobenzyl)hexahydropyrrolo[3,4-c]pyrrole-2(1H)-carboxylate as a clear oil. $^1$H NMR (400 MHz, Chloroform-d) δ 7.11 (d, J=7.9 Hz, 2H), 6.44 (d, J=6.9 Hz, 1H), 6.34 (d, J=8.2 Hz, 1H), 5.69 (hept, J=6.3 Hz, 1H), 4.70 (h, J=7.1 Hz, 1H), 4.23 (q, J=7.5 Hz, 2H), 3.81-3.73 (m, 1H), 3.72-3.58 (m, 3H), 3.54-3.37 (m, 3H), 3.32 (d, J=13.1 Hz, 1H), 2.87 (s, 2H), 2.63 (d, J=9.1 Hz, 1H), 2.56-2.44 (m, 3H), 2.03 (s, 3H). LCMS (ESI, m/z): 543.1 [M+H]$^+$.

Example 8

1,1,1,3,3,3-Hexafluoropropan-2-yl 5-[bis(4-chlorophenyl)methyl]-octahydropyrrolo[3,4-c]pyrrole-2-carboxylate

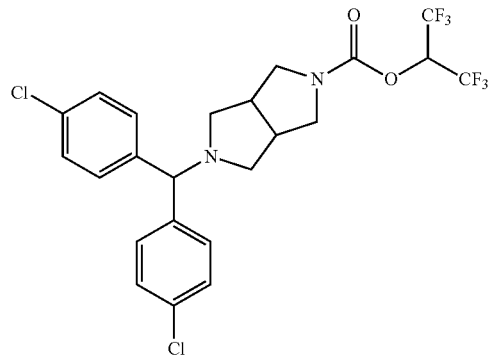 [SMILES: O=C(OC(C(F)(F)F)C(F)(F)F)N1CC2CN(C(c3ccc(Cl)cc3)c3ccc(Cl)cc3)CC2C1]

Step 1: Preparation of 1-chloro-4-[chloro(4-chlorophenyl)methyl]benzene

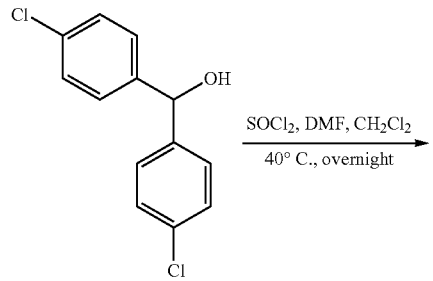

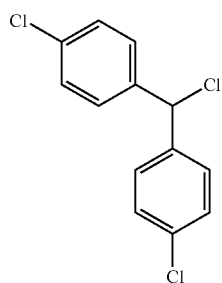

A 1000-mL 3-necked round-bottom flask was charged with bis(4-chlorophenyl)methanol (49.6 g, 196 mmol, 1.00 equiv), N,N-dimethylformamide (5 mL), and dichloromethane (100 mL). Thionyl chloride (93.3 g, 784 mmol, 4.00 equiv) was added dropwise. The resulting solution was stirred overnight at 40° C. The resulting mixture was concentrated under reduced pressure. The residue was chromatographed on a silica gel column with ethyl acetate/petroleum ether (1/5) to provide 47.8 g (90% yield) of 1-chloro-4-[chloro(4-chlorophenyl)methyl]benzene as a gray solid. $^1$H NMR (300 MHz, Chloroform-d): δ 7.30-7.39 (m, 8H), 6.07 (s, 1H). GCMS (EI, m/z): 270 M$^+$.

Step 2: Preparation of tert-butyl 5-[bis(4-chlorophenyl)methyl]-octahydropyrrolo[3,4-c]pyrrole-2-carboxylate

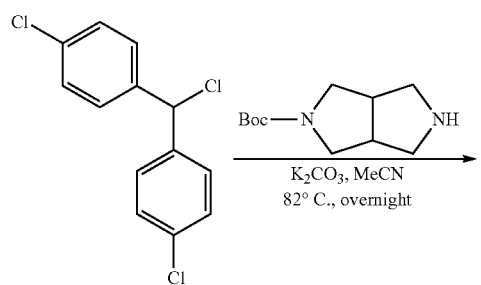

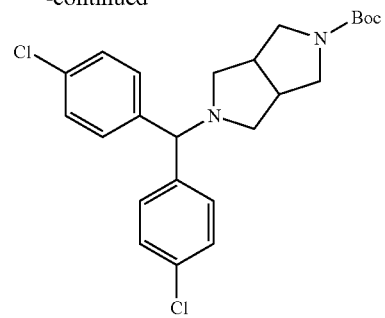

A 100-mL round-bottom flask was charged with tert-butyl octahydropyrrolo[3,4-c]pyrrole-2-carboxylate (2.00 g, 9.42 mmol, 1.00 equiv), 1-chloro-4-[chloro(4-chlorophenyl)methyl]benzene (5.46 g, 20.1 mmol, 2.13 equiv), potassium carbonate (6.90 g, 49.9 mmol, 5.30 equiv), and acetonitrile (30 mL). The resulting solution was stirred overnight at 82° C. and diluted with H$_2$O (50 mL). The resulting solution was extracted with dichloromethane (3×20 mL), and the organic layers were combined, washed with H$_2$O (3×10 mL), dried over anhydrous sodium sulfate, filtered, and concentrated under reduced pressure. The residue was chromatographed on a silica gel column with ethyl acetate/petroleum ether (1/3) to yield 1.80 g (43% yield) of tert-butyl 5-[bis(4-chlorophenyl)methyl]-octahydropyrrolo[3,4-c]pyrrole-2-carboxylate as a yellow solid. LCMS (ESI, m/z): 447 [M+H]$^+$.

Step 3: Preparation of 2-[bis(4-chlorophenyl)methyl]-octahydropyrrolo[3,4-c]pyrrole

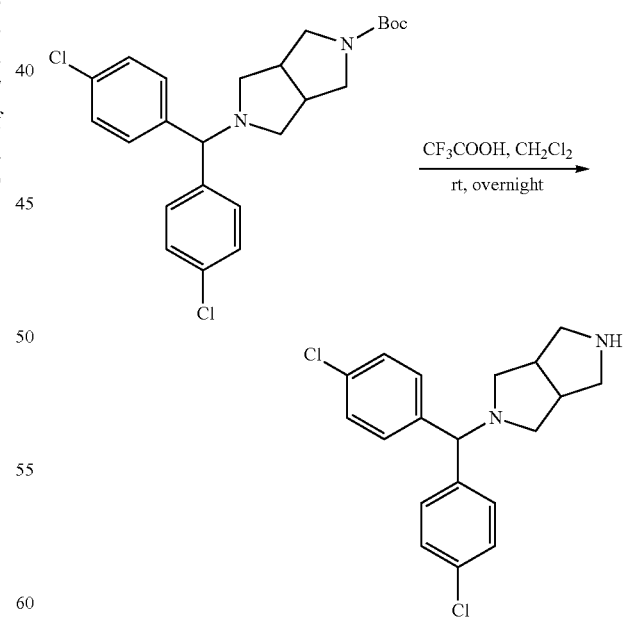

The title compound was synthesized from tert-butyl 5-[bis(4-chlorophenyl)methyl]-octahydropyrrolo[3,4-c]pyrrole-2-carboxylate as described in Example 5 (Step 3) to provide crude of 2-[bis(4-chlorophenyl)methyl]-octahydropyrrolo[3,4-c]pyrrole as brown oil. LCMS (ESI, m/z): 347 [M+H]$^+$.

Step 4: Preparation of 1,1,1,3,3,3-hexafluoropropan-2-yl 5-[bis(4-chlorophenyl)methyl]-octahydropyrrolo[3,4-c]pyrrole-2-carboxylate

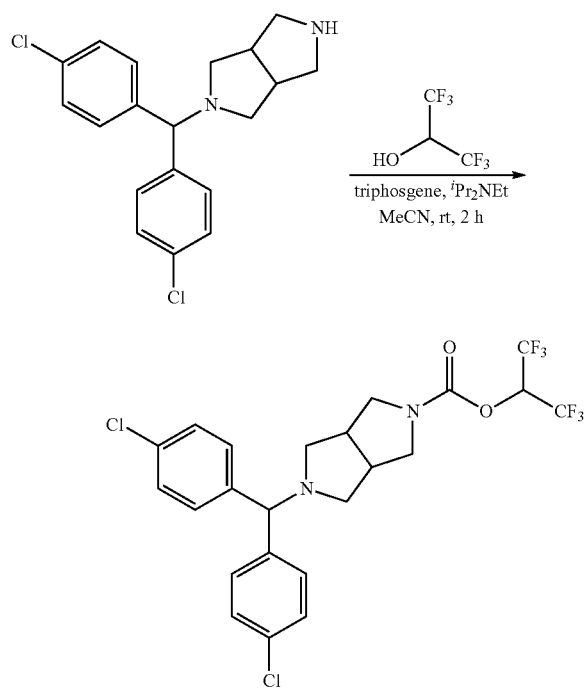 [SMILES: Clc1ccc(C(c2ccc(Cl)cc2)N2CC3CNCC3C2)cc1 ; OC(C(F)(F)F)C(F)(F)F ; O=C(OC(C(F)(F)F)C(F)(F)F)N1CC2CN(C(c3ccc(Cl)cc3)c3ccc(Cl)cc3)CC2C1]

A 50-mL round-bottom flask was charged with 1,1,1,3,3,3-hexafluoropropan-2-ol (336 mg, 2.00 mmol, 1.00 equiv), acetonitrile (20 mL), and triphosgene (198 mg, 0.667 mmol, 0.33 equiv). N,N-Diisopropylethylamine (942 mg, 7.29 mmol, 3.65 equiv) was added dropwise. The mixture was stirred at room temperature for 2 h. 2-[Bis(4-chlorophenyl)methyl]-octahydropyrrolo[3,4-c]pyrrole (694 mg, 2.00 mmol, 1.00 equiv) was added. The resulting solution was stirred for 2 h at room temperature and diluted with $H_2O$ (20 mL). The mixture was extracted with dichloromethane (3×50 mL), and the organic layers were combined, washed with water (3×10 mL), dried over anhydrous sodium sulfate, filtered, and concentrated under reduced pressure. The residue was chromatographed on a silica gel column with ethyl acetate/petroleum ether (1/5). The crude product (198 mg) was purified by preparative HPLC using the following gradient conditions: 20% $CH_3CN$/80% Phase A increasing to 80% $CH_3CN$ over 10 min, then to 100% $CH_3CN$ over 0.1 min, holding at 100% $CH_3CN$ for 1.9 min, then reducing to 20% $CH_3CN$ over 0.1 min, and holding at 20% for 1.9 min, on a Waters 2767-5 Chromatograph. Column: Xbridge Prep C18, 19*150 mm, 5 um. Mobile phase: Phase A: aqueous $NH_4HCO_3$ (0.05%); Phase B: $CH_3CN$. Detector: UV 220 & 254 nm. Purification resulted in 69.6 mg (6% yield) of 1,1,1,3,3,3-hexafluoropropan-2-yl 5-[bis(4-chlorophenyl)methyl]-octahydropyrrolo[3,4-c]pyrrole-2-carboxylate as a colorless oil. $^1$H NMR (300 MHz, Chloroform-d): δ 7.23-7.33 (m, 8H), 5.72-5.85 (m, 1H), 4.11 (s, 1H), 3.65-3.74 (m, 2H), 3.37-3.46 (m, 2H), 2.85 (br, 2H), 2.37-2.52 (m, 4H). LCMS (ESI, m/z): 541 [M+H]$^+$.

Example 9

1,1,1,3,3,3-Hexafluoropropan-2-yl 5-[(4-phenylphenyl)methyl]-octahydropyrrolo[3,4-c]pyrrole-2-carboxylate

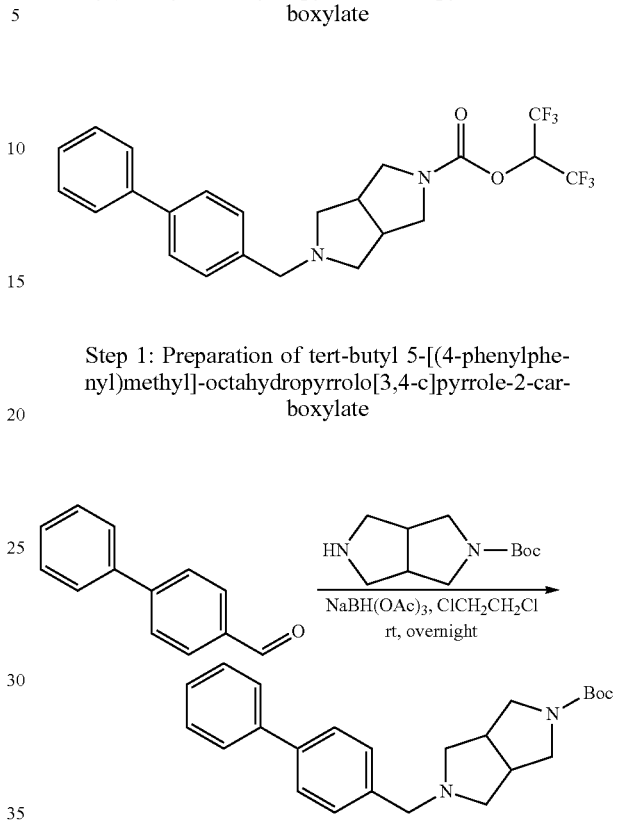

Step 1: Preparation of tert-butyl 5-[(4-phenylphenyl)methyl]-octahydropyrrolo[3,4-c]pyrrole-2-carboxylate A 100-mL round-bottom flask was charged with tert-butyl octahydropyrrolo[3,4-c]pyrrole-2-carboxylate (1.00 g, 4.71 mmol, 1.00 equiv), 4-phenylbenzaldehyde (1.00 g, 5.49 mmol, 1.17 equiv), sodium triacetoxyborohydride (3.18 g, 15.0 mmol, 3.19 equiv), and 1,2-dichloroethane (30 mL). The resulting solution was stirred overnight at room temperature and then diluted with $H_2O$ (30 mL). The resulting solution was extracted with dichloromethane (3×20 mL), and the organic layers were combined, washed with $H_2O$ (3×10 mL), dried over anhydrous sodium sulfate, filtered, and concentrated under reduced pressure. The residue was chromatographed on a silica gel column with ethyl acetate/petroleum ether (1/4) to yield 0.600 g (34% yield) of tert-butyl 5-[(4-phenylphenyl)methyl]-octahydropyrrolo[3,4-c]pyrrole-2-carboxylate as a colorless solid. LCMS (ESI, m/z): 379 [M+H]$^+$.

Step 2-3: Preparation of 1,1,1,3,3,3-hexafluoropropan-2-yl 5-[(4-phenylphenyl)methyl]-octahydropyrrolo[3,4-c]pyrrole-2-carboxylate The title compound was synthesized from tert-butyl 5-[(4-phenylphenyl)methyl]-octahydropyrrolo[3,4-c]pyrrole-2-carboxylate as described in Example 5 (Step 3) followed by Example 8 (Step 4) to afford 1,1,1,3,3,3-hexafluoropropan-2-yl 5-[(4-phenylphenyl)methyl]-octahydropyrrolo[3,4-c]pyrrole-2-carboxylate as a colorless oil. $^1$H NMR (300 MHz, Chloroform-d): δ 7.54-7.68 (m, 4H), 7.35-7.48 (m, 5H), 5.72-5.82 (m, 1H), 3.71-3.76 (m, 4H), 3.44-3.48 (m, 2H), 2.96 (s, 2H), 2.58-2.79 (m, 4H). LCMS (ESI, m/z): 473 [M+H]$^+$.

Example 10

1,1,1,3,3,3-Hexafluoropropan-2-yl 5-[[4-(morpholin-4-yl)-2-(trifluoromethyl)phenyl]methyl]-octahydropyrrolo[3,4-c]pyrrole-2-carboxylate

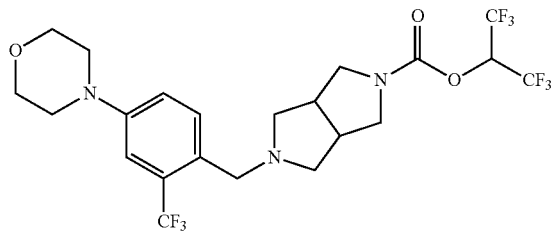 [SMILES: O=C(OC(C(F)(F)F)C(F)(F)F)N1CC2CN(Cc3ccc(N4CCOCC4)cc3C(F)(F)F)CC2C1]

The title compound was synthesized from 4-fluoro-2-(trifluoromethyl)benzaldehyde and morpholine according to the representative procedures of Example 3 (Step 1) followed by Example 9 (Step 1-3) to provide 1,1,1,3,3,3-hexafluoropropan-2-yl 5-[[4-(morpholin-4-yl)-2-(trifluoromethyl)phenyl]methyl]-octahydropyrrolo[3,4-c]pyrrole-2-carboxylate as a yellow oil. $^1$H NMR (300 MHz, Chloroform-d) δ 7.55 (d, J=8.7 Hz, 1H), 7.12 (s, 1H), 7.00-7.03 (m, 1H), 5.70-5.83 (m, 1H), 3.87 (t, J=4.8 Hz, 4H), 3.62-3.77 (m, 4H), 3.35-3.42 (m, 2H), 3.18 (t, J=4.8 Hz, 4H), 2.87 (s, 2H), 2.48-2.63 (m, 4H). LCMS (ESI, m/z): 550 [M+H]$^+$.

Example 11

1,1,1,3,3,3-Hexafluoropropan-2-yl 5-[[4-(morpholin-4-yl)-2-(trifluoromethoxy)phenyl]methyl]-octahydropyrrolo[3,4-c]pyrrole-2-carboxylate

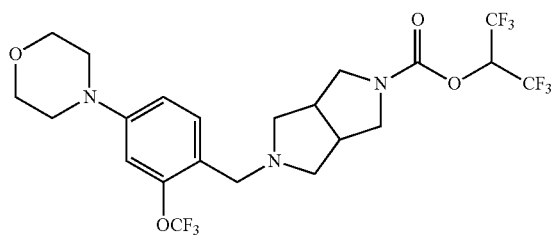 [SMILES: O=C(OC(C(F)(F)F)C(F)(F)F)N1CC2CN(Cc3ccc(N4CCOCC4)cc3OC(F)(F)F)CC2C1]

Step 1: Preparation of 4-(morpholin-4-yl)-2-(trifluoromethoxy)benzaldehyde

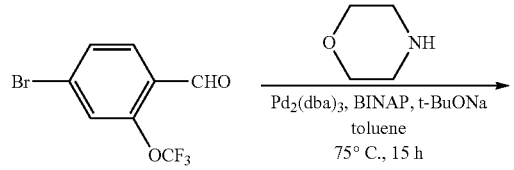

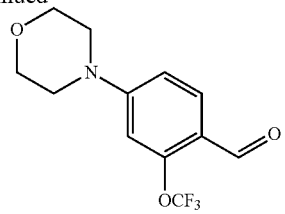

A 500-mL round-bottom flask was purged with and maintained under an inert atmosphere of nitrogen then charged with 4-bromo-2-(trifluoromethoxy)benzaldehyde (8.00 g, 29.7 mmol, 1.00 equiv), morpholine (2.59 g, 29.7 mmol, 1.00 equiv), tert-BuONa (4.28 g, 44.5 mmol, 1.50 equiv), Pd$_2$(dba)$_3$ (1.36 g, 1.49 mmol, 0.05 equiv), BINAP (1.85 g, 2.97 mmol, 0.10 equiv), and toluene (150 mL). The resulting solution was stirred for 15 h at 75° C. in an oil bath. The reaction progress was monitored by LCMS. The resulting solution was diluted with water (50 mL) and extracted with ethyl acetate (3×30 mL). The organic layers were combined, dried over anhydrous sodium sulfate, filtered, and concentrated under reduced pressure. The residue was chromatographed on a silica gel column with ethyl acetate/petroleum ether (¼) to provide 0.800 g (10% yield) of 4-(morpholin-4-yl)-2-(trifluoromethoxy)benzaldehyde as a yellow solid. LCMS (ESI, m/z): 276 [M+H]$^+$.

Steps 2-4: Preparation of 1,1,1,3,3,3-hexafluoropropan-2-yl 5-[[4-(morpholin-4-yl)-2-(trifluoromethoxy)phenyl]methyl]-octahydropyrrolo[3,4-c]pyrrole-2-carboxylate The title compound was synthesized from 4-(morpholin-4-yl)-2-(trifluoromethoxy)benzaldehyde according to the representative procedures of Example 9 (Step 1-3) to provide 1,1,1,3,3,3-hexafluoropropan-2-yl 5-[[4-(morpholin-4-yl)-2-(trifluoromethoxy)phenyl]methyl]-octahydropyrrolo[3,4-c]pyrrole-2-carboxylate as a light yellow oil. $^1$H NMR (300 MHz, Chloroform-d) δ 7.34 (d, J=8.7 Hz, 1H), 6.72-6.82 (m, 2H), 5.69-5.82 (m, 1H), 3.80-3.87 (m, 4H), 3.68-3.75 (m, 2H), 3.58 (s, 2H), 3.33-3.40 (m, 2H), 3.15 (t, J=4.8 Hz, 4H), 2.79-2.92 (m, 2H), 2.53-2.58 (m, 4H). LCMS (ESI, m/z): 566 [M+H]$^+$.

Example 12

1,1,1,3,3,3-Hexafluoropropan-2-yl 5-[(2-phenylphenyl)methyl]-octahydropyrrolo[3,4-c]pyrrole-2-carboxylate

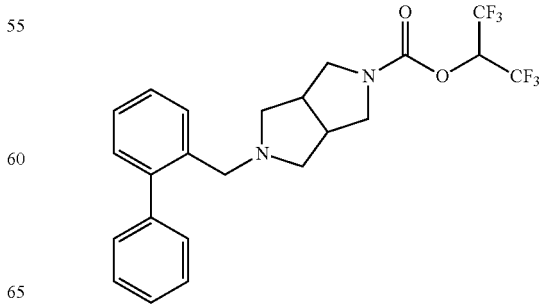

The title compound was synthesized directly from commercially available tert-butyl octahydropyrrolo[3,4-c]pyrrole-2-carboxylate and 2-phenylbenzaldehyde according to the representative procedures of Example 9 (Step 1-3) to provide 1,1,1,3,3,3-hexafluoropropan-2-yl 5-[(2-phenylphenyl)methyl]-octahydropyrrolo[3,4-c]pyrrole-2-carboxylate as a yellow oil. ¹H NMR (400 MHz, Chloroform-d) δ 7.41-7.40 (m, 1H), 7.28-7.39 (m, 8H), 5.76-5.84 (m, 1H), 3.75 (t, J=9.8 Hz, 2H), 3.54 (s, 2H), 3.20-3.27 (m, 2H), 2.82 (s, 2H), 2.52 (t, J=10.6 Hz, 2H), 2.41 (s, 2H). LCMS (ESI, m/z): 473 [M+H]⁺.

Example 13

1,1,1,3,3,3-Hexafluoropropan-2-yl 5-[(3-phenylphenyl)methyl]-octahydropyrrolo[3,4-c]pyrrole-2-carboxylate

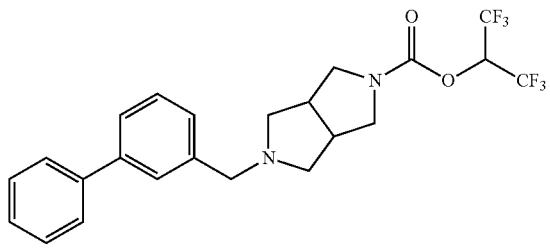 [SMILES: O=C(OC(C(F)(F)F)C(F)(F)F)N1CC2CN(Cc3cccc(-c4ccccc4)c3)CC2C1]

The title compound was synthesized directly from commercially available tert-butyl octahydropyrrolo[3,4-c]pyrrole-2-carboxylate and 3-phenylbenzaldehyde according to the representative procedures of Example 9 (Step 1-3) to provide 1,1,1,3,3,3-hexafluoropropan-2-yl 5-[(3-phenylphenyl)methyl]-octahydropyrrolo[3,4-c]pyrrole-2-carboxylate as a yellow oil. ¹H NMR (300 MHz, Chloroform-d) δ 7.57-7.60 (m, 2H), 7.27-7.52 (m, 7H), 5.72-5.82 (m, 1H), 3.63-3.72 (m, 4H), 3.34-3.42 (m, 2H), 2.84 (br, 2H), 2.47-2.62 (m, 4H). LCMS (ESI, m/z): 473 [M+H]⁺.

Example 14

1,1,1,3,3,3-Hexafluoropropan-2-yl 5-[[4-fluoro-2-(morpholin-4-yl)phenyl]methyl]-octahydropyrrolo[3,4-c]pyrrole-2-carboxylate

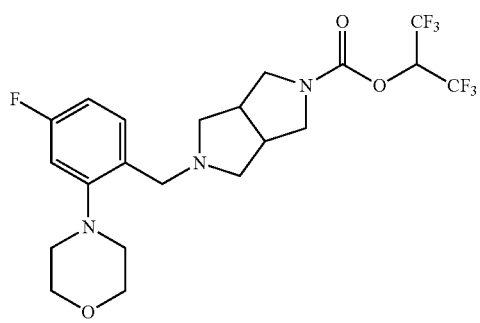 [SMILES: O=C(OC(C(F)(F)F)C(F)(F)F)N1CC2CN(Cc3ccc(F)cc3N3CCOCC3)CC2C1]

The title compound was synthesized directly from commercially available 2,4-difluorobenzaldehyde and morpholine according to the representative procedures of Example 3 (Step 1) followed by Example 9 (Step 1-3) to provide 1,1,1,3,3,3-hexafluoropropan-2-yl 5-[[4-fluoro-2-(morpholin-4-yl)phenyl]methyl]-octahydropyrrolo[3,4-c]pyrrole-2-carboxylate as a yellow oil. ¹H NMR (300 MHz, Chloroform-d) δ 7.26-7.34 (m, 1H), 6.72-6.78 (m, 2H), 5.70-5.78 (m, 1H), 3.82 (t, J=2.2 Hz, 4H), 3.70-3.74 (m, 2H), 3.60-3.67 (m, 2H), 3.28-3.36 (m, 2H), 2.86-2.98 (m, 6H), 2.56-2.61 (m, 4H). LCMS (ESI, m/z): 500 [M+H]⁺.

Example 15

1,1,1,3,3,3-Hexafluoropropan-2-yl 5-[[4-fluoro-2-(pyrrolidin-1-yl)phenyl]methyl]-octahydropyrrolo[3,4-c]pyrrole-2-carboxylate

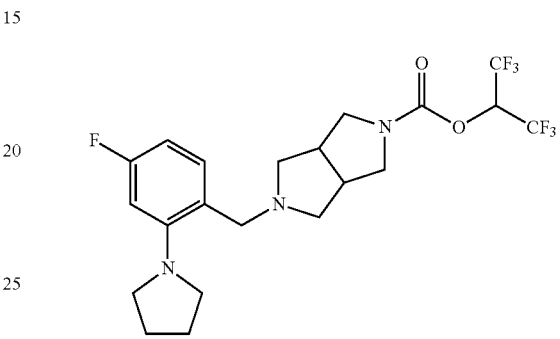

The title compound was synthesized directly from commercially available 2,4-difluorobenzaldehyde and pyrrolidine according to the representative procedures of Example 3 (Step 1) followed by Example 9 (Step 1-3) to provide 1,1,1,3,3,3-hexafluoropropan-2-yl 5-[[4-fluoro-2-(pyrrolidin-1-yl)phenyl]methyl]-octahydropyrrolo[3,4-c]pyrrole-2-carboxylate as a yellow oil. ¹H NMR (300 MHz, Chloroform-d) δ 7.21 (t, J=3.7 Hz, 1H), 6.50-6.56 (m, 2H), 5.67-5.79 (m, 1H), 3.69-3.76 (m, 2H), 3.56 (s, 2H), 3.30-3.37 (m, 2H), 3.24 (t, J=3.3 Hz, 4H), 2.86 (br, 2H), 2.54-2.59 (m, 4H), 1.84-1.96 (m, 4H). LCMS (ESI, m/z): 484 [M+H]⁺.

Example 16

1,1,1,3,3,3-Hexafluoropropan-2-yl 5-[[4-fluoro-2-(3-methylmorpholin-4-yl)phenyl]methyl]-octahydropyrrolo[3,4-c]pyrrole-2-carboxylate

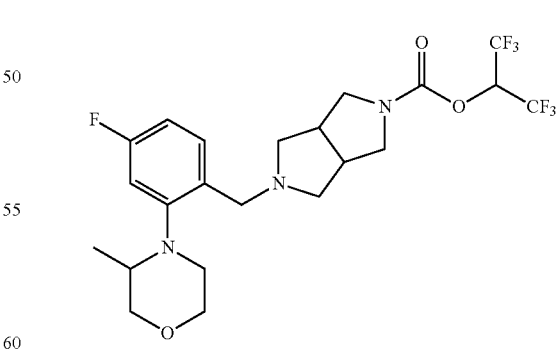

The title compound was synthesized directly from commercially available 2,4-difluorobenzaldehyde and 3-methylmorpholine hydrochloride according to the representative procedures of Example 3 (Step 1) followed by Example 9 (Step 1-3) to provide 1,1,1,3,3,3-hexafluoropropan-2-yl 5-[[4-fluoro-2-(3-methylmorpholin-4-yl)phenyl]methyl]- octahydropyrrolo[3,4-c]pyrrole-2-carboxylate as a colorless oil. $^1$H NMR (300 MHz, Chloroform-d) δ 7.36 (br, 1H), 6.80-6.90 (m, 2H), 5.68-5.76 (m, 1H), 3.66-3.89 (m, 6H), 3.31-3.50 (m, 4H), 3.16-3.21 (m, 1H), 2.87-2.95 (m, 3H), 2.48-2.75 (m, 5H), 0.76 (d, J=3.0 Hz, 3H). LCMS (ESI, m/z): 514 [M+H]$^+$.

Example 17

1,1,1,3,3,3-Hexafluoropropan-2-yl 5-[[2-(4-acetylpiperazin-1-yl)-4-fluorophenyl]methyl]-octahydropyrrolo[3,4-c]pyrrole-2-carboxylate

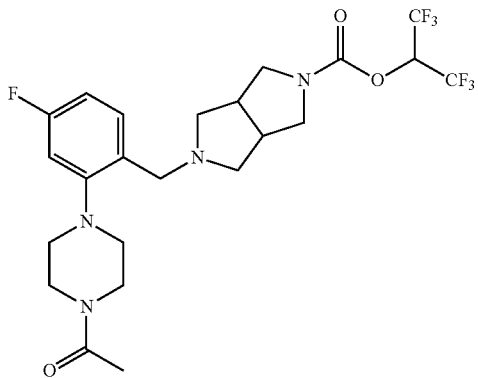 [SMILES: CC(=O)N1CCN(c2cc(F)ccc2CN2CC3CN(C(=O)OC(C(F)(F)F)C(F)(F)F)CC3C2)CC1]

The title compound was synthesized directly from commercially available 2,4-difluorobenzaldehyde and 1-(piperazin-1-yl)ethan-1-one according to the representative procedures of Example 3 (Step 1) followed by Example 9 (Step 1-3) to provide 1,1,1,3,3,3-hexafluoropropan-2-yl 5-[[2-(4-acetylpiperazin-1-yl)-4-fluorophenyl]methyl]-octahydropyrrolo[3,4-c]pyrrole-2-carboxylate as an orange solid. $^1$H NMR (300 MHz, Chloroform-d) δ 7.28-7.33 (m, 1H), 6.72-6.80 (m, 2H), 5.68-5.76 (m, 1H), 3.58-3.81 (m, 8H), 3.30-3.37 (m, 2H), 2.91-3.02 (m, 6H), 2.56-2.59 (m, 4H), 2.13 (s, 3H). LCMS (ESI, m/z): 563 [M+Na]$^+$.

Example 18

1,1,1,3,3,3-Hexafluoropropan-2-yl 5-[[4-chloro-2-(morpholin-4-yl)phenyl]methyl]-octahydropyrrolo[3,4-c]pyrrole-2-carboxylate

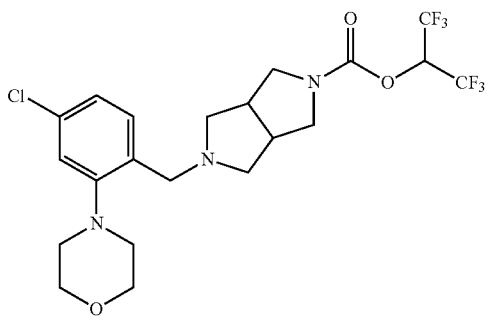 [SMILES: O=C(OC(C(F)(F)F)C(F)(F)F)N1CC2CN(Cc3ccc(Cl)cc3N3CCOCC3)CC2C1]

The title compound was synthesized directly from commercially available 4-chloro-2-fluorobenzaldehyde and morpholine according to the representative procedures of Example 3 (Step 1) followed by Example 9 (Step 1-3) to provide 1,1,1,3,3,3-hexafluoropropan-2-yl 5-[[4-chloro-2-(morpholin-4-yl)phenyl]methyl]-octahydropyrrolo[3,4-c] pyrrole-2-carboxylate as a yellow oil. $^1$H NMR (300 MHz, Chloroform-d) δ 7.31 (d, J=8.4 Hz, 1H), 7.02-7.05 (m, 2H), 5.67-5.79 (m, 1H), 3.80-3.83 (m, 4H), 3.65-3.74 (m, 2H), 3.61 (s, 2H), 3.28-3.37 (m, 2H), 2.87-2.97 (m, 6H), 2.56-2.61 (m, 4H). LCMS (ESI, m/z): 516 [M+H]$^+$.

Example 19

1,1,1,3,3,3-Hexafluoropropan-2-yl 5-[[4-chloro-2-(pyrrolidin-1-yl)phenyl]methyl]-octahydropyrrolo[3,4-c]pyrrole-2-carboxylate

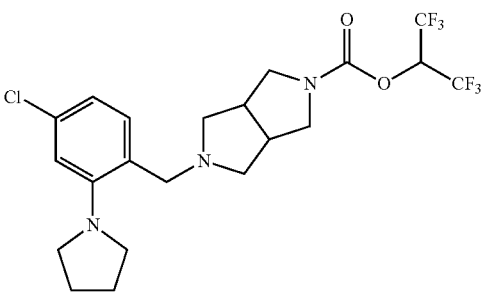 [SMILES: O=C(OC(C(F)(F)F)C(F)(F)F)N1CC2CN(Cc3ccc(Cl)cc3N3CCCC3)CC2C1]

The title compound was synthesized directly from commercially available 4-chloro-2-fluorobenzaldehyde and pyrrolidine according to the representative procedures of Example 3 (Step 1) followed by Example 9 (Step 1-3) to provide 1,1,1,3,3,3-hexafluoropropan-2-yl 5-[[4-chloro-2-(pyrrolidin-1-yl)phenyl]methyl]-octahydropyrrolo[3,4-c] pyrrole-2-carboxylate as a yellow oil. $^1$H NMR (300 MHz, Chloroform-d) δ 7.21-7.26 (m, 1H), 6.77-6.81 (m, 2H), 5.67-5.80 (m, 1H), 3.70-3.76 (m, 2H), 3.56 (s, 2H), 3.27-3.38 (m, 2H), 3.21 (t, J=6.4 Hz, 4H), 2.86 (br, 2H), 2.50-2.59 (m, 4H), 1.84-1.94 (m, 4H). LCMS (ESI, m/z): 500 [M+H]$^+$.

Example 20

1,1,1,3,3,3-Hexafluoropropan-2-yl 5-[[4-chloro-2-(3-methylmorpholin-4-yl)phenyl]methyl]-octahydropyrrolo[3,4-c]pyrrole-2-carboxylate

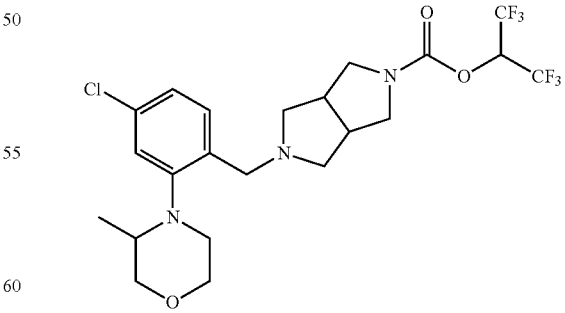

The title compound was synthesized directly from commercially available 4-chloro-2-fluorobenzaldehyde and 3-methylmorpholine according to the representative procedures of Example 3 (Step 1) followed by Example 9 (Step 1-3) to provide 1,1,1,3,3,3-hexafluoropropan-2-yl 5-[[4- chloro-2-(3-methylmorpholin-4-yl)phenyl]methyl]-octahydropyrrolo[3,4-c]pyrrole-2-carboxylate as a yellow oil. ¹H NMR (300 MHz, Chloroform-d) δ 7.36 (d, J=8.7 Hz, 1H), 7.08-7.14 (m, 2H), 5.70-5.78 (m, 1H), 3.60-3.87 (m, 6H), 3.44-3.51 (m, 1H), 3.15-3.39 (m, 4H), 2.70-2.93 (m, 4H), 2.49-2.66 (m, 4H), 0.74 (d, J=6.3 Hz, 3H). LCMS (ESI, m/z): 530 [M+H]⁺.

Example 21

1,1,1,3,3,3-Hexafluoropropan-2-yl 5-[[2-(4-acetylpiperazin-1-yl)-4-chlorophenyl]methyl]-octahydropyrrolo[3,4-c]pyrrole-2-carboxylate

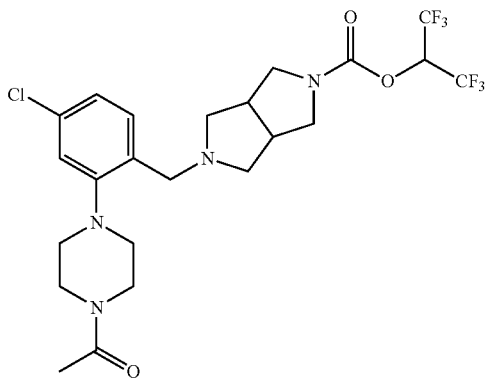 [SMILES: CC(=O)N1CCN(c2cc(Cl)ccc2CN2CC3CN(C(=O)OC(C(F)(F)F)C(F)(F)F)CC3C2)CC1]

The title compound was synthesized directly from commercially available 4-chloro-2-fluorobenzaldehyde and 1-(piperazin-1-yl)ethan-1-one according to the representative procedures of Example 3 (Step 1) followed by Example 9 (Step 1-3) to provide 1,1,1,3,3,3-hexafluoropropan-2-yl 5-[[2-(4-acetylpiperazin-1-yl)-4-chlorophenyl]methyl]-octahydropyrrolo[3,4-c]pyrrole-2-carboxylate as a light yellow solid. ¹H NMR (300 MHz, Chloroform-d) δ 7.30 (d, J=8.1 Hz, 1H), 7.06 (d, J=8.4 Hz, 1H), 7.00 (s, 1H), 5.68-5.77 (m, 1H), 3.56-3.80 (m, 8H), 3.30-3.37 (m, 2H), 2.89-3.05 (m, 6H), 2.56-2.59 (m, 4H), 2.13 (s, 3H). LCMS (ESI, m/z): 557 [M+H]⁺.

Example 22

1,1,1,3,3,3-Hexafluoropropan-2-yl 5-[[2-(morpholin-4-yl)-4-(propan-2-yl)phenyl]methyl]-octahydropyrrolo[3,4-c]pyrrole-2-carboxylate

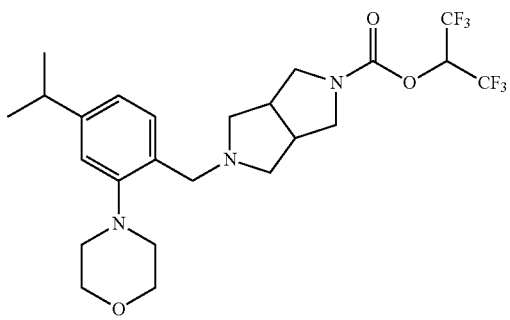 [SMILES: CC(C)c1ccc(CN2CC3CN(C(=O)OC(C(F)(F)F)C(F)(F)F)CC3C2)c(N2CCOCC2)c1]

The title compound was synthesized as from 2-bromo-4-(propan-2-yl)benzaldehyde, tert-butyl octahydropyrrolo[3,4-c]pyrrole-2-carboxylate, and morpholine as described in Example 9 (Step 1), Example 11 (Step 1), Example 5 (Step 3), and Example 8 (Step 4, DCM used instead of MeCN) to provide 1,1,1,3,3,3-hexafluoropropan-2-yl 5-[[2-(morpholin-4-yl)-4-(propan-2-yl)phenyl]methyl]-octahydropyrrolo[3,4-c]pyrrole-2-carboxylate as a yellow oil. ¹H NMR (300 MHz, Chloroform-d) δ 7.25-7.28 (m, 1H), 6.92-6.94 (m, 2H), 5.68-5.76 (m, 1H), 3.63-3.84 (m, 8H), 3.28-3.36 (m, 2H), 2.84-3.01 (m, 7H), 2.58-2.63 (m, 4H), 1.25 (d, J=6.9 Hz, 6H). LCMS (ESI, m/z): 524 [M+H]⁺.

Example 23

1,1,1,3,3,3-Hexafluoropropan-2-yl 5-[[4-(propan-2-yl)-2-(pyrrolidin-1-yl)phenyl]methyl]-octahydropyrrolo[3,4-c]pyrrole-2-carboxylate

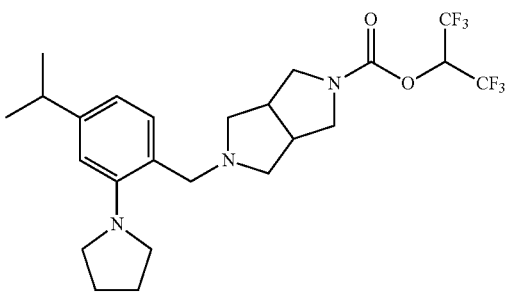 [SMILES: CC(C)c1ccc(CN2CC3CN(C(=O)OC(C(F)(F)F)C(F)(F)F)CC3C2)c(N2CCCC2)c1]

The title compound was synthesized from tert-butyl 5-[[2-bromo-4-(propan-2-yl)phenyl]methyl]-octahydropyrrolo[3,4-c]pyrrole-2-carboxylate as described in Example 9 (Step 1), Example 11 (Step 1), Example 5 (Step 3), and Example 8 (Step 4, DCM used instead of MeCN) to provide 1,1,1,3,3-hexafluoropropan-2-yl 5-[[4-(propan-2-yl)-2-(pyrrolidin-1-yl)phenyl]methyl]-octahydropyrrolo[3,4-c]pyrrole-2-carboxylate as a white solid. ¹H NMR (300 MHz, Chloroform-d) δ 7.23 (d, J=7.5 Hz, 1H), 6.73-6.76 (m, 2H), 5.69-5.77 (m, 1H), 3.59-3.76 (m, 4H), 3.18-3.39 (m, 6H), 2.80-2.89 (m, 3H), 2.54-2.62 (m, 4H), 1.87-1.94 (m, 4H), 1.24 (d, J=6.9 Hz, 6H). LCMS (ESI, m/z): 508 [M+H]⁺.

Example 24

1,1,1,3,3,3-Hexafluoropropan-2-yl 5-[[2-(4-acetylpiperazin-1-yl)-4-(propan-2-yl)phenyl]methyl]-octahydropyrrolo[3,4-c]pyrrole-2-carboxylate

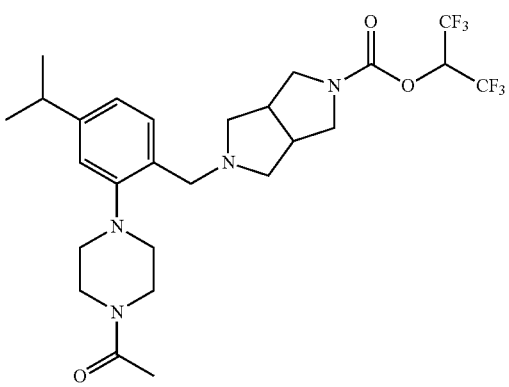 [SMILES: CC(=O)N1CCN(c2cc(C(C)C)ccc2CN2CC3CN(C(=O)OC(C(F)(F)F)C(F)(F)F)CC3C2)CC1]

The title compound was synthesized from 2-bromo-4-(propan-2-yl)benzaldehyde, tert-butyl octahydropyrrolo[3,4-c]pyrrole-2-carboxylate, and 1 (piperazin-1-yl)ethanone as described in Example 9 (Step 1), Example 11 (Step 1), Example 5 (Step 3), and Example 8 (Step 4, DCM used instead of MeCN) to provide 1,1,1,3,3,3-hexafluoropropan-2-yl 5-[[2-(4-acetylpiperazin-1-yl)-4-(propan-2-yl)phenyl]methyl]-octahydropyrrolo[3,4-c]pyrrole-2-carboxylate as a white solid. $^1$H NMR (300 MHz, Chloroform-d) δ 7.27 (d, J=7.8 Hz, 1H), 6.89-6.96 (m, 2H), 5.68-5.76 (m, 1H), 3.55-3.74 (m, 8H), 3.29-3.38 (m, 2H), 2.82-3.08 (m, 7H), 2.59-2.61 (m, 4H), 2.13 (s, 3H), 1.23 (d, J=6.9 Hz, 6H). LCMS (ESI, m/z): 565 [M+H]$^+$.

Example 25

1,1,1,3,3,3-Hexafluoropropan-2-yl 5-[[2-fluoro-4-(3-methylmorpholin-4-yl)phenyl]methyl]-octahydropyrrolo[3,4-c]pyrrole-2-carboxylate

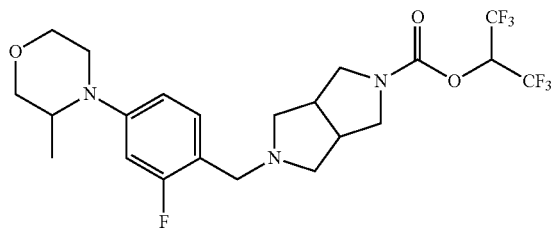 [SMILES: CC1COCCN1c1ccc(CN2CC3CN(C(=O)OC(C(F)(F)F)C(F)(F)F)CC3C2)c(F)c1]

The title compound was synthesized directly from commercially available 2,4-difluorobenzaldehyde and 3-methylmorpholine hydrochloride according to the representative procedures of Example 3 (Step 1) followed by Example 9 (Step 1-3) to provide 1,1,1,3,3,3-hexafluoropropan-2-yl 5-[[2-fluoro-4-(3-methylmorpholin-4-yl)phenyl]methyl]-octahydropyrrolo[3,4-c]pyrrole-2-carboxylate as a light yellow oil. $^1$H NMR (300 MHz, Chloroform-d) δ 7.18 (t, J=3.9 Hz, 1H), 6.48-6.62 (m, 2H), 5.69-5.77 (m, 1H), 3.80-4.01 (m, 1H), 3.66-3.75 (m, 6H), 3.58-3.64 (m, 2H), 3.34-3.40 (m, 2H), 3.08-3.18 (m, 2H), 2.86 (br, 2H), 2.50-2.67 (m, 2H), 2.42-2.48 (m, 2H), 1.12 (d, J=3.3 Hz, 3H). LCMS (ESI, m/z): 514 [M+H]$^+$.

Example 26

1,1,1,3,3,3-Hexafluoropropan-2-yl 5-[[4-(4-acetylpiperazin-1-yl)-2-fluorophenyl]methyl]-octahydropyrrolo[3,4-c]pyrrole-2-carboxylate

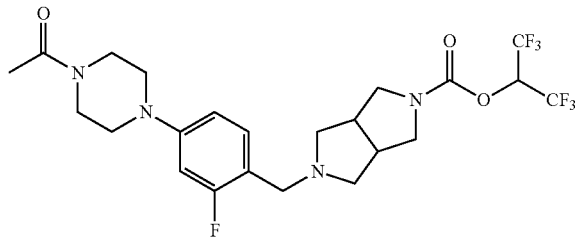 [SMILES: CC(=O)N1CCN(c2ccc(CN3CC4CN(C(=O)OC(C(F)(F)F)C(F)(F)F)CC4C3)c(Cl)c2)CC1]

The title compound was synthesized directly from commercially available 2,4-difluorobenzaldehyde and 1-(piperazin-1-yl)ethan-1-one according to the representative procedures of Example 3 (Step 1) followed by Example 9 (Step 1-3) to provide 1,1,1,3,3,3-hexafluoropropan-2-yl 5-[[4-(4-acetylpiperazin-1-yl)-2-fluorophenyl]methyl]-octahydropyrrolo[3,4-c]pyrrole-2-carboxylate as a yellow oil. $^1$H NMR (300 MHz, Chloroform-d) δ 7.22 (br, 1H), 6.54-6.67 (m, 2H), 5.68-5.76 (m, 1H), 3.60-3.78 (m, 8H), 3.37-3.40 (m, 2H), 3.14-3.21 (m, 4H), 2.87 (br, 2H), 2.50-2.75 (m, 4H), 2.14 (s, 3H). LCMS (ESI, m/z): 563 [M+Na]$^+$.

Example 27

1,1,1,3,3,3-Hexafluoropropan-2-yl 5-[[2-chloro-4-(3-methylmorpholin-4-yl)phenyl]methyl]-octahydropyrrolo[3,4-c]pyrrole-2-carboxylate

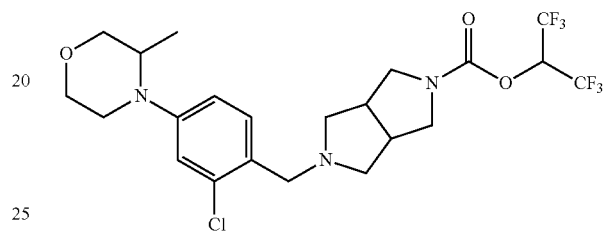

The title compound was synthesized directly from commercially available 2-chloro-4-fluorobenzaldehyde and 3-methylmorpholine according to the representative procedures of Example 3 (Step 1) followed by Example 9 (Step 1-3) to provide 1,1,1,3,3,3-hexafluoropropan-2-yl 5-[[2-chloro-4-(3-methylmorpholin-4-yl)phenyl]methyl]-octahydropyrrolo[3,4-c]pyrrole-2-carboxylate as a yellow oil. $^1$H NMR (300 MHz, Chloroform-d) δ 7.24-7.26 (m, 1H), 6.82-6.83 (m, 1H), 6.72-6.76 (m, 1H), 5.70-5.78 (m, 1H), 3.64-4.00 (m, 9H), 3.34-3.42 (m, 2H), 3.05-3.19 (m, 2H), 2.87 (br, 2H), 2.52-2.65 (m, 4H), 1.10 (d, J=6.3 Hz, 3H). LCMS (ESI, m/z): 530 [M+H]$^+$.

Example 28

1,1,1,3,3,3-Hexafluoropropan-2-yl 5-[[4-(4-acetylpiperazin-1-yl)-2-chlorophenyl]methyl]-octahydropyrrolo[3,4-c]pyrrole-2-carboxylate

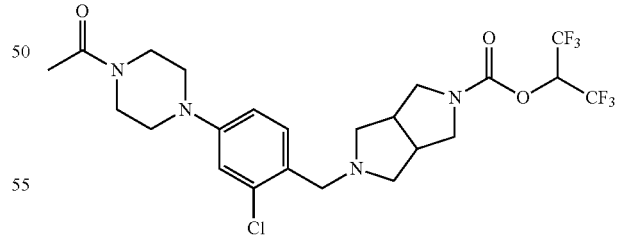

The title compound was synthesized directly from commercially available 2-chloro-4-fluorobenzaldehyde and 1-(piperazin-1-yl)ethan-1-one according to the representative procedures of Example 3 (Step 1) followed by Example 9 (Step 1-3) to provide 1,1,1,3,3,3-hexafluoropropan-2-yl 5-[[4-(4-acetylpiperazin-1-yl)-2-chlorophenyl]methyl]-octahydropyrrolo[3,4-c]pyrrole-2-carboxylate as a yellow oil. $^1$H NMR (300 MHz, Chloroform-d) δ 7.27-7.30 (m, 1H), 6.88 (s, 1H), 6.77-6.81 (m, 1H), 5.71-5.79 (m, 1H), 3.59-

3.77 (m, 8H), 3.34-3.41 (m, 2H), 3.12-3.19 (m, 4H), 2.87 (br, 2H), 2.54-2.64 (m, 4H), 2.14 (s, 3H). LCMS (ESI, m/z): 557 [M+H]⁺.

Example 29

1,1,1,3,3,3-Hexafluoropropan-2-yl 5-[[2-methyl-3-(piperidin-1-yl)phenyl]methyl]-octahydropyrrolo[3,4-c]pyrrole-2-carboxylate

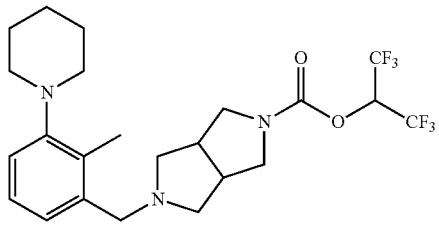 [SMILES: Cc1c(CN2CC3CN(C(=O)OC(C(F)(F)F)C(F)(F)F)CC3C2)cccc1N1CCCCC1]

The title compound was synthesized from 3-bromo-2-methylbenzaldehyde, tert-butyl octahydropyrrolo[3,4-c]pyrrole-2-carboxylate, and piperidine following the procedures described in Example 9 (Step 1), Example 11 (Step 1, Davephos used instead of BINAP), Example 5 (Step 3), and Example 8 (Step 4, DCM used instead of MeCN) to provide 1,1,1,3,3,3-hexafluoropropan-2-yl 5-[[2-methyl-3-(piperidin-1-yl)phenyl]methyl]-octahydropyrrolo[3,4-c]pyrrole-2-carboxylate as a light yellow oil. $^1$H NMR (300 MHz, Chloroform-d) δ 7.07-7.12 (m, 1H), 6.95-6.97 (m, 2H), 5.69-5.77 (m, 1H), 3.68-3.75 (m, 2H), 3.56 (br, 2H), 3.33-3.39 (m, 2H), 2.80-2.86 (m, 6H), 2.53-2.58 (m, 4H), 2.29 (s, 3H), 1.68-1.75 (m, 4H), 1.56-1.64 (br, 2H). LCMS (ESI, m/z): 494 [M+H]⁺.

Example 30

1,1,1,3,3,3-Hexafluoropropan-2-yl 5-[[3-methyl-2-(piperidin-1-yl)phenyl]methyl]-octahydropyrrolo[3,4-c]pyrrole-2-carboxylate

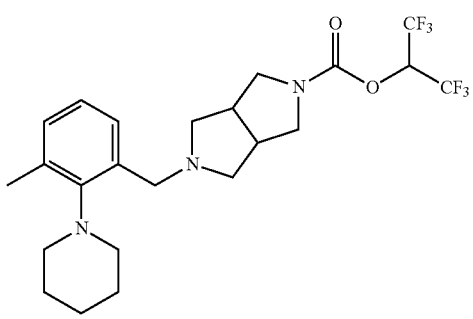 [SMILES: Cc1cccc(CN2CC3CN(C(=O)OC(C(F)(F)F)C(F)(F)F)CC3C2)c1N1CCCCC1]

The title compound was synthesized directly from commercially available 2-bromo-3-methylbenzaldehyde and tert-butyl octahydropyrrolo[3,4-c]pyrrole-2-carboxylate according to the representative procedures of Example 9 (Step 1), Example 11 (Step 1, Davephos used instead of BINAP), Example 5 (Step 3), and Example 8 (Step 4, DCM used instead of MeCN) to provide 1,1,1,3,3,3-hexafluoropropan-2-yl 5-[[3-methyl-2-(piperidin-1-yl)phenyl]methyl]-octahydropyrrolo[3,4-c]pyrrole-2-carboxylate as a light yellow oil. $^1$H NMR (300 MHz, Chloroform-d) δ 7.24-7.29 (m, 1H), 6.97-7.05 (m, 2H), 5.68-5.76 (m, 1H), 3.68-3.75 (m, 4H), 3.38 (br, 2H), 3.05-3.07 (m, 2H), 2.92-2.96 (m, 4H), 2.74 (m, 4H), 2.33 (s, 3H), 1.46-1.54 (m, 6H). LCMS (ESI, m/z): 494 [M+H]⁺.

Example 31

1,1,1,3,3,3-Hexafluoropropan-2-yl 5-[(4-chloro-2-[8-oxa-2-azaspiro[4.5]decan-2-yl]phenyl)methyl]-octahydropyrrolo[3,4-c]pyrrole-2-carboxylate

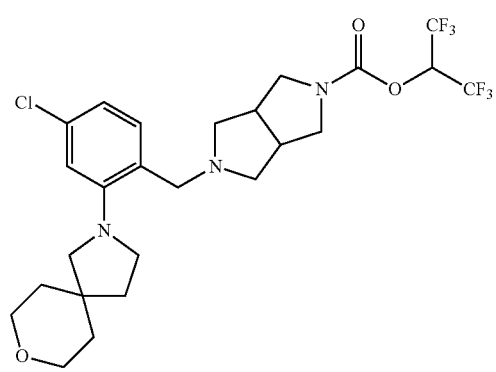 [SMILES: O=C(OC(C(F)(F)F)C(F)(F)F)N1CC2CN(Cc3ccc(Cl)cc3N3CCC4(CCOCC4)C3)CC2C1]

The title compound was synthesized directly from commercially available 4-chloro-2-fluorobenzaldehyde and 8-oxa-2-azaspiro[4.5]decane according to the representative procedures of Example 3 (Step 1) followed by Example 9 (Step 1-3) to provide 1,1,1,3,3,3-hexafluoropropan-2-yl 5-[(4-chloro-2-[8-oxa-2-azaspiro[4.5]decan-2-yl]phenyl)methyl]-octahydropyrrolo[3,4-c]pyrrole-2-carboxylate as a yellow oil. $^1$H NMR (300 MHz, Chloroform-d) δ 7.20-7.23 (m, 1H), 6.80 (s, 2H), 5.66-5.79 (m, 1H), 3.61-3.81 (m, 8H), 3.41-3.46 (m, 4H), 3.13 (s, 2H), 2.87 (br, 2H), 2.52 (br, 4H), 1.82-1.89 (m, 2H), 1.62-1.79 (m, 4H). LCMS (ESI, m/z): 570 [M+H]⁺.

Example 32

1,1,1,3,3,3-Hexafluoropropan-2-yl 5-[(4-chloro-2-[5H,6H,7H-pyrrolo[3,4-b]pyridin-6-yl]phenyl)methyl]-octahydropyrrolo[3,4-c]pyrrole-2-carboxylate

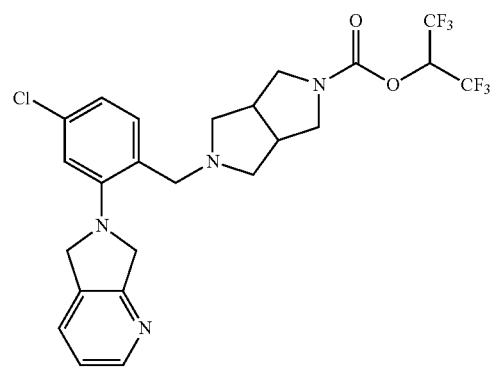 [SMILES: O=C(OC(C(F)(F)F)C(F)(F)F)N1CC2CN(Cc3ccc(Cl)cc3N3Cc4cccnc4C3)CC2C1]

The title compound was synthesized directly from commercially available 4-chloro-2-fluorobenzaldehyde and 5H,6H,7H-pyrrolo[3,4-b]pyridine according to the representative procedures of Example 3 (Step 1) followed by Example 9 (Step 1-3) to provide 1,1,1,3,3,3-hexafluoropropan-2-yl 5-[(4-chloro-2-[5H,6H,7H-pyrrolo[3,4-b]pyridin-6-yl]phenyl)methyl]-octahydropyrrolo[3,4-c]pyrrole-2-carboxylate as a yellow oil. $^1$H NMR (300 MHz, Chloroform-d) δ: 8.48 (d, J=4.8 Hz 1H), 7.59 (d, J=7.5 Hz, 1H), 7.21-7.38 (m, 1H), 7.17-7.20 (m, 1H), 6.99 (s, 1H), 6.88-6.94 (m, 1H), 5.62-5.75 (m, 1H), 4.63-4.81 (m, 4H), 3.67-3.84 (m, 4H), 3.30-3.58 (m, 2H), 2.87 (br, 2H), 2.56 (br, 4H). LCMS (ESI, m/z): 549 [M+H]$^+$.

Example 33

1,1,1,3,3,3-Hexafluoropropan-2-yl 5-[(4-chloro-2-[5H,6H,7H,8H-imidazo[1,2-a]pyrazin-7-yl]phenyl)methyl]-octahydropyrrolo[3,4-c]pyrrole-2-carboxylate

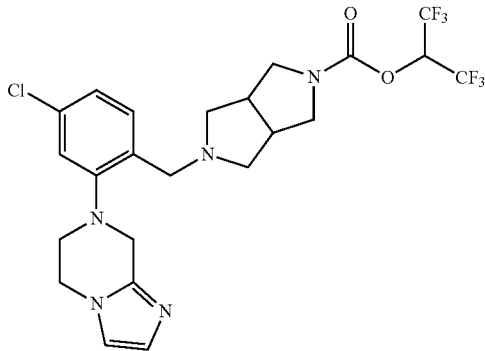 [SMILES: O=C(OC(C(F)(F)F)C(F)(F)F)N1CC2CN(Cc3ccc(Cl)cc3N3CCn4ccnc4C3)CC2C1]

The title compound was synthesized directly from commercially available 4-chloro-2-fluorobenzaldehyde and 5H,6H,7H,8H-imidazo[1,2-a]pyrazine according to the representative procedures of Example 3 (Step 1) followed by Example 9 (Step 1-3) to provide 1,1,1,3,3,3-hexafluoropropan-2-yl 5-[(4-chloro-2-[5H,6H,7H,8H-imidazo[1,2-a]pyrazin-7-yl]phenyl)methyl]-octahydropyrrolo[3,4-c]pyrrole-2-carboxylate as an orange syrup. $^1$H NMR (300 MHz, Chloroform-d) δ 7.34 (d, J=8.1 Hz, 1H), 7.06-7.12 (m, 3H), 6.90 (s, 1H), 5.66-5.79 (m, 1H), 4.23 (br, 2H), 4.05-4.08 (m, 2H), 3.32-3.74 (m, 8H), 2.88 (br, 2H), 2.57-2.62 (m, 4H). LCMS (ESI, m/z): 552 [M+H]$^+$.

Example 34

1,1,1,3,3,3-Hexafluoropropan-2-yl 5-(4-chloro-2-(5,6-dihydro-[1,2,4]triazolo[1,5-a]pyrazin-7(8H)-yl)benzyl)-hexahydropyrrolo[3,4-c]pyrrole-2(1H)-carboxylate

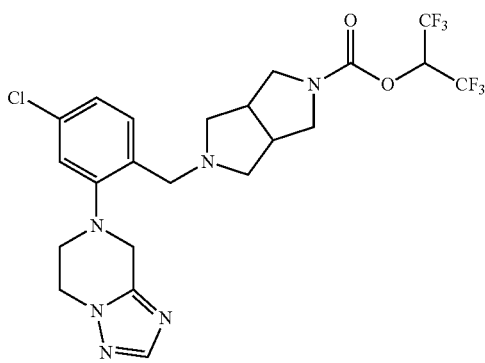 [SMILES: O=C(OC(C(F)(F)F)C(F)(F)F)N1CC2CN(Cc3ccc(Cl)cc3N3CCn4ncnc4C3)CC2C1]

The title compound was synthesized from 4-chloro-2-fluorobenzaldehyde, tert-butyl octahydropyrrolo[3,4-c]pyrrole-2-carboxylate, and 5,6,7,8-tetrahydro-[1,2,4]triazolo[1,5-a]pyrazine as described in Example 9 (Step 1), Example 11 (Step 1), Example 5 (Step 3), and Example 8 (Step 4, DCM used instead of MeCN) to provide 1,1,1,3,3,3-hexafluoropropan-2-yl 5-(4-chloro-2-(5,6-dihydro-[1,2,4]triazolo[1,5-a]pyrazin-7(8H)-yl)benzyl)-hexahydropyrrolo[3,4-c]pyrrole-2(1H)-carboxylate as an off-white solid. $^1$H NMR (300 MHz, Chloroform-d) δ 7.93 (s, 1H), 7.34 (d, J=8.1 Hz, 1H), 7.08-7.15 (m, 2H), 5.66-5.79 (m, 1H), 4.26-4.33 (m, 4H), 3.52-3.74 (m, 6H), 3.23-3.40 (m, 2H), 2.88 (br, 2H), 2.57-2.59 (m, 4H). LCMS (ESI, m/z): 553 [M+H]$^+$.

Example 35

1,1,1,3,3,3-Hexafluoropropan-2-yl 5-(4-chloro-2-((R)-hexahydropyrrolo[1,2-a]pyrazin-2(1H)-yl)benzyl)-hexahydropyrrolo[3,4-c]pyrrole-2(1H)-carboxylate

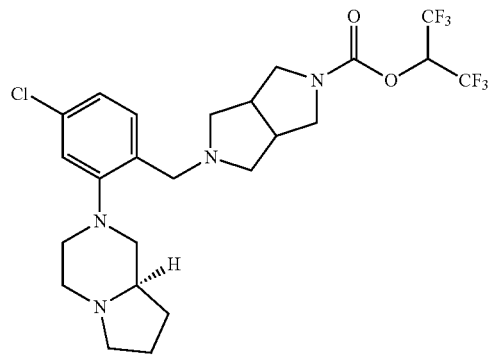 [SMILES: O=C(OC(C(F)(F)F)C(F)(F)F)N1CC2CN(Cc3ccc(Cl)cc3N3CCN4CCC[C@@H]4C3)CC2C1]

The title compound was synthesized directly from commercially available 4-chloro-2-fluorobenzaldehyde and (8aR)-octahydropyrrolo[1,2-a]piperazine according to the representative procedures of Example 3 (Step 1) followed by Example 9 (Step 1-3) to provide 1,1,1,3,3,3-hexafluoropropan-2-yl 5-(4-chloro-2-((R)-hexahydropyrrolo[1,2-a]pyrazin-2(1H)-yl)benzyl)-hexahydropyrrolo[3,4-c]pyrrole-2(1H)-carboxylate as an orange oil. $^1$H NMR (300 MHz, Chloroform-d) δ 7.28 (s, 1H), 6.98-7.04 (m, 2H), 5.69-5.75 (m, 1H), 3.69-3.76 (m, 2H), 3.58 (br, 2H), 3.28-3.34 (m, 3H), 3.05-3.28 (m, 3H), 2.86-2.92 (m, 3H), 2.52-2.62 (m, 5H), 2.36-2.44 (m, 1H), 2.17-2.26 (m, 2H), 1.76-1.91 (m, 3H), 1.42-1.48 (m, 1H). LCMS (ESI, m/z): 555 [M+H]$^+$.

Example 36

1,1,1,3,3,3-Hexafluoropropan-2-yl 5-[[4-chloro-2-(4-methanesulfonylpiperazin-1-yl)phenyl]methyl]-octahydropyrrolo[3,4-c]pyrrole-2-carboxylate

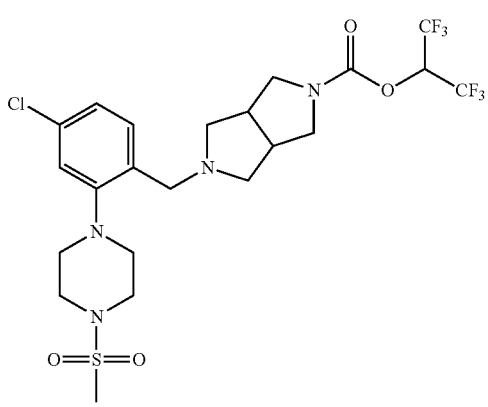 [SMILES: CS(=O)(=O)N1CCN(c2cc(Cl)ccc2CN2CC3CN(C(=O)OC(C(F)(F)F)C(F)(F)F)CC3C2)CC1]

The title compound was synthesized directly from commercially available 4-chloro-2-fluorobenzaldehyde and 1-methanesulfonylpiperazine according to the representative procedures of Example 3 (Step 1) followed by Example 9 (Step 1-3) to provide 1,1,1,3,3,3-hexafluoropropan-2-yl 5-[[4-chloro-2-(4-methanesulfonylpiperazin-1-yl)phenyl]methyl]-octahydropyrrolo[3,4-c]pyrrole-2-carboxylate as an orange syrup. $^1$H NMR (300 MHz, Chloroform-d) δ 7.33 (d, J=8.1 Hz, 1H), 7.02-7.08 (m, 2H), 5.70-5.78 (m, 1H), 3.54-3.74 (m, 4H), 3.31-3.38 (m, 6H), 3.06-3.07 (m, 4H), 2.86 (br, 5H), 2.51-2.58 (m, 4H). LCMS (ESI, m/z): 593 [M+H]$^+$.

Example 37

1,1,1,3,3,3-Hexafluoropropan-2-yl 5-[(4-chloro-2-[4-[(pyrrolidin-1-yl)carbonyl]piperidin-1-yl]phenyl)methyl]-octahydropyrrolo[3,4-c]pyrrole-2-carboxylate

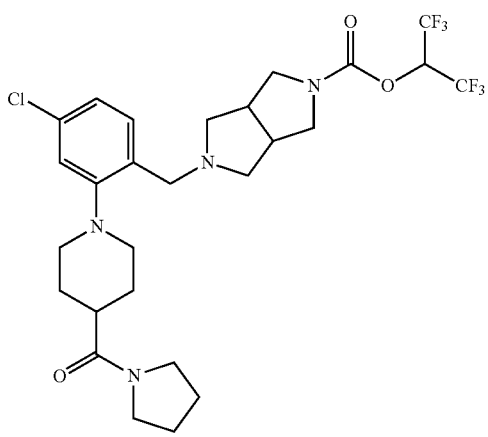 [SMILES: O=C(OC(C(F)(F)F)C(F)(F)F)N1CC2CN(Cc3ccc(Cl)cc3N3CCC(C(=O)N4CCCC4)CC3)CC2C1]

The title compound was synthesized directly from commercially available 4-chloro-2-fluorobenzaldehyde and 4-[(pyrrolidin-1-yl)carbonyl]piperidine hydrochloride according to the representative procedures of Example 3 (Step 1) followed by Example 9 (Step 1-3) to provide 1,1,1,3,3,3-hexafluoropropan-2-yl 5-[(4-chloro-2-[4-[(pyrrolidin-1-yl)carbonyl]piperidin-1-yl]phenyl)methyl]-octahydropyrrolo[3,4-c]pyrrole-2-carboxylate as an orange syrup. $^1$H NMR (300 MHz, Chloroform-d) δ 7.26-7.33 (m, 1H), 6.97-7.00 (m, 2H), 5.68-5.80 (m, 1H), 3.70-3.76 (m, 2H), 3.59 (br, 2H), 3.47-3.53 (m, 4H), 3.26-3.37 (m, 4H), 2.86 (br, 2H), 2.60-2.67 (m, 4H), 2.44-2.48 (m, 3H), 1.78-2.09 (m, 8H). LCMS (ESI, m/z): 611 [M+H]$^+$.

Example 38

1,1,1,3,3,3-Hexafluoropropan-2-yl 5-[(4-chloro-2-[1-oxo-2,8-diazaspiro[4.5]decan-8-yl]phenyl)methyl]-octahydropyrrolo[3,4-c]pyrrole-2-carboxylate

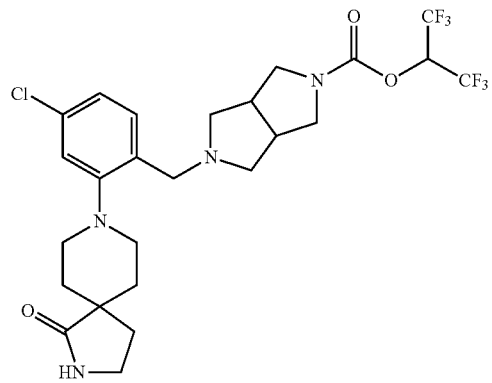 [SMILES: O=C(OC(C(F)(F)F)C(F)(F)F)N1CC2CN(Cc3ccc(Cl)cc3N3CCC4(CCNC4=O)CC3)CC2C1]

The title compound was synthesized directly from commercially available 4-chloro-2-fluorobenzaldehyde and 2,8-diazaspiro[4.5]decan-1-one according to the representative procedures of Example 3 (Step 1) followed by Example 9 (Step 1-3) to provide 1,1,1,3,3,3-hexafluoropropan-2-yl 5-[(4-chloro-2-[1-oxo-2,8-diazaspiro[4.5]decan-8-yl]phenyl)methyl]-octahydropyrrolo[3,4-c]pyrrole-2-carboxylate as an off-white solid. $^1$H NMR (300 MHz, Chloroform-d) δ 7.70 (s, 1H), 7.68-7.32 (m, 1H), 6.98-7.03 (m, 2H), 5.69-5.81 (m, 1H), 3.70-3.76 (m, 2H), 3.61 (br, 2H), 3.25-3.52 (m, 6H), 2.86 (br, 2H), 2.63-2.74 (m, 4H), 2.48-2.52 (m, 2H), 2.08-2.15 (m, 4H), 1.46-1.56 (m, 2H). LCMS (ESI, m/z): 583 [M+H]$^+$.

Example 39

1,1,1,3,3,3-Hexafluoropropan-2-yl 5-[[2-(azetidin-1-yl)-4-chlorophenyl]methyl]-octahydropyrrolo[3,4-c]pyrrole-2-carboxylate

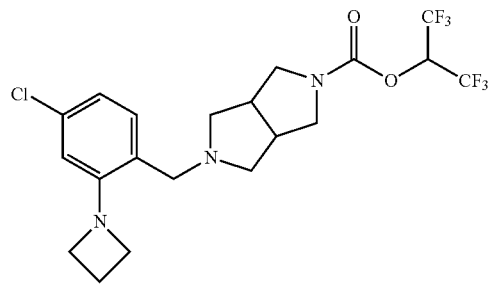 [SMILES: O=C(OC(C(F)(F)F)C(F)(F)F)N1CC2CN(Cc3ccc(Cl)cc3N3CCC3)CC2C1]

The title compound was synthesized from 4-chloro-2-fluorobenzaldehyde, tert-butyl octahydropyrrolo[3,4-c]pyrrole-2-carboxylate, and azetidine as described in Example 9 (Step 1), Example 11 (Step 1), Example 5 (Step 3), and Example 8 (Step 4, DCM used instead of MeCN) to provide 1,1,1,3,3,3-hexafluoropropan-2-yl 5-[[2-(azetidin-1-yl)-4-chlorophenyl]methyl]-octahydropyrrolo[3,4-c]pyrrole-2-carboxylate as a yellow oil. $^1$H NMR (300 MHz, Chloroform-d) δ 7.09 (d, J=7.8 Hz, 1H), 6.72 (d, J=6.6 Hz, 1H), 6.43 (s, 1H), 5.72-5.80 (m, 1H), 3.97 (t, J=7.2 Hz, 4H), 3.70-3.77 (m, 2H), 3.36-3.46 (m, 4H), 2.90 (br, 2H), 2.55-2.56 (m, 4H), 2.24-2.34 (m, 2H). LCMS (ESI, m/z): 486 [M+H]$^+$.

Example 40

1,1,1,3,3,3-Hexafluoropropan-2-yl 5-[(3-methyl-2-[2-oxa-7-azaspiro[4.4]nonan-7-yl]phenyl)methyl]-octahydropyrrolo[3,4-c]pyrrole-2-carboxylate

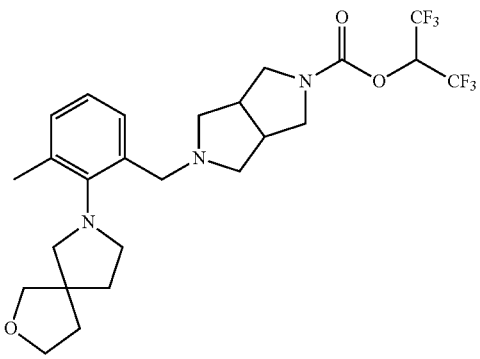 [SMILES: Cc1cccc(CN2CC3CN(C(=O)OC(C(F)(F)F)C(F)(F)F)CC3C2)c1N1CCC2(CCOC2)C1]

The title compound was synthesized from 2-fluoro-3-methylbenzaldehyde, tert-butyl octahydropyrrolo[3,4-c]pyrrole-2-carboxylate, and 2-oxa-7-azaspiro[4.4]nonane as described in Example 9 (Step 1), Example 11 (Step 1), Example 5 (Step 3), and Example 8 (Step 4, DCM used instead of MeCN) to provide 1,1,1,3,3,3-hexafluoropropan-2-yl 5-[(3-methyl-2-[2-oxa-7-azaspiro[4.4]nonan-7-yl]phenyl)methyl]-octahydropyrrolo[3,4-c]pyrrole-2-carboxylate as a yellow oil. $^1$H NMR (300 MHz, Chloroform-d) δ 7.24 (s, 1H), 7.03-7.10 (m, 2H), 5.69-5.78 (m, 1H), 3.66-3.97 (m, 6H), 3.60 (br, 2H), 3.13-3.41 (m, 6H), 2.88 (br, 2H), 2.48-2.57 (m, 4H), 2.26 (s, 3H), 1.91-2.08 (m, 4H). LCMS (ESI, m/z): 536 [M+H]$^+$.

Example 41

1,1,1,3,3,3-Hexafluoropropan-2-yl 5-[[3-methyl-2-(morpholin-4-yl)phenyl]methyl]-octahydropyrrolo[3,4-c]pyrrole-2-carboxylate

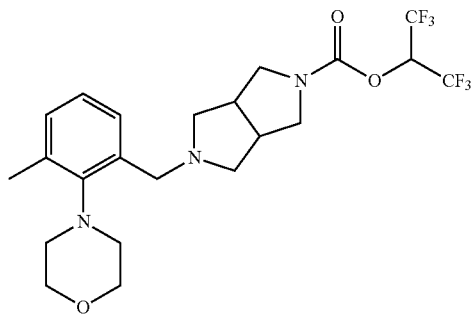 [SMILES: Cc1cccc(CN2CC3CN(C(=O)OC(C(F)(F)F)C(F)(F)F)CC3C2)c1N1CCOCC1]

The title compound was synthesized from 2-fluoro-3-methylbenzaldehyde, tert-butyl octahydropyrrolo[3,4-c]pyrrole-2-carboxylate, and morpholine as described in Example 9 (Step 1), Example 11 (Step 1), Example 5 (Step 3), and Example 8 (Step 4, DCM used instead of MeCN) to provide 1,1,1,3,3,3-hexafluoropropan-2-yl 5-[[3-methyl-2-(morpholin-4-yl)phenyl]methyl]-octahydropyrrolo[3,4-c]pyrrole-2-carboxylate as a yellow oil. $^1$H NMR (300 MHz, Chloroform-d) δ 7.19-7.21 (m, 1H), 7.00-7.09 (m, 2H), 5.68-5.76 (m, 1H), 3.68-3.83 (m, 8H), 3.20-3.38 (m, 4H), 2.88-2.99 (m, 4H), 2.57-2.63 (m, 4H), 2.36 (s, 3H). LCMS (ESI, m/z): 496 [M+H]$^+$.

Example 42

1,1,1,3,3,3-Hexafluoropropan-2-yl 5-[(3-chloro-2-[2-oxa-7-azaspiro[4.4]nonan-7-yl]phenyl)methyl]-octahydropyrrolo[3,4-c]pyrrole-2-carboxylate

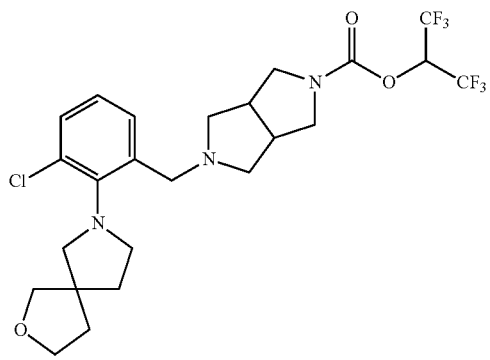 [SMILES: O=C(OC(C(F)(F)F)C(F)(F)F)N1CC2CN(Cc3cccc(Cl)c3N3CCC4(CCOC4)C3)CC2C1]

The title compound was synthesized directly from commercially available 3-chloro-2-fluorobenzaldehyde and 2-oxa-7-azaspiro[4.4]nonane according to the representative procedures of Example 3 (Step 1) followed by Example 9 (Step 1-3) to provide 1,1,1,3,3,3-hexafluoropropan-2-yl 5-[(3-chloro-2-[2-oxa-7-azaspiro[4.4]nonan-7-yl]phenyl)methyl]-octahydropyrrolo[3,4-c]pyrrole-2-carboxylate as a yellow oil. $^1$H NMR (300 MHz, Chloroform-d) δ 7.25-7.29 (m, 2H), 7.05-7.11 (m, 1H), 5.71-5.77 (m, 1H), 3.63-3.94 (m, 8H), 3.16-3.41 (m, 6H), 2.87 (br, 2H), 2.48-2.60 (m, 4H), 1.94-2.06 (m, 4H). LCMS (ESI, m/z): 556 [M+H]$^+$.

Example 43

1,1,1,3,3,3-Hexafluoropropan-2-yl 5-[(3-chloro-2-[3-oxa-8-azabicyclo[3.2.1]octan-8-yl]phenyl)methyl]-octahydropyrrolo[3,4-c]pyrrole-2-carboxylate

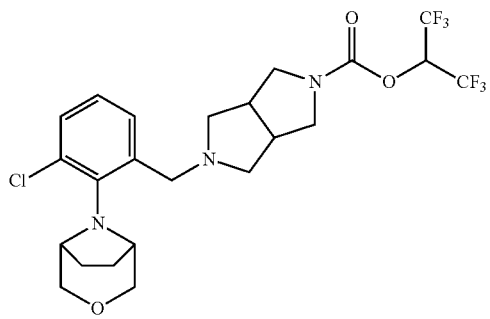 [SMILES: O=C(OC(C(F)(F)F)C(F)(F)F)N1CC2CN(Cc3cccc(Cl)c3N3C4CCC3COC4)CC2C1]

The title compound was synthesized directly from commercially available 3-chloro-2-fluorobenzaldehyde and 3-oxa-8-azabicyclo[3.2.1]octane according to the representative procedures of Example 3 (Step 1) followed by Example 9 (Step 1-3) to provide 1,1,1,3,3,3-hexafluoropropan-2-yl 5-[(3-chloro-2-[3-oxa-8-azabicyclo[3.2.1]octan-8-yl]phenyl)methyl]-octahydropyrrolo[3,4-c]pyrrole-2-carboxylate as a yellow oil. ¹H NMR (300 MHz, Chloroform-d) δ 7.19-7.28 (m, 2H), 6.82-6.87 (m, 1H), 5.68-5.80 (m, 1H), 4.00-4.04 (m, 2H), 3.92 (br, 2H), 3.70-3.76 (m, 4H), 3.60-3.63 (m, 2H), 3.31-3.38 (m, 2H), 2.88 (br, 2H), 2.56-2.65 (m, 4H), 2.09-2.15 (m, 4H). LCMS (ESI, m/z): 542 [M+H]⁺.

Example 44

1,1,1,3,3,3-Hexafluoropropan-2-yl 5-[[3-chloro-2-(morpholin-4-yl)phenyl]methyl]-octahydropyrrolo[3,4-c]pyrrole-2-carboxylate

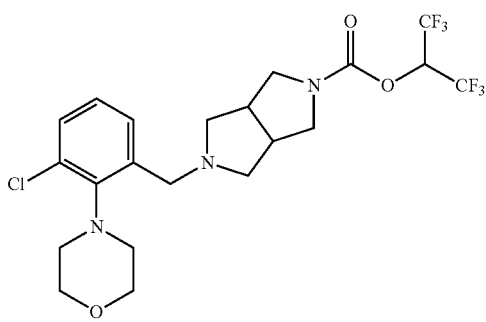 [SMILES: O=C(OC(C(F)(F)F)C(F)(F)F)N1CC2CN(Cc3cccc(Cl)c3N3CCOCC3)CC2C1]

The title compound was synthesized directly from commercially available 3-chloro-2-fluorobenzaldehyde and morpholine according to the representative procedures of Example 3 (Step 1) followed by Example 9 (Step 1-3) to provide 1,1,1,3,3,3-hexafluoropropan-2-yl 5-[[3-chloro-2-(morpholin-4-yl)phenyl]methyl]-octahydropyrrolo[3,4-c]pyrrole-2-carboxylate as a yellow oil. ¹H NMR (300 MHz, Chloroform-d) δ 7.23-7.28 (m, 2H), 7.05-7.10 (m, 1H), 5.66-5.79 (m, 1H), 3.84-3.94 (m, 2H), 3.62-3.75 (m, 8H), 3.31-3.39 (m, 2H), 2.88 (br, 2H), 2.73-2.77 (m, 2H), 2.57-2.62 (m, 4H). LCMS (ESI, m/z): 516 [M+H]⁺.

Example 45

1,1,1,3,3,3-Hexafluoropropan-2-yl 5-[[2-(morpholin-4-yl)-3-(trifluoromethyl)phenyl]methyl]-octahydropyrrolo[3,4-c]pyrrole-2-carboxylate

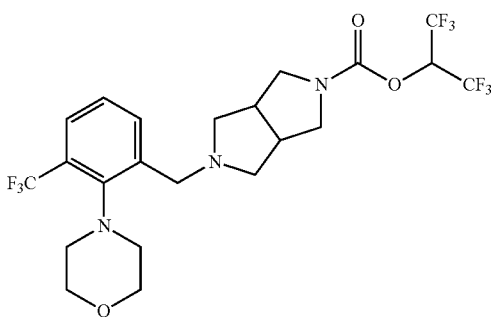 [SMILES: O=C(OC(C(F)(F)F)C(F)(F)F)N1CC2CN(Cc3cccc(C(F)(F)F)c3N3CCOCC3)CC2C1]

The title compound was synthesized directly from commercially available 2-fluoro-3-(trifluoromethyl)benzaldehyde and morpholine according to the representative procedures of Example 3 (Step 1) followed by Example 9 (Step 1-3) to provide 1,1,1,3,3,3-hexafluoropropan-2-yl 5-[[2-(morpholin-4-yl)-3-(trifluoromethyl)phenyl]methyl]-octahydropyrrolo[3,4-c]pyrrole-2-carboxylate as a light yellow oil. ¹H NMR (300 MHz, Chloroform-d) δ 7.71 (d, J=7.5 Hz, 1H), 7.55-7.58 (m, 1H), 7.24-7.29 (m, 1H), 5.70-5.82 (m, 1H), 3.72-3.79 (m, 8H), 3.33-3.50 (m, 4H), 2.81-2.91 (m, 4H), 2.54-2.68 (m, 4H). LCMS (ESI, m/z): 550 [M+H]⁺.

Example 46

1,1,1,3,3,3-Hexafluoropropan-2-yl 5-[(2-methyl-3-[2-oxa-7-azaspiro[4.4]nonan-7-yl]phenyl)methyl]-octahydropyrrolo[3,4-c]pyrrole-2-carboxylate

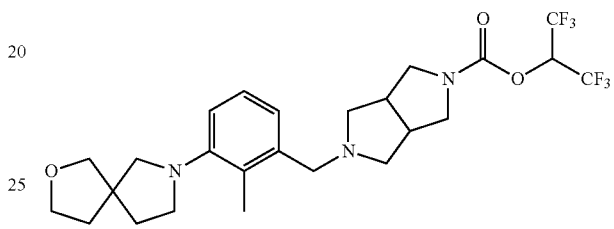

The title compound was synthesized from 3-fluoro-2-methylbenzaldehyde, tert-butyl octahydropyrrolo[3,4-c]pyrrole-2-carboxylate, and 2-oxa-7-azaspiro[4.4]nonane as described in Example 9 (Step 1), Example 11 (Step 1), Example 5 (Step 3), and Example 8 (Step 4, DCM used instead of MeCN) to provide 1,1,1,3,3,3-hexafluoropropan-2-yl 5-[(2-methyl-3-[2-oxa-7-azaspiro[4.4]nonan-7-yl]phenyl)methyl]-octahydropyrrolo[3,4-c]pyrrole-2-carboxylate as a yellow oil. ¹H NMR (300 MHz, Chloroform-d) δ 7.02-7.08 (m, 1H), 6.88-6.91 (m, 2H), 5.73-5.77 (m, 1H), 3.77-3.92 (m, 6H), 3.55 (br, 2H), 3.31-3.37 (m, 2H), 3.03-3.30 (m, 4H), 2.83 (br, 2H), 2.48-2.58 (m, 4H), 2.26 (s, 3H), 1.89-2.06 (m, 4H). LCMS (ESI, m/z): 536 [M+H]⁺.

Example 47

1,1,1,3,3,3-Hexafluoropropan-2-yl 5-[[2-methyl-3-(morpholin-4-yl)phenyl]methyl]-octahydropyrrolo[3,4-c]pyrrole-2-carboxylate

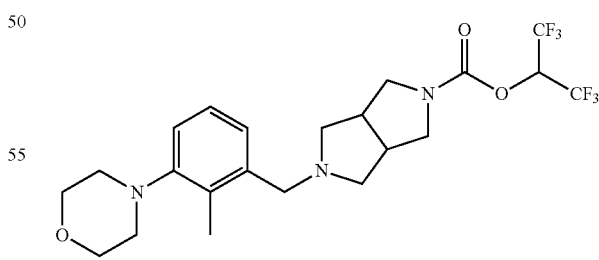

The title compound was synthesized from 3-fluoro-2-methylbenzaldehyde, tert-butyl octahydropyrrolo[3,4-c]pyrrole-2-carboxylate, and morpholine as described in Example 9 (Step 1), Example 11 (Step 1), Example 5 (Step 3), and Example 8 (Step 4, DCM used instead of MeCN) to provide 1,1,1,3,3,3-hexafluoropropan-2-yl 5-[[2-methyl-3-(morpholin-4-yl)phenyl]methyl]-octahydropyrrolo[3,4-c]pyrrole-2- carboxylate as a light yellow solid. $^1$H NMR (300 MHz, Chloroform-d) δ 7.10-7.15 (m, 1H), 7.00-7.02 (m, 2H), 5.67-5.79 (m, 1H), 3.84-3.87 (m, 4H), 3.68-3.74 (m, 2H), 3.56 (br, 2H), 3.30-3.39 (m, 2H), 2.87-2.90 (m, 6H), 2.53-2.58 (m, 4H), 2.31 (s, 3H). LCMS (ESI, m/z): 496 [M+H]$^+$.

Example 48

1,1,1,3,3,3-Hexafluoropropan-2-yl 5-[(2-chloro-3-[2-oxa-7-azaspiro[4.4]nonan-7-yl]phenyl)methyl]-octahydropyrrolo[3,4-c]pyrrole-2-carboxylate

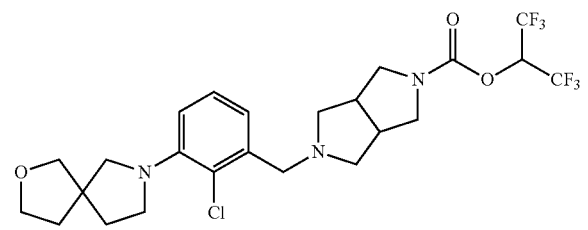 [SMILES: O=C(OC(C(F)(F)F)C(F)(F)F)N1CC2CN(Cc3cccc(N4CCC5(CCOC5)C4)c3Cl)CC2C1]

The title compound was synthesized from 2-chloro-3-fluorobenzaldehyde, tert-butyl octahydropyrrolo[3,4-c]pyrrole-2-carboxylate, and 2-oxa-7-azaspiro[4.4]nonane as described in Example 9 (Step 1), Example 11 (Step 1), Example 5 (Step 3), and Example 8 (Step 4, DCM used instead of MeCN) to provide 1,1,1,3,3,3-hexafluoropropan-2-yl 5-[(2-chloro-3-[2-oxa-7-azaspiro[4.4]nonan-7-yl]phenyl)methyl]-octahydropyrrolo[3,4-c]pyrrole-2-carboxylate as an orange oil. $^1$H NMR (300 MHz, Chloroform-d) δ 7.10-7.15 (m, 1H), 6.99-7.02 (m, 1H), 6.82-6.85 (m, 1H), 5.73-5.77 (m, 1H), 3.87-3.94 (m, 2H), 3.65-3.79 (m, 6H), 3.27-3.46 (m, 6H), 2.85-2.88 (m, 2H), 2.63-2.64 (m, 4H), 1.91-2.05 (m, 4H). LCMS (ESI, m/z): 556 [M+H]$^+$.

Example 49

1,1,1,3,3,3-Hexafluoropropan-2-yl 5-[[2-chloro-3-(morpholin-4-yl)phenyl]methyl]-octahydropyrrolo[3,4-c]pyrrole-2-carboxylate

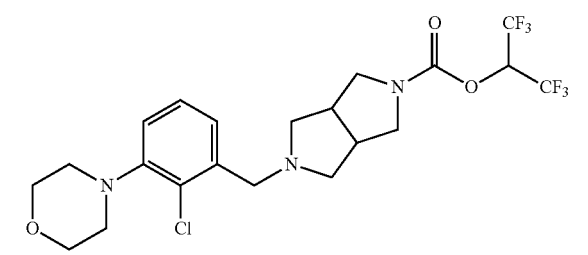 [SMILES: O=C(OC(C(F)(F)F)C(F)(F)F)N1CC2CN(Cc3cccc(N4CCOCC4)c3Cl)CC2C1]

The title compound was synthesized from 2-chloro-3-fluorobenzaldehyde, tert-butyl octahydropyrrolo[3,4-c]pyrrole-2-carboxylate, and morpholine as described in Example 9 (Step 1), Example 11 (Step 1), Example 5 (Step 3), and Example 8 (Step 4, DCM used instead of MeCN) to provide 1,1,1,3,3,3-hexafluoropropan-2-yl 5-[[2-chloro-3-(morpholin-4-yl)phenyl]methyl]-octahydropyrrolo[3,4-c]pyrrole-2-carboxylate as an off-white solid. $^1$H NMR (300 MHz, Chloroform-d) δ 7.19-7.26 (m, 2H), 6.98 (d, J=6.9 Hz, 1H), 5.68-5.80 (m, 1H), 3.87-3.90 (m, 4H), 3.70-3.74 (m, 4H), 3.40 (br, 2H), 3.02-3.05 (m, 4H), 2.90 (br, 2H), 2.62 (br, 4H). LCMS (ESI, m/z): 516 [M+H]$^+$.

Example 50

1,1,1,3,3,3-Hexafluoropropan-2-yl 5-((1-methyl-3-phenyl-1H-pyrazol-4-yl)methyl)hexahydropyrrolo[3,4-c]pyrrole-2(1H)-carboxylate

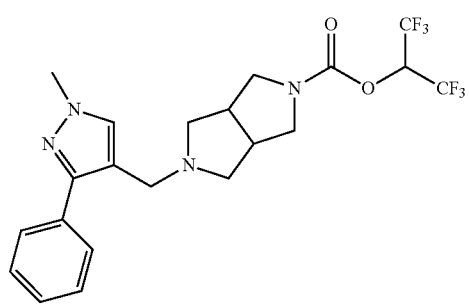 [SMILES: Cn1cc(CN2CC3CN(C(=O)OC(C(F)(F)F)C(F)(F)F)CC3C2)c(-c2ccccc2)n1]

The title compound was synthesized directly from commercially available 1-methyl-3-phenyl-1H-pyrazole-4-carbaldehyde and tert-butyl hexahydropyrrolo[3,4-c]pyrrole-2(1H)-carboxylate according to the representative procedure of Example 1 (Steps 1-3) to provide 1,1,1,3,3,3-hexafluoropropan-2-yl 5-((1-methyl-3-phenyl-1H-pyrazol-4-yl)methyl)hexahydropyrrolo[3,4-c]pyrrole-2(1H)-carboxylate. $^1$H NMR (400 MHz, Chloroform-d) δ 7.76-7.72 (m, 2H), 7.38 (t, J=7.4 Hz, 2H), 7.33-7.28 (m, 2H), 5.72 (hep, J=6.3 Hz, 1H), 3.92 (s, 3H), 3.72 (dd, J=11.6, 8.0 Hz, 2H), 3.55 (s, 2H), 3.34-3.25 (m, 2H), 2.91-2.81 (m, 2H), 2.63-2.47 (m, 4H). LCMS (ESI, m/z): 477.1 [M+H]$^+$.

Example 51

1,1,1,3,3,3-Hexafluoropropan-2-yl 5-[[3-(2-chlorophenyl)-1-methyl-1H-pyrazol-4-yl]methyl]-octahydropyrrolo[3,4-c]pyrrole-2-carboxylate

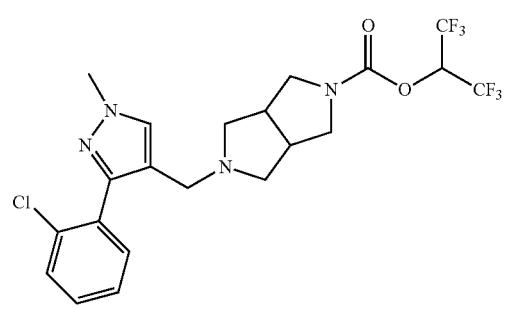 [SMILES: Cn1cc(CN2CC3CN(C(=O)OC(C(F)(F)F)C(F)(F)F)CC3C2)c(-c2ccccc2Cl)n1]

Step 1: Preparation of (E/Z)-1-[1-(2-chlorophenyl) ethylidene]-2-methylhydrazine

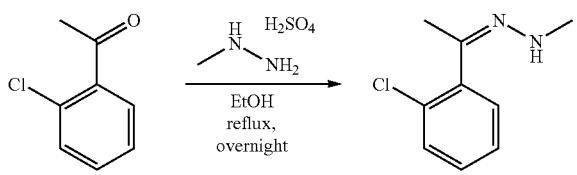

A 100-mL round-bottom flask was charged with 1-(2-chlorophenyl)ethan-1-one (3.80 g, 24.6 mmol, 1.20 equiv), methylhydrazine sulfate (3.00 g, 20.8 mmol, 1.00 equiv), and ethanol (30 mL) under nitrogen. The resulting solution was heated to reflux overnight. Reaction progress was monitored by LCMS. The resulting mixture was concentrated under reduced pressure to provide 7.00 g (crude) of (E/Z)-1-[1-(2-chlorophenyl)ethylidene]-2-methylhydrazine as a yellow oil. LCMS (ESI, m/z): 183 [M+H]$^+$.

Step 2: Preparation of 3-(2-chlorophenyl)-1-methyl-1H-pyrazole-4-carbaldehyde

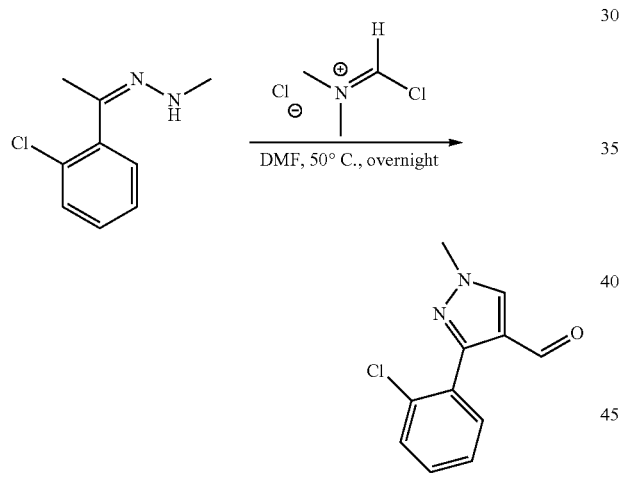

A 100-mL round-bottom flask was charged with (E/Z)-1-[1-(2-chlorophenyl)ethylidene]-2-methylhydrazine (2.00 g, 11.0 mmol, 1.00 equiv), N-(chloromethylene)-N-methyl-methanaminium chloride (12.7 g, 99.2 mmol, 9.06 equiv), and N,N-dimethylformamide (40 mL) under nitrogen. The resulting solution was stirred overnight at 50° C. Reaction progress was monitored by LCMS. The reaction was then quenched with saturated sodium carbonate solution (100 mL). The resulting solution was extracted with ethyl acetate (3×100 mL), and the organic layers were combined, washed with brine (2×100 mL), dried over sodium sulfate, filtered, and concentrated under reduced pressure. The residue was chromatographed on a silica gel column with ethyl acetate/petroleum ether (1/1) to yield 1.00 g (41% yield) of 3-(2-chlorophenyl)-1-methyl-1H-pyrazole-4-carbaldehyde as a yellow solid. LCMS (ESI, m/z): 221 [M+H]$^+$.

Step 3-5: Preparation of 1,1,1,3,3,3-hexafluoropropan-2-yl 5-[[3-(2-chlorophenyl)-1-methyl-1H-pyrazol-4-yl]methyl]-octahydropyrrolo[3,4-c]pyrrole-2-carboxylate The title compound was synthesized from 3-(2-chlorophenyl)-1-methyl-1H-pyrazole-4-carbaldehyde as described in Example 9 (Step 1), Example 5 (Step 3), and Example 8 (Step 4, CDM used instead of MeCN) to provide 1,1,1,3,3,3-hexafluoropropan-2-yl 5-[[3-(2-chlorophenyl)-1-methyl-1H-pyrazol-4-yl]methyl]-octahydropyrrolo[3,4-c]pyrrole-2-carboxylate as a yellow oil. $^1$H NMR (400 MHz, Chloroform-d) δ 7.37-7.45 (m, 3H), 7.30-7.31 (m, 1H), 7.26-7.29 (m, 1H), 5.72-5.78 (m, 1H), 3.98 (s, 3H), 3.66-3.70 (m, 2H), 3.50 (s, 2H), 3.05-3.07 (m, 2H), 2.78 (br, 2H), 2.45-2.51 (m, 2H), 2.33 (br, 2H). LCMS (ESI, m/z): 511 [M+H]$^+$.

Example 52

1,1,1,3,3,3-Hexafluoropropan-2-yl 5-[[3-(1-acetylpiperidin-4-yl)-1-methyl-1H-pyrazol-4-yl]methyl]-octahydropyrrolo[3,4-c]pyrrole-2-carboxylate

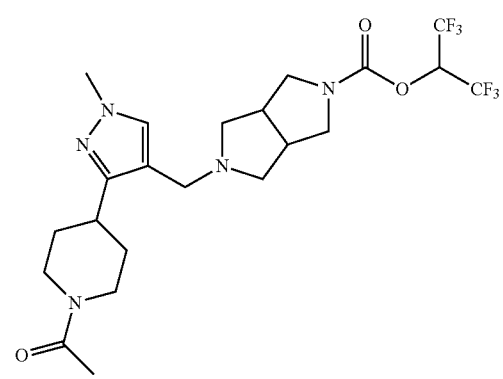 [SMILES: CC(=O)N1CCC(c2nn(C)cc2CN2CC3CN(C(=O)OC(C(F)(F)F)C(F)(F)F)CC3C2)CC1]

Step 1: Preparation of 4-[(E/Z)-1-(2-methylhydrazin-1-ylidene)ethyl]pyridine

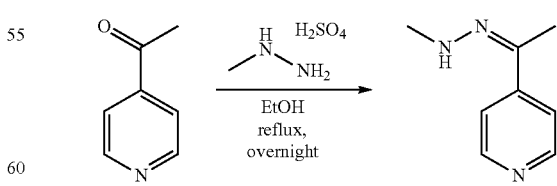

The title compound was synthesized from 1-(pyridin-4-yl)ethan-1-one as described in Example 51 (Step 1) to provide crude 4-[(E/Z)-1-(2-methylhydrazin-1-ylidene)ethyl]pyridine as a yellow solid. LCMS (ESI, m/z): 150 [M+H]$^+$.

Step 2: Preparation of 1-methyl-3-(pyridin-4-yl)-1H-pyrazole-4-carbaldehyde

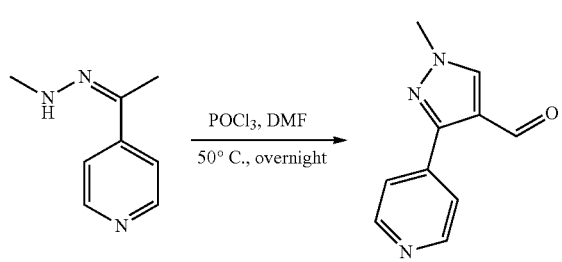

A 500-mL round-bottom flask was charged with N,N-dimethylformamide (250 mL) under nitrogen. Phosphoryl chloride (230 g, 1.50 mol, 8.95 equiv) was added dropwise at 0° C. The resulting solution was stirred for 1 h at room temperature. 4-[(E/Z)-1-(2-Methylhydrazin-1-ylidene)ethyl]pyridine (25.0 g, 168 mmol, 1.00 equiv) was added. The resulting solution was stirred overnight at 50° C. Reaction progress was monitored by LCMS. The reaction was then quenched with water (500 mL). The pH value of the solution was adjusted to 8 with sodium carbonate. The resulting solution was extracted with ethyl acetate (4×500 mL), and the organic layers were combined, washed with brine (2×500 mL), dried over anhydrous sodium sulfate, filtered, and concentrated under reduced pressure. The residue was chromatographed on a silica gel column with dichloromethane/methanol (100/1) to yield 20.0 g (64% yield) of 1-methyl-3-(pyridin-4-yl)-1H-pyrazole-4-carbaldehyde as a yellow solid. LCMS (ESI, m/z): 188 [M+H]$^+$.

Step 3: Preparation of tert-butyl 5-[[1-methyl-3-(pyridin-4-yl)-1H-pyrazol-4-yl]methyl]-octahydro-pyrrolo[3,4-c]pyrrole-2-carboxylate

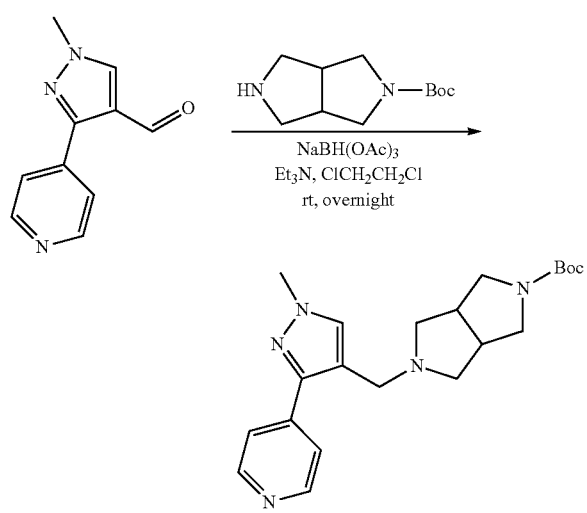

The title compound was synthesized from 1-methyl-3-(pyridin-4-yl)-1H-pyrazole-4-carbaldehyde as described in Example 9 (Step 1) to provide tert-butyl 5-[[1-methyl-3-(pyridin-4-yl)-1H-pyrazol-4-yl]methyl]-octahydropyrrolo[3,4-c]pyrrole-2-carboxylate as a yellow oil. LCMS (ESI, m/z): 384 [M+H]$^+$.

Step 4: Preparation of 1-benzyl-4-[4-([5-[(tert-butoxy)carbonyl]-octahydropyrrolo[3,4-c]pyrrol-2-yl]methyl)-1-methyl-1H-pyrazol-3-yl]pyridin-1-ium bromide

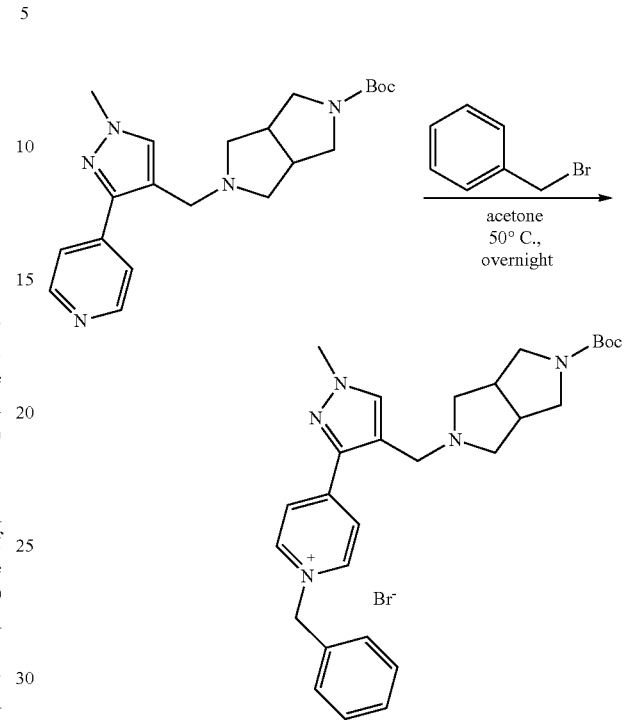

A 250-mL round-bottom flask was charged with tert-butyl 5-[[1-methyl-3-(pyridin-4-yl)-1H-pyrazol-4-yl]methyl]-octahydropyrrolo[3,4-c]pyrrole-2-carboxylate (10.0 g, 26.1 mmol, 1.00 equiv), in acetone (100 mL), and (bromomethyl)benzene (4.70 g, 27.5 mmol, 1.05 equiv). The resulting solution was stirred overnight at 50° C. Reaction progress was monitored by LCMS. The resulting mixture was concentrated under reduced pressure. The crude product was triturated with acetone/ether (1/10) to yield 15.0 g (crude) of 1-benzyl-4-[4-([5-[(tert-butoxy)carbonyl]-octahydropyrrolo[3,4-c]pyrrol-2-yl]methyl)-1-methyl-1H-pyrazol-3-yl]pyridin-1-ium bromide as a yellow solid. LCMS (ESI, m/z): 474 [M-Br]$^+$.

Step 5: Preparation of tert-butyl 5-[[3-(1-benzyl-1,2,3,6-tetrahydropyridin-4-yl)-1-methyl-1H-pyrazol-4-yl]methyl]-octahydropyrrolo[3,4-c]pyrrole-2-carboxylate

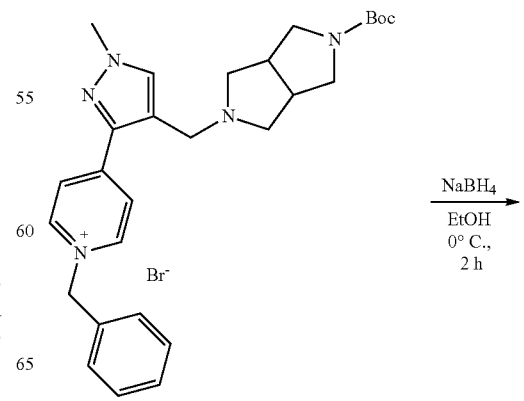

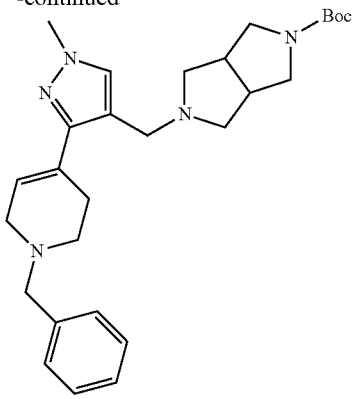

A 250-mL round-bottom flask was charged with 1-benzyl-4-[4-([5-[(tert-butoxy)carbonyl]-octahydropyrrolo[3,4-c]pyrrol-2-yl]methyl)-1-methyl-1H-pyrazol-3-yl]pyridin-1-ium bromide (15.0 g, 27.1 mmol, 1.00 equiv), in ethanol (150 mL), under nitrogen. Sodium borohydride (1.55 g, 41.0 mmol, 1.51 equiv) was added in several batches at 0° C. The resulting solution was stirred for 2 h at room temperature. Reaction progress was monitored by LCMS. The reaction was then quenched with water (10 mL), and the mixture was concentrated under reduced pressure. The residue was chromatographed on a silica gel column with dichloromethane/methanol (10/1) to yield 8.50 g (66% yield) of tert-butyl 5-[[3-(1-benzyl-1,2,3,6-tetrahydropyridin-4-yl)-1-methyl-1H-pyrazol-4-yl]methyl]-octahydropyrrolo[3,4-c]pyrrole-2-carboxylate as a yellow oil. LCMS (ESI, m/z): 478 [M+H]⁺.

Step 6: Preparation of tert-butyl 5-[[1-methyl-3-(piperidin-4-yl)-1H-pyrazol-4-yl]methyl]-octahydropyrrolo[3,4-c]pyrrole-2-carboxylate

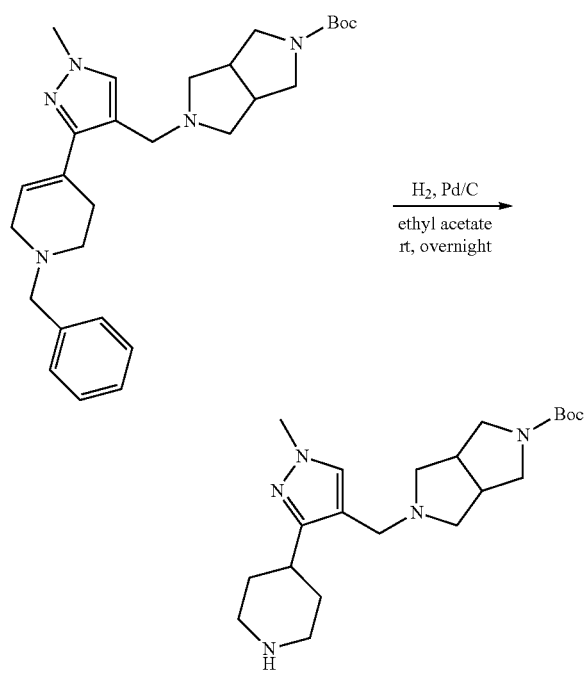

A 250-mL round-bottom flask was charged with tert-butyl 5-[[3-(1-benzyl-1,2,3,6-tetrahydropyridin-4-yl)-1-methyl-1H-pyrazol-4-yl]methyl]-octahydropyrrolo[3,4-c]pyrrole-2-carboxylate (8.50 g, 17.8 mmol, 1.00 equiv), in ethyl acetate (100 mL), and palladium on carbon (2.00 g). Hydrogen was introduced to the flask. The resulting solution was stirred overnight at room temperature. Reaction progress was monitored by LCMS. The solids were filtered out. The resulting mixture was concentrated under reduced pressure to provide 800 mg (12% yield) of tert-butyl 5-[[1-methyl-3-(piperidin-4-yl)-1H-pyrazol-4-yl]methyl]-octahydropyrrolo[3,4-c]pyrrole-2-carboxylate as a yellow oil. LCMS (ESI, m/z): 390 [M+H]⁺.

Step 7: Preparation of tert-butyl 5-[[3-(1-acetylpiperidin-4-yl)-1-methyl-1H-pyrazol-4-yl]methyl]-octahydropyrrolo[3,4-c]pyrrole-2-carboxylate

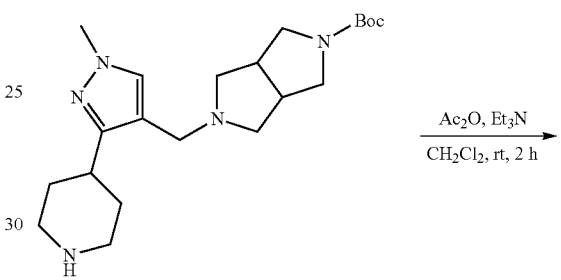

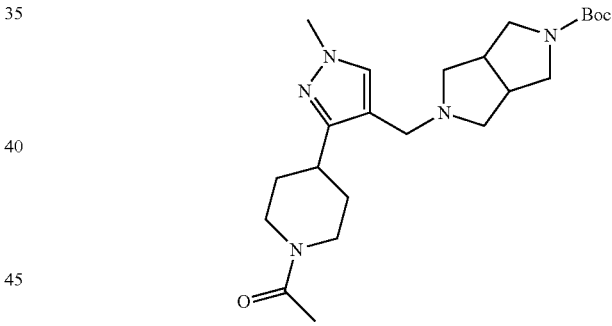

A 50-mL round-bottom flask was charged with tert-butyl 5-[[1-methyl-3-(piperidin-4-yl)-1H-pyrazol-4-yl]methyl]-octahydropyrrolo[3,4-c]pyrrole-2-carboxylate (400 mg, 1.03 mmol, 1.00 equiv), in dichloromethane (10 mL), and triethylamine (202 mg, 2.00 mmol, 1.95 equiv) under nitrogen. Acetic anhydride (153 mg, 1.50 mmol, 1.46 equiv) was added dropwise at 0° C. The resulting solution was stirred for 2 h at room temperature. Reaction progress was monitored by LCMS. The reaction was then quenched with water (20 mL). The mixture was extracted with dichloromethane (3×20 mL), and the organic layers were combined, washed with brine (2×20 mL), dried over anhydrous sodium sulfate, filtered, and concentrated under reduced pressure. The residue was chromatographed on a silica gel column with dichloromethane/methanol (10/1) to yield 220 mg (50% yield) of tert-butyl 5-[[3-(1-acetylpiperidin-4-yl)-1-methyl-1H-pyrazol-4-yl]methyl]-octahydropyrrolo[3,4-c]pyrrole-2-carboxylate as a yellow oil. LCMS (ESI, m/z): 432 [M+H]⁺.

Step 8-9: Preparation of 1,1,1,3,3,3-hexafluoropropan-2-yl 5-[[3-(1-acetylpiperidin-4-yl)-1-methyl-1H-pyrazol-4-yl]methyl]-octahydropyrrolo[3,4-c]pyrrole-2-carboxylate

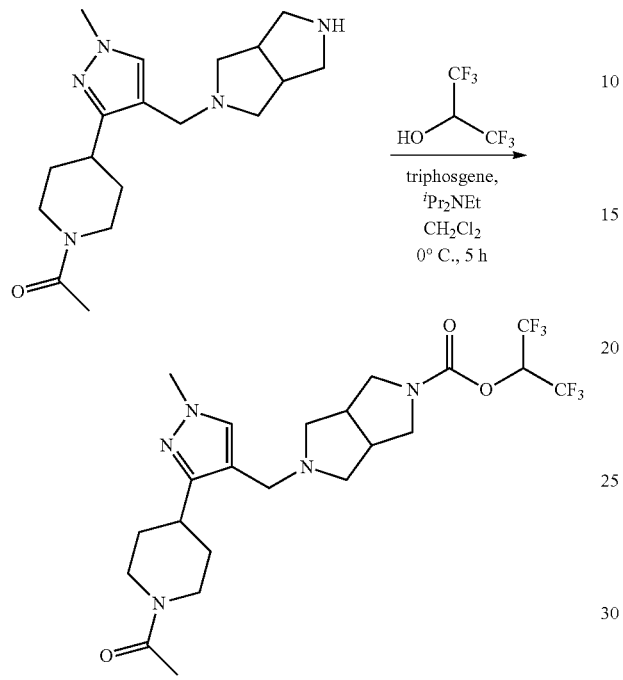

The title compound was synthesized from tert-butyl 5-[[3-(1-acetylpiperidin-4-yl)-1-methyl-1H-pyrazol-4-yl]methyl]-octahydropyrrolo[3,4-c]pyrrole-2-carboxylate as described in Example 5 (Step 3) followed by Example 8 (Step 4, DCM used instead of MeCN) to provide 1,1,1,3,3,3-hexafluoropropan-2-yl 5-[[3-(1-acetylpiperidin-4-yl)-1-methyl-1H-pyrazol-4-yl]methy]-octahydropyrrolo[3,4-c]pyrrole-2-carboxylate as a light yellow oil. $^1$H NMR (300 MHz, Chloroform-d) δ 7.15 (s, 1H), 5.69-5.77 (m, 1H), 4.65-4.69 (m, 1H), 3.85-3.90 (m, 1H), 3.80 (s, 3H), 3.68-3.74 (m, 2H), 3.33-3.48 (m, 4H), 3.06-3.16 (m, 1H), 2.87-2.92 (m, 3H), 2.50-2.68 (m, 5H), 2.09 (s, 3H), 1.86-1.87 (m, 4H). LCMS (ESI, m/z): 526 [M+H]$^+$.

Example 53

1,1,1,3,3,3-Hexafluoropropan-2-yl 5-[[3-phenyl-1-(propan-2-yl)-1H-pyrazol-4-yl]methyl]-octahydropyrrolo[3,4-c]pyrrole-2-carboxylate

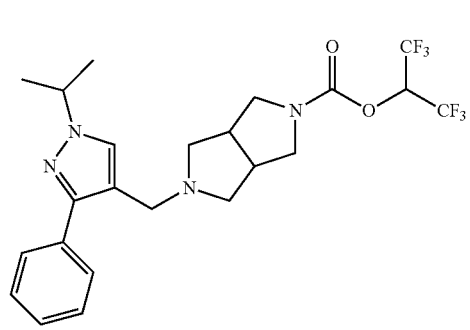 [SMILES: CC(C)n1cc(CN2CC3CN(C(=O)OC(C(F)(F)F)C(F)(F)F)CC3C2)c(-c2ccccc2)n1]

The title compound was synthesized directly from commercially available 1-phenylethan-1-one and propan-2-ylhydrazine hydrochloride according to the representative procedures of Example 51, Steps 1-5 to provide 1,1,1,3,3,3-hexafluoropropan-2-yl 5-[[3-phenyl-1-(propan-2-yl)-1H-pyrazol-4-yl]methyl]-octahydropyrrolo[3,4-c]pyrrole-2-carboxylate as a yellow oil. $^1$H NMR (300 MHz, Chloroform-d) δ 7.76 (d, J=7.2 Hz, 2H), 7.35-7.40 (m, 3H), 7.26-7.31 (m, 1H), 5.68-5.77 (m, 1H), 4.47-4.56 (m, 1H), 3.68-3.75 (m, 2H), 3.56 (s, 2H), 3.26-3.33 (m, 2H), 2.85-2.91 (m, 2H), 2.53-2.58 (m, 4H), 1.53 (d, J=6.6 Hz, 6H). LCMS (ESI, m/z): 505 [M+H]$^+$.

Example 54

1,1,1,3,3,3-Hexafluoropropan-2-yl 5-[[3-(2-chlorophenyl)-1-(propan-2-yl)-1H-pyrazol-4-yl]methyl]-octahydropyrrolo[3,4-c]pyrrole-2-carboxylate

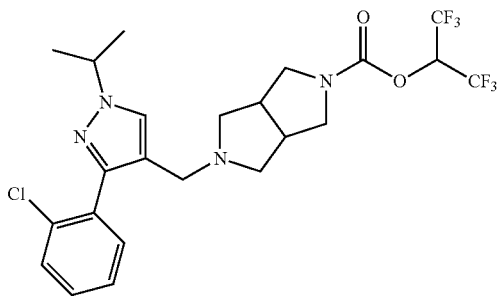 [SMILES: CC(C)n1cc(CN2CC3CN(C(=O)OC(C(F)(F)F)C(F)(F)F)CC3C2)c(-c2ccccc2Cl)n1]

The title compound was synthesized directly from commercially available 1-(2-chlorophenyl)ethan-1-one and propan-2-ylhydrazine hydrochloride according to the representative procedures of Example 51, Steps 1-5 to provide 1,1,1,3,3,3-hexafluoropropan-2-yl 5-[[3-(2-chlorophenyl)-1-(propan-2-yl)-1H-pyrazol-4-yl]methyl]-octahydropyrrolo[3,4-c]pyrrole-2-carboxylate as a yellow oil. $^1$H NMR (400 MHz, Chloroform-d) δ 7.40-7.45 (m, 3H), 7.29 (s, 2H), 5.71-5.78 (m, 1H), 4.51-4.58 (m, 1H), 3.65-3.70 (m, 2H), 3.51 (br, 2H), 3.08 (br, 2H), 2.78 (br, 2H), 2.37-2.47 (m, 4H), 1.58 (d, J=6.8 Hz, 6H). LCMS (ESI, m/z): 539 [M+H]$^+$.

Example 55

1,1,1,3,3,3-Hexafluoropropan-2-yl 5-[[3-(1-acetylpiperidin-4-yl)-1-(propan-2-yl)-1H-pyrazol-4-yl]methyl]-octahydropyrrolo[3,4-c]pyrrole-2-carboxylate

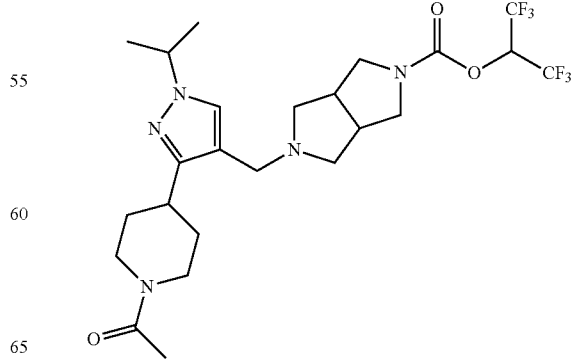

The title compound was synthesized directly from commercially available 1-(pyridin-4-yl)ethan-1-one and propan-2-ylhydrazine hydrochloride according to the representative procedures of Example 52, Steps 1-9 to provide 1,1,1,3,3,3-hexafluoropropan-2-yl 5-[[3-(1-acetylpiperidin-4-yl)-1-(propan-2-yl)-1H-pyrazol-4-yl]methyl]-octahydropyrrolo[3,4-c]pyrrole-2-carboxylate as a yellow oil. $^1$H NMR (300 MHz, Chloroform-d) δ 7.22 (s, 1H), 5.69-5.77 (m, 1H), 4.61-4.66 (m, 1H), 4.34-4.43 (m, 1H), 3.85-3.89 (m, 1H), 3.68-3.74 (m, 2H), 3.34-3.42 (m, 4H), 3.07-3.17 (m, 1H), 2.84-2.94 (m, 3H), 2.68-2.73 (m, 1H), 2.51-2.64 (m, 4H), 2.10 (s, 3H), 1.71-1.88 (m, 4H), 1.45 (d, J=6.8 Hz, 6H). LCMS (ESI, m/z): 554 [M+H]$^+$.

Example 56

1,1,1,3,3,3-Hexafluoropropan-2-yl 5-[[3-(1-methanesulfonylpiperidin-4-yl)-1-methyl-1H-pyrazol-4-yl]methyl]-octahydropyrrolo[3,4-c]pyrrole-2-carboxylate

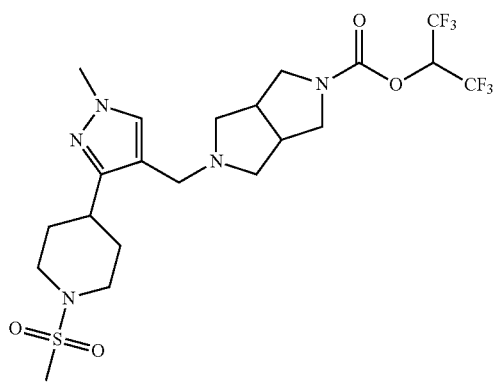 [SMILES: Cn1cc(CN2CC3CN(C(=O)OC(C(F)(F)F)C(F)(F)F)CC3C2)c(C2CCN(S(C)(=O)=O)CC2)n1]

The title compound was synthesized directly from commercially available 1-(pyridin-4-yl)ethan-1-one and methylhydrazine sulfate according to the representative procedures of Example 52, Steps 1-9, with methanesulfonyl chloride substituted for acetic anhydride in Step 7, to provide 1,1,1,3,3,3-hexafluoropropan-2-yl 5-[[3-(1-methanesulfonylpiperidin-4-yl)-1-methyl-1H-pyrazol-4-yl]methyl]-octahydropyrrolo[3,4-c]pyrrole-2-carboxylate as a colorless oil. $^1$H NMR (300 MHz, Chloroform-d) δ 7.16 (s, 1H), 5.68-5.77 (m, 1H), 3.81-3.94 (m, 5H), 3.67-3.73 (m, 2H), 3.34-3.41 (m, 4H), 2.74-2.86 (m, 8H), 2.51-2.57 (m, 4H), 1.93-1.97 (m, 4H). LCMS (ESI, m/z): 562 [M+H]$^+$.

Example 57

1,1,1,3,3,3-Hexafluoropropan-2-yl 5-[[3-(1-methanesulfonylpiperidin-4-yl)-1-(propan-2-yl)-1H-pyrazol-4-yl]methyl]-octahydropyrrolo[3,4-c]pyrrole-2-carboxylate

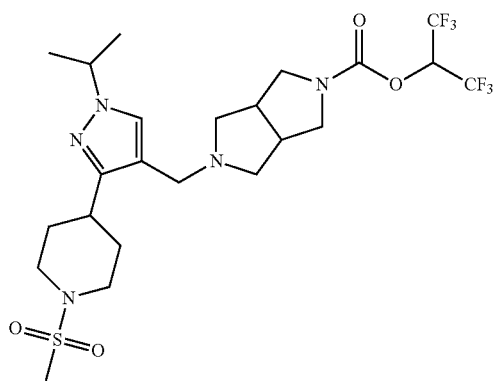 [SMILES: CC(C)n1cc(CN2CC3CN(C(=O)OC(C(F)(F)F)C(F)(F)F)CC3C2)c(C2CCN(S(C)(=O)=O)CC2)n1]

The title compound was synthesized directly from commercially available 1-(pyridin-4-yl)ethan-1-one and propan-2-ylhydrazine hydrochloride according to the representative procedures of Example 52, Steps 1-9, with methanesulfonyl chloride substituted for acetic anhydride in Step 7, to provide 1,1,1,3,3,3-hexafluoropropan-2-yl 5-[[3-(1-methanesulfonylpiperidin-4-yl)-1-(propan-2-yl)-1H-pyrazol-4-yl]methyl]-octahydropyrrolo[3,4-c]pyrrole-2-carboxylate as a light yellow oil. $^1$H NMR (300 MHz, Chloroform-d) δ 7.22 (s, 1H), 5.69-5.77 (m, 1H), 4.34-4.43 (m, 1H), 3.82 (m, 2H), 3.70-3.73 (m, 2H), 3.35-3.42 (m, 4H), 2.77-2.87 (m, 8H), 2.45-2.57 (m, 4H), 1.92-2.04 (m, 4H), 1.46 (d, J=6.8 Hz, 6H). LCMS (ESI, m/z): 590 [M+H]$^+$.

Example 58

1,1,1,3,3,3-Hexafluoropropan-2-yl 5-[(1-cyclohexyl-3-methyl-1H-pyrazol-5-yl)methyl]-octahydropyrrolo[3,4-c]pyrrole-2-carboxylate

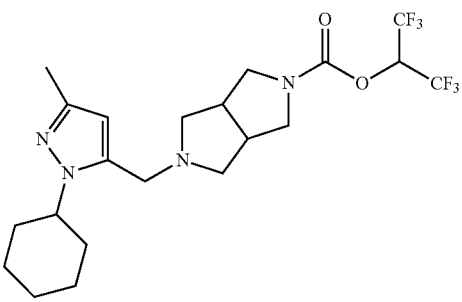 [SMILES: Cc1cc(CN2CC3CN(C(=O)OC(C(F)(F)F)C(F)(F)F)CC3C2)n(C2CCCCC2)n1]

Step 1: Preparation of ethyl(2E)-2-(methoxyimino)-4-oxopentanoate

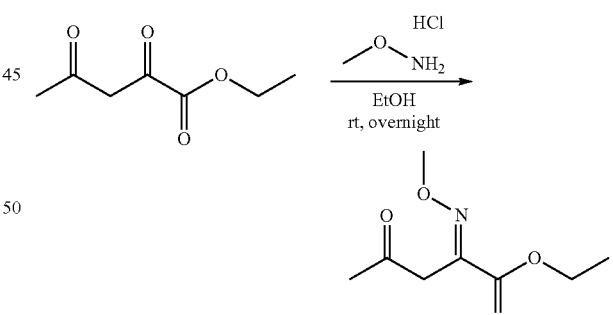

A 100-mL round-bottom flask was charged with ethyl 2,4-dioxopentanoate (15.0 g, 94.8 mmol, 1.00 equiv), in ethanol (100 mL), and methoxylamine hydrochloride (7.90 g, 95.2 mmol, 1.05 equiv) under nitrogen. The resulting solution was stirred overnight at room temperature. Reaction progress was monitored by LCMS. The resulting mixture was concentrated under reduced pressure. The residue was chromatographed on a silica gel column with ethyl acetate/petroleum ether (1/5) to yield 6.50 g (37% yield) of ethyl (2E)-2-(methoxyimino)-4-oxopentanoate as a colorless oil. LCMS (ESI, m/z): 188 [M+H]$^+$.

Step 2: Preparation of ethyl 1-cyclohexyl-3-methyl-1H-pyrazole-5-carboxylate

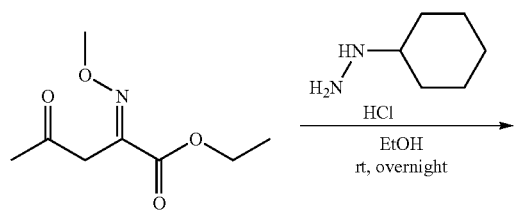

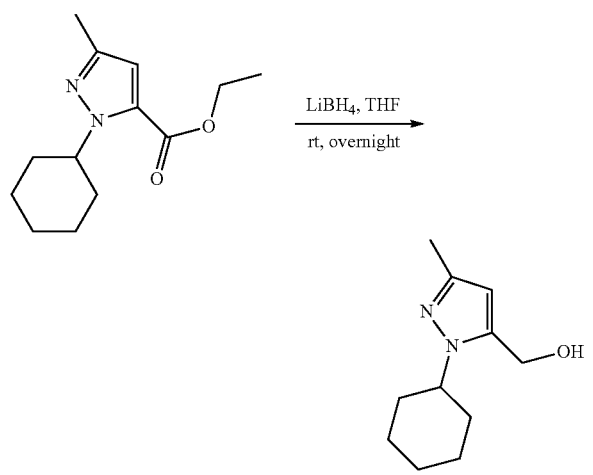

A 100-mL round-bottom flask was charged with ethyl (2E)-2-(methoxyimino)-4-oxopentanoate (1.00 g, 5.34 mmol, 1.00 equiv), in ethanol (20 mL), and cyclohexylhydrazine hydrogen chloride (1.60 g, 10.6 mmol, 2.00 equiv) under nitrogen. The resulting solution was heated to reflux overnight. Reaction progress was monitored by LCMS. The resulting mixture was concentrated under reduced pressure. The residue was chromatographed on a silica gel column with ethyl acetate/petroleum ether (1/10) to yield 1.00 g (79% yield) of ethyl 1-cyclohexyl-3-methyl-1H-pyrazole-5-carboxylate as a colorless oil. LCMS (ESI, m/z): 237 [M+H]+.

Step 3: Preparation of (1-cyclohexyl-3-methyl-1H-pyrazol-5-yl)methanol

A 100-mL round-bottom flask was charged with ethyl 1-cyclohexyl-3-methyl-1H-pyrazole-5-carboxylate (1.00 g, 4.23 mmol, 1.00 equiv), in tetrahydrofuran (20 mL), and lithium borohydride (466 mg, 21.2 mmol, 5.01 equiv) under nitrogen. The resulting solution was stirred overnight at room temperature. Reaction progress was monitored by LCMS. The reaction was then quenched with water (30 mL). The resulting solution was extracted with ethyl acetate (3×50 mL), and the organic layers were combined, washed with brine (2×50 mL), dried over anhydrous sodium sulfate, filtered, and concentrated under reduced pressure to provide 800 mg (97% yield) of (1-cyclohexyl-3-methyl-1H-pyrazol-5-yl)methanol as a white solid. LCMS (ESI, m/z): 195 [M+H]+.

Step 4: Preparation of 1-cyclohexyl-3-methyl-1H-pyrazole-5-carbaldehyde

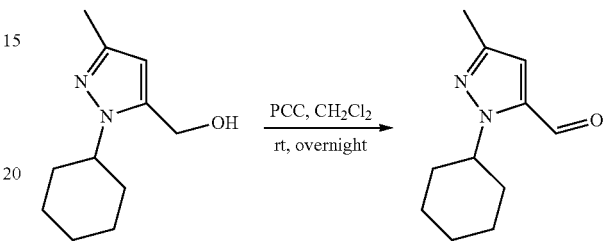

A 100-mL round-bottom flask was charged with (1-cyclohexyl-3-methyl-1H-pyrazol-5-yl)methanol (800 mg, 4.12 mmol, 1.00 equiv), in dichloromethane (20 mL), and pyridinium chlorochromate (1.78 g, 8.26 mmol, 2.01 equiv). The resulting solution was stirred overnight at room temperature. Reaction progress was monitored by LCMS. The resulting mixture was concentrated under reduced pressure. The residue was chromatographed on a silica gel column with ethyl acetate/petroleum ether (1/10) to yield 500 mg (63% yield) of 1-cyclohexyl-3-methyl-1H-pyrazole-5-carbaldehyde as a light-yellow oil. LCMS (ESI, m/z): 193 [M+H]+.

Step 5-7: Preparation of 1,1,1,3,3,3-hexafluoropropan-2-yl 5-[(1-cyclohexyl-3-methyl-1H-pyrazol-5-yl)methyl]-octahydropyrrolo[3,4-c]pyrrole-2-carboxylate

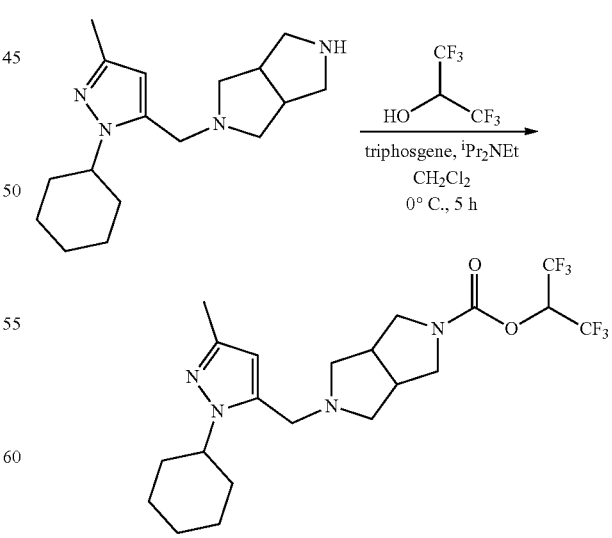

The title compound was synthesized from 1-cyclohexyl-3-methyl-1H-pyrazole-5-carbaldehyde as described in Example 9 (Step 1), Example 5 (Step 3), and Example 8

(Step 4, DCM used instead of MeCN) to provide 1,1,1,3,3,3-hexafluoropropan-2-yl 5-[(1-cyclohexyl-3-methyl-1H-pyrazol-5-yl)methyl]-octahydropyrrolo[3,4-c]pyrrole-2-carboxylate as a light-yellow oil. $^1$H NMR (300 MHz, Chloroform-d) δ 5.83 (s, 1H), 5.67-5.75 (m, 1H), 4.05-4.15 (m, 1H), 3.74-3.77 (m, 2H), 3.55 (br, 2H), 3.27-3.30 (m, 2H), 2.89 (br, 2H), 2.47-2.62 (m, 4H), 2.24 (s, 3H), 1.85-2.00 (m, 6H), 1.68 (br, 1H), 1.26-1.37 (m, 3H). LCMS (ESI, m/z): 483 [M+H]$^+$.

Example 59

1,1,1,3,3,3-Hexafluoropropan-2-yl 5-[[3-methyl-1-(propan-2-yl)-1H-pyrazol-5-yl]methyl]-octahydropyrrolo[3,4-c]pyrrole-2-carboxylate

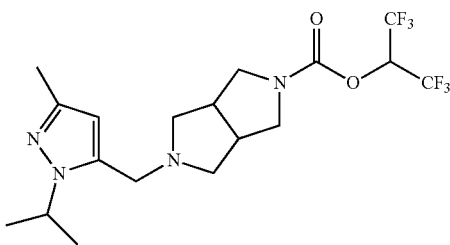 [SMILES: Cc1cc(CN2CC3CN(C(=O)OC(C(F)(F)F)C(F)(F)F)CC3C2)n(C(C)C)n1]

The title compound was synthesized from ethyl(2E)-2-(methoxyimino)-4-oxopentanoate (Example 58, Step 1) and commercially available propan-2-ylhydrazine hydrochloride according to the representative procedures of Example 58, Steps 2-7 to provide 1,1,1,3,3,3-hexafluoropropan-2-yl 5-[[3-methyl-1-(propan-2-yl)-1H-pyrazol-5-yl]methyl]-octahydropyrrolo[3,4-c]pyrrole-2-carboxylate as a yellow oil. $^1$H NMR (300 MHz, Chloroform-d) δ 5.82 (s, 1H), 5.67-5.76 (m, 1H), 4.51-4.60 (m, 1H), 3.69-3.75 (m, 2H), 3.53-3.57 (m, 2H), 3.31-3.38 (m, 2H), 2.88 (br, 2H), 2.49-2.60 (m, 4H), 2.24 (s, 3H), 1.42 (d, J=6.8 Hz, 6H). LCMS (ESI, m/z): 443 [M+H]$^+$.

Example 60

1,1,1,3,3,3-Hexafluoropropan-2-yl 5-[[1-(1-acetylpiperidin-4-yl)-3-methyl-1H-pyrazol-5-yl]methyl]-octahydropyrrolo[3,4-c]pyrrole-2-carboxylate

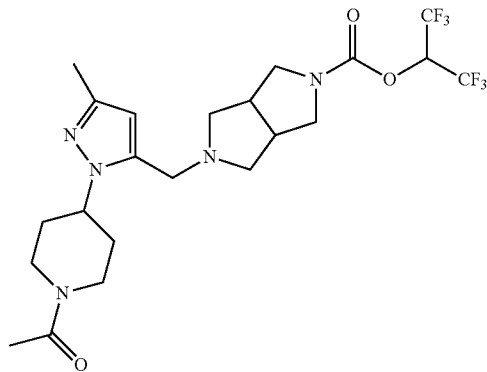 [SMILES: CC(=O)N1CCC(n2nc(C)cc2CN2CC3CN(C(=O)OC(C(F)(F)F)C(F)(F)F)CC3C2)CC1]

The title compound was synthesized from benzyl 4-hydrazinylpiperidine-1-carboxylate dihydrochloride following the procedures described for Example 58 (Step 1-4), Example 9 (Step 1), Example 52 (Step 6-7), Example 5 (Step 3) and Example 8 (Step 4, DCM used instead of MeCN) to provide 1,1,1,3,3,3-hexafluoropropan-2-yl 5-[[1-(1-acetylpiperidin-4-yl)-3-methyl-1H-pyrazol-5-yl]methyl]-octahydropyrrolo[3,4-c]pyrrole-2-carboxylate as a yellow solid. $^1$H NMR (300 MHz, Chloroform-d) δ 5.85 (s, 1H), 5.68-5.76 (m, 1H), 4.75-4.79 (m, 1H), 4.32-4.38 (m, 1H), 3.92-3.95 (m, 1H), 3.61-3.76 (m, 3H), 3.43-3.50 (m, 1H), 3.28-3.35 (m, 2H), 3.05-3.13 (m, 1H), 2.90 (br, 2H), 2.49-2.65 (m, 5H), 2.12-2.22 (m, 8H), 1.80-1.90 (m, 2H). LCMS (ESI, m/z): 526 [M+H]$^+$.

Example 61

1,1,1,3,3,3-Hexafluoropropan-2-yl 5-[[1-cyclohexyl-3-(propan-2-yl)-1H-pyrazol-5-yl]methyl]-octahydropyrrolo[3,4-c]pyrrole-2-carboxylate

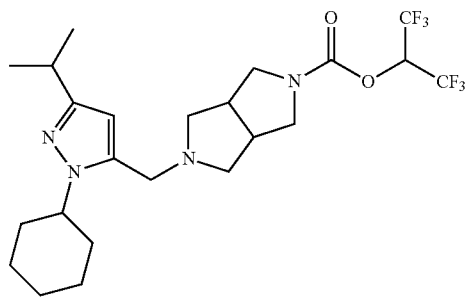 [SMILES: CC(C)c1cc(CN2CC3CN(C(=O)OC(C(F)(F)F)C(F)(F)F)CC3C2)n(C2CCCCC2)n1]

Step 1: Preparation of (E/Z)-1-cyclohexyl-2-(2-methylpropylidene)hydrazine

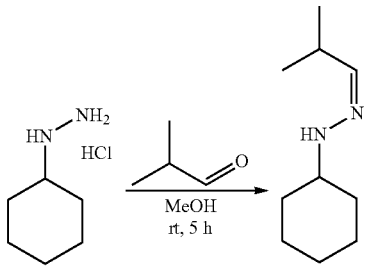

A 100-mL round-bottom flask was charged with cyclohexylhydrazine hydrochloride (1.50 g, 9.96 mmol, 1.00 equiv), in methanol (30 mL), and 2-methylpropanal (720 mg, 9.99 mmol, 1.00 equiv) under nitrogen. The resulting solution was stirred for 5 h at room temperature. Reaction progress was monitored by LCMS. The resulting mixture was concentrated under reduced pressure to provide 1.65 g (98% yield) of (E/Z)-1-cyclohexyl-2-(2-methylpropylidene)hydrazine as a colorless oil. LCMS (ESI, m/z): 169 [M+H]$^+$.

Step 2: Preparation of 1-cyclohexyl-N-methoxy-N-methyl-3-(propan-2-yl)-1H-pyrazole-5-carboxamide

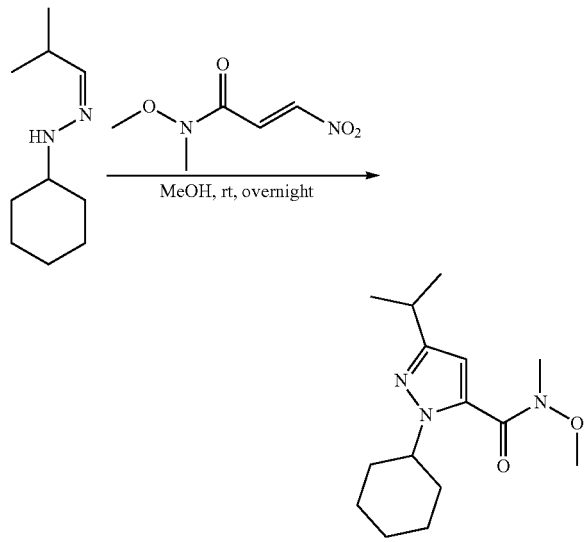

A 100-mL round-bottom flask was charged with (E/Z)-1-cyclohexyl-2-(2-methylpropylidene)hydrazine (1.65 g, 9.81 mmol, 1.00 equiv), in methanol (30 mL), and (2E)-N-methoxy-N-methyl-3-nitroprop-2-enamide (1.60 g, 9.99 mmol, 1.00 equiv). The resulting solution was stirred overnight at room temperature. The resulting mixture was concentrated under reduced pressure. The residue was chromatographed on a silica gel column with ethyl acetate/petroleum ether (1/3) to yield 0.560 g (20% yield) of 1-cyclohexyl-N-methoxy-N-methyl-3-(propan-2-yl)-1H-pyrazole-5-carboxamide as a yellow oil. LCMS (ESI, m/z): 280 [M+H]$^+$.

Step 3: Preparation of 1-cyclohexyl-3-(propan-2-yl)-1H-pyrazole-5-carbaldehyde

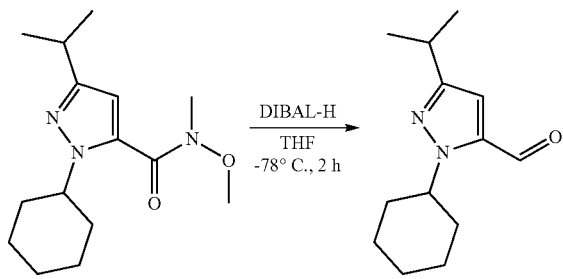 [SMILES: CON(C)C(=O)c1cc(C(C)C)nn1C1CCCCC1 ; CC(C)c1cc(C=O)n(C2CCCCC2)n1]

A 50-mL round-bottom flask was charged with 1-cyclohexyl-N-methoxy-N-methyl-3-(propan-2-yl)-1H-pyrazole-5-carboxamide (560 mg, 2.00 mmol, 1.00 equiv) in tetrahydrofuran (10 mL). Diisobutyl aluminium hydride (1 M in hexane, 4 mL, 4.00 mmol, 2.00 equiv) was added dropwise at −78° C. under nitrogen. The resulting solution was stirred for 2 h at −78° C. Reaction progress was monitored by LCMS. The reaction was then quenched with water (10 mL). The mixture was extracted with ethyl acetate (3×20 mL), and the organic layers were combined, washed with brine (2×20 mL), dried over anhydrous sodium sulfate, filtered, and concentrated under reduced pressure to provide 360 mg (82% yield) of 1-cyclohexyl-3-(propan-2-yl)-1H-pyrazole-5-carbaldehyde as a yellow oil. LCMS (ESI, m/z): 221 [M+H]$^+$.

Step 4-6: Preparation of 1,1,1,3,3,3-hexafluoropropan-2-yl 5-[[1-cyclohexyl-3-(propan-2-yl)-1H-pyrazol-5-yl]methyl]-octahydropyrrolo[3,4-c]pyrrole-2-carboxylate The title compound was synthesized from 1-cyclohexyl-3-(propan-2-yl)-1H-pyrazole-5-carbaldehyde as described in Example 9 (Step 1), Example 52 (Step 6-7), Example 5 (Step 3) and Example 8 (Step 4, DCM used instead of MeCN) to provide 1,1,1,3,3,3-hexafluoropropan-2-yl 5-[[1-cyclohexyl-3-(propan-2-yl)-1H-pyrazol-5-yl]methyl]-octahydropyrrolo[3,4-c]pyrrole-2-carboxylate as a yellow oil. $^1$H NMR (300 MHz, Chloroform-d) δ 5.85 (s, 1H), 5.67-5.76 (m, 1H), 4.05-4.15 (m, 1H), 3.75-3.77 (m, 2H), 3.55-3.59 (m, 2H), 3.27-3.31 (m, 2H), 2.89-3.00 (m, 3H), 2.48-2.61 (m, 4H), 1.81-2.00 (m, 6H), 1.61-1.67 (m, 1H), 1.25-1.40 (m, 3H), 1.21 (d, J=6.8 Hz, 6H). LCMS (ESI, m/z): 511 [M+H]$^+$.

Example 62

1,1,1,3,3,3-Hexafluoropropan-2-yl 5-[[1-(oxan-4-yl)-3-(propan-2-yl)-1H-pyrazol-5-yl]methyl]-octahydropyrrolo[3,4-c]pyrrole-2-carboxylate

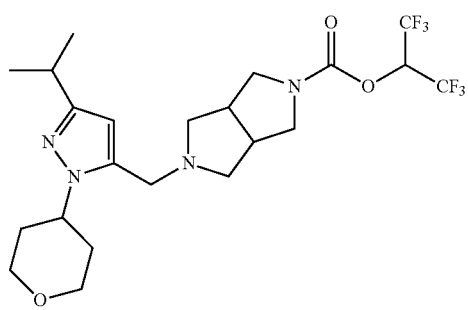 [SMILES: CC(C)c1cc(CN2CC3CN(C(=O)OC(C(F)(F)F)C(F)(F)F)CC3C2)n(C2CCOCC2)n1]

The title compound was synthesized from commercially available oxan-4-ylhydrazine hydrochloride and 2-methylpropanal according to the representative procedures of Example 61 (Steps 1-6) to provide 1,1,1,3,3,3-hexafluoropropan-2-yl 5-[[1-(oxan-4-yl)-3-(propan-2-yl)-1H-pyrazol-5-yl]methyl]-octahydropyrrolo[3,4-c]pyrrole-2-carboxylate as a yellow oil. $^1$H NMR (300 MHz, Chloroform-d) δ 5.88 (s, 1H), 5.67-5.75 (m, 1H), 4.29-4.37 (m, 1H), 4.05-4.09 (m, 2H), 3.70-3.77 (m, 2H), 3.56-3.57 (m, 2H), 3.39-3.48 (m, 2H), 3.28-3.33 (m, 2H), 2.89-2.99 (m, 3H), 2.51-2.59 (m, 4H), 2.28-2.35 (m, 2H), 1.72-1.76 (m, 2H), 1.22 (d, J=6.8 Hz, 6H). LCMS (ESI, m/z): 513 [M+H]$^+$.

Example 63

1,1,1,3,3,3-Hexafluoropropan-2-yl 5-([3-[2-(azetidin-1-yl)phenyl]-1-ethyl-1H-pyrazol-4-yl]methyl)-octahydropyrrolo[3,4-c]pyrrole-2-carboxylate

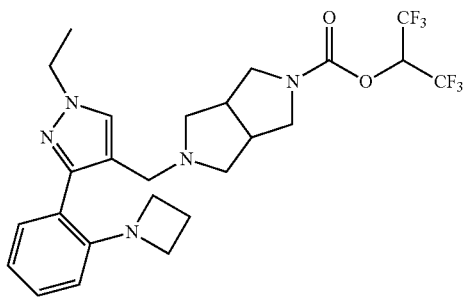 [SMILES: CCn1cc(CN2CC3CN(C(=O)OC(C(F)(F)F)C(F)(F)F)CC3C2)c(-c2ccccc2N2CCC2)n1]

The title compound was synthesized from 1-(2-bromophenyl)ethan-1-one, ethylhydrazine hydrochloride, and azetidine following the procedures described in Example 51 (Step 1), Example 52 (Step 2), Example 9 (Step 1), Example 11 (Step 1), Example 5 (Step 3), and Example 8 (Step 4) to provide 1,1,1,3,3,3-hexafluoropropan-2-yl 5-([3-[2-(azetidin-1-yl)phenyl]-1-ethyl-1H-pyrazol-4-yl]methyl)-octahydropyrrolo[3,4-c]pyrrole-2-carboxylate as a yellow oil. $^1$H NMR (300 MHz, Chloroform-d) δ 7.30 (s, 1H), 7.12-7.26 (m, 2H), 6.76 (t, J=7.4 Hz, 1H), 6.50 (d, J=8.1 Hz, 1H), 5.69-5.77 (m, 1H), 4.14-4.21 (m, 2H), 3.62-3.72 (m, 2H), 3.36-3.68 9 (m, 6H), 3.22-3.30 (m, 2H), 2.82 (br, 2H), 2.47 (br, 4H), 2.04-2.13 (m, 2H), 1.47-1.52 (m, 3H). LCMS (ESI, m/z): 546 [M+H]$^+$.

Example 64

1,1,1,3,3,3-Hexafluoropropan-2-yl 5-([1-ethyl-3-[3-(pyrrolidin-1-yl)phenyl]-1H-pyrazol-4-yl]methyl)-octahydropyrrolo[3,4-c]pyrrole-2-carboxylate

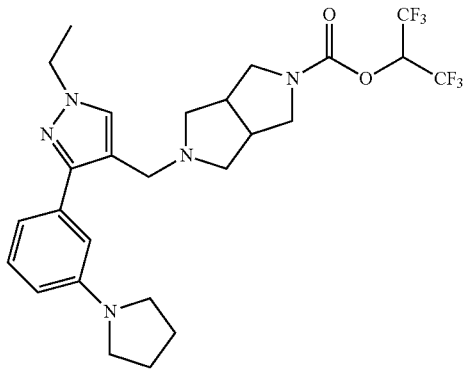 [SMILES: CCn1cc(CN2CC3CN(C(=O)OC(C(F)(F)F)C(F)(F)F)CC3C2)c(-c2cccc(N3CCCC3)c2)n1]

The title compound was synthesized from 1-(3-bromophenyl)ethan-1-one, ethylhydrazine hydrochloride, and pyrrolidine following the procedures described in Example 51 (Step 1), Example 52 (Step 2), Example 9 (Step 1), Example 11 (Step 1), Example 5 (Step 3), and Example 8 (Step 4) to provide 1,1,1,3,3,3-hexafluoropropan-2-yl 5-([1-ethyl-3-[3-(pyrrolidin-1-yl)phenyl]-1H-pyrazol-4-yl]methyl)-octahydropyrrolo[3,4-c]pyrrole-2-carboxylate as an off-white solid. $^1$H NMR (300 MHz, Chloroform-d) δ 7.35 (s, 1H), 7.22 (d, J=8.1 Hz, 1H), 6.99 (s, 2H), 6.53-6.56 (m, 1H), 5.68-5.76 (m, 1H), 4.15-4.22 (m, 2H), 3.69-3.75 (m, 2H), 3.58 (br, 2H), 3.29-3.41 (m, 6H), 2.87 (br, 2H), 2.57 (br, 4H), 1.95-2.04 (m, 4H), 1.49-1.72 (m, 3H). LCMS (ESI, m/z): 560 [M+H]$^+$.

Example 65

1,1,1,3,3,3-Hexafluoropropan-2-yl 5-([1-ethyl-3-[3-(morpholin-4-yl)phenyl]-1H-pyrazol-4-yl]methyl)-octahydropyrrolo[3,4-c]pyrrole-2-carboxylate

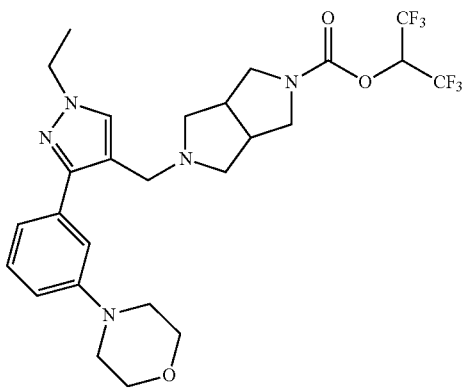 [SMILES: CCn1cc(CN2CC3CN(C(=O)OC(C(F)(F)F)C(F)(F)F)CC3C2)c(-c2cccc(N3CCOCC3)c2)n1]

The title compound was synthesized from 1-(3-bromophenyl)ethan-1-one, ethylhydrazine hydrochloride, and morpholine following the procedures described in Example 51 (Step 1), Example 52 (Step 2), Example 9 (Step 1), Example 11 (Step 1), Example 5 (Step 3), and Example 8 (Step 4) to provide 1,1,1,3,3,3-hexafluoropropan-2-yl 5-([1-ethyl-3-[3-(morpholin-4-yl)phenyl]-1H-pyrazol-4-yl]methyl)-octahydropyrrolo[3,4-c]pyrrole-2-carboxylate as a yellow oil. $^1$H NMR (300 MHz, Chloroform-d) δ 7.33-7.55 (m, 3H), 7.13-7.30 (m, 1H), 6.90 (d, J=6.6 Hz, 1H), 5.68-5.77 (m, 1H), 4.16-4.23 (m, 2H), 3.86-3.89 (m, 4H), 3.60-3.79 (m, 4H), 3.43-3.45 (m, 2H), 3.12-3.23 (m, 4H), 2.78-2.90 (m, 2H), 2.51-2.61 (m, 4H), 1.52-1.60 (m, 3H). LCMS (ESI, m/z): 576 [M+H]$^+$.

Example 66

1,1,1,3,3,3-Hexafluoropropan-2-yl 5-([3-[3-(azetidin-1-yl)phenyl]-1-ethyl-1H-pyrazol-4-yl]methyl)-octahydropyrrolo[3,4-c]pyrrole-2-carboxylate

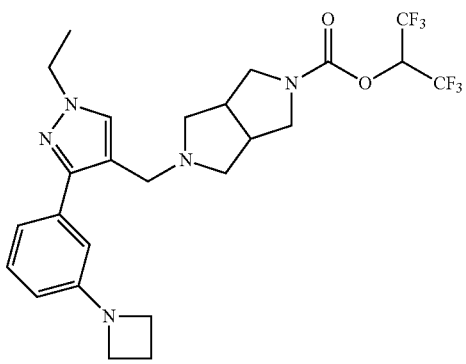 [SMILES: CCn1cc(CN2CC3CN(C(=O)OC(C(F)(F)F)C(F)(F)F)CC3C2)c(-c2cccc(N3CCC3)c2)n1]

The title compound was synthesized from 1-(3-bromophenyl)ethan-1-one, ethylhydrazine hydrochloride, and azetidine following the procedures described in Example 51 (Step 1), Example 52 (Step 2), Example 9 (Step 1), Example 11 (Step 1), Example 5 (Step 3), and Example 8 (Step 4) to provide 1,1,1,3,3,3-hexafluoropropan-2-yl 5-([3-[3-(azetidin-1-yl)phenyl]-1-ethyl-1H-pyrazol-4-yl]methyl)-octahydropyrrolo[3,4-c]pyrrole-2-carboxylate as a white solid. $^{1}$H NMR (300 MHz, Chloroform-d) δ 7.30 (br, 1H), 7.22-7.30 (m, 1H), 6.91 (br, 1H), 6.84 (br, 1H), 6.41-6.44 (m, 1H), 5.68-5.74 (m, 1H), 4.14-4.22 (m, 2H), 3.87 (t, J=9.7 Hz, 4H), 3.70-3.73 (m, 2H), 3.63-3.67 (m, 2H), 3.32-3.45 (m, 2H), 2.83-2.87 (m, 2H), 2.40-2.55 (m, 4H), 2.31-2.38 (m, 2H), 1.49-1.53 (m, 3H). LCMS (ESI, m/z): 546 [M+H]$^{+}$.

Example 67

1,1,1,3,3,3-Hexafluoropropan-2-yl 5-([1-ethyl-3-[4-(pyrrolidin-1-yl)phenyl]-1H-pyrazol-4-yl]methyl)-octahydropyrrolo[3,4-c]pyrrole-2-carboxylate

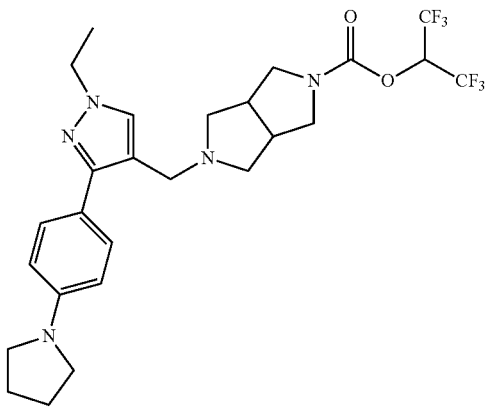 [SMILES: CCn1cc(CN2CC3CN(C(=O)OC(C(F)(F)F)C(F)(F)F)CC3C2)c(-c2ccc(N3CCCC3)cc2)n1]

The title compound was synthesized from 1-(4-bromophenyl)ethan-1-one, ethylhydrazine hydrochloride, and pyrrolidine following the procedures described in Example 51 (Step 1), Example 52 (Step 2), Example 9 (Step 1), Example 11 (Step 1), Example 5 (Step 3), and Example 8 (Step 4) to provide 1,1,1,3,3,3-hexafluoropropan-2-yl 5-([1-ethyl-3-[4-(pyrrolidin-1-yl)phenyl]-1H-pyrazol-4-yl]methyl)-octahydropyrrolo[3,4-c]pyrrole-2-carboxylate as a yellow oil. $^{1}$H NMR (300 MHz, Chloroform-d) δ 7.61 (d, J=8.7 Hz, 2H), 7.31 (s, 1H), 6.85 (d, J=8.7 Hz, 2H), 5.68-5.77 (m, 1H), 4.08-4.19 (m, 2H), 3.70-3.79 (m, 2H), 3.54 (s, 2H), 3.29-3.41 (m, 6H), 2.86-2.87 (m, 2H), 2.56-2.60 (m, 4H), 1.98-2.05 (m, 4H), 1.47-1.53 (m, 3H). LCMS (ESI, m/z): 560 [M+H$^{+}$.

Example 68

1,1,1,3,3,3-Hexafluoropropan-2-yl 5-([1-ethyl-3-[4-(morpholin-4-yl)phenyl]-1H-pyrazol-4-yl]methyl)-octahydropyrrolo[3,4-c]pyrrole-2-carboxylate

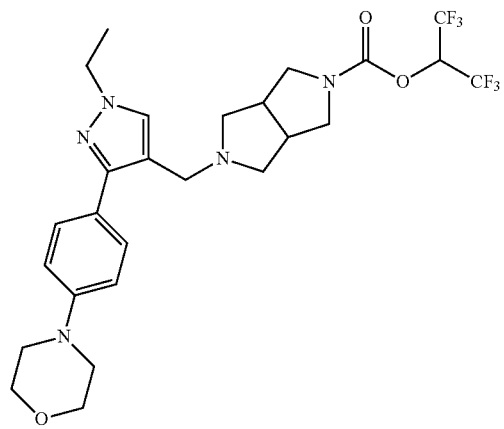 [SMILES: CCn1cc(CN2CC3CN(C(=O)OC(C(F)(F)F)C(F)(F)F)CC3C2)c(-c2ccc(N3CCOCC3)cc2)n1]

The title compound was synthesized from 1-(4-bromophenyl)ethan-1-one, ethylhydrazine hydrochloride, and morpholine following the procedures described in Example 51 (Step 1), Example 52 (Step 2), Example 9 (Step 1), Example 11 (Step 1), Example 5 (Step 3), and Example 8 (Step 4) to provide 1,1,1,3,3,3-hexafluoropropan-2-yl 5-([1-ethyl-3-[4-(morpholin-4-yl)phenyl]-1H-pyrazol-4-yl]methyl)-octahydropyrrolo[3,4-c]pyrrole-2-carboxylate as a yellow oil. $^{1}$H NMR (300 MHz, Chloroform-d) δ 7.64 (br, 2H), 7.47-7.52 (m, 1H), 6.93 (d, J=8.7 Hz, 2H), 5.67-5.73 (m, 1H), 4.14-4.21 (m, 2H), 3.88 (t, J=4.8 Hz, 4H), 3.49-3.71 (m, 4H), 2.29-3.37 (m, 2H), 3.19 (t, J=4.8 Hz, 4H), 2.79-2.95 (m, 2H), 2.44-2.73 (m, 4H), 1.51 (t, J=7.4 Hz, 3H). LCMS (ESI, m/z): 576 [M+H]$^{+}$.

Example 69

1,1,1,3,3,3-Hexafluoropropan-2-yl 5-([3-[4-(azetidin-1-yl)phenyl]-1-ethyl-1H-pyrazol-4-yl]methyl)-octahydropyrrolo[3,4-c]pyrrole-2-carboxylate

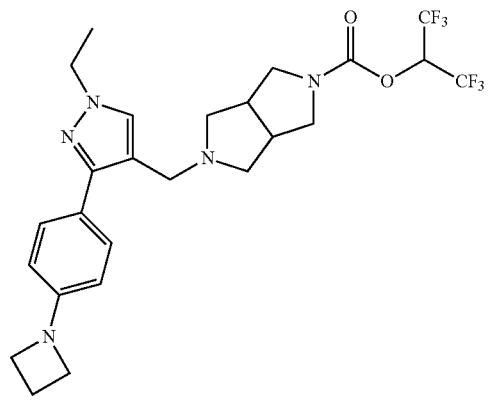 [SMILES: CCn1cc(CN2CC3CN(C(=O)OC(C(F)(F)F)C(F)(F)F)CC3C2)c(-c2ccc(N3CCC3)cc2)n1]

The title compound was synthesized from 1-(4-bromophenyl)ethan-1-one, ethylhydrazine hydrochloride, and azetidine following the procedures described in Example 51 (Step 1), Example 52 (Step 2), Example 9 (Step 1), Example 11 (Step 1), Example 5 (Step 3), and Example 8 (Step 4) to provide 1,1,1,3,3,3-hexafluoropropan-2-yl 5-([3-[4-(azetidin-1-yl)phenyl]-1-ethyl-1H-pyrazol-4-yl]methyl)-octahydropyrrolo[3,4-c]pyrrole-2-carboxylate as a yellow oil. $^1$H NMR (300 MHz, Chloroform-d) δ 7.59 (d, J=8.4 Hz, 2H), 7.34 (s, 1H), 6.44-6.48 (m, 2H), 5.68-5.79 (m, 1H), 4.12-4.19 (m, 2H), 3.90 (t, J=7.4 Hz, 4H), 3.70-3.76 (m, 2H), 3.55 (s, 2H), 3.31-3.48 (m, 2H), 2.88 (br, 2H), 2.57 (br, 4H), 2.32-2.42 (m, 2H), 1.71 (t, J=6.0 Hz, 3H). LCMS (ESI, m/z): 546 [M+H]$^+$.

Example 70

1,1,1,3,3,3-Hexafluoropropan-2-yl 5-[[1-ethyl-3-(pyridin-2-yl)-1H-pyrazol-4-yl]methyl]-octahydropyrrolo[3,4-c]pyrrole-2-carboxylate

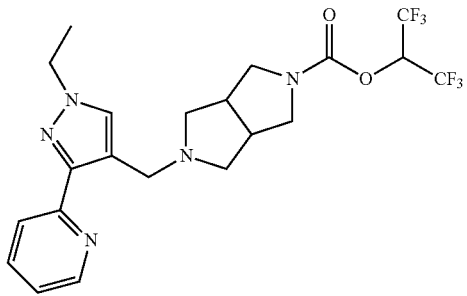 [SMILES: CCn1cc(CN2CC3CN(C(=O)OC(C(F)(F)F)C(F)(F)F)CC3C2)c(-c2ccccn2)n1]

The title compound was synthesized from 1-(pyridin-2-yl)ethan-1-one and ethylhydrazine hydrochloride according to the representative procedures of Example 51, Steps 1-5, with phosphoryl chloride substituted for N-(chloromethylene)-N-methylmethanaminium chloride in Step 2, to provide 1,1,1,3,3,3-hexafluoropropan-2-yl 5-[[1-ethyl-3-(pyridin-2-yl)-1H-pyrazol-4-yl]methyl]-octahydropyrrolo[3,4-c]pyrrole-2-carboxylate as a colorless oil. $^1$H NMR (300 MHz, Chloroform-d) δ 8.62 (s, 1H), 7.92 (d, J=7.8 Hz, 1H), 7.65-7.71 (m, 1H), 7.41 (s, 1H), 7.14-7.18 (m, 1H), 5.67-5.79 (m, 1H), 4.18-4.25 (m, 2H), 3.93 (s, 2H), 3.67-3.73 (m, 2H), 3.29-3.37 (m, 2H), 2.86 (br, 2H), 2.62 (br, 4H), 1.50-1.55 (m, 3H). LCMS (ESI, m/z): 492 [M+H]$^+$.

Example 71

1,1,1,3,3,3-Hexafluoropropan-2-yl 5-[[1-ethyl-3-(pyridin-3-yl)-1H-pyrazol-4-yl]methyl]-octahydropyrrolo[3,4-c]pyrrole-2-carboxylate

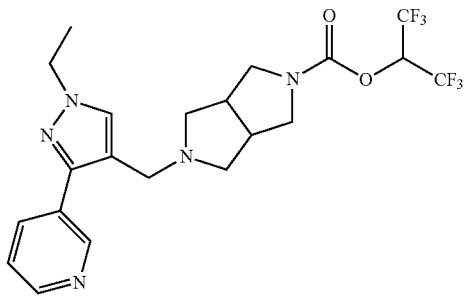 [SMILES: CCn1cc(CN2CC3CN(C(=O)OC(C(F)(F)F)C(F)(F)F)CC3C2)c(-c2cccnc2)n1]

The title compound was synthesized from 1-(pyridin-3-yl)ethan-1-one and ethylhydrazine hydrochloride according to the representative procedures of Example 51, Steps 1-5, with phosphoryl chloride substituted for N-(chloromethylene)-N-methylmethanaminium chloride in Step 2, to provide 1,1,1,3,3,3-hexafluoropropan-2-yl 5-[[1-ethyl-3-(pyridin-3-yl)-1H-pyrazol-4-yl]methyl]-octahydropyrrolo[3,4-c]pyrrole-2-carboxylate as a yellow oil. $^1$H NMR (300 MHz, Chloroform-d) δ 9.00 (s, 1H), 8.54 (d, J=3.3 Hz, 1H), 8.11 (d, J=7.5 Hz, 1H), 7.28-7.39 (m, 2H), 5.66-5.76 (m, 1H), 4.16-4.24 (m, 2H), 3.67-3.74 (m, 2H), 3.56 (s, 2H), 3.27-3.32 (m, 2H), 2.87 (br, 2H), 2.45 (br, 4H), 1.42-1.56 (m, 3H). LCMS (ESI, m/z): 492 [M+H]$^+$.

Example 72

1,1,1,3,3,3-Hexafluoropropan-2-yl 5-[[1-ethyl-3-(pyridin-4-yl)-1H-pyrazol-4-yl]methyl]-octahydropyrrolo[3,4-c]pyrrole-2-carboxylate

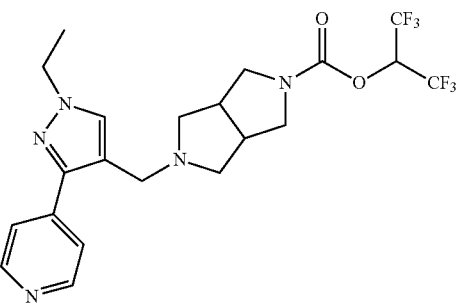 [SMILES: CCn1cc(CN2CC3CN(C(=O)OC(C(F)(F)F)C(F)(F)F)CC3C2)c(-c2ccncc2)n1]

The title compound was synthesized from 1-(pyridin-4-yl)ethan-1-one and ethylhydrazine hydrochloride according to the representative procedures of Example 51, Steps 1-5, with phosphoryl chloride substituted for N-(chloromethylene)-N-methylmethanaminium chloride in Step 2, to provide 1,1,1,3,3,3-hexafluoropropan-2-yl 5-[[1-ethyl-3-(pyridin-4-yl)-1H-pyrazol-4-yl]methyl]-octahydropyrrolo[3,4-c]pyrrole-2-carboxylate as a yellow oil. $^1$H NMR (300 MHz, Chloroform-d) δ 8.59-8.62 (m, 2H), 7.74-7.76 (m, 2H), 7.39 (s, 1H), 5.68-5.76 (m, 1H), 4.16-4.24 (m, 2H), 3.69-3.76 (m, 2H), 3.55 (s, 2H), 3.33-3.40 (m, 2H), 2.90 (br, 2H), 2.60 (br, 4H), 1.51-1.60 (m, 3H). LCMS (ESI, m/z): 492 [M+H]+.

Example 73

1,1,1,3,3,3-Hexafluoropropan-2-yl 5-((1-ethyl-5-(morpholine-4-carbonyl)-1H-pyrazol-4-yl)methyl)hexahydropyrrolo[3,4-c]pyrrole-2(1H)-carboxylate

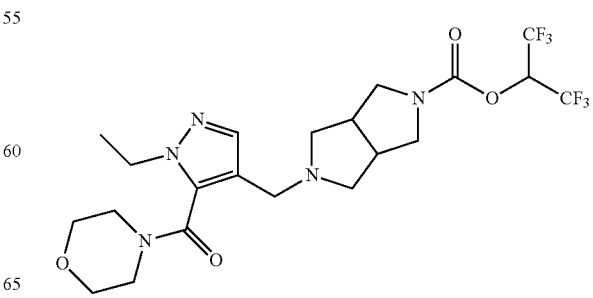

141

Step 1: Preparation of 1,1,1,3,3,3-hexafluoropropan-2-yl 5-((5-(ethoxycarbonyl)-1H-pyrazol-4-yl)methyl)hexahydropyrrolo[3,4-c]pyrrole-2(1H)-carboxylate

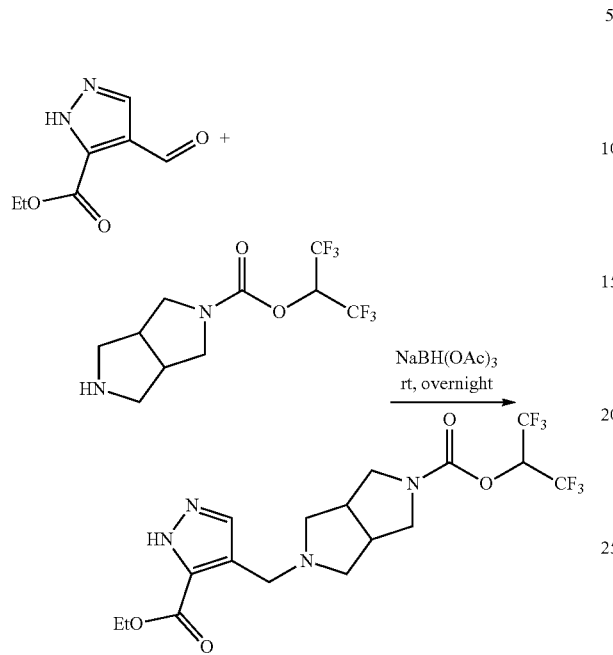

A round-bottom flask was charged with ethyl 4-formyl-1H-pyrazole-5-carboxylate (1.01 g, 6.01 mmol) and 1,1,1,3,3,3-hexafluoropropan-2-yl hexahydropyrrolo[3,4-c]pyrrole-2(1H)-carboxylate (Example 5, Step 3, 1.84 g, 6.01 mmol) and DCM. After stirring the solution at rt for 30 min, NaHB(OAc)₃ (1.89 g, 8.92 mmol) was added. The reaction mixture was stirred at rt for 18 h, after which the reaction was quenched with brine, and the mixture was extracted 3× with DCM. The organics were dried over anhydrous Na₂SO₄ and concentrated. The resulting oil was chromatographed on a silica column with a gradient (100% DCM to 90% DCM/10% MeOH) to provide 1,1,1,3,3,3-hexafluoropropan-2-yl 5-((5-(ethoxycarbonyl)-1H-pyrazol-4-yl)methyl)hexahydropyrrolo[3,4-c]pyrrole-2(1H)-carboxylate (1.8 g, 65%). ¹H NMR (400 MHz, Chloroform-d) δ 7.69 (s, 1H), 5.75 (hept, J=6.3 Hz, 1H), 4.42 (q, J=7.1 Hz, 2H), 3.93 (s, 2H), 3.71 (dd, J=11.4, 8.0 Hz, 2H), 3.43 (dt, J=10.5, 4.6 Hz, 2H), 2.93 (s, 2H), 2.85-2.78 (m, 2H), 2.59 (t, J=10.1 Hz, 2H), 1.42 (t, J=7.1 Hz, 3H). LCMS (ESI, m/z): 459.1 [M+H]⁺.

Step 2: Preparation of 1,1,1,3,3,3-hexafluoropropan-2-yl 5-((5-(ethoxycarbonyl)-1-ethyl-1H-pyrazol-4-yl)methyl)hexahydropyrrolo[3,4-c]pyrrole-2(1H)-carboxylate and 1,1,1,3,3,3-hexafluoropropan-2-yl 5-((3-(ethoxycarbonyl)-1-ethyl-1H-pyrazol-4-yl)methyl)hexahydropyrrolo[3,4-c]pyrrole-2(1H)-carboxylate

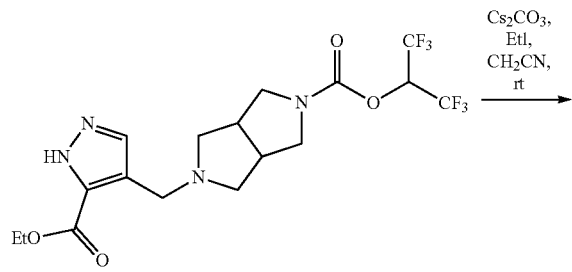

142

-continued

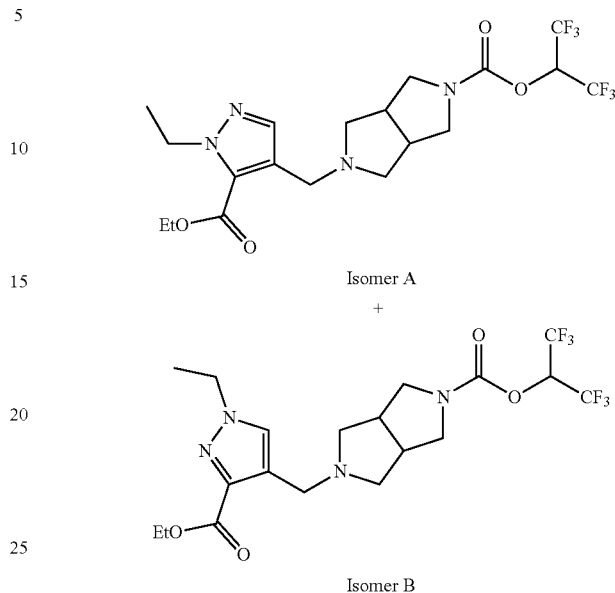

A round bottom flask was charged with 1,1,1,3,3,3-hexafluoropropan-2-yl 5-((5-(ethoxycarbonyl)-1H-pyrazol-4-yl)methyl)hexahydropyrrolo[3,4-c]pyrrole-2(1H)-carboxylate (859 mg, 1.87 mmol) and acetonitrile (20 mL). Cs₂CO₃ (650 mg, 2.00 mmol) and iodoethane (300 μL, 3.75 mmol) were added, and the reaction mixture was stirred at rt. After 30 min, additional Cs₂CO₃ (500 mg, 1.54 mmol) was added, and the mixture was allowed to stir at rt for an additional 2 h. The resulting mixture was concentrated, re-suspended in DCM (150 mL), and washed with brine once. The organics were dried over anhydrous Na₂SO₄ and concentrated. The resulting crude oil was chromatographed on a 80 g silica column with a gradient (100% DCM to 97% DCM/3% MeOH) to provide Isomer A, 1,1,1,3,3,3-hexafluoropropan-2-yl 5-((5-(ethoxycarbonyl)-1-ethyl-1H-pyrazol-4-yl)methyl)hexahydropyrrolo[3,4-c]pyrrole-2(1H)-carboxylate (clear oil, 300 mg, 33%), eluting first, and Isomer B, 1,1,1,3,3,3-hexafluoropropan-2-yl 5-((3-(ethoxycarbonyl)-1-ethyl-1H-pyrazol-4-yl)methyl)hexahydropyrrolo[3,4-c]pyrrole-2(1H)-carboxylate (clear oil, 430 mg, 47%), eluting second. Isomer A: ¹H NMR (400 MHz, Chloroform-d) δ 7.47 (s, 1H), 5.82-5.67 (m, 1H), 4.56 (qd, J=7.1, 1.6 Hz, 2H), 4.38 (qd, J=7.1, 1.7 Hz, 2H), 3.78-3.67 (m, 4H), 3.45-3.34 (m, 2H), 2.89 (br s, 2H), 2.71-2.63 (m, 2H), 2.57-2.46 (m, 2H), 1.48-1.36 (m, 6H). LCMS (ESI, m/z): 487.2 [M+H]⁺. Isomer B: ¹H NMR (400 MHz, Chloroform-d) δ 7.44 (s, 1H), 5.72 (hept, J=6.3 Hz, 1H), 4.37 (q, J=7.1 Hz, 2H), 4.21 (q, J=7.3 Hz, 2H), 3.85 (s, 2H), 3.74-3.64 (m, 2H), 3.40 (ddd, J=11.1, 6.8, 4.1 Hz, 2H), 2.97-2.81 (m, 2H), 2.73-2.55 (m, 4H), 1.48 (t, J=7.3 Hz, 3H), 1.38 (t, J=7.1 Hz, 3H). LCMS (ESI, m/z): 487.2 [M+H]⁺.

143

Step 3: Preparation of 1,1,1,3,3,3-hexafluoropropan-2-yl 5-((1-ethyl-5-(morpholine-4-carbonyl)-1H-pyrazol-4-yl)methyl)hexahydropyrrolo[3,4-c]pyrrole-2(1H)-carboxylate

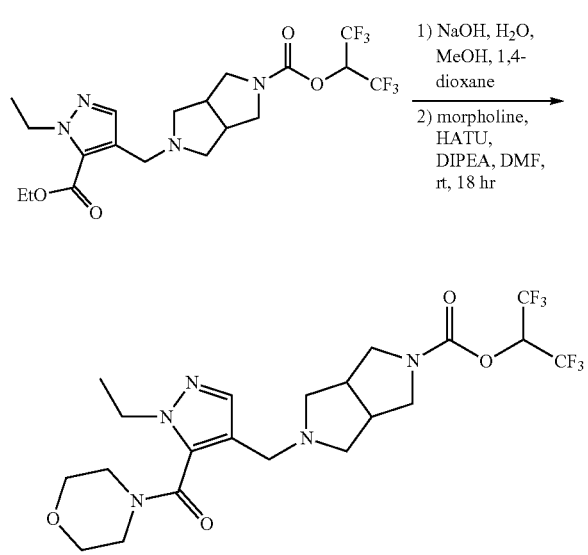

A round-bottom flask was charged with 1,1,1,3,3,3-hexafluoropropan-2-yl 5-((5-(ethoxycarbonyl)-1-ethyl-1H-pyrazol-4-yl)methyl)hexahydropyrrolo[3,4-c]pyrrole-2(1H)-carboxylate (Isomer A, 300 mg, 0.617 mmol), 1,4-dioxane (5 mL), and methanol (1 mL). 1 N NaOH (1.2 mL, 1.2 mmol) was added, and the reaction mixture was stirred for 2 h at rt. The reaction mixture was acidified to pH 2 using 1 N HCl, diluted with brine (20 mL), and extracted with DCM (3×). The organics were dried over anhydrous $Na_2SO_4$, filtered, and concentrated to yield crude 1-ethyl-4-((5-(((1,1,1,3,3,3-hexafluoropropan-2-yl)oxy)carbonyl)hexahydropyrrolo[3,4-c]pyrrol-2(1H)-yl)methyl)-1H-pyrazole-5-carboxylic acid (270 mg, 95%) as a white solid, which was used without further purification. A portion of the crude acid (37 mg, 0.081 mmol) was added to a 4-mL vial and dissolved in DMF (0.5 mL). DIPEA (41 µL, 0.242 mmol), morpholine (14 mg, 0.161 mmol), and HATU (46 mg, 121 mmol) were added, and the reaction mixture was allowed to stir at rt overnight. The reaction mixture was then diluted in DCM and washed with brine (3×). The organics were dried over anhydrous $Na_2SO_4$, filtered, and concentrated. The resulting crude oil was chromatographed on a silica column with a gradient (100% DCM to 90% DCM/10% MeOH) to provide the desired 1,1,1,3,3,3-hexafluoropropan-2-yl 5-((1-ethyl-5-(morpholine-4-carbonyl)-1H-pyrazol-4-yl)methyl)hexahydropyrrolo[3,4-c]pyrrole-2(1H)-carboxylate as a clear oil (20 mg, 47%). $^1$H NMR (400 MHz, Chloroform-d) δ 7.31 (s, 1H), 5.66 (d, J=6.1 Hz, 1H), 4.09 (br s, 2H), 3.95-3.13 (m, 15H), 2.80 (br s, 2H), 2.59-2.25 (m, 4H), 1.36 (td, J=7.2, 1.5 Hz, 5H). LCMS (ESI, m/z): 528.2 [M+H]$^+$.

144

Example 74

1,1,1,3,3,3-Hexafluoropropan-2-yl 5-45-(cyclopropylcarbamoyl)-1-ethyl-1H-pyrazol-4-yl)methyl)hexahydropyrrolo[3,4-c]pyrrole-2(1H)-carboxylate

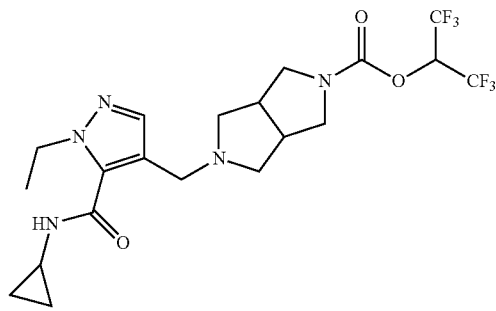 [SMILES: CCn1ncc(CN2CC3CN(C(=O)OC(C(F)(F)F)C(F)(F)F)CC3C2)c1C(=O)NC1CC1]

The title compound was prepared from cyclopropylamine and 1,1,1,3,3,3-hexafluoropropan-2-yl 5-((5-(ethoxycarbonyl)-1-ethyl-1H-pyrazol-4-yl)methyl)hexahydropyrrolo[3,4-c]pyrrole-2(1H)-carboxylate according to the representative procedure of Example 73, Step 3 to provide 1,1,1,3,3,3-hexafluoropropan-2-yl 5-((5-(cyclopropylcarbamoyl)-1-ethyl-1H-pyrazol-4-yl)methyl)hexahydro-pyrrolo[3,4-c]pyrrole-2(1H)-carboxylate as a clear oil. $^1$H NMR (400 MHz, Chloroform-d) δ 7.39 (s, 1H), 6.07 (s, 1H), 4.54 (q, J=6.7 Hz, 2H), 3.78-3.66 (m, 2H), 3.59-3.45 (m, 2H), 3.34 (d, J=12.2 Hz, 2H), 2.95 (d, J=28.0 Hz, 3H), 2.75-2.48 (m, 5H), 1.43-1.33 (m, 3H), 0.81 (d, J=6.3 Hz, 2H), 0.50 (s, 2H). LCMS (ESI, m/z): 498.1 [M+H]$^+$.

Example 75

1,1,1,3,3,3-Hexafluoropropan-2-yl 5-((5-(benzylcarbamoyl)-1-ethyl-1H-pyrazol-4-yl)methyl)hexahydropyrrolo[3,4-c]pyrrole-2(1H)-carboxylate

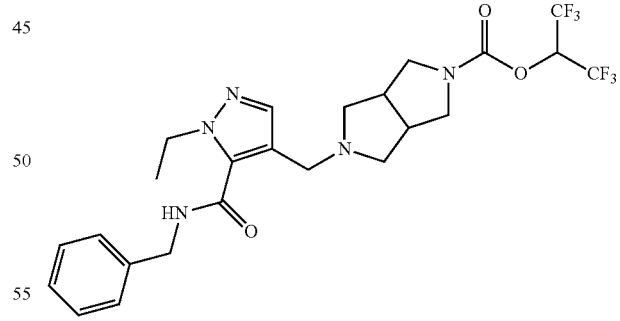

The title compound was prepared from benzylamine and 1,1,1,3,3,3-hexafluoropropan-2-yl 5-((5-(ethoxycarbonyl)-1-ethyl-1H-pyrazol-4-yl)methyl)hexahydropyrrolo[3,4-c]pyrrole-2(1H)-carboxylate according to the representative procedure of Example 73, Step 3 to provide 1,1,1,3,3,3-hexafluoropropan-2-yl 5-((5-(benzylcarbamoyl)-1-ethyl-1H-pyrazol-4-yl)methyl)hexahydropyrrolo[3,4-c]pyrrole-2(1H)-carboxylate as a clear oil. $^1$H NMR (400 MHz, Chloroform-d) δ 7.70 (h, J=8.7, 8.2 Hz, 5H), 6.34 (s, 1H), 4.96-4.87 (m, 2H), 4.76 (d, J=27.9 Hz, 2H), 3.88 (dd, J=12.7, 6.1 Hz, 3H), 3.76 (d, J=12.9 Hz, 1H), 3.65 (s, 2H), 3.43-3.33 (m, 2H), 3.02 (s, 2H), 2.82-2.73 (m, 2H), 2.53 (dd, J=20.0, 9.8 Hz, 2H), 1.77 (t, J=7.1 Hz, 3H). LCMS (ESI, m/z): 548.2 [M+H]⁺.

Example 76

1,1,1,3,3,3-Hexafluoropropan-2-yl 5-((1-ethyl-3-(morpholine-4-carbonyl)-1H-pyrazol-4-yl)methyl)hexahydropyrrolo[3,4-c]pyrrole-2(1H)-carboxylate

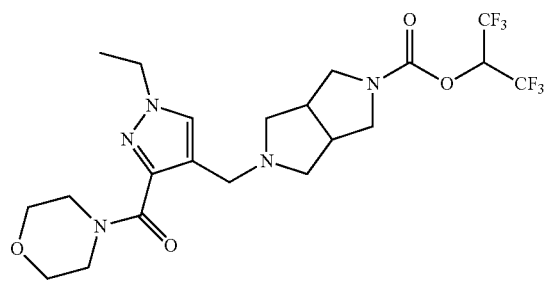 [SMILES: CCn1cc(CN2CC3CN(C(=O)OC(C(F)(F)F)C(F)(F)F)CC3C2)c(C(=O)N2CCOCC2)n1]

The title compound was prepared from morpholine and 1,1,1,3,3,3-hexafluoropropan-2-yl 5-((3-(ethoxycarbonyl)-1-ethyl-1H-pyrazol-4-yl)methyl)hexahydropyrrolo[3,4-c]pyrrole-2(1H)-carboxylate (Isomer B, Example 73, Step 2) according to the representative procedure of Example 73, Step 3 to provide 1,1,1,3,3,3-hexafluoropropan-2-yl 5-((1-ethyl-3-(morpholine-4-carbonyl)-1H-pyrazol-4-yl)methyl)hexahydropyrrolo[3,4-c]pyrrole-2(1H)-carboxylate as a clear oil. ¹H NMR (400 MHz, Chloroform-d) δ 7.71 (s, 1H), 5.61 (hept, J=6.2 Hz, 1H), 4.40-3.82 (m, 6H), 3.85-3.54 (m, 10H), 3.56-2.84 (m, 6H), 1.41 (t, J=7.3 Hz, 3H). LCMS (ESI, m/z): 528.2 [M+H].

Example 77

1,1,1,3,3,3-Hexafluoropropan-2-yl 5-((3-(cyclopropylcarbamoyl)-1-ethyl-1H-pyrazol-4-yl)methyl)hexahydropyrrolo[3,4-c]pyrrole-2(1H)-carboxylate

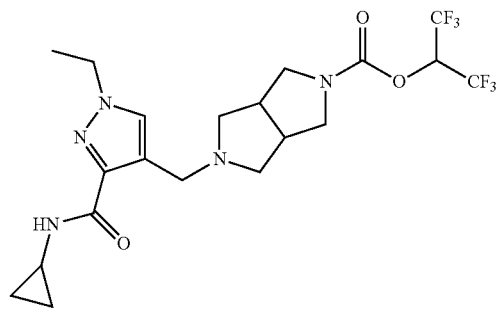 [SMILES: CCn1cc(CN2CC3CN(C(=O)OC(C(F)(F)F)C(F)(F)F)CC3C2)c(C(=O)NC2CC2)n1]

The title compound was prepared from cyclopropylamine and 1,1,1,3,3,3-hexafluoropropan-2-yl 5-((3-(ethoxycarbonyl)-1-ethyl-1H-pyrazol-4-yl)methyl)hexahydropyrrolo[3,4-c]pyrrole-2(1H)-carboxylate (Isomer B, Example 73, Step 4) according to the representative procedure of Example 73, Step 3 to provide 1,1,1,3,3,3-hexafluoropropan-2-yl 5-((3-(cyclopropylcarbamoyl)-1-ethyl-1H-pyrazol-4-yl)methyl)hexahydropyrrolo[3,4-c]pyrrole-2(1H)-carboxylate as a clear oil. ¹H NMR (400 MHz, Chloroform-d) δ 7.60 (s, 1H), 5.64 (hept, J=6.2 Hz, 1H), 4.10 (q, J=7.3 Hz, 4H), 3.71 (dd, J=11.3, 7.3 Hz, 2H), 3.53-2.86 (m, 7H), 2.86-2.69 (m, 2H), 1.42 (t, J=7.3 Hz, 3H), 0.91-0.73 (m, 2H), 0.68-0.47 (m, 2H). LCMS (ESI, m/z): 498.1 [M+H]

Example 78

1,1,1,3,3,3-Hexafluoropropan-2-yl 5-((3-(benzylcarbamoyl)-1-ethyl-1H-pyrazol-4-yl)methyl)hexahydropyrrolo[3,4-c]pyrrole-2(1H)-carboxylate

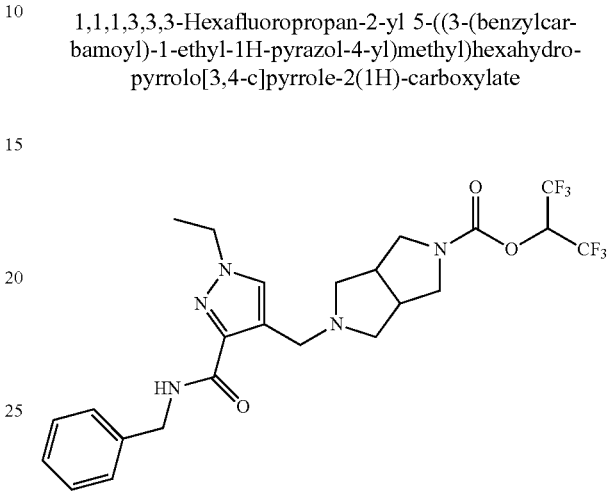

The title compound was prepared from benzylamine and 1,1,1,3,3,3-hexafluoropropan-2-yl 5-((3-(ethoxycarbonyl)-1-ethyl-1H-pyrazol-4-yl)methyl)hexahydropyrrolo[3,4-c]pyrrole-2(1H)-carboxylate (Isomer B, Example 73, Step 4) according to the representative procedure of Example 73, Step 3 to provide 1,1,1,3,3,3-hexafluoropropan-2-yl 5-((3-(benzylcarbamoyl)-1-ethyl-1H-pyrazol-4-yl)methyl)hexahydropyrrolo[3,4-c]pyrrole-2(1H)-carboxylate as a clear oil. ¹H NMR (400 MHz, Chloroform-d) δ 8.89 (br s, 1H), 7.39-7.26 (m, 6H), 5.75 (hept, J=6.3 Hz, 1H), 4.68-4.52 (m, 2H), 4.19 (q, J=7.3 Hz, 2H), 3.72-3.55 (m, 4H), 3.20-3.12 (m, 2H), 2.66 (br s, 2H), 2.62-2.52 (m, 2H), 2.35-2.28 (m, 2H), 1.50 (t, J=7.3 Hz, 3H). LCMS (ESI, m/z): 548.2 [M+H].

Example 79

2,5-Dioxopyrrolidin-1-yl 5-(2-fluoro-4-morpholinobenzyl)hexahydropyrrolo[3,4-c]pyrrole-2(1H)-carboxylate

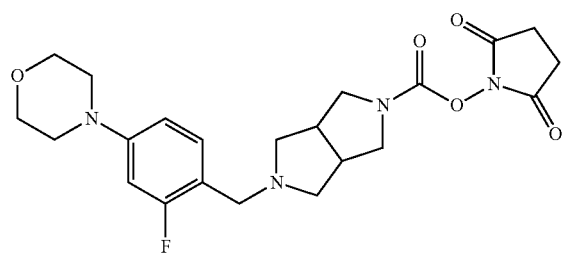 [SMILES: O=C(ON1C(=O)CCC1=O)N1CC2CN(Cc3ccc(N4CCOCC4)cc3F)CC2C1]

Preparation of 2,5-dioxopyrrolidin-1-yl 5-(2-fluoro-4-morpholinobenzyl)hexahydropyrrolo[3,4-c]pyrrole-2(1H)-carboxylate

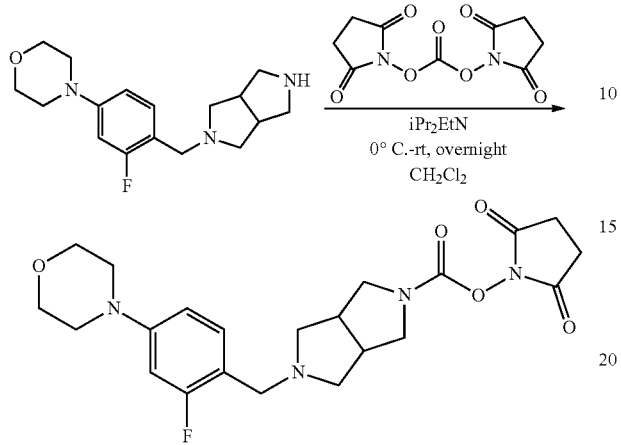

A 10-mL round-bottom flask, equipped with a magnetic stir bar, was charged with 4-(3-fluoro-4-((hexahydropyrrolo[3,4-c]pyrrol-2(1H)-yl)methyl)phenyl)morpholine (Example 1, Step 2, 27.6 mg, 0.0904 mmol) and dichloromethane (1.5 mL) under nitrogen. The resulting suspension was cooled to 0° C., and N,N-diisopropylethylamine (32 µL, 2.0 equiv) was added via syringe, followed by bis(2,5-dioxopyrrolidin-1-yl)carbonate (35 mg, 0.14 mmol, 85% pure). The ice bath was removed, and the suspension was stirred at room temperature overnight. The solvent was removed by rotary evaporation, and the resulting oil was applied to a chromatography column containing 12 g silica and dichloromethane. A gradient solvent was used from 100% dichloromethane to 10% methanol in dichloromethane to provide 32 mg (79%) of 2,5-dioxopyrrolidin-1-yl 5-(2-fluoro-4-morpholinobenzyl)hexahydropyrrolo[3,4-c]pyrrole-2(1H)-carboxylate as a powdery white solid. $^1$H NMR (400 MHz, Chloroform-d) δ 7.16 (t, J=8.6 Hz, 1H), 6.59 (d, J=8.4 Hz, 1H), 6.49 (d, J=13.0 Hz, 1H), 3.85-3.65 (m, 6H), 3.72-3.62 (m, 1H), 3.52 (s, 2H), 3.38-3.25 (m, 2H), 3.15-3.05 (m, 4H), 2.90-2.72 (m, 6H), 2.58-2.42 (m, 4H). LCMS (ESI, m/z): 447.1 [M+H]$^+$.

Example 80

2,5-Dioxopyrrolidin-1-yl 5-(2-chloro-4-morpholinobenzyl)hexahydropyrrolo[3,4-c]pyrrole-2(1H)-carboxylate

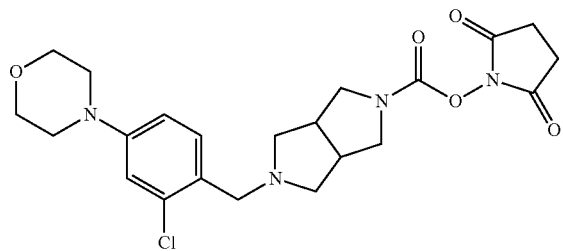 [SMILES: O=C(ON1C(=O)CCC1=O)N1CC2CN(Cc3ccc(N4CCOCC4)cc3Cl)CC2C1]

The title compound was synthesized directly from commercially available 2-chloro-4-morpholinobenzaldehyde and tert-butyl hexahydropyrrolo[3,4-c]pyrrole-2(1H)-carboxylate according to the representative procedures of Example 1, Steps 1 and 2, and Example 79 to provide 2,5-dioxopyrrolidin-1-yl 5-(2-chloro-4-morpholinobenzyl)hexahydropyrrolo[3,4-c]pyrrole-2(1H)-carboxylate as a white solid: $^1$H NMR (400 MHz, Chloroform-d) δ 7.32 (d, J=8.4 Hz, 1H), 6.97-6.70 (m, 2H), 3.96-3.74 (m, 6H), 3.66 (s, 2H), 3.52-3.28 (m, 2H), 3.15 (s, 4H), 3.01-2.76 (m, 6H), 2.60 (br s, 4H). LCMS (ESI, m/z): 463.1 [M+H]$^+$.

Example 81

2,5-Dioxopyrrolidin-1-yl 5-(2-(8-oxa-3-azabicyclo[3.2.1]octan-3-yl)-4-chlorobenzyl)hexahydropyrrolo[3,4-c]pyrrole-2(1H)-carboxylate

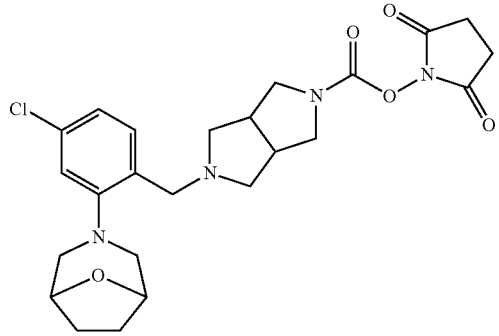 [SMILES: O=C(ON1C(=O)CCC1=O)N1CC2CN(Cc3ccc(Cl)cc3N3CC4CCC(C3)O4)CC2C1]

The title compound was synthesized directly from 2-(8-oxa-3-azabicyclo[3.2.1]octan-3-yl)-4-chlorobenzaldehyde (Example 3, Step 1) and tert-butyl hexahydropyrrolo[3,4-c]pyrrole-2(1H)-carboxylate according to the representative procedures of Example 1, Steps 1 and 2 and Example 79 to provide 2,5-dioxopyrrolidin-1-yl 5-(2-(8-oxa-3-azabicyclo[3.2.1]octan-3-yl)-4-chlorobenzyl)hexahydropyrrolo[3,4-c]pyrrole-2(1H)-carboxylate. $^1$H NMR (400 MHz, Chloroform-d) δ 7.36 (d, J=8.7 Hz, 1H), 7.07 (dt, J=5.2, 1.6 Hz, 2H), 4.41 (s, 2H), 3.81 (dt, J=38.8, 9.8 Hz, 2H), 3.71-3.58 (m, 2H), 3.37 (ddd, J=31.2, 11.2, 4.4 Hz, 2H), 3.04 (d, J=11.2 Hz, 2H), 2.95-2.75 (m, 8H), 2.62 (d, J=9.4 Hz, 2H), 2.52 (t, J=8.0 Hz, 2H), 2.21-2.10 (m, 2H), 2.02-1.96 (m, 2H). LCMS (ESI, m/z): 489.2 [M+H]$^+$.

Example 82

2,5-Dioxopyrrolidin-1-yl 5-(4-chloro-2-(hexahydrocyclopenta[b][1,4]oxazin-4(4aH)-yl)benzyl)hexahydropyrrolo[3,4-c]pyrrole-2(1H)-carboxylate

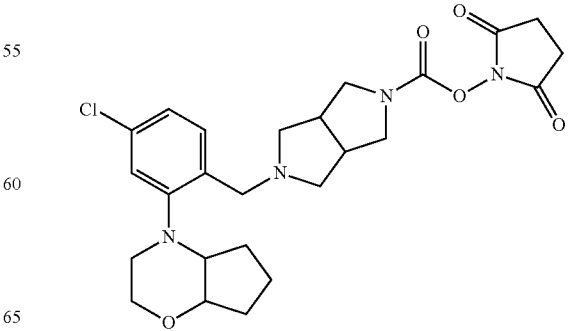

The title compound was synthesized directly from commercially available octahydrocyclopenta[b][1,4]oxazine and tert-butyl hexahydropyrrolo[3,4-c]pyrrole-2(1H)-carboxylate according to the representative procedures of Example 3, Step 1, Example 1, Steps 1 and 2, and Example 79 to provide 2,5-dioxopyrrolidin-1-yl 5-(4-chloro-2-(hexahydrocyclopenta-[b][1,4]oxazin-4(4aH)-yl)benzyl)hexahydropyrrolo[3,4-c]pyrrole-2(1H)-carboxylate as an oil. $^1$H NMR (400 MHz, Chloroform-d) δ 7.43 (d, J=8.6 Hz, 1H), 7.17-6.95 (m, 2H), 4.16 (d, J=12.7 Hz, 1H), 3.92 (dt, J=34.6, 8.9 Hz, 3H), 3.81-3.35 (m, 5H), 3.31-2.98 (m, 4H), 2.97-2.54 (m, 14H). LCMS (ESI, m/z): 503.2 [M+H]$^+$.

Example 83

2,5-Dioxopyrrolidin-1-yl 5-[bis(4-chlorophenyl)methyl]-octahydropyrrolo[3,4-c]pyrrole-2-carboxylate

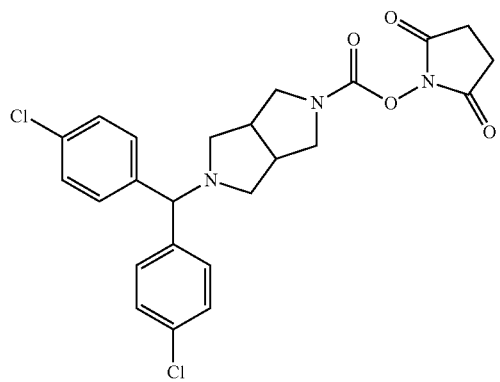 [SMILES: O=C(ON1C(=O)CCC1=O)N1CC2CN(C(c3ccc(Cl)cc3)c3ccc(Cl)cc3)CC2C1]

The title compound was synthesized directly from 2-[bis(4-chlorophenyl)methyl]-octahydropyrrolo[3,4-c]pyrrole (Example 8, Step 3) and bis(2,5-dioxopyrrolidin-1-yl)carbonate according to the general procedure of Example 79 to provide 2,5-dioxopyrrolidin-1-yl 5-[bis(4-chlorophenyl)methyl]-octahydropyrrolo[3,4-c]pyrrole-2-carboxylate as a white solid. $^1$H NMR (300 MHz, Chloroform-d) δ 7.28-7.40 (m, 8H), 7.18 (s, 1H), 3.73-3.89 (m, 2H), 3.39-3.53 (m, 2H), 2.87 (s, 6H), 2.53-2.55 (m, 2H), 2.36-2.41 (m, 2H). LCMS (ESI, m/z): 488 [M+H]$^+$.

Example 84

2,5-Dioxopyrrolidin-1-yl 5-[(4-phenylphenyl)methyl]-octahydropyrrolo[3,4-c]pyrrole-2-carboxylate

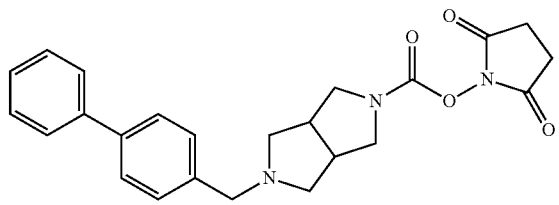 [SMILES: O=C(ON1C(=O)CCC1=O)N1CC2CN(Cc3ccc(-c4ccccc4)cc3)CC2C1]

The title compound was synthesized directly from 2-[(4-phenylphenyl)methyl]-octahydropyrrolo[3,4-c]pyrrole (Example 9, Step 2) and bis(2,5-dioxopyrrolidin-1-yl)carbonate according to the general procedure of Example 79 to provide 2,5-dioxopyrrolidin-1-yl 5-[(4-phenylphenyl)methyl]-octahydropyrrolo[3,4-c]pyrrole-2-carboxylate as a white semi-solid. $^1$H NMR (300 MHz, Chloroform-d) δ 7.33-7.62 (m, 9H), 3.26-3.98 (m, 6H), 2.92-3.10 (m, 2H), 2.85 (br, 4H), 2.61-2.72 (m, 3H), 1.77-2.25 (m, 1H). LCMS (ESI, m/z): 420 [M+H]$^+$.

Example 85

2,5-Dioxopyrrolidin-1-yl 5-[[4-(morpholin-4-yl)-2-(trifluoromethyl)phenyl]methyl]-octahydropyrrolo[3,4-c]pyrrole-2-carboxylate

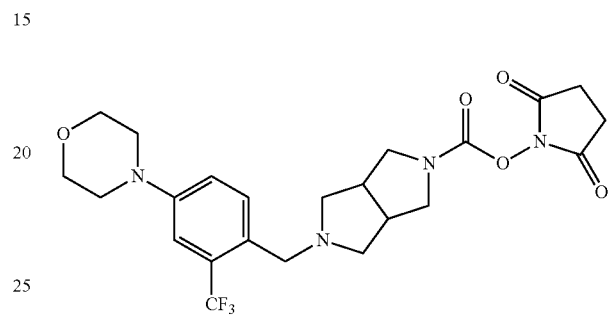

The title compound was synthesized from 4-fluoro-2-(trifluoromethyl)benzaldehyde, morpholine, tert-butyl octahydropyrrolo[3,4-c]pyrrole-2-carboxylate], and bis(2,5-dioxopyrrolidin-1-yl)carbonate according to the general procedures of Example 10 (Step 1), Example 9 (Steps 1 and 2), and Example 79 to provide 2,5-dioxopyrrolidin-1-yl 5-[[4-(morpholin-4-yl)-2-(trifluoromethyl)phenyl]methyl]-octahydropyrrolo[3,4-c]pyrrole-2-carboxylate as a yellow oil. $^1$H NMR (300 MHz, Chloroform-d) δ 7.63 (d, J=8.4 Hz, 1H), 7.05-7.12 (m, 2H), 3.75-3.93 (m, 6H), 3.69 (s, 2H), 3.32-3.46 (m, 2H), 3.19 (t, J=4.8 Hz, 4H), 2.82-2.93 (m, 6H), 2.59-2.67 (m, 2H), 2.47-2.53 (m, 2H). LCMS (ESI, m/z): 497 [M+H]$^+$.

Example 86

2,5-Dioxopyrrolidin-1-yl 5-[[4-(morpholin-4-yl)-2-(trifluoromethoxy)phenyl]methyl]-octahydropyrrolo[3,4-c]pyrrole-2-carboxylate

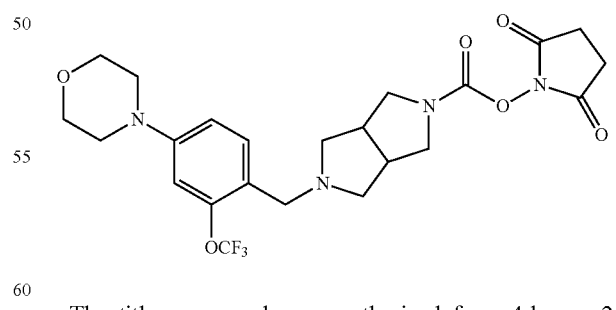

The title compound was synthesized from 4-bromo-2-(trifluoromethoxy)benzaldehyde, morpholine, tert-butyl octahydropyrrolo[3,4-c]pyrrole-2-carboxylate], and bis(2,5-dioxopyrrolidin-1-yl)carbonate according to the general procedures of Example 11 (Step 1), Example 9 (Steps 1 and 2), and Example 79 to provide 2,5-dioxopyrrolidin-1-yl 5-[[4-(morpholin-4-yl)-2-(trifluoromethoxy)phenyl]methyl]-octahydropyrrolo[3,4-c]pyrrole-2-carboxylate as a white solid. $^1$H NMR (300 MHz, Chloroform-d) δ 7.43 (s, 1H), 6.86-6.89 (m, 1H), 6.74 (s, 1H), 3.80-3.90 (m, 6H), 3.64 (s, 2H), 3.40 (br, 2H), 3.18-3.21 (m, 4H), 2.85-3.06 (m, 6H), 2.56-2.72 (m, 4H). LCMS (ESI, m/z): 535 [M+Na]$^+$.

Example 87

2,5-Dioxopyrrolidin-1-yl 5-[(2-phenylphenyl)methyl]-octahydropyrrolo[3,4-c]pyrrole-2-carboxylate

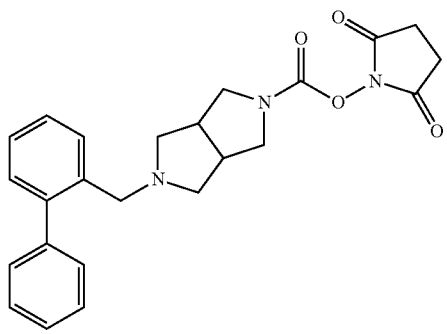 [SMILES: O=C(ON1C(=O)CCC1=O)N1CC2CN(Cc3ccccc3-c3ccccc3)CC2C1]

The title compound was synthesized from commercially available 2-phenylbenzaldehyde, tert-butyl octahydropyrrolo[3,4-c]pyrrole-2-carboxylate], and bis(2,5-dioxopyrrolidin-1-yl)carbonate according to the general procedures of Example 9 (Steps 1 and 2) and Example 79 to provide 2,5-dioxopyrrolidin-1-yl-5-[(2-phenylphenyl)methyl]-octahydropyrrolo[3,4-c]pyrrole-2-carboxylate as a colorless oil. $^1$H NMR (400 MHz, Chloroform-d) δ 7.53 (d, J=7.2 Hz, 1H), 7.29-7.46 (m, 8H), 3.86 (t, J=10.0 Hz, 1H), 3.76 (t, J=10.2 Hz, 1H), 3.60 (s, 2H), 3.24-3.28 (m, 1H), 3.16-3.20 (m, 1H), 2.80-2.84 (m, 5H), 2.61-2.66 (m, 1H), 2.40-2.51 (m, 4H). LCMS (ESI, m/z): 420 [M+H]$^+$.

Example 88

2,5-Dioxopyrrolidin-1-yl 5-[(3-phenylphenyl)methyl]-octahydropyrrolo[3,4-c]pyrrole-2-carboxylate

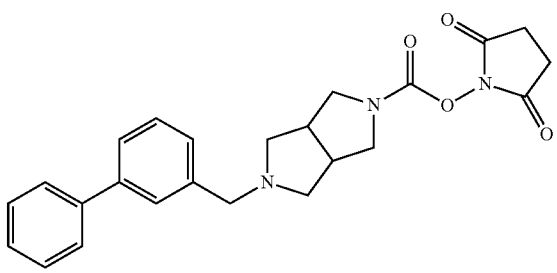 [SMILES: O=C(ON1C(=O)CCC1=O)N1CC2CN(Cc3cccc(-c4ccccc4)c3)CC2C1]

The title compound was synthesized from commercially available 3-phenylbenzaldehyde, tert-butyl octahydropyrrolo[3,4-c]pyrrole-2-carboxylate], and bis(2,5-dioxopyrrolidin-1-yl)carbonate according to the general procedures of Example 9 (Steps 1 and 2) and Example 79 to provide 2,5-dioxopyrrolidin-1-yl 5-[(3-phenylphenyl)methyl]-octahydropyrrolo[3,4-c]pyrrole-2-carboxylate as a colorless oil. $^1$H NMR (300 MHz, Chloroform-d) δ 7.51-7.62 (m, 3H), 7.40-7.49 (m, 4H), 7.31-7.38 (m, 2H), 3.69-3.86 (m, 4H), 3.37-3.50 (m, 2H), 2.92 (br, 2H), 2.81 (s, 4H), 2.68 (t, J=8.1 Hz, 2H), 2.54-2.58 (m, 2H). LCMS (ESI, m/z): 420 [M+H]$^+$.

Example 89

2,5-Dioxopyrrolidin-1-yl 5-[[4-fluoro-2-(morpholin-4-yl)phenyl]methyl]-octahydropyrrolo[3,4-c]pyrrole-2-carboxylate

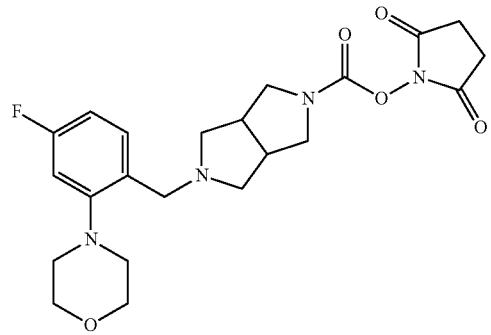 [SMILES: O=C(ON1C(=O)CCC1=O)N1CC2CN(Cc3ccc(F)cc3N3CCOCC3)CC2C1]

The title compound was synthesized from commercially available 2,4-difluorobenzaldehyde, morpholine, tert-butyl octahydropyrrolo[3,4-c]pyrrole-2-carboxylate], and bis(2,5-dioxopyrrolidin-1-yl)carbonate according to the general procedures of Example 10 (Step 1), Example 9 (Steps 1 and 2), and Example 79 to provide 2,5-dioxopyrrolidin-1-yl 5-[[4-fluoro-2-(morpholin-4-yl)phenyl]methyl]-octahydropyrrolo[3,4-c]pyrrole-2-carboxylate as a light yellow semi-solid. $^1$H NMR (300 MHz, Chloroform-d) δ 7.40 (br, 1H), 6.76-6.82 (m, 2H), 3.83-3.86 (m, 5H), 3.66-3.78 (m, 3H), 3.37-3.44 (m, 2H), 2.95-2.98 (m, 6H), 2.82 (s, 4H), 2.62 (br, 4H). LCMS (ESI, m/z): 447 [M+H]$^+$.

Example 90

2,5-Dioxopyrrolidin-1-yl 5-[[4-fluoro-2-(pyrrolidin-1-yl)phenyl]methyl]-octahydropyrrolo[3,4-c]pyrrole-2-carboxylate

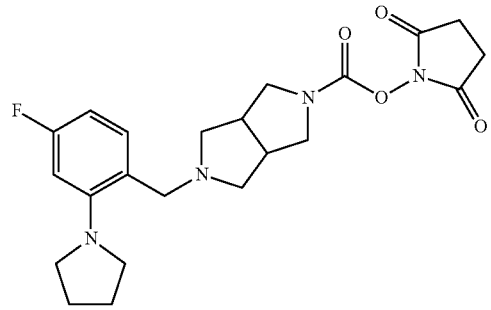 [SMILES: O=C(ON1C(=O)CCC1=O)N1CC2CN(Cc3ccc(F)cc3N3CCCC3)CC2C1]

The title compound was synthesized directly from commercially available 2,4-difluorobenzaldehyde, pyrrolidine, tert-butyl octahydropyrrolo[3,4-c]pyrrole-2-carboxylate], and bis(2,5-dioxopyrrolidin-1-yl)carbonate according to the general procedures of Example 10 (Step 1), Example 9 (Steps 1 and 2), and Example 79 to provide 2,5-dioxopyrrolidin-1-yl 5-[[4-fluoro-2-(pyrrolidin-1-yl)phenyl]methyl]-octahydropyrrolo[3,4-c]pyrrole-2-carboxylate as a light yellow semi-solid. ¹H NMR (300 MHz, Chloroform-d) δ 7.26 (s, 1H), 6.50-6.56 (m, 2H), 3.74-3.89 (m, 2H), 3.59 (s, 2H), 3.22-3.42 (m, 6H), 2.82-2.88 (m, 6H), 2.51-2.57 (m, 4H), 1.91-1.95 (m, 4H). LCMS (ESI, m/z): 431 [M+H]⁺.

Example 91

2,5-Dioxopyrrolidin-1-yl 5-[[4-fluoro-2-(3-methyl-morpholin-4-yl)phenyl]methyl]-octahydropyrrolo[3,4-c]pyrrole-2-carboxylate

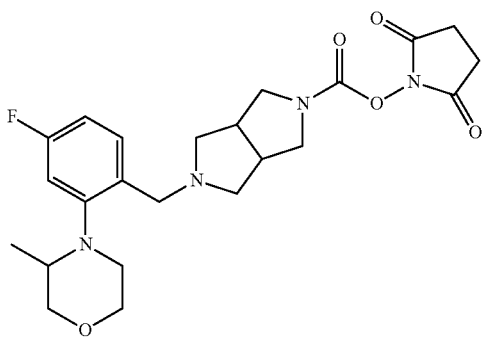 [SMILES: CC1COCCN1c1cc(F)ccc1CN1CC2CN(C(=O)ON3C(=O)CCC3=O)CC2C1]

The title compound was synthesized directly from commercially available 2,4-difluorobenzaldehyde, 3-methyl-morpholine hydrochloride, tert-butyl octahydropyrrolo[3,4-c]pyrrole-2-carboxylate], and bis(2,5-dioxopyrrolidin-1-yl) carbonate according to the general procedures of Example 10 (Step 1), Example 9 (Steps 1 and 2), and Example 79 to provide 2,5-dioxopyrrolidin-1-yl 5-[[4-fluoro-2-(3-methyl-morpholin-4-yl)phenyl]methyl]-octahydropyrrolo[3,4-c]pyrrole-2-carboxylate as a white solid. ¹H NMR (300 MHz, Chloroform-d) δ 7.42 (br, 1H), 6.88 (d, J=4.8 Hz, 2H), 3.72-3.90 (m, 6H), 3.34-3.50 (m, 4H), 3.17-3.19 (m, 1H), 2.75-3.00 (m, 8H), 2.48-2.72 (m, 4H), 0.76 (d, J=3.0 Hz, 3H). LCMS (ESI, m/z): 461 [M+H]⁺.

Example 92

2,5-Dioxopyrrolidin-1-yl 5-[[2-(4-acetylpiperazin-1-yl)-4-fluorophenyl]methyl]-octahydropyrrolo[3,4-c]pyrrole-2-carboxylate

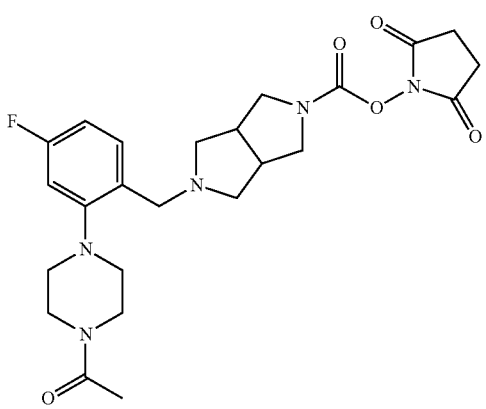 [SMILES: CC(=O)N1CCN(c2cc(F)ccc2CN2CC3CN(C(=O)ON4C(=O)CCC4=O)CC3C2)CC1]

The title compound was synthesized directly from commercially available 2,4-difluorobenzaldehyde, 1-(piperazin-1-yl)ethan-1-one, tert-butyl octahydropyrrolo[3,4-c]pyrrole-2-carboxylate], and bis(2,5-dioxopyrrolidin-1-yl)carbonate according to the general procedures of Example 10 (Step 1), Example 9 (Steps 1 and 2), and Example 79 to provide 2,5-dioxopyrrolidin-1-yl 5-[[2-(4-acetylpiperazin-1-yl)-4-fluorophenyl]methyl]-octahydropyrrolo[3,4-c]pyrrole-2-carboxylate as a white solid. ¹H NMR (300 MHz, Chloroform-d) δ 7.34 (br, 1H), 6.73-6.82 (m, 2H), 3.61-3.80 (m, 8H), 3.34-3.43 (m, 2H), 2.90-3.08 (m, 6H), 2.81 (s, 4H), 2.62-2.69 (m, 4H), 2.13-2.16 (m, 3H). LCMS (ESI, m/z): 510 [M+Na]⁺.

Example 93

2,5-Dioxopyrrolidin-1-yl 5-[[4-chloro-2-(morpholin-4-yl)phenyl]methyl]-octahydropyrrolo[3,4-c]pyrrole-2-carboxylate

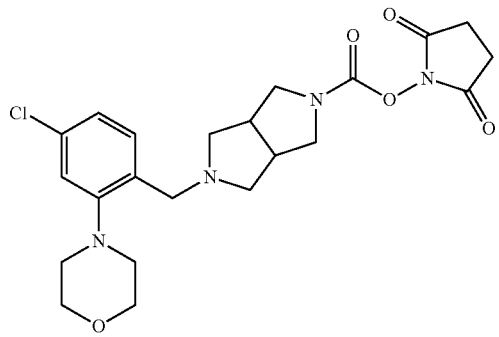 [SMILES: O=C(ON1C(=O)CCC1=O)N1CC2CN(Cc3ccc(Cl)cc3N3CCOCC3)CC2C1]

The title compound was synthesized directly from commercially available 4-chloro-2-fluorobenzaldehyde, morpholine, tert-butyl octahydropyrrolo[3,4-c]pyrrole-2-carboxylate], and bis(2,5-dioxopyrrolidin-1-yl)carbonate according to the general procedures of Example 10 (Step 1), Example 9 (Steps 1 and 2), and Example 79 to provide 2,5-dioxopyrrolidin-1-yl 5-[[4-chloro-2-(morpholin-4-yl)phenyl]methyl]-octahydropyrrolo[3,4-c]pyrrole-2-carboxylate as a white solid. ¹H NMR (300 MHz, Chloroform-d) δ 7.36 (d, J=8.4 Hz, 1H), 7.02-7.08 (m, 2H), 3.70-3.86 (m, 6H), 3.63 (s, 2H), 3.34-3.32 (m, 2H), 2.89-2.98 (m, 6H), 2.82 (s, 4H), 2.59 (br, 4H). LCMS (ESI, m/z): 463 [M+H]⁺.

Example 94

2,5-Dioxopyrrolidin-1-yl 5-[[4-chloro-2-(pyrrolidin-1-yl)phenyl]methyl]-octahydropyrrolo[3,4-c]pyrrole-2-carboxylate

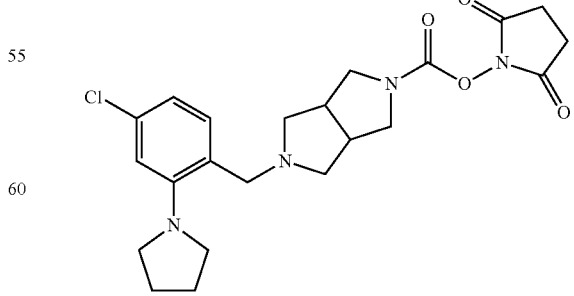

The title compound was synthesized directly from commercially available 4-chloro-2-fluorobenzaldehyde, pyrrolidine, tert-butyl octahydropyrrolo[3,4-c]pyrrole-2-carboxylate], and bis(2,5-dioxopyrrolidin-1-yl)carbonate according to the general procedures of Example 10 (Step 1), Example 9 (Steps 1 and 2), and Example 79 to provide 2,5-dioxopyrrolidin-1-yl 5-[[4-chloro-2-(pyrrolidin-1-yl)phenyl]methyl]-octahydropyrrolo[3,4-c]pyrrole-2-carboxylate as a white semi-solid. $^1$H NMR (300 MHz, Chloroform-d) δ 7.27 (d, J=8.7 Hz, 1H), 6.80-6.82 (m, 2H), 3.73-3.89 (m, 2H), 3.59 (s, 2H), 3.30-3.44 (m, 2H), 3.22 (t, J=6.3 Hz, 4H), 2.81-2.88 (m, 6H), 2.49-2.60 (m, 4H), 1.88-1.97 (m, 4H). LCMS (ESI, m/z): 447 [M+H]$^+$.

Example 95

2,5-Dioxopyrrolidin-1-yl 5-[[4-chloro-2-(3-methylmorpholin-4-yl)phenyl]methyl]-octahydropyrrolo[3,4-c]pyrrole-2-carboxylate

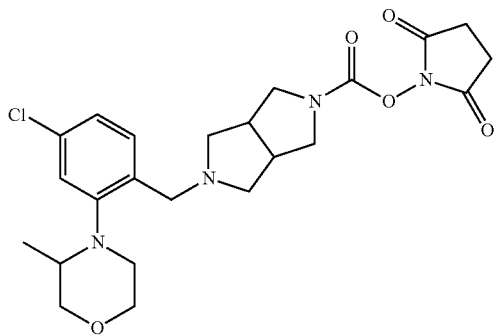 [SMILES: CC1COCCN1c1cc(Cl)ccc1CN1CC2CN(C(=O)ON3C(=O)CCC3=O)CC2C1]

The title compound was synthesized directly from commercially available 4-chloro-2-fluorobenzaldehyde, 3-methylmorpholine, tert-butyl octahydropyrrolo[3,4-c]pyrrole-2-carboxylate], and bis(2,5-dioxopyrrolidin-1-yl)carbonate according to the general procedures of Example 10 (Step 1), Example 9 (Steps 1 and 2), and Example 79 to provide 2,5-dioxopyrrolidin-1-yl 5-[[4-chloro-2-(3-methylmorpholin-4-yl)phenyl]methyl]-octahydropyrrolo[3,4-c]pyrrole-2-carboxylate as a semi-white solid. $^1$H NMR (300 MHz, Chloroform-d) δ 7.41 (d, J=8.7 Hz, 1H), 7.12-7.14 (m, 2H), 3.71-3.88 (m, 6H), 3.16-3.52 (m, 5H), 2.71-2.93 (m, 8H), 2.45-2.66 (m, 4H), 0.74 (d, J=6.3 Hz, 3H). LCMS (ESI, m/z): 477 [M+H]$^+$.

Example 96

2,5-Dioxopyrrolidin-1-yl 5-[[2-(4-acetylpiperazin-1-yl)-4-chlorophenyl]methyl]-octahydropyrrolo[3,4-c]pyrrole-2-carboxylate

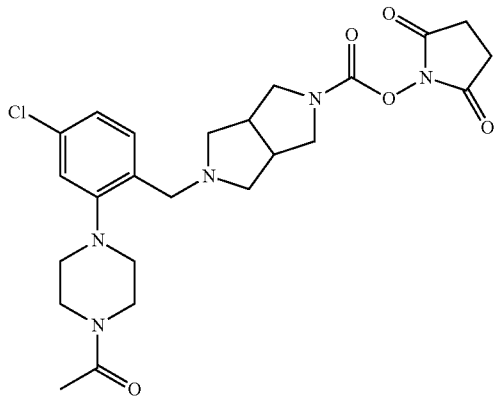 [SMILES: CC(=O)N1CCN(c2cc(Cl)ccc2CN2CC3CN(C(=O)ON4C(=O)CCC4=O)CC3C2)CC1]

The title compound was synthesized directly from commercially available 4-chloro-2-fluorobenzaldehyde, 1-(piperazin-1-yl)ethan-1-one, tert-butyl octahydropyrrolo[3,4-c]pyrrole-2-carboxylate], and bis(2,5-dioxopyrrolidin-1-yl)carbonate according to the general procedures of Example 10 (Step 1), Example 9 (Steps 1 and 2), and Example 79 to provide 2,5-dioxopyrrolidin-1-yl 5-[[2-(4-acetylpiperazin-1-yl)-4-chlorophenyl]methyl]-octahydropyrrolo[3,4-c]pyrrole-2-carboxylate as a white solid. $^1$H NMR (300 MHz, Chloroform-d) δ 7.32 (d, J=8.1 Hz, 1H), 7.07 (d, J=8.1 Hz, 1H), 7.00-7.01 (m, 1H), 3.60-3.85 (m, 8H), 3.34-3.42 (m, 2H), 2.90-2.99 (m, 6H), 2.81 (s, 4H), 2.56-2.64 (m, 4H), 2.13 (s, 3H). LCMS (ESI, m/z): 504.1 [M+H]$^+$.

Example 97

2,5-Dioxopyrrolidin-1-yl 5-[[2-(morpholin-4-yl)-4-(propan-2-yl)phenyl]methyl]-octahydropyrrolo[3,4-c]pyrrole-2-carboxylate

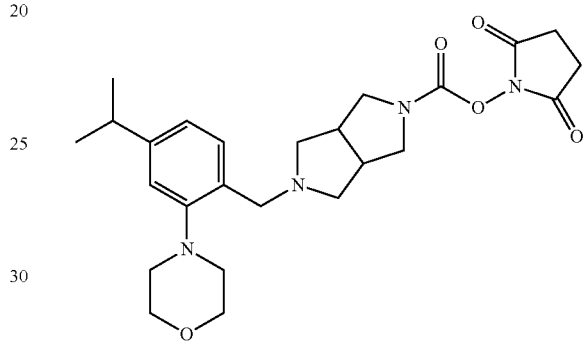

The title compound was synthesized directly from commercially available 2-bromo-4-(propan-2-yl)benzaldehyde, tert-butyl octahydropyrrolo[3,4-c]pyrrole-2-carboxylate], morpholine, and bis(2,5-dioxopyrrolidin-1-yl)carbonate according to the general procedures of Example 22 (Steps 1-3) and Example 79 to provide 2,5-dioxopyrrolidin-1-yl 5-[[2-(morpholin-4-yl)-4-(propan-2-yl)phenyl]methyl]-octahydropyrrolo[3,4-c]pyrrole-2-carboxylate as a yellow oil. $^1$H NMR (300 MHz, Chloroform-d) δ 7.29-7.31 (m, 1H), 6.93-6.96 (m, 2H), 3.65-3.86 (m, 8H), 3.30-3.40 (m, 2H), 2.99-3.02 (m, 4H), 2.81-2.93 (m, 7H), 2.61 (br, 4H), 1.25 (d, J=6.9 Hz, 6H). LCMS (ESI, m/z): 471 [M+H]$^+$.

Example 98

2,5-Dioxopyrrolidin-1-yl 5-[[4-(propan-2-yl)-2-(pyrrolidin-1-yl)phenyl]methyl]-octahydropyrrolo[3,4-c]pyrrole-2-carboxylate

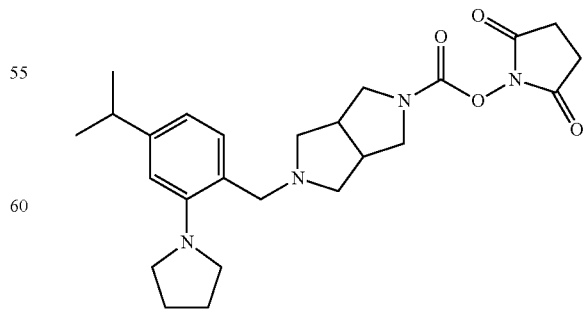

The title compound was synthesized directly from commercially available 2-bromo-4-(propan-2-yl)benzaldehyde, tert-butyl octahydropyrrolo[3,4-c]pyrrole-2-carboxylate], pyrrolidine, and bis(2,5-dioxopyrrolidin-1-yl)carbonate according to the representative procedures of Example 22 (Steps 1-3) and Example 79 to provide 2,5-dioxopyrrolidin-1-yl 5-[[4-(propan-2-yl)-2-(pyrrolidin-1-yl)phenyl]methyl]-octahydropyrrolo[3,4-c]pyrrole-2-carboxylate as a yellow oil. $^1$H NMR (300 MHz, Chloroform-d) δ 7.28 (s, 1H), 6.75-6.77 (m, 2H), 3.62-3.90 (m, 4H), 3.19-3.44 (m, 6H), 2.82-2.92 (m, 7H), 2.60 (br, 4H), 1.91-1.96 (m, 4H), 1.24 (d, J=6.9 Hz, 6H). LCMS (ESI, m/z): 455 [M+H]$^+$.

Example 99

2,5-Dioxopyrrolidin-1-yl 5-[[2-(4-acetylpiperazin-1-yl)-4-(propan-2-yl)phenyl]methyl]-octahydropyrrolo[3,4-c]pyrrole-2-carboxylate

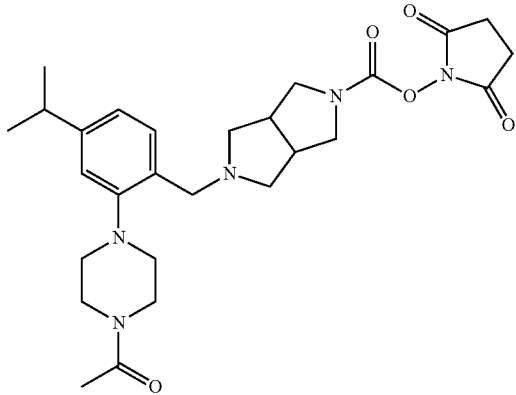 [SMILES: CC(=O)N1CCN(c2cc(C(C)C)ccc2CN2CC3CN(C(=O)ON4C(=O)CCC4=O)CC3C2)CC1]

The title compound was synthesized directly from commercially available 2-bromo-4-(propan-2-yl)benzaldehyde, tert-butyl octahydropyrrolo[3,4-c]pyrrole-2-carboxylate], 1-(piperazin-1-yl)ethan-1-one, and bis(2,5-dioxopyrrolidin-1-yl)carbonate according to the representative procedures of Example 22 (Steps 1-3) and Example 79 to provide 2,5-dioxopyrrolidin-1-yl 5-[[2-(4-acetylpiperazin-1-yl)-4-(propan-2-yl)phenyl]methyl]-octahydropyrrolo[3,4-c]pyrrole-2-carboxylate as a white solid. $^1$H NMR (300 MHz, Chloroform-d) δ 7.28 (s, 1H), 6.90-6.97 (m, 2H), 3.60-3.83 (m, 8H), 3.33-3.41 (m, 2H), 2.81-3.08 (m, 11H), 2.57-2.66 (m, 4H), 2.14 (s, 3H), 1.24 (d, J=6.9 Hz, 6H). LCMS (ESI, m/z): 512 [M+H]$^+$.

Example 100

2,5-Dioxopyrrolidin-1-yl 5-[[2-fluoro-4-(3-methylmorpholin-4-yl)phenyl]methyl]-octahydropyrrolo[3,4-c]pyrrole-2-carboxylate

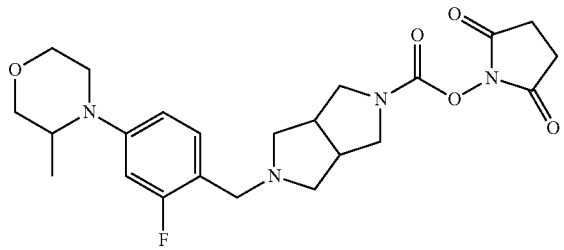 [SMILES: CC1COCCN1c1ccc(CN2CC3CN(C(=O)ON4C(=O)CCC4=O)CC3C2)c(F)c1]

The title compound was synthesized directly from commercially available 2,4-difluorobenzaldehyde, 3-methylmorpholine hydrochloride, tert-butyl octahydropyrrolo[3,4-c]pyrrole-2-carboxylate], and bis(2,5-dioxopyrrolidin-1-yl)carbonate according to the general procedures of Example 10 (Step 1), Example 9 (Steps 1 and 2), and Example 79 to provide 2,5-dioxopyrrolidin-1-yl 5-[[2-fluoro-4-(3-methylmorpholin-4-yl)phenyl]methyl]-octahydropyrrolo[3,4-c]pyrrole-2-carboxylate as a white solid. $^1$H NMR (300 MHz, Chloroform-d) δ 7.29-7.35 (m, 1H), 6.61-6.64 (m, 1H), 6.48-6.54 (m, 1H), 3.97-4.01 (m, 1H), 3.66-3.90 (m, 8H), 3.37-3.57 (m, 2H), 2.82-3.20 (m, 10H), 2.64-2.66 (m, 2H), 1.14 (d, J=3.0 Hz, 3H). LCMS (ESI, m/z): 483 [M+Na]$^+$.

Example 101

2,5-Dioxopyrrolidin-1-yl 5-[[4-(4-acetylpiperazin-1-yl)-2-fluorophenyl]methyl]-octahydropyrrolo[3,4-c]pyrrole-2-carboxylate

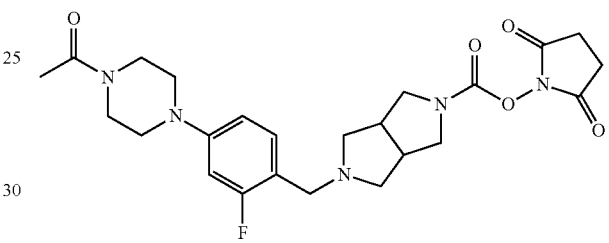

The title compound was synthesized directly from commercially available 2,4-difluorobenzaldehyde, 1-(piperazin-1-yl)ethan-1-one, tert-butyl octahydropyrrolo[3,4-c]pyrrole-2-carboxylate], and bis(2,5-dioxopyrrolidin-1-yl)carbonate according to the general procedures of Example 10 (Step 1), Example 9 (Steps 1 and 2), and Example 79 to provide 2,5-dioxopyrrolidin-1-yl 5-[[4-(4-acetylpiperazin-1-yl)-2-fluorophenyl]methyl]-octahydropyrrolo[3,4-c]pyrrole-2-carboxylate as a white solid. $^1$H NMR (300 MHz, Chloroform-d) δ 7.23-7.28 (m, 1H), 6.66-6.69 (m, 1H), 6.54-6.59 (m, 1H), 3.75-3.86 (m, 4H), 3.60-3.69 (m, 4H), 3.32-3.47 (m, 2H), 3.15-3.19 (m, 4H), 2.82-2.90 (m, 6H), 2.63-2.70 (m, 2H), 2.54-2.61 (m, 2H), 2.14 (s, 3H). LCMS (ESI, m/z): 488 [M+H]$^+$.

Example 102

2,5-Dioxopyrrolidin-1-yl 5-[[2-chloro-4-(3-methylmorpholin-4-yl)phenyl]methyl]-octahydropyrrolo[3,4-c]pyrrole-2-carboxylate

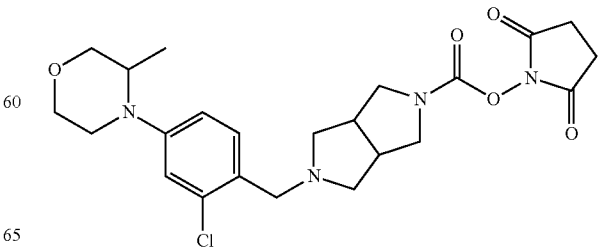

The title compound was synthesized directly from commercially available 2-chloro-4-fluorobenzaldehyde, 3-methylmorpholine, tert-butyl octahydropyrrolo[3,4-c]pyrrole-2-carboxylate], and bis(2,5-dioxopyrrolidin-1-yl)carbonate according to the general procedures of Example 10 (Step 1), Example 9 (Steps 1 and 2), and Example 79 to provide 2,5-dioxopyrrolidin-1-yl 5-[[2-chloro-4-(3-methylmorpholin-4-yl)phenyl]methyl]-octahydropyrrolo[3,4-c]pyrrole-2-carboxylate as a white solid. $^1$H NMR (300 MHz, Chloroform-d) δ 7.28 (d, J=6.6 Hz, 1H), 6.75-6.83 (m, 2H), 3.64-4.00 (m, 9H), 3.32-3.46 (m, 2H), 3.10-3.15 (m, 2H), 2.82-2.94 (m, 6H), 2.60 (br, 4H), 1.11 (d, J=6.3 Hz, 3H). LCMS (ESI, m/z): 477 [M+H]$^+$.

Example 103

2,5-Dioxopyrrolidin-1-yl 5-[[4-(4-acetylpiperazin-1-yl)-2-chlorophenyl]methyl]-octahydropyrrolo[3,4-c]pyrrole-2-carboxylate

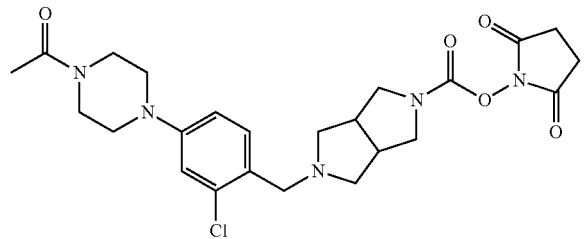 [SMILES: CC(=O)N1CCN(c2ccc(CN3CC4CN(C(=O)ON5C(=O)CCC5=O)CC4C3)c(Cl)c2)CC1]

The title compound was synthesized directly from commercially available 2-chloro-4-fluorobenzaldehyde, 1-(piperazin-1-yl)ethan-1-one, tert-butyl octahydropyrrolo[3,4-c]pyrrole-2-carboxylate], and bis(2,5-dioxopyrrolidin-1-yl)carbonate according to the general procedures of Example 10 (Step 1), Example 9 (Steps 1 and 2), and Example 79 to provide 2,5-dioxopyrrolidin-1-yl 5-[[4-(4-acetylpiperazin-1-yl)-2-chlorophenyl]methyl]-octahydropyrrolo[3,4-c]pyrrole-2-carboxylate as a white solid. $^1$H NMR (300 MHz, Chloroform-d) δ 7.33 (d, J=8.4 Hz, 1H), 6.80-6.88 (m, 2H), 3.60-3.89 (m, 8H), 3.32-3.46 (m, 2H), 3.13-3.20 (m, 4H), 2.82-2.90 (m, 6H), 2.61 (br, 4H), 2.14 (s, 3H). LCMS (ESI, m/z): 504 [M+H$^+$.

Example 104

2,5-Dioxopyrrolidin-1-yl 5-[[2-methyl-3-(piperidin-1-yl)phenyl]methyl]-octahydropyrrolo[3,4-c]pyrrole-2-carboxylate

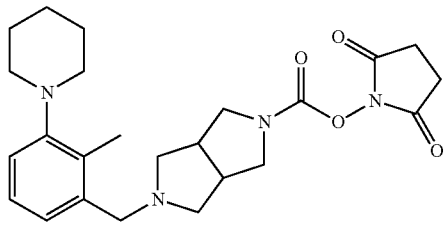 [SMILES: Cc1c(CN2CC3CN(C(=O)ON4C(=O)CCC4=O)CC3C2)cccc1N1CCCCC1]

The title compound was synthesized directly from commercially available 3-bromo-2-methylbenzaldehyde, tert-butyl octahydropyrrolo[3,4-c]pyrrole-2-carboxylate], piperidine, and bis(2,5-dioxopyrrolidin-1-yl)carbonate according to the representative procedures of Example 29 (Steps 1-3) and Example 79 to provide 2,5-dioxopyrrolidin-1-yl 5-[[2-methyl-3-(piperidin-1-yl)phenyl]methyl]-octahydropyrrolo[3,4-c]pyrrole-2-carboxylate as an off-white solid. $^1$H NMR (300 MHz, Chloroform-d) δ 7.09-7.11 (m, 1H), 6.91 (br, 2H), 3.78-3.88 (m, 2H), 3.57 (br, 2H), 3.31-3.49 (m, 2H), 2.82 (br, 10H), 2.55 (br, 4H), 2.31 (br, 3H), 1.68-1.76 (m, 4H), 1.57 (br, 2H). LCMS (ESI, m/z): 441 [M+H]$^+$.

Example 105

2,5-Dioxopyrrolidin-1-yl 5-[[3-methyl-2-(piperidin-1-yl)phenyl]methyl]-octahydropyrrolo[3,4-c]pyrrole-2-carboxylate

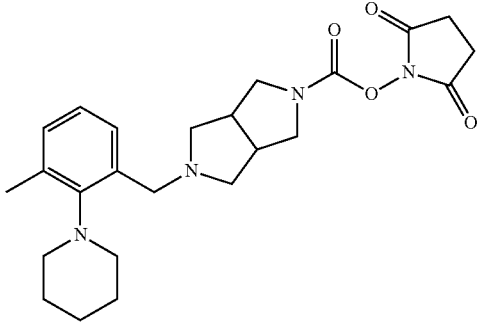 [SMILES: Cc1cccc(CN2CC3CN(C(=O)ON4C(=O)CCC4=O)CC3C2)c1N1CCCCC1]

The title compound was synthesized directly from commercially available 2-bromo-3-methylbenzaldehyde, tert-butyl octahydropyrrolo[3,4-c]pyrrole-2-carboxylate], piperidine, and bis(2,5-dioxopyrrolidin-1-yl)carbonate according to the representative procedures of Example 29 (Steps 1-3) and Example 79 to provide 2,5-dioxopyrrolidin-1-yl 5-[[3-methyl-2-(piperidin-1-yl)phenyl]methyl]-octahydropyrrolo[3,4-c]pyrrole-2-carboxylate as a light yellow solid. $^1$H NMR (300 MHz, Chloroform-d) δ 7.23-7.28 (m, 1H), 7.04 (br, 2H), 3.39-3.76 (m, 6H), 2.82-3.10 (m, 10H), 2.41-2.64 (m, 4H), 2.34 (s, 3H), 1.48-1.64 (m, 6H). LCMS (ESI, m/z): 441 [M+H]$^+$.

Example 106

2,5-Dioxopyrrolidin-1-yl 5-[(4-chloro-2-[8-oxa-2-azaspiro[4.5]decan-2-yl]phenyl)methyl]-octahydropyrrolo[3,4-c]pyrrole-2-carboxylate

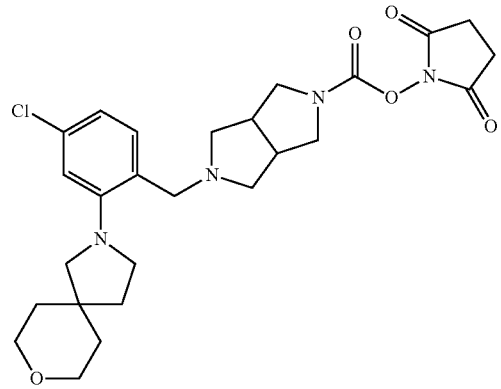 [SMILES: O=C(ON1C(=O)CCC1=O)N1CC2CN(Cc3ccc(Cl)cc3N3CCC4(CCOCC4)C3)CC2C1]

The title compound was synthesized directly from commercially available 4-chloro-2-fluorobenzaldehyde, 8-oxa-2-azaspiro[4.5]decane, tert-butyl octahydropyrrolo[3,4-c]pyrrole-2-carboxylate], and bis(2,5-dioxopyrrolidin-1-yl)carbonate according to the general procedures of Example 10 (Step 1), Example 9 (Steps 1 and 2), and Example 79 to provide 2,5-dioxopyrrolidin-1-yl 5-[(4-chloro-2-[8-oxa-2-azaspiro[4.5]decan-2-yl]phenyl)methyl]-octahydropyrrolo[3,4-c]pyrrole-2-carboxylate as a yellow oil. $^1$H NMR (300 MHz, Chloroform-d) δ 7.24-7.26 (m, 1H), 6.81-6.84 (m, 2H), 3.63-3.86 (m, 6H), 3.24-3.56 (m, 6H), 3.13 (s, 2H), 2.82-2.88 (m, 6H), 2.54 (br, 4H), 1.84 (t, J=7.0 Hz, 2H), 1.64-1.71 (m, 4H). LCMS (ESI, m/z): 517 [M+H]$^+$.

Example 107

2,5-Dioxopyrrolidin-1-yl 5-[(4-chloro-2-[5H,6H,7H-pyrrolo[3,4-b]pyridin-6-yl]phenyl)methyl]-octahydropyrrolo[3,4-c]pyrrole-2-carboxylate

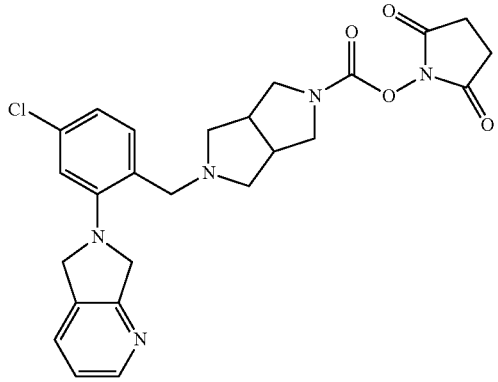 [SMILES: O=C(ON1C(=O)CCC1=O)N1CC2CN(Cc3ccc(Cl)cc3N3Cc4cccnc4C3)CC2C1]

The title compound was synthesized directly from commercially available 4-chloro-2-fluorobenzaldehyde, 5H,6H,7H-pyrrolo[3,4-b]pyridine, tert-butyl octahydropyrrolo[3,4-c]pyrrole-2-carboxylate], and bis(2,5-dioxopyrrolidin-1-yl)carbonate according to the general procedures of Example 10 (Step 1), Example 9 (Steps 1 and 2), and Example 79 to provide 2,5-dioxopyrrolidin-1-yl 5-[(4-chloro-2-[5H,6H,7H-pyrrolo[3,4-b]pyridin-6-yl]phenyl)methyl]-octahydropyrrolo[3,4-c]pyrrole-2-carboxylate as a yellow solid. $^1$H NMR (300 MHz, Chloroform-d) δ 8.48 (d, J=4.8 Hz, 1H), 7.61 (d, J=7.2 Hz, 1H), 7.30-7.32 (m, 1H), 7.18-7.22 (m, 1H), 6.99 (s, 1H), 6.90-6.93 (m, 1H), 4.70-4.80 (m, 4H), 3.69-3.84 (m, 4H), 3.32-3.41 (m, 2H), 2.70-2.88 (m, 6H), 2.57 (br, 4H). LCMS (ESI, m/z): 518 [M+Na]$^+$.

Example 108

2,5-Dioxopyrrolidin-1-yl 5-(4-chloro-2-(5,6-dihydro-[1,2,4]triazolo[1,5-a]pyrazin-7(8H)-yl)benzyl)-hexahydropyrrolo[3,4-c]pyrrole-2(1H)-carboxylate

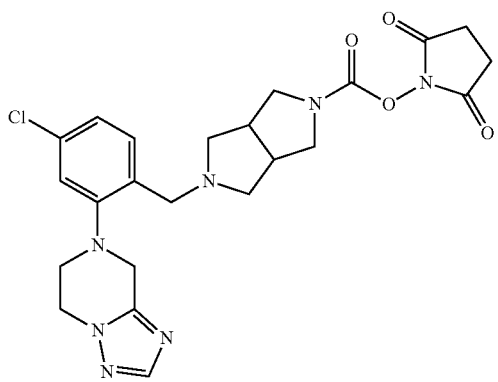 [SMILES: O=C(ON1C(=O)CCC1=O)N1CC2CN(Cc3ccc(Cl)cc3N3CCn4ncnc4C3)CC2C1]

The title compound was synthesized directly from commercially available 2-bromo-4-chlorobenzaldehyde, tert-butyl octahydropyrrolo[3,4-c]pyrrole-2-carboxylate], 5,6,7,8-tetrahydro-[1,2,4]triazolo[1,5-a]pyrazine, and bis(2,5-dioxopyrrolidin-1-yl)carbonate according to the general procedures of Example 22 (Steps 1-3) and Example 79 to provide 2,5-dioxopyrrolidin-1-yl 5-(4-chloro-2-(5,6-dihydro-[1,2,4]triazolo[1,5-a]pyrazin-7(8H)-yl)benzyl)-hexahydropyrrolo[3,4-c]pyrrole-2(1H)-carboxylate as a yellow oil. $^1$H NMR (300 MHz, Chloroform-d) δ 7.93 (s, 1H), 7.35-7.37 (m, 1H), 7.10-7.16 (m, 2H), 4.33-4.38 (m, 4H), 3.62-3.82 (m, 6H), 3.37-3.48 (m, 2H), 2.84-2.96 (m, 6H), 2.55-2.75 (m, 4H). LCMS (ESI, m/z): 522 [M+Na]$^+$.

Example 109

2,5-Dioxopyrrolidin-1-yl 5-(4-chloro-2-((R)-hexahydropyrrolo[1,2-a]pyrazin-2(1H)-yl)benzyl)-hexahydropyrrolo[3,4-c]pyrrole-2(1H)-carboxylate

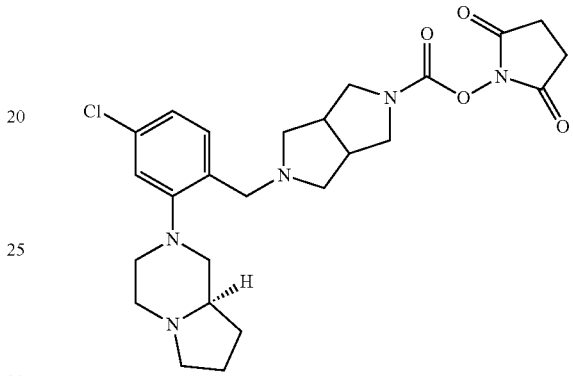

The title compound was synthesized directly from commercially available 4-chloro-2-fluorobenzaldehyde, (8aR)-octahydropyrrolo[1,2-a]piperazine, tert-butyl octahydropyrrolo[3,4-c]pyrrole-2-carboxylate], and bis(2,5-dioxopyrrolidin-1-yl)carbonate according to the general procedures of Example 10 (Step 1), Example 9 (Steps 1 and 2), and Example 79 to provide 2,5-dioxopyrrolidin-1-yl 5-(4-chloro-2-((R)-hexahydropyrrolo[1,2-a]pyrazin-2(1H)-yl)benzyl)-hexahydropyrrolo[3,4-c]pyrrole-2(1H)-carboxylate as a pink solid. $^1$H NMR (300 MHz, Chloroform-d) δ 7.32 (d, J=9.0 Hz, 1H), 7.03-7.05 (m, 2H), 3.53-3.88 (m, 4H), 3.26-3.42 (M, 3H), 3.14 (br, 3H), 3.00-3.02 (m, 2H), 2.91 (br, 4H), 2.42-2.58 (m, 6H), 2.26 (br, 2H), 1.84-1.97 (m, 2H), 1.66 (br, 3H). LCMS (ESI, m/z): 502 [M+H]$^+$.

Example 110

2,5-Dioxopyrrolidin-1-yl 5-[[4-chloro-2-(4-methanesulfonylpiperazin-1-yl)phenyl]methyl]-octahydropyrrolo[3,4-c]pyrrole-2-carboxylate

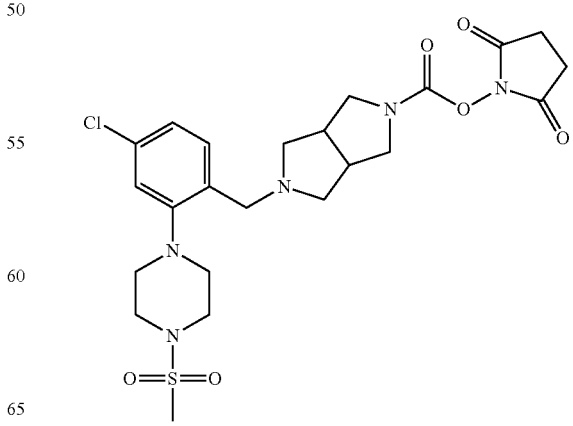

The title compound was synthesized directly from commercially available 4-chloro-2-fluorobenzaldehyde, 1-methanesulfonylpiperazine, tert-butyl octahydropyrrolo[3,4-c]pyrrole-2-carboxylate], and bis(2,5-dioxopyrrolidin-1-yl)carbonate according to the general procedures of Example 10 (Step 1), Example 9 (Steps 1 and 2), and Example 79 to provide 2,5-dioxopyrrolidin-1-yl 5-[[4-chloro-2-(4-methanesulfonylpiperazin-1-yl)phenyl]methyl]-octahydropyrrolo[3,4-c]pyrrole-2-carboxylate as a white solid. $^1$H NMR (300 MHz, Chloroform-d) δ 7.33-7.36 (m, 1H), 7.03-7.10 (m, 2H), 3.55-3.81 (m, 4H), 3.38-3.46 (m, 6H), 3.08-3.09 (m, 4H), 2.82-2.88 (m, 9H), 2.57-2.64 (m, 4H). LCMS (ESI, m/z): 540 [M+H]$^+$.

Example 111

2,5-Dioxopyrrolidin-1-yl 5-[(4-chloro-2-[4-[(pyrrolidin-1-yl)carbonyl]piperidin-1-yl]phenyl)methyl]-octahydropyrrolo[3,4-c]pyrrole-2-carboxylate

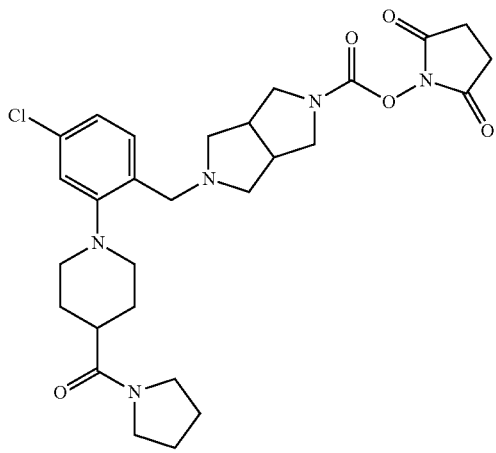 [SMILES: O=C(ON1C(=O)CCC1=O)N1CC2CN(Cc3ccc(Cl)cc3N3CCC(C(=O)N4CCCC4)CC3)CC2C1]

The title compound was synthesized directly from commercially available 4-chloro-2-fluorobenzaldehyde, 4-[(pyrrolidin-1-yl)carbonyl]piperidine hydrochloride, tert-butyl octahydropyrrolo[3,4-c]pyrrole-2-carboxylate], and bis(2,5-dioxopyrrolidin-1-yl)carbonate according to the general procedures of Example 10 (Step 1), Example 9 (Steps 1 and 2), and Example 79 to provide 2,5-dioxopyrrolidin-1-yl 5-[(4-chloro-2-[4-[(pyrrolidin-1-yl)carbonyl]piperidin-1-yl]phenyl)methyl]-octahydropyrrolo[3,4-c]pyrrole-2-carboxylate as a light yellow oil. $^1$H NMR (300 MHz, Chloroform-d) δ 7.31-7.33 (m, 1H), 7.00-7.03 (m, 2H), 3.81-3.91 (m, 2H), 3.46-3.78 (m, 6H), 3.24-3.38 (m, 4H), 2.80-2.91 (m, 6H), 2.59-2.80 (m, 4H), 2.44-2.72 (m, 3H), 1.78-2.07 (m, 8H). LCMS (ESI, m/z): 558 [M+H]$^+$.

Example 112

2,5-Dioxopyrrolidin-1-yl 5-[(4-chloro-2-[1-oxo-2,8-diazaspiro[4.5]decan-8-yl]phenyl)methyl]-octahydropyrrolo[3,4-c]pyrrole-2-carboxylate

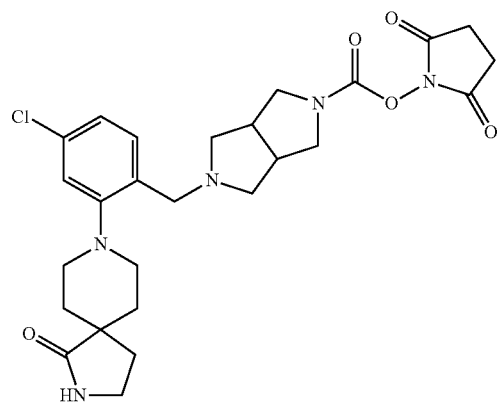 [SMILES: O=C(ON1C(=O)CCC1=O)N1CC2CN(Cc3ccc(Cl)cc3N3CCC4(CCNC4=O)CC3)CC2C1]

The title compound was synthesized directly from commercially available 4-chloro-2-fluorobenzaldehyde, 2,8-diazaspiro[4.5]decan-1-one, tert-butyl octahydropyrrolo[3,4-c]pyrrole-2-carboxylate], and bis(2,5-dioxopyrrolidin-1-yl)carbonate according to the general procedures of Example 10 (Step 1), Example 9 (Steps 1 and 2), and Example 79 to provide 2,5-dioxopyrrolidin-1-yl 5-[(4-chloro-2-[1-oxo-2,8-diazaspiro[4.5]decan-8-yl]phenyl)methyl]-octahydropyrrolo[3,4-c]pyrrole-2-carboxylate as a light yellow oil. $^1$H NMR (300 MHz, Chloroform-d) δ 7.34 (s, 1H), 7.04 (s, 2H), 6.00 (s, 1H), 3.65-3.86 (m, 4H), 3.28-3.54 (m, 6H), 2.72-2.92 (m, 10H), 2.46 (br, 2H), 2.02-2.18 (m, 4H), 1.43-1.58 (m, 2H). LCMS (ESI, m/z): 530 [M+H]$^+$.

Example 113

2,5-Dioxopyrrolidin-1-yl 5-[[2-(azetidin-1-yl)-4-chlorophenyl]methyl]-octahydropyrrolo[3,4-c]pyrrole-2-carboxylate

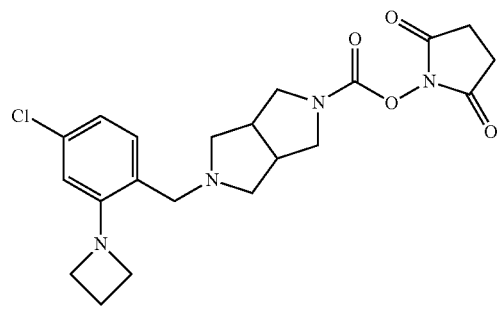 [SMILES: O=C(ON1C(=O)CCC1=O)N1CC2CN(Cc3ccc(Cl)cc3N3CCC3)CC2C1]

The title compound was synthesized directly from commercially available 2-bromo-4-chlorobenzaldehyde, tert-butyl octahydropyrrolo[3,4-c]pyrrole-2-carboxylate], azetidine, and bis(2,5-dioxopyrrolidin-1-yl)carbonate according to the general procedures of Example 22 (Steps 1-3) and Example 79 to provide 2,5-dioxopyrrolidin-1-yl 5-[[2-(azetidin-1-yl)-4-chlorophenyl]methyl]-octahydropyrrolo[3,4-c]

pyrrole-2-carboxylate as a yellow oil. ¹H NMR (300 MHz, Chloroform-d) δ 7.09 (br, 1H), 6.70-6.73 (m, 1H), 6.41 (s, 1H), 3.97 (t, J=7.2 Hz, 4H), 3.72-3.84 (m, 2H), 3.45-3.64 (m, 4H), 2.82-2.87 (m, 6H), 2.50-2.66 (m, 4H), 2.28-2.41 (m, 2H). LCMS (ESI, m/z): 455 [M+Na]⁺.

Example 114

2,5-Dioxopyrrolidin-1-yl 5-((1-methyl-3-phenyl-1H-pyrazol-4-yl)methyl)hexahydropyrrolo[3,4-c]pyrrole-2(1H)-carboxylate

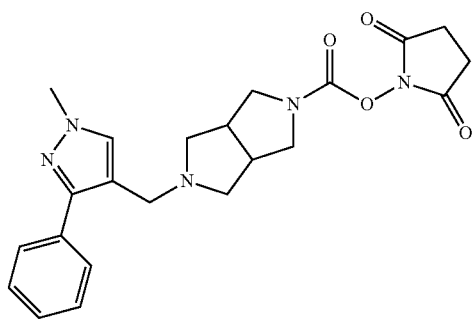 [SMILES: Cn1cc(CN2CC3CN(C(=O)ON4C(=O)CCC4=O)CC3C2)c(-c2ccccc2)n1]

The title compound was synthesized directly from commercially available 1-methyl-3-phenyl-1H-pyrazole-4-carbaldehyde, tert-butyl hexahydropyrrolo[3,4-c]pyrrole-2(1H)-carboxylate, and bis(2,5-dioxopyrrolidin-1-yl)carbonate according to the representative procedures of Example 1 (Steps 1 and 2) and Example 79 to provide 2,5-dioxopyrrolidin-1-yl 5-((1-methyl-3-phenyl-1H-pyrazol-4-yl)methyl)hexahydropyrrolo[3,4-c]pyrrole-2(1H)-carboxylate. ¹H NMR (400 MHz, Chloroform-d) δ 7.66-7.62 (m, 2H), 7.53 (s, 1H), 7.41 (t, J=7.5 Hz, 2H), 7.37-7.32 (m, 1H), 3.94 (s, 3H), 3.85-3.65 (m, 4H), 3.45-3.28 (m, 2H), 3.02-2.85 (m, 2H), 2.85-2.72 (m, 4H), 2.65-2.52 (m, 4H). LCMS (ESI, m/z): 424.1 [M+H]⁺.

Example 115

2,5-Dioxopyrrolidin-1-yl 5-[[3-(2-chlorophenyl)-1-methyl-1H-pyrazol-4-yl]methyl]-octahydropyrrolo[3,4-c]pyrrole-2-carboxylate

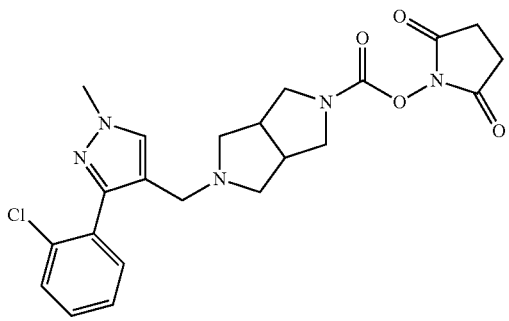 [SMILES: Cn1cc(CN2CC3CN(C(=O)ON4C(=O)CCC4=O)CC3C2)c(-c2ccccc2Cl)n1]

The title compound was synthesized directly from commercially available 1-(2-chlorophenyl)ethan-1-one, methylhydrazine sulfate, tert-butyl hexahydropyrrolo[3,4-c]pyrrole-2(1H)-carboxylate, and bis(2,5-dioxopyrrolidin-1-yl) carbonate according to the representative procedures of Example 51 (Steps 1-4) and Example 79 to provide 2,5-dioxopyrrolidin-1-yl 5-[[3-(2-chlorophenyl)-1-methyl-1H-pyrazol-4-yl]methyl]-octahydropyrrolo[3,4-c]pyrrole-2-carboxylate as a colorless oil. ¹H NMR (300 MHz, Chloroform-d) δ 7.28-7.51 (m, 5H), 3.95 (s, 3H), 3.64-3.81 (m, 2H), 3.50 (br, 2H), 3.05-3.13 (m, 2H), 2.82 (s, 6H), 2.52 (br, 2H), 2.29 (br, 2H). LCMS (ESI, m/z): 458 [M+H]⁺.

Example 116

2,5-Dioxopyrrolidin-1-yl 5-[[3-(1-acetylpiperidin-4-yl)-1-methyl-1H-pyrazol-4-yl]methyl]-octahydropyrrolo[3,4-c]pyrrole-2-carboxylate

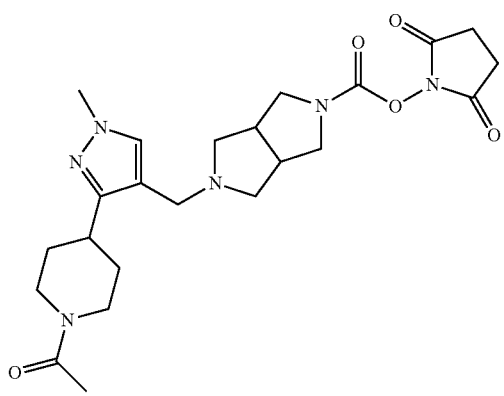 [SMILES: CC(=O)N1CCC(c2nn(C)cc2CN2CC3CN(C(=O)ON4C(=O)CCC4=O)CC3C2)CC1]

The title compound was synthesized directly from commercially available 1-(pyridin-4-yl)ethan-1-one, methylhydrazine sulfate, tert-butyl hexahydropyrrolo[3,4-c]pyrrole-2(1H)-carboxylate, and bis(2,5-dioxopyrrolidin-1-yl) carbonate according to the representative procedures of Example 52 (Steps 1-8) and Example 79 to provide 2,5-dioxopyrrolidin-1-yl 5-[[3-(1-acetylpiperidin-4-yl)-1-methyl-1H-pyrazol-4-yl]methyl]-octahydropyrrolo[3,4-c]pyrrole-2-carboxylate as a yellow oil. ¹H NMR (300 MHz, Chloroform-d) δ 7.57 (s, 1H), 4.64-4.68 (m, 1H), 4.15 (br, 2H), 3.88-4.08 (m, 8H), 3.42-3.60 (m, 2H), 3.12-3.28 (m, 3H), 2.50-2.87 (m, 8H), 2.11 (s, 3H), 1.66-1.85 (m, 4H). LCMS (ESI, m/z): 473 [M+H]⁺.

Example 117

2,5-Dioxopyrrolidin-1-yl 5-[[3-phenyl-1-(propan-2-yl)-1H-pyrazol-4-yl]methyl]-octahydropyrrolo[3,4-c]pyrrole-2-carboxylate

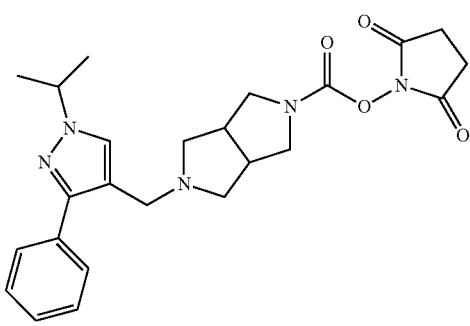 [SMILES: CC(C)n1cc(CN2CC3CN(C(=O)ON4C(=O)CCC4=O)CC3C2)c(-c2ccccc2)n1]

The title compound was synthesized directly from commercially available 1-phenylethan-1-one, propan-2-ylhydrazine hydrochloride, tert-butyl hexahydropyrrolo[3,4-c]pyrrole-2(1H)-carboxylate, and bis(2,5-dioxopyrrolidin-1-yl)carbonate according to the representative procedures of Example 51 (Steps 1-4) and Example 79 to provide 2,5-dioxopyrrolidin-1-yl 5-[[3-phenyl-1-(propan-2-yl)-1H-pyrazol-4-yl]methyl]-octahydropyrrolo[3,4-c]pyrrole-2-carboxylate as a white solid. ¹H NMR (400 MHz, Chloroform-d) δ 7.63-7.71 (m, 2H), 7.58 (s, 1H), 7.38-7.47 (m, 2H), 7.30-7.34 (m, 1H), 4.49-4.54 (m, 1H), 3.80-3.85 (m, 1H), 3.70-3.75 (m, 1H), 3.64 (s, 2H), 3.28-3.41 (m, 2H), 2.81-2.91 (m, 1H), 2.72 (s, 4H), 2.49-2.65 (m, 5H), 1.53 (d, J=7.2 Hz, 6H). LCMS (ESI, m/z): 474 [M+Na]⁺.

Example 118

2,5-Dioxopyrrolidin-1-yl 5-[[3-(2-chlorophenyl)-1-(propan-2-yl)-1H-pyrazol-4-yl]methyl]-octahydropyrrolo[3,4-c]pyrrole-2-carboxylate

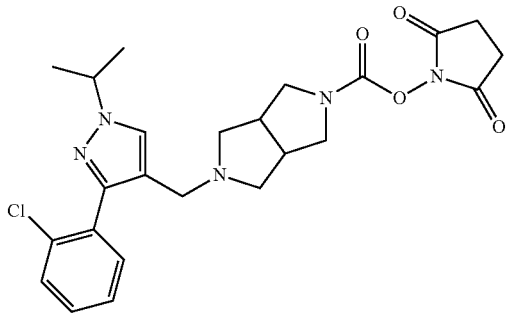 [SMILES: CC(C)n1cc(CN2CC3CN(C(=O)ON4C(=O)CCC4=O)CC3C2)c(-c2ccccc2Cl)n1]

The title compound was synthesized directly from commercially available 1-(2-chlorophenyl)ethan-1-one, propan-2-ylhydrazine hydrochloride, tert-butyl hexahydropyrrolo[3,4-c]pyrrole-2(1H)-carboxylate, and bis(2,5-dioxopyrrolidin-1-yl)carbonate according to the representative procedures of Example 51 (Steps 1-4) and Example 79 to provide 2,5-dioxopyrrolidin-1-yl 5-[[3-(2-chlorophenyl)-1-(propan-2-yl)-1H-pyrazol-4-yl]methyl]-octahydropyrrolo[3,4-c]pyrrole-2-carboxylate as a colorless oil. ¹H NMR (300 MHz, Chloroform-d) δ 7.38-7.46 (m, 3H), 7.30-7.37 (m, 2H), 4.48-4.57 (m, 1H), 3.66-3.80 (m, 2H), 3.50 (br, 2H), 3.01-3.12 (m, 2H), 2.82 (s, 6H), 2.48 (br, 2H), 2.29 (br, 2H), 1.55 (d, J=6.8 Hz, 6H). LCMS (ESI, m/z): 486 [M+H]⁺.

Example 119

2,5-Dioxopyrrolidin-1-yl 5-[[3-(1-acetylpiperidin-4-yl)-1-(propan-2-yl)-1H-pyrazol-4-yl]methyl]-octahydropyrrolo[3,4-c]pyrrole-2-carboxylate

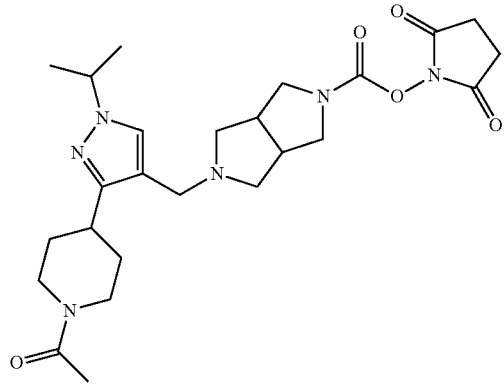 [SMILES: CC(=O)N1CCC(c2nn(C(C)C)cc2CN2CC3CN(C(=O)ON4C(=O)CCC4=O)CC3C2)CC1]

The title compound was synthesized directly from commercially available 1-(pyridin-4-yl)ethan-1-one, propan-2-ylhydrazine hydrochloride, tert-butyl hexahydropyrrolo[3,4-c]pyrrole-2(1H)-carboxylate, and bis(2,5-dioxopyrrolidin-1-yl)carbonate according to the representative procedures of Example 52 (Steps 1-8) and Example 79 to provide 2,5-dioxopyrrolidin-1-yl 5-[[3-(1-acetylpiperidin-4-yl)-1-(propan-2-yl)-1H-pyrazol-4-yl]methyl]-octahydropyrrolo[3,4-c]pyrrole-2-carboxylate as a colorless oil. ¹H NMR (300 MHz, Chloroform-d) δ 7.26 (s, 1H), 4.62-4.66 (m, 1H), 4.36-4.45 (m, 1H), 3.74-3.93 (m, 3H), 3.26-3.74 (m, 4H), 3.03-3.20 (m, 1H), 2.83-2.90 (m, 6H), 2.71-2.75 (m, 1H), 2.67 (br, 3H), 2.13 (s, 3H), 1.69-1.89 (m, 6H), 1.45 (d, J=6.8 Hz, 6H). LCMS (ESI, m/z): 501 [M+H]⁺.

Example 120

2,5-Dioxopyrrolidin-1-yl 5-[[3-(1-methanesulfonylpiperidin-4-yl)-1-(propan-2-yl)-1H-pyrazol-4-yl]methyl]-octahydropyrrolo[3,4-c]pyrrole-2-carboxylate

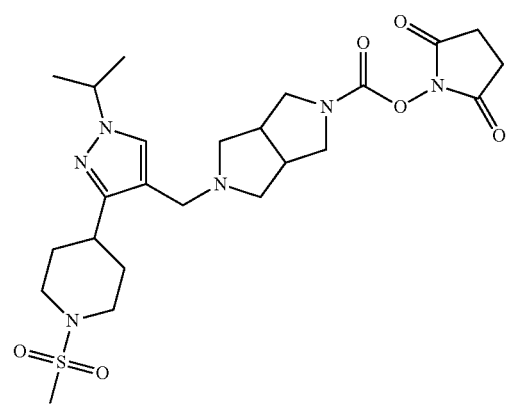 [SMILES: CC(C)n1cc(CN2CC3CN(C(=O)ON4C(=O)CCC4=O)CC3C2)c(C2CCN(S(C)(=O)=O)CC2)n1]

The title compound was synthesized directly from commercially available 1-(pyridin-4-yl)ethan-1-one, propan-2-ylhydrazine hydrochloride, tert-butyl hexahydropyrrolo[3,4-c]pyrrole-2(1H)-carboxylate, and bis(2,5-dioxopyrrolidin-1-yl)carbonate according to the representative procedures of Example 52 (Steps 1-8) and Example 79 to provide 2,5-dioxopyrrolidin-1-yl 5-[[3-(1-methanesulfonylpiperidin-4-yl)-1-(propan-2-yl)-1H-pyrazol-4-yl]methyl]-octahydropyrrolo[3,4-c]pyrrole-2-carboxylate as a white solid. ¹H NMR (300 MHz, Chloroform-d) δ 7.20 (s, 1H), 4.36-4.44 (m, 1H), 3.78-3.87 (m, 3H), 3.25-3.62 (m, 4H), 2.82-3.00 (m, 11H), 2.44-2.74 (m, 3H), 2.03 (br, 4H), 1.54-1.75 (m, 3H), 1.44 (d, J=6.8 Hz, 6H). LCMS (ESI, m/z): 537 [M+H]⁺.

Example 121

2,5-Dioxopyrrolidin-1-yl 5-[[3-methyl-1-(propan-2-yl)-1H-pyrazol-5-yl]methyl]-octahydropyrrolo[3,4-c]pyrrole-2-carboxylate

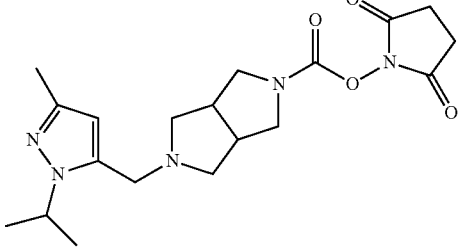

The title compound was synthesized from commercially available ethyl 2,4-dioxopentanoate, methoxylamine hydrochloride, propan-2-ylhydrazine hydrochloride, tert-butyl hexahydropyrrolo[3,4-c]pyrrole-2(1H)-carboxylate, and bis(2,5-dioxopyrrolidin-1-yl)carbonate according to the representative procedures of Example 58 (Steps 1-6) and Example 79 to provide 2,5-dioxopyrrolidin-1-yl 5-[[3-methyl-1-(propan-2-yl)-1H-pyrazol-5-yl]methyl]-octahydropyrrolo[3,4-c]pyrrole-2-carboxylate as a white solid. $^1$H NMR (300 MHz, Chloroform-d) δ 5.84 (s, 1H), 4.55-4.64 (m, 1H), 3.71-3.87 (m, 2H), 3.55 (br, 2H), 3.32-3.44 (m, 2H), 2.81-2.90 (m, 6H), 2.46-2.57 (m, 4H), 2.24 (s, 3H), 1.46 (d, J=6.8 Hz, 6H). LCMS (ESI, m/z): 390 [M+H]$^+$.

Example 122

2,5-Dioxopyrrolidin-1-yl 5-[[1-(1-acetylpiperidin-4-yl)-3-methyl-1H-pyrazol-5-yl]methyl]-octahydropyrrolo[3,4-c]pyrrole-2-carboxylate

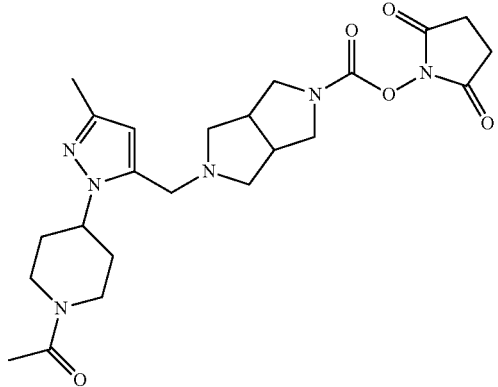 [SMILES: CC(=O)N1CCC(n2nc(C)cc2CN2CC3CN(C(=O)ON4C(=O)CCC4=O)CC3C2)CC1]

The title compound was synthesized from commercially available ethyl 2,4-dioxopentanoate, methoxylamine hydrochloride, benzyl 4-hydrazinylpiperidine-1-carboxylate dihydrochloride, tert-butyl hexahydropyrrolo[3,4-c]pyrrole-2 (1H)-carboxylate, and bis(2,5-dioxopyrrolidin-1-yl) carbonate according to the representative procedures of Example 58 (Steps 1-5), Example 60 (Steps 6 and 7), Example 58 (Step 6), and Example 79 to provide 2,5-dioxopyrrolidin-1-yl 5-[[1-(1-acetylpiperidin-4-yl)-3-methyl-1H-pyrazol-5-yl]methyl]-octahydropyrrolo[3,4-c] pyrrole-2-carboxylate as a white solid. $^1$H NMR (300 MHz, Chloroform-d) δ 5.86 (s, 1H), 4.75-4.79 (m, 1H), 4.37 (br, 1H), 3.98-4.02 (m, 1H), 3.68-3.82 (m, 3H), 3.21-3.46 (m, 3H), 3.06-3.15 (m, 1H), 2.68-2.91 (m, 6H), 2.41-2.62 (m, 5H), 2.01-2.22 (m, 8H), 1.83-1.90 (m, 2H). LCMS (ESI, m/z): 473 [M+H]$^+$.

Example 123

2,5-Dioxopyrrolidin-1-yl 5-[[1-cyclohexyl-3-(propan-2-yl)-1H-pyrazol-5-yl]methyl]-octahydropyrrolo[3,4-c]pyrrole-2-carboxylate

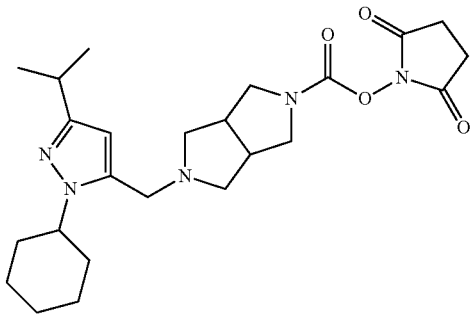 [SMILES: CC(C)c1cc(CN2CC3CN(C(=O)ON4C(=O)CCC4=O)CC3C2)n(C2CCCCC2)n1]

The title compound was synthesized from commercially available cyclohexylhydrazine hydrochloride, 2-methylpropanal, (2E)-N-methoxy-N-methyl-3-nitroprop-2-enamide, tert-butyl hexahydropyrrolo[3,4-c]pyrrole-2(1H)-carboxylate, and bis(2,5-dioxopyrrolidin-1-yl)carbonate according to the representative procedures of Example 61 (Steps 1-5) and Example 79 to provide 2,5-dioxopyrrolidin-1-yl 5-[[1-cyclohexyl-3-(propan-2-yl)-1H-pyrazol-5-yl]methyl]-octahydropyrrolo[3,4-c]pyrrole-2-carboxylate as a white solid. $^1$H NMR (300 MHz, Chloroform-d) δ 5.87 (s, 1H), 4.09-4.58 (m, 1H), 3.76-3.88 (m, 2H), 3.57 (s, 2H), 3.29-3.41 (m, 2H), 2.81-2.98 (m, 7H), 2.55 (br, 4H), 1.84-2.01 (m, 6H), 1.67-1.71 (m, 1H), 1.25-1.44 (m, 3H), 1.21 (d, J=6.8 Hz, 6H). LCMS (ESI, m/z): 458 [M+H]$^+$.

Example 124

2,5-Dioxopyrrolidin-1-yl 5-[[1-(oxan-4-yl)-3-(propan-2-yl)-1H-pyrazol-5-yl]methyl]-octahydropyrrolo[3,4-c]pyrrole-2-carboxylate

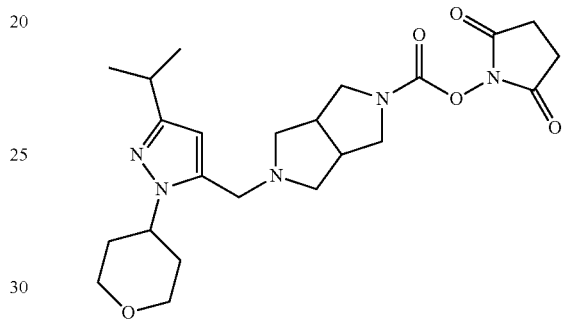

The title compound was synthesized from commercially available oxan-4-ylhydrazine hydrochloride, 2-methylpropanal, (2E)-N-methoxy-N-methyl-3-nitroprop-2-enamide, tert-butyl hexahydropyrrolo[3,4-c]pyrrole-2(1H)-carboxylate, and bis(2,5-dioxopyrrolidin-1-yl)carbonate according to the representative procedures of Example 61 (Steps 1-5) and Example 79 to provide 2,5-dioxopyrrolidin-1-yl 5-[[1-(oxan-4-yl)-3-(propan-2-yl)-1H-pyrazol-5-yl]methyl]-octahydropyrrolo[3,4-c]pyrrole-2-carboxylate as a yellow oil. $^1$H NMR (300 MHz, Chloroform-d) δ 5.90 (s, 1H), 4.30-4.41 (m, 1H), 4.08-4.13 (m, 2H), 3.70-3.85 (m, 2H), 3.31-3.59 (m, 6H), 2.92-2.99 (m, 3H), 2.81-2.90 (m, 4H), 2.56-2.70 (m, 4H), 2.30-2.50 (m, 2H), 1.70-1.82 (m, 2H), 1.22 (d, J=6.8 Hz, 6H). LCMS (ESI, m/z): 460 [M+H]$^+$.

Example 125

2,2,2-Trifluoro-1-(methylcarbamoyl)ethyl 5-[bis(4-chlorophenyl)methyl]-octahydropyrrolo[3,4-c]pyrrole-2-carboxylate

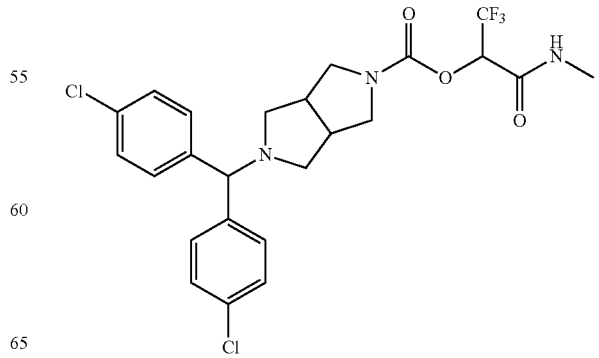

Step 1: Preparation of ethyl 3,3,3-trifluoro-2-hydroxypropanoate

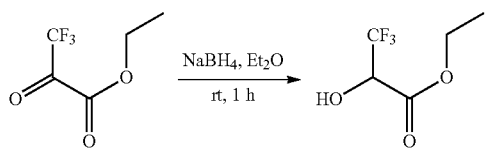

A 100-mL round-bottom flask was charged with ethyl 3,3,3-trifluoro-2-oxopropanoate (5.00 g, 29.4 mmol, 1.00 equiv), ether (50 mL). The mixture was cooled to 0° C. $NaBH_4$ (559 mg, 14.8 mmol, 0.50 equiv) was added in portions. The resulting solution was stirred for 1 h at room temperature and diluted with $H_2O$ (20 mL). The mixture was extracted with dichloromethane (3×50 mL), and the organic layers were combined, dried over anhydrous sodium sulfate, filtered, and concentrated under reduced pressure to provide 4.20 g (83% yield) of ethyl 3,3,3-trifluoro-2-hydroxypropanoate as a colorless solid. GCMS (EI, m/z): 172 [M]$^+$.

Steps 2-4: Preparation of 2-[bis(4-chlorophenyl)methyl]-octahydropyrrolo[3,4-c]pyrrole 2-[Bis(4-chlorophenyl)methyl]-octahydropyrrolo[3,4-c]pyrrole was synthesized from commercially available bis(4-chlorophenyl)methanol and tert-butyl hexahydropyrrolo[3,4-c]pyrrole-2(1H)-carboxylate according to the representative procedures of Example 8 (Steps 1-3).

Step 5: Preparation of ethyl 2-([5-[bis(4-chlorophenyl)methyl]-octahydropyrrolo[3,4-c]pyrrol-2-yl]carbonyloxy)-3,3,3-trifluoropropanoate

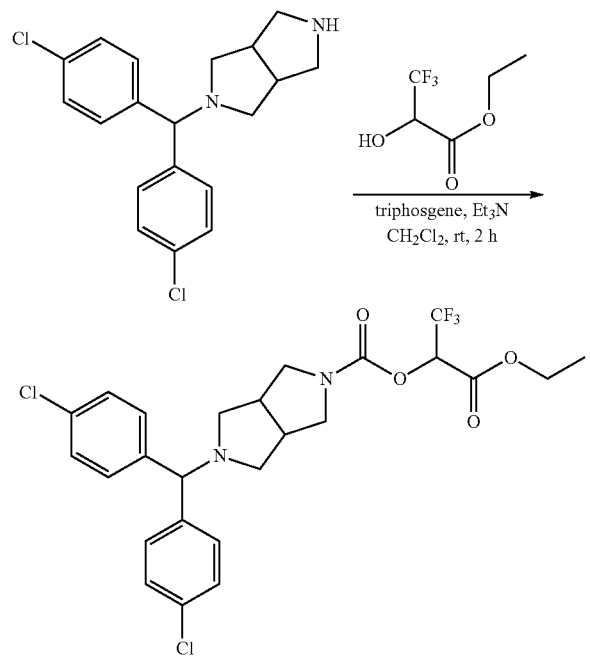

A 25-mL round-bottom flask was charged with ethyl 3,3,3-trifluoro-2-hydroxypropanoate (74.0 mg, 0.430 mmol, 1.00 equiv), triphosgene (43.0 mg, 0.145 mmol, 0.33 equiv), and dichloromethane (5 mL). Triethylamine (131 mg, 1.29 mmol, 3.00 equiv) was added dropwise. The mixture was stirred at room temperature for 2 h. 2-[Bis(4-chlorophenyl)methyl]-octahydropyrrolo[3,4-c]pyrrole (150 mg, 0.432 mmol, 1.00 equiv) was added. The resulting solution was stirred for 2 h at room temperature and diluted with $H_2O$ (20 mL). The mixture was extracted with dichloromethane (3×20 mL), and the organic layers were combined, washed with water (3×10 mL), dried over anhydrous sodium sulfate, and concentrated under reduced pressure. The residue was chromatographed on a silica gel column with ethyl acetate/petroleum ether (1/5) to provide 100 mg (36% yield) of ethyl 2-([5-[bis(4-chlorophenyl)methyl]-octahydropyrrolo[3,4-c]pyrrol-2-yl]carbonyloxy)-3,3,3-trifluoropropanoate as a colorless oil. LCMS (ESI, m/z): 545 [M+H]$^+$.

Step 6: Preparation of 2,2,2-trifluoro-1-(methylcarbamoyl)ethyl 5-[bis(4-chlorophenyl)methyl]-octahydropyrrolo[3,4-c]pyrrole-2-carboxylate

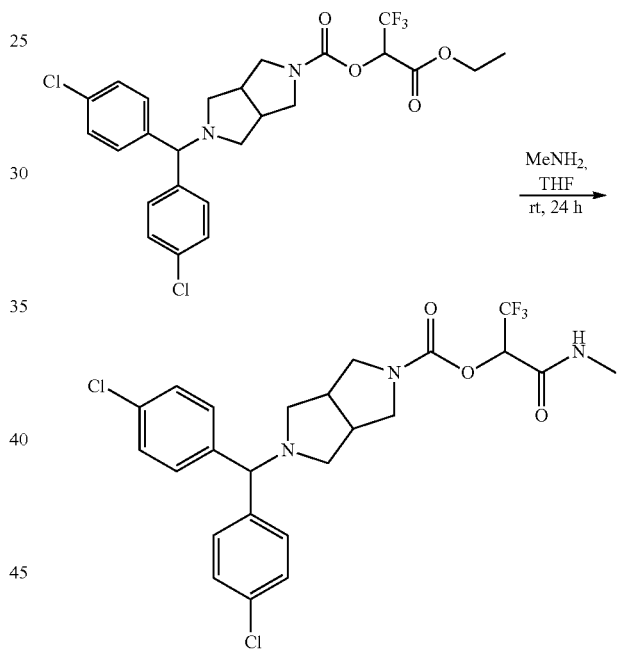

A 25-mL round-bottom flask was charged with ethyl 2-([5-[bis(4-chlorophenyl)methyl]-octahydropyrrolo[3,4-c]pyrrol-2-yl]carbonyloxy)-3,3,3-trifluoropropanoate (100 mg, 0.183 mmol, 1.00 equiv), tetrahydrofuran (5 mL), and methylamine (2 M in tetrahydrofuran, 0.90 mL, 1.80 mmol, 10.0 equiv). The resulting solution was stirred for 24 h at room temperature. The resulting mixture was concentrated under reduced pressure. The crude product (125 mg) was purified by preparative HPLC using the following gradient conditions: 20% $CH_3CN$/80% Phase A increasing to 80% $CH_3CN$ over 10 min, then to 100% $CH_3CN$ over 0.1 min, holding at 100% $CH_3CN$ for 1.9 min, then reducing to 20% $CH_3CN$ over 0.1 min, and holding at 20% for 1.9 min, on a Waters 2767-5 Chromatograph. Column: Xbridge Prep C18, 19*150 mm, 5 um. Mobile phase: Phase A: aqueous $NH_4HCO_3$ (0.05%); Phase B: $CH_3CN$. Detector: UV 220 & 254 nm. Purification resulted in 27.1 mg (28% yield) of 2,2,2-trifluoro-1-(methylcarbamoyl)ethyl 5-[bis(4-chlorophenyl)methyl]-octahydropyrrolo[3,4-c]pyrrole-2-carboxylate as a white solid. ¹H NMR (300 MHz, Chloroform-d) δ 7.23-7.33 (m, 8H), 6.20 (br, 1H), 5.53-5.64 (m, 1H), 4.11-4.16 (m, 1H), 3.57-3.80 (m, 2H), 3.33-3.47 (m, 2H), 2.89-2.95 (m, 5H), 2.43-2.50 (m, 4H). LCMS (ESI, m/z): 530 [M+H]⁺.

Example 126

2,2,2-Trifluoro-1-(methylcarbamoyl)ethyl 5-[(4-phenylphenyl)methyl]-octahydropyrrolo[3,4-c]pyrrole-2-carboxylate

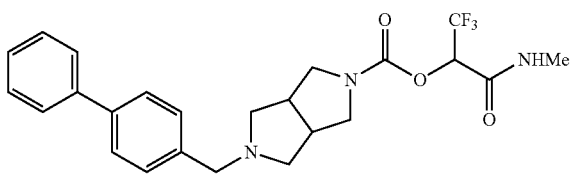 [SMILES: CNC(=O)C(OC(=O)N1CC2CN(Cc3ccc(-c4ccccc4)cc3)CC2C1)C(F)(F)F]

The title compound was synthesized from 2-[(4-phenylphenyl)methyl]-octahydropyrrolo[3,4-c]pyrrole (Example 9, Steps 1 and 2) and ethyl 3,3,3-trifluoro-2-hydroxypropanoate (Example 125, Step 1) according to the representative procedures of Example 125, Steps 5 and 6, to provide 2,2,2-trifluoro-1-(methylcarbamoyl)ethyl 5-[(4-phenylphenyl)methyl]-octahydropyrrolo[3,4-c]pyrrole-2-carboxylate as a light yellow oil. ¹H NMR (300 MHz, Chloroform-d) δ 7.37-7.62 (m, 9H), 6.19 (s, 1H), 5.55-5.60 (m, 1H), 3.40-3.95 (m, 6H), 2.55-3.19 (m, 9H). LCMS (ESI, m/z): 462 [M+H]⁺.

Example 127

1,1,1,3,3,3-hexafluoropropan-2-yl 5-[(2-methyl-3-[3-oxa-8-azabicyclo[3.2.1]octan-8-yl]phenyl)methyl]-octahydropyrrolo[3,4-c]pyrrole-2-carboxylate

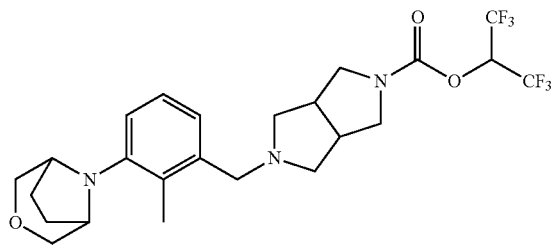 [SMILES: Cc1c(CN2CC3CN(C(=O)OC(C(F)(F)F)C(F)(F)F)CC3C2)cccc1N1C2CCC1COC2]

Step 1: Preparation of potassium ((5-(tert-butoxycarbonyl)-hexahydropyrrolo[3,4-c]pyrrol-2(1H)-yl)methyl)trifluoroborate as a brown solid

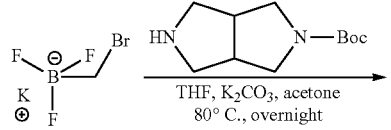

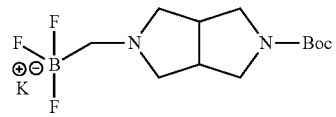

A 250-mL round-bottom flask was charged with potassium (bromomethyl)trifluoroborate (2.00 g, 9.96 mmol, 1.00 equiv), tert-butyl octahydropyrrolo[3,4-c]pyrrole-2-carboxylate (2.32 g, 10.9 mmol, 1.10 equiv), tetrahydrofuran (20 mL). The mixture was stirred overnight at 80° C. The solid was filtered out and the organic layer was concentrated under reduced pressure. Potassium carbonate (1.37 g, 9.91 mmol, 1.00 equiv), acetone (20 mL) was added. The resulting solution was stirred for 1.5 hours at room temperature. The reaction progress was monitored by LCMS. The resulting mixture was concentrated under reduced pressure. The crude product was re-crystallized from acetone/n-hexane (2/20) to provide 2.20 g (67% yield) of potassium ((5-(tert-butoxycarbonyl)-hexahydropyrrolo[3,4-c]pyrrol-2(1H)-yl)methyl)trifluoroborate as a brown solid. LCMS (ESI, m/z): 333 [M+H]⁺.

Step 2: Preparation of 8-(3-chloro-2-methylphenyl)-3-oxa-8-azabicyclo[3.2.1]octane

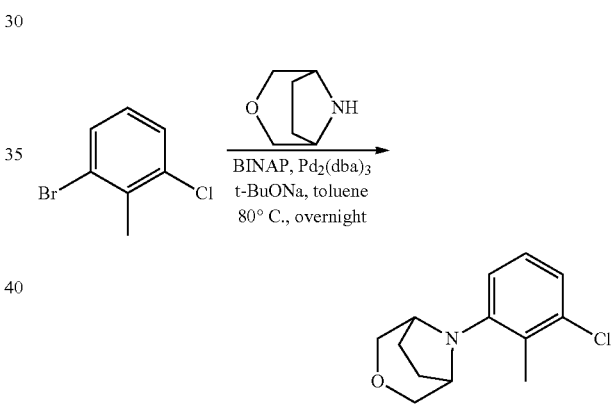

The title compound was synthesized from 1-bromo-3-chloro-2-methylbenzene as described in Example 11 (Step 1) to provide 8-(3-chloro-2-methylphenyl)-3-oxa-8-azabicyclo[3.2.1]octane as yellow oil. LCMS (ESI, m/z): 238 [M+H]⁺.

Step 3: Preparation of tert-butyl 5-[(2-methyl-3-[3-oxa-8-azabicyclo[3.2.1]octan-8-yl]phenyl)methyl]-octahydropyrrolo[3,4-c]pyrrole-2-carboxylate

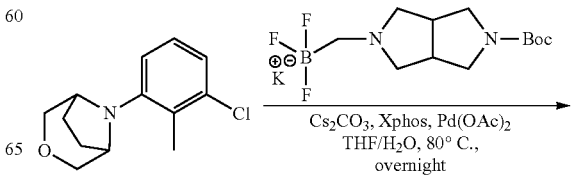

-continued

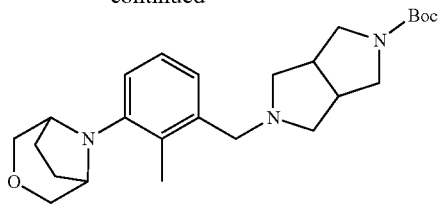

A 25-mL round-bottom flask was charged with 8-(3-chloro-2-methylphenyl)-3-oxa-8-azabicyclo[3.2.1]octane (200 mg, 0.840 mmol, 1.00 equiv), potassium ((5-(tert-butoxycarbonyl)-hexahydropyrrolo[3,4-c]pyrrol-2(1H)-yl)methyl)trifluoroborate (335 mg, 1.01 mmol, 1.20 equiv), cesium carbonate (822 mg, 2.52 mmol, 3.00 equiv), 2-(dicyclohexylphosphino)-2',4',6'-triisopropylbiphenyl (24.0 mg, 0.0503 mmol, 0.06 equiv), palladium acetate (6.00 mg, 0.0267 mmol, 0.03 equiv), tetrahydrofuran (4 mL), H$_2$O (1 mL) under nitrogen. The resulting solution was stirred overnight at 80° C. The reaction progress was monitored by LCMS. The resulting mixture was diluted with H$_2$O (20 mL). The mixture was extracted with dichloromethane (3×30 mL) and the organic layers were combined, washed with water (3×10 mL), dried over anhydrous sodium sulfate, filtered and concentrated under reduced pressure. The residue was chromatographed on a silica gel column with ethyl acetate/petroleum ether (3/7) to provide 149 mg (41% yield) of tert-butyl 5-[(2-methyl-3-[3-oxa-8-azabicyclo[3.2.1]octan-8-yl]phenyl)methyl]-octahydropyrrolo[3,4-c]pyrrole-2-carboxylate as yellow oil. LCMS (ESI, m/z): 428 [M+H]$^+$ Steps 4-5: Preparation of 1,1,1,3,3,3-hexafluoropropan-2-yl 5-[(2-methyl-3-[3-oxa-8-azabicyclo[3.2.1]octan-8-yl]phenyl)methyl]-octahydropyrrolo[3,4-c]pyrrole-2-carboxylate The title compound was synthesized from tert-butyl 5-[(2-methyl-3-[3-oxa-8-azabicyclo[3.2.1]octan-8-yl]phenyl)methyl]-octahydropyrrolo[3,4-c]pyrrole-2-carboxylate as described in Example 5 (Step 3) followed by Example 8 (Step 4, DCM used instead of MeCN) to 1,1,1,3,3,3-hexafluoropropan-2-yl 5-[(2-methyl-3-[3-oxa-8-azabicyclo[3.2.1]octan-8-yl]phenyl)methyl]-octahydropyrrolo[3,4-c]pyrrole-2-carboxylate as orange oil. $^1$H NMR (300 MHz, Chloroform-d) δ: 7.01-7.06 (m, 1H), 6.91-6.93 (m, 1H), 6.78 (d, J=7.8 Hz, 1H), 5.66-5.79 (m, 1H), 3.94-3.97 (m, 2H), 3.65-3.74 (m, 4H), 3.55 (br, 4H), 3.36-3.38 (m, 2H), 2.86 (br, 2H), 2.55 (br, 4H), 2.37 (s, 3H), 1.94-2.05 (m, 4H). LCMS (ESI, m/z): 522 [M+H]$^+$.

Example 128

1,1,1,3,3,3-hexafluoropropan-2-yl 5-[(3-[2-oxa-7-azaspiro[4.4]nonan-7-yl]-2-(trifluoromethyl)phenyl)methyl]-octahydropyrrolo[3,4-c]pyrrole-2-carboxylate

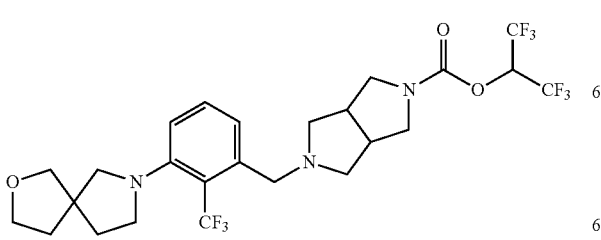

The title compound was synthesized from 1-bromo-3-chloro-2-(trifluoromethyl)benzene, 2-oxa-7-azaspiro[4.4]nonane and tert-butyl octahydropyrrolo[3,4-c]pyrrole-2-carboxylate according to the general procedure of Example 127 (Step 1-5) to provide 1,1,1,3,3,3-hexafluoropropan-2-yl 5-[(3-[2-oxa-7-azaspiro[4.4]nonan-7-yl]-2-(trifluoromethyl)phenyl)methyl]-octahydropyrrolo[3,4-c]pyrrole-2-carboxylate as an orange oil. $^1$H NMR (300 MHz, Chloroform-d) δ 7.29-7.36 (m, 1H), 7.21 (s, 1H), 6.95 (d, J=8.1 Hz, 1H), 5.68-5.79 (m, 1H), 3.87-3.96 (m, 2H), 3.63-3.75 (m, 6H), 3.30-3.38 (m, 4H), 3.19 (br, 2H), 2.87 (br, 2H), 2.59-2.64 (br, 2H), 2.48 (br, 2H), 1.92-2.05 (m, 4H). LCMS (ESI, m/z): 590 [M+H]$^+$.

Example 129

1,1,1,3,3,3-hexafluoropropan-2-yl 5-[[3-(morpholin-4-yl)-2-(trifluoromethyl)phenyl]methyl]-octahydropyrrolo[3,4-c]pyrrole-2-carboxylate

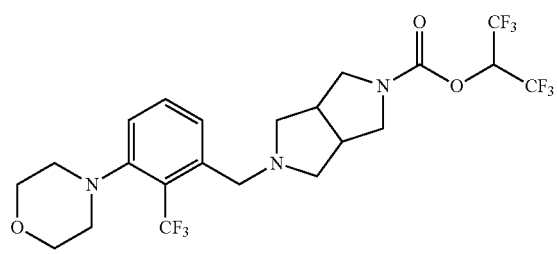 [SMILES: O=C(OC(C(F)(F)F)C(F)(F)F)N1CC2CN(Cc3cccc(N4CCOCC4)c3C(F)(F)F)CC2C1]

The title compound was synthesized from 1-bromo-3-chloro-2-(trifluoromethyl)benzene, morpholine and tert-butyl octahydropyrrolo[3,4-c]pyrrole-2-carboxylate according to the general procedure of Example 127 (Step 1-5) to provide 1,1,1,3,3,3-hexafluoropropan-2-yl 5-[[3-(morpholin-4-yl)-2-(trifluoromethyl)phenyl]methyl]-octahydropyrrolo[3,4-c]pyrrole-2-carboxylate as an orange syrup. $^1$H NMR (300 MHz, Chloroform-d) δ 7.42-7.46 (m, 2H), 7.19-7.22 (m, 1H), 5.68-5.80 (m, 1H), 3.70-3.84 (m, 8H), 3.34-3.40 (m, 2H), 2.89-2.92 (m, 6H), 2.40-2.63 (m, 4H). LCMS (ESI, m/z): 550 [M+H]$^+$.

Example 130

1,1,1,3,3,3-hexafluoropropan-2-yl 5-([1-ethyl-3-[2-(piperidin-1-yl)phenyl]-1H-pyrazol-4-yl]methyl)-octahydropyrrolo[3,4-c]pyrrole-2-carboxylate

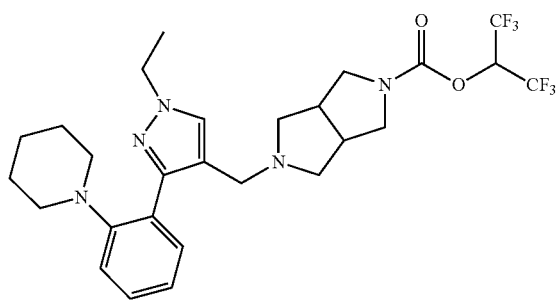 [SMILES: CCn1cc(CN2CC3CN(C(=O)OC(C(F)(F)F)C(F)(F)F)CC3C2)c(-c2ccccc2N2CCCCC2)n1]

The title compound was synthesized from 1-(2-fluorophenyl)ethan-1-one and piperidine according to the representative procedures of Example 3 (Step 1), Example 51 (Step 1), Example 52 (Step 2), Example 9 (Step 1), and Example 127 (Steps 4-5) to afford 1,1,1,3,3,3-hexafluoropropan-2-yl 5-([1-ethyl-3-[2-(piperidin-1-yl)phenyl]-1H-pyrazol-4-yl]methyl)-octahydropyrrolo[3,4-c]pyrrole-2-carboxylate as a yellow oil. $^1$H NMR (300 MHz, Chloroform-d) δ 7.34 (s, 1H), 7.22-7.29 (m, 2H), 6.94-7.00 (m, 2H), 5.68-5.76 (m, 1H), 4.14-4.22 (m, 2H), 3.58-3.67 (m, 4H), 3.05-3.14 (m, 2H), 2.72-2.78 (m, 6H), 2.31-2.38 (m, 4H), 1.49-1.51 (m, 9H). LCMS (ESI, m/z): 574 [M+H]$^+$.

Example 131

1,1,1,3,3,3-hexafluoropropan-2-yl 5-([1-ethyl-3-[2-(morpholin-4-yl)phenyl]-1H-pyrazol-4-yl]methyl)-octahydropyrrolo[3,4-c]pyrrole-2-carboxylate

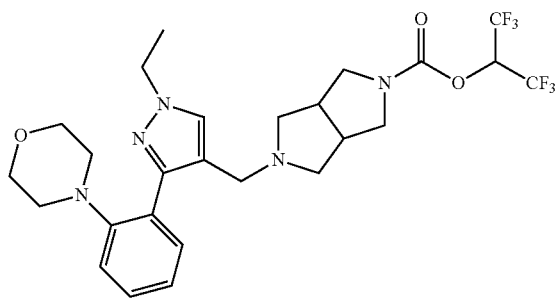 [SMILES: CCn1cc(CN2CC3CN(C(=O)OC(C(F)(F)F)C(F)(F)F)CC3C2)c(-c2ccccc2N2CCOCC2)n1]

The title compound was synthesized from 1-(2-fluorophenyl)ethan-1-one, morpholine, and tert-butyl octahydropyrrolo[3,4-c]pyrrole-2-carboxylate according to the general procedure described in Example 3 (Step 1), Example 51 (Step 1), Example 52 (Step 2), Example 9 (Step 1), and Example 127 (Steps 4-5) to afford 1,1,1,3,3,3-hexafluoropropan-2-yl 5-([1-ethyl-3-[2-(morpholin-4-yl)phenyl]-1H-pyrazol-4-yl]methyl)-octahydropyrrolo[3,4-c]pyrrole-2-carboxylate as a yellow oil. $^1$H NMR (300 MHz, Chloroform-d) δ 7.36 (s, 1H), 7.26-7.32 (m, 2H), 7.00-7.06 (m, 2H), 5.68-5.76 (m, 1H), 4.14-4.21 (m, 2H), 3.57-3.67 (m, 8H), 3.07-3.15 (m, 2H), 2.82-2.85 (m, 4H), 2.74 (br, 2H), 2.32-2.35 (m, 4H), 1.46-1.51 (m, 3H). LCMS (ESI, m/z): 576 [M+H]$^+$.

Example 132

1,1,1,3,3,3-hexafluoropropan-2-yl 5-([1-ethyl-3-[3-(piperidin-1-yl)phenyl]-1H-pyrazol-4-yl]methyl)-octahydropyrrolo[3,4-c]pyrrole-2-carboxylate

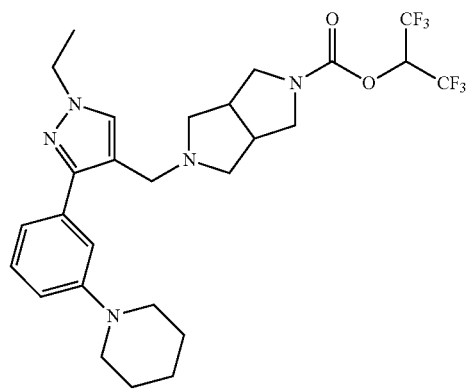 [SMILES: CCn1cc(CN2CC3CN(C(=O)OC(C(F)(F)F)C(F)(F)F)CC3C2)c(-c2cccc(N3CCCCC3)c2)n1]

Step 1-3: Preparation of tert-butyl 5-[[3-(3-bromophenyl)-1-ethyl-1H-pyrazol-4-yl]methyl]-octahydropyrrolo[3,4-c]pyrrole-2-carboxylate The title compound was synthesized from 1-(3-bromophenyl)ethan-1-one according to procedures analogous to those described in Example 3 (Step 1), Example 51 (Step 1), Example 52 (Step 2), Example 9 (Step 1), and Example 127 (Steps 4-5) to afford tert-butyl 5-[[3-(3-bromophenyl)-1-ethyl-1H-pyrazol-4-yl]methyl]-octahydropyrrolo[3,4-c]pyrrole-2-carboxylate as yellow oil. LCMS (ESI, m/z): 475 [M+H]$^+$ Step 4: Preparation of tert-butyl 5-([1-ethyl-3-[3-(piperidin-1-yl)phenyl]-1H-pyrazol-4-yl]methyl)-octahydropyrrolo[3,4-c]pyrrole-2-carboxylate

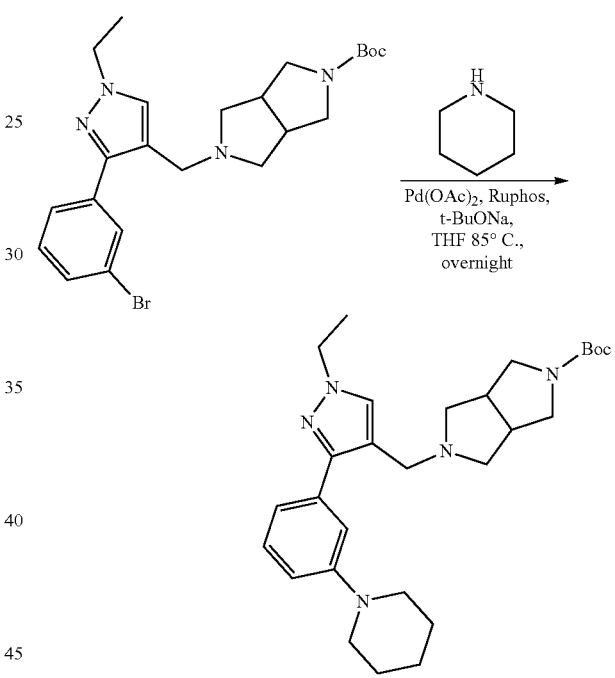

A 100-mL round-bottom flask was charged with tert-butyl 5-[[3-(3-bromophenyl)-1-ethyl-1H-pyrazol-4-yl]methyl]-octahydropyrrolo[3,4-c]pyrrole-2-carboxylate (500 mg, 1.05 mmol, 1.00 equiv), piperidine (135 mg, 1.59 mmol, 1.51 equiv), dicyclohexyl(2',6'-diisopropoxybiphenyl-2-yl)phosphine (98.0 mg, 0.210 mmol, 0.20 equiv), sodium tert-butoxide (153 mg, 1.59 mmol, 1.51 equiv), palladium acetate (12.0 mg, 0.0540 mmol, 0.05 equiv), tetrahydrofuran (20 mL) under nitrogen. The resulting solution was stirred overnight at 85° C. and then diluted with water (20 mL). The resulting solution was extracted with ethyl acetate (3×20 mL) and the organic layers were combined, dried over anhydrous sodium sulfate, filtered and concentrated under reduced pressure. The residue was chromatographed on a silica gel column with ethyl acetate/petroleum ether (57/43) to provide 300 mg (59% yield) of tert-butyl 5-([1-ethyl-3-[3-(piperidin-1-yl)phenyl]-1H-pyrazol-4-yl]methyl)-octahydropyrrolo[3,4-c]pyrrole-2-carboxylate as yellow oil. LCMS (ESI, m/z): 480 [M+H]$^+$

Step 5-6: Preparation of 1,1,1,3,3,3-hexafluoropropan-2-yl 5-([1-ethyl-3-[3-(piperidin-1-yl)phenyl]-1H-pyrazol-4-yl]methyl)-octahydropyrrolo[3,4-c]pyrrole-2-carboxylate The title compound was synthesized from tert-butyl 5-([1-ethyl-3-[3-(piperidin-1-yl)phenyl]-1H-pyrazol-4-yl]methyl)-octahydropyrrolo[3,4-c]pyrrole-2-carboxylate following the general procedures described in Example 127 (Steps 4-5) to afford 1,1,1,3,3,3-hexafluoropropan-2-yl 5-([1-ethyl-3-[3-(piperidin-1-yl)phenyl]-1H-pyrazol-4-yl]methyl)-octahydropyrrolo[3,4-c]pyrrole-2-carboxylate as a yellow oil. $^1$H NMR (300 MHz, Chloroform-d) δ 7.35-7.54 (m, 2H), 7.05-7.24 (m, 2H), 6.91-6.93 (m, 1H), 5.68-5.71 (m, 1H), 4.13-4.30 (m, 2H), 3.50-3.89 (m, 4H), 3.35-3.43 (m, 2H), 3.02-3.35 (m, 4H), 2.77-2.88 (m, 2H), 2.33-2.69 (m, 3H), 1.70-1.71 (m, 4H), 1.49-1.58 (m, 6H). LCMS (ESI, m/z): 574 [M+H]$^+$.

Example 133

1,1,1,3,3,3-hexafluoropropan-2-yl 5-([1-ethyl-3-[4-(piperidin-1-yl)phenyl]-1H-pyrazol-4-yl]methyl)-octahydropyrrolo[3,4-c]pyrrole-2-carboxylate

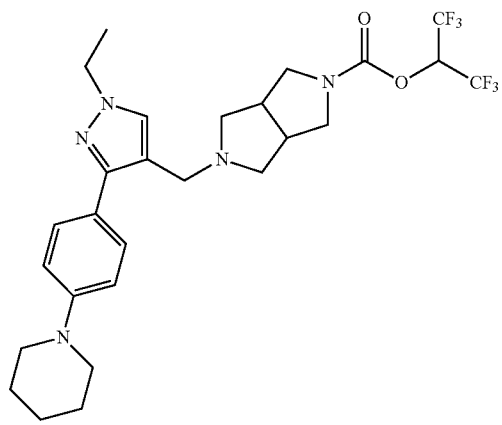 [SMILES: CCn1cc(CN2CC3CN(C(=O)OC(C(F)(F)F)C(F)(F)F)CC3C2)c(-c2ccc(N3CCCCC3)cc2)n1]

The title compound was synthesized from 1-(4-bromophenyl)ethan-1-one, tert-butyl octahydropyrrolo[3,4-c]pyrrole-2-carboxylate, and piperidine as analogously described for Example 132 to afford 1,1,1,3,3,3-hexafluoropropan-2-yl 5-([1-ethyl-3-[4-(piperidin-1-yl)phenyl]-1H-pyrazol-4-yl]methyl)-octahydropyrrolo[3,4-c]pyrrole-2-carboxylate as a white solid. $^1$H NMR (300 MHz, Chloroform-d) δ 7.61-7.63 (m, 2H), 7.33 (br, 1H), 6.91-6.96 (m, 2H), 5.68-5.76 (m, 1H), 4.12-4.20 (m, 2H), 3.70-3.76 (m, 2H), 3.55 (br, 2H), 3.31-3.38 (m, 2H), 3.17-3.21 (m, 4H), 2.87 (br, 2H), 2.56 (br, 4H), 1.70-1.75 (m, 4H), 1.62-1.68 (m, 2H), 1.52-1.60 (m, 3H). LCMS (ESI, m/z): 574 [M+H]$^+$.

Example 134

1,1,1,3,3,3-hexafluoropropan-2-yl 5-[(2-[7-methanesulfonyl-2,7-diazaspiro[4.4]nonan-2-yl]phenyl)methyl]-octahydropyrrolo[3,4-c]pyrrole-2-carboxylate

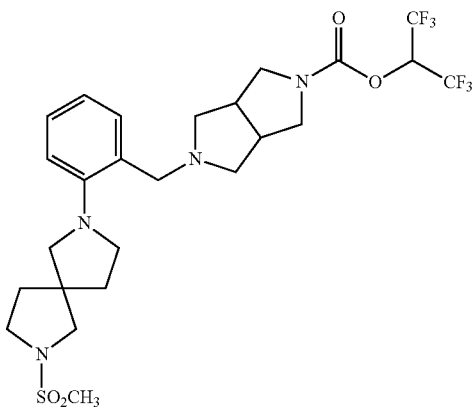 [SMILES: CS(=O)(=O)N1CCC2(CCN(c3ccccc3CN3CC4CN(C(=O)OC(C(F)(F)F)C(F)(F)F)CC4C3)C2)C1]

Step 1-2: Preparation of 2-[2,7-diazaspiro[4.4]nonan-2-yl]benzaldehyde

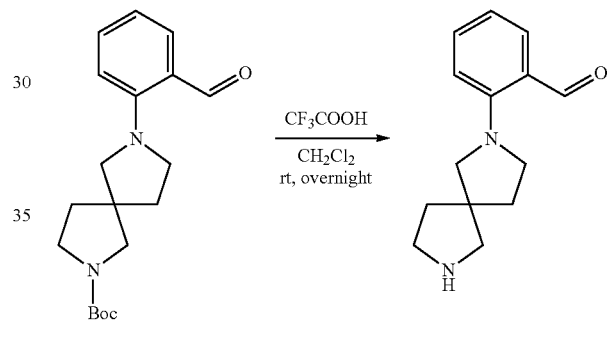

The title compound was synthesized from 2-fluorobenzaldehyde and tert-butyl 2,7-diazaspiro[4.4]nonane-2-carboxylate following the procedure analogously described in Example 3 (Step 1) followed by Example 5 (Step 3) to provide 2-[2,7-diazaspiro[4.4]nonan-2-yl]benzaldehyde as a yellow solid. LCMS (ESI, m/z): 231 [M+H]$^+$

Step 3: Preparation of 2-[7-methanesulfonyl-2,7-diazaspiro[4.4]nonan-2-yl]benzaldehyde

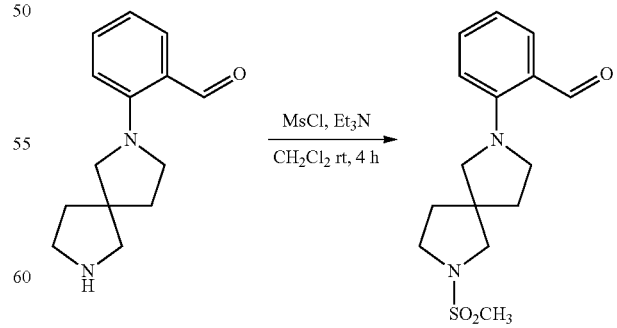

A 100-mL round-bottom flask was charged with 2-[2,7-diazaspiro[4.4]nonan-2-yl]benzaldehyde (500 mg, 2.17 mmol, 1.00 equiv) in dichloromethane (10 mL), triethylamine (659 mg, 6.51 mmol, 3.00 equiv) under nitrogen. Methanesulfonyl chloride (375 mg, 3.26 mmol, 1.50 equiv) was added dropwise 0° C. The resulting solution was stirred for 4 h at room temperature. The reaction progress was monitored by LCMS. The reaction was then quenched with water (20 mL). The resulting solution was extracted with dichloromethane (3×20 mL) and the organic layers were combined, washed with brine (2×20 mL), dried over anhydrous sodium sulfate, filtered and concentrated under reduced pressure to provide 600 mg (90% yield) of 2-[7-methanesulfonyl-2,7-diazaspiro[4.4]nonan-2-yl]benzaldehyde as yellow oil. LCMS (ESI, m/z): 309 [M+H]

Step 4-6. Preparation of 1,1,1,3,3,3-hexafluoropropan-2-yl 5-[(2-[7-methanesulfonyl-2,7-diazaspiro[4.4]nonan-2-yl]phenyl)methyl]-octahydropyrrolo[3,4-c]pyrrole-2-carboxylate The title compound was synthesized from 2-[7-methanesulfonyl-2,7-diazaspiro[4.4]nonan-2-yl]benzaldehyde following procedures analogous to those described in Example 9 (Step 1), and Example 127 (Steps 4-5) to afford 1,1,1,3,3,3-hexafluoropropan-2-yl 5-[(2-[7-methanesulfonyl-2,7-diazaspiro[4.4]nonan-2-yl]phenyl)methyl]-octahydropyrrolo[3,4-c]pyrrole-2-carboxylate as a white solid. $^1$H NMR (300 MHz, Chloroform-d) δ 7.33 (br, 1H), 7.16-7.22 (m, 1H), 6.90-6.96 (m, 2H), 5.68-5.77 (m, 1H), 3.70-3.76 (m, 2H), 3.59 (br, 2H), 3.23-3.51 (m, 9H), 3.09-3.12 (m, 1H), 2.86-2.88 (m, 5H), 2.54-2.63 (m, 4H), 1.90-2.07 (m, 4H). LCMS (ESI, m/z): 599 [M+H]

Example 135

1,1,1,3,3,3-hexafluoropropan-2-yl 5-[(2-[7-acetyl-2,7-diazaspiro[4.4]nonan-2-yl]phenyl)methyl]-octahydropyrrolo[3,4-c]pyrrole-2-carboxylate

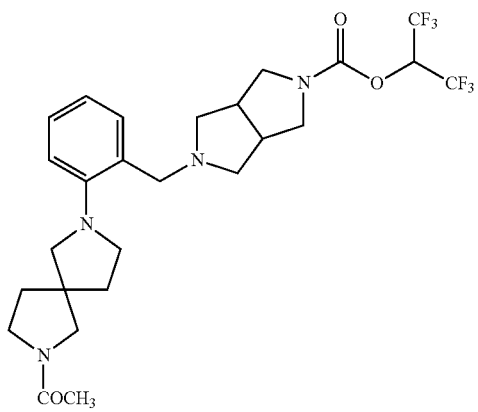 [SMILES: CC(=O)N1CCC2(CCN(c3ccccc3CN3CC4CN(C(=O)OC(C(F)(F)F)C(F)(F)F)CC4C3)C2)C1]

The title compound was synthesized from 2-[2,7-diazaspiro[4.4]nonan-2-yl]benzaldehyde (Example 134, Step 3) following the procedure analogously described in Example 52 (Step 7) followed by Example 130 (Step 4-6) to afford 1,1,1,3,3,3-hexafluoropropan-2-yl 5-[(2-[7-acetyl-2,7-diazaspiro[4.4]nonan-2-yl]phenyl)methyl]-octahydropyrrolo[3,4-c]pyrrole-2-carboxylate as a yellow oil. $^1$H NMR (300 MHz, Chloroform-d) δ 7.31-7.46 (m, 1H), 7.09-7.25 (m, 1H), 6.89-6.94 (m, 2H), 5.71-5.75 (m, 1H), 3.69-3.77 (m, 2H), 3.44-3.60 (m, 5H), 3.10-3.40 (m, 7H), 2.87-2.88 (m, 2H), 2.51-2.62 (m, 4H), 1.89-2.06 (m, 7H). LCMS (ESI, m/z): 563 [M+H].

Example 136

1,1,1,3,3,3-hexafluoropropan-2-yl 5-[(2-[2-methanesulfonyl-2,6-diazaspiro[3.4]octan-6-yl]phenyl)methyl]-octahydropyrrolo[3,4-c]pyrrole-2-carboxylate

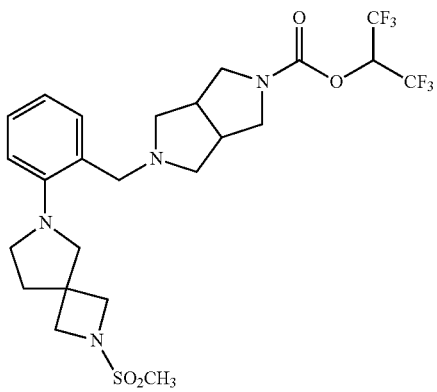 [SMILES: CS(=O)(=O)N1CC2(CCN(c3ccccc3CN3CC4CN(C(=O)OC(C(F)(F)F)C(F)(F)F)CC4C3)C2)C1]

The title compound was synthesized from 2-fluorobenzaldehyde, tert-butyl 2,6-diazaspiro[3.4]octane-2-carboxylate, and tert-butyl octahydropyrrolo[3,4-c]pyrrole-2-carboxylate according to the general procedure described in Example 134 (Steps 1-6) to afford 1,1,1,3,3,3-hexafluoropropan-2-yl 5-[(2-[2-methanesulfonyl-2,6-diazaspiro[3.4]octan-6-yl]phenyl)methyl]-octahydropyrrolo[3,4-c]pyrrole-2-carboxylate as a yellow oil. $^1$H NMR (300 MHz, Chloroform-d) δ 7.34-7.36 (m, 1H), 7.17-7.22 (m, 1H), 6.90-6.98 (m, 2H), 5.69-5.77 (m, 1H), 3.91-3.94 (m, 4H), 3.57-3.89 (m, 4H), 3.34-3.46 (m, 4H), 3.21-3.26 (m, 2H), 2.81-2.95 (m, 5H), 2.56-2.65 (m, 4H), 2.13-2.18 (m, 2H). LCMS (ESI, m/z): 585 [M+H]$^+$.

Example 137

1,1,1,3,3,3-hexafluoropropan-2-yl 5-[(2-[2-acetyl-2,6-diazaspiro[3.4]octan-6-yl]phenyl)methyl]-octahydropyrrolo[3,4-c]pyrrole-2-carboxylate

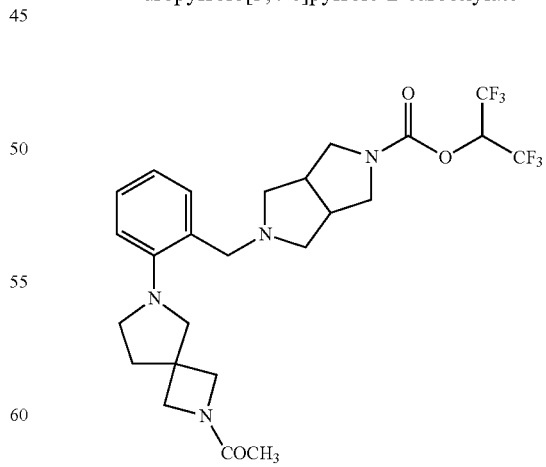

The title compound was synthesized from 2-fluorobenzaldehyde, tert-butyl 2,6-diazaspiro[3.4]octane-2-carboxylate, and tert-butyl octahydropyrrolo[3,4-c]pyrrole-2-carboxylate according to the general procedure described in Example 52 (Step 7) followed by Example 130 (Step 4-6) to afford 1,1,1,3,3,3-hexafluoropropan-2-yl 5-[(2-[2-acetyl-2,6-diazaspiro[3.4]octan-6-yl]phenyl)methyl]-octahydropyrrolo[3,4-c]pyrrole-2-carboxylate as yellow oil. $^1$H NMR (300 MHz, Chloroform-d) δ 7.32-7.41 (m, 1H), 7.17-7.22 (m, 1H), 6.89-6.97 (m, 2H), 5.69-5.78 (m, 1H), 3.94-4.10 (m, 4H), 3.52-3.76 (m, 4H), 3.23-3.47 (m, 6H), 2.88 (br, 2H), 2.56-2.58 (m, 4H), 2.13-2.18 (m, 2H), 1.89 (s, 3H). LCMS (ESI, m/z): 549 [M+H]$^+$.

Example 138

2,5-dioxopyrrolidin-1-yl 5-[[3-methyl-2-(4-methyl-piperazin-1-yl)phenyl]methyl]-octahydropyrrolo[3,4-c]pyrrole-2-carboxylate

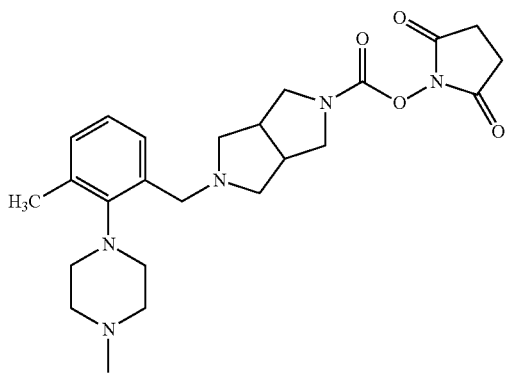 [SMILES: Cc1cccc(CN2CC3CN(C(=O)ON4C(=O)CCC4=O)CC3C2)c1N1CCN(C)CC1]

Step 1-4: Preparation of 1-methyl-4-(2-methyl-6-[octahydropyrrolo[3,4-c]pyrrol-2-ylmethyl]phenyl)piperazine The title compound was synthesized from 2-bromo-1-chloro-3-methylbenzene, 1-methylpiperazine, and tert-butyl octahydropyrrolo[3,4-c]pyrrole-2-carboxylate following procedures analogous to those described in Example 127 (Steps 1-4) to afford 1-methyl-4-(2-methyl-6-[octahydropyrrolo[3,4-c]pyrrol-2-ylmethyl]phenyl)piperazine as yellow oil. LCMS (ESI, m/z): 315 [M+H]$^+$.

Step 5: Preparation of 2,5-dioxopyrrolidin-1-yl 5-[[3-methyl-2-(4-methylpiperazin-1-yl)phenyl]methyl]-octahydropyrrolo[3,4-c]pyrrole-2-carboxylate

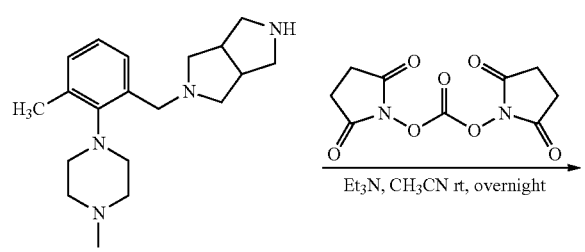

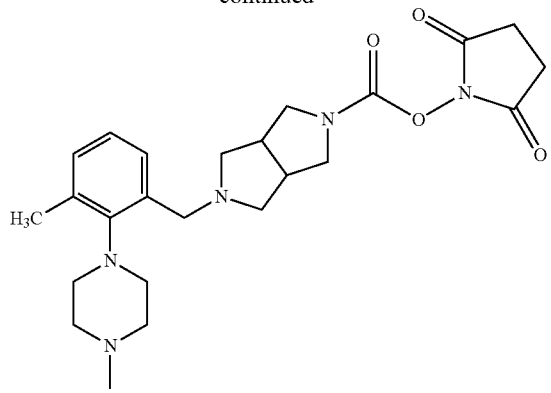

A 100-mL round-bottom flask was charged with 1-methyl-4-(2-methyl-6-[octahydropyrrolo[3,4-c]pyrrol-2-ylmethyl]phenyl)piperazine (39.0 mg, 0.120 mmol, 1.00 equiv), bis(2,5-dioxopyrrolidin-1-yl)carbonate (38.0 mg, 0.150 mmol, 1.20 equiv), triethylamine (25.0 mg, 0.250 mmol, 2.00 equiv), CH$_3$CN (5 mL). The resulting solution was stirred overnight at room temperature and concentrated under reduced pressure. The crude product (100 mg) was purified by preparative HPLC using the following gradient conditions: 20% CH$_3$CN/60% Phase A increasing to 80% CH$_3$CN over 10 min, then to 100% CH$_3$CN over 0.1 min, holding at 100% CH$_3$CN for 1.9 min, then reducing to 20% CH$_3$CN over 0.1 min, and holding at 20% for 1.9 min, on a Waters 2767-5 Chromatograph. Column: Xbridge Prep C$_{13}$, 19*150 mm Sum; Mobile phase: Phase A: H$_2$O; Phase B: CH$_3$CN; Detector, UV220 & 254 nm. Purification resulted in 47.5 mg (76% yield) of formic acid 2,5-dioxopyrrolidin-1-yl 5-[[3-methyl-2-(4-methylpiperazin-1-yl)phenyl]methyl]-octahydropyrrolo[3,4-c]pyrrole-2-carboxylate as yellow oil. $^1$H NMR (300 MHz, Chloroform-d) δ 8.40 (br, 2H), 7.05-7.17 (m, 3H), 2.95-3.78 (m, 16H), 2.56-2.82 (m, 11H), 2.36 (s, 3H). LCMS (ESI, m/z): 456 [M+H]$^+$.

Example 139

2,5-dioxopyrrolidin-1-yl 5-[[2-(4-ethylpiperazin-1-yl)-3-methylphenyl]methyl]-octahydropyrrolo[3,4-c]pyrrole-2-carboxylate

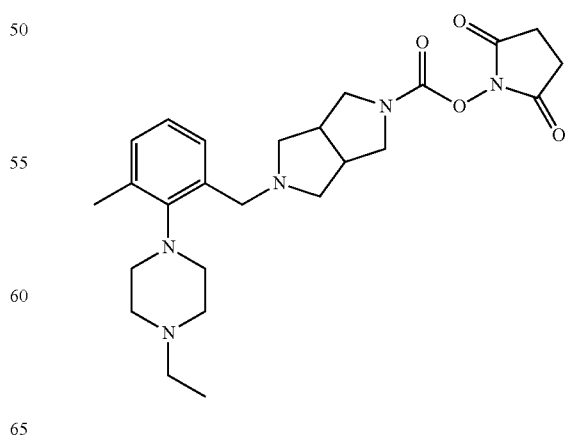

The title compound was synthesized from 2-bromo-1-chloro-3-methylbenzene, 1-ethylpiperazine, and tert-butyl octahydropyrrolo[3,4-c]pyrrole-2-carboxylate following procedures analogous to those described in Example 138 (Steps 1-5) to afford 2,5-dioxopyrrolidin-1-yl 5-[[2-(4-ethylpiperazin-1-yl)-3-methylphenyl]methyl]-octahydropyrrolo[3,4-c]pyrrole-2-carboxylate as brown oil. $^1$H NMR (300 MHz, Chloroform-d) δ 8.46 (s, 1H), 7.04-7.27 (m, 3H), 6.50-6.88 (br, 2H), 3.62-3.78 (m, 4H), 3.30-3.50 (m, 6H), 3.06-3.22 (m, 6H), 2.92 (br, 2H), 2.81 (s, 4H), 2.60-2.67 (m, 4H), 2.36-2.64 (s, 3H), 1.32-1.40 (m, 3H). LCMS (ESI, m/z): 470 [M+H]$^+$.

Example 140

2,5-dioxopyrrolidin-1-yl 5-[[3-(4-methanesulfonamidopiperidin-1-yl)-2-methylphenyl]methyl]-octahydropyrrolo[3,4-c]pyrrole-2-carboxylate

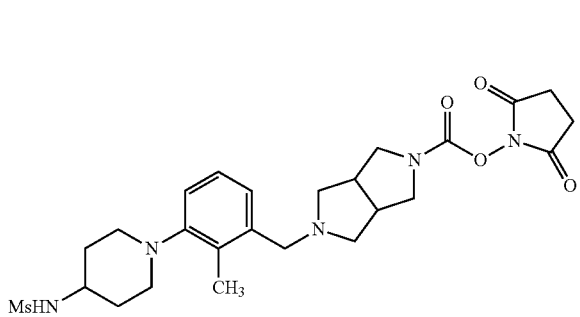

The title compound was synthesized 1-bromo-3-chloro-2-methylbenzene and tert-butyl piperidin-4-ylcarbamate as analogously described in the procedures for Example 11 (Step 1), Example 1 Step (Step 2), Example 134 (Step 3), Example 127 (Steps 3-4) and Example 138 (Step 5) to afford 2,5-dioxopyrrolidin-1-yl 5-[[3-(4-methanesulfonamidopiperidin-1-yl)-2-methylphenyl]methyl]-octahydropyrrolo[3,4-c]pyrrole-2-carboxylate as a white solid. $^1$H NMR (300 MHz, Chloroform-d) δ 6.95-7.26 (m, 3H), 4.30 (d, J=7.5 Hz, 1H), 3.76-3.86 (m, 2H), 3.29-3.58 (m, 5H), 3.03-3.10 (m, 5H), 2.74-2.89 (m, 8H), 2.58-2.70 (m, 4H), 2.31-2.56 (s, 3H), 2.09-2.14 (m, 2H), 1.73-1.81 (m, 2H). LCMS (ESI, m/z): 534 [M+H]$^+$.

Example 141

2,5-dioxopyrrolidin-1-yl 5-[[3-(4-methanesulfonylpiperazin-1-yl)-2-methylphenyl]methyl]-octahydropyrrolo[3,4-c]pyrrole-2-carboxylate

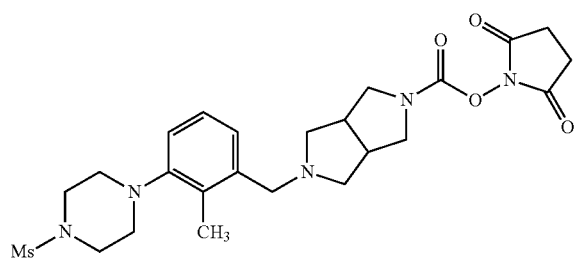 [SMILES: Cc1c(CN2CC3CN(C(=O)ON4C(=O)CCC4=O)CC3C2)cccc1N1CCN(S(C)(=O)=O)CC1]

The title compound was synthesized from 1-bromo-3-chloro-2-methylbenzene, 1-methanesulfonylpiperazine, and tert-butyl octahydropyrrolo[3,4-c]pyrrole-2-carboxylate following the general procedures described in Example 138 (Steps 1-5) to afford 2,5-dioxopyrrolidin-1-yl 5-[[3-(4-methanesulfonylpiperazin-1-yl)-2-methylphenyl]methyl]-octahydropyrrolo[3,4-c]pyrrole-2-carboxylate as a yellow oil. $^1$H NMR (300 MHz, Chloroform-d) δ 7.12-7.26 (s, 1H), 6.97-7.05 (m, 2H), 3.75-3.88 (m, 2H), 3.48-3.57 (s, 2H), 3.27-3.40 (m, 6H), 3.01-3.08 (m, 4H), 2.82-3.00 (d, J=7.5 Hz, 9H), 2.57-2.65 (m, 4H), 2.33-2.48 (s, 3H). LCMS (ESI, m/z): 520 [M+H]$^+$.

Example 142

2,5-dioxopyrrolidin-1-yl 5-[[3-(4-acetamidopiperidin-1-yl)-2-methylphenyl]methyl]-octahydropyrrolo[3,4-c]pyrrole-2-carboxylate

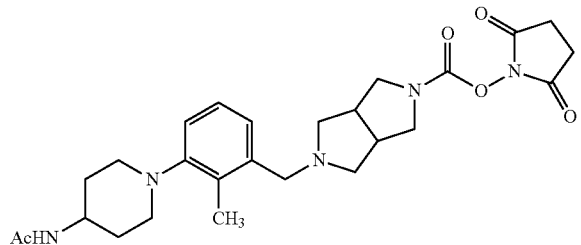 [SMILES: CC(=O)NC1CCN(c2cccc(CN3CC4CN(C(=O)ON5C(=O)CCC5=O)CC4C3)c2C)CC1]

The title compound was synthesized from 3-bromo-2-methylbenzaldehyde and N-(piperidin-4-yl)acetamide according to the procedure analogously described for Example 9 (Step 1), Example 11 (Step 1), and Example 138 (Steps 4-5) to afford 2,5-dioxopyrrolidin-1-yl 5-[[3-(4-acetamidopiperidin-1-yl)-2-methylphenyl]methyl]-octahydropyrrolo[3,4-c]pyrrole-2-carboxylate as a white solid. $^1$H NMR (300 MHz, Chloroform-d) δ 7.03-7.19 (m, 3H), 5.57-5.59 (m, 1H), 3.88-4.03 (m, 3H), 3.44-3.64 (m, 6H), 3.01-3.12 (m, 4H), 2.85 (s, 4H), 2.62-2.78 (m, 4H), 2.34 (s, 3H), 2.00-2.09 (m, 5H), 1.59-1.67 (m, 2H). LCMS (ESI, m/z): 498 [M+H]$^+$.

Example 143

2,5-dioxopyrrolidin-1-yl 5-[[3-(4-acetylpiperazin-1-yl)-2-methylphenyl]methyl]-octahydropyrrolo[3,4-c]pyrrole-2-carboxylate

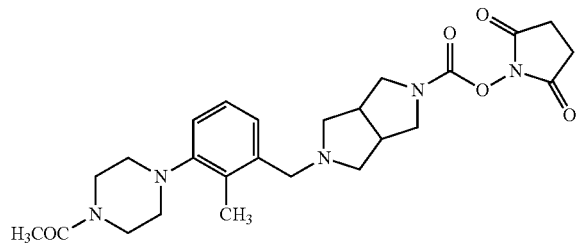

The title compound was synthesized from 3-bromo-2-methylbenzaldehyde, tert-butyl octahydropyrrolo[3,4-c]pyrrole-2-carboxylate, and 1-(piperazin-1-yl)ethan-1-one following the general procedures described in Example 9 (Step 1), Example 11 (Step 1), and Example 138 (Steps 4-5) to afford 2,5-dioxopyrrolidin-1-yl 5-[[3-(4-acetylpiperazin-1-yl)-2-methylphenyl]methyl]-octahydropyrrolo[3,4-c]pyrrole-2-carboxylate as a white solid. $^1$H NMR (300 MHz, Chloroform-d) δ 7.09-7.20 (m, 2H), 7.00 (d, J=7.2 Hz, 1H), 3.53-3.99 (m, 10H), 3.08-3.23 (m, 3H), 2.84-2.87 (m, 8H), 2.62-2.73 (m, 3H), 2.38 (s, 3H), 2.14 (s, 3H). LCMS (ESI, m/z): 484 [M+H]⁺.

Example 144

2,5-dioxopyrrolidin-1-yl 5-[[3-(4,4-difluoropiperidin-1-yl)-2-methylphenyl]methyl]-octahydropyrrolo[3,4-c]pyrrole-2-carboxylate

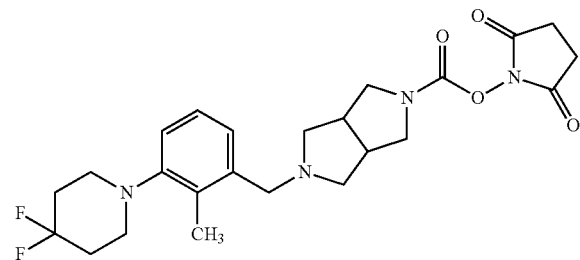 [SMILES: Cc1c(CN2CC3CN(C(=O)ON4C(=O)CCC4=O)CC3C2)cccc1N1CCC(F)(F)CC1]

The title compound was synthesized from 3-bromo-2-methylbenzaldehyde, tert-butyl octahydropyrrolo[3,4-c]pyrrole-2-carboxylate, and 4,4-difluoropiperidine following the general procedures described in Example 19 (Step 1), Example 11 (Step 1), and Example 138 (Steps 4-5) to afford 2,5-dioxopyrrolidin-1-yl 5-[[3-(4,4-difluoropiperidin-1-yl)-2-methylphenyl]methyl]-octahydropyrrolo[3,4-c]pyrrole-2-carboxylate as a yellow oil. ¹H NMR (300 MHz, Chloroform-d) δ 6.99-7.16 (m, 3H), 3.34-3.84 (m, 6H), 2.82-3.01 (m, 10H), 2.45-2.68 (m, 4H), 2.34-2.38 (m, 3H), 2.10-2.20 (m, 4H). LCMS (ESI, m/z): 477 [M+H]⁺.

Example 145

2,5-dioxocyclopentyl 5-[[2-methyl-3-(4-methylpiperazin-1-yl)phenyl]methyl]-octahydropyrrolo[3,4-c]pyrrole-2-carboxylate

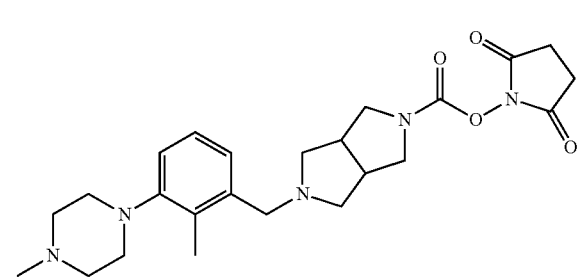 [SMILES: Cc1c(CN2CC3CN(C(=O)ON4C(=O)CCC4=O)CC3C2)cccc1N1CCN(C)CC1]

The title compound was synthesized from 3-bromo-2-methylbenzaldehyde, tert-butyl octahydropyrrolo[3,4-c]pyrrole-2-carboxylate, and 1-methylpiperazine following the general procedures described in Example 9 (Step 1), Example 11 (Step 1), and Example 138 (Steps 4-5) to afford 2,5-dioxocyclopentyl 5-[[2-methyl-3-(4-methylpiperazin-1-yl)phenyl]methyl]-octahydropyrrolo[3,4-c]pyrrole-2-carboxylate as red oil. ¹HNMR (400 MHz, Chloroform-d): δ 7.24-7.28 (m, 1H), 7.18-7.20 (m, 2H), 4.25-4.50 (m, 2H), 3.72-4.14 (m, 4H), 3.49-3.71 (m, 2H), 3.25-3.41 (m, 6H), 3.01-3.14 (m, 4H), 2.84-2.95 (m, 7H), 2.67 (br, 1H), 2.37 (s, 3H), 2.11-2.29 (m, 1H). LCMS (ESI, m/z): 456 [M+H]⁺.

Example 146

2,5-dioxocyclopentyl 5-[[3-(4-ethylpiperazin-1-yl)-2-methylphenyl]methyl]-octahydropyrrolo[3,4-c]pyrrole-2-carboxylate

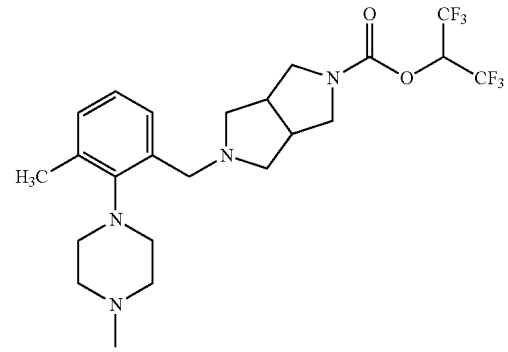 [SMILES: Cc1cccc(CN2CC3CN(C(=O)OC(C(F)(F)F)C(F)(F)F)CC3C2)c1N1CCN(C)CC1]

The title compound was synthesized from 3-bromo-2-methylbenzaldehyde, tert-butyl octahydropyrrolo[3,4-c]pyrrole-2-carboxylate, and 1-ethylpiperazine following the general procedures described in Example 9 (Step 1), Example 11 (Step 1), and Example 138 (Steps 4-5) to afford 2,5-dioxocyclopentyl 5-[[3-(4-ethylpiperazin-1-yl)-2-methylphenyl]methyl]-octahydropyrrolo[3,4-c]pyrrole-2-carboxylate as yellow oil. ¹H NMR (400 MHz, Chloroform-d): δ 7.02-7.14 (m, 1H), 6.96-7.00 (m, 2H), 3.76-3.91 (m, 2H), 3.57 (s, 2H), 3.27-3.39 (m, 2H), 3.02 (br, 4H), 2.82 (br, 10H), 2.50-2.65 (m, 6H), 2.24-2.39 (m, 3H), 1.19-1.28 (m, 3H). LCMS (ESI, m/z): 470 [M+H]⁺.

Example 147

1,1,1,3,3,3-hexafluoropropan-2-yl 5-[[3-methyl-2-(4-methylpiperazin-1-yl)phenyl]methyl]-octahydropyrrolo[3,4-c]pyrrole-2-carboxylate The title compound was synthesized from 2-bromo-1-chloro-3-methylbenzene, 1-methylpiperazine, and tert-butyl octahydropyrrolo[3,4-c]pyrrole-2-carboxylate following the general procedures described in Example 127 (Steps 1-5) to afford 1,1,1,3,3,3-hexafluoropropan-2-yl 5-[[3-methyl-2-(4-methylpiperazin-1-yl)phenyl]methyl]-octahydropyrrolo[3,4-c]pyrrole-2-carboxylate as a yellow semi-solid. ¹H NMR (300 MHz, Chloroform-d) δ 7.18-7.21 (m, 1H), 6.98-7.06 (m, 2H), 5.69-5.77 (m, 1H), 3.66-3.75 (m, 4H), 3.31-3.39

(m, 2H), 3.21-3.27 (m, 2H), 3.01-3.05 (m, 2H), 2.85-2.86 (m, 2H), 2.51-2.62 (m, 6H), 2.36-2.49 (m, 8H). LCMS (ESI, m/z): 509 [M+H]+.

Example 148

1,1,1,3,3,3-hexafluoropropan-2-yl 5-[[2-(4-ethylpiperazin-1-yl)-3-methylphenyl]methyl]-octahydropyrrolo[3,4-c]pyrrole-2-carboxylate

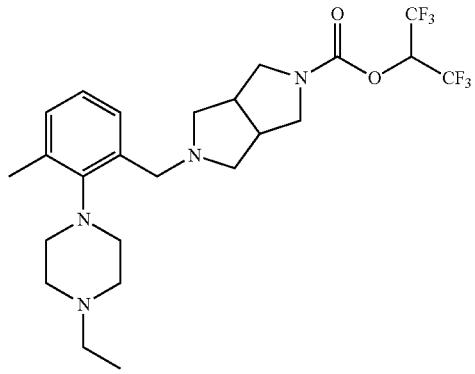 [SMILES: CCN1CCN(c2c(C)cccc2CN2CC3CN(C(=O)OC(C(F)(F)F)C(F)(F)F)CC3C2)CC1]

The title compound was synthesized from 2-bromo-1-chloro-3-methylbenzene, 1-ethylpiperazine, and tert-butyl octahydropyrrolo[3,4-c]pyrrole-2-carboxylate following the general procedures described in Example 127 (Steps 1-5) to afford 1,1,1,3,3,3-hexafluoropropan-2-yl 5-[[2-(4-ethylpiperazin-1-yl)-3-methylphenyl]methyl]-octahydropyrrolo[3,4-c]pyrrole-2-carboxylate as a light yellow solid. $^1$H NMR (300 MHz, Chloroform-d) δ 7.18-7.26 (m, 1H), 7.00-7.06 (m, 2H), 5.68-5.76 (m, 1H), 3.62-3.74 (m, 4H), 3.09-3.39 (m, 6H), 2.80-2.86 (s, 2H), 2.72 (s, 2H), 2.56-2.62 (m, 8H), 2.35-2.56 (s, 3H), 1.60-1.84 (m, 3H). LCMS (ESI, m/z): 523 [M+H]+.

Example 149

1,1,1,3,3,3-hexafluoropropan-2-yl 5-[[3-(4-methanesulfonamidopiperidin-1-yl)-2-methylphenyl]methyl]-octahydropyrrolo[3,4-c]pyrrole-2-carboxylate

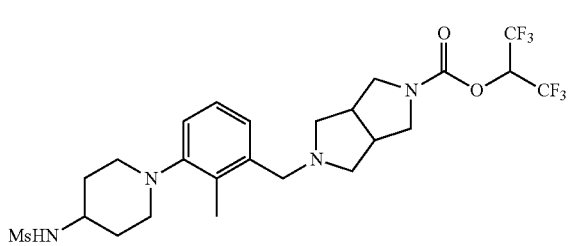

The title compound was synthesized from N-[1-(3-chloro-2-methylphenyl)piperidin-4-yl]methanesulfonamide (Example 140, Step 3) following the general procedures described in Example 127 (Steps 3-5) to afford 1,1,1,3,3,3-hexafluoropropan-2-yl 5-[[3-(4-methanesulfonamidopiperidin-1-yl)-2-methylphenyl]methyl]-octahydropyrrolo[3,4-c]pyrrole-2-carboxylate as a yellow syrup. $^1$H NMR (300 MHz, Chloroform-d) δ 6.91-7.31 (m, 3H), 5.69-5.77 (m, 1H), 4.28 (d, J=7.5 Hz, 1H), 3.25-3.70 (m, 7H), 3.03-3.08 (m, 5H), 2.70-2.86 (m, 4H), 2.55 (br, 4H), 2.28 (s, 3H), 2.10-2.13 (m, 2H), 1.68-1.79 (m, 2H). LCMS (ESI, m/z): 587 [M+H]+.

Example 150

1,1,1,3,3,3-hexafluoropropan-2-yl 5-[[3-(4-methanesulfonylpiperazin-1-yl)-2-methylphenyl]methyl]-octahydropyrrolo[3,4-c]pyrrole-2-carboxylate

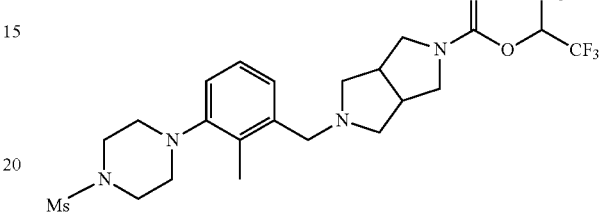

The title compound was synthesized from tert-butyl 5-[(3-bromo-2-methylphenyl)methyl]-octahydropyrrolo[3,4-c]pyrrole-2-carboxylate (Example 142, Step 1) and 1-methanesulfonylpiperazine following the general procedures described in Example 11 (Step 1) followed by Example 127 (Steps 4-5) to afford 1,1,1,3,3,3-hexafluoropropan-2-yl 5-[[3-(4-methanesulfonylpiperazin-1-yl)-2-methylphenyl]methyl]-octahydropyrrolo[3,4-c]pyrrole-2-carboxylate as yellow oil. $^1$H NMR (400 MHz, Chloroform-d) δ 7.26 (t, J=8.0 Hz, 1H), 7.10-7.16 (m, 2H), 5.69-5.75 (m, 1H), 4.30 (m, 2H), 4.03 (br, 2H), 3.60 (s, 4H), 3.15-3.40 (m, 6H), 3.03 (br, 4H), 2.86 (br, 3H), 2.49-2.75 (m, 2H), 2.34 (s, 3H). LCMS (ESI, m/z): 573[M+H]+.

Example 151

1,1,1,3,3,3-hexafluoropropan-2-yl 5-[[3-(4-acetamidopiperidin-1-yl)-2-methylphenyl]methyl]-octahydropyrrolo[3,4-c]pyrrole-2-carboxylate

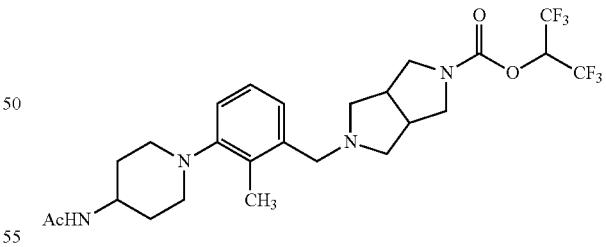

The title compound was synthesized from tert-butyl 5-[(3-bromo-2-methylphenyl)methyl]-octahydropyrrolo[3,4-c]pyrrole-2-carboxylate and N-(piperidin-4-yl)acetamide following the general procedures described for Example 11 (Step 1) followed by Example 127 (Steps 4-5) to afford 1,1,1,3,3,3-hexafluoropropan-2-yl 5-[[3-(4-acetamidopiperidin-1-yl)-2-methylphenyl]methyl]-octahydropyrrolo[3,4-c]pyrrole-2-carboxylate as a white solid. $^1$H NMR (300 MHz, Chloroform-d) δ 7.07-7.12 (m, 1H), 6.95-6.98 (m, 2H), 5.69-5.77 (m, 1H), 5.43-5.46 (m, 1H), 3.89-3.98 (m, 1H), 3.67-3.74 (m, 2H), 3.55 (s, 2H), 3.30-3.39 (m, 2H), 3.02-3.06 (m, 2H), 2.70-2.86 (m, 4H), 2.53-2.58 (m, 4H), 2.28 (s, 3H), 2.00-2.10 (m, 5H), 1.66-1.70 (m, 2H). LCMS (ESI, m/z): 551 [M+H]⁺.

Example 152

1,1,1,3,3,3-hexafluoropropan-2-yl 5-[[3-(4-acetylpiperazin-1-yl)-2-methylphenyl]methyl]-octahydropyrrolo[3,4-c]pyrrole-2-carboxylate

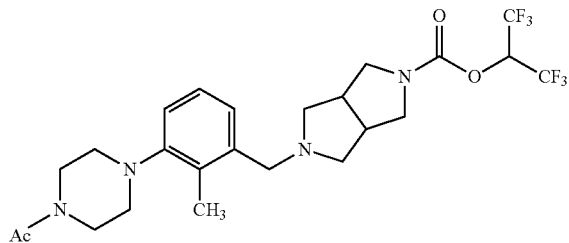 [SMILES: CC(=O)N1CCN(c2cccc(CN3CC4CN(C(=O)OC(C(F)(F)F)C(F)(F)F)CC4C3)c2C)CC1]

The title compound was synthesized from tert-butyl 5-[(3-bromo-2-methylphenyl)methyl]-octahydropyrrolo[3,4-c]pyrrole-2-carboxylate and 1-(piperazin-1-yl)ethan-1-one following the general procedures described for Example 11 (Step 1) followed by Example 127 (Steps 4-5) to afford 1,1,1,3,3,3-hexafluoropropan-2-yl 5-[[3-(4-acetylpiperazin-1-yl)-2-methylphenyl]methyl]-octahydropyrrolo[3,4-c]pyrrole-2-carboxylate as light yellow oil. ¹H NMR (300 MHz, Chloroform-d) δ 7.09-7.14 (m, 1H), 7.02 (d, J=6.9 Hz, 1H), 6.94 (d, J=7.8 Hz, 1H), 5.69-5.78 (m, 1H), 3.56-3.74 (m, 8H), 3.31-3.39 (m, 2H), 2.83-2.89 (m, 6H), 2.55 (br, 4H), 2.32 (s, 3H), 2.14 (s, 3H). LCMS (ESI, m/z): 537 [M+H]⁺.

Example 153

1,1,1,3,3,3-hexafluoropropan-2-yl 5-[[3-(4,4-difluoropiperidin-1-yl)-2-methylphenyl]methyl]-octahydropyrrolo[3,4-c]pyrrole-2-carboxylate

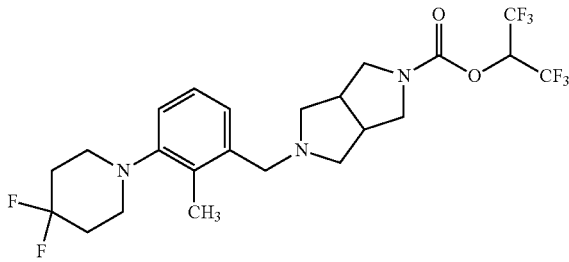 [SMILES: Cc1c(CN2CC3CN(C(=O)OC(C(F)(F)F)C(F)(F)F)CC3C2)cccc1N1CCC(F)(F)CC1]

The title compound was synthesized from tert-butyl 5-[(3-bromo-2-methylphenyl)methyl]-octahydropyrrolo[3,4-c]pyrrole-2-carboxylate and 4,4-difluoropiperidine following the general procedures described for Example 11 (Step 1) followed by Example 127 (Steps 4-5) to afford 1,1,1,3,3,3-hexafluoropropan-2-yl 5-[[3-(4,4-difluoropiperidin-1-yl)-2-methylphenyl]methyl]-octahydropyrrolo[3,4-c]pyrrole-2-carboxylate as a white solid. ¹H NMR (300 MHz, Chloroform-d) δ 7.08-7.14 (m, 1H), 6.98-7.02 (m, 2H), 5.67-5.79 (m, 1H), 3.67-3.74 (m, 2H), 3.56 (s, 2H), 3.31-3.40 (m, 2H), 2.86-2.99 (m, 6H), 2.42-2.58 (m, 4H), 2.30 (s, 3H), 2.07-2.20 (m, 4H). LCMS (ESI, m/z): 530 [M+H]⁺.

Example 154

1,1,1,3,3,3-hexafluoropropan-2-yl 5-[[2-methyl-3-(4-methylpiperazin-1-yl)phenyl]methyl]-octahydropyrrolo[3,4-c]pyrrole-2-carboxylate

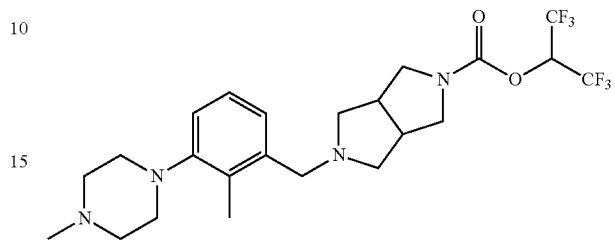 [SMILES: CCN1CCN(c2cccc(CN3CC4CN(C(=O)OC(C(F)(F)F)C(F)(F)F)CC4C3)c2C)CC1]

The title compound was synthesized from tert-butyl 5-[(3-bromo-2-methylphenyl)methyl]-octahydropyrrolo[3,4-c]pyrrole-2-carboxylate and 1-methylpiperazine following the general procedures described for Example 11 (Step 1) followed by Example 127 (Steps 4-5) to afford 1,1,1,3,3,3-hexafluoropropan-2-yl 5-[[2-methyl-3-(4-methylpiperazin-1-yl)phenyl]methyl]-octahydropyrrolo[3,4-c]pyrrole-2-carboxylate as a white solid. ¹H NMR (400 MHz, Chloroform-d) δ 7.12 (t, J=8.0 Hz, 1H), 7.00-7.02 (m, 2H), 5.70-5.76 (m, 1H), 3.76-3.82 (m, 1H), 3.68-3.73 (m, 2H), 3.55 (s, 2H), 3.31-3.38 (m, 2H), 3.07 (br, 4H), 2.86 (br, 5H), 2.51-2.56 (m, 7H), 2.28 (s, 3H). LCMS (ESI, m/z): 509 [M+H]⁺.

Example 155

1,1,1,3,3,3-hexafluoropropan-2-yl 5-[[3-(4-ethylpiperazin-1-yl)-2-methylphenyl]methyl]-octahydropyrrolo[3,4-c]pyrrole-2-carboxylate

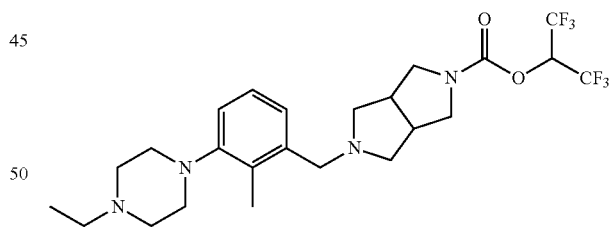

The title compound was synthesized from tert-butyl 5-[(3-bromo-2-methylphenyl)methyl]-octahydropyrrolo[3,4-c]pyrrole-2-carboxylate and 1-ethylpiperazine following the general procedures described for Example 11 (Step 1) followed by Example 127 (Steps 4-5) to afford 1,1,1,3,3,3-hexafluoropropan-2-yl 5-[[3-(4-ethylpiperazin-1-yl)-2-methylphenyl]methyl]-octahydropyrrolo[3,4-c]pyrrole-2-carboxylate as yellow oil. ¹H NMR (400 MHz, Chloroform-d) δ 7.09-7.13 (m, 1H), 6.98-7.01 (m, 2H), 5.70-5.76 (m, 1H), 3.71-3.74 (m, 2H), 3.58 (s, 2H), 3.31-3.38 (m, 2H), 2.97 (t, J=4.0 Hz, 4H), 2.88 (br, 2H), 2.68 (br, 3H), 2.45-2.58 (m, 7H), 2.29 (s, 3H), 1.17 (t, J=8.0 Hz, 3H). LCMS (ESI, m/z): 523 [M+H]⁺.

Example 156

1,1,1,3,3,3-hexafluoropropan-2-yl 5-[[3-ethyl-1-(oxan-4-yl)-1H-pyrazol-5-yl]methyl]-octahydropyrrolo[3,4-c]pyrrole-2-carboxylate

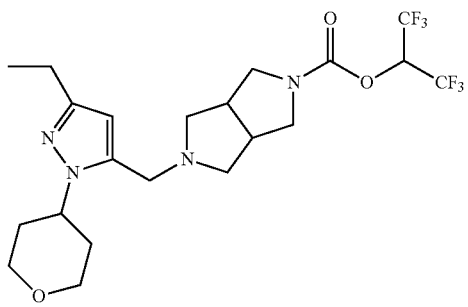 [SMILES: CCc1cc(CN2CC3CN(C(=O)OC(C(F)(F)F)C(F)(F)F)CC3C2)n(C2CCOCC2)n1]

The title compound was synthesized from 2,4-dioxohexanoate and oxan-4-ylhydrazine hydrochloride following the procedures analogously described for Example 58 (Steps 1-7) to afford 1,1,1,3,3,3-hexafluoropropan-2-yl 5-[[3-ethyl-1-(oxan-4-yl)-1H-pyrazol-5-yl]methyl]-octahydropyrrolo[3,4-c]pyrrole-2-carboxylate as yellow oil. $^1$H NMR (300 MHz, Chloroform-d) δ 5.89 (s, 1H), 5.67-5.76 (m, 1H), 4.30-4.38 (m, 1H), 4.04-4.09 (m, 2H), 3.70-3.78 (m, 2H), 3.28-3.57 (m, 6H), 2.90 (br, 2H), 2.49-2.65 (m, 6H), 2.28-2.35 (m, 2H), 1.72-1.92 (m, 2H), 1.19-1.24 (m, 3H). LCMS (ESI, m/z): 499 [M+H]$^+$.

Example 157

1,1,1,3,3,3-hexafluoropropan-2-yl 5-[[3-tert-butyl-1-(oxan-4-yl)-1H-pyrazol-5-yl]methyl]-octahydropyrrolo[3,4-c]pyrrole-2-carboxylate

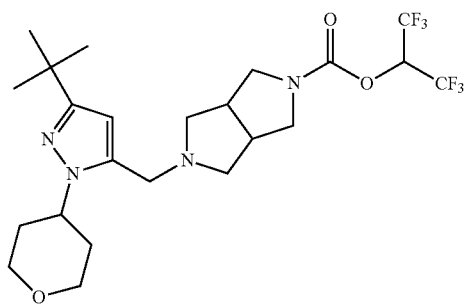 [SMILES: CC(C)(C)c1cc(CN2CC3CN(C(=O)OC(C(F)(F)F)C(F)(F)F)CC3C2)n(C2CCOCC2)n1]

The title compound was synthesized from ethyl 5,5-dimethyl-2,4-dioxohexanoate, oxan-4-ylhydrazine hydrochloride, and tert-butyl octahydropyrrolo[3,4-c]pyrrole-2-carboxylate according to the general procedures described in Example 58 (Steps 1-7) to afford 1,1,1,3,3,3-hexafluoropropan-2-yl 5-[[3-tert-butyl-1-(oxan-4-yl)-1H-pyrazol-5-yl] methyl]-octahydropyrrolo[3,4-c]pyrrole-2-carboxylate as yellow oil. $^1$H NMR (300 MHz, Chloroform-d) δ5.87 (s, 1H), 5.71-5.78 (m, 1H), 4.35-4.43 (m, 1H), 4.09-4.14 (m, 2H), 3.65-3.71 (m, 2H), 3.38-3.57 (m, 6H), 2.75-2.89 (m, 4H), 2.35-2.49 (m, 4H), 1.72-1.80 (m, 2H), 1.38 (s, 9H). LCMS (ESI, m/z): 527 [M+H]$^+$.

Example 158

1,1,1,3,3,3-hexafluoropropan-2-yl 5-[[3-chloro-2-(4,4-difluoropiperidin-1-yl)phenyl]methyl]-octahydropyrrolo[3,4-c]pyrrole-2-carboxylate

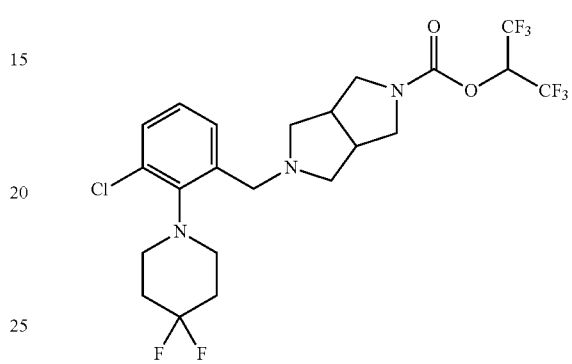

Step 1-2: Preparation of tert-butyl 5-[[3-chloro-2-(4-hydroxypiperidin-1-yl)phenyl]methyl]-octahydropyrrolo[3,4-c]pyrrole-2-carboxylate

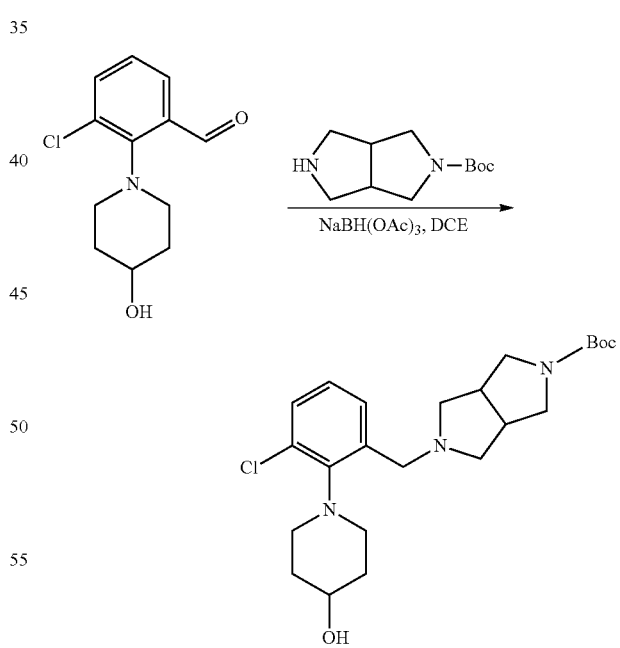

The title compound was synthesized from 3-chloro-2-fluorobenzaldehyde and piperidin-4-ol following procedures analogous to those described in Example 3 (Step 1) followed by Example 9 (Step 1) to provide tert-butyl 5-[[3-chloro-2-(4-hydroxypiperidin-1-yl)phenyl]methyl]-octahydropyrrolo[3,4-c]pyrrole-2-carboxylate as yellow oil. LCMS (ESI, m/z): 436 [M+H]$^+$.

Step 3: Preparation of tert-butyl 5-[[3-chloro-2-(4-oxopiperidin-1-yl)phenyl]methyl]-octahydropyrrolo[3,4-c]pyrrole-2-carboxylate

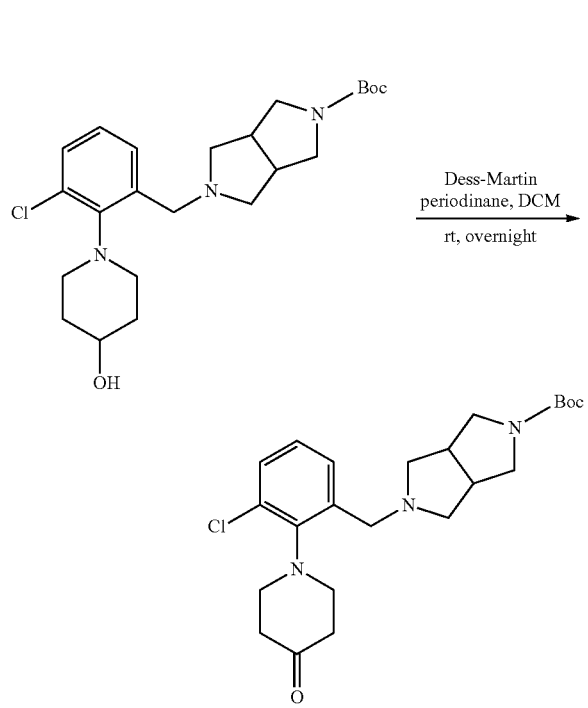

A 100-mL round-bottom flask was charged with tert-butyl 5-[[3-chloro-2-(4-hydroxypiperidin-1-yl)phenyl]methyl]-octahydropyrrolo[3,4-c]pyrrole-2-carboxylate (630 mg, 1.44 mmol, 1.00 equiv), (1,1,1-triacetoxy)-1,1-dihydro-1,2-benziodoxol-3(1H)-one (919 mg, 2.17 mmol, 1.50 equiv), dichloromethane (20 mL). The resulting solution was stirred overnight at room temperature and quenched by water (10 mL). The mixture was extracted with dichloromethane (3×15 mL) and the organic layers were combined, dried over anhydrous sodium sulfate, filtered and concentrated under reduced pressure. The residue was chromatographed on a silica gel column with ethyl acetate/petroleum ether (55/45) to provide 250 mg (40% yield) of tert-butyl 5-[[3-chloro-2-(4-oxopiperidin-1-yl)phenyl]methyl]-octahydropyrrolo[3,4-c]pyrrole-2-carboxylate as yellow oil. LCMS (ESI, m/z): 434 [M+H]$^+$.

Step 4: Preparation of tert-butyl 5-[[3-chloro-2-(4,4-difluoropiperidin-1-yl)phenyl]methyl]-octahydropyrrolo[3,4-c]pyrrole-2-carboxylate

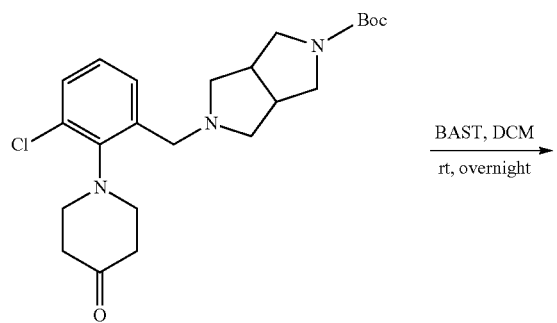

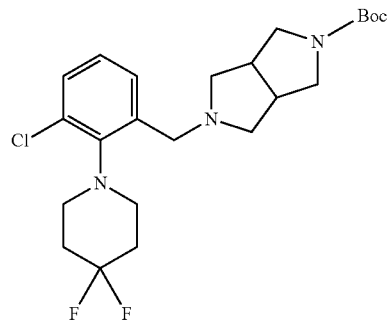

A 100-mL round-bottom flask was charged with tert-butyl 5-[[3-chloro-2-(4-oxopiperidin-1-yl)phenyl]methyl]-octahydropyrrolo[3,4-c]pyrrole-2-carboxylate (250 mg, 0.580 mmol, 1.00 equiv) and dichloromethane (10 mL) under nitrogen. Bis(2-methoxyethyl)amino]sulfur trifluoride (383 mg, 1.73 mmol, 3.01 equiv) was added at 0° C. The resulting solution was stirred overnight at room temperature and quenched by water (10 mL). The mixture was extracted with dichloromethane (3×15 mL) and the organic layers were combined, dried over anhydrous sodium sulfate, filtered and concentrated under reduced pressure. The crude product (300 mg) was purified by preparative HPLC using the following gradient conditions: 20% CH$_3$CN/80% Phase A increasing to 80% CH$_3$CN over 10 min, then to 100% CH$_3$CN over 0.1 min, holding at 100% CH$_3$CN for 1.9 min, then reducing to 20% CH$_3$CN over 0.1 min, and holding at 20% for 1.9 min, on a Waters 2767-5 Chromatograph. Column: Xbridge Prep C$_{18}$, 19*150 mm 5 um; Mobile phase: Phase A: water with 0.05% NH$_4$HCO$_3$; Phase B: CH$_3$CN; Detector, UV220 & 254 nm. Purification resulted in 80.0 mg (30% yield) of tert-butyl 5-[[3-chloro-2-(4,4-difluoropiperidin-1-yl)phenyl]methyl]-octahydropyrrolo[3,4-c]pyrrole-2-carboxylate as yellow oil. LCMS (ESI, m/z): 456 [M+H]$^+$.

Step 5-6: Preparation of 1,1,1,3,3,3-hexafluoropropan-2-yl 5-[[3-chloro-2-(4,4-difluoropiperidin-1-yl)phenyl]methyl]-octahydropyrrolo[3,4-c]pyrrole-2-carboxylate The title compound was synthesized from tert-butyl 5-[[3-chloro-2-(4,4-difluoropiperidin-1-yl)phenyl]methyl]-octahydropyrrolo[3,4-c]pyrrole-2-carboxylate following the general procedures described in Example 127 (Steps 4-5) to afford 1,1,1,3,3,3-hexafluoropropan-2-yl 5-[[3-chloro-2-(4,4-difluoropiperidin-1-yl)phenyl]methyl]-octahydropyrrolo[3,4-c]pyrrole-2-carboxylate as yellow oil. $^1$H NMR (300 MHz, Chloroform-d) δ 7.24-7.31 (m, 2H), 7.06 (t, J=7.8 Hz, 1H), 5.66-5.79 (m, 1H), 3.66-3.75 (m, 4H), 3.49-3.55 (m, 2H), 3.34-3.38 (m, 2H), 2.89-3.10 (m, 4H), 2.54-2.59 (m, 4H), 1.96-2.23 (m, 4H). LCMS (ESI, m/z): 550 [M+H]$^+$.

Example 159

1,1,1,3,3,3-hexafluoropropan-2-yl 5-[[3-chloro-2-(4-fluoropiperidin-1-yl)phenyl]methyl]-octahydropyrrolo[3,4-c]pyrrole-2-carboxylate

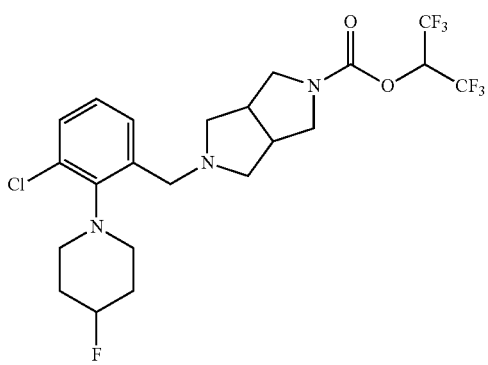 [SMILES: O=C(OC(C(F)(F)F)C(F)(F)F)N1CC2CN(Cc3cccc(Cl)c3N3CCC(F)CC3)CC2C1]

The title compound was synthesized from 3-chloro-2-fluorobenzaldehyde and 4-fluoropiperidine following the procedures analogously described in Example 3 (Step 1) followed by Example 9 (Step 1), and Example 127 (Steps 4-5) to afford 1,1,1,3,3,3-hexafluoropropan-2-yl 5-[[3-chloro-2-(4-fluoropiperidin-1-yl)phenyl]methyl]-octahydropyrrolo[3,4-c]pyrrole-2-carboxylate as a yellow oil. $^1$H NMR (300 MHz, Chloroform-d) δ 7.21-7.25 (m, 2H), 7.04 (t, J=7.5 Hz, 1H), 5.69-5.77 (m, 1H), 4.59-4.98 (m, 1H), 3.72-3.76 (m, 5H), 3.34-3.69 (m, 3H), 2.89-3.03 (m, 3H), 2.70-2.77 (m, 1H), 2.55-2.63 (m, 4H), 1.78-2.11 (m, 4H). LCMS (ESI, m/z): 532 [M+H]$^+$.

Example 160

2,5-dioxopyrrolidin-1-yl 5-[[3-chloro-2-(4-fluoropiperidin-1-yl)phenyl]methyl]-octahydropyrrolo[3,4-c]pyrrole-2-carboxylate

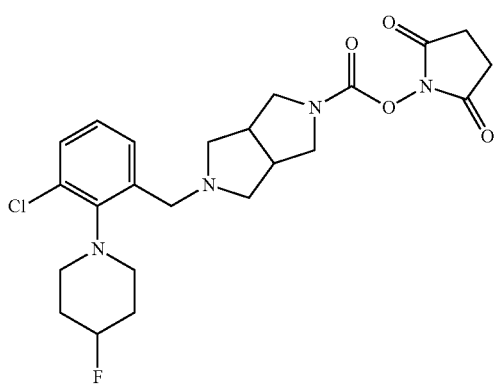 [SMILES: O=C(ON1C(=O)CCC1=O)N1CC2CN(Cc3cccc(Cl)c3N3CCC(F)CC3)CC2C1]

The title compound was synthesized from 1-(2-chloro-6-[octahydropyrrolo[3,4-c]pyrrol-2-ylmethyl]phenyl)-4-fluoropiperidine (Example 159, Step 3) following the general procedure described in Example 138 (Step 5) to afford 2,5-dioxopyrrolidin-1-yl 5-[[3-chloro-2-(4-fluoropiperidin-1-yl)phenyl]methyl]-octahydropyrrolo[3,4-c]pyrrole-2-carboxylate as a white solid. $^1$H NMR (300 MHz, Chloroform-d) δ 7.31 (br, 1H), 7.22-7.24 (m, 1H), 7.05-7.10 (m, 1H), 4.56-4.98 (m, 1H), 3.71-3.86 (m, 5H), 3.37-3.44 (m, 3H), 2.73-3.02 (m, 8H), 2.57-2.64 (m, 4H), 1.64-2.11 (m, 4H). LCMS (ESI, m/z): 479 [M+H]$^+$.

Example 161

2,5-dioxopyrrolidin-1-yl 5-([2-chloro-4-[(piperidin-1-yl)carbonyl]phenyl]methyl)-octahydropyrrolo[3,4-c]pyrrole-2-carboxylate

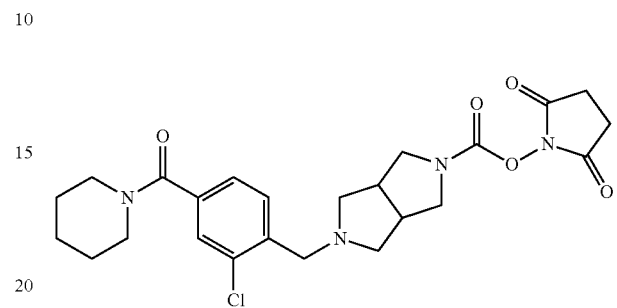

Step 1: Preparation of methyl 3-chloro-4-formylbenzoate

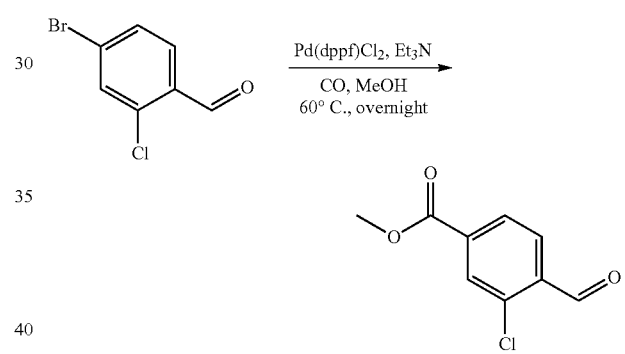

A 500-mL round-bottom flask was charged with 4-bromo-2-chlorobenzaldehyde (20.0 g, 91.1 mmol, 1.00 equiv), methanol (300 mL), [1,1'-bis(diphenylphosphino)ferrocene]dichloropalladium (6.68 g, 9.13 mmol, 0.10 equiv), triethylamine (27.7 g, 274 mmol, 3.00 equiv). CO was introduced in. The resulting solution was stirred overnight at 60° C. and concentrated under reduced pressure. The residue was chromatographed on a silica gel column with ethyl acetate/petroleum ether (15/85) to provide 14.5 g (80% yield) of methyl 3-chloro-4-formylbenzoate as a white solid.

Step 2: Preparation of tert-butyl 5-[[2-chloro-4-(methoxycarbonyl)phenyl]methyl]-octahydropyrrolo[3,4-c]pyrrole-2-carboxylate

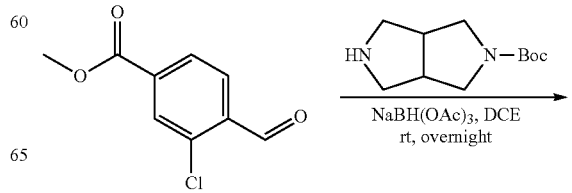

-continued

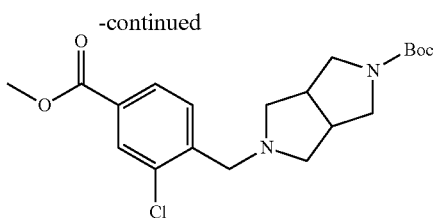

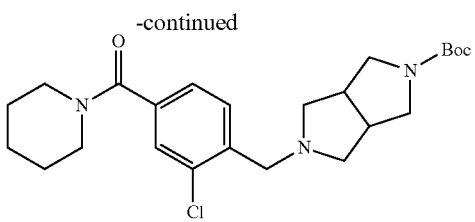

The title compound was synthesized from methyl 3-chloro-4-formylbenzoate and tert-butyl octahydropyrrolo[3,4-c]pyrrole-2-carboxylate following the procedure analogously described in Example 9 (Step 1) to afford tert-butyl 5-[[2-chloro-4-(methoxycarbonyl)phenyl]methyl]-octahydropyrrolo[3,4-c]pyrrole-2-carboxylate as yellow oil. LCMS (ESI, m/z): 395 [M+H]+.

Step 3: Preparation of 4-([5-[(tert-butoxy)carbonyl]-octahydropyrrolo[3,4-c]pyrrol-2-yl]methyl)-3-chlorobenzoic acid

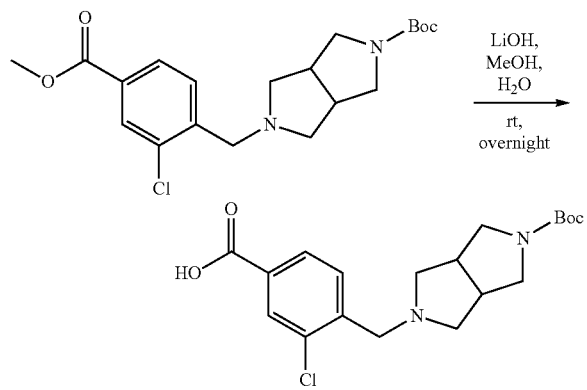

A 100-mL round-bottom flask was charged with tert-butyl 5-[[2-chloro-4-(methoxycarbonyl)phenyl]methyl]-octahydropyrrolo[3,4-c]pyrrole-2-carboxylate (2.50 g, 6.33 mmol, 1.00 equiv), lithium hydroxide (759 mg, 31.7 mmol, 5.01 equiv), methanol (20 mL), water (7 mL). The resulting solution was stirred overnight at room temperature. The pH value of the solution was adjusted to 6 with hydrochloric acid (1 mol/L). The resulting solution was extracted with dichloromethane (3×25 mL) and the organic layers were combined, dried over anhydrous sodium sulfate, filtered and concentrated under reduced pressure to provide 2.4 g (100% yield) of 4-([5-[(tert-butoxy)carbonyl]-octahydropyrrolo[3,4-c]pyrrol-2-yl]methyl)-3-chlorobenzoic acid as a white solid. LCMS (ESI, m/z): 381 [M+H]+.

Step 4: Preparation of tert-butyl 5-([2-chloro-4-[(piperidin-1-yl)carbonyl]phenyl]methyl)-octahydropyrrolo[3,4-c]pyrrole-2-carboxylate

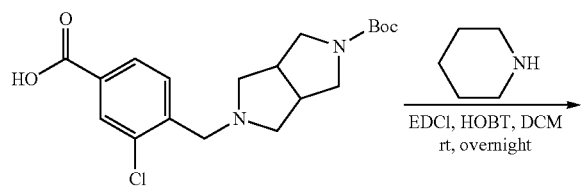

A 40-mL round-bottom flask was charged with 4-([5-[(tert-butoxy)carbonyl]-octahydropyrrolo[3,4-c]pyrrol-2-yl]methyl)-3-chlorobenzoic acid (480 mg, 1.26 mmol, 1.00 equiv), dichloromethane (15 mL), N-(3-dimethylaminopropyl)-N'-ethylcarbodiimide hydrochloride (363 mg, 1.89 mmol, 1.50 equiv), 1-hydroxybenzotrizole (255 mg, 1.89 mmol, 1.50 equiv). The resulting solution was stirred for 2 h at room temperature and piperidine (214 mg, 2.51 mmol, 1.99 equiv) was added. The resulting solution was stirred overnight at room temperature and quenched by water (10 mL). The resulting solution was extracted with dichloromethane (3×15 mL) and the organic layers were combined, dried over anhydrous sodium sulfate, concentrated under reduced pressure. The residue was chromatographed on a silica gel column with ethyl acetate/petroleum ether (93/7) to provide 400 mg (71% yield) of tert-butyl 5-([2-chloro-4-[(piperidin-1-yl)carbonyl]phenyl]methyl)-octahydropyrrolo[3,4-c]pyrrole-2-carboxylate as yellow oil. LCMS (ESI, m/z): 448 [M+H]+.

Step 5-6: Preparation of 2,5-dioxopyrrolidin-1-yl 5-([2-chloro-4-[(piperidin-1-yl)carbonyl]phenyl]methyl)-octahydropyrrolo[3,4-c]pyrrole-2-carboxylate The title compound was synthesized from tert-butyl 5-([2-chloro-4-[(piperidin-1-yl)carbonyl]phenyl]methyl)-octahydropyrrolo[3,4-c]pyrrole-2-carboxylate following the procedure analogously described for Example 127 (Step 4) followed by a procedure analogous to that which was described for Example 138 (Step 5) to provide 2,5-dioxopyrrolidin-1-yl 5-([2-chloro-4-[(piperidin-1-yl)carbonyl]phenyl]methyl)-octahydropyrrolo[3,4-c]pyrrole-2-carboxylate as a white solid. 1H NMR (300 MHz, Chloroform-d) δ 7.54-7.56 (m, 1H), 7.40 (d, J=1.5 Hz, 1H), 7.27-7.31 (m, 1H), 3.70-3.91 (m, 6H), 3.37-3.49 (m, 4H), 2.83-2.94 (m, 6H), 2.66 (br, 4H), 1.56-1.68 (m, 6H). LCMS (ESI, m/z): 489 [M+H]+.

Example 162

2,5-dioxopyrrolidin-1-yl 5-(2-chloro-4-(4-methylpiperazine-1-carbonyl)benzyl)-hexahydropyrrolo[3,4-c]pyrrole-2(1H)-carboxylate

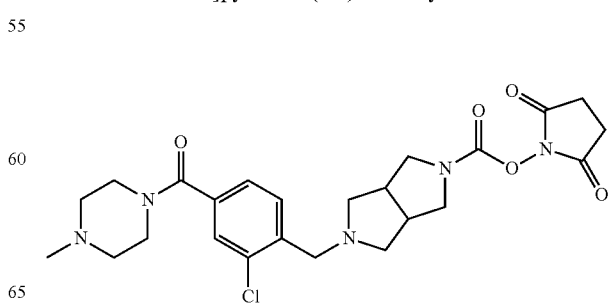

The title compound was synthesized from 4-bromo-2-chlorobenzaldehyde, tert-butyl octahydropyrrolo[3,4-c]pyrrole-2-carboxylate, and 1-methylpiperazine following the general procedure described in Example 161 (Steps 1-6) to afford 2,5-dioxopyrrolidin-1-yl5-(2-chloro-4-(4-methylpiperazine-1-carbonyl)benzyl)-hexahydropyrrolo[3,4-c]pyrrole-2(1H)-carboxylate as a white solid. ¹H NMR (300 MHz, Chloroform-d) δ 7.55 (d, J=7.8 Hz, 1H), 7.41 (d, J=1.5 Hz, 1H), 7.27-7.33 (m, 1H), 3.74-3.92 (m, 6H), 3.36-3.50 (m, 4H), 2.89-2.93 (m, 6H), 2.63-2.83 (m, 4H), 2.34-2.60 (m, 7H). LCMS (ESI, m/z): 504 [M+H]⁺.

Example 163

2,5-dioxopyrrolidin-1-yl 5-(2-chloro-4-(morpholine-4-carbonyl)benzyl)-hexahydropyrrolo[3,4-c]pyrrole-2(1H)-carboxylate

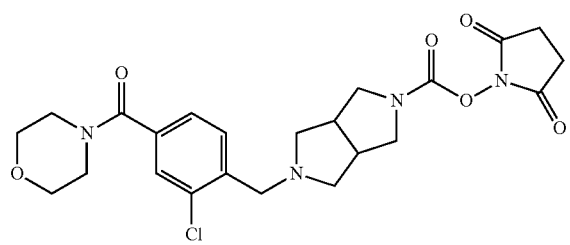 [SMILES: O=C(ON1C(=O)CCC1=O)N1CC2CN(Cc3ccc(C(=O)N4CCOCC4)cc3Cl)CC2C1]

The title compound was synthesized from 4-bromo-2-chlorobenzaldehyde, tert-butyl octahydropyrrolo[3,4-c]pyrrole-2-carboxylate, and morpholine following the general procedure described in Example 161 (Steps 1-6) to afford 2,5-dioxopyrrolidin-1-yl5-(2-chloro-4-(morpholine-4-carbonyl)benzyl)-hexahydropyrrolo[3,4-c]pyrrole-2(1H)-carboxylate as a white solid. ¹H NMR (300 MHz, Chloroform-d) δ 7.62 (br, 1H), 7.43 (s, 1H), 7.31-7.34 (m, 1H), 3.45-3.76 (m, 14H), 2.96 (br, 2H), 2.83 (s, 4H), 2.70 (br, 4H). LCMS (ESI, m/z): 491 [M+H]⁺.

Example 164

2,5-dioxopyrrolidin-1-yl 5-(2-chloro-4-(pyrrolidine-1-carbonyl)benzyl)-hexahydropyrrolo[3,4-c]pyrrole-2(1H)-carboxylate

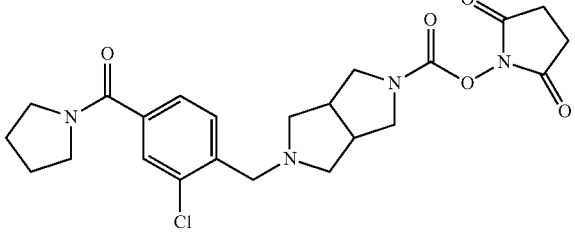

The title compound was synthesized from 4-bromo-2-chlorobenzaldehyde, tert-butyl octahydropyrrolo[3,4-c]pyrrole-2-carboxylate, and pyrrolidine following the general procedure described in Example 161 (Steps 1-6) to afford 2,5-dioxopyrrolidin-1-yl5-(2-chloro-4-(pyrrolidine-1-carbonyl)benzyl)-hexahydropyrrolo[3,4-c]pyrrole-2(1H)-carboxylate as a white solid. ¹H NMR (300 MHz, Chloroform-d) δ 7.52-7.56 (m, 2H), 7.41-7.44 (m, 1H), 3.75-3.92 (m, 4H), 3.64 (t, J=6.8 Hz, 2H), 3.36-3.49 (m, 4H), 2.83-2.92 (m, 6H), 2.58-2.69 (m, 4H), 1.85-2.01 (m, 4H). LCMS (ESI, m/z): 475 [M+H]⁺.

Example 165

2,5-dioxopyrrolidin-1-yl5-(4-(azetidine-1-carbonyl)-2-chlorobenzyl)-hexahydropyrrolo[3,4-c]pyrrole-2(1H)-carboxylate

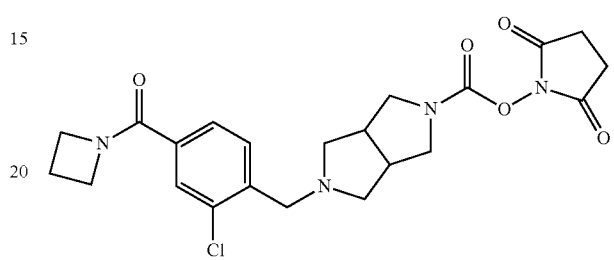

The title compound was synthesized from 4-bromo-2-chlorobenzaldehyde, tert-butyl octahydropyrrolo[3,4-c]pyrrole-2-carboxylate, and azetidine following the general procedure described in Example 161 (Steps 1-6) to afford 2,5-dioxopyrrolidin-1-yl5-(4-(azetidine-1-carbonyl)-2-chlorobenzyl)-hexahydropyrrolo[3,4-c]pyrrole-2(1H)-carboxylate as a white solid. ¹H NMR (300 MHz, Chloroform-d) δ 7.65 (s, 1H), 7.50-7.57 (m, 2H), 4.20-4.36 (m, 4H), 3.76-3.92 (m, 4H), 3.36-3.50 (m, 2H), 2.83-2.92 (m, 6H), 2.58-2.69 (m, 4H), 2.31-2.41 (m, 2H). LCMS (ESI, m/z): 461 [M+H]⁺.

Example 166

2,5-dioxopyrrolidin-1-yl5-(2-fluoro-4-(piperidine-1-carbonyl)benzyl)-hexahydropyrrolo[3,4-c]pyrrole-2(1H)-carboxylate

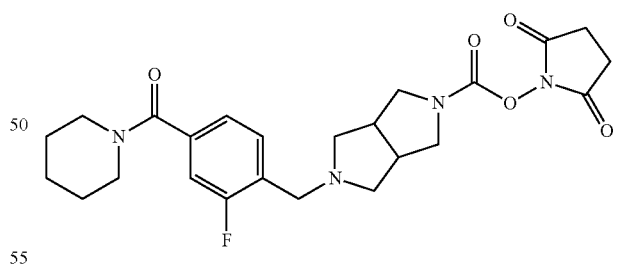

The title compound was synthesized from 4-bromo-2-fluorobenzaldehyde, tert-butyl octahydropyrrolo[3,4-c]pyrrole-2-carboxylate, and piperidine following the general procedure described in Example 161 (Steps 1-6) to afford 2,5-dioxopyrrolidin-1-yl5-(2-fluoro-4-(piperidine-1-carbonyl)benzyl)-hexahydropyrrolo[3,4-c]pyrrole-2(1H)-carboxylate as a white solid. ¹H NMR (300 MHz, Chloroform-d) δ 7.49 (br, 1H), 7.16-7.19 (m, 1H), 7.07-7.11 (m, 1H), 3.72-3.88 (m, 6H), 3.36-3.49 (m, 4H), 2.83-2.93 (m, 6H), 2.62 (br, 4H), 1.55-1.68 (m, 6H). LCMS (ESI, m/z): 473 [M+H]⁺.

Example 167

2,5-dioxopyrrolidin-1-yl 5-(2-fluoro-4-(pyrrolidine-1-carbonyl)benzyl)-hexahydropyrrolo[3,4-c]pyrrole-2(1H)-carboxylate

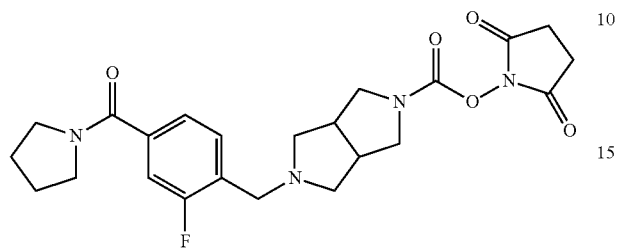

The title compound was synthesized from 4-bromo-2-fluorobenzaldehyde, tert-butyl octahydropyrrolo[3,4-c]pyrrole-2-carboxylate, and pyrrolidine following the general procedure described in Example 161 (Steps 1-6) to afford 2,5-dioxopyrrolidin-1-yl 5-(2-fluoro-4-(pyrrolidine-1-carbonyl)benzyl)-hexahydropyrrolo[3,4-c]pyrrole-2(1H)-carboxylate as a yellow oil. $^1$H NMR (300 MHz, Chloroform-d) δ 7.61 (br, 1H), 7.30-7.33 (m, 1H), 7.22-7.25 (m, 1H), 3.62-3.77 (m, 6H), 3.42-3.50 (m, 4H), 2.83-2.97 (m, 7H), 2.53-2.63 (m, 3H), 1.87-2.01 (m, 4H). LCMS (ESI, m/z): 459 [M+H]$^+$.

Example 168

2,5-dioxopyrrolidin-1-yl 5-(4-(azetidine-1-carbonyl)-2-fluorobenzyl)-hexahydropyrrolo[3,4-c]pyrrole-2(1H)-carboxylate

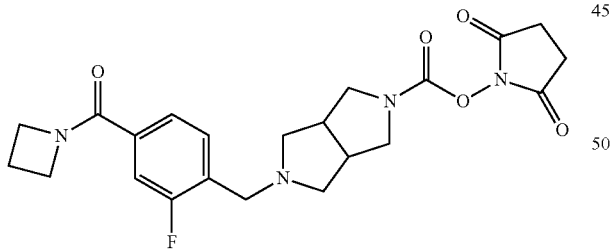

The title compound was synthesized from 4-bromo-2-fluorobenzaldehyde, tert-butyl octahydropyrrolo[3,4-c]pyrrole-2-carboxylate, and azetidine following the general procedure described in Example 161 (Steps 1-6) to afford 2,5-dioxopyrrolidin-1-yl 5-(4-(azetidine-1-carbonyl)-2-fluorobenzyl)-hexahydropyrrolo[3,4-c]pyrrole-2(1H)-carboxylate as a white solid. $^1$H NMR (300 MHz, Chloroform-d) δ 7.56 (br, 1H), 7.34-7.43 (m, 2H), 4.21-4.36 (m, 4H), 3.73-3.79 (m, 4H), 3.41-3.52 (m, 2H), 2.90-2.99 (m, 2H), 2.83 (s, 5H), 2.64-2.76 (m, 3H), 2.31-2.42 (m, 2H). LCMS (ESI, m/z): 445 [M+H]$^+$.

Example 169

1,1,1,3,3,3-hexafluoropropan-2-yl 5-[[1-(2-chlorophenyl)-3-ethyl-1H-pyrazol-5-yl]methyl]-octahydropyrrolo[3,4-c]pyrrole-2-carboxylate

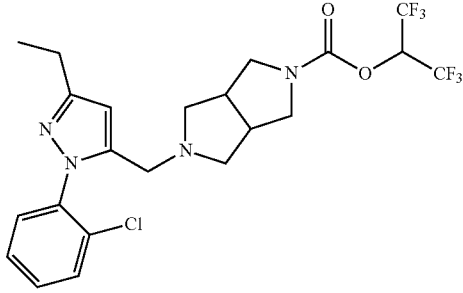 [SMILES: CCc1cc(CN2CC3CN(C(=O)OC(C(F)(F)F)C(F)(F)F)CC3C2)n(-c2ccccc2Cl)n1]

The title compound was synthesized from 2,4-dioxohexanoate, (2-chlorophenyl)hydrazine hydrochloride following the general procedure described for Example 58 (Step 1-7) to afford 1,1,1,3,3,3-hexafluoropropan-2-yl 5-[[1-(2-chlorophenyl)-3-ethyl-1H-pyrazol-5-yl]methyl]-octahydropyrrolo[3,4-c]pyrrole-2-carboxylate as a yellow solid. $^1$H NMR (300 MHz, Chloroform-d) δ 7.43-7.49 (m, 1H), 7.27-7.39 (m, 3H), 6.14 (s, 1H), 5.70-5.78 (m, 1H), 3.64-3.71 (m, 2H), 3.50 (s, 2H), 3.02-3.07 (m, 2H), 2.66-2.84 (m, 4H), 2.32-2.48 (m, 4H), 1.29-1.33 (m, 3H). LCMS (ESI, m/z): 525 [M+H]$^+$.

Example 170

1,1,1,3,3,3-hexafluoropropan-2-yl 5-[[3-tert-butyl-1-(2-chlorophenyl)-1H-pyrazol-5-yl]methyl]-octahydropyrrolo[3,4-c]pyrrole-2-carboxylate

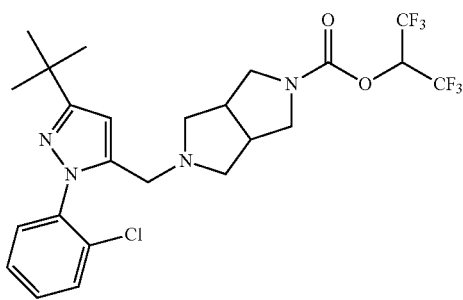 [SMILES: CC(C)(C)c1cc(CN2CC3CN(C(=O)OC(C(F)(F)F)C(F)(F)F)CC3C2)n(-c2ccccc2Cl)n1]

The title compound was synthesized from 5,5-dimethyl-2,4-dioxohexanoate, (2-chlorophenyl)hydrazine hydrochloride following the general procedure described for Example 58 (Step 1-7) to afford 1,1,1,3,3,3-hexafluoropropan-2-yl 5-[[3-tert-butyl-1-(2-chlorophenyl)-1H-pyrazol-5-yl]methyl]-octahydropyrrolo[3,4-c]pyrrole-2-carboxylate as yellow oil. $^1$H NMR (300 MHz, Chloroform-d) δ 7.44-7.47 (m, 1H), 7.28-7.41 (m, 3H), 6.16 (s, 1H), 5.72-5.76 (m, 1H), 3.64-3.70 (m, 2H), 3.48 (s, 2H), 3.01-3.06 (m, 2H), 2.78 (br, 2H), 2.36-2.46 (m, 4H), 1.34 (s, 9H). LCMS (ESI, m/z): 553 [M+H]$^+$.

Example 171

1,1,1,3,3,3-hexafluoropropan-2-yl 5-[[3-chloro-2-(4-methylpiperazin-1-yl)phenyl]methyl]-octahydropyrrolo[3,4-c]pyrrole-2-carboxylate

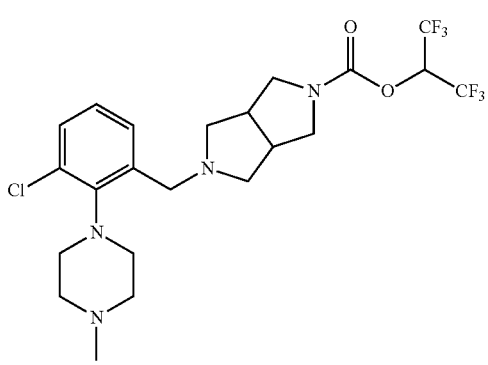 [SMILES: CN1CCN(c2c(Cl)cccc2CN2CC3CN(C(=O)OC(C(F)(F)F)C(F)(F)F)CC3C2)CC1]

The title compound was synthesized from 3-chloro-2-fluorobenzaldehyde, 1-methylpiperazine, and tert-butyl octahydropyrrolo[3,4-c]pyrrole-2-carboxylate as analogously described in Example 159 (Steps 1-4) to afford 1,1,1,3,3,3-hexafluoropropan-2-yl 5-[[3-chloro-2-(4-methylpiperazin-1-yl)phenyl]methyl]-octahydropyrrolo[3,4-c]pyrrole-2-carboxylate as a yellow oil. $^1$H NMR (300 MHz, Chloroform-d) δ 7.21-7.30 (m, 2H), 7.02-7.08 (m, 1H), 5.70-5.78 (m, 1H), 3.57-3.74 (m, 6H), 3.32-3.40 (m, 2H), 2.76-2.93 (m, 6H), 2.52-2.61 (m, 4H), 2.36-2.41 (m, 5H). LCMS (ESI, m/z): 529 [M+H]$^+$.

Example 172

1,1,1,3,3,3-hexafluoropropan-2-yl 5-[(3-chloro-2-[8-oxa-2-azaspiro[4.5]decan-2-yl]phenyl)methyl]-octahydropyrrolo[3,4-c]pyrrole-2-carboxylate

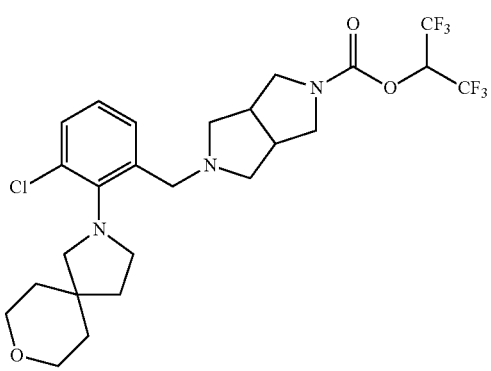 [SMILES: O=C(OC(C(F)(F)F)C(F)(F)F)N1CC2CN(Cc3cccc(Cl)c3N3CCC4(CCOCC4)C3)CC2C1]

The title compound was synthesized from 3-chloro-2-fluorobenzaldehyde, 8-oxa-2-azaspiro[4.5]decane, and tert-butyl octahydropyrrolo[3,4-c]pyrrole-2-carboxylate as analogously described in Example 159 (Steps 1-4) to afford 1,1,1,3,3,3-hexafluoropropan-2-yl 5-[(3-chloro-2-[8-oxa-2-azaspiro[4.5]decan-2-yl]phenyl)methyl]-octahydropyrrolo[3,4-c]pyrrole-2-carboxylate as colorless oil. $^1$H NMR (400 MHz, Chloroform-d) δ 7.26-7.31 (m, 2H), 7.06-7.10 (m, 1H), 5.70-5.76 (m, 1H), 3.62-3.78 (m, 8H), 3.31-3.57 (m, 4H), 3.13 (s, 2H), 2.87 (br, 2H), 2.52-2.56 (m, 4H), 1.89 (t, J=6.8 Hz, 2H), 1.66-1.78 (m, 4H). LCMS (ESI, m/z): 570 [M+H]$^+$.

Example 173

1,1,1,3,3,3-hexafluoropropan-2-yl 5-([3-chloro-2-[(3S)-3-(fluoromethyl)pyrrolidin-1-yl]phenyl]methyl)-octahydropyrrolo[3,4-c]pyrrole-2-carboxylate

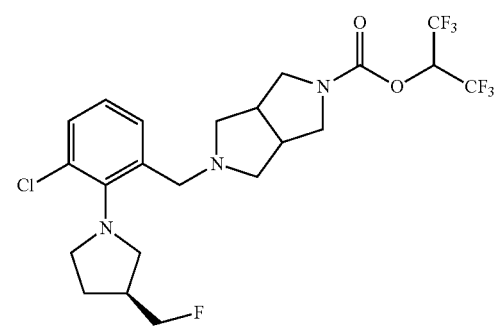 [SMILES: O=C(OC(C(F)(F)F)C(F)(F)F)N1CC2CN(Cc3cccc(Cl)c3N3CC[C@H](CF)C3)CC2C1]

Step 1-2: Preparation of tert-butyl 5-([3-chloro-2-[(3S)-3-(hydroxymethyl)pyrrolidin-1-yl]phenyl]methyl)-octahydropyrrolo[3,4-c]pyrrole-2-carboxylate The title compound was synthesized from 3-chloro-2-fluorobenzaldehyde, (3S)-pyrrolidin-3-ylmethanol, and tert-butyl octahydropyrrolo[3,4-c]pyrrole-2-carboxylate following the procedure analogously described for Example 158 (Step 1) followed by the procedure analogously described in Example 130 (Step 4) to afford tert-butyl 5-([3-chloro-2-[(3S)-3-(hydroxymethyl)pyrrolidin-1-yl]phenyl]methyl)-octahydropyrrolo[3,4-c]pyrrole-2-carboxylate as yellow oil. LCMS (ESI, m/z): 436 [M+H]$^+$.

Step 3: Preparation of tert-butyl 5-([3-chloro-2-[(3S)-3-([[(4-methylbenzene)sulfonyl]oxy]methyl)pyrrolidin-1-yl]phenyl]methyl)-octahydropyrrolo[3,4-c]pyrrole-2-carboxylate

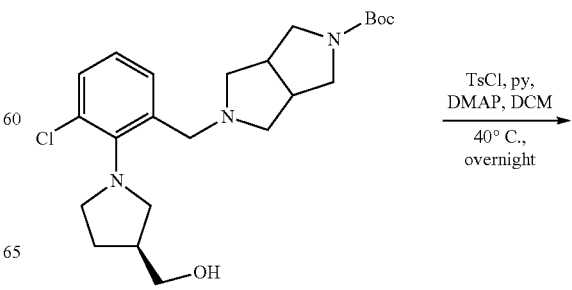

-continued

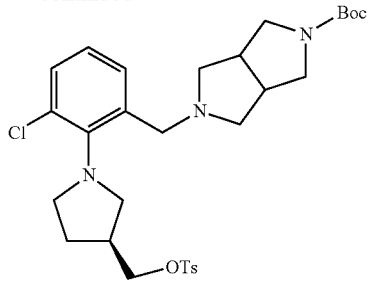

A 100-mL round-bottom flask was charged with tert-butyl 5-([3-chloro-2-[(3S)-3-(hydroxymethyl)pyrrolidin-1-yl]phenyl]methyl)-octahydropyrrolo[3,4-c]pyrrole-2-carboxylate (1.30 g, 2.98 mmol, 1.00 equiv), 4-methylbenzene-1-sulfonyl chloride (0.856 g, 4.49 mmol, 1.50 equiv), pyridine (0.472 g, 5.97 mmol, 2.00 equiv), 4-dimethylaminopyridine (0.0360 g, 0.290 mmol, 0.10 equiv), dichloromethane (20 mL). The resulting solution was stirred overnight at 40° C. and then diluted with H$_2$O (10 mL). The resulting mixture was extracted with dichloromethane (3×10 mL). The organic layers were combined and washed with brine (1×50 mL), dried over anhydrous sodium sulfate, filtered and concentrated under reduced pressure. The residue was chromatographed on a silica gel column with ethyl acetate/petroleum ether (50/50) to provide 1.20 g (68% yield) of tert-butyl 5-([3-chloro-2-[(3S)-3-([[(4-methylbenzene)sulfonyl]oxy]methyl)pyrrolidin-1-yl]phenyl]methyl)-octahydropyrrolo[3,4-c]pyrrole-2-carboxylate as yellow oil. LCMS (ESI, m/z): 590 [M+H]$^+$.

Step 4: Preparation of tert-butyl 5-([3-chloro-2-[(3S)-3-(fluoromethyl)pyrrolidin-1-yl]phenyl]methyl)-octahydropyrrolo[3,4-c]pyrrole-2-carboxylate

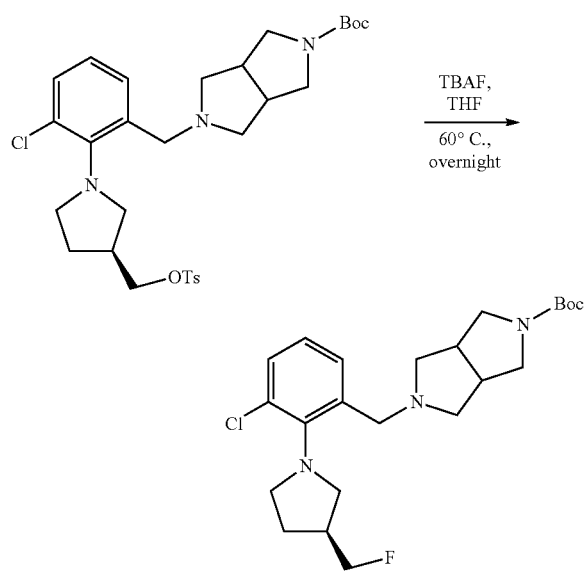

A 100-mL round-bottom flask was charged with tert-butyl 5-([3-chloro-2-[(3S)-3-([[(4-methylbenzene)sulfonyl]oxy]methyl)pyrrolidin-1-yl]phenyl]methyl)-octahydropyrrolo[3,4-c]pyrrole-2-carboxylate (1.70 g, 2.88 mmol, 1.00 equiv), tetrabutylammonium fluoride (3.00 g, 11.5 mmol, 4.00 equiv), tetrahydrofuran (20 mL). The resulting solution was stirred overnight at 60° C. and concentrated under reduced pressure. The residue was chromatographed on a silica gel column with ethyl acetate/petroleum ether (25/75) to provide 1.00 g (79% yield) of tert-butyl 5-([3-chloro-2-[(3S)-3-(fluoromethyl)pyrrolidin-1-yl]phenyl]methyl)-octahydropyrrolo[3,4-c]pyrrole-2-carboxylate as yellow oil. LCMS (ESI, m/z): 438 [M+H]$^+$.

Step 5-6. Preparation of 1,1,1,3,3,3-hexafluoropropan-2-yl 5-([3-chloro-2-[(3S)-3-(fluoromethyl)pyrrolidin-1-yl]phenyl]methyl)-octahydropyrrolo[3,4-c]pyrrole-2-carboxylate The title compound was synthesized from tert-butyl 5-([3-chloro-2-[(3S)-3-(fluoromethyl)pyrrolidin-1-yl]phenyl]methyl)-octahydropyrrolo[3,4-c]pyrrole-2-carboxylate following procedures analogous to those described in Example 127 (Steps 4-5) to afford 1,1,1,3,3,3-hexafluoropropan-2-yl 5-([3-chloro-2-[(3S)-3-(fluoromethyl)pyrrolidin-1-yl]phenyl]methyl)-octahydropyrrolo[3,4-c]pyrrole-2-carboxylate as yellow oil. $^1$H NMR (300 MHz, Chloroform-d) δ 7.25-7.31 (m, 2H), 7.06-7.11 (m, 1H), 5.34-5.78 (m, 1H), 4.54-4.56 (m, 1H), 4.38-4.40 (m, 1H), 3.65-3.76 (m, 4H), 3.22-3.44 (m, 5H), 3.04-3.09 (m, 1H), 2.88 (br, 2H), 2.73-2.80 (m, 1H), 2.55-2.57 (m, 4H), 2.09-2.14 (m, 1H), 1.76-1.82 (m, 1H). LCMS (ESI, m/z): 532 [M+H]$^+$.

Example 174

1,1,1,3,3,3-hexafluoropropan-2-yl 5-[[3-(3-chlorophenyl)-1-(propan-2-yl)-1H-pyrazol-4-yl]methyl]-octahydropyrrolo[3,4-c]pyrrole-2-carboxylate

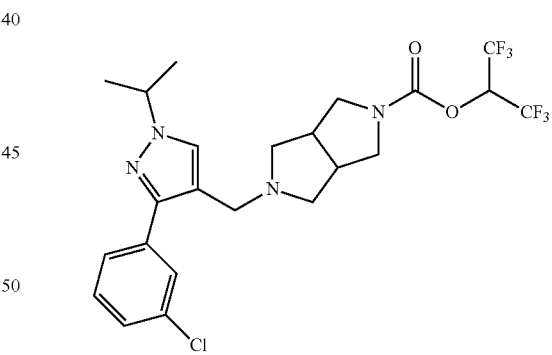

The title compound was synthesized from 1-(3-chlorophenyl)ethanone and propan-2-ylhydrazine hydrochloride following procedures analogous to those described in Example 51 (Step 1), Example 52 (Step 2), Example 9 (Step 1), and Example 127 (Steps 4-5) to afford 1,1,1,3,3,3-hexafluoropropan-2-yl 5-[[3-(3-chlorophenyl)-1-(propan-2-yl)-1H-pyrazol-4-yl]methyl]-octahydropyrrolo[3,4-c]pyrrole-2-carboxylate as colorless oil. $^1$H NMR (300 MHz, Chloroform-d) δ 7.96 (br, 1H), 7.68-7.70 (m, 1H), 7.24-7.36 (m, 3H), 5.67-5.75 (m, 1H), 4.46-4.55 (m, 1H), 3.72-3.79 (m, 2H), 3.52 (br, 2H), 3.30-3.34 (m, 2H), 2.88 (br, 2H), 2.54-2.59 (m, 4H), 1.53 (d, J=6.6 Hz, 6H). LCMS (ESI, m/z): 539 [M+H]$^+$

Example 175

1,1,1,3,3,3-hexafluoropropan-2-yl 5-[(2-chlorophenyl)methyl]-octahydropyrrolo[3,4-c]pyrrole-2-carboxylate

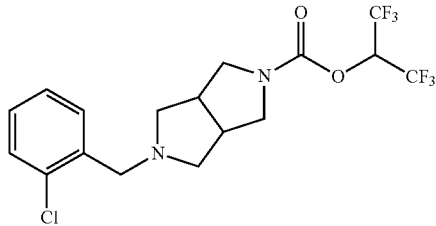 [SMILES: O=C(OC(C(F)(F)F)C(F)(F)F)N1CC2CN(Cc3ccccc3Cl)CC2C1]

The title compound was synthesized from 2-chlorobenzaldehyde and tert-butyl octahydropyrrolo[3,4-c]pyrrole-2-carboxylate following procedures analogous to those described in Example 9 (Step 1), and Example 127 (Steps 4-5) to afford 1,1,1,3,3,3-hexafluoropropan-2-yl 5-[(2-chlorophenyl)methyl]-octahydropyrrolo[3,4-c]pyrrole-2-carboxylate as yellow oil. $^1$H NMR (300 MHz, Chloroform-d) δ 7.43 (d, J=6.9 Hz, 1H), 7.33-7.36 (m, 1H), 7.16-7.24 (m, 2H), 5.68-5.80 (m, 1H), 3.73 (t, J=9.9 Hz, 4H), 3.36-3.44 (m, 2H), 2.90 (br, 2H), 2.58-2.64 (m, 4H). LCMS (ESI, m/z): 431 [M+H]$^+$.

Example 176

1,1,1,3,3,3-hexafluoropropan-2-yl 5-[(3-chlorophenyl)methyl]-octahydropyrrolo[3,4-c]pyrrole-2-carboxylate

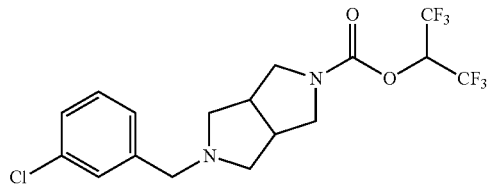 [SMILES: O=C(OC(C(F)(F)F)C(F)(F)F)N1CC2CN(Cc3cccc(Cl)c3)CC2C1]

The title compound was synthesized from 3-chlorobenzaldehyde and tert-butyl octahydropyrrolo[3,4-c]pyrrole-2-carboxylate following procedures analogous to those described in Example 9 (Step 1), and Example 127 (Steps 4-5) to afford 1,1,1,3,3,3-hexafluoropropan-2-yl 5-[(3-chlorophenyl)methyl]-octahydropyrrolo[3,4-c]pyrrole-2-carboxylate as a yellow oil. $^1$H NMR (300 MHz, Chloroform-d) δ 7.29 (s, 1H), 7.19-7.27 (m, 3H), 5.68-5.80 (m, 1H), 3.66-3.78 (m, 2H), 3.56 (s, 2H), 3.35-3.43 (m, 2H), 2.89 (br, 2H), 2.57-2.62 (m, 2H), 2.46-2.53 (m, 2H). LCMS (ESI, m/z): 431 [M+H]$^+$.

Example 177

1,1,1,3,3,3-hexafluoropropan-2-yl 5-[(4-chlorophenyl)methyl]-octahydropyrrolo[3,4-c]pyrrole-2-carboxylate

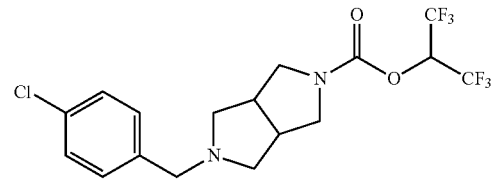 [SMILES: O=C(OC(C(F)(F)F)C(F)(F)F)N1CC2CN(Cc3ccc(Cl)cc3)CC2C1]

The title compound was synthesized from 4-chlorobenzaldehyde and tert-butyl octahydropyrrolo[3,4-c]pyrrole-2-carboxylate following procedures analogous to those described in Example 9 (Step 1), and Example 127 (Steps 4-5) to afford 1,1,1,3,3,3-hexafluoropropan-2-yl 5-[(4-chlorophenyl)methyl]-octahydropyrrolo[3,4-c]pyrrole-2-carboxylate as a yellow solid. $^1$H NMR (300 MHz, Chloroform-d) δ 7.23-7.31 (m, 4H), 5.69-5.82 (m, 1H), 3.71-3.79 (m, 2H), 3.57-3.68 (m, 2H), 3.36-3.44 (m, 2H), 2.89 (br, 2H), 2.48-2.58 (m, 4H). LCMS (ESI, m/z): 431 [M+H]$^+$.

Example 178

1,1,1,3,3,3-hexafluoropropan-2-yl 5-((1-ethyl-3-(prop-2-yn-1-ylcarbamoyl)-1H-pyrazol-4-yl)methyl)hexahydropyrrolo[3,4-c]pyrrole-2(1H)-carboxylate

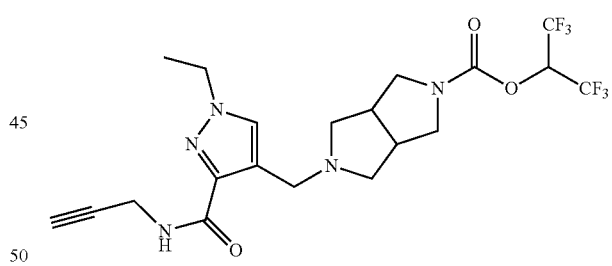

The title compound was prepared from propargylamine and 1,1,1,3,3,3-hexafluoro-propan-2-yl 5-((3-(ethoxycarbonyl)-1-ethyl-1H-pyrazol-4-yl)methyl)hexahydro-pyrrolo[3,4-c]pyrrole-2(1H)-carboxylate (Isomer B, Example 73, Step 2) according to a procedure analogous to that which was described in Example 73 (Step 3) to provide 1,1,1,3,3,3-hexafluoropropan-2-yl 5-((1-ethyl-3-(prop-2-yn-1-ylcarbamoyl)-1H-pyrazol-4-yl)methyl)hexahydropyrrolo[3,4-c]pyrrole-2(1H)-carboxylate as a clear oil. $^1$H NMR (400 MHz, Chloroform-d) δ 9.18 (br s, 1H), 7.33 (s, 1H), 5.74 (hept, J=6.3 Hz, 1H), 4.28-4.14 (m, 4H), 3.78-3.63 (m, 4H), 3.41 (dt, J=11.7, 4.8 Hz, 2H), 2.99-2.87 (m, 2H), 2.79-2.70 (m, 2H), 2.67-2.49 (m, 2H), 2.22 (td, J=2.6, 0.6 Hz, 1H), 1.50 (t, J=7.3 Hz, 3H). LCMS (ESI, m/z): 496.1 [M+H].

Example 179

1,1,1,3,3,3-hexafluoropropan-2-yl 5-((5-((cyclopropylmethyl)carbamoyl)-1-ethyl-1H-pyrazol-4-yl)methyl)hexahydropyrrolo[3,4-c]pyrrole-2(1H)-carboxylate

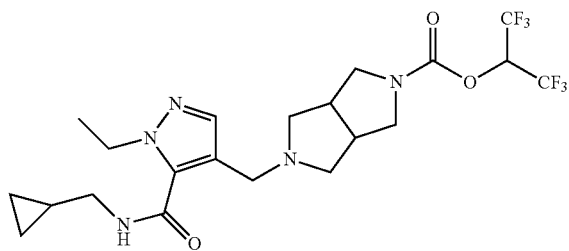 [SMILES: CCn1ncc(CN2CC3CN(C(=O)OC(C(F)(F)F)C(F)(F)F)CC3C2)c1C(=O)NCC1CC1]

The title compound was prepared from cyclopropylmethanamine and 1,1,1,3,3,3-hexafluoropropan-2-yl 5-((5-(ethoxycarbonyl)-1-ethyl-1H-pyrazol-4-yl)methyl)hexahydropyrrolo[3,4-c]pyrrole-2(1H)-carboxylate (Isomer A, Example 73, Step 2) according to a procedure analogous to that which was described in Example 73 (Step 3) to provide 1,1,1,3,3,3-hexafluoropropan-2-yl 5-((5-((cyclopropylmethyl)carbamoyl)-1-ethyl-1H-pyrazol-4-yl)methyl)hexahydropyrrolo[3,4-c]pyrrole-2(1H)-carboxylate as a clear oil. $^1$H NMR (400 MHz, Chloroform-d) δ 9.67 (s, 1H), 7.31 (s, 1H), 5.70 (hept, J=6.2 Hz, 1H), 4.57 (q, J=7.2 Hz, 2H), 3.75-3.61 (m, 2H), 3.53 (s, 2H), 3.38-3.30 (m, 2H), 3.24-3.16 (m, 2H), 2.97-2.87 (m, 2H), 2.83-2.71 (m, 2H), 2.52-2.41 (m, 2H), 1.48-1.40 (m, 3H), 1.02-0.87 (m, 1H), 0.56-0.44 (m, 2H), 0.27-0.14 (m, 2H). LCMS (ESI, m/z): 512.3 [M+H].

Example 180

1,1,1,3,3,3-hexafluoropropan-2-yl 5-((5-((3-chlorophenethyl)carbamoyl)-1-ethyl-1H-pyrazol-4-yl)methyl)hexahydropyrrolo[3,4-c]pyrrole-2(1H)-carboxylate

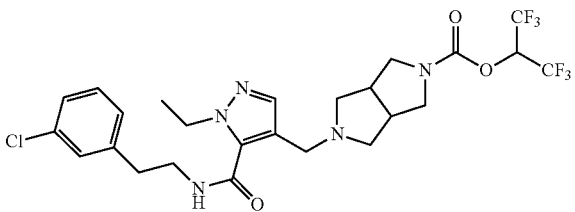 [SMILES: CCn1ncc(CN2CC3CN(C(=O)OC(C(F)(F)F)C(F)(F)F)CC3C2)c1C(=O)NCCc1cccc(Cl)c1]

The title compound was prepared from 2-(3-chlorophenyl)ethanamine and 1,1,1,3,3,3-hexafluoropropan-2-yl 5-((5-(ethoxycarbonyl)-1-ethyl-1H-pyrazol-4-yl)methyl)hexahydropyrrolo[3,4-c]pyrrole-2(1H)-carboxylate (Isomer A, Example 73, Step 2) according to a procedure analogous to that which was described in Example 73 (Step 3) to provide 1,1,1,3,3,3-hexafluoropropan-2-yl 5-((5-((3-chlorophenethyl)carbamoyl)-1-ethyl-1H-pyrazol-4-yl)methyl)hexahydropyrrolo[3,4-c]pyrrole-2(1H)-carboxylate as a clear oil. $^1$H NMR (400 MHz, Chloroform-d) δ 9.86 (t, J=5.7 Hz, 1H), 7.31-7.19 (m, 4H), 7.10 (dt, J=7.1, 1.6 Hz, 1H), 5.74 (hept, J=6.2 Hz, 1H), 4.61 (q, J=7.2 Hz, 2H), 3.65 (tt, J=12.2, 5.5 Hz, 2H), 3.59-3.39 (m, 2H), 3.29 (s, 2H), 3.12 (ddd, J=11.2, 7.2, 3.8 Hz, 2H), 2.88 (t, J=6.2 Hz, 2H), 2.85-2.69 (m, 2H), 2.33-2.24 (m, 2H), 2.16-2.04 (m, 2H), 1.48 (t, J=7.2 Hz, 3H). LCMS (ESI, m/z): 596.3 [M+H]$^+$.

Example 181

1,1,1,3,3,3-hexafluoropropan-2-yl 5-((1-ethyl-5-(((tetrahydro-2H-pyran-4-yl)methyl)carbamoyl)-1H-pyrazol-4-yl)methyl)hexahydropyrrolo[3,4-c]pyrrole-2(1H)-carboxylate

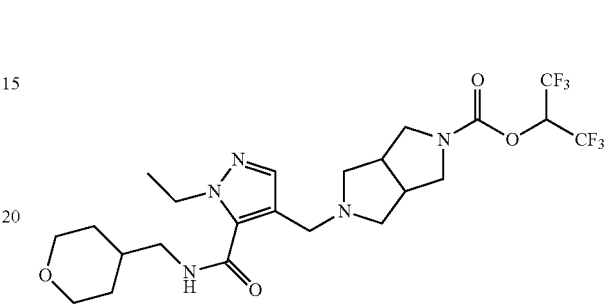

The title compound was prepared from (tetrahydro-2H-pyran-4-yl)methanamine and 1,1,1,3,3,3-hexafluoropropan-2-yl 5-((5-(ethoxycarbonyl)-1-ethyl-1H-pyrazol-4-yl)methyl)hexahydropyrrolo[3,4-c]pyrrole-2(1H)-carboxylate (Isomer A, Example 73, Step 2) according to a procedure analogous to that which was described in Example 73 (Step 3) to provide 1,1,1,3,3,3-hexafluoropropan-2-yl 5-((1-ethyl-5-(((tetrahydro-2H-pyran-4-yl)methyl)carbamoyl)-1H-pyrazol-4-yl)methyl)hexahydropyrrolo[3,4-c]pyrrole-2(1H)-carboxylate. $^1$H NMR (400 MHz, Chloroform-d) δ 9.69 (t, J=5.5 Hz, 1H), 7.25 (s, 1H), 5.66 (hept, J=6.2 Hz, 1H), 4.52 (q, J=7.2 Hz, 2H), 3.92 (dd, J=11.3, 3.6 Hz, 2H), 3.72-3.62 (m, 2H), 3.54-3.41 (m, 2H), 3.36-3.23 (m, 4H), 3.13 (t, J=6.3 Hz, 2H), 2.91-2.85 (m, 2H), 2.67-2.61 (m, 2H), 2.43 (t, J=11.1 Hz, 2H), 1.82-1.72 (m, 1H), 1.62-1.52 (m, 2H), 1.38 (t, J=7.2 Hz, 3H), 1.33-1.16 (m, 2H). LCMS (ESI, m/z): 556.3 [M+H]$^+$.

Example 182

1,1,1,3,3,3-hexafluoropropan-2-yl 5-((1-ethyl-5-((tetrahydro-2H-pyran-4-yl)carbamoyl)-1H-pyrazol-4-yl)methyl)hexahydropyrrolo[3,4-c]pyrrole-2(1H)-carboxylate

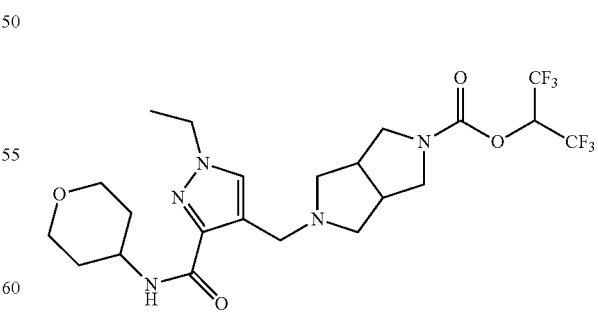

The title compound was prepared from tetrahydro-2H-pyran-4-amine and 1,1,1,3,3,3-hexafluoropropan-2-yl 5-((5-(ethoxycarbonyl)-1-ethyl-1H-pyrazol-4-yl)methyl)hexahydropyrrolo[3,4-c]pyrrole-2(1H)-carboxylate (Isomer B, Example 73, Step 2) according to a procedure analogous to that which was described in Example 73 (Step 3) to provide 1,1,1,3,3,3-hexafluoropropan-2-yl 5-((1-ethyl-5-((tetrahydro-2H-pyran-4-yl)carbamoyl)-1H-pyrazol-4-yl)methyl)hexahydropyrrolo[3,4-c]pyrrole-2(1H)-carboxylate as a clear oil. $^1$H NMR (400 MHz, Chloroform-d) δ 9.67 (d, J=7.0 Hz, 1H), 7.33 (s, 1H), 5.81-5.68 (m, 1H), 4.58 (q, J=7.2 Hz, 2H), 4.18-4.04 (m, 1H), 3.99 (d, J=10.1 Hz, 2H), 3.66 (dd, J=11.3, 6.5 Hz, 2H), 3.58-3.38 (m, 6H), 2.93 (br s, 4H), 2.37-2.20 (m, 2H), 2.02-1.92 (m, 2H), 1.50-1.34 (m, 5H). LCMS (ESI, m/z): 542.3 [M+H]$^+$.

Example 183

1,1,1,3,3,3-hexafluoropropan-2-yl 5-(3-(morpholinomethyl)-5-(trifluoromethoxy)benzyl)hexahydropyrrolo[3,4-c]pyrrole-2(1H)-carboxylate

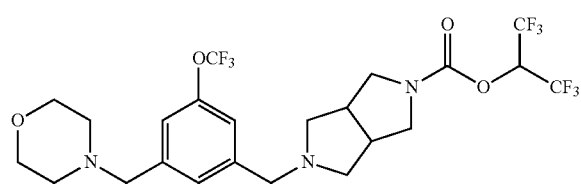 [SMILES: O=C(OC(C(F)(F)F)C(F)(F)F)N1CC2CN(Cc3cc(CN4CCOCC4)cc(OC(F)(F)F)c3)CC2C1]

Step 1: Preparation of potassium trifluoro((5-((1,1,1,3,3,3-hexafluoropropan-2-yloxy)carbonyl)hexahydropyrrolo[3,4-c]pyrrol-2(1H)-yl)methyl)borate

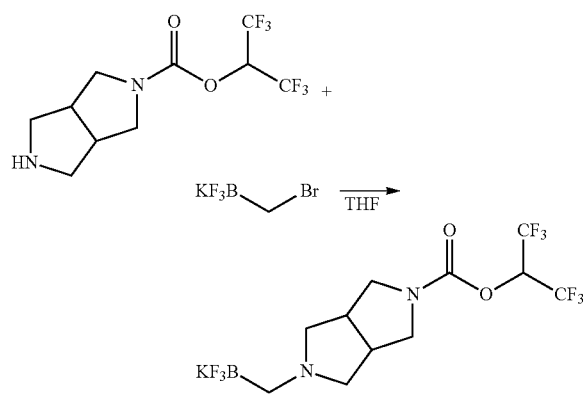

Potassium bromomethyltrifloroborate (8.4 g, 42.2 mmol) was added to a solution of HFIP piperazine carbamate (Example 5, Step 3, 42.2 mmol, crude from last step) in THF (1.0 M) at r.t. the mixture was heated at 80° C. for 3 hours and then concentrated under reduced pressure. The residue was dissolved in a mixture of acetone (300 ml) and MeOH (500 mL), K$_2$CO$_3$ (5.82 g, 42.2 mmol) was added. The mixture was stirred for 3 hours at rt. The insoluble salts were filtrated off and the filtrate was concentrated under reduced pressure. The crude potassium trifluoro((5-((1,1,1,3,3,3-hexafluoropropan-2-yloxy)carbonyl)hexahydropyrrolo[3,4-c]pyrrol-2(1H)-yl)methyl)borate is used for the coupling reaction directly. $^1$H NMR (400 MHz, (CD$_3$)$_2$SO) δ 1.73-1.77 (m, 1H), 1.98-2.02 (m, 2H), 2.50 (m, 1H), 2.80-2.95 (m, 4H), 3.22-3.26 (m, 2H), 3.35-3.39 (m, 2H), 3.43-3.46 (m, 2H), 3.58-3.61 (m, 1H).

Step 2-3: Preparation of 1,1,1,3,3,3-hexafluoropropan-2-yl 5-(3-(morpholinomethyl)-5-(trifluoromethoxy)benzyl)hexahydropyrrolo[3,4-c]pyrrole-2(1H)-carboxylate The title compound was synthesized from 3-bromo-5-trifluoromethoxylbenzaldehyde, morpholine, and potassium trifluoro((5-((1,1,1,3,3,3-hexafluoropropan-2-yloxy)carbonyl)hexahydropyrrolo[3,4-c]pyrrol-2(1H)-yl)methyl)borate following a procedure analogous to that which was described in Example 8 (Step 4, DCM was used instead of MeCN) followed by Example 127 (Step 3) to 1,1,1,3,3,3-hexafluoropropan-2-yl 5-(3-(morpholinomethyl)-5-(trifluoromethoxy)benzyl)hexahydropyrrolo[3,4-c]pyrrole-2(1H)-carboxylate as a pale yellow oil (141 mg, 81%). $^1$H NMR (400 MHz, Chloroform-d) δ 1.22-1.40 (m, 2H), 2.38-2.43 (m, 4H), 2.59-2.64 (m, 2H), 2.80-2.87 (m, 2H), 3.26-3.37 (m, 2H), 3.47 (s, 2H), 3.56 (s, 2H), 3.61-3.72 (m, 6H), 5.67 (hept, J=6.0 Hz, 1H), 7.04 (s, 1H), 7.06 (s, 1H), 7.14 (s, 1H). LCMS (ESI, m/z): 580.2 (M+H).

Example 184

1,1,1,3,3,3-hexafluoropropan-2-yl 5-(3-(piperidin-1-ylmethyl)-5-(trifluoromethoxy)benzyl)hexahydropyrrolo[3,4-c]pyrrole-2(1H)-carboxylate

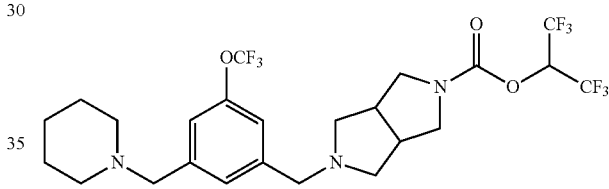

The title compound was synthesized from 3-bromo-5-trifluoromethoxylbenzaldehyde and piperidine following procedures analogous to those described in Example 183 (Steps 1-3) to afford 1,1,1,3,3,3-hexafluoropropan-2-yl 5-(3-(piperidin-1-ylmethyl)-5-(trifluoromethoxy)benzyl)hexahydropyrrolo[3,4-c]pyrrole-2(1H)-carboxylate. $^1$H NMR (400 MHz, Chloroform-d) δ 1.34-1.39 (m, 2H), 1.49-1.55 (m, 4H), 2.31 (br, 2H), 2.40-2.53 (m, 4H), 2.81 (m, 2H), 2.98-3.06 (m, 1H), 3.16-3.21 (m, 1H), 3.27-3.57 (m, 4H), 3.40 (s, 2H), 3.63-3.75 (m, 2H), 5.67 (hept, J=6.0 Hz, 1H), 6.99 (s, 1H), 7.02 (s, 1H), 7.19 (s, 1H). LCMS (ESI, m/z): 578.1 (M+H).

Example 185

1,1,1,3,3,3-hexafluoropropan-2-yl 5-(3-(pyrrolidin-1-ylmethyl)-5-(trifluoromethoxy)benzyl)hexahydropyrrolo[3,4-c]pyrrole-2(1H)-carboxylate

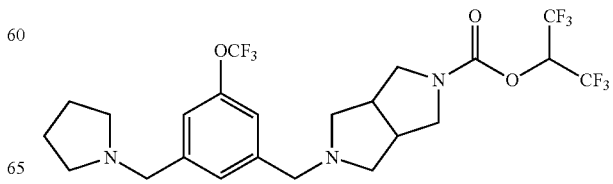

The title compound was synthesized from 3-bromo-5-trifluoromethoxylbenzaldehyde and pyrrolidine following procedures analogous to those described in Example 183 (Steps 1-3) to afford 1,1,1,3,3,3-hexafluoropropan-2-yl 5-(3-(pyrrolidin-1-ylmethyl)-5-(trifluoromethoxy)benzyl)hexahydropyrrolo[3,4-c]pyrrole-2(1H)-carboxylate. $^1$H NMR (400 MHz, Chloroform-d) δ 1.73 (br, 4H), 2.40-2.53 (m, 6H), 2.55-2.67 (m, 1H), 2.81 (m, 2H), 2.99-3.07 (m 1H), 3.16-3.22 (m, 1H), 3.27-3.3.41 (m, 2H), 3.47-3.77 (m, 2H), 3.51 (s, br, 2H), 3.56 (s, 2H), 5.66 (hept, J=6.4 Hz, 1H), 7.01 (s, 1H), 7.02, (s, 1H), 7.14 (s, 1H). LCMS (ESI, m/z): 564.2 (M+H).

Example 186

1,1,1,3,3,3-hexafluoropropan-2-yl 5-(3-(pyrrolidin-1-ylmethyl)-5-(trifluoromethoxy)benzyl)hexahydropyrrolo[3,4-c]pyrrole-2(1H)-carboxylate

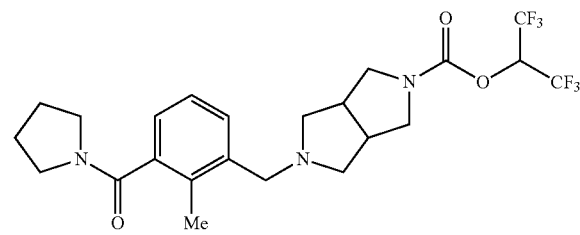 [SMILES: Cc1c(CN2CC3CN(C(=O)OC(C(F)(F)F)C(F)(F)F)CC3C2)cccc1C(=O)N1CCCC1]

Step 1: Preparation of (3-bromo-2-methylphenyl)(pyrrolidin-1-yl)methanone

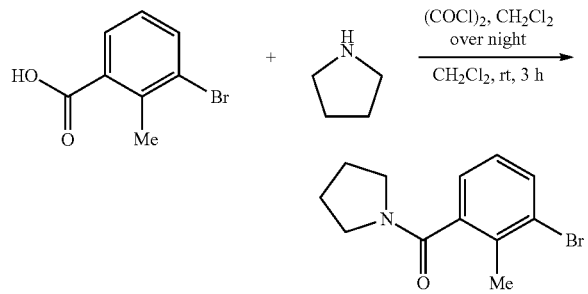

A 50-mL round-bottom flask, equipped with a magnetic stir bar, was charged with 3-bromo-2-methylbenzoic acid (2.14 g, 10 mmol). The aldehyde was dissolved in 20 mL dichloromethane (anhydrous). Oxalyl chloride (25 mmol) was added. The reaction was allowed to continue to stir at room temperature overnight. At that point, the solvent was removed under vacuum. The residue was diluted in 20 mL methylene chloride. Pyrrolidine (20 mmol) and Et$_3$N (50 mmol) were added to the flask. The reaction mixture was stir at room temperature for 4 hours. The reaction was quenched with 2 N HCl. The aqueous phase was extracted twice with dichloromethane (25 mL*3). The combined organic layers were dried over anhydrous sodium sulfate, filtered and concentrated. The crude mixture was applied to a chromatography column. A gradient solvent was used from 100% hexanes to 100% ethyl acetate to provide 1.89 g (79%) of (3-bromo-2-methylphenyl)(pyrrolidin-1-yl)methanone as a white solid.

Step 2: Preparation of 1,1,1,3,3,3-hexafluoropropan-2-yl 5-(2-methyl-3-(pyrrolidine-1-carbonyl)benzyl)hexahydropyrrolo[3,4-c]pyrrole-2(1H)-carboxylate

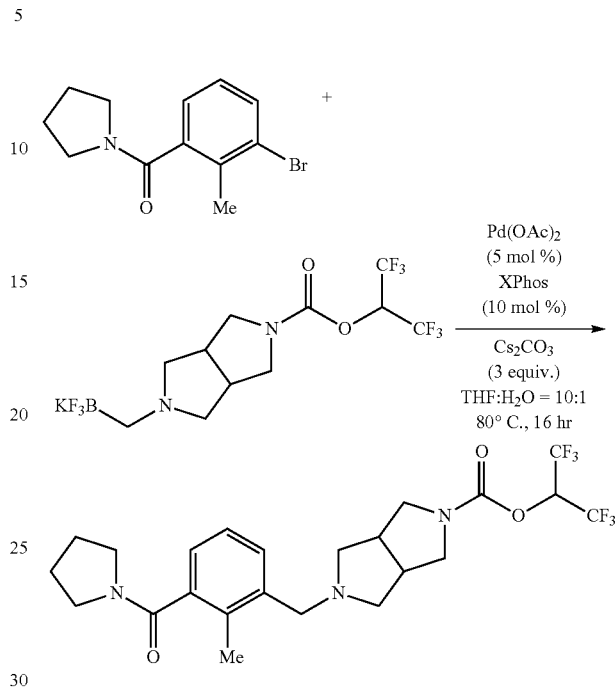

The title compound was synthesized from (3-bromo-2-methylphenyl)(pyrrolidin-1-yl)methanone and potassium trifluoro((5-((1,1,1,3,3,3-hexafluoropropan-2-yloxy)carbonyl)hexahydropyrrolo[3,4-c]pyrrol-2(1H)-yl)methyl)borate following a procedure analogous to that which was described in Example 127 (Step 3) to afford 1,1,1,3,3,3-hexafluoropropan-2-yl 5-(2-methyl-3-(pyrrolidine-1-carbonyl)benzyl)hexahydropyrrolo[3,4-c]pyrrole-2(1H)-carboxylate. $^1$H NMR (400 MHz, CDCl$_3$) δ 1.84-1.90 (m, 2H), 1.93-2.00 (m, 2H), 2.28 (s, 3H), 2.54 (br, 4H), 2.88 (m, 2H), 3.10 (m, 2H), 3.31-3.38 (m, 2H), 3.58 (s, 2H), 3.65-3.73 (m, 4H), 5.74 (hept, J=6.4 Hz, 1H), 7.11 (dd, J1=1.6 Hz, J2=7.6 Hz, 1H), 7.17 (t, J=7.6 Hz, 1H), 7.26 (dd, J1=1.6 Hz, J2=7.6 Hz, 1H). $^{13}$C NMR (100 MHz, CDCl$_3$) δ 15.27, 24.63, 25.94, 41.08, 42.05, 45.31, 48.27, 52.22, 53.15, 57.44, 59.96, 67.75 (hept, J=34.1 Hz), 77.27, 124.52, 125.83, 129.51, 132.64, 137.92, 138.75, 150.25, 170.25. LCMS (ESI, m/z): 508.4 (M+H).

Example 187

1,1,1,3,3,3-hexafluoropropan-2-yl 5-(2-methyl-3-(piperidine-1-carbonyl)benzyl)hexahydropyrrolo[3,4-c]pyrrole-2(1H)-carboxylate

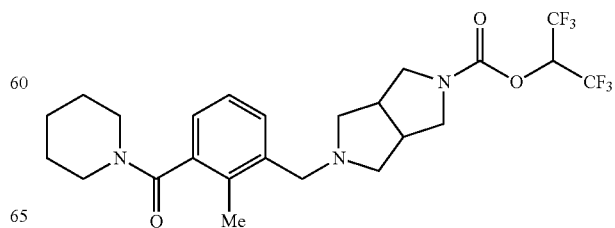

The title compound was synthesized from 3-bromo-2-methylbenzoic acid, piperidine and potassium trifluoro((5-((1,1,1,3,3,3-hexafluoropropan-2-yloxy)carbonyl)hexahydropyrrolo[3,4-c]pyrrol-2(1H)-yl)methyl)borate according to procedures analogous to those described for Example 186 (Steps 1-2) to afford 1,1,1,3,3,3-hexafluoropropan-2-yl 5-(2-methyl-3-(piperidine-1-carbonyl)benzyl)hexahydropyrrolo[3,4-c]pyrrole-2(1H)-carboxylate. $^1$H NMR (400 MHz, Chloroform-d) δ 1.45 (br, 2H), 1.66 (br, 4H), 2.27 (s, 3H), 2.50 (m, 2H), 2.58 (m, 2H), 2.88 (m, 2H), 3.11-3.15 (m, 2H), 3.26-3.40 (m, 2H), 3.50-3.55 (m, 2H), 3.62-3.86 (m, 6H), 5.70-5.77 (double hept, 1H), 7.07 (d, J=7.6 Hz, 1H), 7.16 (t, J=7.6 Hz, 1H), 7.26 (d, J=7.6 Hz, 1H). $^{13}$C NMR (100 MHz, CDCl$_3$) δ 15.38, 15.40, 24.52, 25.71, 26.43, 41.03, 41.10, 42.01, 42.07, 42.33, 47.83, 52.15, 52.21, 53.10, 53.15, 57.32, 57.39, 59.65, 59.74, 60.10, 60.13, 67.74 (hept, J=34.4 Hz), 77.56, 119.33, 122.15, 124.53, 124.55, 125.77, 129.28, 129.30, 132.90, 132.95, 137.55, 137.84, 150.20, 150.25, 170.11. LCMS (ESI, m/z): 522.4 (M+H).

Example 188

1,1,1,3,3,3-hexafluoropropan-2-yl 5-(5-(morpholinomethyl)-2-(trifluoromethoxy)benzyl)hexahydropyrrolo[3,4-c]pyrrole-2(1H)-carboxylate

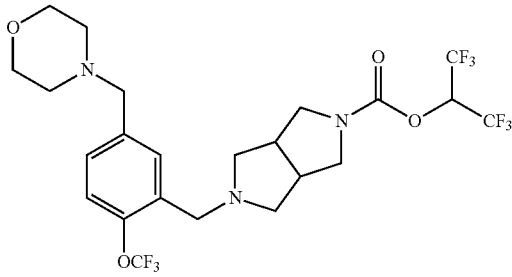 [SMILES: O=C(OC(C(F)(F)F)C(F)(F)F)N1CC2CN(Cc3cc(CN4CCOCC4)ccc3OC(F)(F)F)CC2C1]

The title compound was synthesized from 3-bromo-4-(trifluoromethoxy)benzaldehyde and morpholine following procedures analogous to those described in Example 183 (Steps 1-3) to afford 1,1,1,3,3,3-hexafluoropropan-2-yl 5-(5-(morpholinomethyl)-2-(trifluoromethoxy)benzyl)hexahydropyrrolo[3,4-c]pyrrole-2(1H)-carboxylate. $^1$H NMR (400 MHz, CDCl3) δ 2.45 (br, 4H), 2.56-2.61 (m, 4H), 2.90 (m, 2H), 3.36-3.42 (m, 2H), 3.50 (s, 2H), 3.66 (s, 2H), 3.71-3.78 (m, 6H); $^{13}$C NMR (100 MHz, CDCl$_3$) δ 41.07, 42.05, 44.71, 52.12, 52.39, 53.10, 53.59, 59.74, 62.46, 62.57, 66.95, 67.76 (hept, J=34.1 Hz), 120.58 (q, J=255.3 Hz), 120.44, 128.83, 131.16, 136.60, 114.43, 150.29. The rotamer was observed from NMR experiments. LCMS (ESI, m/z): 580.2 (M+H).

Example 189

1,1,1,3,3,3-hexafluoropropan-2-yl 5-(5-(piperidin-1-ylmethyl)-2-(trifluoromethoxy)benzyl)hexahydropyrrolo[3,4-c]pyrrole-2(1H)-carboxylate

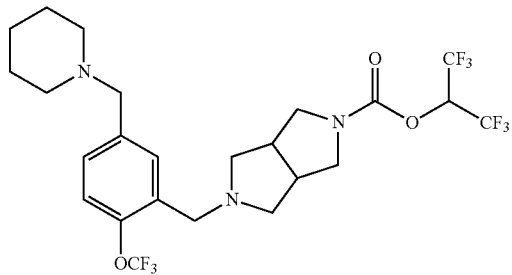 [SMILES: O=C(OC(C(F)(F)F)C(F)(F)F)N1CC2CN(Cc3cc(CN4CCCCC4)ccc3OC(F)(F)F)CC2C1]

The title compound was synthesized from 3-bromo-4-(trifluoromethoxy)benzaldehyde and piperidine following procedures analogous those described in Example 183 (Steps 1-3) to afford 1,1,1,3,3,3-hexafluoropropan-2-yl 5-(5-(piperidin-1-ylmethyl)-2-(trifluoromethoxy)benzyl)hexahydropyrrolo[3,4-c]pyrrole-2(1H)-carboxylate. $^1$H NMR (400 MHz, CDCl$_3$) δ 1.45 (br, 2H), 1.56-1.61 (m, 4H), 2.37 (br, 2H), 2.56-2.59 (m, 4H), 2.90 (m, 2H), 3.34-3.40 (m, 2H), 3.46 (s, 2H), 3.67 (s, 2H), 3.74-3.79 (m, 2H), 5.76 (hept, J=6.4 Hz, 1H), 7.15-7.26 (m, 2H), 7.44 (s, 1H). $^{13}$C NMR (100 MHz, CDCl$_3$) δ 24.30, 25.94, 41.07, 42.08, 44.82, 52.08, 52.34, 53.08, 54.46, 54.53, 59.57, 59.68, 62.08, 62.98, 67.76 (hept, J=34.2 Hz), 120.31, 121.12 (q, J=200 Hz), 120.60 (q, J=255 Hz), 126.81, 128.78, 129.25, 130.89, 131.13, 132.42, 137.54, 137.71, 146.22, 146.43, 150.27. The rotamer was observed from NMR experiments. LCMS (ESI, m/z): 578.1 (M+H).

Example 190

1,1,1,3,3,3-hexafluoropropan-2-yl 5-(5-(pyrrolidin-1-ylmethyl)-2-(trifluoromethoxy)benzyl)hexahydropyrrolo[3,4-c]pyrrole-2(1H)-carboxylate

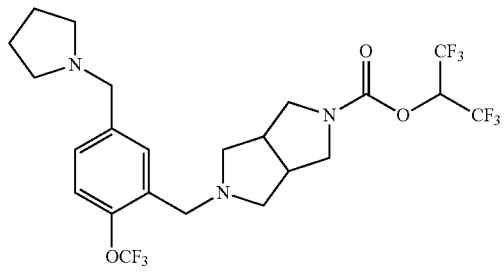 [SMILES: O=C(OC(C(F)(F)F)C(F)(F)F)N1CC2CN(Cc3cc(CN4CCCC4)ccc3OC(F)(F)F)CC2C1]

The title compound was synthesized from 3-bromo-4-(trifluoromethoxy)benzaldehyde and pyrrolidine following procedures analogous to those described in Example 183 (Steps 1-3) to afford 1,1,1,3,3,3-hexafluoropropan-2-yl 5-(5-(pyrrolidin-1-ylmethyl)-2-(trifluoromethoxy)benzyl)hexahydropyrrolo[3,4-c]pyrrole-2(1H)-carboxylate. $^1$H NMR (400 MHz, CDCl$_3$) δ 1.80 (br, 4H), 2.51 (br, 4H), 2.56-2.59 (m, 4H), 2.89 (m, 2H), 3.34-3.40 (m, 2H), 3.61 (s, 2H), 3.66 (s, 2H), 3.74-3.78 (m, 2H), 5.76 (hept, J=6.4 Hz, 1H), 7.16-7.30 (m, 2H), 7.45 (s, 1H). $^{13}$C NMR (100 MHz, CDCl$_3$) δ 29.56, 41.08, 42.06, 44.80, 52.12, 52.36, 53.11, 54.14, 54.21, 59.64, 59.70, 59.81, 59.92, 67.76 (hept, J=34.2 Hz), 120.44, 120.60 (q, J=255 Hz), 121.24 (q, J=280.2 Hz), 126.95, 128.59, 128.98, 130.92, 131.06, 132.20, 138.23, 138.36, 146.25, 146.26, 150.28. The rotamer was observed from NMR experiments. LCMS (ESI, m/z): 564.2 (M+H).

Example 191

1,1,1,3,3,3-hexafluoropropan-2-yl 5-(4-(morpholine-4-carbonyl)-3-(trifluoromethoxy)benzyl)hexahydropyrrolo[3,4-c]pyrrole-2(1H)-carboxylate

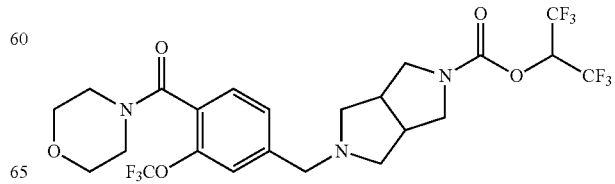

The title compound was synthesized from 4-bromo-2-(trifluoromethoxy)benzoic acid, morpholine and potassium trifluoro((5-((1,1,1,3,3,3-hexafluoropropan-2-yloxy)carbonyl)hexahydropyrrolo[3,4-c]pyrrol-2(1H)-yl)methyl)borate according to procedures analogous to those described in Example 186 (Steps 1-2) to afford 1,1,1,3,3,3-hexafluoropropan-2-yl 5-(4-(morpholine-4-carbonyl)-3-(trifluoromethoxy)benzyl)hexahydropyrrolo[3,4-c]pyrrole-2(1H)-carboxylate. $^1$H NMR (400 MHz, Chloroform-d) δ 2.54-2.64 (m, 4H), 2.82 (br, 4H), 2.95 (m, 2H), 3.35-3.48 (m, 2H), 3.63-3.75 (m, 2H), 3.70-3.92 (m, 2H), 3.95 (br, 4H), 5.66 (hept, J=6 Hz, 1H), 7.27-7.31 (m, 1H), 7.39 (m, 1H), 7.78 (M, 1H). LCMS (ESI, m/z): 594.9 (M+H).

Example 192

1,1,1,3,3,3-hexafluoropropan-2-yl 5-(4-(piperidine-1-carbonyl)-3-(trifluoromethoxy)benzyl)hexahydropyrrolo[3,4-c]pyrrole-2(1H)-carboxylate

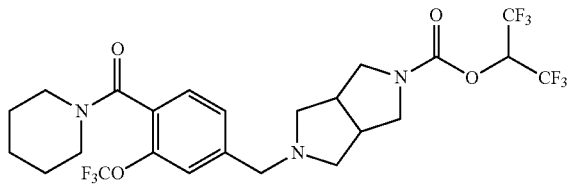 [SMILES: O=C(OC(C(F)(F)F)C(F)(F)F)N1CC2CN(Cc3ccc(C(=O)N4CCCCC4)c(OC(F)(F)F)c3)CC2C1]

The title compound was synthesized from 4-bromo-2-(trifluoromethoxy)benzoic acid, piperidine and potassium trifluoro((5-((1,1,1,3,3,3-hexafluoropropan-2-yloxy)carbonyl)hexahydropyrrolo[3,4-c]pyrrol-2(1H)-yl)methyl)borate according to procedures analogous to those described for Example 186 (Steps 1-2) to afford 1,1,1,3,3,3-hexafluoropropan-2-yl 5-(4-(piperidine-1-carbonyl)-3-(trifluoromethoxy)benzyl)hexahydropyrrolo[3,4-c]pyrrole-2(1H)-carboxylate. $^1$H NMR (400 MHz, CDCl$_3$) δ 1.19 (br, 2H), 1.61-1.91 (m, 6H), 3.07 (m, 2H), 3.17-3.23 (m, 4H), 3.37-3.42 (m, 2H), 3.51-3.56 (m, 4H), 3.73-3.79 (m, 2H), 5.66 (hept, J=6 Hz, 1H), 6.29 (s, 1H), 6.40 (dd, J1=8.8 Hz, J2=2.4 Hz, 1H), 7.22 (d, J=8.8 Hz, 1H). $^{13}$C NMR (100 MHz, CDCl$_3$) δ 24.55, 25.93, 29.26, 31.74, 41.11, 42.01, 45.75, 48.05, 50.29, 51.10, 51.67, 51.72, 53.77, 67.89 (hept, J=34.2 Hz), 69.52, 104.13, 110.40, 119.08, 120.45, 122.04, 129.74, 146.11, 146.13, 148.87, 150.69, 166.18. LCMS (ESI, m/z): 592.2 (M+H).

Example 193

1,1,1,3,3,3-hexafluoropropan-2-yl 5-(4-(pyrrolidine-1-carbonyl)-3-(trifluoromethoxy)benzyl)hexahydropyrrolo[3,4-c]pyrrole-2(1H)-carboxylate

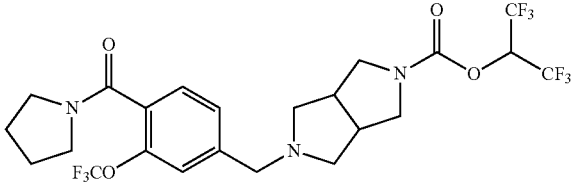 [SMILES: O=C(OC(C(F)(F)F)C(F)(F)F)N1CC2CN(Cc3ccc(C(=O)N4CCCC4)c(OC(F)(F)F)c3)CC2C1]

The title compound was synthesized from 4-bromo-2-(trifluoromethoxy)benzoic acid, pyrrolidine and potassium trifluoro((5-((1,1,1,3,3,3-hexafluoropropan-2-yloxy)carbonyl)hexahydropyrrolo[3,4-c]pyrrol-2(1H)-yl)methyl)borate according to procedures analogous to those described for Example 186 (Steps 1-2) to afford 1,1,1,3,3,3-hexafluoropropan-2-yl 5-(4-(pyrrolidine-1-carbonyl)-3-(trifluoromethoxy)benzyl)hexahydropyrrolo[3,4-c]pyrrole-2(1H)-carboxylate. $^1$H NMR (400 MHz, CDCl$_3$) δ 1.55-1.66 (m, 6H), 3.12-3.13 (m, 2H), 3.23-3.28 (m, 4H), 3.43-3.48 (m, 2H), 3.57-3.62 (m, 2H), 3.79 (s, 2H), 3.84-3.85 (m, 2H), 5.72 (hept, J=6.0 Hz, 1H), 6.35 (d, J=12.4 Hz, 1H), 6.46 (dd, J1=2.4 Hz, J2=8.4 Hz, 1H), 7.24 (d, J=8.4 Hz, 1H). $^{13}$C NMR (100 MHz, CDCl$_3$) δ 24.56, 25.58, 26.22, 41.12, 42.01, 42.92, 48.23, 50.30, 51.11, 51.69, 51.74, 67.90 (hept, J=34.4 Hz), 103.80, 108.01, 109.98, 110.49, 117.77, 120.74 (q, J=256.3 Hz), 129.95, 146.07, 148.79, 150.68. The rotamer was observed from NMR experiments. LCMS (ESI, m/z): 578.2 (M+H).

Example 194

1,1,1,3,3,3-hexafluoropropan-2-yl 5-((1-methyl-3-phenyl-1H-pyrazol-5-yl)methyl)hexahydropyrrolo[3,4-c]pyrrole-2(1H)-carboxylate

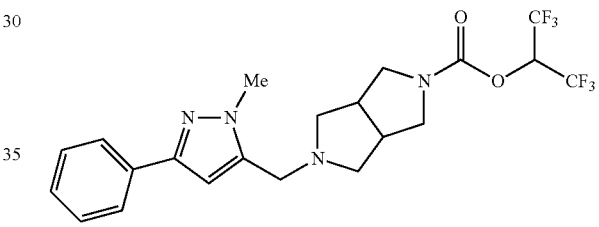

A 16-mL screw cap-seal vial with a thick septa, equipped with a magnetic stir bar, was charged in turn with Pd(OAc)$_2$ (3.4 mg, 0.015 mmol, 5 mol %), XPhos (14.3 mg, 0.03 mmol, 10 mol %), 5-bromo-1-methyl-3-phenyl-1H-pyrazole (0.3 mol, 1 equiv.), potassium trifluoro((5-((1,1,1,3,3,3-hexafluoropropan-2-yloxy)carbonyl)hexahydropyrrolo[3,4-c]pyrrol-2(1H)-yl)methyl)borate (0.45 mmol, 1.5 equiv.) and Cs$_2$CO$_3$ (294 mg, 0.9 mmol, 3 equiv.). The vial was tight sealed and vacuum and back filled with N$_2$ through a needle for 3 circles. 2.5 mL of THF/H$_2$O=10:1 was added via syringe. The reaction mixture was heated at 80° C. for 16 hours. After cooled to room temperature, the reaction mixture was quenched with 15 mL H$_2$O, the aqueous solution was extracted with dichloromethane (15 mL*3). The combined organic layered was washed with water and brine, dried over sodium sulfate and concentrated. The resulting yellow oil was chromatographed on a 24 g silica column with a gradient (100% dichloromethane to 90% dichloromethane/10% methanol containing 2M ammonia) to provide 1,1,1,3,3,3-hexafluoropropan-2-yl 5-((1-methyl-3-phenyl-1H-pyrazol-5-yl)methyl)hexahydropyrrolo[3,4-c]pyrrole-2(1H)-carboxylate as a pale yellow oil (123 mg, 86%). 1H NMR (400 MHz, CDCl3) δ 2.55-2.64 (m, 4H), 2.88-2.95 (m, 2H), 3.36-3.43 (m, 2H), 3.64 (s, 2H), 3.71-3.76 (m, 2H), 3.92 (s, 3H), 5.75 (hept, J=6.0 Hz, 1H), 6.43 (s, 1H), 7.31 (d, J=7.6 Hz, 1H), 7.40 (t, J=7.6 Hz, 1H), 7.79 (d, J=7.6 Hz, 1H)). LCMS (ESI, m/z): 477.1 (M+H).

Example 195

1,1,1,3,3,3-hexafluoropropan-2-yl 5-43-(3-fluorophenyl)-1-methyl-1H-pyrazol-5-yl)methyl)hexahydropyrrolo[3,4-c]pyrrole-2(1H)-carboxylate

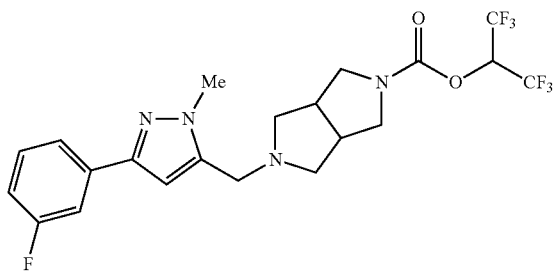 [SMILES: Cn1nc(-c2cccc(F)c2)cc1CN1CC2CN(C(=O)OC(C(F)(F)F)C(F)(F)F)CC2C1]

The title compound was synthesized from 5-bromo-3-(3-fluorophenyl)-1-methyl-1H-pyrazole and potassium trifluoro((5-((1,1,1,3,3,3-hexafluoropropan-2-yloxy)carbonyl)hexahydropyrrolo[3,4-c]pyrrol-2(1H)-yl)methyl)borate according to a procedure analogous to that which was described in Example 194 to afford 1,1,1,3,3,3-hexafluoropropan-2-yl 5-((3-(3-fluorophenyl)-1-methyl-1H-pyrazol-5-yl)methyl)hexahydropyrrolo[3,4-c]pyrrole-2(1H)-carboxylate. 1H NMR (400 MHz, Chloroform-d) δ 2.43-2.54 (m, 4H), 2.85 (m, 2H), 3.24-3.29 (m, 2H), 3.78 (s, 2H), 3.71-3.76 (m, 2H), 3.83 (s, 3H), 5.74 (kept, J=6.4 Hz, 1H), 7.12-7.23 (m, 3H), 7.42-7.47 (m, 1H), 7.49 (s, 1H). LCMS (ESI, m/z): 495.1 (M+H).

Example 196

1,1,1,3,3,3-hexafluoropropan-2-yl 5-((1-methyl-3-(m-tolyl)-1H-pyrazol-5-yl)methyl)hexahydropyrrolo[3,4-c]pyrrole-2(1H)-carboxylate

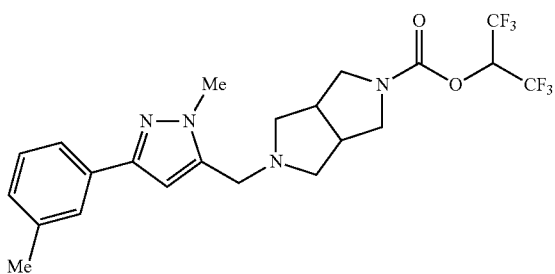 [SMILES: Cc1cccc(-c2cc(CN3CC4CN(C(=O)OC(C(F)(F)F)C(F)(F)F)CC4C3)n(C)n2)c1]

The title compound was synthesized from 5-bromo-1-methyl-3-m-tolyl-1H-pyrazole and potassium trifluoro((5-((1,1,1,3,3,3-hexafluoropropan-2-yloxy)carbonyl)hexahydropyrrolo[3,4-c]pyrrol-2(1H)-yl)methyl)borate according to a procedure analogous to that which was described in Example 194 to afford 1,1,1,3,3,3-hexafluoropropan-2-yl 5-((1-methyl-3-(m-tolyl)-1H-pyrazol-5-yl)methyl)hexahydropyrrolo[3,4-c]pyrrole-2(1H)-carboxylate. $^1$H NMR (400 MHz, Chloroform-d) δ 2.39 (s, 3H), 2.50-2.64 (m, 4H), 2.89 (m, 2H), 3.30-3.35 (m, 2H), 3.57 (s, 2H), 3.74-3.79 (m, 2H), 3.94 (s, 3H), 5.75 (kept, J=6.4 Hz, 1H), 7.14-7.16 (m, 1H), 7.28 (t, J=7.6 Hz, 1H), 7.33 (s, 1H), 7.55 (d, J=7.6 Hz, 1H), 7.62 (s, 1H). LCMS (ESI, m/z): 491.1 (M+H).

Example 197

2,5-dioxopyrrolidin-1-yl 5-((1-methyl-3-phenyl-1H-pyrazol-5-yl)methyl)hexahydropyrrolo[3,4-c]pyrrole-2(1H)-carboxylate

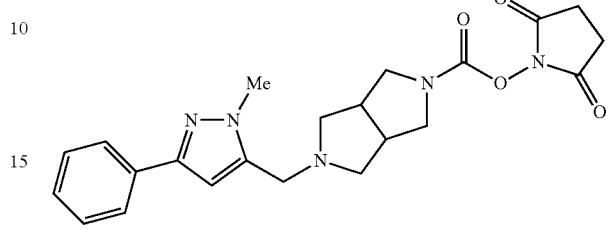

Step 1-2: Preparation of 2-((1-methyl-3-phenyl-1H-pyrazol-5-yl)methyl)octahydropyrrolo[3,4-c]pyrrole The title compound was synthesized from 5-bromo-1-methyl-3-phenyl-1H-pyrazole and potassium ((5-(tert-butoxycarbonyl)-hexahydropyrrolo[3,4-c]pyrrol-2(1H)-yl)methyl)trifluoroborate following procedures analogous to those described in Example 127 (Step 3) followed by Example 5 (Step 3) to provide crude 24(1-methyl-3-phenyl-1H-pyrazol-5-yl)methyl)octahydropyrrolo[3,4-c]pyrrole.

Step 3: Preparation of 2,5-dioxopyrrolidin-1-yl 5-((1-methyl-3-phenyl-1H-pyrazol-5-yl)methyl) hexahydropyrrolo[3,4-c]pyrrole-2(1H)-carboxylate

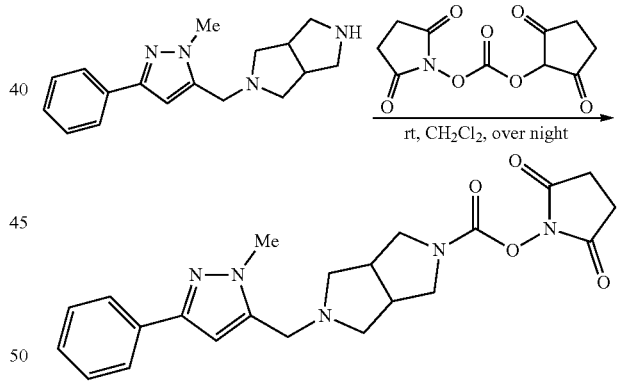

A 10-mL round-bottom flask, equipped with a magnetic stir bar, was charged with 2-((1-methyl-3-phenyl-1H-pyrazol-5-yl)methyl)octahydropyrrolo[3,4-c]pyrrole (crude product from last step, about 0.25 mmol) and dichloromethane (1.5 mL) under nitrogen. The resulting suspension was cooled to 0° C. and N,N-diisopropylethylamine (32 μL, 2.0 equiv) was added via syringe, followed by N,N'-disuccinimidyl carbonate (105 mg, 0.42 mmol, 85% pure). The ice bath was removed and the suspension was stirred at room temperature for overnight. The solvent was removed by rotary evaporation and the resulting oil was applied to a chromatography column containing 12 g silica and dichloromethane. A gradient solvent was used from 100% dichloromethane to 10% methanol in dichloromethane to provide 2,5-dioxopyrrolidin-1-yl 5-((1-methyl-3-phenyl-1H-pyrazol-5-yl)methyl)hexahydropyrrolo[3,4-c]pyrrole-2(1H)-carboxylate a powdery white solid. ¹H NMR (400 MHz, Chloroform-d) δ 2.54-2.64 (m, 4H), 2.83 (s, 4H), 2.89-2.95 (m, 2H), 3.35-3.47 (m, 2H), 3.65 (s, 2H), 3.70-3.92 (m, 2H), 3.95 (s, 3H), 6.44 (s, 1H), 7.29 (m, 1H), 7.39 (t, J=7.2 Hz, 1H), 7.78 (d, J=7.6 Hz, 2H). LCMS (ESI, m/z): 424.1 (M+H).

Example 198

2,5-dioxopyrrolidin-1-yl 5-43-(3-fluorophenyl)-1-methyl-1H-pyrazol-5-yl)methyl)hexahydropyrrolo[3,4-c]pyrrole-2(1H)-carboxylate

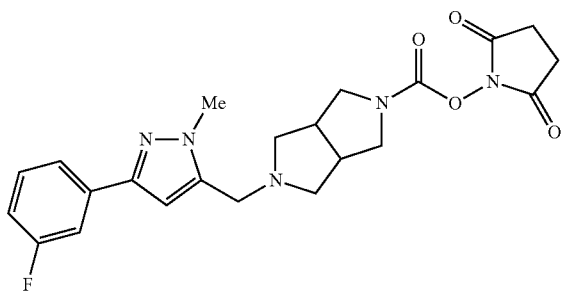 [SMILES: Cn1nc(-c2cccc(F)c2)cc1CN1CC2CN(C(=O)ON3C(=O)CCC3=O)CC2C1]

The title compound was synthesized from 5-bromo-3-(3-fluorophenyl)-1-methyl-1H-pyrazole and potassium ((5-(tert-butoxycarbonyl)-hexahydropyrrolo[3,4-c]pyrrol-2(1H)-yl)methyl)trifluoroborate following procedures analogous to those described in Example 197 (Steps 1-3) to afford 2,5-dioxopyrrolidin-1-yl 5-((3-(3-fluorophenyl)-1-methyl-1H-pyrazol-5-yl)methyl)hexahydropyrrolo[3,4-c]pyrrole-2(1H)-carboxylate. 1H NMR (400 MHz, Chloroform-d) δ 2.59-2.60 (m, 4H), 2.78 (s, 4H), 3.01 (m, 2H), 3.62-3.71 (m, 6H), 3.74 (s, 3H), 7.00-7.18 (m, 3H), 7.44-7.50 (m, 1H), 7.58 (s, 1H). LCMS (ESI, m/z): 442.1 (M+H).

Example 199

2,5-dioxopyrrolidin-1-yl 5-((1-methyl-3-(m-tolyl)-1H-pyrazol-5-yl)methyl)hexahydropyrrolo[3,4-c]pyrrole-2(1H)-carboxylate

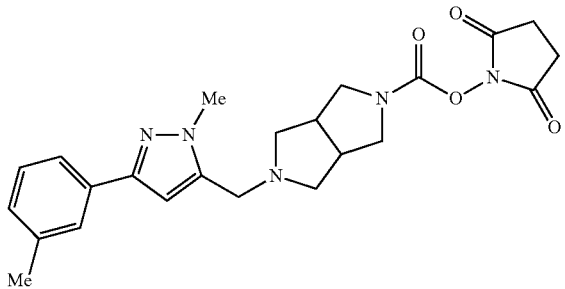

The title compound was synthesized from 5-bromo-1-methyl-3-m-tolyl-1H-pyrazole and potassium ((5-(tert-butoxycarbonyl)-hexahydropyrrolo[3,4-c]pyrrol-2(1H)-yl)methyl)trifluoroborate following procedures analogous to those described in Example 197 (Steps 1-3) to afford 2,5-dioxopyrrolidin-1-yl 5-((1-methyl-3-(m-tolyl)-1H-pyrazol- 5-yl)methyl)hexahydropyrrolo[3,4-c]pyrrole-2(1H)-carboxylate. ¹H NMR (400 MHz, Chloroform-d) δ 2.31 (s, 3H), 2.44-2.56 (m, 4H), 2.70-2.78 (m, 2H), 2.14-2.22 (m, 2H), 3.45-3.63 (m, 6H), 3.60 (s, 2H), 3.85 (s, 3H), 7.06 (d, J=7.2 Hz, 1H), 7.19-7.25 (m, 2H), 7.49 (d, J=7.2 Hz, 1H), 7.54 (s, 1H). LCMS (ESI, m/z): 438.1 (M+H).

Example 200

1,1,1,3,3,3-hexafluoropropan-2-yl 5-(2-(difluoromethyl)-4-morpholinobenzyl)hexahydropyrrolo[3,4-c]pyrrole-2(1H)-carboxylate

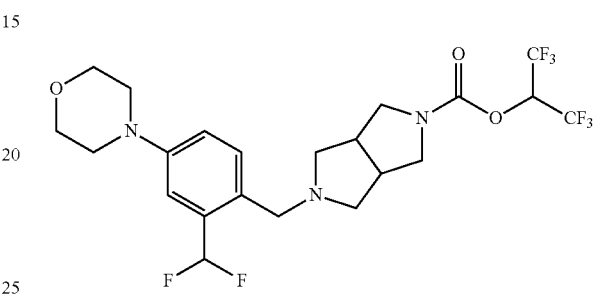

The title compound was synthesized from 1-bromo-2-difluoromethyl-4-fluorobenzene, morpholine, and potassium trifluoro((5-((1,1,1,3,3,3-hexafluoropropan-2-yloxy)carbonyl)hexahydropyrrolo[3,4-c]pyrrol-2(1H)-yl)methyl)borate following a procedure analogous to that which was described in Example 158 (Step 2) followed by a procedure analogously described in Example 127 (Step 3) to afford 1,1,1,3,3,3-hexafluoropropan-2-yl 5-(2-(difluoromethyl)-4-morpholinobenzyl)hexahydropyrrolo[3,4-c]pyrrole-2(1H)-carboxylate. ¹H NMR (400 MHz, Chloroform-d) δ 2.48-2.56 (m, 4H), 2.87 (m, 2H), 3.19-3.22 (m, 4H), 3.31-3.37 (m, 2H), 3.63 (s, 2H), 3.71-3.76 (m, 2H), 3.88-3.90 (m, 4H), 6.91 (d, J=8.4 Hz, 1H), 7.12 (t, J=56 Hz, 1H), 7.17 (s, 1H), 7.10 (d, J=8.4 Hz, 1H). LCMS (ESI, m/z): 532.2 (M+H).

Example 201

1,1,1,3,3,3-hexafluoropropan-2-yl 5-(2-(difluoromethyl)-4-(piperidin-1-yl)benzyl)hexahydropyrrolo[3,4-c]pyrrole-2(1H)-carboxylate

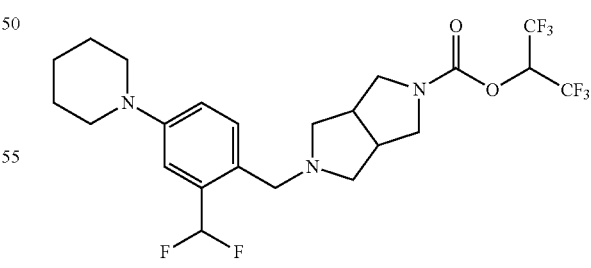

The title compound was synthesized from 1-bromo-2-difluoromethyl-4-fluorobenzene, piperidine, and potassium trifluoro((5-((1,1,1,3,3,3-hexafluoropropan-2-yloxy)carbonyl)hexahydropyrrolo[3,4-c]pyrrol-2(1H)-yl)methyl)borate following procedures analogous to those described in Example 200 to afford 1,1,1,3,3,3-hexafluoropropan-2-yl 5-(2-(difluoromethyl)-4-(piperidin-1-yl)benzyl)hexahydropyrrolo[3,4-c]pyrrole-2(1H)-carboxylate. ¹H NMR (400 MHz, Chloroform-d) δ 1.41-1.47 (m, 2H), 1.53-1.59 (m, 4H), 2.29-2.39 (m, 4H), 2.70 (m, 2H), 3.02-3.05 (m, 4H), 3.14-3.20 (m, 2H), 3.44 (s, 2H), 3.54-3.59 (m, 2H), 5.59 (hept, J=6 Hz, 1H), 6.76 (dd, J1=2.4 Hz, J2=8.4 Hz, 1H), 6.95 (t, J=56 Hz, 1H), 6.99 (d, J=8.4 Hz, 1H), 7.02 (d, J=2.4 Hz, 1H). LCMS (ESI, m/z): 530.2 (M+H).

Example 202

1,1,1,3,3,3-hexafluoropropan-2-yl 5-(2-(difluoromethyl)-4-(pyrrolidin-1-yl)benzyl)hexahydropyrrolo[3,4-c]pyrrole-2(1H)-carboxylate

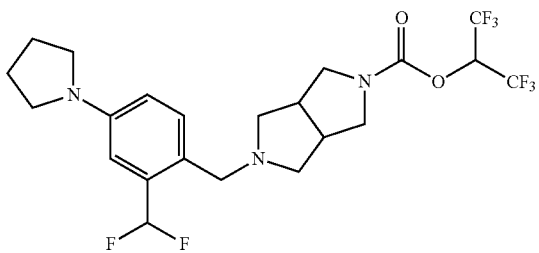 [SMILES: O=C(OC(C(F)(F)F)C(F)(F)F)N1CC2CN(Cc3ccc(N4CCCC4)cc3C(F)F)CC2C1]

The title compound was synthesized from 1-bromo-2-difluoromethyl-4-fluorobenzene, pyrrolidine, and potassium trifluoro((5-((1,1,1,3,3,3-hexafluoropropan-2-yloxy)carbonyl)hexahydropyrrolo[3,4-c]pyrrol-2(1H)-yl)methyl)borate following procedures analogous to those described in Example 200 to afford 1,1,1,3,3,3-hexafluoropropan-2-yl 5-(2-(difluoromethyl)-4-(pyrrolidin-1-yl)benzyl)hexahydropyrrolo[3,4-c]pyrrole-2(1H)-carboxylate. ¹H NMR (400 MHz, Chloroform-d) δ 2.02-2.05 (m, 4H), 2.48-2.53 (m, 4H), 2.87 (m, 2H), 3.30-3.37 (m, 6H), 3.60 (s, 2H), 3.71-3.76 (m, 2H), 5.76 (hept, J=6.0 Hz, 1H), 6.55 (dd, J1=2.4 Hz, J2=8.4 Hz, 1H), 6.82 (d, J=2.4 Hz, 1H), 7.12 (d, J=8.4 Hz, 1H), 7.13 (t, J=56.0 Hz, 1H). LCMS (ESI, m/z): 516.3 (M+H).

Example 203

1,1,1,3,3,3-hexafluoropropan-2-yl 5-(4-(difluoromethyl)-2-morpholinobenzyl)hexahydropyrrolo[3,4-c]pyrrole-2(1H)-carboxylate

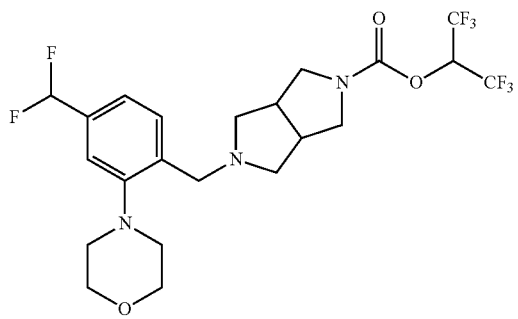 [SMILES: O=C(OC(C(F)(F)F)C(F)(F)F)N1CC2CN(Cc3ccc(C(F)F)cc3N3CCOCC3)CC2C1]

The title compound was synthesized from 1-bromo-4-(difluoromethyl)-2-fluorobenzene, morpholine, and potassium trifluoro((5-((1,1,1,3,3,3-hexafluoropropan-2-yloxy)carbonyl)hexahydropyrrolo[3,4-c]pyrrol-2(1H)-yl)methyl)borate following procedures analogous to those described in Example 200 to afford 1,1,1,3,3,3-hexafluoropropan-2-yl 5-(4-(difluoromethyl)-2-morpholinobenzyl)hexahydropyrrolo[3,4-c]pyrrole-2(1H)-carboxylate. ¹H NMR (400 MHz, Chloroform-d) δ 2.47-2.56 (m, 4H), 2.81 (m, 2H), 2.91-2.92 (m, 4H), 3.23-3.31 (m, 2H), 3.60 (s, 2H), 3.60-3.67 (m, 2H), 3.75-3.78 (m, 4H), 5.66 (hept, J=6.0 Hz, 1H), 6.54 (t, J=56.4 Hz, 1H), 7.11-7.13 (m, 2H), 7.41 (d, J=8.4 Hz, 1H). LCMS (ESI, m/z): 532.2 (M+H).

Example 204

1,1,1,3,3,3-hexafluoropropan-2-yl 5-(4-(difluoromethyl)-2-(piperidin-1-yl)benzyl)hexahydropyrrolo[3,4-c]pyrrole-2(1H)-carboxylate

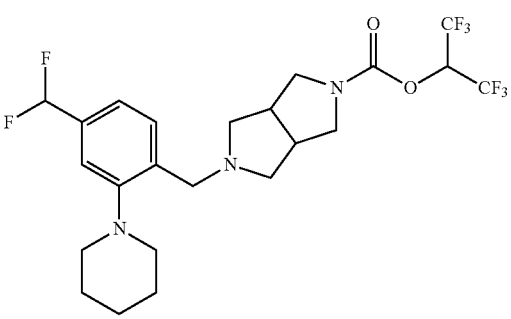 [SMILES: O=C(OC(C(F)(F)F)C(F)(F)F)N1CC2CN(Cc3ccc(C(F)F)cc3N3CCCCC3)CC2C1]

The title compound was synthesized from 1-bromo-4-(difluoromethyl)-2-fluorobenzene, piperidine, and potassium trifluoro((54(1,1,1,3,3,3-hexafluoropropan-2-yloxy)carbonyl)hexahydropyrrolo[3,4-c]pyrrol-2(1H)-yl)methyl)borate following procedures analogous to those described in Example 200 to afford 1,1,1,3,3,3-hexafluoropropan-2-yl 5-(4-(difluoromethyl)-2-(piperidin-1-yl)benzyl)hexahydropyrrolo[3,4-c]pyrrole-2(1H)-carboxylate. 1H NMR (400 MHz, Chloroform-d) δ 1.47-1.52 (m, 2H), 1.59-1.65 (m 4H), 2.45-2.56 (m, 4H), 2.79-2.82 (m, 6H), 3.24-3.31 (m, 2H), 3.58 (m, 2H), 3.62-3.67 (m, 2H), 5.66 (hept, J=6.4 Hz, 1H), 6.52 (t, J=56.4 Hz, 1H), 7.07 (d, J=8.0 Hz, 1H), 7.10 (s, 1H), 7.39 (d, J=8.0 Hz, 1H). LCMS (ESI, m/z): 530.2 (M+H).

Example 205

1,1,1,3,3,3-hexafluoropropan-2-yl 5-(4-(difluoromethyl)-2-(pyrrolidin-1-yl)benzyl)hexahydropyrrolo[3,4-c]pyrrole-2(1H)-carboxylate

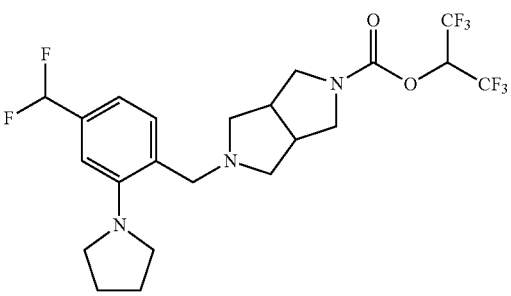 [SMILES: O=C(OC(C(F)(F)F)C(F)(F)F)N1CC2CN(Cc3ccc(C(F)F)cc3N3CCCC3)CC2C1]

The title compound was synthesized from 1-bromo-4-(difluoromethyl)-2-fluorobenzene, pyrrolidine, and potassium trifluoro((5-((1,1,1,3,3,3-hexafluoropropan-2-yloxy)carbonyl)hexahydropyrrolo[3,4-c]pyrrol-2(1H)-yl)methyl)borate following procedures analogous to those described in Example 200 to afford 1,1,1,3,3,3-hexafluoropropan-2-yl 5-(4-(difluoromethyl)-2-(pyrrolidin-1-yl)benzyl)hexahydropyrrolo[3,4-c]pyrrole-2(1H)-carboxylate. 1H NMR (400 MHz, Chloroform-d) δ 1.81-1.84 (m, 4H), 2.39-2.52 (m, 4H), 2.77 (m, 2H), 3.13-3.16 (m, 4H), 3.24-3.30 (m, 2H), 2.53 (s, 2H), 3.62-3.67 (m, 2H), 5.65 (hept, J=6.4 Hz, 1H), 6.49 (t, J=56.8 Hz, 1H), 6.87 (d, J=8.0 Hz, 1H), 6.89 (s, 1H), 7.32 (d, J=8.0 Hz, 1H). LCMS (ESI, m/z): 516.3 (M+H).

Example 206

1,1,1,3,3,3-hexafluoropropan-2-yl 5-((6-methyl-[1,1'-biphenyl]-3-yl)methyl)hexahydropyrrolo[3,4-c]pyrrole-2(1H)-carboxylate

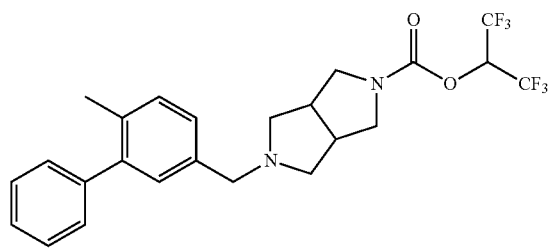 [SMILES: Cc1ccc(CN2CC3CN(C(=O)OC(C(F)(F)F)C(F)(F)F)CC3C2)cc1-c1ccccc1]

Step 1: Preparation of 5-chloro-2-methyl-1,1'-biphenyl

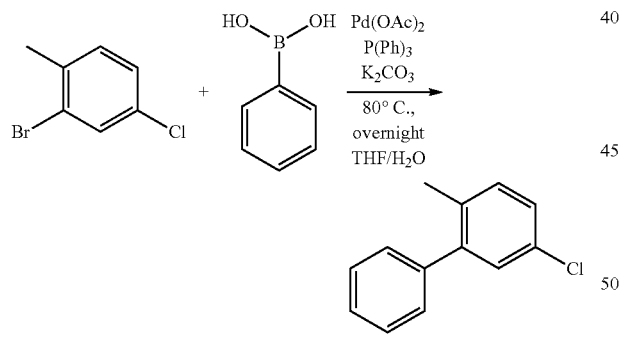

A 12 mL vial equipped with a magnetic stir bar was charged with 2-bromo-4-chloro-methylbenzene (357.3 mg, 1.74 mmol). To this vial was added phenyl boronic acid (233 mg, 1.91 mmol), Pd(OAc)₂ (19.5 mg, 0.09 mmol), P(Ph)₃ (91.2 mg, 0.35 mmol), and K₂CO₃ (480 mg, 3.58 mmol). The vial was flushed with nitrogen and evacuated 3 times. A 10:1 mixture of anhydrous THF:H₂O was then added by syringe. The resulting mixture was heated at 80° C. for 18 hours. The reaction was then cooled to rt whereupon 5 mL H₂O was added. The reaction was extracted with EtOAc (3×10 mL) and the combined organic layers were dried over Na₂SO₄, filtered and concentrated under reduced pressure to yield an oil. The oil was purified using a 12 g ISCO SiO₂ column eluting with pure hexanes over a 30 minute period. The desired fractions were combined and concentrated under reduced pressure to yield 5-chloro-2-methyl-1,1'-biphenyl as a clear oil (332 mg, 94% yield). ¹H NMR (400 MHz, Chloroform-d) δ 7.37-7.30 (m, 2H), 7.30-7.24 (m, 1H), 7.23-7.18 (m, 2H), 7.16-7.09 (m, 3H), 2.14 (s, 3H).

Step 2: Preparation of 1,1,1,3,3,3-hexafluoropropan-2-yl 5-((6-methyl-[1,1'-biphenyl]-3-yl)methyl)hexahydropyrrolo[3,4-c]pyrrole-2(1H)-carboxylate

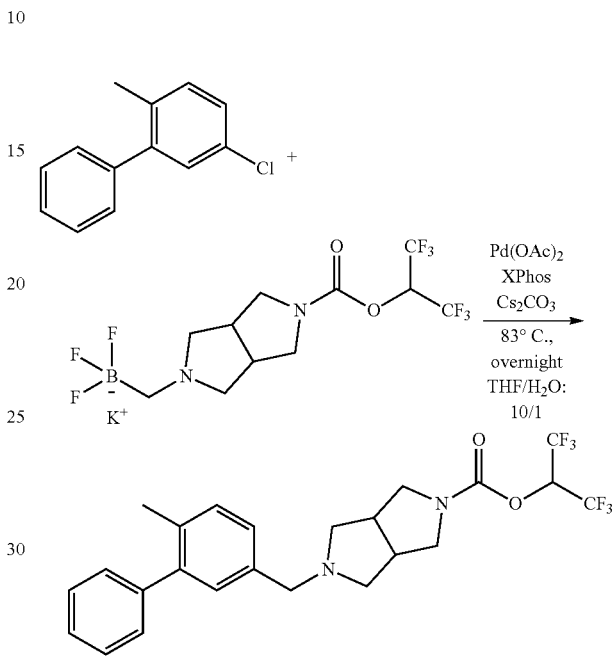

The title compound was synthesized from 5-chloro-2-methyl-1,1'-biphenyl and potassium trifluoro((5-((1,1,1,3,3-hexafluoropropan-2-yloxy)carbonyl)hexahydropyrrolo[3,4-c]pyrrol-2(1H)-yl)methyl)borate as analogously described in Example 127 (Step 3) to afford 1,1,1,3,3,3-hexafluoropropan-2-yl 5-((6-methyl-[1,1'-biphenyl]-3-yl)methyl)hexahydropyrrolo[3,4-c]pyrrole-2(1H)-carboxylate as a clear oil (43 mg, 33% yield). ¹H NMR (400 MHz, Chloroform-d) δ 7.48-7.40 (m, 2H), 7.39-7.32 (m, 3H), 7.25-7.22 (m, 2H), 7.17 (s, 1H), 5.86-5.59 (m, 0H), 3.80-3.67 (m, 2H), 3.61 (s, 2H), 3.45-3.35 (m, 2H), 2.96-2.83 (m, 2H), 2.68-2.59 (m, 2H), 2.58-2.47 (m, 2H), 2.29 (s, 3H). LCMS (ESI, m/z): 487.5 (M+H).

Example 207

1,1,1,3,3,3-hexafluoropropan-2-yl 5-((1-methyl-3-phenyl-1H-pyrazol-4-yl)methyl)hexahydropyrrolo[3,4-c]pyrrole-2(1H)-carboxylate

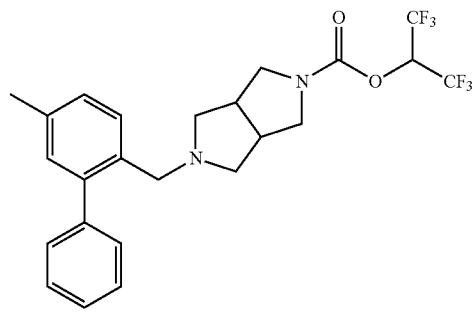 [SMILES: Cc1ccc(CN2CC3CN(C(=O)OC(C(F)(F)F)C(F)(F)F)CC3C2)c(-c2ccccc2)c1]

The title compound was synthesized from 2-bromo-1-chloro-4-methyl-benzene and potassium trifluoro((5-((1,1,1,3,3,3-hexafluoropropan-2-yloxy)carbonyl)hexahydropyrrolo[3,4-c]pyrrol-2(1H)-yl)methyl)borate as analogously described in Example 183 (Step 5) to afford 1,1,1,3,3,3-hexafluoropropan-2-yl 5-((5-methyl-[1,1'-biphenyl]-2-yl)methyl)hexahydropyrrolo[3,4-c]pyrrole-2(1H)-carboxylate as an oil. ¹H NMR (400 MHz, Chloroform-d) δ 7.40-7.31 (m, 5H), 7.28 (s, 1H), 7.17-7.13 (m, 1H), 7.11-7.09 (m, 1H), 5.83-5.68 (m, 1H), 3.77-3.67 (m, 2H), 3.50 (s, 2H), 3.25-3.13 (m, 2H), 2.88-2.72 (m, 2H), 2.54-2.43 (m, 2H), 2.43-2.31 (m, 5H). LCMS (ESI, m/z): 487.5 (M+H).

Example 208

1,1,1,3,3,3-hexafluoropropan-2-yl 5-(4-chloro-2-(tetrahydro-1H-furo[3,4-c]pyrrol-5(3H)-yl)benzyl)hexahydropyrrolo[3,4-c]pyrrole-2(1H)-carboxylate

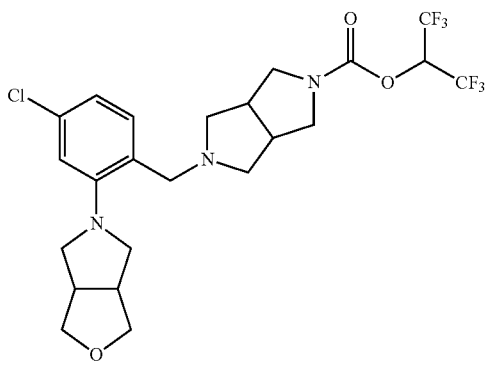 [SMILES: O=C(OC(C(F)(F)F)C(F)(F)F)N1CC2CN(Cc3ccc(Cl)cc3N3CC4COCC4C3)CC2C1]

The title compound was synthesized directly from commercially available hexahydro-1H-furo[3,4-c]pyrrole and tert-butyl hexahydropyrrolo[3,4-c]pyrrole-2(1H)-carboxylate according to the general procedures of Example 3 (Step 1) and Example 1 (Steps 1-3) to provide 1,1,1,3,3,3-hexafluoropropan-2-yl 5-(4-chloro-2-(tetrahydro-1H-furo[3,4-c]pyrrol-5(3H)-yl)benzyl)hexahydropyrrolo[3,4-c]pyrrole-2(1H)-carboxylate as an oil. ¹H NMR (400 MHz, Chloroform-d) δ 7.25-7.20 (m, 1H), 6.93-6.88 (m, 2H), 5.73-5.59 (m, 1H), 4.00-3.93 (m, 2H), 3.70-3.62 (m, 2H), 3.54-3.46 (m, 4H), 3.33-3.22 (m, 2H), 3.04-2.92 (m, 4H), 2.88-2.75 (m, 4H), 2.57-2.48 (m, 2H), 2.48-2.39 (m, 2H). LCMS (ESI, m/z): 543.0 (M+H).

Example 209

1,1,1,3,3,3-hexafluoropropan-2-yl 5-(2-(tetrahydro-1H-furo[3,4-c]pyrrol-5(3H)-yl)-6-(trifluoromethyl)benzyl)hexahydropyrrolo[3,4-c]pyrrole-2(1H)-carboxylate

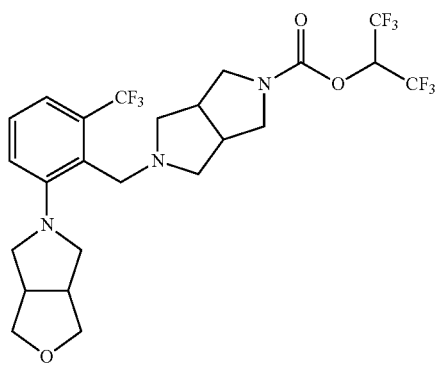 [SMILES: O=C(OC(C(F)(F)F)C(F)(F)F)N1CC2CN(Cc3c(N4CC5COCC5C4)cccc3C(F)(F)F)CC2C1]

The title compound was synthesized directly from commercially available hexahydro-1H-furo[3,4-c]pyrrole and tert-butyl hexahydropyrrolo[3,4-c]pyrrole-2(1H)-carboxylate according to the general procedures of Example 3 (Step 1) and Example 1 (Steps 1-3) to provide 1,1,1,3,3,3-hexafluoropropan-2-yl 5-(2-(tetrahydro-1H-furo[3,4-c]pyrrol-5(3H)-yl)-6-(trifluoromethyl)benzyl)hexahydropyrrolo[3,4-c]pyrrole-2(1H)-carboxylate as an oil. ¹H NMR (400 MHz, Chloroform-d) δ 7.37-7.32 (m, 1H), 7.28-7.23 (m, 2H), 5.70-5.59 (m, 1H), 3.99-3.91 (m, 2H), 3.82-3.76 (m, 2H), 3.68-3.60 (m, 2H), 3.59-3.51 (m, 2H), 3.21-3.10 (m, 2H), 3.05-2.98 (m, 2H), 2.90-2.78 (m, 4H), 2.77-2.66 (m, 2H), 2.48-2.41 (m, 2H), 2.38-2.31 (m, 2H). LCMS (ESI, m/z): 576.2 (M+H).

Example 210

1,1,1,3,3,3-hexafluoropropan-2-yl 5-(2-(tetrahydro-1H-furo[3,4-c]pyrrol-5(3H)-yl)-4-(trifluoromethyl)benzyl)hexahydropyrrolo[3,4-c]pyrrole-2(1H)-carboxylate

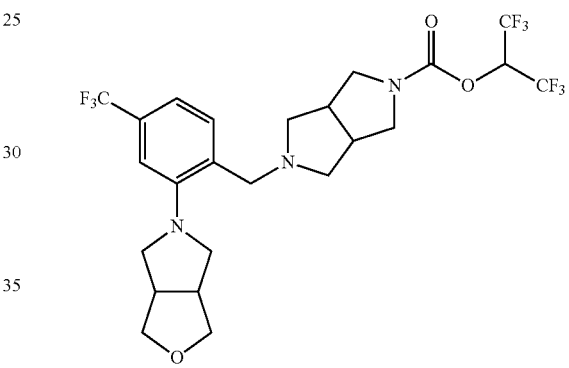

The title compound was synthesized directly from commercially available hexahydro-1H-furo[3,4-c]pyrrole and tert-butyl hexahydropyrrolo[3,4-c]pyrrole-2(1H)-carboxylate according to the general procedures of Example 3 (Step 1) and Example 1 (Steps 1-3) to provide 1,1,1,3,3,3-hexafluoropropan-2-yl 5-(2-(tetrahydro-1H-furo[3,4-c]pyrrol-5(3H)-yl)-4-(trifluoromethyl)benzyl)hexahydropyrrolo[3,4-c]pyrrole-2(1H)-carboxylate as an oil. ¹H NMR (400 MHz, Chloroform-d) δ 7.58-7.48 (m, 1H), 7.32-7.19 (m, 2H), 5.82-5.70 (m, 1H), 4.12-3.98 (m, 2H), 3.82-3.72 (m, 2H), 3.70-3.58 (m, 4H), 3.45-3.34 (m, 2H), 3.18-2000 3.02 (m, 4H), 3.01-2.84 (m, 4H), 2.70-2.51 (m, 4H). LCMS (ESI, m/z): 576.2 (M+H).

Example 211

Biological Activity Assays to Asses MAGL & Serine Hydrolase Activity

Compounds were tested to assess their MAGL and serine hydrolase activity using the following in vitro and in vivo assays.

In Vitro Competitive Activity-based Protein Profiling

Proteomes (mouse brain membrane fraction or cell lysates) (50 µL, 1.0 mg/ml total protein concentration) were preincubated with varying concentrations of inhibitors at 37° C. After 30 min, FP—Rh (1.0 µL, 50 µM in DMSO) was added and the mixture was incubated for another 30 min at 37° C. Reactions were quenched with SDS loading buffer (50 μL-4×) and run on SDS-PAGE. Following gel imaging, serine hydrolase activity was determined by measuring fluorescent intensity of gel bands corresponding to MAGL, ABHD6 and FAAH using ImageJ 1.43 u software.

Preparation of Mouse Brain Proteomes from Inhibitor Treated Mice.

Inhibitors were administered to wild-type C57Bl/6J by oral gavage in a vehicle of polyethylene glycol. Each animal was sacrificed 4 h following administration and brain proteomes were prepared and analyzed according to previously established methods (See Niphakis, M. J., et al. (2011) *ACS Chem. Neurosci.* and Long, J. Z., et al. *Nat. Chem. Biol.* 5:37-44).

Recombinant Expression of Human MAGL in HEK293T Cells.

hMAGL was expressed in HEK293T cells according to previously reported methods (see Niphakis, Long, and Blankman, J. L., et al. (2007) *Chem. Biol.* 14:1347-1356). Cell lysates were diluted with mock proteomes for use in competitive ABPP experiments.

Compounds demonstrated activity in the assays of this Example as indicated in the following tables (Tables 1 and 2).

TABLE 1

In vitro and in vivo serine hydrolase profiles for carbamate MAGL inhibitors.

| Compound from Example No. | Mouse (IC$_{50}$ value, nM) | | | Mouse brain MAGL (% inhibition at 5 mg/kg, p.o.) |
|---|---|---|---|---|
| | ABHD6 | FAAH | MAGL | |
| 1 | * | ** | *** | — |
| 2 | * | ** | *** | — |
| 3 | * | * | *** | C |
| 4 | * | * | ** | C |
| 5 | * | * | ** | — |
| 6 | * | * | ** | — |
| 7 | * | * | *** | — |
| 10 | * | ** | *** | — |
| 11 | ** | ** | *** | — |
| 12 | X | * | *** | — |
| 13 | * | ** | *** | — |
| 15 | * | * | ** | — |
| 16 | * | * | *** | — |
| 17 | * | * | ** | — |
| 19 | * | * | *** | — |
| 20 | * | * | *** | — |
| 21 | ** | * | *** | — |
| 22 | * | * | ** | — |
| 23 | * | * | ** | — |
| 24 | * | X | *** | C |
| 25 | * | * | *** | — |
| 26 | * | * | ** | — |
| 27 | * | * | *** | — |
| 28 | * | ** | *** | — |
| 29 | X | * | *** | C |
| 30 | * | X | ** | — |
| 31 | * | * | *** | — |
| 32 | * | * | *** | — |
| 33 | * | * | *** | — |
| 34 | ** | * | *** | — |
| 35 | * | X | ** | — |
| 36 | ** | * | *** | B |
| 37 | * | * | *** | C |
| 38 | * | X | *** | C |
| 39 | * | ** | *** | — |
| 40 | * | * | *** | B |
| 41 | * | * | ** | — |
| 42 | * | * | *** | B |
| 43 | * | * | *** | — |
| 44 | * | * | *** | — |

TABLE 1-continued

In vitro and in vivo serine hydrolase profiles for carbamate MAGL inhibitors.

| Compound from Example No. | Mouse (IC$_{50}$ value, nM) | | | Mouse brain MAGL (% inhibition at 5 mg/kg, p.o.) |
|---|---|---|---|---|
| | ABHD6 | FAAH | MAGL | |
| 45 | * | * | *** | A |
| 46 | * | * | *** | — |
| 47 | * | * | *** | A |
| 48 | * | * | *** | — |
| 49 | * | * | *** | — |
| 50 | * | * | *** | B |
| 51 | * | X | *** | C |
| 53 | * | * | *** | — |
| 54 | ** | X | *** | B |
| 55 | * | X | ** | — |
| 57 | * | X | *** | C |
| 58 | * | X | *** | A |
| 59 | * | * | ** | — |
| 60 | * | X | ** | — |
| 61 | * | X | *** | A |
| 62 | * | * | *** | A |
| 63 | ** | X | *** | A |
| 64 | * | * | *** | B |
| 65 | * | * | *** | C |
| 66 | * | * | *** | C |
| 67 | * | * | *** | B |
| 68 | * | * | *** | — |
| 69 | * | * | *** | C |
| 71 | * | * | *** | B |
| 72 | * | * | *** | — |
| 73 | X | X | ** | — |
| 74 | ** | X | *** | B |
| 75 | ** | * | *** | — |
| 77 | * | X | ** | — |
| 78 | * | X | *** | B |
| 79 | * | * | * | — |
| 80 | * | * | ** | — |
| 81 | * | * | ** | — |
| 82 | * | * | ** | — |
| 85 | * | ** | ** | — |
| 86 | * | * | ** | — |
| 87 | * | ** | ** | — |
| 88 | * | ** | *** | — |
| 102 | * | * | ** | — |
| 104 | * | ** | *** | — |
| 114 | * | X | ** | — |
| 127 | * | * | *** | B |
| 128 | * | * | *** | C |
| 129 | * | * | *** | A |
| 130 | * | X | *** | C |
| 131 | * | X | *** | A |
| 132 | * | * | *** | C |
| 133 | * | * | *** | C |
| 134 | * | * | *** | C |
| 135 | * | * | *** | C |
| 136 | * | * | *** | C |
| 137 | * | * | *** | C |
| 144 | * | ** | *** | — |
| 147 | X | X | ** | — |
| 148 | * | X | ** | — |
| 149 | * | * | *** | — |
| 150 | * | * | *** | — |
| 151 | * | * | *** | — |
| 152 | * | * | *** | C |
| 153 | X | * | *** | — |
| 154 | * | X | ** | — |
| 155 | * | * | ** | — |
| 156 | * | * | *** | — |
| 157 | * | X | ** | — |
| 158 | * | X | ** | — |
| 159 | * | X | *** | C |
| 160 | * | * | ** | — |
| 169 | * | * | *** | C |
| 170 | * | X | *** | B |
| 171 | * | X | ** | — |
| 172 | * | X | *** | C |

TABLE 1-continued

In vitro and in vivo serine hydrolase profiles for carbamate MAGL inhibitors.

| Compound from Example No. | Mouse (IC$_{50}$ value, nM) | | | Mouse brain MAGL (% inhibition at 5 mg/kg, p.o.) |
|---|---|---|---|---|
| | ABHD6 | FAAH | MAGL | |
| 173 | X | * | *** | B |
| 174 | * | * | *** | C |
| 178 | * | X | ** | — |
| 179 | ** | X | *** | — |
| 180 | * | X | *** | C |
| 181 | ** | X | *** | — |
| 182 | ** | X | *** | — |
| 183 | * | * | ** | — |
| 184 | * | * | ** | — |
| 185 | * | X | ** | — |
| 186 | * | * | *** | — |
| 187 | * | * | *** | — |
| 188 | * | * | *** | A |
| 189 | * | * | ** | — |
| 190 | * | * | ** | — |
| 192 | * | X | ** | — |
| 193 | * | X | ** | — |
| 194 | * | * | *** | — |
| 195 | ** | * | *** | — |
| 196 | * | * | *** | — |
| 200 | * | * | ** | — |
| 201 | * | * | ** | — |
| 202 | * | * | ** | — |
| 203 | * | * | *** | — |
| 204 | * | * | *** | — |
| 205 | * | * | *** | — |
| 206 | * | * | ** | — |
| 207 | * | * | ** | A |
| 208 | * | * | ** | — |
| 209 | * | X | ** | — |
| 210 | * | * | *** | — |

Mouse IC$_{50}$ data: * is less than 100 nM;  is between 100 and 1,000 nM; * is between 1,000 and 10,000 nM; X is greater than 10,000 nM
Mouse brain MAGL data: A is 75% or greater; B is between 25% and 75%; C is 25% or lower

TABLE 2

In vitro serine hydrolase profiles for carbamate MAGL inhibitors.

| Compound from Example No. | % Inhibition at 1 µM | | |
|---|---|---|---|
| | ABHD6 | FAAH | MAGL |
| 1 | * | ** | *** |
| 2 | * | ** | *** |
| 3 | ** | ** | *** |
| 4 | * | * | *** |
| 8 | ** | * | ** |
| 9 | ** | ** | *** |
| 10 | * | ** | *** |
| 11 | * | *** | *** |
| 12 | * | ** | *** |
| 13 | * | ** | *** |
| 14 | * | ** | *** |
| 15 | * | ** | *** |
| 16 | * | * | *** |
| 17 | * | ** | *** |
| 18 | ** | ** | *** |
| 19 | * | ** | *** |
| 20 | * | * | *** |
| 21 | ** | ** | *** |
| 22 | * | * | *** |
| 23 | * | * | *** |
| 24 | ** | * | *** |
| 25 | ** | ** | *** |
| 26 | ** | * | *** |
| 27 | * | ** | *** |
| 28 | * | ** | *** |
| 29 | * | ** | *** |
| 30 | * | * | *** |
| 31 | * | * | *** |
| 32 | ** | ** | *** |
| 33 | ** | ** | *** |
| 34 | ** | ** | *** |
| 35 | * | * | *** |
| 36 | ** | * | *** |
| 37 | * | ** | *** |
| 38 | * | * | *** |
| 39 | * | ** | *** |
| 40 | * | * | *** |
| 41 | * | * | *** |
| 42 | * | * | *** |
| 43 | * | * | *** |
| 44 | * | * | *** |
| 45 | * | * | *** |
| 46 | * | ** | *** |
| 47 | ** | ** | *** |
| 48 | * | ** | *** |
| 49 | * | ** | *** |
| 50 | ** | * | *** |
| 51 | ** | * | *** |
| 52 | * | * | ** |
| 53 | ** | * | *** |
| 54 | ** | * | *** |
| 55 | * | * | *** |
| 56 | * | * | *** |
| 57 | ** | * | *** |
| 58 | ** | * | *** |
| 59 | ** | ** | *** |
| 60 | * | * | *** |
| 61 | ** | * | *** |
| 62 | ** | * | *** |
| 63 | ** | * | *** |
| 64 | * | * | *** |
| 65 | * | * | *** |
| 66 | ** | * | *** |
| 67 | * | * | *** |
| 68 | * | * | *** |
| 69 | ** | * | *** |
| 70 | * | * | ** |
| 71 | ** | * | *** |
| 72 | ** | * | *** |
| 74 | ** | * | *** |
| 75 | *** | * | *** |
| 76 | * | * | ** |
| 77 | * | * | *** |
| 78 | ** | * | *** |
| 80 | * | ** | ** |
| 81 | ** | * | ** |
| 82 | ** | * | ** |
| 83 | * | * | ** |
| 84 | ** | *** | *** |
| 85 | * | ** | *** |
| 86 | * | ** | *** |
| 87 | ** | ** | *** |
| 88 | ** | *** | *** |
| 89 | * | * | * |
| 90 | * | ** | ** |
| 91 | * | * | * |
| 92 | * | * | * |
| 93 | ** | * | ** |
| 94 | * | ** | ** |
| 95 | * | * | ** |
| 96 | * | * | * |
| 97 | * | * | * |
| 98 | * | * | ** |
| 99 | * | * | * |
| 100 | * | * | ** |
| 101 | * | * | * |
| 102 | * | ** | ** |
| 103 | * | * | * |
| 104 | * | *** | *** |

TABLE 2-continued

In vitro serine hydrolase profiles for carbamate MAGL inhibitors.

| Compound from Example No. | % Inhibition at 1 μM | | |
|---|---|---|---|
| | ABHD6 | FAAH | MAGL |
| 105 | * | * | ** |
| 106 | * | * | ** |
| 107 | ** | ** | ** |
| 108 | * | * | * |
| 109 | * | * | * |
| 110 | * | * | * |
| 111 | * | * | ** |
| 112 | * | * | ** |
| 113 | ** | * | *** |
| 115 | * | * | ** |
| 116 | * | * | * |
| 117 | ** | * | ** |
| 118 | ** | * | ** |
| 119 | * | * | * |
| 120 | * | * | * |
| 121 | * | * | * |
| 122 | * | * | * |
| 123 | *** | * | ** |
| 124 | * | * | ** |
| 125 | * | * | ** |
| 126 | * | ** | ** |
| 127 | ** | * | *** |
| 128 | * | * | *** |
| 129 | * | * | *** |
| 130 | * | * | *** |
| 131 | * | * | *** |
| 132 | * | * | *** |
| 133 | * | * | *** |
| 134 | * | ** | *** |
| 135 | * | * | *** |
| 136 | * | * | *** |
| 137 | * | * | *** |
| 138 | * | * | * |
| 139 | * | * | * |
| 140 | * | * | ** |
| 141 | * | * | ** |
| 142 | * | * | * |
| 143 | * | * | * |
| 144 | * | *** | *** |
| 145 | * | * | * |
| 146 | * | * | ** |
| 147 | * | * | *** |
| 148 | * | * | *** |
| 149 | * | ** | *** |
| 150 | * | ** | *** |
| 151 | ** | * | *** |
| 152 | ** | * | *** |
| 153 | * | ** | *** |
| 154 | * | * | *** |
| 155 | ** | ** | *** |
| 156 | * | * | *** |
| 157 | * | * | *** |
| 158 | * | * | *** |
| 159 | * | * | *** |
| 160 | ** | ** | *** |
| 161 | ** | ** | ** |
| 163 | * | * | * |
| 164 | ** | * | ** |
| 165 | * | * | ** |
| 167 | * | — | — |
| 168 | * | — | — |
| 169 | ** | * | *** |
| 170 | ** | * | *** |
| 171 | * | * | *** |
| 172 | * | * | *** |
| 173 | ** | * | *** |
| 174 | ** | * | *** |
| 178 | * | * | *** |
| 179 | ** | * | *** |
| 180 | * | * | *** |
| 181 | ** | * | *** |
| 182 | ** | * | *** |
| 183 | * | * | *** |
| 184 | * | * | *** |
| 185 | * | * | *** |
| 186 | ** | * | *** |
| 187 | ** | * | *** |
| 188 | * | * | *** |
| 189 | * | * | *** |
| 190 | * | * | *** |
| 191 | * | * | * |
| 192 | ** | * | *** |
| 193 | ** | * | *** |
| 194 | * | ** | *** |
| 195 | ** | * | *** |
| 196 | * | * | *** |
| 197 | * | * | * |
| 198 | * | * | * |
| 199 | * | * | ** |
| 200 | * | ** | *** |
| 201 | * | ** | *** |
| 202 | * | ** | *** |
| 203 | ** | * | *** |
| 204 | * | * | *** |
| 205 | * | * | *** |
| 206 | ** | ** | *** |
| 207 | * | * | *** |
| 208 | * | * | *** |
| 209 | ** | * | *** |
| 210 | * | * | *** |

\*\*\* is >75%;
\*\* is between 25 and 75%;
\* is <25%

Example 212

Biological Activity Assays for Antimicrobial and Antiparasitic Activity

Compounds were tested to assess their antimicrobial and antiparasitic activity using the following in vitro assays.
In vitro Assay for Determining Percent Inhibition at 100 μM for Compounds Against *Mycobacterium Tuberculosis* (Mtb) Using a Low Oxygen Recovery Assay (LORA)

The ability of disclosed compounds to inhibit Mtb can be assessed using a low oxygen recovery assay (LORA) (Cho et al., 2007. Low-oxygen-recovery assay for high-throughput screening of compounds against nonreplicating *Mycobacterium tuberculosis*. Antimicrobial Agents and Chemotherapy 51, 1380-1385). This assay employs *Mycobacterium tuberculosis* H37Rv (pFCA-luxAB), which synthesises luciferase when actively growing (Changsen et al., 2003. Improved green fluorescent protein reporter gene-based microplate screening for antituberculosis compounds by utilizing an acetamidase promoter. Antimicrobial Agents and Chemotherapy 47, 3682-3687; Snewin et al., 1999. Assessment of immunity to mycobacterial infection with luciferase reporter constructs. Infection and Immunity 67, 4586-4593). For example, a selected strain can be cultured in Dubos Tween-albumin broth in a fermentor and agitated with no detectable perturbation of the medium surface. The dissolved oxygen concentration (DOC) is monitored with an oxygen sensor probe. Cells are harvested when the desired growth phase (i.e., late non-replicating persistence) is achieved. Aliquots of bacterial culture can be centrifuged, washed, and resuspended. Serial dilutions of disclosed compounds are prepared in microplates, and an aliquot of the cell suspension is subsequently added. The microplate cultures are placed under anaerobic conditions and incubated for a period of time. Luminescence is then measured. Compounds that reduce the viability of Mtb under these non-growth conditions lead to a decreased luciferase signal.

In vitro Assay for Determining Minimum Inhibitory Concentration (MIC) for Compounds Against *Mycobacterium Tuberculosis* (Mtb) Using a Microplate Alamar Blue Assay (MABA)

The activity of disclosed compounds against Mtb can be assessed according to a method based on the microplate Alamar Blue® assay (MABA) (Collins and Franzblau, 1997. Microplate alamar blue assay versus BACTEC 460 system for high-throughput screening of compounds against *Mycobacterium tuberculosis* and *Mycobacterium avium*. *Antimicrobial Agents and Chemotherapy* 41, 1004-1009). Briefly, stock solutions of disclosed compounds are prepared and added to, for example, two wells of a microplate. One well is inoculated with broth containing Mtb. The second well receives only media in order to assess background fluorescence. For MICs, serial dilutions are performed in media. Each microplate is incubated for a period of time. After incubation, one control growth is developed with a mixture of Alamar Blue® solution and Tween 80. The plates are then reincubated. Afterwards, if the well turns pink, the dye mixture is placed into all wells and the plates are reincubated for an additional period of time. The mean fluorescence units (FU) of media-only wells are subtracted from all other wells. The results are expressed in terms of % inhibition defined as 1-(test well FU/mean FU of triplicate bacteria-only wells)×100. The MIC is defined as the lowest concentration effecting a reduction in fluorescence of ≥90% relative to bacteria-only controls.

In vitro Assay for Determining $IC_{50}$ of Compounds Against *Trypanosoma Brucei*

The ability of disclosed compounds to inhibit *Trypanosoma brucei* (*T. brucei*) can be assessed using the Alamar Blue® assay (Räz et al., 1997. The Alamar Blue® assay to determine drug sensitivity of African trypanosomes (*T.b. rhodesiense* and *T.b. gambiense*) in vitro. *Acta Tropica* 68, 139-147). Bloodstream form trypanosomes are cultivated in Minimum Essential Medium (MEM). Standard curves can be generated by serially diluting *T. brucei* in culture medium and measuring fluorescence and absorbance after a period of incubation with Alamar Blue®. A drug sensitivity assay can be performed as described for the LILIT (long incubation low inoculation test) previously described (Brun and Lun, 1994. Drug sensitivity of Chinese *Trypanosoma evansi* and *Trypanosoma equiperdum* isolates. Vet. Parasitol. 52, 37-46) with minor modifications. Briefly, bloodstream form trypanosomes can be inoculated into microtiter plates and incubated in the presence of various disclosed compound concentrations for a period of time. Background fluorescence and absorbance of the drug-containing medium are determined for each drug dilution. Wells without drug serve as controls. Alamar Blue® is added after a period of time and fluorescence and colorimetric development is later determined. $IC_{50}$ values for disclosed compounds can be calculated by linear interpolation selecting values above and below the 50% mark (Hills et al., 1986. WHO document, WHO working paper No. 2.8.5).

Activity against Mtb and *T. brucei* for exemplary compounds is provided in the following table (Table 3).

TABLE 3

In vitro pathogen profiles for exemplary carbamate inhibitors.

| Compound from | % Inhibition at 100 μM | MIC | | $IC_{50}$ |
|---|---|---|---|---|
| Example No. | Mtb LORA | Mtb MABA | Mtb LORA | *T. brucei* |
| 9 | *** | +++ | +++ | ND |
| 83 | *** | +++ | ND | ND |
| 84 | *** | ++ | ND | ND |
| 106 | ND | ND | ND | ### |
| 125 | *** | +++ | ND | ND |
| 126 | *** | ++ | ND | ND |

*** is >80%;
** is between 51 and 80%;
* is ≤50%
+++ is ≤50 μM;
++ is between 51 and 100 μM;
+ >100 μM
is <5 μM;
is between 5 and 10 μM;
is >10 μM
ND = Not determined

INCORPORATION BY REFERENCE

The entire disclosure of each of the patent documents and scientific articles referred to herein is incorporated by reference for all purposes.

Equivalents

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

We claim:

1. A compound represented by Formula (I):

Formula (I)

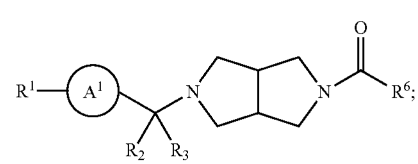

wherein:

$A^1$ is arylene or heteroarylene, each of which is optionally substituted with 1 or 2 substituents independently selected from the group consisting of halogen, alkyl, haloalkyl, cycloalkyl, hydroxyl, alkoxy, and haloalkoxy;

$R^1$ is one of the following:

(a) heterocyclyl optionally substituted with 1, 2, or 3 substituents independently selected from the group consisting of alkyl, —$N(R^7)C(O)R^8$, —$N(R^7)SO_2R^8$, —$C(O)R^8$, —$SO_2R^8$, oxo, halogen, haloalkyl, hydroxyl, and alkoxy;

(b) aryl, heteroaryl, or a fused heterocyclyl-heteroaryl, each of which is optionally substituted with 1, 2, or 3 substituents independently selected from the group consisting of halogen, —$C(O)R^8$, —$SO_2R^8$, heterocycloalkyl, and alkyl; or (c) alkyl, halogen, —C(O)N(R⁹)(R¹⁰), or -alkylene-heterocyclyl;

R² is hydrogen or unsubstituted alkyl;

R³ is hydrogen, alkyl, or aryl, wherein alkyl or aryl is optionally substituted with 1, 2, or 3 halogen substituents;

R⁶ is —O-haloalkyl, —O—C(R¹¹)(haloalkyl)C(O)N(R¹²)(R¹³), or

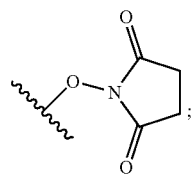 [SMILES: *ON1C(=O)CCC1=O]

R⁷ is hydrogen or alkyl;
R⁸ is alkyl;
R⁹ is hydrogen or alkyl;
R¹⁰ is hydrogen, alkyl, aryl, aralkyl, -alkylene-heterocyclyl, or -alkylene-cycloalkyl, wherein alkyl, aryl, aralkyl, -alkylene-heterocyclyl, or -alkylene-cycloalkyl are optionally substituted with 1 or more substituents selected from the group consisting of alkyl, alkenyl, alkynyl, halogen, and haloalkyl; or R⁹ and R¹⁰ are taken together with the nitrogen atom to which they are attached to form a 4-7 membered heterocyclic ring;
R¹¹ is hydrogen or alkyl;
R¹² is hydrogen or alkyl; and
R¹³ is alkyl;
wherein the stereochemical configuration at any stereocenter in a compound of Formula (I) is R, S, or a mixture thereof;
or a pharmaceutically acceptable salt, solvate, hydrate, tautomer, or N-oxide thereof.

2. The compound of claim 1, wherein R² is hydrogen.

3. The compound of claim 2, wherein R³ is hydrogen.

4. The compound of claim 3, wherein R⁶ is —O-haloalkyl.

5. The compound of claim 4, wherein R⁶ is —O—C(H)(CF₃)₂.

6. The compound of claim 5, wherein A¹ is phenylene substituted with 1 or 2 substituents independently selected from the group consisting of halogen, alkyl, haloalkyl, cycloalkyl, hydroxyl, alkoxy, and haloalkoxy.

7. The compound of claim 6, wherein A¹ is phenylene substituted with 1 or 2 substituents independently selected from the group consisting of halogen, methyl, —CF₃, and —O—CF₃.

8. The compound of claim 7, wherein A¹ is phenylene substituted with 1 substituent selected from the group consisting of halogen, methyl, —CF₃, and —O—CF₃.

9. The compound of claim 5, wherein A¹ is a 5-membered or 6-membered heteroarylene substituted with 1 or 2 substituents independently selected from the group consisting of halogen, alkyl, haloalkyl, cycloalkyl, hydroxyl, alkoxy, and haloalkoxy.

10. The compound of claim 9, wherein A¹ is pyridinylene or pyrazolylene, each of which is substituted with 1 or 2 substituents independently selected from the group consisting of halogen, alkyl, haloalkyl, cycloalkyl, hydroxyl, alkoxy, and haloalkoxy.

11. The compound of claim 8, wherein R¹ is heterocyclyl optionally substituted with 1, 2, or 3 substituents independently selected from the group consisting of alkyl, —N(R⁷)C(O)R⁸, —N(R⁷)SO₂R⁸, —C(O)R⁸, —SO₂R⁸, oxo, halogen, haloalkyl, hydroxyl, and alkoxy.

12. The compound of claim 11, wherein R¹ is tetrahydropyranyl, morpholinyl, piperidinyl, pyrrolidinyl, piperizinyl, or azetidinyl, each of which is optionally substituted with 1, 2, or 3 substituents independently selected from the group consisting of alkyl, —N(R⁷)C(O)R⁸, —N(R⁷)SO₂R⁸, —C(O)R⁸, —SO₂R⁸, and oxo.

13. The compound of claim 8, wherein R¹ is a heterocyclyl selected from:

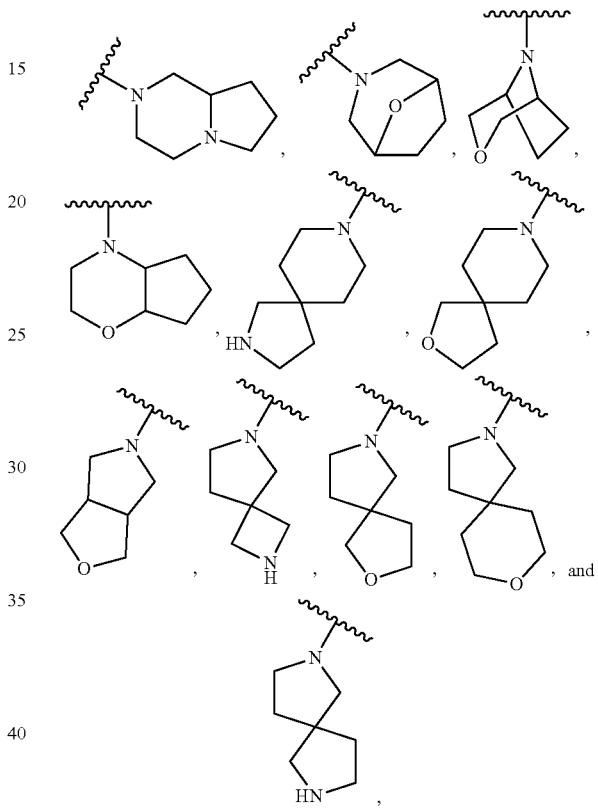

each of which is optionally substituted with 1 or 2 substituents independently selected from the group consisting of alkyl, —N(R⁷)C(O)R⁸, —N(R⁷)SO₂R⁸, —C(O)R⁸, —SO₂R⁸, and oxo.

14. The compound of claim 8, wherein R¹ is aryl, heteroaryl, or a fused heterocyclyl-heteroaryl, each of which is optionally substituted with 1, 2, or 3 substituents independently selected from the group consisting of halogen, heterocycloalkyl, and alkyl.

15. The compound of claim 14, wherein R¹ is phenyl, pyridinyl, pyrazolyl, or a fused heterocyclyl-heteroaryl, each of which is optionally substituted with 1, 2, or 3 substituents independently selected from the group consisting of halogen, heterocycloalkyl, and alkyl, wherein the fused heterocyclyl-heteroaryl is:

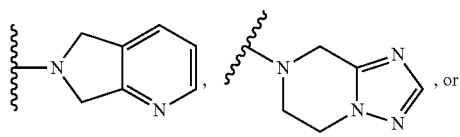

-continued

[Chemical structure]

16. The compound of claim 1, wherein the compound is 1,1,1,3,3,3-hexafluoropropan-2-yl 5-({1-ethyl-3-[3-(morpholin-4-yl)phenyl]-1H-pyrazol-4-yl}methyl)-octahydropyrrolo[3,4-c]pyrrole-2-carboxylate; 1,1,1,3,3,3-hexafluoropropan-2-yl 5-((1-methyl-3-phenyl-1H-pyrazol-4-yl)methyl)hexahydropyrrolo[3,4-c]pyrrole-2(1H)-carboxylate; 1,1,1,3,3,3-hexafluoropropan-2-yl 5-{[3-phenyl-1-(propan-2-yl)-1H-pyrazol-4-yl]methyl}-octahydropyrrolo[3,4-c]pyrrole-2-carboxylate; 1,1,1,3,3,3-hexafluoropropan-2-yl 5-{[3-(2-chlorophenyl)-1-(propan-2-yl)-1H-pyrazol-4-yl]methyl}-octahydropyrrolo[3,4-c]pyrrole-2-carboxylate; 1,1,1,3,3,3-hexafluoropropan-2-yl 5-[(3-chloro-2-{2-oxa-7-azaspiro[4.4]nonan-7-yl}phenyl)methyl]-octahydropyrrolo[3,4-c]pyrrole-2-carboxylate; 1,1,1,3,3,3-hexafluoropropan-2-yl 5-[(3-phenylphenyl)methyl]-octahydropyrrolo[3,4-c]pyrrole-2-carboxylate; 1,1,1,3,3,3-hexafluoropropan-2-yl 5-[(3-methyl-2-{2-oxa-7-azaspiro[4.4]nonan-7-yl}phenyl)methyl]-octahydropyrrolo[3,4-c]pyrrole-2-carboxylate; 1,1,1,3,3,3-hexafluoropropan-2-yl 5-{[3-(2-chlorophenyl)-1-methyl-1H-pyrazol-4-yl]methyl}-octahydropyrrolo[3,4-c]pyrrole-2-carboxylate; 1,1,1,3,3,3-hexafluoropropan-2-yl 5-(2-(8-oxa-3-azabicyclo[3.2.1]octan-3-yl)-4-chlorobenzyl)hexahydropyrrolo[3,4-c]pyrrole-2(1H)-carboxylate; 1,1,1,3,3,3-hexafluoropropan-2-yl 5-{[1-cyclohexyl-3-(propan-2-yl)-1H-pyrazol-5-yl]methyl}-octahydropyrrolo[3,4-c]pyrrole-2-carboxylate; 1,1,1,3,3,3-hexafluoropropan-2-yl 5-(2-chloro-4-morpholinobenzyl) hexahydro-pyrrolo[3,4-c]pyrrole-2(1H)-carboxylate; 1,1,1,3,3,3-hexafluoropropan-2-yl 5-{[2-(morpholin-4-yl)-3-(trifluoromethyl)phenyl]methyl}-octahydropyrrolo[3,4-c]pyrrole-2-carboxylate; 1,1,1,3,3,3-hexafluoropropan-2-yl 5-{[2-methyl-3-(morpholin-4-yl)phenyl]methy}-octahydropyrrolo[3,4-c]pyrrole-2-carboxylate; 1,1,1,3,3,3-hexafluoropropan-2-yl 5-(2-(3-acetamidoazetidin-1-yl)-5-chlorobenzyl)hexahydro-pyrrolo[3,4-c]pyrrole-2(1H)-carboxylate; 1,1,1,3,3,3-hexafluoropropan-2-yl 5-{[1-(oxan-4-yl)-3-(propan-2-yl)-1H-pyrazol-5-yl]methyl}-octahydropyrrolo[3,4-c]pyrrole-2-carboxylate; 1,1,1,3,3,3-hexafluoropropan-2-yl 5-{[2-methyl-3-(piperidin-1-yl)phenyl]methyl}-octahydropyrrolo[3,4-c]pyrrole-2-carboxylate; 1,1,1,3,3,3-hexafluoropropan-2-yl 5-(4-chloro-2-(5,6-dihydro-[1,2,4]triazolo[1,5-a]pyrazin-7(8H)-yl)benzyl)-hexahydropyrrolo[3,4-c]pyrrole-2(1H)-carboxylate; 1,1,1,3,3,3-hexafluoropropan-2-yl 5-{[2-(azetidin-1-yl)-4-chlorophenyl]methyl}-octahydropyrrolo[3,4-c]pyrrole-2-carboxylate; 1,1,1,3,3,3-hexafluoropropan-2-yl 5-{[2-(4-acetylpiperazin-1-yl)-4-chlorophenyl]methyl}-octahydropyrrolo[3,4-c]pyrrole-2-carboxylate; 1,1,1,3,3,3-hexafluoropropan-2-yl 5-[(1-cyclohexyl-3-methyl-1H-pyrazol-5-yl)methyl]-octahydropyrrolo[3,4-c]pyrrole-2-carboxylate; 1,1,1,3,3,3-hexafluoropropan-2-yl 5-[(2-phenylphenyl)methyl]-octahydropyrrolo[3,4-c]pyrrole-2-carboxylate; 1,1,1,3,3,3-hexafluoropropan-2-yl 5-{[2-chloro-4-(3-methylmorpholin-4-yl)phenyl]methyl}-octahydropyrrolo[3,4-c]pyrrole-2-carboxylate; 1,1,1,3,3,3-hexafluoropropan-2-yl 5-[(3-chloro-2-{3-oxa-8-azabicyclo[3.2.1]octan-8-yl}phenyl)methyl]-octahydropyrrolo[3,4-c]pyrrole-2-carboxylate; 1,1,1,3,3,3-hexafluoropropan-2-yl 5-{[4-(morpholin-4-yl)-2-(trifluoromethoxy)phenyl]methyl}-octahydropyrrolo[3,4-c]pyrrole-2-carboxylate; 1,1,1,3,3,3-hexafluoropropan-2-yl 5-{[4-(4-acetylpiperazin-1-yl)-2-chlorophenyl]methyl}-octahydropyrrolo[3,4-c]pyrrole-2-carboxylate; 1,1,1,3,3,3-hexafluoropropan-2-yl 5-{[1-ethyl-3-(pyridin-3-yl)-1H-pyrazol-4-yl]methyl}-octahydropyrrolo[3,4-c]pyrrole-2-carboxylate; 1,1,1,3,3,3-hexafluoropropan-2-yl 5-[(2-methyl-3-{2-oxa-7-azaspiro[4.4]nonan-7-yl}phenyl)methyl]-octahydropyrrolo[3,4-c]pyrrole-2-carboxylate; 1,1,1,3,3,3-hexafluoropropan-2-yl 5-(4-chloro-2-(hexahydrocyclopenta[b][1,4]oxazin-4(4aH)-yl)benzyl)hexahydropyrrolo[3,4-c]pyrrole-2(1H)-carboxylate; 1,1,1,3,3,3-hexafluoropropan-2-yl 5-{[4-(morpholin-4-yl)-2-(trifluoromethyl)phenyl]methyl}-octahydropyrrolo[3,4-c]pyrrole-2-carboxylate; 1,1,1,3,3,3-hexafluoropropan-2-yl 5-{[4-fluoro-2-(3-methylmorpholin-4-yl)phenyl]methyl}-octahydropyrrolo[3,4-c]pyrrole-2-carboxylate; 1,1,1,3,3,3-hexafluoropropan-2-yl 5-({1-ethyl-3-[4-(morpholin-4-yl)phenyl]-1H-pyrazol-4-yl}methyl)-octahydropyrrolo[3,4-c]pyrrole-2-carboxylate; 1,1,1,3,3,3-hexafluoropropan-2-yl 5-{[2-(4-acetylpiperazin-1-yl)-4-(propan-2-yl)phenyl]methyl}-octahydropyrrolo[3,4-c]pyrrole-2-carboxylate; 1,1,1,3,3,3-hexafluoropropan-2-yl 5-{[2-chloro-3-(morpholin-4-yl)phenyl]methyl}-octahydropyrrolo[3,4-c]pyrrole-2-carboxylate; 1,1,1,3,3,3-hexafluoropropan-2-yl 5-(2-fluoro-4-morpholinobenzyl)hexahydro-pyrrolo[3,4-c]pyrrole-2(1H)-carboxylate; 1,1,1,3,3,3-hexafluoropropan-2-yl 5-[(4-chloro-2-{5H,6H,7H,8H-imidazo[1,2-a]pyrazin-7-yl}phenyl)methyl]-octahydropyrrolo[3,4-c]pyrrole-2-carboxylate; 1,1,1,3,3,3-hexafluoropropan-2-yl 5-[(4-chloro-2-{5H,6H,7H-pyrrolo[3,4-b]pyridin-6-yl}phenyl)methyl]-octahydropyrrolo[3,4-c]pyrrole-2-carboxylate; 1,1,1,3,3,3-hexafluoropropan-2-yl 5-{[3-chloro-2-(morpholin-4-yl)phenyl]methyl}-octahydropyrrolo[3,4-c]pyrrole-2-carboxylate; 1,1,1,3,3,3-hexafluoropropan-2-yl 5-{[1-ethyl-3-(pyridin-4-yl)-1H-pyrazol-4-yl]methyl}-octahydropyrrolo[3,4-c]pyrrole-2-carboxylate; 1,1,1,3,3,3-hexafluoropropan-2-yl 5-({1-ethyl-3-[4-(pyrrolidin-1-yl)phenyl]-1H-pyrazol-4-yl}methyl)-octahydropyrrolo[3,4-c]pyrrole-2-carboxylate; 1,1,1,3,3,3-hexafluoropropan-2-yl 5-{[3-(1-methanesulfonylpiperidin-4-yl)-1-(propan-2-yl)-1H-pyrazol-4-yl]methyl}-octahydropyrrolo[3,4-c]pyrrole-2-carboxylate; 1,1,1,3,3,3-hexafluoropropan-2-yl 5-{[4-chloro-2-(3-methylmorpholin-4-yl)phenyl]methyl}-octahydropyrrolo[3,4-c]pyrrole-2-carboxylate; 1,1,1,3,3,3-hexafluoropropan-2-yl 5-[(4-chloro-2-{1-oxo-2,8-diazaspiro[4.5]decan-8-yl}phenyl)methyl]-octahydropyrrolo[3,4-c]pyrrole-2-carboxylate; 1,1,1,3,3,3-hexafluoropropan-2-yl 5-{[2-fluoro-4-(3-methylmorpholin-4-yl)phenyl]methyl}-octahydropyrrolo[3,4-c]pyrrole-2-carboxylate; 1,1,1,3,3,3-hexafluoropropan-2-yl 5- [(4-chloro-2-{8-oxa-2-azaspiro[4.5]decan-2-yl}phenyl)methyl]-octahydropyrrolo[3,4-c]pyrrole-2-carboxylate; 1,1,1,3,3,3-hexafluoropropan-2-yl 5-{[4-chloro-2-(pyrrolidin-1-yl)phenyl]methyl}-octahydropyrrolo[3,4-c]pyrrole-2-carboxylate; 1,1,1,3,3,3-hexafluoropropan-2-yl 5-{[4-chloro-2-(4-methanesulfonylpiperazin-1-yl)phenyl]methyl}-octahydropyrrolo[3,4-c]pyrrole-2-carboxylate; 1,1,1,3,3,3-hexafluoropropan-2-yl 5-[(2-chloro-3-{2-oxa-7-azaspiro[4.4]nonan-7-yl}phenyl)methyl]-octahydropyrrolo[3,4-c]pyrrole-2-carboxylate; 1,1,1,3,3,3-hexafluoropropan-2-yl 5-(5-chloro-2-(4-(methylsulfonamido)piperidin-1-yl)benzyl)hexahydropyrrolo[3,4-c]pyrrole-2(1H)-carboxylate; 1,1,1,3,3,3-hexafluoropropan-2-yl 5-{[2-(4-acetylpiperazin-1-yl)-4-fluorophenyl]methyl}-octahydropyrrolo[3,4-c]pyrrole-2-carboxylate; 1,1,1,3,3,3-hexafluoropropan-2-yl 5-{[4-fluoro-2-(pyrrolidin-1-yl)phenyl]methyl}-octahydropyrrolo[3,4-c]pyrrole-2-carboxylate; 1,1,1,3,3,3-

Hexafluoropropan-2-yl 5-(4-chloro-2-((R)-hexahydropyrrolo[1,2-a]pyrazin-2(1H)-yl)benzyl)-hexahydropyrrolo[3,4-c]pyrrole-2(1H)-carboxylate; 1,1,1,3,3,3-hexafluoropropan-2-yl 5-{[3-methyl-2-(morpholin-4-yl)phenyl]methyl}-octahydropyrrolo[3,4-c]pyrrole-2-carboxylate; 1,1,1,3,3,3-hexafluoropropan-2-yl 5-{[3-(1-acetylpiperidin-4-yl)-1-(propan-2-yl)-1H-pyrazol-4-yl]methyl}-octahydropyrrolo[3,4-c]pyrrole-2-carboxylate; 1,1,1,3,3,3-hexafluoropropan-2-yl 5-{[2-(morpholin-4-yl)-4-(propan-2-yl)phenyl]methyl}-octahydropyrrolo[3,4-c]pyrrole-2-carboxylate; 1,1,1,3,3,3-hexafluoropropan-2-yl 5-{[4-(4-acetylpiperazin-1-yl)-2-fluorophenyl]methyl}-octahydropyrrolo[3,4-c]pyrrole-2-carboxylate; 1,1,1,3,3,3-hexafluoropropan-2-yl 5-{[1-(1-acetylpiperidin-4-yl)-3-methyl-1H-pyrazol-5-yl]methyl}-octahydropyrrolo[3,4-c]pyrrole-2-carboxylate; 1,1,1,3,3,3-hexafluoropropan-2-yl 5-(2-(4-acetamidopiperidin-1-yl)-5-chlorobenzyl)hexahydro-pyrrolo[3,4-c]pyrrole-2(1H)-carboxylate; 1,1,1,3,3,3-hexafluoropropan-2-yl 5-{[3-methyl-1-(propan-2-yl)-1H-pyrazol-5-yl]methyl}-octahydropyrrolo[3,4-c]pyrrole-2-carboxylate; 1,1,1,3,3,3-hexafluoropropan-2-yl 5-{[4-(propan-2-yl)-2-(pyrrolidin-1-yl)phenyl]methyl}-octahydropyrrolo[3,4-c]pyrrole-2-carboxylate; 1,1,1,3,3,3-hexafluoropropan-2-yl 5-{[3-methyl-2-(piperidin-1-yl)phenyl]methyl}-octahydropyrrolo[3,4-c]pyrrole-2-carboxylate; 1,1,1,3,3,3-hexafluoropropan-2-yl 5-((1-ethyl-5-(morpholine-4-carbonyl)-1H-pyrazol-4-yl)methyl)hexahydropyrrolo[3,4-c]pyrrole-2(1H)-carboxylate; 1,1,1,3,3,3-hexafluoropropan-2-yl 5-[bis(4-chlorophenyl)methyl]-octahydropyrrolo[3,4-c]pyrrole-2-carboxylate; 1,1,1,3,3,3-hexafluoropropan-2-yl 5-[(4-phenylphenyl)methyl]-octahydropyrrolo[3,4-c]pyrrole-2-carboxylate; 1,1,1,3,3,3-hexafluoropropan-2-yl 5-{[4-fluoro-2-(morpholin-4-yl)phenyl]methyl}-octahydropyrrolo[3,4-c]pyrrole-2-carboxylate; 1,1,1,3,3,3-hexafluoropropan-2-yl 5-{[4-chloro-2-(morpholin-4-yl)phenyl]methyl}-octahydropyrrolo[3,4-c]pyrrole-2-carboxylate; 1,1,1,3,3,3-hexafluoropropan-2-yl 5-{[3-(1-acetylpiperidin-4-yl)-1-methyl-1H-pyrazol-4-yl]methyl}-octahydropyrrolo[3,4-c]pyrrole-2-carboxylate; 1,1,1,3,3,3-hexafluoropropan-2-yl 5-{[3-(1-methanesulfonyl-piperidin-4-yl)-1-methyl-1H-pyrazol-4-yl]methyl}-octahydropyrrolo[3,4-c]pyrrole-2-carboxylate; 1,1,1,3,3,3-hexafluoropropan-2-yl 5-({3-[2-(azetidin-1-yl)phenyl]-1-ethyl-1H-pyrazol-4-yl}methyl)-octahydropyrrolo[3,4-c]pyrrole-2-carboxylate; 1,1,1,3,3,3-hexafluoropropan-2-yl 5-({1-ethyl-3-[3-(pyrrolidin-1-yl)phenyl]-1H-pyrazol-4-yl}methyl)-octahydropyrrolo[3,4-c]pyrrole-2-carboxylate; 1,1,1,3,3,3-hexafluoropropan-2-yl 5-({3-[3-(azetidin-1-yl)phenyl]-1-ethyl-1H-pyrazol-4-yl}methyl)-octahydro-pyrrolo[3,4-c]pyrrole-2-carboxylate; 1,1,1,3,3,3-hexafluoropropan-2-yl 5-({3-[4-(azetidin-1-yl)phenyl]-1-ethyl-1H-pyrazol-4-yl}methyl)-octahydropyrrolo[3,4-c]pyrrole-2-carboxylate; 1,1,1,3,3,3-hexafluoropropan-2-yl 5-{[1-ethyl-3-(pyridin-2-yl)-1H-pyrazol-4-yl]methyl}-octahydropyrrolo[3,4-c]pyrrole-2-carboxylate; 1,1,1,3,3,3-hexafluoropropan-2-yl 5-((5-(benzylcarbamoyl)-1-ethyl-1H-pyrazol-4-yl)methyl)hexahydropyrrolo[3,4-c]pyrrole-2(1H)-carboxylate; 1,1,1,3,3,3-Hexafluoropropan-2-yl 5-((1-ethyl-3-(morpholine-4-carbonyl)-1H-pyrazol-4-yl)methyl)hexahydropyrrolo[3,4-c]pyrrole-2(1H)-carboxylate; 1,1,1,3,3,3-hexafluoropropan-2-yl 5-((3-(benzylcarbamoyl)-1-ethyl-1H-pyrazol-4-yl)methyl)hexa-hydropyrrolo[3,4-c]pyrrole-2(1H)-carboxylate; 2,5-dioxopyrrolidin-1-yl 5-{[2-methyl-3-(piperidin-1-yl)phenyl]methyl}-octahydropyrrolo[3,4-c]pyrrole-2-carboxylate; 2,5-dioxopyrrolidin-1-yl 5-[(3-phenylphenyl)methyl]-octahydropyrrolo[3,4-c]pyrrole-2-carboxylate; 2,5-dioxopyrrolidin-1-yl 5-{[4-(morpholin-4-yl)-2-(trifluoromethoxy)phenyl]methyl}-octahydropyrrolo[3,4-c]pyrrole-2-carboxylate; 2,5-dioxopyrrolidin-1-yl 5-[(2-phenylphenyl)methyl]-octahydropyrrolo[3,4-c]pyrrole-2-carboxylate; 2,5-dioxopyrrolidin-1-yl 5-{[4-(morpholin-4-yl)-2-(trifluoromethyl)phenyl]methyl}-octahydropyrrolo[3,4-c]pyrrole-2-carboxylate; 2,5-dioxopyrrolidin-1-yl 5-(2-(8-oxa-3-azabicyclo[3.2.1]octan-3-yl)-4-chlorobenzyl)hexahydropyrrolo[3,4-c]pyrrole-2(1H)-carboxylate; 2,5-dioxopyrrolidin-1-yl 5-(2-chloro-4-morpholinobenzyl)hexahydro-pyrrolo[3,4-c]pyrrole-2(1H)-carboxylate; 2,5-dioxopyrrolidin-1-yl 5-(4-chloro-2-(hexahydrocyclopenta[b][1,4]oxazin-4(4aH)-yl)benzyl)hexahydropyrrolo[3,4-c]pyrrole-2(1H)-carboxylate; 2,5-dioxopyrrolidin-1-yl 5-{[2-chloro-4-(3-methylmorpholin-4-yl)phenyl]methyl}-octahydropyrrolo[3,4-c]pyrrole-2-carboxylate; 2,5-dioxopyrrolidin-1-yl 5-((1-methyl-3-phenyl-1H-pyrazol-4-yl)methyl)hexahydropyrrolo[3,4-c]pyrrole-2(1H)-carboxylate; 2,5-dioxopyrrolidin-1-yl 5-(2-fluoro-4-morpholinobenzyl)hexahydro-pyrrolo[3,4-c]pyrrole-2(1H)-carboxylate; 2,5-dioxopyrrolidin-1-yl 5-[bis(4-chlorophenyl)methyl]-octahydropyrrolo[3,4-c]pyrrole-2-carboxylate; 2,5-dioxopyrrolidin-1-yl 5-[(4-phenylphenyl)methyl]-octahydropyrrolo[3,4-c]pyrrole-2-carboxylate; 2,5-dioxopyrrolidin-1-yl 5-{[4-fluoro-2-(morpholin-4-yl)phenyl]methyl}-octahydro-pyrrolo[3,4-c]pyrrole-2-carboxylate; 2,5-dioxopyrrolidin-1-yl 5-{[4-fluoro-2-(pyrrolidin-1-yl)phenyl]methyl}-octahydropyrrolo[3,4-c]pyrrole-2-carboxylate; 2,5-dioxopyrrolidin-1-yl 5-{[4-fluoro-2-(3-methylmorpholin-4-yl)phenyl]methyl}-octahydropyrrolo[3,4-c]pyrrole-2-carboxylate; 2,5-dioxopyrrolidin-1-yl 5-{[2-(4-acetylpiperazin-1-yl)-4-fluorophenyl]methyl}-octahydropyrrolo[3,4-c]pyrrole-2-carboxylate; 2,5-dioxopyrrolidin-1-yl 5-{[4-chloro-2-(morpholin-4-yl)phenyl]methyl}-octahydro-pyrrolo[3,4-c]pyrrole-2-carboxylate; 2,5-dioxopyrrolidin-1-yl 5-{[4-chloro-2-(pyrrolidin-1-yl)phenyl]methyl}-octahydropyrrolo[3,4-c]pyrrole-2-carboxylate; 2,5-dioxopyrrolidin-1-yl 5-{[4-chloro-2-(3-methylmorpholin-4-yl)phenyl]methyl}-octahydropyrrolo[3,4-c]pyrrole-2-carboxylate; 2,5-dioxopyrrolidin-1-yl 5-{[2-(4-acetylpiperazin-1-yl)-4-chlorophenyl]methyl}-octahydropyrrolo[3,4-c]pyrrole-2-carboxylate; 2,5-dioxopyrrolidin-1-yl 5-{[2-(morpholin-4-yl)-4-(propan-2-yl)phenyl]methyl}-octahydropyrrolo[3,4-c]pyrrole-2-carboxylate; 2,5-dioxopyrrolidin-1-yl 5-{[4-(propan-2-yl)-2-(pyrrolidin-1-yl)phenyl]methyl}-octahydropyrrolo[3,4-c]pyrrole-2-carboxylate; 2,5-dioxopyrrolidin-1-yl 5-{[2-(4-acetylpiperazin-1-yl)-4-(propan-2-yl)phenyl]methyl}-octahydropyrrolo[3,4-c]pyrrole-2-carboxylate; 2,5-dioxopyrrolidin-1-yl 5-{[2-fluoro-4-(3-methylmorpholin-4-yl)phenyl]methyl}-octahydropyrrolo[3,4-c]pyrrole-2-carboxylate; 2,5-dioxopyrrolidin-1-yl 5-{[4-(4-acetylpiperazin-1-yl)-2-fluorophenyl]methyl}-octahydropyrrolo[3,4-c]pyrrole-2-carboxylate; 2,5-dioxopyrrolidin-1-yl 5-{[4-(4-acetylpiperazin-1-yl)-2-chlorophenyl]methyl}-octahydropyrrolo[3,4-c]pyrrole-2-carboxylate; 2,5-dioxopyrrolidin-1-yl 5-{[3-methyl-2-(piperidin-1-yl)phenyl]methyl}-octahydropyrrolo[3,4-c]pyrrole-2-carboxylate; 2,5-dioxopyrrolidin-1-yl 5-[(4-chloro-2-{8-oxa-2-azaspiro[4.5]decan-2-yl}phenyl)methyl]-octahydropyrrolo[3,4-c]pyrrole-2-carboxylate; 2,5-dioxopyrrolidin-1-yl 5-[(4-chloro-2-{5H,6H,7H-pyrrolo[3,4-b]pyridin-6-yl}phenyl)methyl]-octahydropyrrolo[3,4-c]pyrrole-2-carboxylate; 2,5-Dioxopyrrolidin-1-yl 5-(4-chloro-2-(5,6-dihydro-[1,2,4]triazolo[1,5-a]pyrazin-7(8H)-yl)benzyl)-hexahydropyrrolo[3,4-c]pyrrole-2(1H)- carboxylate; 2,5-Dioxopyrrolidin-1-yl 5-(4-chloro-2-((R)-hexahydropyrrolo[1,2-a]pyrazin-2(1H)-yl)benzyl)-hexahydropyrrolo[3,4-c]pyrrole-2(1H)-carboxylate; 2,5-dioxopyrrolidin-1-yl 5-{[4-chloro-2-(4-methanesulfonylpiperazin-1-yl)phenyl]methyl}-octahydropyrrolo[3,4-c]pyrrole-2-carboxylate; 2,5-dioxopyrrolidin-1-yl 5-[(4-chloro-2-{1-oxo-2,8-diazaspiro[4.5]decan-8-yl}phenyl)methyl]-octahydro-pyrrolo[3,4-c]pyrrole-2-carboxylate; 2,5-dioxopyrrolidin-1-yl 5-{[2-(azetidin-1-yl)-4-chlorophenyl]methyl}-octahydropyrrolo[3,4-c]pyrrole-2-carboxylate; 2,5-dioxopyrrolidin-1-yl 5-{[3-(2-chlorophenyl)-1-methyl-1H-pyrazol-4-yl]methyl}-octahydropyrrolo[3,4-c]pyrrole-2-carboxylate; 2,5-dioxopyrrolidin-1-yl 5-{[3-(1-acetylpiperidin-4-yl)-1-methyl-1H-pyrazol-4-yl]methyl}-octahydropyrrolo[3,4-c]pyrrole-2-carboxylate; 2,5-dioxopyrrolidin-1-yl 5-{[3-phenyl-1-(propan-2-yl)-1H-pyrazol-4-yl]methyl}-octahydropyrrolo[3,4-c]pyrrole-2-carboxylate; 2,5-dioxopyrrolidin-1-yl 5-{[3-(2-chlorophenyl)-1-(propan-2-yl)-1H-pyrazol-4-yl]methyl}-octahydropyrrolo[3,4-c]pyrrole-2-carboxylate; 2,5-dioxopyrrolidin-1-yl 5-{[3-(1-acetylpiperidin-4-yl)-1-(propan-2-yl)-1H-pyrazol-4-yl]methyl}-octahydropyrrolo[3,4-c]pyrrole-2-carboxylate; 2,5-dioxopyrrolidin-1-yl 5-{[3-(1-methanesulfonylpiperidin-4-yl)-1-(propan-2-yl)-1H-pyrazol-4-yl]methyl}-octahydropyrrolo[3,4-c]pyrrole-2-carboxylate; 2,5-dioxopyrrolidin-1-yl 5-{[3-methyl-1-(propan-2-yl)-1H-pyrazol-5-yl]methyl}-octahydropyrrolo[3,4-c]pyrrole-2-carboxylate; 2,5-dioxopyrrolidin-1-yl 5-{[1-(1-acetylpiperidin-4-yl)-3-methyl-1H-pyrazol-5-yl]methyl}-octahydropyrrolo[3,4-c]pyrrole-2-carboxylate; 2,5-dioxopyrrolidin-1-yl 5-{[1-cyclohexyl-3-(propan-2-yl)-1H-pyrazol-5-yl]methyl}-octahydropyrrolo[3,4-c]pyrrole-2-carboxylate; 2,5-dioxopyrrolidin-1-yl 5-{[1-(oxan-4-yl)-3-(propan-2-yl)-1H-pyrazol-5-yl]methyl}-octahydropyrrolo[3,4-c]pyrrole-2-carboxylate; 2,2,2-trifluoro-1-(methylcarbamoyl)ethyl 5-[bis(4-chlorophenyl)methyl]-octahydropyrrolo[3,4-c]pyrrole-2-carboxylate; 2,2,2-trifluoro-1-(methylcarbamoyl)ethyl 5-[(4-phenylphenyl)methyl]-octahydropyrrolo[3,4-c]pyrrole-2-carboxylate; 1,1,1,3,3,3-hexafluoropropan-2-yl 5-[(2-methyl-3-[3-oxa-8-azabicyclo[3.2.1]octan-8-yl]phenyl)methyl]-octahydropyrrolo[3,4-c]pyrrole-2-carboxylate; 1,1,1,3,3,3-hexafluoro-propan-2-yl 5-[(3-[2-oxa-7-azaspiro[4.4]nonan-7-yl]-2-(trifluoromethyl)phenyl)methyl]-octahydropyrrolo[3,4-c]pyrrole-2-carboxylate; 1,1,1,3,3,3-hexafluoropropan-2-yl 5-[[3-(morpholin-4-yl)-2-(trifluoromethyl)phenyl]methyl]-octahydropyrrolo[3,4-c]pyrrole-2-carboxylate; 1,1,1,3,3,3-hexafluoropropan-2-yl 5-([1-ethyl-3-[2-(piperidin-1-yl)phenyl]-1H-pyrazol-4-yl]methyl)-octahydropyrrolo[3,4-c]pyrrole-2-carboxylate; 1,1,1,3,3,3-hexafluoropropan-2-yl 5-([1-ethyl-3-[2-(morpholin-4-yl)phenyl]-1H-pyrazol-4-yl]methyl)-octahydropyrrolo[3,4-c]pyrrole-2-carboxylate; 1,1,1,3,3,3-hexafluoropropan-2-yl 5-([1-ethyl-3-[3-(piperidin-1-yl)phenyl]-1H-pyrazol-4-yl]methyl)-octahydro-pyrrolo[3,4-c]pyrrole-2-carboxylate; 1,1,1,3,3,3-hexafluoro-propan-2-yl 5-([1-ethyl-3-[4-(piperidin-1-yl)phenyl]-1H-pyrazol-4-yl]methyl)-octahydropyrrolo[3,4-c]pyrrole-2-carboxylate; 1,1,1,3,3,3-hexafluoropropan-2-yl 5-[(2-[7-methanesulfonyl-2,7-diazaspiro[4.4]nonan-2-yl]phenyl)methyl]-octahydropyrrolo[3,4-c]pyrrole-2-carboxylate; 1,1,1,3,3,3-hexafluoropropan-2-yl 5-[(2-[7-acetyl-2,7-diazaspiro[4.4]nonan-2-yl]phenyl)methyl]-octahydropyrrolo[3,4-c]pyrrole-2-carboxylate; 1,1,1,3,3,3-hexafluoropropan-2-yl 5-[(2-[2-methanesulfonyl-2,6-diazaspiro[3.4]octan-6-yl]phenyl)methyl]-octahydropyrrolo[3,4-c]pyrrole-2-carboxylate; 1,1,1,3,3,3-hexafluoropropan-2-yl 5-[(2-[2-acetyl-2,6-diazaspiro[3.4]octan-6-yl]phenyl) methyl]-octahydropyrrolo [3,4-c]pyrrole-2-carboxylate; 2,5-dioxopyrrolidin-1-yl 5-[[3-methyl-2-(4-methylpiperazin-1-yl)phenyl]methyl]-octahydropyrrolo[3,4-c]pyrrole-2-carboxylate; 2,5-dioxopyrrolidin-1-yl 5-[[2-(4-ethylpiperazin-1-yl)-3-methylphenyl]methyl]-octahydropyrrolo [3,4-c]pyrrole-2-carboxylate; 2,5-dioxopyrrolidin-1-yl 5-[[3-(4-methanesulfonamidopiperidin-1-yl)-2-methylphenyl] methyl]-octahydropyrrolo[3,4-c]pyrrole-2-carboxylate; 2,5-dioxopyrrolidin-1-yl 5-[[3-(4-methanesulfonylpiperazin-1-yl)-2-methylphenyl]methyl]-octahydropyrrolo[3,4-c]pyrrole-2-carboxylate; 2,5-dioxopyrrolidin-1-yl 5-[[3-(4-acetamidopiperidin-1-yl)-2-methylphenyl]methyl]-octahydropyrrolo [3,4-c]pyrrole-2-carboxylate; 2,5-dioxopyrrolidin-1-yl 5-[[3-(4-acetylpiperazin-1-yl)-2-methylphenyl]methyl]-octahydropyrrolo[3,4-c]pyrrole-2-carboxylate; 2,5-dioxopyrrolidin-1-yl 5-[[3-(4,4-difluoropiperidin-1-yl)-2-methylphenyl]methyl] octahydropyrrolo[3,4-c]pyrrole-2-carboxylate; 2,5-dioxocyclopentyl 5-[[2-methyl-3-(4-methylpiperazin-1-yl) phenyl]methyl]-octahydropyrrolo[3,4-c]pyrrole-2-carboxylate; 2,5-dioxocyclopentyl 5-[[3-(4-ethylpiperazin-1-yl)-2-methylphenyl]methyl]-octahydropyrrolo[3,4-c] pyrrole-2-carboxylate; 1,1,1,3,3,3-hexafluoropropan-2-yl 5-[[3-methyl-2-(4-methylpiperazin-1-yl)phenyl]methyl]-octahydropyrrolo[3,4-c]pyrrole-2-carboxylate; 1,1,1,3,3,3-hexafluoropropan-2-yl 5-[[2-(4-ethylpiperazin-1-yl)-3-methylphenyl]methyl]-octahydropyrrolo[3,4-c]pyrrole-2-carboxylate; 1,1,1,3,3,3-hexafluoropropan-2-yl 5-[[3-(4-methanesulfonamidopiperidin-1-yl)-2-methylphenyl] methyl]-octahydropyrrolo[3,4-c]pyrrole-2-carboxylate; 1,1,1,3,3,3-hexafluoropropan-2-yl 5-[[3-(4-methanesulfonylpiperazin-1-yl)-2-methylphenyl]methyl]-octahydropyrrolo [3,4-c]pyrrole-2-carboxylate; 1,1,1,3,3,3-hexafluoropropan-2-yl 5-[[3-(4-acetamidopiperidin-1-yl)-2-methylphenyl]methyl]-octahydropyrrolo[3,4-c]pyrrole-2-carboxylate; 1,1,1,3,3,3-hexafluoropropan-2-yl 5-[[3-(4-acetylpiperazin-1-yl)-2-methylphenyl]methyl]-octahydropyrrolo[3,4-c]pyrrole-2-carboxylate; 1,1,1,3,3,3-hexafluoropropan-2-yl 5-[[3-(4,4-difluoropiperidin-1-yl)-2-methylphenyl]methyl]-octahydropyrrolo [3,4-c]pyrrole-2-carboxylate; 1,1,1,3,3,3-hexafluoropropan-2-yl 5-[[2-methyl-3-(4-methylpiperazin-1-yl)phenyl]methyl]-octahydropyrrolo[3,4-c]pyrrole-2-carboxylate; 1,1,1,3,3,3-hexafluoropropan-2-yl 5-[[3-(4-ethylpiperazin-1-yl)-2-methylphenyl]methyl]-octahydropyrrolo[3,4-c]pyrrole-2-carboxylate; 1,1,1,3,3,3-hexafluoropropan-2-yl 5-[[3-ethyl-1-(oxan-4-yl)-1H-pyrazol-5-yl]methyl]-octahydropyrrolo [3,4-c]pyrrole-2-carboxylate; 1,1,1,3,3,3-hexafluoropropan-2-yl 5-[[3-tert-butyl-1-(oxan-4-yl)-1H-pyrazol-5-yl] methyl]-octahydropyrrolo[3,4-c]pyrrole-2-carboxylate; 1,1,1,3,3,3-hexafluoropropan-2-yl 5-[[3-chloro-2-(4,4-difluoropiperidin-1-yl)phenyl]methyl]-octahydropyrrolo[3,4-c]pyrrole-2-carboxylate; 1,1,1,3,3,3-hexafluoropropan-2-yl 5-[[3-chloro-2-(4-fluoropiperidin-1-yl)phenyl]methyl]-octahydropyrrolo [3,4-c]pyrrole-2-carboxylate; 2,5-dioxopyrrolidin-1-yl 5-[[3-chloro-2-(4-fluoropiperidin-1-yl) phenyl]methyl]-octahydropyrrolo[3,4-c]pyrrole-2-carboxylate; 2,5-dioxopyrrolidin-1-yl 5-([2-chloro-4-[(piperidin-1-yl)carbonyl]phenyl]methyl)-octahydropyrrolo [3,4-c]pyrrole-2-carboxylate; 2,5-dioxopyrrolidin-1-yl 5-(2-chloro-4-(morpholine-4-carbonyl)benzyl)-hexahydropyrrolo[3,4-c]pyrrole-2(1H)-carboxylate; 2,5-dioxopyrrolidin-1-yl5-(2-chloro-4-(pyrrolidine-1-carbonyl)benzyl)-hexahydropyrrolo[3,4-c]pyrrole-2(1H)-carboxylate; 2,5-dioxopyrrolidin-1-yl 5-(4-(azetidine-1-carbonyl)-2-chlorobenzyl)-hexahydro-pyrrolo[3,4-c]pyrrole-2(1H)-carboxylate; 2,5-dioxopyrrolidin-1-yl5-(2-fluoro-4-(piperidine-1-carbonyl)benzyl)-hexahydropyrrolo[3,4-c]pyrrole-2 (1H)-carboxylate; 2,5-dioxopyrrolidin-1-yl 5-(2-fluoro-4-(pyrrolidine-1-carbonyl)benzyl)-hexahydropyrrolo [3,4-c] pyrrole-2(1H)-carboxylate; 2,5-dioxopyrrolidin-1-yl 5-(4-(azetidine-1-carbonyl)-2-fluorobenzyl)-hexahydropyrrolo [3,4-c]pyrrole-2(1H)-carboxylate; 1,1,1,3,3,3-hexafluoropropan-2-yl 5-[[1-(2-chlorophenyl)-3-ethyl-1H-pyrazol-5-yl]methyl]-octahydropyrrolo [3,4-c]pyrrole-2-carboxylate; 1,1,1,3,3,3-hexafluoropropan-2-yl 5-[[3-tert-butyl-1-(2-chlorophenyl)-1H-pyrazol-5-yl]methyl]-octahydropyrrolo[3,4-c]pyrrole-2-carboxylate; 1,1,1,3,3,3-hexafluoropropan-2-yl 5-[[3-chloro-2-(4-methylpiperazin-1-yl)phenyl]methyl]-octahydropyrrolo[3,4-c]pyrrole-2-carboxylate; 1,1,1,3,3,3-hexafluoropropan-2-yl 5-[(3-chloro-2-[8-oxa-2-azaspiro[4.5]decan-2-yl]phenyl)methyl]-octahydropyrrolo[3,4-c]pyrrole-2-carboxylate; 1,1,1,3,3,3-hexafluoropropan-2-yl 5([3-chloro-2-[(3S)-3-(fluoromethyl)pyrrolidin-1-yl]phenyl]methyl)-octahydropyrrolo[3,4-c]pyrrole-2-carboxylate; 1,1,1,3,3,3-hexafluoropropan-2-yl 5-[[3-(3-chlorophenyl)-1-(propan-2-yl)-1H-pyrazol-4-yl]methyl]-octahydropyrrolo[3,4-c] pyrrole-2-carboxylate; 1,1,1,3,3,3-hexafluoropropan-2-yl 5-[(2-chlorophenyl)methyl]-octahydropyrrolo[3,4-c]pyrrole-2-carboxylate; 1,1,1,3,3,3-hexafluoropropan-2-yl 5-[(3-chlorophenyl)methyl]-octahydropyrrolo [3,4-c]pyrrole-2-carboxylate; 1,1,1,3,3,3-hexafluoropropan-2-yl 5-[(4-chlorophenyl)methyl]-octahydropyrrolo[3,4-c]pyrrole-2-carboxylate; 1,1,1,3,3,3-hexafluoropropan-2-yl 5-((1-ethyl-3-(prop-2-yn-1-ylcarbamoyl)-1H-pyrazol-4-yl)methyl) hexahydropyrrolo[3,4-c]pyrrole-2(1H)-carboxylate; 1,1,1,3,3,3-hexafluoropropan-2-yl 5-((5-((cyclopropylmethyl) carbamoyl)-1-ethyl-1H-pyrazol-4-yl)methyl) hexahydropyrrolo[3,4-c]pyrrole-2(1H)-carboxylate; 1,1,1,3,3,3-hexafluoropropan-2-yl 5-((5-((3-chlorophenethyl) carbamoyl)-1-ethyl-1H-pyrazol-4-yl)methyl) hexahydropyrrolo[3,4-c]pyrrole-2(1H)-carboxylate; 1,1,1,3,3,3-hexafluoropropan-2-yl 5-((1-ethyl-5-(((tetrahydro-2H-pyran-4-yl)methyl)carbamoyl)-1H-pyrazol-4-yl)methyl) hexahydropyrrolo[3,4-c]pyrrole-2(1H)-carboxylate; 1,1,1,3,3,3-hexafluoropropan-2-yl 5-(3-(morpholinomethyl)-5-(trifluoromethoxy)benzyl)hexahydropyrrolo[3,4-c]pyrrole-2(1H)-carboxylate; 1,1,1,3,3,3-hexafluoropropan-2-yl 5-(3-(piperidin-1-ylmethyl)-5-(trifluoro-methoxy)benzyl) hexahydropyrrolo[3,4-c]pyrrole-2(1H)-carboxylate; 1,1,1,3,3,3-hexafluoro-propan-2-yl 5-(3-(pyrrolidin-1-ylmethyl)-5-(trifluoromethoxy)benzyl)hexahydro-pyrrolo[3,4-c]pyrrole-2(1H)-carboxylate; 1,1,1,3,3,3-hexafluoropropan-2-yl 5-(3-(pyrrolidin-1-ylmethyl)-5-(trifluoromethoxy) benzyl)hexahydropyrrolo[3,4-c]pyrrole-2(1H)-carboxylate; 1,1,1,3,3,3-hexafluoro-propan-2-yl 5-(2-methyl-3-(piperidine-1-carbonyl)benzyl)hexahydro-pyrrolo[3,4-c]pyrrole-2(1H)-carboxylate; 1,1,1,3,3,3-hexafluoropropan-2-yl 5-(5-(morpholinomethyl)-2-(trifluoromethoxy)benzyl) hexahydropyrrolo[3,4-c]pyrrole-2(1H)-carboxylate; 1,1,1,3,3,3-hexafluoropropan-2-yl 5-(5-(piperidin-1-ylmethyl)-2-(trifluoromethoxy)benzyl)hexa-hydropyrrolo[3,4-c]pyrrole-2(1H)-carboxylate; 1,1,1,3,3,3-hexafluoropropan-2-yl 5-(5-(pyrrolidin-1-ylmethyl)-2-(trifluoromethoxy) benzyl)hexahydropyrrolo[3,4-c]pyrrole-2(1H)-carboxylate; 1,1,1,3,3,3-hexafluoropropan-2-yl 5-(4-(morpholine-4-carbonyl)-3-(trifluoro-methoxy)benzyl) hexahydropyrrolo[3,4-c] pyrrole-2(1H)-carboxylate; 1,1,1,3,3,3-hexafluoro-propan-2-yl 5-(4-(piperidine-1-carbonyl)-3-(trifluoromethoxy) benzyl)hexahydropyrrolo[3,4-c]pyrrole-2(1H)-carboxylate; 1,1,1,3,3,3-hexafluoropropan-2-yl 5-(4-(pyrrolidine-1-carbonyl)-3-(trifluoromethoxy)benzyl)hexahydropyrrolo[3,4-c]pyrrole-2(1H)-carboxylate; 1,1,1,3,3,3-hexafluoropropan-2-yl 5-((1-methyl-3-phenyl-1H-pyrazol-5-yl)methyl) hexahydropyrrolo[3,4-c]pyrrole-2(1H)-carboxylate; 1,1,1,3,3,3-hexafluoropropan-2-yl 5-((3-(3-fluorophenyl)-1-methyl-1H-pyrazol-5-yl)methyl)hexahydropyrrolo[3,4-c]pyrrole-2(1H)-carboxylate; 1,1,1,3,3,3-hexafluoropropan-2-yl 5-((1-methyl-3-(m-tolyl)-1H-pyrazol-5-yl)methyl)hexahydro-pyrrolo[3,4-c]pyrrole-2(1H)-carboxylate; 2,5-dioxopyrrolidin-1-yl 5-((1-methyl-3-phenyl-1H-pyrazol-5-yl)methyl)hexahydropyrrolo[3,4-c]pyrrole-2(1H)-carboxylate; 2,5-dioxopyrrolidin-1-yl 5-((3-(3-fluorophenyl)-1-methyl-1H-pyrazol-5-yl)methyl)hexa-hydropyrrolo[3,4-c]pyrrole-2(1H)-carboxylate; 2,5-dioxopyrrolidin-1-yl 5-((1-methyl-3-(m-tolyl)-1H-pyrazol-5-yl)methyl)hexa-hydropyrrolo[3,4-c]pyrrole-2(1H)-carboxylate; 1,1,1,3,3,3-hexafluoropropan-2-yl 5-(2-(difluoromethyl)-4-morpholinobenzyl)hexa-hydropyrrolo [3,4-c]pyrrole-2(1H)-carboxylate; 1,1,1,3,3,3-hexafluoropropan-2-yl 5-(2-(difluoromethyl)-4-(piperidin-1-yl)benzyl)hexahydro-pyrrolo[3,4-c]pyrrole-2(1H)-carboxylate; 1,1,1,3,3,3-hexafluoropropan-2-yl 5-(2-(difluoro-methyl)-4-(pyrrolidin-1-yl)benzyl) hexahydropyrrolo[3,4-c]pyrrole-2(1H)-carboxylate; 1,1,1,3,3,3-hexafluoropropan-2-yl 5-(4-(difluoromethyl)-2-morpholinobenzyl)hexahydro-pyrrolo[3,4-c]pyrrole-2(1H)-carboxylate; 1,1,1,3,3,3-hexafluoropropan-2-yl 5-(4-(difluoro-methyl)-2-(piperidin-1-yl)benzyl) hexahydropyrrolo[3,4-c]pyrrole-2(1H)-carboxylate; 1,1,1,3,3,3-hexafluoropropan-2-yl 5-(4-(difluoromethyl)-2-(pyrrolidin-1-yl)benzyl)hexahydropyrrolo[3,4-c]pyrrole-2 (1H)-carboxylate; 1,1,1,3,3,3-hexafluoropropan-2-yl 5-((6-methyl-[1,1'-biphenyl]-3-yl)methyl)hexahydropyrrolo[3,4-c]pyrrole-2(1H)-carboxylate; 1,1,1,3,3,3-hexafluoropropan-2-yl 5-((1-methyl-3-phenyl-1H-pyrazol-4-yl)methyl) hexahydropyrrolo[3,4-c]pyrrole-2(1H)-carboxylate; 1,1,1,3,3,3-hexafluoropropan-2-yl 5-(4-chloro-2-(tetrahydro-1H-furo[3,4-c]pyrrol-5(3H)-yl) benzyl)hexahydropyrrolo[3,4-c]pyrrole-2(1H)-carboxylate; 1,1,1,3,3,3-hexafluoro-propan-2-yl 5-(2-(tetrahydro-1H-furo[3,4-c]pyrrol-5(3H)-yl)-6-(trifluoromethyl)benzyl) hexahydropyrrolo[3,4-c] pyrrole-2(1H)-carboxylate; or 1,1,1,3,3,3-hexafluoropropan-2-yl 5-(2-(tetrahydro-1H-furo[3,4-c]pyrrol-5(3H)-yl)-4-(trifluoromethyl)benzyl)hexahydro-pyrrolo[3,4-c]pyrrole-2(1H)-carboxylate; or a pharmaceutically acceptable salt thereof.

17. A pharmaceutical composition comprising a compound of claim 1, or a pharmaceutically acceptable salt, solvate, hydrate, tautomer, or N-oxide thereof, and a pharmaceutically acceptable carrier.

18. A method of treating pain in a patient, comprising administering a therapeutically effective amount of a compound of claim 1, or a pharmaceutically acceptable salt, solvate, hydrate, tautomer, or N-oxide thereof, to a patient in need thereof to treat said pain.

* * * * *